United States Patent
Freier et al.

(10) Patent No.: US 11,781,143 B2
(45) Date of Patent: *Oct. 10, 2023

(54) MODULATORS OF PNPLA3 EXPRESSION

(71) Applicant: Ionis Pharmaceuticals, Inc., Carlsbad, CA (US)

(72) Inventors: Susan M. Freier, San Marcos, CA (US); Huynh-Hoa Bui, San Diego, CA (US)

(73) Assignee: IONIS PHARMACEUTICALS, INC., Carlsbad, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 16/936,060

(22) Filed: Jul. 22, 2020

(65) Prior Publication Data

US 2021/0079401 A1 Mar. 18, 2021

Related U.S. Application Data

(63) Continuation of application No. 16/574,407, filed on Sep. 18, 2019, now Pat. No. 10,774,333.

(60) Provisional application No. 62/733,152, filed on Sep. 19, 2018.

(51) Int. Cl.
*C12N 15/113* (2010.01)
*A61P 1/16* (2006.01)

(52) U.S. Cl.
CPC .......... *C12N 15/1137* (2013.01); *A61P 1/16* (2018.01); *C12N 2310/315* (2013.01); *C12N 2310/32* (2013.01)

(58) Field of Classification Search
CPC .......... C12N 15/1137; C12N 2310/315; C12N 2310/32; A61P 1/16
See application file for complete search history.

(56) References Cited

U.S. PATENT DOCUMENTS

| | | | | |
|---|---|---|---|---|
| 10,774,333 | B2 * | 9/2020 | Freier | C12Y 203/01051 |
| 2010/0056384 | A1 | 3/2010 | Hobbs et al. | |
| 2012/0277284 | A1 * | 11/2012 | Swayze | A61P 35/00 536/24.5 |
| 2017/0349903 | A1 * | 12/2017 | Liu | A61K 47/6923 |
| 2018/0201936 | A1 | 7/2018 | Hinkle | |

FOREIGN PATENT DOCUMENTS

| | | |
|---|---|---|
| WO | 2008050329 A2 | 5/2008 |
| WO | 2010028110 A2 | 3/2010 |
| WO | 2015010135 A2 | 1/2015 |
| WO | 2016130806 A2 | 8/2016 |
| WO | 2017048620 A1 | 3/2017 |
| WO | 2017106283 A1 | 6/2017 |
| WO | 2019118638 A2 | 6/2019 |
| WO | 2020061200 A1 | 3/2020 |
| WO | 2020126780 A1 | 6/2020 |
| WO | 2021074772 A1 | 4/2021 |
| WO | 2021126734 A1 | 6/2021 |

OTHER PUBLICATIONS

Bruschi et al (Hepatic Medicine: Evidence and Research 2017:9 55-66) (Year: 2017).*
International Search Report and Written Opinion for International Application No. PCT/US2019/051743 dated Feb. 28, 2020.
International Search Report and Written Opinion for International Application No. PCT/EP2019/084791 dated Mar. 30, 2020.
Lee, Joseph J., et al, "Palmitoleic acid is elevated in fatty liver disease and reflects hepatic lipogenesis1-4", Am J Clin Nutr; 2015; 101:34-43.
Hoekstra, Menno, et al., "The expression level of non-alcoholic fatty liver disease-related gene PNPLA3 in hepatocytes is highly influenced by hepatic lipid status", Journal of Hepatology, 2010; vol. 52; 244-251.
Naoki Kumashiro et al: "Role of patatin-like phospholipase domain-containing 3 on lipid-induced hepatic steatosis and insulin resistance in rats", Hepatology, vol. 57, No. 5, May 25, 2013 (May 25, 2013), pp. 1763-1772.
Linden, D. et al. Molecular Metabolism, 22:49-61 (Apr. 2019).
International Search Report for PCT/IB2020/059566 dated Mar. 15, 2021.
Supplementary European Search Report for EP 19861898 dated Apr. 28, 2022.
Schmidt, K. et al., Nucleic Acids Research, 45(5): 2294-2306 (2017).
Sandhu et al., "Quantitative digital pathology reveals association of cell-specific PNPLA3 transcription with NAFLD disease activity", JHEP Reports, 1:199-202 (2019).
International Search Report and Written Opinion for International Application No. PCT/IB2022/055292 dated Sep. 2, 2022.

* cited by examiner

*Primary Examiner* — Richard A Schnizer

(57) ABSTRACT

The present embodiments provide methods, compounds, and compositions useful for inhibiting PNPLA3 expression, which may be useful for treating, preventing, or ameliorating a disease associated with PNPLA3.

14 Claims, No Drawings
Specification includes a Sequence Listing.

SEQUENCE LISTING

<160> NUMBER OF SEQ ID NOS: 2172

<210> SEQ ID NO 1
<211> LENGTH: 2805
<212> TYPE: DNA
<213> ORGANISM: Homo sapiens

<400> SEQUENCE: 1

| | | | | | |
|---|---|---|---|---|---|
| atggtccgag | ggggcgggg | ctgacgtcgc | gctgggaatg | ccctggccga | gacactgagg | 60 |
| cagggtagag | agcgcttgcg | ggcgccgggc | ggagctgctg | cggatcagga | cccgagccga | 120 |
| ttcccgatcc | cgacccagat | cctaacccgc | gccccgccc | cgccgccgcc | gccatgtacg | 180 |
| acgcagagcg | cggctggagc | ttgtccttcg | cgggctgcgg | cttcctgggc | ttctaccacg | 240 |
| tcggggcgac | ccgctgcctg | agcgagcacg | ccccgcacct | cctccgcgac | gcgcgcatgt | 300 |
| tgttcggcgc | ttcggccggg | gcgttgcact | gcgtcggcgt | cctctccggt | atcccgctgg | 360 |
| agcagactct | gcaggtcctc | tcagatcttg | tgcggaaggc | caggagtcgg | aacattggca | 420 |
| tcttccatcc | atccttcaac | ttaagcaagt | tcctccgaca | gggtctctgc | aaatgcctcc | 480 |
| cggccaatgt | ccaccagctc | atctccggca | aaataggcat | ctctcttacc | agagtgtctg | 540 |
| atggggaaaa | cgttctggtg | tctgactttc | ggtccaaaga | cgaagtcgtg | gatgccttgg | 600 |
| tatgttcctg | cttcatcccc | ttctacagtg | gccttatccc | tccttccttc | agaggcgtgc | 660 |
| gatatgtgga | tggaggagtg | agtgacaacg | tacccttcat | tgatgccaaa | acaaccatca | 720 |
| ccgtgtcccc | cttctatggg | gagtacgaca | tctgccctaa | agtcaagtcc | acgaactttc | 780 |
| ttcatgtgga | catcaccaag | ctcagtctac | gcctctgcac | agggaacctc | taccttctct | 840 |
| cgagagcttt | tgtcccccg | gatctcaagg | tgctgggaga | gatatgcctt | cgaggatatt | 900 |
| tggatgcatt | caggttcttg | gaagagaagg | gcatctgcaa | caggcccag | ccaggcctga | 960 |
| agtcatcctc | agaagggatg | gatcctgagg | tcgccatgcc | cagctgggca | acatgagtc | 1020 |
| tggattcttc | cccggagtcg | gctgccttgg | ctgtgaggct | ggagggagat | gagctgctag | 1080 |
| accacctgcg | tctcagcatc | ctgccctggg | atgagagcat | cctggacacc | ctctcgccca | 1140 |
| ggctcgctac | agcactgagt | gaagaaatga | agacaaagg | tggatacatg | agcaagattt | 1200 |
| gcaacttgct | acccattagg | ataatgtctt | atgtaatgct | gccctgtacc | ctgcctgtgg | 1260 |
| aatctgccat | tgcgattgtc | cagagactgg | tgacatggct | tccagatatg | cccgacgatg | 1320 |
| tcctgtggtt | gcagtgggtg | acctcacagg | tgttcactcg | agtgctgatg | tgtctgctcc | 1380 |
| ccgcctccag | gtcccaaatg | ccagtgagca | gccaacaggc | ctcccatgc | acacctgagc | 1440 |
| aggactggcc | ctgctggact | ccctgctccc | ccaagggctg | tccagcagag | accaaagcag | 1500 |
| aggccaccc | gcggtccatc | ctcaggtcca | gcctgaactt | cttcttgggc | aataaagtac | 1560 |
| ctgctggtgc | tgaggggctc | tccacctttc | ccagtttttc | actagagaag | agtctgtgag | 1620 |
| tcacttgagg | aggcgagtct | agcagattct | ttcagaggtc | ctaaagtttc | ccatctttgt | 1680 |
| gcagctacct | ccgcattgct | gtgtagtgac | ccctgcctgt | gacgtggagg | atcccagcct | 1740 |
| ctgagctgag | ttggttttat | gaaaagctag | gaagcaacct | ttcgcctgtg | cagcggtcca | 1800 |
| gcacttaact | ctaatacatc | agcatgcgtt | aattcagctg | gttgggaaat | gacaccagga | 1860 |
| agcccagtgc | agagggtccc | ttactgactg | tttcgtggcc | ctattaatgg | tcagactgtt | 1920 |
| ccagcatgag | gttcttagaa | tgacaggtgt | ttggatgggt | ggggccttg | tgatgggggg | 1980 |
| taggctggcc | catgtgtgat | cttgtggggt | ggagggaaga | gaatagcatg | atcccacttc | 2040 |
| cccatgctgt | gggaagggt | gcagttcgtc | cccaagaacg | acactgcctg | tcaggtggtc | 2100 |

| | |
|---|---|
| tgcaaagatg ataaccttga ctactaaaaa cgtctccatg gcgggggtaa caagatgata | 2160 |
| atctacttaa ttttagaaca ccttttttcac ctaactaaaa taatgtttaa agagttttgt | 2220 |
| ataaaaatgt aaggaagcgt tgttacctgt tgaattttgt attatgtgaa tcagtgagat | 2280 |
| gttagtagaa taagccttaa aaaaaaaaaa atcggttggg tgcagtggca cacggctgta | 2340 |
| atcccagcac tttgggaggc caaggttggg agatcacctg aggtcaggag ttcaagacca | 2400 |
| gtctggccaa catagcaaaa ccctgtctct actaaaaata caaaaattat ctgggcatgg | 2460 |
| tggtgcatgc ctgtaatccc agctattcgg aaggctgagg caggagaatc acttgaaccc | 2520 |
| aggaggcgga ggttgcggtg agctgagatt gcaccatttc attccagcct gggcaacatg | 2580 |
| agtgaaagtc tgactcaaaa aaaaaaaatt taaaaaacaa ataatctag tgtgcagggc | 2640 |
| attcacctca gcccccccagg caggagccaa gcacagcagg agcttccgcc tcctctccac | 2700 |
| tggagcacac aacttgaacc tggcttatt tctgcaggga ccagccccac atggtcagtg | 2760 |
| agtttctccc catgtgtggc gatgagagag tgtagaaata aagac | 2805 |

<210> SEQ ID NO 2
<211> LENGTH: 33500
<212> TYPE: DNA
<213> ORGANISM: Homo sapiens

<400> SEQUENCE: 2

| | |
|---|---|
| gaacactgag ttcaagataa gaaatgttta taactctgtg ctggcagcca agagctggat | 60 |
| cccagttgca gatggggcta tgcgtagcag tgagagtggg agacacagag acagggactg | 120 |
| agagagagag agagagagat gggatcaggg ataagggcag tactgccagg cactgggctg | 180 |
| ggtgctttct gttcatcaca tttaacttca caatgcccct cacacaactg ttttctcccc | 240 |
| catggtacag atataaaaag tgaagctctg agagatgaaa tgatgcttgc gagtcttgtg | 300 |
| cactggctgt ctgatgccaa agcttgcagt ctcaaccatg atatcatgtg cctgtcccac | 360 |
| tggaggctgg atgggggct gagagagctg gaccatgaaa cccttgccca gctgggtcct | 420 |
| ctctttgtct ctggaaagtg gggagggccc ccagctgctg tctacatgca gtgacgaaga | 480 |
| ggggggtgagt cctcagccct gctcctgtcc tgcccacatc tgggtcacac tggggatgac | 540 |
| agatgtccag tgtggctggc caagaatgaa tgccggtgga caggaagaga atatgaatgc | 600 |
| ctgtggctgt tggcagggtg actcatctcg ggccttcggt cacagcctca aattcctgtg | 660 |
| ccagagcctg gccctcctgt cattagtcct aagactggtc atgcaatgca ggagggatgg | 720 |
| atgggtacag gaggctagag gttctgaccc cagctgtccc ctccagaagc ctcagttccg | 780 |
| ccgcagccct gagcgtgagg tgggggtgga gggcagttag gcaggactg taggtaatgc | 840 |
| ccctctccag caaagccaac acgtcaggaa tagatgggac ccctgtctg cttctcagct | 900 |
| ctcctgacct tccccgggac ttaggacctg accctgcctt gctctgggcc tccatctaca | 960 |
| aagtgtctat gtgatgaggc agtcagccca ggtattcact aaggcctgaa gctcccatgc | 1020 |
| cctgggattc ctgcccagag aaaggaggca gccctgctcc cagctcccct acccctccag | 1080 |
| gcaaggcaaa agcaaggact gcagcagaat ggggaagctc agttgaacat gaaccaccca | 1140 |
| accaatccag gtgcttctca ggtgacattt ggaatcctga cagcaatgtc acctgttta | 1200 |
| caacaccacc agtcattctg cagttgagga cactgagcca caagagggc agaggcctga | 1260 |
| ccccaaagct cacatactct gcattcctcc aggtctcacg gagaaggggg agggcttcct | 1320 |
| ggtccactcc agctggggc gctatggccc ggcagaccag ggtcctccag tgaggagctc | 1380 |

-continued

```
tggaccaagg tctaacttgg ctccatgtac tgctgtgggc ttgctccacc cagtgccagg    1440
ggtaggtcaa ggtcaagggg cctcttaggc atctcctaag ggcatgctac tatccaaatg    1500
tttgtgtccc cactaaaggt catctgttga atcctacac cttaaggtga tgatctttgg     1560
aggcgggggc ctttggaagg tgatttgatg agagggtggc acccttatga atgggattgg    1620
tgcccttatc aaagaggccc agaggtgagg atgtggcaag atggcacctt ctacgagcca    1680
tacctctcac cagggaccaa atctgctggt atcttgaact tgggctttcc agcctccaga    1740
actgtgagac agagaaataa gccaggcgaa gtggctcacc cctgtaatcc cagcattttg    1800
ggaggctgag gtgggtgatg acttgaggtc aggagttcta gactagcctg gccaacatgg    1860
tgaaacccca tctctactaa aaatacaaaa aattagtcag gcatggtggc gcatgcttgt    1920
aatcccagct actcgtgagg ctgaggcagg agaatccctt gaacccggga ggaagaggct    1980
gcagtgggcc aagatcgtgc cattgcactc cagcctgggg ggaaaaagat agaaataaat    2040
ctcttgtttg taagccctc cgctttaagg tgttttgttt tcgcacctga acggactaag     2100
ggactaaggg accaggaatc atccaggcct cagcttccca aagcactccc cactccccag    2160
ttcctacagg gccccgaccc cagccccagc acccgtcatt cacattttt acttacaaag     2220 gaaactttga aatggacact tcctgttact ttcattcaat gaaaaaatc cccagcactt     2280 gaaggcaatc atacagaaag cctgcaacaa cgcagagagt agactcttca ggtggtggtg    2340
cctgctttag gctggctctc cccgggtcaa aagggacgtg ataaagtgtt aaagtgatgt    2400
taaggatcaa gtgggcacca actgcgactc ccctcccacc ccccgactta acagatgtca    2460
aggaaaacag aaggaagccg tttctctcca ggacatgcag tgtctgctgg agttttggaa    2520
aaatgctttc tctcgagtcg ctgcggggag ctcccaggct ggacccccc gcacaggtcc     2580 tccgccatcg ccctcccagc ccccgccccc aatcccctc ccagaccgg tccccgcccc      2640 catccccgc cagacgtcgt ccccaccccc atcccctcc aagcccgcc cgggagggcg       2700 tcctgcccgc tcattgggcc tcccgccggc tcatttgcat ggtccgaggg gggcggggct    2760
gacgtcgcgc tgggaatgcc ctggccgaga cactgaggca gggtagagag cgcttgcggg    2820 cgccgggcg agctgctgcg gatcaggacc cgagccgatt cccgatcccg acccagatcc     2880
taacccgcgc cccgcccg ccgccgccgc catgtacgac gcagagcgcg gctggagctt      2940
gtccttcgcg ggctgcggct tcctgggctt ctaccacgtc ggggcgaccc gctgcctgag    3000
cgagcacgcc ccgcacctcc tccgcgacgc gcgcatgttg ttcggcgctt cggccggggc    3060
gttgcactgc gtcggcgtcc tctccggtat cccgctgggt gcgtctgggg acgctgcccg    3120
ggctccacgt gcggagtggg tgcccctag gccggggagc gggggatccc caggggtcgc     3180
ggggccctgg aggagcgggc atcggacgcg gacacggcgg ggtgcatccc gagggccccc    3240
tccgaggcag atgcttcctg cgggggcgct gttcctgggc ccgggaaggg ggcgttggaa    3300
ccccgagcgg tccgggccga agctgggac tctcgtgcgt ccccacccct accccatca     3360 ggcgcccgtg catgaaggga gaccctcacc tccggactga gagtcggagc gtctcggagc    3420
gacggggagt agggagcggg accggggcg gagggtagtg ctggcccctg cggactccgg     3480 gtccctgtg tcctctcggg aggggctgga cgggctgagc tgccgagggg ccgatttgcc     3540
ctgggccgga caaagagtgg ggctttggcc ggtccccac ggtgggctcc ttccctctgg     3600
ggattgaggg actcaagaca ccccgcgcct gcgcttttct tttctttttt tcttttttt     3660 ttttttgagac ggagtttcgc tcagtcgccc aggctggagt gcagtggcgt gatctcaact   3720
cactgcaagc tccacctccc aggttcacgc cattctcctg cctcagcctc ccgagtagct    3780
```

```
gggactacag gcgccagcca ccaagcccgg ctaattttttt gtattttttta gtagagacgg   3840 ggtttcaccg tgttagccag gatggtctcg atctcctgac ctcgtgatct gcccacctcg   3900
gcctcccaga atgctggggt tacaggcgtg agccactgct ccctgctgcc tacgctctct   3960
gggtcgcagc ccagccttct gggggctggg tagcctccca gaagggcaac cctgggcatc   4020
ctccagggca ggctaactgg agtctagtgg ggaggggtac cttgaaagag gaaagttgtt   4080
tcctcctcct cctcctcctc cagtgtttgg gaccctttcct gggggctgga gtgcatccct   4140
ggacaccccc caatcccatc ctcttctcta gtttccactg acctaggccc accctcccct   4200
ctccggctca gtactcctgg aaatgagatt ccgtacattt gaatcttgtc ctaatgaaat   4260
atttgtccat gtgggtacct gtgtgtgtgt ggtgggggtg cagacggagg gtttgtttct   4320
cactagctgg aactactggg gtgtggtatg cttcctggga atttgtgtgc cacagtcctg   4380
gaggcgagga gggggttgtg agccagtagg caggggctgg ggcaagtagc attgtgaagc   4440
tattgacacc cagacgtccc caggcaggag attatgcccc cattagcccc cttttatctg   4500
ggcttcctta acaatggact cttttgccctg cctgccagag ccagcaggga gtgactgttc   4560
agtggtgagg aagcgggcag aggaagccct gccattgggt aggagcagtg ggcagcccct   4620
gggctgactg ggaggtgggg attagggatt agacagtcct ggctgtctgc cttcccctaa   4680
gccaggggga gaggagcaaa gggcacgaaa tgtggcctcc aggaggatta gaccgccaca   4740
tgatcatttg cacaccctgg ggtttagcaa caataaaagt cagcttttt gtatcccaag   4800 gtggcctgtg gacacccaca tggacaaatg tttacactgg gacagaattc aaatgcagag   4860
gtcccaggag cctaaagtac actcactctg gtatagaaag gattccttac tgggcagagg   4920
acaggtgcag cctggggctt tcccaggcag gacacaggga ggctcaggaa ccaccaagtc   4980
cctggaaggt ggatctggag gcgttggcag gagccactcc ctgggttcca gggctccagg   5040
ttcctgcttt aacccctgt ctcacagagg gctgtgcact tggggctgc tgagcatgtc   5100 ccagaggctg catcctggac acagcacctc agtgcatctg agctgaggct aacttggcag   5160
gagggacagg cagaacctgc cagccacgtg caattccacc cctctggcca ctcagggaag   5220
gagagctgtg agtcaagatc agatttgggt caggacaggc tggggcctgc ctgtccctgt   5280
gcatcccaag atttatggct ggccaggggt tgggctggga ggggtggtct tgcatgccag   5340
gagagtgcag atcagcctga gaggccaggc cagtaagtga ggtcagatct cctgcacctg   5400
atagcattaa ggccatctac accaaagctc taatgctgat atgttcctgg cctctatgtg   5460
gggcatggag gtggggcatg gaggtgaggc ctgctcgcct gggcttctgg aagtgggaga   5520
ctcattcctg tggctgaggc ctacagcagt gctgtgtggt aggaatacac tggaagccat   5580
gatgtcattg tgcattttct agaagccaca ttgaataaag taaaagacac aggtagaatt   5640
aatttcattg agcccaatat atccaaaata atatcatttt cacatctatt caatataaaa   5700
atttactaat gagatatttc atactaagcc actgaaatcc agtttgtatc ttacacatct   5760
cagttttgac gagccacatt tcaagggcgt gatagccaca tgtggctccc atagtagaca   5820
gtactggtct agagaaatgt tggtggcatc cttgctgtct ggtttctggc cttgccaaaa   5880
gtattaccat cccagtgtgg tacattcttt catgtatttg tctcctgtcc ccagagcaga   5940
ctctgcaggt cctctcagat cttgtgcgga aggccaggag tcggaacatt ggcatcttcc   6000
atccatcctt caacttaagc aagttcctcc gacagggtc ctgcaaatgc ctcccggcca   6060
atgtccacca gctcatctcc ggcaaaatag gcatctctct taccagagtg tctgatgggg   6120
```

```
aaaacgttct ggtgtctgac tttcggtcca aagacgaagt cgtggatgta agcagtttgc   6180
ttatctggac gttgtcaagt tagaaaagct gttttgggat gggtgtggtg gctcatgcct   6240
gtcatcccgg cactttggga ggccgaagcg ggtgggttgc ttgagcccag gagctcgaga   6300
ccaacatgat gaaacccagt ctctacaaaa attacagaaa aattagctag gcatggtgtt   6360
gtgggcccat agtcccagct actagggagg ctgaggcagg agaattgctt gagcctggga   6420
ggtggaggtt gcagtaagtc atgatcatgc cactgtactc cagcccgggt gacagtgaga   6480
tgctgtctgg aaaaaaaaaa aaagaaaga ctgttttgtt ttggaagcaa cacaggcagt   6540
tgtaggcccc ctgtgccaga gtgacataaa ctctgtacac ctccagtgat ttggtccatg   6600
tttgtaaacc ctgaatgttc caggcagtt tcttttcttc acttttatc tcttttttt   6660 gggtggggg gcgggtaca gagtcttgct ctgtctccca ggctggagtg cagtggcgca   6720
atctcaacct cccgaggagc tgggactaca ggcacaggcc atcacacctt gctaatgttt   6780 gtacttttg tagagacggg gttttgccct gttgccagg ctggtcccaa actcctgcac   6840
ccaagtaatc tgcccacctc tgcctggcag ttacaatttc aaataattcc tccctttcct   6900
tcaacacttg gctcatgacc gtccagtcca aggaacctgt cctgcaggtg tgcctctccc   6960
gagcttcctc tatgcatctt ccataatgaa gatgccttct cactggaaac cctacaaggg   7020
tgggaacgtg ccttatttgc ctgtatcctc agggtctagc agagagaaga taatttgtaa   7080
taccaaaaca ccattaaatt cagctgatgc tttcataagc gctccttgga ggaaggactc   7140
catttacttg acagatctgt gcaagacagc agcctggcgc gtctaacctg cagccagttg   7200
catcctctgt ttaaccttgt ttgcggaagc tttctctaaa cagccagcac ttgtctgttc   7260
ccacatgggt ccgttctccc agtgaatcac cgtggtgcct gctgactgct ctgtagcaca   7320
gtgcttcgca aagtgtgatc ctgggaccag cagagcagca gctcctttga gcttattgga   7380
atggcagacc ctcaggtccc acctctgacc tgctgcatgg gaattctggg gagggacgca   7440
gaatctctgg ttccacaggc tctccggtga tgctaatgaa taccggcatt tgaacagcac   7500
cgatctagcc cctttcagtc catgagccaa caaccccttgg tcctgtctgt ggtgacccag   7560
tgtgactctc atggggagca aggagaggaa gttgaagttc actgacaggg ttgttaaggg   7620
gattatgcaa tagatgagac ccatgggcct gaagtccgag ggtgtatgtt agttccccgt   7680
tcttttgacc catggattaa cctactctgt gcaaagggca ttttcaagtt tgttgccctg   7740
ctcacttgga gaaagcttat gaaggatcag gaaaattaaa agggtgctct cgcctataac   7800
ttctctctcc tttgctttca caggccttgg tatgttcctg cttcatcccc ttctacagtg   7860
gccttatccc tccttccttc agaggcgtgg taagtcggct ttctctgcta gcgctgagtc   7920 ctggggcct ctgaagtgtg ctcacacatc tcctgcctgc agggcactgg tgtcgggcac   7980
ctcagggtct gtcccatggt ggagccccat gcctcactgc ctttcagaca gagtagccac   8040 agctggcct atttccaggc tacccgggca gcaaaactta ctgcatgtgt aattaattat   8100
ttggctatct gtaaggtaaa ctggctggtt cacttaatct gcaccttaag catcagatag   8160
cttctcagtg atctagttaa actatatgat gttggccagg cgcggtggct catgtctgta   8220
atcccagcac tttgggagcc tgaagcaggc agatcacttg aggtcaggag ttcgagacca   8280
gcctggccaa cagtgtgaaa ctctgtctct cctaaaaata caaaaattag ctgggcatgg   8340
tggtgtgcac ctgtaatccc agctgctcgg gaggctgagg caggagaatt gcttgaactt   8400
gggaggcgga agttgcagtg agccaagatc gcaccactgc actccatcct gggtgacaga   8460
gcgagactct atctcaaaaa gaaaaaaaa aaaaggtaa ataaagtata tgacactgaa   8520
```

```
gaatctgtta cccctggaag gtggagcttt actcttaggg ggaactataa cagtcatata   8580
tatatatttt tttcttttct ttttttttt ttttgagatg gagtctggct ctgtcgccca    8640
ggctggagtg cagtggtgca atctcggctc actgcaacct ccacctcaca ggttcaggca   8700
attctcctgc ctcaacctcc cgagtagctg ggattacagg tgcctgccgt cacgccaagc   8760
taatttttgt attttagta gagacagggt ttcatcatat tggccaggct ggtctccaac    8820
tcctgacctc aggtgatccg cccgccttgg cctcccaaag tgctgagatt acaggcgtga   8880
gccatggtgc ccggccaaca atcacatgtg ttgtaaacaa caacaaaaat ctgtcagcct   8940
ggtctaacct agatttgtgc tttgttttgt tttgccactt tgtgatgcac aggaggaagt   9000
ttaggctgta aaatactagc cttttagggt aattttgaa ctcacaagag cagcagcgga    9060
acctttgatg caatcctgta tgtagcacca gcagagccac gtggcagagg gactcgcatt   9120
aggagcctcc cattacagac tacgtgctcc tgtgcgttat cttataggt ccccacaacc    9180
aaggggagat gtgattattc atcctgtgtg gctgtgggga acttgagagt catacttgcc   9240
caaagagcac ggccagcgag cttgcaccca ggtcactctc tgctcctctg tcagaacagg   9300
gcatgtcttg gttcactgca gggcggctct tctcattctc tgtagtttgg ggtccaggat   9360
agtggtccac ggagccactg gagtgcccag ctactgagtg accaaagcat attttggatt   9420
tccgacattg ccacagcatg gttgggcatc agcaggaccc caaccccttg ttatgctggt   9480
ggctttatgt ggttatttga tcttccccag aactcagcag gagtgcaccc agcagcaccg   9540
tagtgatgct ctctggctcc ccagtgcacg gttctggctt tccttcctgg tcgagagttt   9600
caagccctct gggtcctact ctgtcctttt cagcccatag ctttgttcaa aagctgctgg   9660
cagtgttcag atttggctga gttcagtgaa tatgtgcatt ggctgatttc tgagccatgc   9720
caggggatg gagaagccga agcaggagtg tttgttctgc aggctctgga gtaggcattg    9780
ggtctgtgcc ggctcacttg ctagtcttgc atccttcccc aacccctct ggggatgtct    9840
ggccacatca gaagacagtt tgggttgtca gaactggggg agtaccaggc cgaggtgggt   9900
ggatcatgag gtcaggagat cgagaccatc ctggctaaca cagtgaaacc tcatctctac   9960
taaacatacg aaaaaaatta gctgggcgtg gtggcgggcg cctgtagtcc cagctactcg  10020
ggaggctgag gcaggagaat ggtgtgaacc cggggggcgg agcttgcagt gagctgagat  10080
cctgccactg cactccagcc tgggcaacaa agcgagactc cgtctcacaa acaaaacaaa  10140
acaaaacaaa acaaaatctg ggggagtgcc actggcatct gatgtataga ggcccgagat  10200
gctgtgtcat cacccgttga gtgcgctcat aggcatcttc ctgacaatta gaacccatta  10260
ttcttcaaat tcaatgcaag caaattcaaa gcattactgt gtacataccg catgctaatc  10320
aattgcacca ctgagctcc taaattcaaa acattactat aaaaaagttc aaaatgcatg    10380
gaaaagttgt acatggcagg agaatatttg ggcttctgac taccccttga atgaagatga  10440
tccaccagcc gccttcctcc ttggtcttca ctccagattc ctagcatttc attctgtgtc  10500
tctttatgca gtgaggtttt tgtttgtttt ttgagacaga gtctcactgt atcacctagg  10560
cctggagtgc agtggcgcga tctcagctca ctgcaaccct cggctcctgg gtttaagcga  10620
ttctcctgcc tcagcctccc gagcagctga gattacaagc acacatcccc atgcccagct  10680
aattttgta ttttagcag agacagggt tcaccatgtt gcccaggctg gtctcgaact     10740
cctgcctca agtgatccat gtgcctcagc cttccaaagt gctgggatta caggcgtgag   10800
ccaccatgcc cagctcctag tgaggttttt gatgccttgc tacatctgcc ctagaaattg  10860
```

```
tgtgactacg attttggaaa tgttgctgtg taaacttgtg atcatttctg gactccaggc   10920
aagaatcttg atggctaagg tgtggctgaa catgtctgat tctctcctgg acctgtttta   10980
ggccaaactc tgctctgaaa ttcctccgtg tggaagggcg ggctggggag agcctcccag   11040
ctggaatctt ttggatgcct ttctctgtgg gtatctgatg gctggctctg atggctggct   11100
gtgatggctg tggctggaaa tcattgttga catgagtttc acagatgcag gctctgtcca   11160
aattgtagca aaagctgcct gccccagccg agctatgggc aataaggtgg tttaaggata   11220
tagatgaagg aaaactcacc cttagaataa tttatccaaa atgctgctgt gttgtgggtt   11280
agaggacatt ttctgaggtc ccaggttcat tgtttcattt aagtctcaaa agtccctcca   11340
ggtgttggtt ctaattgtca aagcatgggg ggagatgggc tcatgggtta aaggtcttat   11400
cccagatttc tgtatcctcc ttgcaagcag caaaggggtc tggatttgaa tccatgacca   11460
tgtttctcct ttgggtttcc atcacactct gtccccgtgc actgagcacc ctttagttca   11520
tatgaccccc ttaggcatgt tacatgggca ctcctatagg tgcccatctg gcccctaggac  11580
ttggccaaca caacatggac tccagtttcc atctgcctct tgccaggca cttttgtgca   11640
gtgcacacac tgtacaacag tagacggcaa ccctgagagc cagagtagag cctgtcctag   11700
caccggaatg ctcggtaagg atttgtcgca ggagtgattc caaagccaat gtcctccctc   11760
catatcagcc tgtttgtggc tctgagaagc tctgcccaca tgtgaaagct tgttaagcac   11820
ttaagcacta acccagagct tcagacagtg ccagtccttt ttcccttct ttaaaagcga   11880
tatgtggatg gaggagtgag tgacaacgta cccttcattg atgccaaaac aaccatcacc   11940
gtgtcccct tctatgggga gtacgacatc tgccctaaag tcaagtccac gaactttctt   12000
catgtggaca tcaccaagct cagtctacgc ctctgcacag ggaacctcta ccttctctcg   12060
agagcttttg tcccccgga tctcaaggtg agttggtggt gaggggcag gtgttctggg   12120
gtgcagctct tctttgcctc cctgattgcc aggagctacc agttactgtc tgcacaatca   12180
aacagaaata gacctgtcct tgatggttaa cggaaataaa aggcgcttgt cccagaagct   12240
caggtgaggc accaccctga ttatgggaat cacctgggaa catatacccca gacctaaaac   12300
tcagatccac ttcccaggct gtggttatat agtcaggggg gtgcagtatg ggtattagga   12360
tttttattt tttagttata aagatttttt tttggtttgt ttttgagaca gggtcttgct   12420
ctgccgctta ggctggagtg cagtggtgca atcatagctc actgaagcct cagactcctg   12480
ggttcaagca gtcctcccac ctcagcctcc taaggagctg ggacccacag gcatgcagca   12540
ccacacctgg ctaattttta aaattttgt ggagtgttgc ccaggctggt ctcacactcc   12600
tggcctcaag cgatcctccc accccagcct cccaatgtgt tgggattaca ggcatgagcc   12660
attgtaccca gccactaaga tgattcttat ttggaaacac ggtcaagaac aactgcgttc   12720
ggtagtttaa cctttttttga ttgtggtggt tttagtatgc cttaccactc taccatagta   12780
agaaatttgc agaccatgta caccaacctt tggtgctcct ggggagaaag aaagaaggct   12840
atgcaatgca atgcatgctc acagtccaag ggagagggaa agctgtctaa caggattggt   12900
tttcccgtgt gctttataag cagatgagta gaggagacag ctcttattgt cctagtggca   12960
attgggatag gctgcaaagt ttgttagggt ggaggcttat tccgggacca agggagccca   13020
aagaaacaag ctcctgccag gcgcggtggc tcacgcctgt aatcccagca ctttgggagg   13080
ctgaggcagg tggatcacct gaggtcagga gtttgagacc agcctggcca acatggtgaa   13140
accccgtctc catgaaaaat acaaaaatta cccgggcatg gtggcgggca cctgtaatcc   13200
cagctactag ggaggctgag gcaggaaaat ggcttgaacc tcggaagtgg aggtggccgt   13260
```

```
tagccgagat cacgccactg cactccagcc tgggcaacag agcaagactc tgccttaaaa    13320
aaaaaaaaaa aaaaaagaaa agtaaaagga aaaaaaagag gctctggcct gctggggtgc    13380
ctgcaaagtc tccgtggaag ggtgacattc aagccgagac ctccagggaa ctgtctcctg    13440
ggagcacaga gcccttttgct cagccccccag gtggctcagt gcccccagcc agcagactca   13500
gagcttgcat gattctttgg tgctctctgc ggtcttccaa tgatgctgaa ataaatggtg    13560
cttggtgtct ccctgctgta gtccccttgc ttgctttgct cacaggtgct gggagagata    13620
tgccttcgag gatatttgga tgcattcagg ttcttggaag agaagggtat gtatgggctg    13680
ggaggatcag ccatgccctt ttgacaagca tttactagcg gtcttggtaa agacttgaga    13740
tttgccttag ttctaacact tagtgcccaa cgccttcctt gtgttgctca acctactcat    13800
gagcccagga gataggaaat ctccgtccca ttgtacagat ggggaaacag aattttggaa    13860
aggagagcca agcagcacac accccctccct gaggggcaga gccgagattt gaactgggat    13920
gtcatgactc cagggccctc tccctccccca gggtccccctt atctgaaggc ggttttttctt  13980 tccagctcga cctcttgtga cccttagttt aacaagggcc gaagttaaag agtttctgcg    14040
cctggacccc aaatgaagca atcagatttc tcatctccag tcaggtgtgg gtccaagccc    14100
actagacaag tttgctcttc ccagagcaca tttctgcctt caagtcatcc tggcttgtca    14160
gggctggggg agttctgctg tagaaatatt agagtggaag gaaaaagatg tgttgggagc    14220 tattttttctt taatactaaa agttggttga tgaatttgtc gttggccaag accaaggaga    14280
ctgcattttt aaggacatat gtgtatttat ctgctcagaa aatgttcatt gctgtgtgct    14340
agggatactg cagtgaacac agaggtgtga cccttgccag ccttgtgaga gaagtgagca    14400
gataagtaag cagaagggtg atgctgtgtc gatgggaaag tacaggtgcc aatgagaagg    14460
cacaggtgtc aaggagaaga cacaggatgc tggaggctca tgcaggatgg atctccaagg    14520
cccaggggaa gaagggcctc tcggaggacg tgaatccaca ttaagacttt ggggataagt    14580
aggagcgcct taggcatggg gacccatgga tgcgaggcct gtaggacaca gacaggatgg    14640
catgaaggcc tgtgcaactg gaggggtggg gatgggggaca ctaagagatg gctggaagtg   14700
tgggggtggg gacactaaga gatgactgga gaagagggg tcaggagtgg tgaaaaatgg    14760
gagaggaggg caggctgggc cttttggata caggggatt gcatcctgca gtggtaggga    14820
gccactgagg gctgctgcag taggagtgag gggatcagag gagagctttg gaagcccccct   14880 ggatgcggga caggaagcga gataccagtg tctaggaggc cagtgaggca gccacaggct    14940
ccaccaggat cagggctgcg agggtcatga ggaggaaacc aatttgaagg agtccagggg    15000
aataggactt ggaaatgacc gatgggacat ttgggaagag gaagacagaa gagcgcagtc    15060
ccggcttctg gctttagcag ttgggcaagg ggagatgggg agatgtgccc atgggttgag    15120
ggttgaggac attaggaggg agccggtatg gcaggaagag ctggtgtgcc agagatgctg    15180
gaagcagcat ctgcctgaga acagatacct ggcaatattc ctaagggaaa gtgacatctc    15240
ggagggtgag gagggcatct gatagggcct ggaaagagcc ggggcaagca tgaatgtgag    15300
gttatcttgg ggggcaaggc tcaggcgttg aggagcagcc cctggtctct tcagcctgaa    15360
gttggaagcc agagttgggc caggtgcagc tgtggttgtc tgaagtcccc ctccccccagc   15420 ccagtgtgcc aatgctgtaa gagcaagggc cgctcactgg tgctggtggc tgagtcccag   15480
cacccaggac agggcctggc acatactggt gcccaatcct cccttctggg tgcttcttcc    15540
aaggccttgt gatggaagtg agtaccctct tcgacatcag acccagcttc aaatcctggc    15600
```

```
tctgctatgt attggctgcg tggctttaga caagtcttt  aaccttgctg tgcttctgat    15660
ttctcagctg aaaaatggag atgatgatag tggtttctgt aaggccttat ggtgaagcac    15720
ctagctcagg gcctggaagg caggtgtaac cagtggttca gttgttataa accaacacta    15780
accctcgcct ttgcacctca tgaaaccaga tatgtagatg gagcccacaa agctagcagg    15840
agccaagctc acgtgtgtcc tgctttaaag ccccatacc  ctttctccgg gtgacaaaca    15900
cctgtgctcg ttctcttccc ttcccctctt ccccttgcat ttggctaata acaggccagc    15960
tgcctgcctc cctgcagttt ggtagatggg tgggtaacga ccaccactcc cacgttcgcc    16020
tgatgggctt gttttccgtg cccttcacag gcatctgcaa caggcccag  ccaggcctga    16080 agtcatcctc agaagggatg gatcctgagg tcgccatgcc cagctgggca acatgagtc     16140 tggattcttc cccggagtcg gctgccttgg ctgtgaggct ggagggagat gagctgctag    16200
accacctgcg tctcagcatc ctgccctggg atgagagcat cctggacacc ctctcgccca    16260
ggctcgctac aggtacccac tcctcggggt gagcacgggc agcaccttgt tttctttctt    16320
gtgcattatg gaggaagatg gtactgccac atgggagcga taggggtgagg caaccatgac   16380 aggtggttgg gaacatctcc ttccatgtgt acagcctggg ctgctgccat cactcccagc    16440
acagccccca accccccaa  tcctggaacc ttgccaagtc tcccttccca tggggtcatg    16500
accaggagga aaacaaactc cagctgagcc ccttgggtt  ccccatatag gctcctgcct    16560
gtggcagctg ggccctctgt accccttt c aactctgtct ccctaacatg gcacctgagc    16620
tcctgccatc ctggatttca tggaccccaa ggatgggggt cctgcatctg ggacttggcc    16680
tattactcgg agctccttt  cagccgcctc cctccacctg tccacccacc tcaaggctcc    16740
tttcttgaga cctctcctaa tttctccctt ccctaaacc  cacaattttg aacctccatc    16800
gaatggtgct gtattttata atgtcatcaa atatcaaatg gagacagtgc tatggtccaa    16860
atgattgtgt accccccaga atttgtcttt tgaaatccta acccccaaca tgatggtctt    16920
aggaggtggg gcctttggga ggagattagg tcatgaggaa agggctgtca tgaatgggat    16980 tggtgcccet attaaacaga cccaagagag gtcccttgtc ccttctactg tgtgaggact    17040
cagaaggtgt tgtctatgaa gaagcaggcc ctcaccagac accaacatgt ctgctgcccc    17100
ttgatctggg accttgcagc ctctagaact ctgaaaaatc gatgtttgtt gttttataag    17160
ccactcagtt ggtggcattt tgttagagta gcctgaacac ggactaagtc aaacagaaga    17220
acccacaaac cagctacaga gttgggcatt tggagaaatt caaaaatgag tcagacataa    17280
ctccttattc ttgaggtgcc ctaagagatg ggacacagca gctgcccagg tgcattagtt    17340
tgttctcaca ttgctataaa gaaataccctg agactgggta actcataaag aaagaggttg    17400
aattggctca cagttgcaca ggctggacag gaagcatggt gctggcatct gtcagcttc     17460 tggggaggcc tcaggaaact tacaatcatg gcagaaggtg aacgggaagc atgcacatcc    17520
catgactgga gcaggagtga gagagagagg gaaatagagg gaaggtgcca tacacttta     17580 aacaaccaga tctcatgaga acacattcac tatcaagaga acagcaccag tggggaaatc    17640
cgcccccatg atccaatcac ctcccatcag gctccgcctc caacactggg aattacaatt    17700
tgacatgaga tgtgggcagg gacacagatc caaaccatat gaccagatta atacgatttg    17760
aggcatcacg aggtcattaa agagagggaa taaaagactg gggctccagg aagaaggctc    17820
tggaatccag cagagggtca aggaccagct tgtaaagctg gtggtgcctg agaagtacct    17880
aggagaacat agatgctgtg acgtttgatg tagctgtttt ttgttttgtg ttttggtttt    17940
tgagacagag tctcactctg ttgcccaggc tggagtgtgc agtggcgtga tcttggctca    18000
```

```
ctggagcctc catctcccag gttcaaatga tcctcatgcc tcagcctcct gagttgctgg    18060
gattacaggt gcacaccacc acgcctggct aattttgtg ttttcagtag agacagggt    18120 tcaccatgtt ggccaggctg gtcttgaact cctgacctca agtgatccaa caacttcagc    18180
ctcccaaagt gctgggatga caggcatgag ccaccatgcc cagcctgatg tagctgtttc    18240
tgtgcacatt atttgctgtg gggtatattc agatttctta atacaagatg attctttgcc    18300
tcatgactta cacaccattt tctatttaat ttcagctatg atattggaaa tggacatgtc    18360
ttttcaagga aaataaaagc aggctttctg gaatggcgac ttccaaacat atttgtcaat    18420
ttaaaggagc tgggagtggg gaccctatgc tccgtaagca ctctcttagc tgttcttggc    18480
tgtgctcccc gcttcagctt cacactgccc ttgctgtgaa gggagcagcc tgggccgggc    18540
gcggtggctt acacctgtaa tcctagcact ttgggaggcc gaggtgggtg gatcacctga    18600
ggtcaggagt tcaagaccag cctggccaac atggtgaaac tccatctcta ctaaaaatac    18660
aaaaaattag ctgggcatgg tggcaggtgc ctgtaatccc agctacttgg gaggctgagg    18720
cagaagaatc gcttgaaccc aggaggcgga ggttgcagtg agccgagatt gcgccattgc    18780
actccagcct gggggcaaca agagcaaaac tctgtctgga aaaaaagaa aggagcagct    18840 tggcaaaccc caccttgtcg cttttgtgag tgcctctgac cctttggctg ccaggacggg    18900
cgtattttat ggaaatgcta agcaccaaca gagtaaagtg gtttggtttt tcacagtggt    18960
gggagataat agctccaaat tgtcttttc agcactgagt gaagaaatga aagacaaagg    19020
tggatacatg agcaagattt gcaacttgct acccattagg ataatgtctt atgtaatgct    19080
gccctgtacc ctgcctgtgg aatctgccat tgcgattgtc cagaggtgag catttaggt    19140 ggctccgtgt cttcctcaca gggttgatat gaggatgaaa caagatgata gatcatggtg    19200
gcatgtagtc tgggacctgg attgtcgtgc cacagatcac agctcacagt ctatgtgcaa    19260 tgccctgaa tgttgcccac ctgtcctcaa gccacacatg cacctgtaac tcagtgcaag    19320
cccagaaact ccccgtgggg actcctagag ctgtcagtgg cctcacatag cagctggtcc    19380
agtctcttgt gattgcccaa ggaaactgag gcctggagag cttggggtca ctgctctgag    19440
gccatagaga tgcctagtag aagggccagg cctagaagca ggatccttgc tgcccctctg    19500 agctgttcc attaaaatc acatgaaggc cggcgccgtg gctcacggct gtaatcccag    19560
cattttggga ggcaaggtg ggtggatcat gtgaggtcag gagtttgaga ccagcttggc    19620
caacatggtg aaatgccatc tgtactaaaa atacaaaat tagtggagca tggtggcacg    19680
tgcctgtact cccagctact tggaaggctg ggcagaagaa atcgcttgag cctgggaggc    19740
agaggttgta gtgagccaag attgtaccac tgcactccag cctgggtgac aggagagaaa    19800
ccctatctca aaataaaatg aaaggtaatg aaatgaataa aataataaat caagtcacgg    19860
ccgggcacgg tggctcacac ctgtaatccc agcgctttgg gaggccgagg tgggtggata    19920
atgaggtcag gagttcaaga ccagcctggc caacatggtg aaaccatgtc tctactaaaa    19980
atacaaaaat tagctgggca tggtggtgca tgcctgtaat cccagctact ccggaggcta    20040
aggcaggaga attgcttgaa gcaggaccta ggaggcggag gttggttgca gtgagccgag    20100
atcatgccac tgcactctag cctgggctac agagcgaaac tccgactcaa aaaaaaaaa    20160 aaaaaaaat caaatcacat gaaagtagaa cataggggaat tccatctttc gttctaggca    20220
tagtttgtta atatgattca gagccagcag ttaggagaac acagtgtgac tctcctagaa    20280
cttcttgatt gggcttcctc tgattgggtt tcctctgatt gggcttcctc tgaaagtggg    20340
```

```
gggatgggg ggtggggagc agaatggtca gagcttggct cagcagtcag actgctcttc    20400
ttcaaatcct ggctgcattg cttactacag ctgtgtgact ccagatgact gaatccacct    20460
ctctgtgctg cagcttcccg tctagagaga tcacctggag cagagggtgg tcaggagact    20520
caatctggtt actgactcac agtgcaggag tactcatccc atagtaagca tccagctaga    20580
gatgttgatt tctattttca ggtaataatg atgatcgtaa aattagagac agataaaagg    20640
tatgggcatt aggccagggc actgcaattt ctaagctgtg tgacctcagg caagttactc    20700
gacttctctg agcctcagcg gtttcatccg caatatatgg ataggaaaac cgacctcagt    20760
gggttgtctg acagtggagg gcacttgatt aaaaaaaaaa aaattaccct ggtctgaata    20820
ttaccctgga ctgaaagaaa aatattgagc taatacaggc atcaggaatg gggctgcagg    20880
gagtccaggg aagggagaac gaagagcctg aaggtgtgag gaggtgcgag tgctgatctg    20940
tctgctacaa agaggctgct gagcctcctg tggatgtggc cctggacttg gcagtttaat    21000
acctgagctg ttaaaataac ctcagatgct gtgttcttta aggggtagga ttcagattcc    21060
tgctgaaatg cttctgaaag ggagggaatg agccagccca tccccagttg cttttttaaga    21120 tcattgggaa gttctggtct tgccatttgt ccctggacca ctcttaggtc ctcctgcccc    21180
acttccatct gggtgtgtgc cctgggctgt ccaccacaca gctacatcct gccatcttcc    21240
ctcctggagc cactgtgcca tgcatggatc tgtagcttca ttttcttgg cttttccctg    21300 gttttctgg agcagagtct ctagtaaact cccaaggaag aaaacgtttg actttatgtg    21360
tgttgggaaa cgtgcttttt ttctattaca tctcagtgat aggttggcca tgtctagaat    21420
tgcaggttga aaatcatttc ctctcagtat attggttagt gagaagcctg ggactgagac    21480
agtcacattc tcacttcttt gcaggtgagt gctcttagga ctgtcttttt atcccttata    21540
ctctgaaatg tcatatgtct tggtgtaagt ccttatttca gttattgagc tggacaagta    21600
ctggagaccc cttcagtcaa agccttctgt cattctccag ctctaggaaa ttatcttcta    21660
ttgttatttc tgttattcct tcccttccat tttcttttt cttttttttt ttttttttt    21720 gagacagggt cttactctgg tgcccaggct ggaatgcagt gacctgatca tggtacactg    21780
cagcctgaac ctcccagact caagtgatcc tcccacctca acctcctaag tagctgggac    21840
tgcaagcaca catcaccaca cccaacaaat attttttaaa aattttgtaa gatgggatct    21900
tactatgttg cccagacttt ttcttcctct tcctggggct cttattagga agatgtttga    21960
cttcctgggt tggattcctg tctccgtgtc tgactttctc tctttgtcat attttttcatc    22020 actcgttgtc ttttttgcgtc tgctctgaca gatttcctca aattttgtct tctagtccta    22080
tcctacagtt tttactttca gcaaatataa tttaatctcc aagagtactc tcttgttctt    22140
ttttcttagc attctgttct tgttttatgg atgtaacatt ctcttggaat atttgctgtc    22200
ctctagatca tcccttctcc atttcttctt gggctagttt ttctgttct tcatctttct    22260 cttttatgct acttattctg ggcgtgttct tggtgggttt tttcccatat agcaacagag    22320
gacttggagc tcaggagaa aagggtaggt gcatcacctg gcagagctcc cagacagtga    22380
caggcaggct gcgggaagga tgtctacttg gcggtgctac cgctttccta gaaacccttt    22440
ccctggagct ggttgaactg ttgggttttg ccctggtggt gaacgctggc tcccgtgct    22500 ctgcctgttt catcaccagc cccctcccct tctgcctggg gtccagtaat ctgttgaaat    22560
atatatcttg ctcattggtg agctcctgct ccttcctcgt tgctcttgca gatttatcac    22620
ttctcgtaag gctgcgcttg tacttcggga ttttctctgt gccacactgg gaaacatagg    22680
gtggttgcat gctgcagtcc tgagcactta tttcactcac atctttacac gaagatttgg    22740
```

```
tgggtgttta ctttgttttt agtaagttag tctgtcatgt cctttgatcc ttttttttg    22800 tttttttgaga tggagtctct ctgtgtcctc caggctggag tgcaatgtcg cgatctcagc   22860
tcactgcaac ctccacctcc tgggctcaag agattctcct gcttcagtct cctgagtagc   22920
tgggattaca ggcatgtgcc accacacctg gctaattttt gtattttag tagaggtggg    22980 gtttggcatg ttggccagcc tggtctcaaa ctcctgacct cctgacctgc ctgccttggc   23040
ctcccaaagt gctgggatta caggtgtgag ccaccacacc tggccctgat taatctttta   23100
atgcccagtc tctccttcaa aagccggctc cttctctcc ctcgccttcc tagattcctt    23160
ctccactccc caggatcagc ctcctcctcc ccacccacc actgccgggg ggatgtctgt    23220
ggtcaggcat ttatcagaga ccctgaggtg ggggtccttt atgtgtctgg gggatggaga   23280
gtctagagga ggtagcgttc agacctctcc atggtgcctc tgctgggctc acatgtgacc   23340
aagcacagca aaccatgagg caggggatgg tcttgaccat gagagcccett gcagcagctg   23400 ccatgggcct cagctcctct ccaagctggg aagagccctg aaaagccaag gtgttttttt   23460
ttccctcttt atttcagtgt aagtcccttg agctttcttg aaccagaagt gggctcattt   23520
tgctttagag atttcaggtg ggcttgtcct tgtcctagca tcccagatcc accttctggg   23580
aagtcatcag attggaggtg atgttggcag cttttgtaaa caagggtag tgttgtaagc    23640 tgttgtgtct gcctatgtgt gtgtttgtgt acttggtctc atctctgcag actggtgaca   23700
tggcttccag atatgcccga cgatgtcctg tggttgcagt gggtgacctc acaggtgttc   23760
actcgagtgc tgatgtgtct gctccccgcc tccaggtaaa tactttggct gtgggtgtgt   23820
gggccggacg ggcacctctc tcatctgatg aggcctcaca cgacattcta gaaacagctg   23880
gctgaacacc aagcaaggag cttgcccttg ggtgtgggga ccctgtctca tgggaggcag   23940
ctgagtcagt cagaggtcct ggcacacctg ctgagagctg ccacccaggc caacctgaac   24000
cggagcctgg gaagacttcc cgtcggatga gtctctttga gtgcagcatt gatggtggaa   24060
gagcagagag gccccagata agcagggaaa ggtgcttcag acagagtggc tgggatgagg   24120
actggggagt gtcagatagc gctggcgtgt ctgagcgaag gagctctggc acccatggca   24180
caggaaggag gtgggaccct ggaggggcag ggctagcaga gctcctcgga gcgtgtggct   24240
aggtgcctgg taatgcaagc cccctgtcct ccaccctctg ttgtactgag tcacagtctc   24300
cggggtgaag cctagcagtc tgcgttgaca ggccccaggg gatgccgcta cttcctgaat   24360
tctgaattct ggaaactgag ccggagttca gggcctggct cccattacca gggttgggcg   24420
ttatcctgaa aatcataggc cttggttttcc tcacttggct aacaggggtg atccccatcc   24480
cctcaatggg tttccgtgag ctcctgagag cccgtagcat ggtacttggc acatgctggg   24540
catcaggagg tatggcctct cttgctattg ttgttattgg tagacacaga aggatttaaa   24600 agtagggaa tgcaaagatc cgatttgcta gggaagaggg cagtagtggc caagtagagg    24660
gtggatcctg ggccctggct ggcagcaggc agcaaggggg gctgccaggg cccaggcagg   24720
gacgatctgt agaccgagag gcttcctaag gctcttggac aggaggaggt gtcggttcca   24780
agcctaagga gtggggcagc cctggtgact ggtggtcagt ggtgccaggc ggtgggtggt   24840
aggacaccct ggcaggcaag taggtttgtg tgggggaaac tgataggccc ctccaggat    24900 tcgttggtgg acaacacctg tgatgtccag tgggaggtgt ccaggtagct gggagggcca   24960
caggcttgga agacctaggt ggtgacatca gcccagcact gagggctaga agaagctgtg   25020
tctctggctg tgacggcacc ctagagtgtg tgtggtgccc tctactggcc ggcaatgtgg   25080
```

```
gtccaccgta gctcagactg cacactgcag cagcgggaac ggcctctaag ccaacttcct    25140
ccatgtgttt caggtcccaa atgccagtga gcagccaaca ggcctcccca tgcacacctg    25200
agcaggactg gccctgctgg actccctgct cccccaaggg ctgtccagca gagaccaaag    25260
cagaggccac cccgcggtcc atcctcaggt ccagcctgaa cttcttcttg gcaataaag     25320 tacctgctgg tgctgagggg ctctccacct ttcccagttt ttcactagag aagagtctgt    25380
gagtcacttg aggaggcgag tctagcagat tctttcagag gtgctaaagt ttcccatctt    25440
tgtgcagcta cctccgcatt gctgtgtagt gaccccctgcc tgtgacgtgg aggatcccag   25500
cctctgagct gagttggttt tatgaaaagc taggaagcaa cctttcgcct gtgcagcggt    25560
ccagcactta actctaatac atcagcatgc gttaattcag ctggttggga aatgacacca    25620
ggaagcccag tgcagagggt cccttactga ctgtttcgtg gccctattaa tggtcagact    25680
gttccagcat gaggttctta aatgacagg tgtttggatg ggtgggggcc ttgtgatggg     25740
gggtaggctg gccatgtgt gatcttgtgg ggtggaggga agagaatagc atgatcccac     25800
ttccccatgc tgtgggaagg ggtgcagttc gtccccaaga acgacactgc ctgtcaggtg    25860
gtctgcaaag atgataacct tgactactaa aaacgtctcc atggcggggg taacaagatg    25920
ataatctact taattttaga acaccttttt cacctaacta aaataatgtt taagagtttt    25980
tgtataaaaa tgtaaggaag cgttgttacc tgttgaattt tgtattatgt gaatcagtga    26040
gatgttagta gaataagcct taaaaaaaaa aaaatcggtt gggtgcagtg gcacacggct    26100
gtaatcccag cactttggga ggccaaggtt ggcagatcac ctgaggtcag gagttcaaga    26160
ccagtctggc caacatagca aaaccctgtc tctactaaaa atacaaaaat tatctgggca    26220
tggtggtgca tgcctgtaat cccagctatt cggaaggctg aggcaggaga atcacttgaa    26280
cccaggaggc ggaggttgcg gtgagctgag attgcaccat tcattccag cctgggcaac     26340 atgagtgaaa gtctgactca aaaaaaaaaa atttaaaaaa caaaataatc tagtgtgcag    26400
ggcattcacc tcagccccccc aggcaggagc caagcacagc aggagcttcc gcctcctctc    26460
cactggagca cacaacttga acctggctta ttttctgcag ggaccagccc cacatggtca    26520
gtgagttcct cccatgtgt ggcgatgaga gagtgtagaa ataaagacac aagacaaaga     26580 gataaagaa aagacagctg ggcccggggg accactacca ccaatgcgcg gagaccggta     26640
gtggccctga atgtctggct gcgctgttat ttattggata caaagcaaaa ggggcagggt    26700
aaagagtgtg actcatctcc aatgataggt aaggtcacgt gggtcacgtg tccactggac    26760
aggggtccct tccctgcctg gcagctgagg cagagagaga gaggagacaa agagaaagac    26820
agcttacgcc attatttctg catatcagag acttttagta ctttcaataa tttactactg    26880
ctatctagaa ggcagagcca ggtgtacagg atggaacatg aaggtggact aggagcgtga    26940
ccactgaagc acagcatcac agggagacag ttaggcctcc agataactgt gggcgagcct    27000
gactgatgcc aggccctcca caagaggtgg aagagcagag tcttctctaa actccccag     27060 ggaaagggag actctctttc ctcgtctgct aagtagcggg tgttgttcct tgacactttt    27120
tgctaccgct agaccacggt ccgcctggca atgggcgtct tcccagatgt tggtgtcacc    27180
gctagaccaa ggagccctct gatggccctg tccaggcata acagaaggct cgcactcctg    27240
tcttctggtc acttctcgct acgtcccctc agctcctatc tctgtatggc ctggtttttc    27300
ctaggttatg attgtagagt gaggattatt ataatattgg aataaagagt aattgctaca    27360
aataatgatt aatgatattc atatataatc atatctaaga tctatatctg gtataactat    27420
tcttgtttta tattttatta tactggaaca gctcgtgtcc tcagtctctt gcctcagcac    27480
```

```
ctgggtggtt tgccacccac aattttccac atgcttctgg tctgcgttct tttttctcc    27540
ttgcatcttc tcattctctg atcaccccaa cctctctctg tcttccctac tctgccagcc    27600
ttgatggaga caagcccttg agaccagaac tcaccttttc cccaggtgtg ataatctatt    27660
agcaaggtca gtgtaatatg actgacggtg aaacgtgtat ttttttctat ttatgcattt    27720
gagtacagta cgtacaagaa aaataatggt gtgctcaaac tgttaaatgt tggaaaagaa    27780
agatacaacc cttacccata ttgtgtaagt gccctggagt agaagaacca gcaagctcag    27840
acaaagcact tgactgagaa gacagaccct ttaaaggaaa cgggttctag ggacaaactc    27900
tacgtgggcc tgttctcttg ataagaccgt gaactctttg agaaaagagg ctacttgtga    27960
aaataatgag cccccttcgg ggcaggagtt ccggggtttg aacctgcctt cttacatctt    28020
gagggctaag tgagttccca aggcctctgt tcagtggttg ctccgtcagt gagctcaggt    28080
ctggtgagtg gcagggtctt ccacccccaa ccccaccggg tgtcagagca agacactgtc    28140
ccccatggag ctggaatggg gtggaggagc ccacatctgg cacccacgtg gcctccttgt    28200
gacggaccca cccttgcaat gttggaaagg aaagttacaa gtttcttttc ccaagtttcc    28260
cagtaggctt tgttctgtta gcttcacgcc ttcggtcatt agcagacata aataaacttt    28320
aaccattgtt ttttatcttt tttttttttt tttgagatgg agtttcactc ttgttgccca    28380
ggctggagta caatggcaca atctcggctc accacaacct ccgcctcccg ggttcaaacg    28440
tttctcctgc ctcagcctcc caagtagatg ccaagcctcc caagtagata caggcatgtg    28500
ccaccacgcc cagctaattt tttgtatttt tagtagagat ggggtttctc caggttggtc    28560
aggctgatct cgaattcccg acctcagatg atccacccgc ctcggtctcc caaagtgttg    28620
ggattccagg tgtgagccac cacgcccggc caacagtatt ttctaataac cagtatattt    28680
ccatatacat gtgtacatgg gtattgtgat tgttatcagg aaaaaatata ttaaatggct    28740
gataggagac catgggacgt attttctttc tgcttttaaa aattattcag gccgggtgcg    28800
gtggctcatg cctgtaatcc cagcccttg ggaggccaac gtggacagat cacctgaggt    28860
caggagttcg ggacaagcct ggccaacatg gtgaaaccct gtctactaaa aaacacaaa    28920
aattagccag gtgtggtggc aggcgcctgt aatcccaatt agtgggttgg ctgaggcagg    28980
agaatcactt gaacccagga ggtggtggtt gcagtgagct gagatcgtgc cactgcaccc    29040
cagcccgggt gacagagtga gactccatct caaaaaata aaaataaaa aataaaaaat    29100
aaattattca atcttctttta tttttattgt tttaatgact aaagttattt ttagtagaaa    29160
cagggtcttg ctatgttacc cacgctagtc ttgaactcat tggcttaagc agtcttcctg    29220
ccttagcctc ccaaagtgct gggattacag gcatgcctgg ctcctccacc ttcttaaaat    29280
aagcatttgt tttataattt tttccaagtg tgtatcaaga taaggaaatc aggaagtgta    29340
atattcttat agaaatggcc aaggcctccc ccttcacctg tgcctcagat gctacccaat    29400
cccgccttct ctgtccctcc agaaggcacc ctttgcttag gcctccctct cttcctgaac    29460
cacctctgga agtttcttat tggcctatga atgcattctt atttcttctt atcaaataaa    29520
gccttccctt taatttatgg cacatttatg ctttggaatc cactctcagg aataatcagt    29580
atgtagcata ttacacgtca gcggcaaca ttcttttttt tttttttttt ttttgaggca    29640
gggtcccgct ctgtcatcca ggctagagta cggtggtgca atcatagttc actgcagcct    29700
caacttcctg gggtcaagcc atcttcccac ctcagtctcc caagtagctg gaaccacatg    29760
tgtgcactac cacacccagc tagttttttt ttgtagagac agggccttgc cttgttgccc    29820
```

```
aggctggtct ccaagtcctg ggctcaagtg atgctcctgc cttggccttc caaagtgcta   29880
ggattacagg tgtgagctac catgcctggt ccaacattct tcatttggta aatggctaaa   29940
cttagtgcag agtatgagcc tgattttgtt taaaaaaaaa atgtgtgtgg gtgtgtatat   30000
gtatctttga gtgtatataa aaagactgaa agagggctgg gcacggtggc tcatgcctgt   30060
aatcccagca ctttgggagg ctgagggagg cggatcactt aagtcaggag tttgagacca   30120
gactgggtga acccatct ctactaaaaa atgcaaaaat tagctgggca tggtggcggg   30180
cacctgtaat cccagcaacc agggaggctg aggcaggaga atcacttgaa cccaggaggt   30240
ggaggttgca gtgacccgag atgcagtgag actccacctc aaaaaaaaaa aaaaaaaaa    30300 aaaaaaagac taaggatata tatcaaaacc cttatggcag actgttattt gtaattgtat   30360
tttatttgtc gtgcttatat gtgttgccca agtttctatg gtgaacggta tgcatcactt   30420
tcagcatgag aaaataactc ctaataaacg tgattcttaa aggactctcc ctgtgtacat   30480
cctttccaag gagccccgat gtaccctgct tccctcacag ccaagctcct ctaggacagt   30540
cctccctagg gggttacggc cttgctcctt tgatggccct gccacagccc aggggctctt   30600
tcctgggcac tgtggaccag accctcctag aatccctctc cttcctcaac cccagactct   30660
caggcacccc atctctatcc tggacaccga gcttgtcacc aaggcccagc tgcagctgct   30720
gtgctgagtg tgcacagcca cctctgggaa ggctgtgctc cccctgagga cctgggtcct   30780
cagtctctga ctctgggggg attcgggcc acctacccac cttctggctc tactcaacac   30840
cagcagcccc tcaacatcaa gccctccagc tcacagcacc tcagctctgc agctccaaag   30900 ccacccagc ctggaactgg ggactcaggg agactccctc gctccaactc cagctggtcc   30960
cagcactgcc tctgctgtca tctctggaat ctggtctctt gtcccagcc cactgctgcc   31020 agggtcagcc ctggtacttt ctacctgggt tgctgcaaca gcttccctct ggggccgcc   31080 tgttttcagc cttgggccca tctgccctcc acgttgctgc tgggcaagct gaggccccac   31140
cacaccccca gcaccttcct gtgcctccag gccttccctg ccagtacacc ccctccagcc   31200
cctgaagccc tgtcagcagc tcagagcctt tccccggagt caccctgctt cccgagggga   31260
cccacgttgc tgctgggcaa gctgaggccc cgccacaacc ccagcgcctt cctctgcctc   31320
cagactccct cctagcacac cctctccagc tcctgcagtc ccaccagcag ctcagagcct   31380
cttccctgag tcaccctgct tcccgagggg acctccaccc agggaatgcc cttccaggct   31440
cctctcactg attcaccttc actcctcaga ggtcaggtgc tggctgatag aggcaatgag   31500
gtgagcccct cacctcaggg cgctcagccc ctgggaaggt gatgaaaaag gcaccccaa    31560 ggggtgtccc aaactaatag gtggatgact cccgtgggaa gatccagtct cccctcccca   31620 tgccaatta aatttgggt gttttctttt actttttga ggcaaggtct tgctttgttg      31680
ctcaggctgg agtgcagtgg cacaatcaca gctcactgca gccttgacct cctgggctca   31740
agcaatcctc ctccttcagc ttcctgagga ggttttaatt aaataaatta aaagctaatt   31800
aaaaacattt ttttttttttt ttggtagaga tggggtctca ctgttttcca ggctgatctt   31860
gaactcctgg actcaagcaa tcctcttgct tcagcctctg gagtagctgg gactacaggt   31920
gcttgctact atgcccagct atttttttta tttttattt ttattttgta gtgatgggt     31980 gtgtttccta ggctgatctt gaactcctgg gctcaagcaa tcctcctgcc tcggcctccc   32040
aaagtgctga gattataggt atgagccatt gcactcagcc tggattgtat taaggaaact   32100
agcttagtca ctaaactgca cttctacttc tgattggaca agattggcac tttgtaaacc   32160
aggttttctg ggatgctggt ttccttgaag atgtttctag ctggtattat catataggat   32220
```

```
aggctgagtt atgctgcatt aacaagcaaa acccaaaagg tttatttctc attcgtgctg   32280
tatgtccagc aaatgtggct gggcttcatt ttaagtcgtc ctcactccca gacctagcct   32340
gtaggtgccc caccattggg ggatcgctga ttgccatggc atggttagag aaatatggtt   32400
cttaaaggtt ctcatccaga gtggcacatc tctcttctgc tcacaatgtg ttgaccaaag   32460
caagtcacat ggatgggagc agggagatgc aatcctctct tgtgcccaaa agaggagcac   32520
aagaaatact gttgaatagc attgccagag gccacagaaa aatctccaaa accaaaaatc   32580
tctatgaccc aataaattca agaaatactg ggttaaagag aaggaaacca gtatatgcac   32640
tgtgagactt ctcagtcttt attatataca ttgtaaccat cacagacagc ctttaatata   32700
tacatcttaa ctatcacaga cagccttcag tatattatat acattataac catcacagac   32760
agccttcaat atattatata cattataacc atcacagaca gcctttaata tatacattat   32820
aactatcaca gcctttaata tattatgtac attgtaacta tcacagcctt taatatatta   32880
tatacattgt aactaccacc gcctttaata tagtataccc attgtaacta tcacagcctt   32940
taatatacac attgttaact accacagaca gcctttaata tattatatac attgtaacta   33000
tcacagatag cctttaatat atacattgta actatcgcag acagcccttt gtttgagggt   33060
aaagcatgtg actttgtttt cctcctgttc cctctgccat cctccagggc ctcacacaca   33120
ataggctctc aaatattgca accatcttgc actctgcagg gcaacctcat ggcttatcct   33180
ttacaagtgg catactcaga agaataacga ggaagaaagt gtaagaaaag agggctgttt   33240
gggcaaagaa aatctggttg attcgatgtt tacagagtgc caggcccat gcttgatctc   33300 atgaggtcct cagaccttat gccttaggct atcatttcca ttttacagat aaggaattga   33360
ggctcaggga actgagagtg agggaagggc aggggcctgg ctggtgctgg gttctgtctc   33420
tttccaggca agaagggaca tgtggacttg aatatttagc tcagggatgt tggaggccta   33480
gggtgctgct atttaaatgg                                              33500
```

<210> SEQ ID NO 3
<211> LENGTH: 2222
<212> TYPE: DNA
<213> ORGANISM: Homo sapiens

<400> SEQUENCE: 3

```
gtagagagcg cttgcgggcg ccgggcggag ctgctgcgga tcaggacccg agccgattcc     60
cgatcccgac ccagatccta acccgcgccc ccgccccgcc gccgccgcca tgtacgacgc    120
agagcgcggc tggagcttgt ccttcgcggg ctgcggcttc ctgggcttct accacgtcgg    180
ggcgacccgc tgcctgagcg agcacgcccc gcacctcctc cgcgacgcgc gcatgttgtt    240
cggcgcttcg gccggggcgt tgcactgcgt cggcgtcctc tccgagcaga ctctgcaggt    300
cctctcagat cttgtgcgga aggccaggag tcggaacatt ggcatcttcc atccatcctt    360
caacttaagc aagttcctcc gacagggtct ctgcaaatgc ctcccggcca atgtccacca    420
gctcatctcc ggcaaaatat gcatctctct taccagagtg tctgatgggg aaaacgttct    480
ggtgtctgac tttcggtcca agacgaagt cgtggatgcc ttggtatgtt cctgcttcat    540
gcctttctac agtggcctta tccctccttc cttcagaggc gtgcgatatg tggatggagg    600
agtgagtgac aacgtaccct tcattgatgc caaaacaacc atcaccgtgt ccccccttcta    660 tggggagtac gacatctgcc ctaaagtcaa gtccacgaac tttcttcatg tggacatcac    720
caagctcagt ctacgcctct gcacagggaa cctctacctt ctctcgagag cttttgtccc    780
```

| | |
|---|---|
| cccggatctc aaggtgctgg gagagatatg ccttcgagga tatttggatg cattcaggtt | 840 |
| cttggaagag aagggcatct gcaacaggcc ccagccaggc ctgaagtcat cctcagaagg | 900 |
| gatggatcct gaggtcgcca tgcccagctg ggcaaacatg agtctggatt cttccccgga | 960 |
| gtcggctgcc ttggctgtga ggctggaggg agatgagctg ctagaccacc tgcgtctcag | 1020 |
| catcctgccc tgggatgaga gcatcctgga caccctctcg cccaggctcg ctacagcact | 1080 |
| gagtgaagaa atgaaagaca aaggtggata catgagcaag atttgcaact tgctacccat | 1140 |
| taggataatg tcttatgtaa tgctgccctg taccctgcct gtggaatctg ccattgcgat | 1200 |
| tgtccagaga ctggtgacat ggcttccaga tatgcccgac gatgtcctgt ggttgcagtg | 1260 |
| ggtgacctca caggtgttca ctcgagtgct gatgtgtctg ctccccgcct ccaggtccca | 1320 |
| aatgccagtg agcagccaac aggcctcccc atgcacacct gagcaggact ggccctgctg | 1380 |
| gactccctgc tcccccgagg gctgtccagc agagaccaaa gcagaggcca cccgcggtc | 1440 |
| catcctcagg tccagcctga acttcttctt gggcaataaa gtacctgctg gtgctgaggg | 1500 |
| gctctccacc tttcccagtt tttcactaga gaagagtctg tgagtcactt gaggaggcga | 1560 |
| gtctagcaga ttctttcaga ggtgctaaag tttcccatct ttgtgcagct acctccgcat | 1620 |
| tgctgtgtag tgacccctgc ctgtgacgtg gaggatccca gcctctgagc tgagttggtt | 1680 |
| ttatgaaaag ctaggaagca acctttcgcc tgtgcagcgg tccagcactt aactctaata | 1740 |
| catcagcatg cgttaattca gctggttggg aaatgacacc aggaagccca gtgcagaggg | 1800 |
| tcccttactg actgtttcgt ggccctatta atggtcagac tgttccagca tgaggttctt | 1860 |
| agaatgacag gtgtttggat gggtgggggc cttgtgatgg gggtaggct ggcccatgtg | 1920 |
| tgatcttgtg gggtggaggg aagagaatag catgatccca cttccccatg ctgtgggaag | 1980 |
| gggtgcagtt cgtccccaag aacgacactg cctgtcaggt ggtctgcaaa gatgataacc | 2040 |
| ttgactacta aaaacgtctc catggcgggg gtaacaagat gataatctac ttaattttag | 2100 |
| aacacctttt tcacctaact aaaataatgt ttaaagagtt ttgtataaaa atgtaaggaa | 2160 |
| gcgttgttac ctgttgaatt ttgtattatg tgaatcagtg agatgttagt agaataagcc | 2220 |
| tt | 2222 |

```
<210> SEQ ID NO 4
<211> LENGTH: 886
<212> TYPE: DNA
<213> ORGANISM: Homo sapiens
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t

<400> SEQUENCE: 4
```

| | |
|---|---|
| ctgcccgggc tcccgtgcgg agtgggtgcc ccctaggccg gggagcgggg gatccccagg | 60 |
| ggtcgcgggg ccctggagga gcgggcatcg gacgcggaca cggcggggtg catcccgagg | 120 |
| gccccctccg aggcagatgc ttcctgcggg ggcgctgttc ctgggcccgg aaggggggcg | 180 |
| ttggaacccc gagcggtccg ggccgaagcc tgggactctc agcagactct gcaggtcctc | 240 |
| tcagatcttg tgcggaaggc caggagtcgg aacattggca tcttccatcc atccttcaac | 300 |
| ttaagcaagt tcctccgaca gggtctcggc aaatgcctcc cggccaatgt ccaccagctc | 360 |
| atctccggca aaatatgcat ctctcttacc agagtgtctg atgggaaaaa cgttctggtg | 420 |

```
tctgactttc ggtccaaaga cgaagtcgtg gatgccttgg tatgttcctg cttcatcccc      480
ttctacagtg gccttatccc tccttccttc agaggcgtgc gatatgtgga tggaggagtg      540
agtgacaacg tacccttca ttgatgccaa acaaccatc accgtgtccc ccttnctatg        600
ggagtacgac atctgcccta nagtcaagtc cacgaacttt cttcatgtgg acatcaccaa      660
gctcagtcta cgcctctgca cagggaaacc tctaccttct ctcgagagct tttgtccccc      720
cggatctcaa ggcatctgca acaggcccca gcccaggccc tgaagtcctc ctcaaaaggg      780
gatgggatcc tggaggtcgc ccttgccccg gctgggccaa acattgagtt ctggatttct      840 tcccccgag tccgcctgcc cttggcctgt gaacgcttga aagggc                      886

<210> SEQ ID NO 5
<211> LENGTH: 423
<212> TYPE: DNA
<213> ORGANISM: Homo sapiens

<400> SEQUENCE: 5
tttcaaccca cgatcacggc tcactgcacc tccatctccc tggttcaagc gattctcctg       60
cctccgcctc ccgagtagct gggattacag gcatgtgcta ccaagccctg ctatgggtc       120 cccttatctg aaggcggttt ttcttttccag ctcgacctct tgtgacccct agtttaacaa     180
gggccgaagt taaagagttt ctgcgcctgg acccctaatg aagcaatcag atttctcatc     240
tccagtcagg tgtgggtcca agcccactag acaagtttgc tcttcccaga gcacatttct    300
gccttcaagt catcctggct tgtcagggct gggggagttc tgctgtagaa atattagagt     360
ggaaggaaaa agatgtgttg ggagctattt ttctttaata ctaaaagttg gttgatgaat     420
ttg                                                                   423

<210> SEQ ID NO 6
<211> LENGTH: 568
<212> TYPE: DNA
<213> ORGANISM: Homo sapiens

<400> SEQUENCE: 6
actgaggcag ggtagagagc gcttgcgggc gccggcgga gctgctgcgg atcaggaccc       60
gagccgattc ccgatcccga cccagatcct aacccgcgcc cccgccccgc cgccgccgcc      120
atgtacgacg cagagcagcg gctggagcct tgtccttcgc gggcctgcgg cttcctgggc      180
ttctaccacg tcggggcgac ccgctgcctg agcgagcacg ccccgcacct cctccgcgac     240
gcgcgcatgt tgttcggcgc ttcggccggg gcgttgcact gcgtcggcgt cctctccggt     300
atcccgctgg actctgcagg tcctctcaga tcttgtgcgg aaggccagga gtcggaacat    360
tggcatcttc catccatcct tcaacttaag caagttcctc cgacagggtc tcggcaaatg    420
cctcccggcc aatgtccacc agctcatctc cggcaaaata tgcatctctc ttaccagagt    480
gtctgatggg gaaaacgttc tggtgtctga ctttcggtcc aaagacgaag tcgtggatgc    540
cttggtactt tcctgcttca tccccttc                                       568

<210> SEQ ID NO 7

<400> SEQUENCE: 7

000

<210> SEQ ID NO 8
```

```
<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
ccttggtatg ttcctgcttc a                                              21

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
gttgtcactc actcctccat c                                              21

<210> SEQ ID NO 13
<211> LENGTH: 25
<212> TYPE: DNA
<213> ORGANISM: Artificial sequence
<220> FEATURE:
<223> OTHER INFORMATION: Probe

<400> SEQUENCE: 13
tggccttatc cctccttcct tcaga                                          25

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
tgaggctgga gggagatg                                                  18

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
gctcatgtat ccacctttgt ct                                             22
```

```
<210> SEQ ID NO 16
<211> LENGTH: 24
<212> TYPE: DNA
<213> ORGANISM: Artificial sequence
<220> FEATURE:
<223> OTHER INFORMATION: Probe

<400> SEQUENCE: 16
ctagaccacc tgcgtctcag catc                                            24

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
ggcattccca gcgcga                                                     16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
tcctgatccg cagcag                                                     16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
ggctcgggtc ctgatc                                                     16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
gttaggatct gggtcg                                                     16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
gtacatggcg gcggcg                                                     16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 22
tccagccgcg ctctgc                                                     16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
gcgaaggaca agctcc                                                     16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
cgcgaaggac aagctc                                                     16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
gcggaggagg tgcggg                                                     16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
cgcggaggag gtgcgg                                                     16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
tcgcggagga ggtgcg                                                     16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
gaacaacatg cgcgcg                                                     16

<210> SEQ ID NO 29
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 29
cgaacaacat gcgcgc                                                    16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
ccgaacaaca tgcgcg                                                    16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
gccgaacaac atgcgc                                                    16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
cgccgaacaa catgcg                                                    16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33
gccgacgcag tgcaac                                                    16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
cgccgacgca gtgcaa                                                    16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
```
gggataccgg agagga 16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
tctgagagga cctgca 16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
caagatctga gaggac 16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
gccaatgttc cgactc 16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
gaagatgcca atgttc 16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
ttaagttgaa ggatgg 16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
tgcttaagtt gaagga 16

<210> SEQ ID NO 42
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 42
tggacattgg ccggga                                               16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
gtggacattg gccggg                                               16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
agctggtgga cattgg                                               16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
catcagacac tctggt                                               16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ccccatcaga cactct                                               16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
agtcagacac cagaac                                               16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
tggcatcaat gaaggg                                               16
```

```
<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
tgttttggca tcaatg                                                       16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
tttagggcag atgtcg                                                       16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
ctttagggca gatgtc                                                       16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
gtagactgag cttggt                                                       16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
aggtagaggt tccctg                                                       16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
gggacaaaag ctctcg                                                       16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 55
ggcatatctc tcccag                                                          16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
aggcatatct ctccca                                                          16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
aaatatcctc gaaggc                                                          16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
ccaaatatcc tcgaag                                                          16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
tccaaatatc ctcgaa                                                          16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
atgcatccaa atatcc                                                          16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
ttgcagatgc ccttct                                                          16

<210> SEQ ID NO 62

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
atccatccct tctgag                                                    16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
gggcatggcg acctca                                                    16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
actcatgttt gcccag                                                    16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
ggtctagcag ctcatc                                                    16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
cgcaggtggt ctagca                                                    16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
acgcaggtgg tctagc                                                    16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
```
tgagacgcag gtggtc                                                  16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
ggatgctgag acgcag                                                  16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
gtatccacct ttgtct                                                  16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
gctcatgtat ccacct                                                  16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
gcaaatcttg ctcatg                                                  16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
tgcaaatctt gctcat                                                  16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
ttgcaaatct tgctca                                                  16

<210> SEQ ID NO 75
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 75
agcaagttgc aaatct                                              16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
gggtagcaag ttgcaa                                              16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
cctaatgggt agcaag                                              16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
tcctaatggg tagcaa                                              16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
atcctaatgg gtagca                                              16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
cattatccta atgggt                                              16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
acattatcct aatggg                                              16
```

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
gacattatcc taatgg                                                         16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
tacataagac attatc                                                         16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
gcattacata agacat                                                         16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
ccacaggcag ggtaca                                                         16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
tccacaggca gggtac                                                         16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
ggcagattcc acaggc                                                         16

<210> SEQ ID NO 88
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 88
cgcaatggca gattcc                                                        16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
gacaatcgca atggca                                                        16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
ggacaatcgc aatggc                                                        16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
tggacaatcg caatgg                                                        16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
agccatgtca ccagtc                                                        16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
tggaagccat gtcacc                                                        16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
ctggaagcca tgtcac                                                        16
```

```
<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
ggcatatctg gaagcc                                                16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
gggcatatct ggaagc                                                16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
agcactcgag tgaaca                                                16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
gcatttggga cctgga                                                16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
ggcatttggg acctgg                                                16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
tggcatttgg gacctg                                                16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 101
gctcactggc atttgg                                                   16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
gttcaggctg gacctg                                                   16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
aggtacttta ttgccc                                                   16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
agcaggtact ttattg                                                   16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
aactttagca cctctg                                                   16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
gaaactttag cacctc                                                   16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
ggaaacttta gcacct                                                   16

<210> SEQ ID NO 108
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 108
ctgcacaaag atggga                                                        16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
agctgcacaa agatgg                                                        16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
agcaatgcgg aggtag                                                        16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
accaactcag ctcaga                                                        16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
aaccaactca gctcag                                                        16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
tcctagcttt tcataa                                                        16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
```
tgctggaccg ctgcac                                          16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
gagttaagtg ctggac                                          16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
gtattagagt taagtg                                          16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
tgtattagag ttaagt                                          16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
tgatgtatta gagtta                                          16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
gctgatgtat tagagt                                          16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
tgaattaacg catgct                                          16

<210> SEQ ID NO 121
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 121
ctgaattaac gcatgc                                                   16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
agtaagggac cctctg                                                   16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
cagtaaggga ccctct                                                   16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
tcagtaaggg accctc                                                   16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
agtcagtaag ggaccc                                                   16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
attaataggg ccacga                                                   16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
ccattaatag ggccac                                                   16
```

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
accattaata gggcca                                               16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
gaacagtctg accatt                                               16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
tggaacagtc tgacca                                               16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
ctggaacagt ctgacc                                               16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
tgctggaaca gtctga                                               16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
cctcatgctg gaacag                                               16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 134
tcattctaag aacctc                                                   16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
acccatccaa acacct                                                   16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
acacatgggc cagcct                                                   16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
caagatcaca catggg                                                   16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
gggacgaact gcaccc                                                   16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
tatcatcttt gcagac                                                   16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
gtttttagta gtcaag                                                   16

<210> SEQ ID NO 141
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
cgtttttagt agtcaa                                                    16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
tatcatcttg ttaccc                                                    16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
gattatcatc ttgtta                                                    16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
tagattatca tcttgt                                                    16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
gtagattatc atcttg                                                    16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
agtagattat catctt                                                    16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
```

```
gtgaaaaagg tgttct                                                    16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
tagttaggtg aaaaag                                                    16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
ttattttagt taggtg                                                    16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
cattatttta gttagg                                                    16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
ctactaacat ctcact                                                    16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
tctactaaca tctcac                                                    16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
ttattctact aacatc                                                    16

<210> SEQ ID NO 154
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 154
gcttattcta ctaaca                                                    16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
ggcttattct actaac                                                    16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
ggtgaatgcc ctgcac                                                    16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
ttcaagttgt gtgctc                                                    16

<210> SEQ ID NO 158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 158
gggagaaact cactga                                                    16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
tgctacttgc cccagc                                                    16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
cacaatgcta cttgcc                                                    16
```

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
cccaatggca gggctt                                          16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
tgctcctacc caatgg                                          16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
gacttttatt gttgct                                          16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
ttctatacca gagtga                                          16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
tttctatacc agagtg                                          16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
gtagatggcc ttaatg                                          16

<210> SEQ ID NO 167
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 167
tacatccacg acttcg         16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
ttacatccac gacttc         16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
ggaacattca gggttt         16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
attacttggg tgcagg         16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
gcagattact tgggtg         16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
tgcaggacag gttcct         16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
cacactgggt caccac         16

```
<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
agtcacactg ggtcac                                                     16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
ggtatatgtt cccagg                                                     16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
tataaccaca gcctgg                                                     16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
ctgactatat aaccac                                                     16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
atcttagtgg ctgggt                                                     16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
cttactatgg tagagt                                                     16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 180
tcttactatg gtagag                                                        16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
tgcattgcat agcctt                                                        16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
ttgcattgca tagcct                                                        16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
tgcttataaa gcacac                                                        16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
ggaataagcc tccacc                                                        16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
gaaatctgat tgcttc                                                        16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
tacttatctg ctcact                                                        16

<210> SEQ ID NO 187
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 187
tctcttagtg tcccca                                                     16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
atctcttagt gtcccc                                                     16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
tcacattcat gcttgc                                                     16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
gataacctca cattca                                                     16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
gagctaggtg cttcac                                                     16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
ataacaactg aaccac                                                     16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
```
gttattagcc aaatgc                                                 16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
ggagacttgg caaggt                                                 16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
attcatgaca gccctt                                                 16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
atcgattttt cagagt                                                 16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
acaaacatcg attttt                                                 16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
ctctttaatg acctcg                                                 16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
gtcagaggca ctcaca                                                 16

<210> SEQ ID NO 200
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 200
agctattatc tcccac                                                        16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
agtttctggg cttgca                                                        16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
ggcaatcaca agagac                                                        16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 203
agaggaagcc caatca                                                        16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
cagaggaagc ccaatc                                                        16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
tagaaattgc agtgcc                                                        16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
tcctatccat atattg                                                        16
```

```
<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 207
gcaattctag acatgg                                                       16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 208
aggacttaca ccaaga                                                       16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 209
ttcctaataa gagccc                                                       16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 210
gtcaaacatc ttccta                                                       16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 211
aaaactgtag gatagg                                                       16

<210> SEQ ID NO 212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 212
gttacatcca taaaac                                                       16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 213
agagaatgtt acatcc                                                         16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
aaagattaat cagggc                                                         16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 215
gtatttacct ggaggc                                                         16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 216
ggcctatgat tttcag                                                         16

<210> SEQ ID NO 217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 217
atacttttgg caaggc                                                         16

<210> SEQ ID NO 218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 218
aatacttttg gcaagg                                                         16

<210> SEQ ID NO 219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 219
tgcttacatc cacgac                                                         16

<210> SEQ ID NO 220
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 220
catcatgttg gtctcg                                                         16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 221
gattacttgg gtgcag                                                         16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 222
cagattactt gggtgc                                                         16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 223
tttaatggtg ttttgg                                                         16

<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 224
tcaaatgccg gtattc                                                         16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 225
gtgaacttca acttcc                                                         16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 226
```
ctatataacc acagcc                                                            16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
gactatataa ccacag                                                            16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 228
aatcatctta gtggct                                                            16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 229
tactatggta gagtgg                                                            16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 230
gtacatggtc tgcaaa                                                            16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 231
tgtacatggt ctgcaa                                                            16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
gcatgcattg cattgc                                                            16

<210> SEQ ID NO 233
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 233
accaatcctg ttagac                                                   16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 234
ggagacacca agcacc                                                   16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 235
gcactaagtg ttagaa                                                   16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 236
gcttacttat ctgctc                                                   16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 237
ggagatccat cctgca                                                   16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 238
catctcttag tgtccc                                                   16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 239
tcctaatgtc ctcaac                                                   16
```

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 240
aagataacct cacatt                                                          16

<210> SEQ ID NO 241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 241
caagataacc tcacat                                                          16

<210> SEQ ID NO 242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 242
tataacaact gaacca                                                          16

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 243
gctttaaagc aggaca                                                          16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 244
aaaattgtgg gtttag                                                          16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 245
atcatttgga ccatag                                                          16

<210> SEQ ID NO 246
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 246
acatcgattt ttcaga                                                      16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 247
caaacatcga tttttc                                                      16

<210> SEQ ID NO 248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 248
gctttacaag ctggtc                                                      16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 249
atctatgttc tcctag                                                      16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 250
acctaaaatg ctcacc                                                      16

<210> SEQ ID NO 251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 251
ccagactaca tgccac                                                      16

<210> SEQ ID NO 252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 252
tctactaggc atctct                                                      16

```
<210> SEQ ID NO 253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 253
ttctactagg catctc                                                     16

<210> SEQ ID NO 254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 254
tcagaggaag cccaat                                                     16

<210> SEQ ID NO 255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 255
gaaattgcag tgccct                                                     16

<210> SEQ ID NO 256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 256
gccaacctat cactga                                                     16

<210> SEQ ID NO 257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 257
agacatggcc aaccta                                                     16

<210> SEQ ID NO 258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 258
tgaaataagg acttac                                                     16

<210> SEQ ID NO 259
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 259
cctaataaga gcccca                                                      16

<210> SEQ ID NO 260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 260
gaaatctgtc agagca                                                      16

<210> SEQ ID NO 261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 261
tgtaggatag gactag                                                      16

<210> SEQ ID NO 262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 262
gaatgttaca tccata                                                      16

<210> SEQ ID NO 263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 263
gagaatgtta catcca                                                      16

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 264
gtgataaatc tgcaag                                                      16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 265
agattaatca gggcca                                                      16

<210> SEQ ID NO 266
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 266
aagattaatc agggcc                                                     16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 267
ggtcacatgt gagccc                                                     16

<210> SEQ ID NO 268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 268
cacttctggt tcaaga                                                     16

<210> SEQ ID NO 269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 269
ccaatctgat gacttc                                                     16

<210> SEQ ID NO 270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 270
aagtatttac ctggag                                                     16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 271
cactcaaaga gactca                                                     16

<210> SEQ ID NO 272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 272
```

-continued

```
gcctatgatt ttcagg                                                        16

<210> SEQ ID NO 273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 273
cactactgcc ctcttc                                                        16

<210> SEQ ID NO 274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 274
tgctgggctg atgtca                                                        16

<210> SEQ ID NO 275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 275
ggcatttggg acctga                                                        16

<210> SEQ ID NO 276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 276
gcccccctcg gaccat                                                        16

<210> SEQ ID NO 277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 277
cctcagtgtc tcggcc                                                        16

<210> SEQ ID NO 278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 278
aatcggctcg ggtcct                                                        16

<210> SEQ ID NO 279
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 279
gacaagctcc agccgc                                                    16

<210> SEQ ID NO 280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 280
cgctcaggca gcgggt                                                    16

<210> SEQ ID NO 281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 281
ctccagcggg ataccg                                                    16

<210> SEQ ID NO 282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 282
ggccttccgc acaaga                                                    16

<210> SEQ ID NO 283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 283
tggatggaag atgcca                                                    16

<210> SEQ ID NO 284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 284
gagaccctgt cggagg                                                    16

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 285
gatgagctgg tggaca                                                    16
```

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 286
gagagatgcc tatttt                                                      16

<210> SEQ ID NO 287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 287
gaccgaaagt cagaca                                                      16

<210> SEQ ID NO 288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 288
gttttggcat caatga                                                      16

<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 289
gacttgactt tagggc                                                      16

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 290
cgagagaagg tagagg                                                      16

<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 291
ctcgaaggca tatctc                                                      16

<210> SEQ ID NO 292
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 292
gggcctgttg cagatg                                                       16

<210> SEQ ID NO 293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 293
ggcatggcga cctcag                                                       16

<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 294
agccaaggca gccgac                                                       16

<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 295
gcgagcctgg gcgaga                                                       16

<210> SEQ ID NO 296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 296
ctcatgtatc cacctt                                                       16

<210> SEQ ID NO 297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 297
gggcagcatt acataa                                                       16

<210> SEQ ID NO 298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 298
aagccatgtc accagt                                                       16

<210> SEQ ID NO 299
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 299
actcgagtga acacct                                                       16

<210> SEQ ID NO 300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 300
gcctgttggc tgctca                                                       16

<210> SEQ ID NO 301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 301
ctgctggaca gccctt                                                       16

<210> SEQ ID NO 302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 302
ctttattgcc caagaa                                                       16

<210> SEQ ID NO 303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 303
cagactcttc tctagt                                                       16

<210> SEQ ID NO 304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 304
aatctgctag actcgc                                                       16

<210> SEQ ID NO 305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 305
```
cagcaatgcg gaggta                                          16

<210> SEQ ID NO 306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 306
gaaaggttgc ttccta                                          16

<210> SEQ ID NO 307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 307
gtgctggacc gctgca                                          16

<210> SEQ ID NO 308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 308
aacgcatgct gatgta                                          16

<210> SEQ ID NO 309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 309
gcttcctggt gtcatt                                          16

<210> SEQ ID NO 310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 310
gccacgaaac agtcag                                          16

<210> SEQ ID NO 311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 311
catgctggaa cagtct                                          16

<210> SEQ ID NO 312
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 312
aaggccccca cccatc                                                     16

<210> SEQ ID NO 313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 313
tgggccagcc tacccc                                                     16

<210> SEQ ID NO 314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 314
ggaagtggga tcatgc                                                     16

<210> SEQ ID NO 315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 315
gttatcatct ttgcag                                                     16

<210> SEQ ID NO 316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 316
cttgttaccc ccgcca                                                     16

<210> SEQ ID NO 317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 317
tctcactgat tcacat                                                     16

<210> SEQ ID NO 318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 318
ccctgcacac tagatt                                                     16
```

<210> SEQ ID NO 319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 319
gaggcggaag ctcctg                                                  16

<210> SEQ ID NO 320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 320
caggttcaag ttgtgt                                                  16

<210> SEQ ID NO 321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 321
aaatgtacgg aatctc                                                  16

<210> SEQ ID NO 322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 322
gtgtaaacat ttgtcc                                                  16

<210> SEQ ID NO 323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 323
agctttggtg tagatg                                                  16

<210> SEQ ID NO 324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 324
tactatggga gccaca                                                  16

<210> SEQ ID NO 325
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 325
tgaaattgta actgcc                                                    16

<210> SEQ ID NO 326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 326
tagatcggtg ctgttc                                                    16

<210> SEQ ID NO 327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 327
gttataggcg agagca                                                    16

<210> SEQ ID NO 328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 328
tatataacca cagcct                                                    16

<210> SEQ ID NO 329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 329
ataagagctg tctcct                                                    16

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 330
ctagtaaatg cttgtc                                                    16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
ctaatatttc tacagc                                                    16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
ctcttagtgt ccccat                                              16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
ttccatcaca aggcct                                              16

<210> SEQ ID NO 334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 334
tccataatgc acaaga                                              16

<210> SEQ ID NO 335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
tgtagctggt ttgtgg                                              16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336
aacagctaca tcaggc                                              16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
ggcattgcac atagac                                              16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 338
gtaagcaatg cagcca                                              16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
ttagaaattg cagtgc                                              16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
aggtattaaa ctgcca                                              16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
gtcctaagag cactca                                              16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
gataaatctg caagag                                              16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
gggacttaca ctgaaa                                              16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
gtcaacgcag actgct                                              16

<210> SEQ ID NO 345
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 345
cgcccccctc ggacca                                                        16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
gcctcagtgt ctcggc                                                        16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
gaatcggctc gggtcc                                                        16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 348
ggacaagctc cagccg                                                        16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
tcgctcaggc agcggg                                                        16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
gctccagcgg gatacc                                                        16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
```
tggccttccg cacaag                                                          16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
taagttgaag gatgga                                                          16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
agagaccctg tcggag                                                          16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
agatgagctg gtggac                                                          16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
aagagagatg cctatt                                                          16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
ggaccgaaag tcagac                                                          16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
gttgttttgg catcaa                                                          16

<210> SEQ ID NO 358
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 358
ggacttgact ttaggg                                                    16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
tcgagagaag gtagag                                                    16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
cctcgaaggc atatct                                                    16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 361
gatgacttca ggcctg                                                    16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
tgggcatggc gacctc                                                    16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
cagccaaggc agccga                                                    16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
agcgagcctg ggcgag                                                    16
```

```
<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
tgctcatgta tccacc                                                      16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
agggcagcat tacata                                                      16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
tatctggaag ccatgt                                                      16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
cactcgagtg aacacc                                                      16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
ggcctgttgg ctgctc                                                      16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
gtctctgctg gacagc                                                      16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 371
gtactttatt gcccaa                                                         16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
gactcacaga ctcttc                                                         16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
gaatctgcta gactcg                                                         16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 374
acagcaatgc ggaggt                                                         16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
cgaaaggttg cttcct                                                         16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
agtgctggac cgctgc                                                         16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
taacgcatgc tgatgt                                                         16

<210> SEQ ID NO 378
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
ggcttcctgg tgtcat                                                    16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
ggccacgaaa cagtca                                                    16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
tcatgctgga acagtc                                                    16

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 381
tcacaaggcc cccacc                                                    16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
atgggccagc ctaccc                                                    16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
cgaactgcac cccttc                                                    16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
```
ggttatcatc tttgca                                                16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
tcttgttacc cccgcc                                                16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
atctcactga ttcaca                                                16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
gccctgcaca ctagat                                                16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
ggaggcggaa gctcct                                                16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
gccaggttca agttgt                                                16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
caaatgtacg gaatct                                                16

<210> SEQ ID NO 391
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 391
tactttaggc tcctgg                                                       16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
agcattagag ctttgg                                                       16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
tctactatgg gagcca                                                       16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
ggacaggttc cttgga                                                       16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
ctagatcggt gctgtt                                                       16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
agttataggc gagagc                                                       16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
actatataac cacagc                                                       16
```

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
gacaataaga gctgtc                                               16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
gctagtaaat gcttgt                                               16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
ccaactttta gtatta                                               16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
agccatctct tagtgt                                               16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
tctgatgtcg aagagg                                               16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 403
tcccatgtgg cagtac                                               16

<210> SEQ ID NO 404
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 404
tccaaatgcc caactc                                                         16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 405
gcaaataatg tgcaca                                                         16

<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 406
gggcattgca cataga                                                         16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 407
gtagtaagca atgcag                                                         16

<210> SEQ ID NO 408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 408
cttagaaatt gcagtg                                                         16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 409
attttaacag ctcagg                                                         16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 410
tatgacattt cagagt                                                         16

```
<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 411
agtacaagcg cagcct                                                   16

<210> SEQ ID NO 412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 412
acaaggacaa gcccac                                                   16

<210> SEQ ID NO 413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 413
gaagtagcgg catccc                                                   16

<210> SEQ ID NO 414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 414
ccgcccccct cggacc                                                   16

<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 415
tgcctcagtg tctcgg                                                   16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 416
ggaatcggct cgggtc                                                   16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 417
aaggacaagc tccagc                                                    16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 418
ctcgctcagg cagcgg                                                    16

<210> SEQ ID NO 419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 419
tgctccagcg ggatac                                                    16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 420
ctggccttcc gcacaa                                                    16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 421
cttaagttga aggatg                                                    16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 422
cagagaccct gtcgga                                                    16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 423
cggagatgag ctggtg                                                    16

<210> SEQ ID NO 424
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 424
taagagagat gcctat                                                   16

<210> SEQ ID NO 425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 425
tggaccgaaa gtcaga                                                   16

<210> SEQ ID NO 426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 426
ggttgttttg gcatca                                                   16

<210> SEQ ID NO 427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 427
tggacttgac tttagg                                                   16

<210> SEQ ID NO 428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 428
ctcgagagaa ggtaga                                                   16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 429
tcctcgaagg catatc                                                   16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 430
```

```
ggatgacttc aggcct                                               16

<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 431
ctgggcatgg cgacct                                               16

<210> SEQ ID NO 432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 432
acagccaagg cagccg                                               16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 433
tagcgagcct gggcga                                               16

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 434
caagttgcaa atcttg                                               16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 435
cagggcagca ttacat                                               16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 436
tcgggcatat ctggaa                                               16

<210> SEQ ID NO 437
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 437
gcactcgagt gaacac                                                      16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 438
aggcctgttg gctgct                                                      16

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 439
ttggtctctg ctggac                                                      16

<210> SEQ ID NO 440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 440
ggtactttat tgccca                                                      16

<210> SEQ ID NO 441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 441
gtgactcaca gactct                                                      16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 442
agaatctgct agactc                                                      16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 443
cacagcaatg cggagg                                                      16

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 444
gcgaaaggtt gcttcc                                                16

<210> SEQ ID NO 445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 445
aagtgctgga ccgctg                                                16

<210> SEQ ID NO 446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 446
ttaacgcatg ctgatg                                                16

<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 447
gggcttcctg gtgtca                                                16

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 448
gggccacgaa acagtc                                                16

<210> SEQ ID NO 449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 449
ctcatgctgg aacagt                                                16

<210> SEQ ID NO 450
<211> LENGTH: 16
<212> TYPE: DNA
<213> ORGANISM: Artificial sequence
<220> FEATURE:
<223> OTHER INFORMATION: Synthetic oligonucleotide -continued

<400> SEQUENCE: 450
atcacaaggc ccccac                                                  16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 451
catgggccag cctacc                                                  16

<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 452
acgaactgca cccctt                                                  16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 453
aggttatcat ctttgc                                                  16

<210> SEQ ID NO 454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 454
atcttgttac ccccgc                                                  16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 455
catctcactg attcac                                                  16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 456
tgccctgcac actaga                                                  16

<210> SEQ ID NO 457

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 457
gaggaggcgg aagctc                                                       16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 458
agccaggttc aagttg                                                       16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 459
tcaaatgtac ggaatc                                                       16

<210> SEQ ID NO 460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 460
gtactttagg ctcctg                                                       16

<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 461
acatatcagc attaga                                                       16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 462
gtctactatg ggagcc                                                       16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 463
```

```
gaagatgcat agagga                                              16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 464
tcacactggg tcacca                                              16

<210> SEQ ID NO 465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 465
ggcaatcagg gaggca                                              16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 466
tgactatata accaca                                              16

<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 467
cccaattgcc actagg                                              16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 468
tctttaccaa gaccgc                                              16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 469
gacaaattca tcaacc                                              16

<210> SEQ ID NO 470
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 470
ctgtatccaa aaggcc                                                        16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 471
atacatagca gagcca                                                        16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 472
caccctatcg ctccca                                                        16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 473
agttatgtct gactca                                                        16

<210> SEQ ID NO 474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 474
aatatacccc acagca                                                        16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 475
gtgcatgtgt ggcttg                                                        16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 476
tgtagtaagc aatgca                                                        16
```

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 477
catatattgc ggatga                                                    16

<210> SEQ ID NO 478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 478
gttattttaa cagctc                                                    16

<210> SEQ ID NO 479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 479
ataaggactt acacca                                                    16

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 480
cagcatgcaa ccaccc                                                    16

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 481
tgggatgcta ggacaa                                                    16

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 482
ggaagtagcg gcatcc                                                    16

<210> SEQ ID NO 483
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 483
cattcccagc gcgacg  16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 484
taccctgcct cagtgt  16

<210> SEQ ID NO 485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 485
tcgggaatcg gctcgg  16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 486
cgaaggacaa gctcca  16

<210> SEQ ID NO 487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 487
gctcgctcag gcagcg  16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 488
ctgctccagc gggata  16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 489
cctggccttc cgcaca  16

```
<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 490
gcttaagttg aaggat                                                      16

<210> SEQ ID NO 491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 491
gcagagaccc tgtcgg                                                      16

<210> SEQ ID NO 492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 492
ccggagatga gctggt                                                      16

<210> SEQ ID NO 493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 493
gtaagagaga tgccta                                                      16

<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 494
ttggaccgaa agtcag                                                      16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 495
tggttgtttt ggcatc                                                      16

<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 496
gtggacttga ctttag                                               16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 497
tctcgagaga aggtag                                               16

<210> SEQ ID NO 498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 498
atcctcgaag gcatat                                               16

<210> SEQ ID NO 499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 499
tgaggatgac ttcagg                                               16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 500
gctgggcatg gcgacc                                               16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 501
tagcagctca tctccc                                               16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 502
gtagcgagcc tgggcg                                               16

<210> SEQ ID NO 503
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 503
tagcaagttg caaatc                                                      16

<210> SEQ ID NO 504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 504
acagggcagc attaca                                                      16

<210> SEQ ID NO 505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 505
cgtcgggcat atctgg                                                      16

<210> SEQ ID NO 506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 506
cagcactcga gtgaac                                                      16

<210> SEQ ID NO 507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 507
gaggcctgtt ggctgc                                                      16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 508
gaggatggac cgcggg                                                      16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 509
```

-continued

```
gcaggtactt tattgc                                                16

<210> SEQ ID NO 510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 510
agtgactcac agactc                                                16

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 511
aagaatctgc tagact                                                16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 512
acacagcaat gcggag                                                16

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 513
ggcgaaaggt tgcttc                                                16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 514
taagtgctgg accgct                                                16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 515
attaacgcat gctgat                                                16

<210> SEQ ID NO 516
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 516
tgggcttcct ggtgtc                                              16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 517
agggccacga aacagt                                              16

<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 518
acctcatgct ggaaca                                              16

<210> SEQ ID NO 519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 519
catcacaagg ccccca                                              16

<210> SEQ ID NO 520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 520
acatgggcca gcctac                                              16

<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 521
gacgaactgc acccct                                              16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 522
tcaaggttat catctt                                              16

```
<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 523
catcttgtta cccccg                                                      16

<210> SEQ ID NO 524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 524
ctaacatctc actgat                                                      16

<210> SEQ ID NO 525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 525
atgccctgca cactag                                                      16

<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 526
agaggaggcg gaagct                                                      16

<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 527
aagccaggtt caagtt                                                      16

<210> SEQ ID NO 528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 528
attaggacaa gattca                                                      16

<210> SEQ ID NO 529
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 529
tgtactttag gctcct                                                        16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 530
aacatatcag cattag                                                        16

<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 531
caaggatgcc accaac                                                        16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 532
tcattatgga agatgc                                                        16

<210> SEQ ID NO 533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 533
ttaacaaccc tgtcag                                                        16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 534
gtaactggta gctcct                                                        16

<210> SEQ ID NO 535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 535
acccatactg cacccc                                                        16

<210> SEQ ID NO 536
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 536
gcctatccca attgcc                                                         16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 537
gtctttacca agaccg                                                         16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 538
aacgacaaat tcatca                                                         16

<210> SEQ ID NO 539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 539
tgcaatcccc ctgtat                                                         16

<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 540
aatacatagc agagcc                                                         16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
tgtcatggtt gcctca                                                         16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 542
```
ataaggagtt atgtct                                                    16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543
gaatataccc cacagc                                                    16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 544
gttacaggtg catgtg                                                    16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
agtcatctgg agtcac                                                    16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 546
tcagacaacc cactga                                                    16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
aggaatctga atccta                                                    16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 548
gataatttcc tagagc                                                    16

<210> SEQ ID NO 549
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 549
gaaataagtg ctcagg                                                    16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
ctccaatctg atgact                                                    16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
gaattcagga agtagc                                                    16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 552
gcattcccag cgcgac                                                    16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 553
gctctctacc ctgcct                                                    16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
atcgggaatc ggctcg                                                    16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
ccgcgaagga caagct                                                    16
```

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
tgctcgctca ggcagc                                                     16

<210> SEQ ID NO 557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 557
tctgctccag cgggat                                                     16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
ctcctggcct tccgca                                                     16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559
ttgcttaagt tgaagg                                                     16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
tgcagagacc ctgtcg                                                     16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 561
gccggagatg agctgg                                                     16

<210> SEQ ID NO 562
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 562
ggtaagagag atgcct                                                    16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
tttggaccga aagtca                                                    16

<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
atggttgttt tggcat                                                    16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 565
cgtggacttg acttta                                                    16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 566
ctctcgagag aaggta                                                    16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
tatcctcgaa ggcata                                                    16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
ttctgaggat gacttc                                                    16

```
<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
ttgcccagct gggcat                                                      16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 570
ctagcagctc atctcc                                                      16

<210> SEQ ID NO 571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 571
tgtagcgagc ctgggc                                                      16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
gtagcaagtt gcaaat                                                      16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
tacagggcag cattac                                                      16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
caaccacagg acatcg                                                      16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 575
tcagcactcg agtgaa                          16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
ggaggcctgt tggctg                          16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
tgaggatgga ccgcgg                          16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
accagcaggt acttta                          16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 579
aagtgactca cagact                          16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
aaagaatctg ctagac                          16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 581
tacacagcaa tgcgga                          16

<210> SEQ ID NO 582
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 582
aggcgaaagg ttgctt                                                        16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 583
ttaagtgctg gaccgc                                                        16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 584
aattaacgca tgctga                                                        16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 585
ggaccctctg cactgg                                                        16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586
tagggccacg aaacag                                                        16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587
aacctcatgc tggaac                                                        16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
```
ccatcacaag gccccc                                              16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
cacatgggcc agccta                                              16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 590
ggacgaactg cacccc                                              16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
gtcaaggtta tcatct                                              16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
tcatcttgtt accccc                                              16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
tactaacatc tcactg                                              16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 594
aatgccctgc acacta                                              16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 595
gagaggaggc ggaagc                                                    16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
taagccaggt tcaagt                                                    16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
tttcattagg acaaga                                                    16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 598
gtgtacttta ggctcc                                                    16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 599
gaacatatca gcatta                                                    16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
gtaatacttt tggcaa                                                    16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
ggtattacaa attatc                                                    16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
cttaacaacc ctgtca                                                    16

<210> SEQ ID NO 603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 603
agtaactggt agctcc                                                    16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 604 ctaatacccaｰtactgc                                                    16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
aactttgcag cctatc                                                    16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
agaactaagg caaatc                                                    16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 607
gtcttggcca acgaca                                                    16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide -continued

<400> SEQUENCE: 608
caggatgcaa tccccc                                                    16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
gccaatacat agcaga                                                    16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
gtccatgaaa tccagg                                                    16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 611
tctcttaggg cacctc                                                    16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 612
tgaatatacc ccacag                                                    16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
agctctagga gtcccc                                                    16

<210> SEQ ID NO 614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 614
ccagattgag tctcct                                                    16

<210> SEQ ID NO 615

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615
aatcaagtgc cctcca                                               16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 616
tgtagctgtg tggtgg                                               16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 617
taccatgatc aggtca                                               16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 618
gtaaagatgt gagtga                                               16

<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 619
gtttacaaaa gctgcc                                               16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 620
tgaactccgg ctcagt                                               16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 621
```
gggcattccc agcgcg                                           16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 622
cgctctctac cctgcc                                           16

<210> SEQ ID NO 623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 623
gatcgggaat cggctc                                           16

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 624
cccgcgaagg acaagc                                           16

<210> SEQ ID NO 625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 625
gtcgcggagg aggtgc                                           16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 626
gtctgctcca gcggga                                           16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 627
actcctggcc ttccgc                                           16

<210> SEQ ID NO 628
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 628
cttgcttaag ttgaag                                                    16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 629
ttgcagagac cctgtc                                                    16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 630
tgccggagat gagctg                                                    16

<210> SEQ ID NO 631
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 631
tggtaagaga gatgcc                                                    16

<210> SEQ ID NO 632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 632
ctttggaccg aaagtc                                                    16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 633
gatggttgtt ttggca                                                    16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 634
acatgaagaa agttcg                                                    16
```

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 635
gctctcgaga gaaggt                                                      16

<210> SEQ ID NO 636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 636
atatcctcga aggcat                                                      16

<210> SEQ ID NO 637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 637
cccttctgag gatgac                                                      16

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 638
gtttgcccag ctgggc                                                      16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 639
gtctagcagc tcatct                                                      16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 640
ctgtagcgag cctggg                                                      16

<210> SEQ ID NO 641
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 641
ggtagcaagt tgcaaa                                                      16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 642
gtacagggca gcatta                                                      16

<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 643
gcaaccacag gacatc                                                      16

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 644
atcagcactc gagtga                                                      16

<210> SEQ ID NO 645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 645
gggaggcctg ttggct                                                      16

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 646
ctgaggatgg accgcg                                                      16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 647
caccagcagg tacttt                                                      16

<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 648
caagtgactc acagac                                                    16

<210> SEQ ID NO 649
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 649
tgaaagaatc tgctag                                                    16

<210> SEQ ID NO 650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 650
ctacacagca atgcgg                                                    16

<210> SEQ ID NO 651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 651
caggcgaaag gttgct                                                    16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 652
gttaagtgct ggaccg                                                    16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 653
gaattaacgc atgctg                                                    16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 654
gggaccctct gcactg                                                  16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 655
atagggccac gaaaca                                                  16

<210> SEQ ID NO 656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 656
gaacctcatg ctggaa                                                  16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 657
cccatcacaa ggcccc                                                  16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 658
tcacacatgg gccagc                                                  16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 659
ctgacaggca gtgtcg                                                  16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 660
agtcaaggtt atcatc                                                  16

<210> SEQ ID NO 661
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 661
atcatcttgt tacccc                                                    16

<210> SEQ ID NO 662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 662
attctactaa catctc                                                    16

<210> SEQ ID NO 663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 663
gaatgccctg cacact                                                    16

<210> SEQ ID NO 664
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 664
gctccagtgg agagga                                                    16

<210> SEQ ID NO 665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 665
ataagccagg ttcaag                                                    16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 666
gtgagaaaca aaccct                                                    16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 667
```

```
tctataccag agtgag                                                   16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 668
aggaatgagt ctccca                                                   16

<210> SEQ ID NO 669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 669
ggtaatactt ttggca                                                   16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 670
cgcttatgaa agcatc                                                   16

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 671
cccttaacaa ccctgt                                                   16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 672
tttgattgtg cagaca                                                   16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 673
tcctaatacc catact                                                   16

<210> SEQ ID NO 674
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 674
acaaactttg cagcct                                                       16

<210> SEQ ID NO 675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 675
gttagaacta aggcaa                                                       16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 676
gagcagataa atacac                                                       16

<210> SEQ ID NO 677
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 677
tggtatctcg cttcct                                                       16

<210> SEQ ID NO 678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 678
taaagccacg cagcca                                                       16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 679
ccagatgcag gacccc                                                       16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 680
aaactaatgc acctgg                                                       16
```

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 681
ctgaatatac cccaca                                           16

<210> SEQ ID NO 682
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 682
agctgctatg tgaggc                                           16

<210> SEQ ID NO 683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 683
tcagtaacca gattga                                           16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 684
tttaatcaag tgccct                                           16

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 685
caggatgtag ctgtgt                                           16

<210> SEQ ID NO 686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 686
taagatccca tcttac                                           16

<210> SEQ ID NO 687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 687
aaagtaaaca cccacc                                                           16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 688
gcttacaaca ctaccc                                                           16

<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 689
gtaatgggag ccaggc                                                           16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 690
agggcattcc cagcgc                                                           16

<210> SEQ ID NO 691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 691
gcgctctcta ccctgc                                                           16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 692
ggatcgggaa tcggct                                                           16

<210> SEQ ID NO 693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 693
gcccgcgaag gacaag                                                           16

<210> SEQ ID NO 694

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 694
cgtcgcggag gaggtg                                                         16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 695
aggacctgca gagtct                                                         16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 696
cgactcctgg ccttcc                                                         16

<210> SEQ ID NO 697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 697
acttgcttaa gttgaa                                                         16

<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 698
gggaggcatt tgcaga                                                         16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 699
ttgccggaga tgagct                                                         16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 700
```

```
tctggtaaga gagatg                                                    16
```

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 701

```
tctttggacc gaaagt                                                    16
```

<210> SEQ ID NO 702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 702

```
tgatggttgt tttggc                                                    16
```

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 703

```
gtccacatga agaaag                                                    16
```

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 704

```
agctctcgag agaagg                                                    16
```

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 705

```
aatatcctcg aaggca                                                    16
```

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 706

```
gatccatccc ttctga                                                    16
```

<210> SEQ ID NO 707
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 707
tgtttgccca gctggg                                                   16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 708
gacgcaggtg gtctag                                                   16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 709
gctgtagcga gcctgg                                                   16

<210> SEQ ID NO 710
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 710
tgggtagcaa gttgca                                                   16

<210> SEQ ID NO 711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 711
ggtacagggc agcatt                                                   16

<210> SEQ ID NO 712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 712
tgcaaccaca ggacat                                                   16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 713
catcagcact cgagtg                                                   16
```

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 714
ctcaggtgtg catggg                                                   16

<210> SEQ ID NO 715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 715
cctgaggatg gaccgc                                                   16

<210> SEQ ID NO 716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 716
agcaccagca ggtact                                                   16

<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 717
tcaagtgact cacaga                                                   16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 718
cacctctgaa agaatc                                                   16

<210> SEQ ID NO 719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 719
actacacagc aatgcg                                                   16

<210> SEQ ID NO 720
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 720
acaggcgaaa ggttgc                                                   16

<210> SEQ ID NO 721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 721
agttaagtgc tggacc                                                   16

<210> SEQ ID NO 722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 722
gctgaattaa cgcatg                                                   16

<210> SEQ ID NO 723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 723
agggaccctc tgcact                                                   16

<210> SEQ ID NO 724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 724
aatagggcca cgaaac                                                   16

<210> SEQ ID NO 725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 725
agaacctcat gctgga                                                   16

<210> SEQ ID NO 726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 726
ccccatcaca aggccc                                                   16
```

```
<210> SEQ ID NO 727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 727
atcacacatg ggccag                                                       16

<210> SEQ ID NO 728
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 728
cctgacaggc agtgtc                                                       16

<210> SEQ ID NO 729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 729
tagtcaaggt tatcat                                                       16

<210> SEQ ID NO 730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 730
ttatcatctt gttacc                                                       16

<210> SEQ ID NO 731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 731
cttattctac taacat                                                       16

<210> SEQ ID NO 732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 732
tgaatgccct gcacac                                                       16

<210> SEQ ID NO 733
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 733
tgctccagtg gagagg                                              16

<210> SEQ ID NO 734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 734
gtccctgcag aaaata                                              16

<210> SEQ ID NO 735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 735
agcataccac acccca                                              16

<210> SEQ ID NO 736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 736
ggacatgctc agcagc                                              16

<210> SEQ ID NO 737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 737
tgctgtaggc ctcagc                                              16

<210> SEQ ID NO 738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 738
tggtaatact tttggc                                              16

<210> SEQ ID NO 739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 739
gtaaatggag tccttc                                              16

<210> SEQ ID NO 740
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 740
cataatcccc ttaaca                                                   16

<210> SEQ ID NO 741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 741
ttaaccatca aggaca                                                   16

<210> SEQ ID NO 742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 742
tcttagtggc tgggta                                                   16

<210> SEQ ID NO 743
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 743
cctaacaaac tttgca                                                   16

<210> SEQ ID NO 744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 744
actaagtgtt agaact                                                   16

<210> SEQ ID NO 745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 745
ctgcagtatc cctagc                                                   16

<210> SEQ ID NO 746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 746
```

```
tcccatcggt catttc                                                      16

<210> SEQ ID NO 747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 747
gaaaccacta tcatca                                                      16

<210> SEQ ID NO 748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 748
gtaataggcc aagtcc                                                      16

<210> SEQ ID NO 749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 749
caaactaatg cacctg                                                      16

<210> SEQ ID NO 750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 750
ccaatatcat agctga                                                      16

<210> SEQ ID NO 751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 751
cacaagagac tggacc                                                      16

<210> SEQ ID NO 752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 752
tactatggga tgagta                                                      16

<210> SEQ ID NO 753
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 753
ttttaatcaa gtgccc                                                     16

<210> SEQ ID NO 754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 754
ggcaggatgt agctgt                                                     16

<210> SEQ ID NO 755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 755
agtcaaacat cttcct                                                     16

<210> SEQ ID NO 756
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 756
cagactaact tactaa                                                     16

<210> SEQ ID NO 757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 757
agcttacaac actacc                                                     16

<210> SEQ ID NO 758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 758
atgctacggg ctctca                                                     16

<210> SEQ ID NO 759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 759
cagggcattc ccagcg                                                     16

<210> SEQ ID NO 760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 760
cagctccgcc cggcgc                                                        16

<210> SEQ ID NO 761
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 761
ttaggatctg ggtcgg                                                        16

<210> SEQ ID NO 762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 762
agcccgcgaa ggacaa                                                        16

<210> SEQ ID NO 763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 763
gcgccgaaca acatgc                                                        16

<210> SEQ ID NO 764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 764
agaggacctg cagagt                                                        16

<210> SEQ ID NO 765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 765
ccgactcctg gccttc                                                        16

<210> SEQ ID NO 766
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 766
aacttgctta agttga                                              16

<210> SEQ ID NO 767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 767
cgggaggcat ttgcag                                              16

<210> SEQ ID NO 768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 768
tttgccggag atgagc                                              16

<210> SEQ ID NO 769
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 769
ctctggtaag agagat                                              16

<210> SEQ ID NO 770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 770
gtctttggac cgaaag                                              16

<210> SEQ ID NO 771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 771
gagggataag gccact                                              16

<210> SEQ ID NO 772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 772
gtgatggttg ttttgg                                              16

<210> SEQ ID NO 773
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 773
ggtgatgtcc acatga                                                    16

<210> SEQ ID NO 774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 774
aagctctcga gagaag                                                    16

<210> SEQ ID NO 775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 775
caaatatcct cgaagg                                                    16

<210> SEQ ID NO 776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 776
ggatccatcc cttctg                                                    16

<210> SEQ ID NO 777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 777
ctcatgtttg cccagc                                                    16

<210> SEQ ID NO 778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 778
agacgcaggt ggtcta                                                    16

<210> SEQ ID NO 779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 779
```
tgctgtagcg agcctg                                                    16

<210> SEQ ID NO 780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 780
atgggtagca agttgc                                                    16

<210> SEQ ID NO 781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 781
ttccacaggc agggta                                                    16

<210> SEQ ID NO 782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 782
actgcaacca caggac                                                    16

<210> SEQ ID NO 783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 783
acatcagcac tcgagt                                                    16

<210> SEQ ID NO 784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 784
ctgctcaggt gtgcat                                                    16

<210> SEQ ID NO 785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 785
acctgaggat ggaccg                                                    16

<210> SEQ ID NO 786
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 786
cagcaccagc aggtac                                                   16

<210> SEQ ID NO 787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 787
ctcctcaagt gactca                                                   16

<210> SEQ ID NO 788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 788
tagcacctct gaaaga                                                   16

<210> SEQ ID NO 789
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 789
cactacacag caatgc                                                   16

<210> SEQ ID NO 790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 790
cacaggcgaa aggttg                                                   16

<210> SEQ ID NO 791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 791
agagttaagt gctgga                                                   16

<210> SEQ ID NO 792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 792
agctgaatta acgcat                                                   16
```

<210> SEQ ID NO 793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 793
aagggaccct ctgcac                                                          16

<210> SEQ ID NO 794
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 794
taatagggcc acgaaa                                                          16

<210> SEQ ID NO 795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 795
aagaacctca tgctgg                                                          16

<210> SEQ ID NO 796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 796
cccccatcac aaggcc                                                          16

<210> SEQ ID NO 797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 797
gatcacacat gggcca                                                          16

<210> SEQ ID NO 798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 798
acctgacagg cagtgt                                                          16

<210> SEQ ID NO 799
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 799
gtagtcaagg ttatca                                                  16

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
taagtagatt atcatc                                                  16

<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
aggcttattc tactaa                                                  16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 802
gtgaatgccc tgcaca                                                  16

<210> SEQ ID NO 803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 803
gtgctccagt ggagag                                                  16

<210> SEQ ID NO 804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 804
ggtccctgca gaaaat                                                  16

<210> SEQ ID NO 805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 805
aagcatacca cacccc                                                  16

```
<210> SEQ ID NO 806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 806
aatcttggga tgcaca                                                     16

<210> SEQ ID NO 807
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 807
catcatggct tccagt                                                     16

<210> SEQ ID NO 808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 808
tgggatggta atactt                                                     16

<210> SEQ ID NO 809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 809
aagtaaatgg agtcct                                                     16

<210> SEQ ID NO 810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 810
ttgcataatc ccctta                                                     16

<210> SEQ ID NO 811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 811
ttaactagat cactga                                                     16

<210> SEQ ID NO 812
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 812
tcctaatgcg agtccc                                                      16

<210> SEQ ID NO 813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 813
tgctgctggg tgcact                                                      16

<210> SEQ ID NO 814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 814
ggtgatgaca cagcat                                                      16

<210> SEQ ID NO 815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 815
gccatgtaca actttt                                                      16

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 816
tacaatttgg acagag                                                      16

<210> SEQ ID NO 817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 817
acctatagga gtgccc                                                      16

<210> SEQ ID NO 818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 818
ttatttccgt taacca                                                      16

<210> SEQ ID NO 819
<211> LENGTH: 16
```

-continued

<210> SEQ ID NO 819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 819
agaatcatct tagtgg                                                   16

<210> SEQ ID NO 820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 820
cggaataagc ctccac                                                   16

<210> SEQ ID NO 821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 821
ggcactaagt gttaga                                                   16

<210> SEQ ID NO 822
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 822
tctcacaagg ctggca                                                   16

<210> SEQ ID NO 823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 823
gccataccgg ctccct                                                   16

<210> SEQ ID NO 824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 824
ggccttacag aaacca                                                   16

<210> SEQ ID NO 825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 825
agtaataggc caagtc                          16

<210> SEQ ID NO 826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 826
acaaactaat gcacct                          16

<210> SEQ ID NO 827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 827
tccaatatca tagctg                          16

<210> SEQ ID NO 828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 828
ctactaggca tctcta                          16

<210> SEQ ID NO 829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 829
cttactatgg gatgag                          16

<210> SEQ ID NO 830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 830
taatattcag accagg                          16

<210> SEQ ID NO 831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 831
ccatgcatgg cacagt                          16

<210> SEQ ID NO 832
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 832
agacaggaat ccaacc                                                       16

<210> SEQ ID NO 833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 833
ggacatgaca gactaa                                                       16

<210> SEQ ID NO 834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 834
gcagacacaa cagctt                                                       16

<210> SEQ ID NO 835
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 835
ccatgctacg ggctct                                                       16

<210> SEQ ID NO 836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 836
ggccagggca ttccca                                                       16

<210> SEQ ID NO 837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 837
gcagctccgc ccggcg                                                       16

<210> SEQ ID NO 838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 838
ggttaggatc tgggtc                                                       16
```

```
<210> SEQ ID NO 839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 839
ggtagaagcc caggaa                                                    16

<210> SEQ ID NO 840
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 840
cgacgcagtg caacgc                                                    16

<210> SEQ ID NO 841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 841
tgagaggacc tgcaga                                                    16

<210> SEQ ID NO 842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 842
atgttccgac tcctgg                                                    16

<210> SEQ ID NO 843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 843
gaacttgctt aagttg                                                    16

<210> SEQ ID NO 844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 844
ccgggaggca tttgca                                                    16

<210> SEQ ID NO 845
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 845
ttttgccgga gatgag                                                       16

<210> SEQ ID NO 846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 846
actctggtaa gagaga                                                       16

<210> SEQ ID NO 847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 847
cgtctttgga ccgaaa                                                       16

<210> SEQ ID NO 848
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 848
cggtgatggt tgtttt                                                       16

<210> SEQ ID NO 849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 849
tggtgatgtc cacatg                                                       16

<210> SEQ ID NO 850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 850
aaagctctcg agagaa                                                       16

<210> SEQ ID NO 851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 851
atccaaatat cctcga                                                       16

<210> SEQ ID NO 852
```

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 852
aggatccatc ccttct                                                    16

<210> SEQ ID NO 853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 853
gactcatgtt tgccca                                                    16

<210> SEQ ID NO 854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 854
gagacgcagg tggtct                                                    16

<210> SEQ ID NO 855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 855
gtgctgtagc gagcct                                                    16

<210> SEQ ID NO 856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 856
aatgggtagc aagttg                                                    16

<210> SEQ ID NO 857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 857
attccacagg cagggt                                                    16

<210> SEQ ID NO 858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 858
```

```
gtcacccact gcaacc                                              16

<210> SEQ ID NO 859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 859
cacatcagca ctcgag                                              16

<210> SEQ ID NO 860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 860
tcctgctcag gtgtgc                                              16

<210> SEQ ID NO 861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 861
gacctgagga tggacc                                              16

<210> SEQ ID NO 862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 862
tcagcaccag caggta                                              16

<210> SEQ ID NO 863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 863
cgcctcctca agtgac                                              16

<210> SEQ ID NO 864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 864
actttagcac ctctga                                              16

<210> SEQ ID NO 865
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 865
gtcactacac agcaat                                                   16

<210> SEQ ID NO 866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 866
gcacaggcga aaggtt                                                   16

<210> SEQ ID NO 867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 867
tagagttaag tgctgg                                                   16

<210> SEQ ID NO 868
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 868
cagctgaatt aacgca                                                   16

<210> SEQ ID NO 869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 869
taagggaccc tctgca                                                   16

<210> SEQ ID NO 870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 870
ttaatagggc cacgaa                                                   16

<210> SEQ ID NO 871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 871
taagaacctc atgctg                                                   16
```

<210> SEQ ID NO 872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 872 cccccccatca caaggc                                                        16

<210> SEQ ID NO 873
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 873
agatcacaca tgggcc                                                         16

<210> SEQ ID NO 874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 874
accacctgac aggcag                                                         16

<210> SEQ ID NO 875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 875
agtagtcaag gttatc                                                         16

<210> SEQ ID NO 876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 876
tgaaaaaggt gttcta                                                         16

<210> SEQ ID NO 877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 877
aaggcttatt ctacta                                                         16

<210> SEQ ID NO 878
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 878
aggtgaatgc cctgca                    16

<210> SEQ ID NO 879
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 879
tgtgctccag tggaga                    16

<210> SEQ ID NO 880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 880
tggtccctgc agaaaa                    16

<210> SEQ ID NO 881
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 881
tgcctactgg ctcaca                    16

<210> SEQ ID NO 882
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 882
aaatcttggg atgcac                    16

<210> SEQ ID NO 883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 883
tgacatcatg gcttcc                    16

<210> SEQ ID NO 884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 884
gcttacatcc acgact                    16

```
<210> SEQ ID NO 885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 885
caagtaaatg gagtcc                                                     16

<210> SEQ ID NO 886
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 886
atctattgca taatcc                                                     16

<210> SEQ ID NO 887
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 887
tttatttccg ttaacc                                                     16

<210> SEQ ID NO 888
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 888
ttcttgaccg tgtttc                                                     16

<210> SEQ ID NO 889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 889
ccggaataag cctcca                                                     16

<210> SEQ ID NO 890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 890
tgtacaatgg gacgga                                                     16

<210> SEQ ID NO 891
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 891
atcgacacag catcac                                                        16

<210> SEQ ID NO 892
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 892
tgccataccg gctccc                                                        16

<210> SEQ ID NO 893
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 893
ggtttataac aactga                                                        16

<210> SEQ ID NO 894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 894
gccttgaggt gggtgg                                                        16

<210> SEQ ID NO 895
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 895
agtcatggga tgtgca                                                        16

<210> SEQ ID NO 896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 896
atgtttggaa gtcgcc                                                        16

<210> SEQ ID NO 897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 897
aaggatcctg cttcta                                                        16

<210> SEQ ID NO 898
<211> LENGTH: 16

-continued

<212> TYPE: DNA
<213> ORGANISM: Artificial sequence
<220> FEATURE:
<223> OTHER INFORMATION: Synthetic oligonucleotide

<400> SEQUENCE: 898
gcttactatg ggatga                                                   16

<210> SEQ ID NO 899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 899
gtaatattca gaccag                                                   16

<210> SEQ ID NO 900
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 900
atccatgcat ggcaca                                                   16

<210> SEQ ID NO 901
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 901
gtcagacacg gagaca                                                   16

<210> SEQ ID NO 902
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 902
ggcttttgaa ggagag                                                   16

<210> SEQ ID NO 903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 903
tatttacctg gaggcg                                                   16

<210> SEQ ID NO 904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 904
caaatcggat ctttgc                                                    16

<210> SEQ ID NO 905
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 905
cggccagggc attccc                                                    16

<210> SEQ ID NO 906
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 906
gcagcagctc cgcccg                                                    16

<210> SEQ ID NO 907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 907
gcgggttagg atctgg                                                    16

<210> SEQ ID NO 908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 908
cgtggtagaa gcccag                                                    16

<210> SEQ ID NO 909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 909
ccgacgcagt gcaacg                                                    16

<210> SEQ ID NO 910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 910
atctgagagg acctgc                                                    16

<210> SEQ ID NO 911
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 911
aatgttccga ctcctg                                                        16

<210> SEQ ID NO 912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 912
ggaacttgct taagtt                                                        16

<210> SEQ ID NO 913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 913
gccgggaggc atttgc                                                        16

<210> SEQ ID NO 914
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 914
attttgccgg agatga                                                        16

<210> SEQ ID NO 915
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 915
cactctggta agagag                                                        16

<210> SEQ ID NO 916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 916
acggtgatgg ttgttt                                                        16

<210> SEQ ID NO 917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 917
agcttggtga tgtcca                                                        16

<210> SEQ ID NO 918
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 918
aaaagctctc gagaga                                                          16

<210> SEQ ID NO 919
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 919
catccaaata tcctcg                                                          16

<210> SEQ ID NO 920
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 920
caggatccat cccttc                                                          16

<210> SEQ ID NO 921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 921
agactcatgt ttgccc                                                          16

<210> SEQ ID NO 922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 922
ctgagacgca ggtggt                                                          16

<210> SEQ ID NO 923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 923
agtgctgtag cgagcc                                                          16

<210> SEQ ID NO 924
<211> LENGTH: 16
<212> TYPE: DNA
<213> ORGANISM: Artificial sequence
<220> FEATURE:
<223> OTHER INFORMATION: Synthetic oligonucleotide -continued

<400> SEQUENCE: 924
taatgggtag caagtt                                                        16

<210> SEQ ID NO 925
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 925
caatggcaga ttccac                                                        16

<210> SEQ ID NO 926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 926
ggtcacccac tgcaac                                                        16

<210> SEQ ID NO 927
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 927
acacatcagc actcga                                                        16

<210> SEQ ID NO 928
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 928
gtcctgctca ggtgtg                                                        16

<210> SEQ ID NO 929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 929
ggctggacct gaggat                                                        16

<210> SEQ ID NO 930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 930
gtggagagcc cctcag                                                        16

<210> SEQ ID NO 931

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 931
tcgcctcctc aagtga                                                        16

<210> SEQ ID NO 932
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 932
aaactttagc acctct                                                        16

<210> SEQ ID NO 933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 933
ggtcactaca cagcaa                                                        16

<210> SEQ ID NO 934
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 934
tgcacaggcg aaaggt                                                        16

<210> SEQ ID NO 935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 935
ttagagttaa gtgctg                                                        16

<210> SEQ ID NO 936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 936
ccagctgaat taacgc                                                        16

<210> SEQ ID NO 937
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 937
```
gtaagggacc ctctgc        16

<210> SEQ ID NO 938
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 938
cattaatagg gccacg        16

<210> SEQ ID NO 939
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 939
ctaagaacct catgct        16

<210> SEQ ID NO 940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 940 acccccatc acaagg         16

<210> SEQ ID NO 941
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 941
aagatcacac atgggc        16

<210> SEQ ID NO 942
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 942
gaccacctga caggca        16

<210> SEQ ID NO 943
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 943
tagtagtcaa ggttat        16

<210> SEQ ID NO 944
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 944
ggtgaaaaag gtgttc                                                     16

<210> SEQ ID NO 945
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 945
taaggcttat tctact                                                     16

<210> SEQ ID NO 946
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 946
gaggtgaatg ccctgc                                                     16

<210> SEQ ID NO 947
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 947
gtgtgctcca gtggag                                                     16

<210> SEQ ID NO 948
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 948
ctggtccctg cagaaa                                                     16

<210> SEQ ID NO 949
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 949
caatgctact tgcccc                                                     16

<210> SEQ ID NO 950
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 950
taaatcttgg gatgca                                                     16
```

<210> SEQ ID NO 951
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 951
acaatgacat catggc                                                      16

<210> SEQ ID NO 952
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 952
gcaaactgct tacatc                                                      16

<210> SEQ ID NO 953
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 953
gttagacgcg ccaggc                                                      16

<210> SEQ ID NO 954
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 954
tctcatctat tgcata                                                      16

<210> SEQ ID NO 955
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 955
ttttatttcc gttaac                                                      16

<210> SEQ ID NO 956
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 956
taaactaccg aacgca                                                      16

<210> SEQ ID NO 957
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 957
cccggaataa gcctcc        16

<210> SEQ ID NO 958
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 958
ctgtacaatg ggacgg        16

<210> SEQ ID NO 959
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 959
tcccatcgac acagca        16

<210> SEQ ID NO 960
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 960
ggaatattgc caggta        16

<210> SEQ ID NO 961
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 961
tggtttataa caactg        16

<210> SEQ ID NO 962
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 962
attaggagag gtctca        16

<210> SEQ ID NO 963
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 963
cttgatagtg aatgtg        16

```
<210> SEQ ID NO 964
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 964
ggcactcaca aaagcg                                                        16

<210> SEQ ID NO 965
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 965
ccctatgttc tacttt                                                        16

<210> SEQ ID NO 966
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 966
caacatctct agctgg                                                        16

<210> SEQ ID NO 967
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 967
ggtaatattc agacca                                                        16

<210> SEQ ID NO 968
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 968
tgaagctaca gatcca                                                        16

<210> SEQ ID NO 969
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 969
ggaaatctgt cagagc                                                        16

<210> SEQ ID NO 970
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 970
gaatctagga aggcga                                               16

<210> SEQ ID NO 971
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 971
agtatttacc tggagg                                               16

<210> SEQ ID NO 972
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 972
agccttagga agcctc                                               16

<210> SEQ ID NO 973
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 973
tcggccaggg cattcc                                               16

<210> SEQ ID NO 974
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 974
cgcagcagct ccgccc                                               16

<210> SEQ ID NO 975
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 975
cgcgggttag gatctg                                               16

<210> SEQ ID NO 976
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 976
gcgggtcgcc ccgacg                                               16

<210> SEQ ID NO 977
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 977
acgccgacgc agtgca                                              16

<210> SEQ ID NO 978
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 978
gatctgagag gacctg                                              16

<210> SEQ ID NO 979
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 979
caatgttccg actcct                                              16

<210> SEQ ID NO 980
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 980
ggaggaactt gcttaa                                              16

<210> SEQ ID NO 981
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 981
ggccgggagg catttg                                              16

<210> SEQ ID NO 982
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 982
tattttgccg gagatg                                              16

<210> SEQ ID NO 983
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 983
```
acactctggt aagaga                                                  16

<210> SEQ ID NO 984
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 984
cacggtgatg gttgtt                                                  16

<210> SEQ ID NO 985
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 985
gagcttggtg atgtcc                                                  16

<210> SEQ ID NO 986
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 986
caaaagctct cgagag                                                  16

<210> SEQ ID NO 987
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 987
gcatccaaat atcctc                                                  16

<210> SEQ ID NO 988
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 988
tcaggatcca tccctt                                                  16

<210> SEQ ID NO 989
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 989
cagactcatg tttgcc                                                  16

<210> SEQ ID NO 990
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 990
gctgagacgc aggtgg                                                    16

<210> SEQ ID NO 991
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 991
cagtgctgta gcgagc                                                    16

<210> SEQ ID NO 992
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 992
ctaatgggta gcaagt                                                    16

<210> SEQ ID NO 993
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 993
gcaatggcag attcca                                                    16

<210> SEQ ID NO 994
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 994
aggtcaccca ctgcaa                                                    16

<210> SEQ ID NO 995
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 995
gacacatcag cactcg                                                    16

<210> SEQ ID NO 996
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 996
agtcctgctc aggtgt                                                    16
```

```
<210> SEQ ID NO 997
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 997
aagttcaggc tggacc                                                      16

<210> SEQ ID NO 998
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 998
ggtggagagc ccctca                                                      16

<210> SEQ ID NO 999
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 999
ctcgcctcct caagtg                                                      16

<210> SEQ ID NO 1000
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1000
gatgggaaac tttagc                                                      16

<210> SEQ ID NO 1001
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1001
gggtcactac acagca                                                      16

<210> SEQ ID NO 1002
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1002
ctgcacaggc gaaagg                                                      16

<210> SEQ ID NO 1003
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1003
attagagtta agtgct                                                    16

<210> SEQ ID NO 1004
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1004
accagctgaa ttaacg                                                    16

<210> SEQ ID NO 1005
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1005
gtcagtaagg gaccct                                                    16

<210> SEQ ID NO 1006
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1006
gaccattaat agggcc                                                    16

<210> SEQ ID NO 1007
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1007
tctaagaacc tcatgc                                                    16

<210> SEQ ID NO 1008
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1008 tacccccat cacaag                                                     16

<210> SEQ ID NO 1009
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1009
acaagatcac acatgg                                                    16

<210> SEQ ID NO 1010

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1010
agaccacctg acaggc                                                   16

<210> SEQ ID NO 1011
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1011
ttagtagtca aggtta                                                   16

<210> SEQ ID NO 1012
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1012
aggtgaaaaa ggtgtt                                                   16

<210> SEQ ID NO 1013
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1013
ttaaggctta ttctac                                                   16

<210> SEQ ID NO 1014
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1014
tgaggtgaat gccctg                                                   16

<210> SEQ ID NO 1015
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1015
tgtgtgctcc agtgga                                                   16

<210> SEQ ID NO 1016
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1016
```
gctggtccct gcagaa                                                    16

<210> SEQ ID NO 1017
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1017
gggacgcacg agagtc                                                    16

<210> SEQ ID NO 1018
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1018
gtcaatagct tcacaa                                                    16

<210> SEQ ID NO 1019
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1019
ataaatcttg ggatgc                                                    16

<210> SEQ ID NO 1020
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1020
cacaatgaca tcatgg                                                    16

<210> SEQ ID NO 1021
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1021
gataagcaaa ctgctt                                                    16

<210> SEQ ID NO 1022
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1022
gaggatgcaa ctggct                                                    16

<210> SEQ ID NO 1023
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1023
tcggacttca ggccca                                                   16

<210> SEQ ID NO 1024
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1024
ccttttattt ccgtta                                                   16

<210> SEQ ID NO 1025
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1025
gcatactaaa accacc                                                   16

<210> SEQ ID NO 1026
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1026
gactttgcag gcaccc                                                   16

<210> SEQ ID NO 1027
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1027
tgacatccca gttcaa                                                   16

<210> SEQ ID NO 1028
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1028
tactttccca tcgaca                                                   16

<210> SEQ ID NO 1029
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1029
aggaatattg ccaggt                                                   16
```

```
<210> SEQ ID NO 1030
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1030
ggttagtgtt ggttta                                                   16

<210> SEQ ID NO 1031
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1031
cattcgatgg aggttc                                                   16

<210> SEQ ID NO 1032
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1032
ggcggatttc cccact                                                   16

<210> SEQ ID NO 1033
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1033
taaaatacgc ccgtcc                                                   16

<210> SEQ ID NO 1034
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1034
tccctatgtt ctactt                                                   16

<210> SEQ ID NO 1035
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1035
atcaacatct ctagct                                                   16

<210> SEQ ID NO 1036
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 1036
gggtaatatt cagacc                                                     16

<210> SEQ ID NO 1037
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1037
tttactagag actctg                                                     16

<210> SEQ ID NO 1038
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1038
gtaggatagg actaga                                                     16

<210> SEQ ID NO 1039
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1039
ataaatgcct gaccac                                                     16

<210> SEQ ID NO 1040
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1040
tgtttctaga atgtcg                                                     16

<210> SEQ ID NO 1041
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1041
gcctatcagt ttcccc                                                     16

<210> SEQ ID NO 1042
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1042
ctcggccagg gcattc                                                     16

```
<210> SEQ ID NO 1043
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1043
tccgcagcag ctccgc                                                     16

<210> SEQ ID NO 1044
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1044
gcgcgggtta ggatct                                                     16

<210> SEQ ID NO 1045
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1045
agcgggtcgc cccgac                                                     16

<210> SEQ ID NO 1046
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1046
ataccggaga ggacgc                                                     16

<210> SEQ ID NO 1047
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1047
aagatctgag aggacc                                                     16

<210> SEQ ID NO 1048
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1048
ccaatgttcc gactcc                                                     16

<210> SEQ ID NO 1049
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 1049
cggaggaact tgctta                          16

<210> SEQ ID NO 1050
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1050
tggccgggag gcattt                          16

<210> SEQ ID NO 1051
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1051
ctattttgcc ggagat                          16

<210> SEQ ID NO 1052
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1052
gacactctgg taagag                          16

<210> SEQ ID NO 1053
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1053
acacggtgat ggttgt                          16

<210> SEQ ID NO 1054
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1054
actgagcttg gtgatg                          16

<210> SEQ ID NO 1055
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1055
acaaaagctc tcgaga                          16

<210> SEQ ID NO 1056
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1056
acctgaatgc atccaa                                                   16

<210> SEQ ID NO 1057
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1057
ctcaggatcc atccct                                                   16

<210> SEQ ID NO 1058
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1058
ccagactcat gtttgc                                                   16

<210> SEQ ID NO 1059
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1059
tgctgagacg caggtg                                                   16

<210> SEQ ID NO 1060
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1060
tcagtgctgt agcgag                                                   16

<210> SEQ ID NO 1061
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1061
tatcctaatg ggtagc                                                   16

<210> SEQ ID NO 1062
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1062
```

```
tcgcaatggc agattc                                              16

<210> SEQ ID NO 1063
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1063
tgtgaggtca cccact                                              16

<210> SEQ ID NO 1064
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1064
agacacatca gcactc                                              16

<210> SEQ ID NO 1065
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1065
cagtcctgct caggtg                                              16

<210> SEQ ID NO 1066
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1066
gaagttcagg ctggac                                              16

<210> SEQ ID NO 1067
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1067
aggtggagag cccctc                                              16

<210> SEQ ID NO 1068
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1068
actcgcctcc tcaagt                                              16

<210> SEQ ID NO 1069
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 1069
agatgggaaa ctttag                                                   16

<210> SEQ ID NO 1070
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1070
ggctgggatc ctccac                                                   16

<210> SEQ ID NO 1071
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1071
gctgcacagg cgaaag                                                   16

<210> SEQ ID NO 1072
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1072
tattagagtt aagtgc                                                   16

<210> SEQ ID NO 1073
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1073
aaccagctga attaac                                                   16

<210> SEQ ID NO 1074
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1074
cagtcagtaa gggacc                                                   16

<210> SEQ ID NO 1075
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1075
tgaccattaa tagggc                                                   16

-continued

<210> SEQ ID NO 1076
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1076
ttctaagaac ctcatg                                                    16

<210> SEQ ID NO 1077
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1077 ctaccccca tcacaa                                                     16

<210> SEQ ID NO 1078
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1078
ccacaagatc acacat                                                    16

<210> SEQ ID NO 1079
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1079
cagaccacct gacagg                                                    16

<210> SEQ ID NO 1080
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1080
tttagtagtc aaggtt                                                    16

<210> SEQ ID NO 1081
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1081
taggtgaaaa aggtgt                                                    16

<210> SEQ ID NO 1082
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1082
acccaaccga tttttt                                                       16

<210> SEQ ID NO 1083
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1083
ctgaggtgaa tgccct                                                       16

<210> SEQ ID NO 1084
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1084
ttgtgtgctc cagtgg                                                       16

<210> SEQ ID NO 1085
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1085
tcactgacca tgtggg                                                       16

<210> SEQ ID NO 1086
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1086
cttcatgcac gggcgc                                                       16

<210> SEQ ID NO 1087
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1087
gcataatctc ctgcct                                                       16

<210> SEQ ID NO 1088
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1088
gccataaatc ttggga                                                       16

<210> SEQ ID NO 1089
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1089
ctttattcaa tgtggc                                                         16

<210> SEQ ID NO 1090
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1090
tacaactgcc tgtgtt                                                         16

<210> SEQ ID NO 1091
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1091
aaagcttccg caaaca                                                         16

<210> SEQ ID NO 1092
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1092
ctaacataca ccctcg                                                         16

<210> SEQ ID NO 1093
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1093
agcttctggg acaagc                                                         16

<210> SEQ ID NO 1094
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1094
ggcatactaa aaccac                                                         16

<210> SEQ ID NO 1095
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1095
```
ttgaatgtca cccttc                                                  16

<210> SEQ ID NO 1096
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1096
agtcatgaca tcccag                                                  16

<210> SEQ ID NO 1097
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1097
tctcattggc acctgt                                                  16

<210> SEQ ID NO 1098
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1098
ccctatcaga tgccct                                                  16

<210> SEQ ID NO 1099
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1099
catatctggt ttcatg                                                  16

<210> SEQ ID NO 1100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1100
gaccatagca ctgtct                                                  16

<210> SEQ ID NO 1101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1101
attaatctgg tcatat                                                  16

<210> SEQ ID NO 1102
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1102
tccataaaat acgccc                                                    16

<210> SEQ ID NO 1103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1103
gaaagatgga attccc                                                    16

<210> SEQ ID NO 1104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1104
tacgatcatc attatt                                                    16

<210> SEQ ID NO 1105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1105
gtattagctc aatatt                                                    16

<210> SEQ ID NO 1106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1106
gtttactaga gactct                                                    16

<210> SEQ ID NO 1107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1107
gtaaaaactg taggat                                                    16

<210> SEQ ID NO 1108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1108
gataaatgcc tgacca                                                    16
```

<210> SEQ ID NO 1109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1109
ccgacgggaa gtcttc                                                    16

<210> SEQ ID NO 1110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1110
ggcctatcag tttccc                                                    16

<210> SEQ ID NO 1111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1111
tctcggccag ggcatt                                                    16

<210> SEQ ID NO 1112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1112
atccgcagca gctccg                                                    16

<210> SEQ ID NO 1113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1113
ggcgcgggtt aggatc                                                    16

<210> SEQ ID NO 1114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1114
cagcgggtcg ccccga                                                    16

<210> SEQ ID NO 1115
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1115
gataccggag aggacg                                            16

<210> SEQ ID NO 1116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1116
gcacaagatc tgagag                                            16

<210> SEQ ID NO 1117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1117
tgccaatgtt ccgact                                            16

<210> SEQ ID NO 1118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1118
tcggaggaac ttgctt                                            16

<210> SEQ ID NO 1119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1119
ttggccggga ggcatt                                            16

<210> SEQ ID NO 1120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1120
cctattttgc cggaga                                            16

<210> SEQ ID NO 1121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1121
agacactctg gtaaga                                            16

```
<210> SEQ ID NO 1122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1122
gacacggtga tggttg                                                        16

<210> SEQ ID NO 1123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1123
gactgagctt ggtgat                                                        16

<210> SEQ ID NO 1124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1124
gacaaaagct ctcgag                                                        16

<210> SEQ ID NO 1125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1125
aacctgaatg catcca                                                        16

<210> SEQ ID NO 1126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1126
cctcaggatc catccc                                                        16

<210> SEQ ID NO 1127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1127
aatccagact catgtt                                                        16

<210> SEQ ID NO 1128
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1128
caggatgctg agacgc                                                            16

<210> SEQ ID NO 1129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1129
ctcagtgctg tagcga                                                            16

<210> SEQ ID NO 1130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1130
ttatcctaat gggtag                                                            16

<210> SEQ ID NO 1131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1131
atcgcaatgg cagatt                                                            16

<210> SEQ ID NO 1132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1132
cacctgtgag gtcacc                                                            16

<210> SEQ ID NO 1133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1133
cagacacatc agcact                                                            16

<210> SEQ ID NO 1134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1134
ccagtcctgc tcaggt                                                            16

<210> SEQ ID NO 1135
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1135
agaagaagtt caggct                                                    16

<210> SEQ ID NO 1136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1136
aaaggtggag agcccc                                                    16

<210> SEQ ID NO 1137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1137
gactcgcctc ctcaag                                                    16

<210> SEQ ID NO 1138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1138
ggtagctgca caaaga                                                    16

<210> SEQ ID NO 1139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1139
gaggctggga tcctcc                                                    16

<210> SEQ ID NO 1140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1140
cgctgcacag gcgaaa                                                    16

<210> SEQ ID NO 1141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1141
```

```
gatgtattag agttaa                                                    16

<210> SEQ ID NO 1142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1142
caaccagctg aattaa                                                    16

<210> SEQ ID NO 1143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1143
acagtcagta agggac                                                    16

<210> SEQ ID NO 1144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1144
ctgaccatta ataggg                                                    16

<210> SEQ ID NO 1145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1145
gtcattctaa gaacct                                                    16

<210> SEQ ID NO 1146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1146
cctacccccc atcaca                                                    16

<210> SEQ ID NO 1147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1147
accccacaag atcaca                                                    16

<210> SEQ ID NO 1148
<211> LENGTH: 16
<212> TYPE: DNA
<213> ORGANISM: Artificial sequence
```

-continued

```
<220> FEATURE:
<223> OTHER INFORMATION: Synthetic oligonucleotide

<400> SEQUENCE: 1148
gcagaccacc tgacag                                                   16

<210> SEQ ID NO 1149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1149
ccccgccatg gagacg                                                   16

<210> SEQ ID NO 1150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1150
gttaggtgaa aaaggt                                                   16

<210> SEQ ID NO 1151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1151
gcacccaacc gatttt                                                   16

<210> SEQ ID NO 1152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1152
gctgaggtga atgccc                                                   16

<210> SEQ ID NO 1153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1153
gttgtgtgct ccagtg                                                   16

<210> SEQ ID NO 1154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1154
ctcactgacc atgtgg                                                   16
```

<210> SEQ ID NO 1155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1155
gcaaatcggc ccctcg                                              16

<210> SEQ ID NO 1156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1156
ggcataatct cctgcc                                              16

<210> SEQ ID NO 1157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1157
tggcatgcaa gaccac                                              16

<210> SEQ ID NO 1158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1158
actttattca atgtgg                                              16

<210> SEQ ID NO 1159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1159
gtttatgtca ctctgg                                              16

<210> SEQ ID NO 1160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1160
gaacagacaa gtgctg                                              16

<210> SEQ ID NO 1161
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1161
actaacatac accctc                                                    16

<210> SEQ ID NO 1162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1162
ataatcaggg tggtgc                                                    16

<210> SEQ ID NO 1163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1163
aggcatacta aaacca                                                    16

<210> SEQ ID NO 1164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1164
gaatcatgca agctct                                                    16

<210> SEQ ID NO 1165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1165
taaactaagg gtcaca                                                    16

<210> SEQ ID NO 1166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1166
atccatcctg catgag                                                    16

<210> SEQ ID NO 1167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1167
ggccctatca gatgcc                                                    16

<210> SEQ ID NO 1168
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1168
ctacatatct ggtttc                                                    16

<210> SEQ ID NO 1169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1169
tggaccatag cactgt                                                    16

<210> SEQ ID NO 1170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1170
tattaatctg gtcata                                                    16

<210> SEQ ID NO 1171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1171
ccactttact ctgttg                                                    16

<210> SEQ ID NO 1172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1172
aactatgcct agaacg                                                    16

<210> SEQ ID NO 1173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1173
tttacgatca tcatta                                                    16

<210> SEQ ID NO 1174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1174
```
tgtattagct caatat         16

<210> SEQ ID NO 1175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1175
tgggagttta ctagag         16

<210> SEQ ID NO 1176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1176
agagagtact cttgga         16

<210> SEQ ID NO 1177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1177
ctgataaatg cctgac         16

<210> SEQ ID NO 1178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1178
atcaatgctg cactca         16

<210> SEQ ID NO 1179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1179
acgaatccct ggaggg         16

<210> SEQ ID NO 1180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1180
gtctcggcca gggcat         16

<210> SEQ ID NO 1181
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1181
ctgatccgca gcagct                                                    16

<210> SEQ ID NO 1182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1182
cgtacatggc ggcggc                                                    16

<210> SEQ ID NO 1183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1183
gcagcgggtc gccccg                                                    16

<210> SEQ ID NO 1184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1184
ggataccgga gaggac                                                    16

<210> SEQ ID NO 1185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1185
cgcacaagat ctgaga                                                    16

<210> SEQ ID NO 1186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1186
atgccaatgt tccgac                                                    16

<210> SEQ ID NO 1187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1187
gtcggaggaa cttgct                                                    16
```

<210> SEQ ID NO 1188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1188
attggccggg aggcat                                               16

<210> SEQ ID NO 1189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1189
gcctattttg ccggag                                               16

<210> SEQ ID NO 1190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1190
cagacactct ggtaag                                               16

<210> SEQ ID NO 1191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1191
tactccccat agaagg                                               16

<210> SEQ ID NO 1192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1192
tagactgagc ttggtg                                               16

<210> SEQ ID NO 1193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1193
ggacaaaagc tctcga                                               16

<210> SEQ ID NO 1194
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1194
gaacctgaat gcatcc                                                    16

<210> SEQ ID NO 1195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1195
cgacctcagg atccat                                                    16

<210> SEQ ID NO 1196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1196
gaatccagac tcatgt                                                    16

<210> SEQ ID NO 1197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1197
gcaggatgct gagacg                                                    16

<210> SEQ ID NO 1198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1198
actcagtgct gtagcg                                                    16

<210> SEQ ID NO 1199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1199
attatcctaa tgggta                                                    16

<210> SEQ ID NO 1200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1200
aatcgcaatg gcagat                                                    16
```

<210> SEQ ID NO 1201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1201
aacacctgtg aggtca                                                        16

<210> SEQ ID NO 1202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1202
ggagcagaca catcag                                                        16

<210> SEQ ID NO 1203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1203
gccagtcctg ctcagg                                                        16

<210> SEQ ID NO 1204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1204
aagaagaagt tcaggc                                                        16

<210> SEQ ID NO 1205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1205
gaaaggtgga gagccc                                                        16

<210> SEQ ID NO 1206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1206
tagactcgcc tcctca                                                        16

<210> SEQ ID NO 1207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1207
gaggtagctg cacaaa                                                   16

<210> SEQ ID NO 1208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1208
aactcagctc agaggc                                                   16

<210> SEQ ID NO 1209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1209
ccgctgcaca ggcgaa                                                   16

<210> SEQ ID NO 1210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1210
ctgatgtatt agagtt                                                   16

<210> SEQ ID NO 1211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1211
ccaaccagct gaatta                                                   16

<210> SEQ ID NO 1212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1212
aacagtcagt aaggga                                                   16

<210> SEQ ID NO 1213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1213
tctgaccatt aatagg                                                   16

<210> SEQ ID NO 1214
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1214
tgtcattcta agaacc                                                      16

<210> SEQ ID NO 1215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1215 gcctacccccc catcac                                                      16

<210> SEQ ID NO 1216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1216
caccccacaa gatcac                                                      16

<210> SEQ ID NO 1217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1217
tgcagaccac ctgaca                                                      16

<210> SEQ ID NO 1218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1218
cccccgccat ggagac                                                      16

<210> SEQ ID NO 1219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1219
cgcttcctta cattttt                                                     16

<210> SEQ ID NO 1220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1220
```

| | |
|---|---|
| tgcacccaac cgattt | 16 |

<210> SEQ ID NO 1221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1221

| | |
|---|---|
| ggctgaggtg aatgcc | 16 |

<210> SEQ ID NO 1222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1222

| | |
|---|---|
| agttgtgtgc tccagt | 16 |

<210> SEQ ID NO 1223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1223

| | |
|---|---|
| actcactgac catgtg | 16 |

<210> SEQ ID NO 1224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1224

| | |
|---|---|
| ggccaaagcc ccactc | 16 |

<210> SEQ ID NO 1225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1225

| | |
|---|---|
| gggcataatc tcctgc | 16 |

<210> SEQ ID NO 1226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1226

| | |
|---|---|
| ggctgatctg cactct | 16 |

<210> SEQ ID NO 1227
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1227
taattctacc tgtgtc                                                     16

<210> SEQ ID NO 1228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1228
agtttatgtc actctg                                                     16

<210> SEQ ID NO 1229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1229
acactttgcg aagcac                                                     16

<210> SEQ ID NO 1230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1230
gaactaacat acaccc                                                     16

<210> SEQ ID NO 1231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1231
cccataatca gggtgg                                                     16

<210> SEQ ID NO 1232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1232
gtagagtggt aaggca                                                     16

<210> SEQ ID NO 1233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1233
aagaatcatg caagct                                                     16
```

```
<210> SEQ ID NO 1234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1234
ttaaactaag ggtcac                                                       16

<210> SEQ ID NO 1235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1235
ttaatgtgga ttcacg                                                       16

<210> SEQ ID NO 1236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1236
ccaagataac ctcaca                                                       16

<210> SEQ ID NO 1237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1237
ccatctacat atctgg                                                       16

<210> SEQ ID NO 1238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1238
cacaatcatt tggacc                                                       16

<210> SEQ ID NO 1239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1239
gtattaatct ggtcat                                                       16

<210> SEQ ID NO 1240
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1240
cacctctgga caatcg                                                    16

<210> SEQ ID NO 1241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1241
caaactatgc ctagaa                                                    16

<210> SEQ ID NO 1242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1242
attttacgat catcat                                                    16

<210> SEQ ID NO 1243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1243
tgcctgtatt agctca                                                    16

<210> SEQ ID NO 1244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1244
cacataaagt caaacg                                                    16

<210> SEQ ID NO 1245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1245
agaacaagag agtact                                                    16

<210> SEQ ID NO 1246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1246
cacataaagg accccc                                                    16

<210> SEQ ID NO 1247
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1247
cgctatctga cactcc                                                  16

<210> SEQ ID NO 1248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1248
tccaccaacg aatccc                                                  16

<210> SEQ ID NO 1249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1249
tgtctcggcc agggca                                                  16

<210> SEQ ID NO 1250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1250
cctgatccgc agcagc                                                  16

<210> SEQ ID NO 1251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1251
ccagccgcgc tctgcg                                                  16

<210> SEQ ID NO 1252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1252
ggcagcgggt cgcccc                                                  16

<210> SEQ ID NO 1253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1253
```
cgggataccg gagagg 16

<210> SEQ ID NO 1254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1254
ccgcacaaga tctgag 16

<210> SEQ ID NO 1255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1255
gatgccaatg ttccga 16

<210> SEQ ID NO 1256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1256
tgtcggagga acttgc 16

<210> SEQ ID NO 1257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1257
cattggccgg gaggca 16

<210> SEQ ID NO 1258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1258
tgcctatttt gccgga 16

<210> SEQ ID NO 1259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1259
tcagacactc tggtaa 16

<210> SEQ ID NO 1260
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1260
cgtactcccc atagaa                                                          16

<210> SEQ ID NO 1261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1261
cgtagactga gcttgg                                                          16

<210> SEQ ID NO 1262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1262
caccttgaga tccggg                                                          16

<210> SEQ ID NO 1263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1263
agaacctgaa tgcatc                                                          16

<210> SEQ ID NO 1264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1264
gcgacctcag gatcca                                                          16

<210> SEQ ID NO 1265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1265
ggcagccgac tccggg                                                          16

<210> SEQ ID NO 1266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1266
caggatgctc tcatcc                                                          16
```

```
<210> SEQ ID NO 1267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1267
cactcagtgc tgtagc                                                16

<210> SEQ ID NO 1268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1268
agacattatc ctaatg                                                16

<210> SEQ ID NO 1269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1269
caatcgcaat ggcaga                                                16

<210> SEQ ID NO 1270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1270
gaacacctgt gaggtc                                                16

<210> SEQ ID NO 1271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1271
ggctgctcac tggcat                                                16

<210> SEQ ID NO 1272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1272
ggccagtcct gctcag                                                16

<210> SEQ ID NO 1273
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 1273
cccaagaaga agttca                                                         16

<210> SEQ ID NO 1274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1274
ggaaaggtgg agagcc                                                         16

<210> SEQ ID NO 1275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1275
ctagactcgc ctcctc                                                         16

<210> SEQ ID NO 1276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1276
gcggaggtag ctgcac                                                         16

<210> SEQ ID NO 1277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1277
caactcagct cagagg                                                         16

<210> SEQ ID NO 1278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1278
accgctgcac aggcga                                                         16

<210> SEQ ID NO 1279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1279
tgctgatgta ttagag                                                         16

-continued

```
<210> SEQ ID NO 1280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1280
cccaaccagc tgaatt                                                    16

<210> SEQ ID NO 1281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1281
aaacagtcag taaggg                                                    16

<210> SEQ ID NO 1282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1282
gtctgaccat taatag                                                    16

<210> SEQ ID NO 1283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1283
ctgtcattct aagaac                                                    16

<210> SEQ ID NO 1284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1284
agcctacccc ccatca                                                    16

<210> SEQ ID NO 1285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1285
ccaccccaca agatca                                                    16

<210> SEQ ID NO 1286
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1286
ttgcagacca cctgac                                              16

<210> SEQ ID NO 1287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1287 accccccgcca tggaga                                             16

<210> SEQ ID NO 1288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1288
acgcttcctt acattt                                              16

<210> SEQ ID NO 1289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1289
ctgcacccaa ccgatt                                              16

<210> SEQ ID NO 1290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1290
gggctgaggt gaatgc                                              16

<210> SEQ ID NO 1291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1291
aagttgtgtg ctccag                                              16

<210> SEQ ID NO 1292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1292
gaaactcact gaccat                                              16

<210> SEQ ID NO 1293
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1293
ggaaacaact ttcctc                                               16

<210> SEQ ID NO 1294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1294
gatcatgtgg cggtct                                               16

<210> SEQ ID NO 1295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1295
cacttactgg cctggc                                               16

<210> SEQ ID NO 1296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1296
atattgggct caatga                                               16

<210> SEQ ID NO 1297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1297
atcactggag gtgtac                                               16

<210> SEQ ID NO 1298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1298
caggatcaca ctttgc                                               16

<210> SEQ ID NO 1299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1299
```
ggaactaaca tacacc                                           16

<210> SEQ ID NO 1300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1300
gtatatgttc ccaggt                                           16

<210> SEQ ID NO 1301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1301
gtgtacatgg tctgca                                           16

<210> SEQ ID NO 1302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1302
atcattggaa gaccgc                                           16

<210> SEQ ID NO 1303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1303
gttaaactaa gggtca                                           16

<210> SEQ ID NO 1304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1304
cttaatgtgg attcac                                           16

<210> SEQ ID NO 1305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1305
tccaacttca ggctga                                           16

<210> SEQ ID NO 1306
<211> LENGTH: 16
<212> TYPE: DNA
<213> ORGANISM: Artificial sequence -continued

```
<220> FEATURE:
<223> OTHER INFORMATION: Synthetic oligonucleotide

<400> SEQUENCE: 1306
agctttgtgg gctcca                                                    16

<210> SEQ ID NO 1307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1307
gtttaataag ggcacc                                                    16

<210> SEQ ID NO 1308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1308
cgtattaatc tggtca                                                    16

<210> SEQ ID NO 1309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1309
cacctaaaat gctcac                                                    16

<210> SEQ ID NO 1310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1310
acaaactatg cctaga                                                    16

<210> SEQ ID NO 1311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1311
aattttacga tcatca                                                    16

<210> SEQ ID NO 1312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1312
gacagatcag cactcg                                                    16
```

<210> SEQ ID NO 1313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1313
caattctaga catggc                                                       16

<210> SEQ ID NO 1314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1314
tgcacctacc cttttc                                                       16

<210> SEQ ID NO 1315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1315
acacataaag gacccc                                                       16

<210> SEQ ID NO 1316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1316
gcattaccag gcacct                                                       16

<210> SEQ ID NO 1317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1317
gacatcacag gtgttg                                                       16

<210> SEQ ID NO 1318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1318
gtgtctcggc cagggc                                                       16

<210> SEQ ID NO 1319
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1319
gtcctgatcc gcagca                                               16

<210> SEQ ID NO 1320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1320
ctccagccgc gctctg                                               16

<210> SEQ ID NO 1321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1321
aggcagcggg tcgccc                                               16

<210> SEQ ID NO 1322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1322
gcgggatacc ggagag                                               16

<210> SEQ ID NO 1323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1323
tccgcacaag atctga                                               16

<210> SEQ ID NO 1324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1324
agatgccaat gttccg                                               16

<210> SEQ ID NO 1325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1325
ctgtcggagg aacttg                                               16

<210> SEQ ID NO 1326
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1326
acattggccg ggaggc                                                    16

<210> SEQ ID NO 1327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1327
atgcctattt tgccgg                                                    16

<210> SEQ ID NO 1328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1328
atcagacact ctggta                                                    16

<210> SEQ ID NO 1329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1329
actttagggc agatgt                                                    16

<210> SEQ ID NO 1330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1330
gtagaggttc cctgtg                                                    16

<210> SEQ ID NO 1331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1331
agcaccttga gatccg                                                    16

<210> SEQ ID NO 1332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1332
```
gttgcagatg cccttc                                                    16

<210> SEQ ID NO 1333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1333
ggcgacctca ggatcc                                                    16

<210> SEQ ID NO 1334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1334
aggcagccga ctccgg                                                    16

<210> SEQ ID NO 1335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1335
gtgtccagga tgctct                                                    16

<210> SEQ ID NO 1336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1336
tcactcagtg ctgtag                                                    16

<210> SEQ ID NO 1337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1337
ataagacatt atccta                                                    16

<210> SEQ ID NO 1338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1338
acaatcgcaa tggcag                                                    16

<210> SEQ ID NO 1339
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1339
gtgaacacct gtgagg                                                       16

<210> SEQ ID NO 1340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1340
ttggctgctc actggc                                                       16

<210> SEQ ID NO 1341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1341
gggccagtcc tgctca                                                       16

<210> SEQ ID NO 1342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1342
gcccaagaag aagttc                                                       16

<210> SEQ ID NO 1343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1343
ctagtgaaaa actggg                                                       16

<210> SEQ ID NO 1344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1344
gctagactcg cctcct                                                       16

<210> SEQ ID NO 1345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1345
tgcggaggta gctgca                                                       16
```

<210> SEQ ID NO 1346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1346
cctagctttt cataaa                                                        16

<210> SEQ ID NO 1347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1347
gaccgctgca caggcg                                                        16

<210> SEQ ID NO 1348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1348
atgctgatgt attaga                                                        16

<210> SEQ ID NO 1349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1349
tcccaaccag ctgaat                                                        16

<210> SEQ ID NO 1350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1350
gaaacagtca gtaagg                                                        16

<210> SEQ ID NO 1351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1351
agtctgacca ttaata                                                        16

<210> SEQ ID NO 1352
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1352
acctgtcatt ctaaga                                                         16

<210> SEQ ID NO 1353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1353
cagcctaccc cccatc                                                         16

<210> SEQ ID NO 1354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1354
ctccacccca caagat                                                         16

<210> SEQ ID NO 1355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1355
ctttgcagac cacctg                                                         16

<210> SEQ ID NO 1356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1356
tacccccgcc atggag                                                         16

<210> SEQ ID NO 1357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1357
caacaggtaa caacgc                                                         16

<210> SEQ ID NO 1358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1358
gtcagacttt cactca                                                         16

```
<210> SEQ ID NO 1359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1359
gtgcttggct cctgcc                                                   16

<210> SEQ ID NO 1360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1360
caagttgtgt gctcca                                                   16

<210> SEQ ID NO 1361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1361
catcgccaca catggg                                                   16

<210> SEQ ID NO 1362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1362
aggaagggtc ccaaac                                                   16

<210> SEQ ID NO 1363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1363
tgatcatgtg gcggtc                                                   16

<210> SEQ ID NO 1364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1364
tgctatcagg tgcagg                                                   16

<210> SEQ ID NO 1365
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 1365
tatattgggc tcaatg                                                   16

<210> SEQ ID NO 1366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1366
gtttacaaac atggac                                                   16

<210> SEQ ID NO 1367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1367
tcattagcat caccgg                                                   16

<210> SEQ ID NO 1368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1368
gggaactaac atacac                                                   16

<210> SEQ ID NO 1369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1369
gggtatatgt tcccag                                                   16

<210> SEQ ID NO 1370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1370
tgcatagcct tctttc                                                   16

<210> SEQ ID NO 1371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1371
catcattgga agaccg                                                   16

<210> SEQ ID NO 1372
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1372
tctttaactt cggccc                                                 16

<210> SEQ ID NO 1373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1373
tcttaatgtg gattca                                                 16

<210> SEQ ID NO 1374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1374
tcagacaacc acagct                                                 16

<210> SEQ ID NO 1375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1375
taaagcagga cacacg                                                 16

<210> SEQ ID NO 1376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1376
agacatgttg gtgtct                                                 16

<210> SEQ ID NO 1377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1377
ccccagtctt ttattc                                                 16

<210> SEQ ID NO 1378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1378
```
ggaagacacg gagcca                                                          16

<210> SEQ ID NO 1379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1379
cctaactgct ggctct                                                          16

<210> SEQ ID NO 1380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1380
taattttacg atcatc                                                          16

<210> SEQ ID NO 1381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1381
ctctttgtag cagaca                                                          16

<210> SEQ ID NO 1382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1382
caatatactg agagga                                                          16

<210> SEQ ID NO 1383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1383
gtagacatcc ttcccg                                                          16

<210> SEQ ID NO 1384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1384
gacacataaa ggaccc                                                          16

<210> SEQ ID NO 1385
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1385
tgcattacca ggcacc                                                        16

<210> SEQ ID NO 1386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1386
ggacatcaca ggtgtt                                                        16

<210> SEQ ID NO 1387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1387
agtgtctcgg ccaggg                                                        16

<210> SEQ ID NO 1388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1388
ggtcctgatc cgcagc                                                        16

<210> SEQ ID NO 1389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1389
gctccagccg cgctct                                                        16

<210> SEQ ID NO 1390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1390
caggcagcgg gtcgcc                                                        16

<210> SEQ ID NO 1391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1391
agcgggatac cggaga                                                        16
```

<210> SEQ ID NO 1392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1392
ttccgcacaa gatctg                                                   16

<210> SEQ ID NO 1393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1393
aagatgccaa tgttcc                                                   16

<210> SEQ ID NO 1394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1394
ccctgtcgga ggaact                                                   16

<210> SEQ ID NO 1395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1395
ggacattggc cgggag                                                   16

<210> SEQ ID NO 1396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1396
gatgcctatt ttgccg                                                   16

<210> SEQ ID NO 1397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1397
ccatcagaca ctctgg                                                   16

<210> SEQ ID NO 1398
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1398
caggaacata ccaagg                                                    16

<210> SEQ ID NO 1399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1399
gttgtcactc actcct                                                    16

<210> SEQ ID NO 1400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1400
gactttaggg cagatg                                                    16

<210> SEQ ID NO 1401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1401
ggtagaggtt ccctgt                                                    16

<210> SEQ ID NO 1402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1402
cagcaccttg agatcc                                                    16

<210> SEQ ID NO 1403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1403
ctgttgcaga tgccct                                                    16

<210> SEQ ID NO 1404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1404
tggcgacctc aggatc                                                    16

<210> SEQ ID NO 1405
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1405
aaggcagccg actccg                                                    16

<210> SEQ ID NO 1406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1406
ggtgtccagg atgctc                                                    16

<210> SEQ ID NO 1407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1407
ttcactcagt gctgta                                                    16

<210> SEQ ID NO 1408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1408
acataagaca ttatcc                                                    16

<210> SEQ ID NO 1409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1409
ctggacaatc gcaatg                                                    16

<210> SEQ ID NO 1410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1410
gagtgaacac ctgtga                                                    16

<210> SEQ ID NO 1411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1411
```
gttggctgct cactgg                                                    16

<210> SEQ ID NO 1412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1412
agggccagtc ctgctc                                                    16

<210> SEQ ID NO 1413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1413
attgcccaag aagaag                                                    16

<210> SEQ ID NO 1414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1414
tctagtgaaa aactgg                                                    16

<210> SEQ ID NO 1415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1415
tgctagactc gcctcc                                                    16

<210> SEQ ID NO 1416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1416
atgcggaggt agctgc                                                    16

<210> SEQ ID NO 1417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1417
ggttgcttcc tagctt                                                    16

<210> SEQ ID NO 1418
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1418
ggaccgctgc acaggc                                              16

<210> SEQ ID NO 1419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1419
catgctgatg tattag                                              16

<210> SEQ ID NO 1420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1420
ttcccaacca gctgaa                                              16

<210> SEQ ID NO 1421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1421
cgaaacagtc agtaag                                              16

<210> SEQ ID NO 1422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1422
aacagtctga ccatta                                              16

<210> SEQ ID NO 1423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1423
cacctgtcat tctaag                                              16

<210> SEQ ID NO 1424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1424
ccagcctacc ccccat                                              16
```

-continued

<210> SEQ ID NO 1425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1425
gtgggatcat gctatt                                                 16

<210> SEQ ID NO 1426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1426
tctttgcaga ccacct                                                 16

<210> SEQ ID NO 1427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1427 ttaccccgc catgga                                                  16

<210> SEQ ID NO 1428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1428
tcaacaggta acaacg                                                 16

<210> SEQ ID NO 1429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1429
gcacactaga ttattt                                                 16

<210> SEQ ID NO 1430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1430
cggaagctcc tgctgt                                                 16

<210> SEQ ID NO 1431
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1431
tcaagttgtg tgctcc                                                    16

<210> SEQ ID NO 1432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1432
tcatcgccac acatgg                                                    16

<210> SEQ ID NO 1433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1433
tcatttccag gagtac                                                    16

<210> SEQ ID NO 1434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1434
caaatgatca tgtggc                                                    16

<210> SEQ ID NO 1435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1435
taatgctatc aggtgc                                                    16

<210> SEQ ID NO 1436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1436
gatatattgg gctcaa                                                    16

<210> SEQ ID NO 1437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1437
gggtttacaa acatgg                                                    16

```
<210> SEQ ID NO 1438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1438
ttcattagca tcaccg                                                      16

<210> SEQ ID NO 1439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1439
gttaatccat gggtca                                                      16

<210> SEQ ID NO 1440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1440
agcctaaact tcctcc                                                      16

<210> SEQ ID NO 1441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1441
agaagagccg ccctgc                                                      16

<210> SEQ ID NO 1442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1442
gcaagactag caagtg                                                      16

<210> SEQ ID NO 1443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1443
agcatgcggt atgtac                                                      16

<210> SEQ ID NO 1444
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1444
cacacaattt ctaggg                                                    16

<210> SEQ ID NO 1445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1445
ttgacaatta gaacca                                                    16

<210> SEQ ID NO 1446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1446
acaaatcctt accgag                                                    16

<210> SEQ ID NO 1447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1447
gttttaggtc tgggta                                                    16

<210> SEQ ID NO 1448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1448
ttgcatagcc ttcttt                                                    16

<210> SEQ ID NO 1449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1449
catacatacc cttctc                                                    16

<210> SEQ ID NO 1450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1450
cgcagaaact ctttaa                                                    16

<210> SEQ ID NO 1451
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1451
gtcttaatgt ggattc                                              16

<210> SEQ ID NO 1452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1452
agcattggca cactgg                                              16

<210> SEQ ID NO 1453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1453
ggctttaaag caggac                                              16

<210> SEQ ID NO 1454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1454
gcagacatgt tggtgt                                              16

<210> SEQ ID NO 1455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1455
tacaagctgg tccttg                                              16

<210> SEQ ID NO 1456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1456
gacaatccag gtccca                                              16

<210> SEQ ID NO 1457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1457
```

-continued

```
gaggaagccc aatcaa                                                       16

<210> SEQ ID NO 1458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1458
ctaattttac gatcat                                                       16

<210> SEQ ID NO 1459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1459
ttaaactgcc aagtcc                                                       16

<210> SEQ ID NO 1460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1460
ccaatatact gagagg                                                       16

<210> SEQ ID NO 1461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1461
ggtagcaccg ccaagt                                                       16

<210> SEQ ID NO 1462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1462
caccatggag aggtct                                                       16

<210> SEQ ID NO 1463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1463
ttgcattacc aggcac                                                       16

<210> SEQ ID NO 1464
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 1464
gctacctgga cacctc                                                   16

<210> SEQ ID NO 1465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1465
atctttgcag accacc                                                   16

<210> SEQ ID NO 1466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1466
cagtgtctcg gccagg                                                   16

<210> SEQ ID NO 1467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1467
gggtcctgat ccgcag                                                   16

<210> SEQ ID NO 1468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1468
agctccagcc gcgctc                                                   16

<210> SEQ ID NO 1469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1469
tcaggcagcg ggtcgc                                                   16

<210> SEQ ID NO 1470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1470
cagcgggata ccggag                                                   16
```

<210> SEQ ID NO 1471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1471
cttccgcaca agatct                                              16

<210> SEQ ID NO 1472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1472
ggaagatgcc aatgtt                                              16

<210> SEQ ID NO 1473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1473
accctgtcgg aggaac                                              16

<210> SEQ ID NO 1474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1474
ggtggacatt ggccgg                                              16

<210> SEQ ID NO 1475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1475
agatgcctat tttgcc                                              16

<210> SEQ ID NO 1476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1476
cgaaagtcag acacca                                              16

<210> SEQ ID NO 1477
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1477
tgactttagg gcagat                                                    16

<210> SEQ ID NO 1478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1478
aaggtagagg ttccct                                                    16

<210> SEQ ID NO 1479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1479
aaggcatatc tctccc                                                    16

<210> SEQ ID NO 1480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1480
cctgttgcag atgccc                                                    16

<210> SEQ ID NO 1481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1481
atggcgacct caggat                                                    16

<210> SEQ ID NO 1482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1482
caaggcagcc gactcc                                                    16

<210> SEQ ID NO 1483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1483
cgagagggtg tccagg                                                    16

<210> SEQ ID NO 1484
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1484
cttcactcag tgctgt                                                   16

<210> SEQ ID NO 1485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1485
cagcattaca taagac                                                   16

<210> SEQ ID NO 1486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1486
ctctggacaa tcgcaa                                                   16

<210> SEQ ID NO 1487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1487
cgagtgaaca cctgtg                                                   16

<210> SEQ ID NO 1488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1488
tgttggctgc tcactg                                                   16

<210> SEQ ID NO 1489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1489
ctggacagcc cttggg                                                   16

<210> SEQ ID NO 1490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1490
```

```
tattgcccaa gaagaa                                              16

<210> SEQ ID NO 1491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1491
actcttctct agtgaa                                              16

<210> SEQ ID NO 1492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1492
ctgctagact cgcctc                                              16

<210> SEQ ID NO 1493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1493
aatgcggagg tagctg                                              16

<210> SEQ ID NO 1494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1494
aggttgcttc ctagct                                              16

<210> SEQ ID NO 1495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1495
tggaccgctg cacagg                                              16

<210> SEQ ID NO 1496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1496
gcatgctgat gtatta                                              16

<210> SEQ ID NO 1497
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 1497
tcatttccca accagc                                                      16

<210> SEQ ID NO 1498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1498
acgaaacagt cagtaa                                                      16

<210> SEQ ID NO 1499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1499
ggaacagtct gaccat                                                      16

<210> SEQ ID NO 1500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1500
aacacctgtc attcta                                                      16

<210> SEQ ID NO 1501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1501
gccagcctac ccccca                                                      16

<210> SEQ ID NO 1502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1502
agtgggatca tgctat                                                      16

<210> SEQ ID NO 1503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1503 gttaccccg ccatgg                                                       16
```

<210> SEQ ID NO 1504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1504
ttcaacaggt aacaac                                          16

<210> SEQ ID NO 1505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1505
tgcacactag attatt                                          16

<210> SEQ ID NO 1506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1506
gcggaagctc ctgctg                                          16

<210> SEQ ID NO 1507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1507
gttcaagttg tgtgct                                          16

<210> SEQ ID NO 1508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1508
ctcatcgcca cacatg                                          16

<210> SEQ ID NO 1509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1509
cggaatctca tttcca                                          16

<210> SEQ ID NO 1510
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1510
gcaaatgatc atgtgg        16

<210> SEQ ID NO 1511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1511
cttaatgcta tcaggt        16

<210> SEQ ID NO 1512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1512
ggatatattg ggctca        16

<210> SEQ ID NO 1513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1513
agggtttaca aacatg        16

<210> SEQ ID NO 1514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1514
attcattagc atcacc        16

<210> SEQ ID NO 1515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1515
ggttaatcca tgggtc        16

<210> SEQ ID NO 1516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1516
agttttaggt ctgggt        16

```
<210> SEQ ID NO 1517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1517
cattgcatag ccttct                                                    16

<210> SEQ ID NO 1518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1518
ccatacatac ccttct                                                    16

<210> SEQ ID NO 1519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1519
acccacacct gactgg                                                    16

<210> SEQ ID NO 1520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1520
cgctcctact tatccc                                                    16

<210> SEQ ID NO 1521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1521
tcttacagca ttggca                                                    16

<210> SEQ ID NO 1522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1522
catctaccaa actgca                                                    16

<210> SEQ ID NO 1523
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1523
aacaaacatc gatttt                                                    16

<210> SEQ ID NO 1524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1524
agctttacaa gctggt                                                    16

<210> SEQ ID NO 1525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1525
acgacaatcc aggtcc                                                    16

<210> SEQ ID NO 1526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1526
tctaatttta cgatca                                                    16

<210> SEQ ID NO 1527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1527
attaaactgc caagtc                                                    16

<210> SEQ ID NO 1528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1528
accaatatac tgagag                                                    16

<210> SEQ ID NO 1529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1529
agcggtagca ccgcca                                                    16

<210> SEQ ID NO 1530
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1530
tcacatgtga gcccag                                                  16

<210> SEQ ID NO 1531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1531
gtacaacaga gggtgg                                                  16

<210> SEQ ID NO 1532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1532
ggctgatgtc accacc                                                  16

<210> SEQ ID NO 1533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1533
tcagtgtctc ggccag                                                  16

<210> SEQ ID NO 1534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1534
tcggctcggg tcctga                                                  16

<210> SEQ ID NO 1535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1535
caagctccag ccgcgc                                                  16

<210> SEQ ID NO 1536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1536
```
ctcaggcagc gggtcg                                          16

<210> SEQ ID NO 1537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1537
ccagcgggat accgga                                          16

<210> SEQ ID NO 1538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1538
ccttccgcac aagatc                                          16

<210> SEQ ID NO 1539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1539
gatggaagat gccaat                                          16

<210> SEQ ID NO 1540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1540
gaccctgtcg gaggaa                                          16

<210> SEQ ID NO 1541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1541
ctggtggaca ttggcc                                          16

<210> SEQ ID NO 1542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1542
gagatgccta ttttgc                                          16

<210> SEQ ID NO 1543
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1543
ccgaaagtca gacacc                                               16

<210> SEQ ID NO 1544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1544
gcatcaatga agggta                                               16

<210> SEQ ID NO 1545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1545
ttgactttag ggcaga                                               16

<210> SEQ ID NO 1546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1546
gaaggtagag gttccc                                               16

<210> SEQ ID NO 1547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1547
gaaggcatat ctctcc                                               16

<210> SEQ ID NO 1548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1548
gcctgttgca gatgcc                                               16

<210> SEQ ID NO 1549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1549
catggcgacc tcagga                                               16
```

<210> SEQ ID NO 1550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1550
ccaaggcagc cgactc                                                  16

<210> SEQ ID NO 1551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1551
gcgagagggt gtccag                                                  16

<210> SEQ ID NO 1552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1552
tcttcactca gtgctg                                                  16

<210> SEQ ID NO 1553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1553
gcagcattac ataaga                                                  16

<210> SEQ ID NO 1554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1554
agtctctgga caatcg                                                  16

<210> SEQ ID NO 1555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1555
tcgagtgaac acctgt                                                  16

<210> SEQ ID NO 1556
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1556
ctgttggctg ctcact                                                    16

<210> SEQ ID NO 1557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1557
gctggacagc ccttgg                                                    16

<210> SEQ ID NO 1558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1558
ttattgccca agaaga                                                    16

<210> SEQ ID NO 1559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1559
gactcttctc tagtga                                                    16

<210> SEQ ID NO 1560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1560
tctgctagac tcgcct                                                    16

<210> SEQ ID NO 1561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1561
caatgcggag gtagct                                                    16

<210> SEQ ID NO 1562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1562
aaggttgctt cctagc                                                    16

<210> SEQ ID NO 1563
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1563
ctggaccgct gcacag                                                  16

<210> SEQ ID NO 1564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1564
cgcatgctga tgtatt                                                  16

<210> SEQ ID NO 1565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1565
gtgtcatttc ccaacc                                                  16

<210> SEQ ID NO 1566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1566
cacgaaacag tcagta                                                  16

<210> SEQ ID NO 1567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1567
gctggaacag tctgac                                                  16

<210> SEQ ID NO 1568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1568
catccaaaca cctgtc                                                  16

<210> SEQ ID NO 1569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1569
```

```
ggccagccta cccccc                                              16

<210> SEQ ID NO 1570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1570
aagtgggatc atgcta                                              16

<210> SEQ ID NO 1571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1571
catctttgca gaccac                                              16

<210> SEQ ID NO 1572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1572 tgttacccccc gccatg                                             16

<210> SEQ ID NO 1573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1573
gattcacata atacaa                                              16

<210> SEQ ID NO 1574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1574
ctgcacacta gattat                                              16

<210> SEQ ID NO 1575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1575
ggcggaagct cctgct                                              16

<210> SEQ ID NO 1576
<211> LENGTH: 16
<212> TYPE: DNA
```

<213> ORGANISM: Artificial sequence
<220> FEATURE:
<223> OTHER INFORMATION: Synthetic oligonucleotide

<400> SEQUENCE: 1576
ggttcaagtt gtgtgc                                            16

<210> SEQ ID NO 1577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1577
tctcatcgcc acacat                                            16

<210> SEQ ID NO 1578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1578
tacggaatct catttc                                            16

<210> SEQ ID NO 1579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1579
ggccaccttg ggatac                                            16

<210> SEQ ID NO 1580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1580
gccttaatgc tatcag                                            16

<210> SEQ ID NO 1581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1581
tggatatatt gggctc                                            16

<210> SEQ ID NO 1582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1582
acattcaggg tttaca                                            16

<210> SEQ ID NO 1583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1583
gtattcatta gcatca                                                  16

<210> SEQ ID NO 1584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1584
aggttaatcc atgggt                                                  16

<210> SEQ ID NO 1585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1585
gagttttagg tctggg                                                  16

<210> SEQ ID NO 1586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1586
cttataaagc acacgg                                                  16

<210> SEQ ID NO 1587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1587
gggcatggct gatcct                                                  16

<210> SEQ ID NO 1588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1588
caaacttgtc tagtgg                                                  16

<210> SEQ ID NO 1589
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1589
tcgcatccat gggtcc                                                             16

<210> SEQ ID NO 1590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1590
gctcttacag cattgg                                                             16

<210> SEQ ID NO 1591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1591
ccatctacca aactgc                                                             16

<210> SEQ ID NO 1592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1592
gacttagtcc gtgttc                                                             16

<210> SEQ ID NO 1593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1593
cagcatctat gttctc                                                             16

<210> SEQ ID NO 1594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1594
atagactgtg agctgt                                                             16

<210> SEQ ID NO 1595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1595
gaccattctg ctcccc                                                             16

```
<210> SEQ ID NO 1596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1596
gcccatacct tttatc                                                     16

<210> SEQ ID NO 1597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1597
gtattaaact gccaag                                                     16

<210> SEQ ID NO 1598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1598
ctaaccaata tactga                                                     16

<210> SEQ ID NO 1599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1599
ggctggtgat gaaaca                                                     16

<210> SEQ ID NO 1600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1600
cctcatggtt tgctgt                                                     16

<210> SEQ ID NO 1601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1601
cagtacaaca gagggt                                                     16

<210> SEQ ID NO 1602
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1602
cacattgccg gccagt                                                    16

<210> SEQ ID NO 1603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1603
ctcagtgtct cggcca                                                    16

<210> SEQ ID NO 1604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1604
atcggctcgg gtcctg                                                    16

<210> SEQ ID NO 1605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1605
acaagctcca gccgcg                                                    16

<210> SEQ ID NO 1606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1606
gctcaggcag cgggtc                                                    16

<210> SEQ ID NO 1607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1607
tccagcggga taccgg                                                    16

<210> SEQ ID NO 1608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1608
gccttccgca caagat                                                    16

<210> SEQ ID NO 1609
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1609
ggatggaaga tgccaa                                                         16

<210> SEQ ID NO 1610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1610
agaccctgtc ggagga                                                         16

<210> SEQ ID NO 1611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1611
atgagctggt ggacat                                                         16

<210> SEQ ID NO 1612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1612
agagatgcct attttg                                                         16

<210> SEQ ID NO 1613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1613
accgaaagtc agacac                                                         16

<210> SEQ ID NO 1614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1614
ggcatcaatg aagggt                                                         16

<210> SEQ ID NO 1615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1615
```
cttgacttta gggcag                                                              16

<210> SEQ ID NO 1616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1616
gagaaggtag aggttc                                                              16

<210> SEQ ID NO 1617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1617
tcgaaggcat atctct                                                              16

<210> SEQ ID NO 1618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1618
ggcctgttgc agatgc                                                              16

<210> SEQ ID NO 1619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1619
gcatggcgac ctcagg                                                              16

<210> SEQ ID NO 1620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1620
gccaaggcag ccgact                                                              16

<210> SEQ ID NO 1621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1621
ggcgagaggg tgtcca                                                              16

<210> SEQ ID NO 1622
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1622
tgtatccacc tttgtc                                                   16

<210> SEQ ID NO 1623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1623
ggcagcatta cataag                                                   16

<210> SEQ ID NO 1624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1624
ccatgtcacc agtctc                                                   16

<210> SEQ ID NO 1625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1625
ctcgagtgaa cacctg                                                   16

<210> SEQ ID NO 1626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1626
cctgttggct gctcac                                                   16

<210> SEQ ID NO 1627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1627
tgctggacag cccttg                                                   16

<210> SEQ ID NO 1628
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1628
tttattgccc aagaag                                                   16
```

```
<210> SEQ ID NO 1629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1629
agactcttct ctagtg                                                     16

<210> SEQ ID NO 1630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1630
atctgctaga ctcgcc                                                     16

<210> SEQ ID NO 1631
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1631
gcaatgcgga ggtagc                                                     16

<210> SEQ ID NO 1632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1632
aaaggttgct tcctag                                                     16

<210> SEQ ID NO 1633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1633
gctggaccgc tgcaca                                                     16

<210> SEQ ID NO 1634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1634
acgcatgctg atgtat                                                     16

<210> SEQ ID NO 1635
<211> LENGTH: 16
<212> TYPE: DNA
<213> ORGANISM: Artificial sequence
<220> FEATURE:
<223> OTHER INFORMATION: Synthetic oligonucleotide
```

-continued

```
<400> SEQUENCE: 1635
ggtgtcattt cccaac                                                     16

<210> SEQ ID NO 1636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1636
ccacgaaaca gtcagt                                                     16

<210> SEQ ID NO 1637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1637
atgctggaac agtctg                                                     16

<210> SEQ ID NO 1638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1638
ccatccaaac acctgt                                                     16

<210> SEQ ID NO 1639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1639
gggccagcct accccc                                                     16

<210> SEQ ID NO 1640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1640
gaagtgggat catgct                                                     16

<210> SEQ ID NO 1641
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1641
atcatctttg cagacc                                                     16

<210> SEQ ID NO 1642
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1642 ttgttaccccc cgccat                                                    16

<210> SEQ ID NO 1643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1643
ctgattcaca taatac                                                     16

<210> SEQ ID NO 1644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1644
cctgcacact agatta                                                     16

<210> SEQ ID NO 1645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1645
aggcggaagc tcctgc                                                     16

<210> SEQ ID NO 1646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1646
aggttcaagt tgtgtg                                                     16

<210> SEQ ID NO 1647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1647
aatgtacgga atctca                                                     16

<210> SEQ ID NO 1648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1648
```
gtccatgtgg gtgtcc                                                    16

<210> SEQ ID NO 1649
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1649
ggccttaatg ctatca                                                    16

<210> SEQ ID NO 1650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1650
tagtatgaaa tatctc                                                    16

<210> SEQ ID NO 1651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1651
attgtaactg ccaggc                                                    16

<210> SEQ ID NO 1652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1652
ccggtattca ttagca                                                    16

<210> SEQ ID NO 1653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1653
gagcagggca acaaac                                                    16

<210> SEQ ID NO 1654
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1654
atataaccac agcctg                                                    16

<210> SEQ ID NO 1655
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1655
gcttataaag cacacg                                                     16

<210> SEQ ID NO 1656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1656
tagtaaatgc ttgtca                                                     16

<210> SEQ ID NO 1657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1657
ggcagaaatg tgctct                                                     16

<210> SEQ ID NO 1658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1658
cttcatgcca tcctgt                                                     16

<210> SEQ ID NO 1659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1659
tgctcttaca gcattg                                                     16

<210> SEQ ID NO 1660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1660
ggtacctgta gcgagc                                                     16

<210> SEQ ID NO 1661
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1661
ttgacttagt ccgtgt                                                     16

<210> SEQ ID NO 1662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1662
agctacatca ggctgg                                                        16

<210> SEQ ID NO 1663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1663
tgcacataga ctgtga                                                        16

<210> SEQ ID NO 1664
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1664
gactgctgag ccaagc                                                        16

<210> SEQ ID NO 1665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1665
agaaattgca gtgccc                                                        16

<210> SEQ ID NO 1666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1666
ggtattaaac tgccaa                                                        16

<210> SEQ ID NO 1667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1667
tcactaacca atatac                                                        16

<210> SEQ ID NO 1668
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1668
ataaatctgc aagagc                                               16

<210> SEQ ID NO 1669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1669
tctcatggtc aagacc                                               16

<210> SEQ ID NO 1670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1670
gactgctagg cttcac                                               16

<210> SEQ ID NO 1671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1671
cgctgctgca gtgtgc                                               16

<210> SEQ ID NO 1672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1672
ggcatccacg acttcg                                               16

<210> SEQ ID NO 1673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1673
aggcatccac gacttc                                               16

<210> SEQ ID NO 1674
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1674
caaggcatcc acgact                                               16

<210> SEQ ID NO 1675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1675
aacataccaa ggcatc                                               16

<210> SEQ ID NO 1676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1676
ggaacatacc aaggca                                               16

<210> SEQ ID NO 1677
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1677
aggaacatac caaggc                                               16

<210> SEQ ID NO 1678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1678
gggataaggc cactgt                                               16

<210> SEQ ID NO 1679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1679
agggataagg ccactg                                               16

<210> SEQ ID NO 1680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1680
aaggagggat aaggcc                                               16

<210> SEQ ID NO 1681
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1681
acatatcgca cgcctc                                                  16

<210> SEQ ID NO 1682
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1682
cacatatcgc acgcct                                                  16

<210> SEQ ID NO 1683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1683
ccacatatcg cacgcc                                                  16

<210> SEQ ID NO 1684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1684
atccacatat cgcacg                                                  16

<210> SEQ ID NO 1685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1685
ctccatccac atatcg                                                  16

<210> SEQ ID NO 1686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1686
atcaatgaag ggtacg                                                  16

<210> SEQ ID NO 1687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1687
catcaatgaa gggtac                                                  16

<210> SEQ ID NO 1688
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1688
atggaagatg ccaatg                                                     16

<210> SEQ ID NO 1689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1689
ggagatgagc tggtgg                                                     16

<210> SEQ ID NO 1690
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1690
agactgagct tggtga                                                     16

<210> SEQ ID NO 1691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1691
cctgaatgca tccaaa                                                     16

<210> SEQ ID NO 1692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1692
atgctgagac gcaggt                                                     16

<210> SEQ ID NO 1693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1693
aatggcagat tccaca                                                     16

<210> SEQ ID NO 1694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1694
```

-continued ctctgaaaga atctgc                                                16

<210> SEQ ID NO 1695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1695
atgggaaact ttagca                                                16

<210> SEQ ID NO 1696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1696
tgtcatttcc caacca                                                16

<210> SEQ ID NO 1697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1697
ttttagtagt caaggt                                                16

<210> SEQ ID NO 1698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1698
gcttccttac attttt                                                16

<210> SEQ ID NO 1699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1699
taacatctca ctgatt                                                16

<210> SEQ ID NO 1700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1700
ctagtgagaa acaaac                                                16

<210> SEQ ID NO 1701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1701
ttattgttgc taaacc                                                    16

<210> SEQ ID NO 1702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1702
actttaggct cctggg                                                    16

<210> SEQ ID NO 1703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1703
agccataaat cttggg                                                    16

<210> SEQ ID NO 1704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1704
atgacatcat ggcttc                                                    16

<210> SEQ ID NO 1705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1705
ttattcaatg tggctt                                                    16

<210> SEQ ID NO 1706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1706
gggctcaatg aaatta                                                    16

<210> SEQ ID NO 1707
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1707
cttagtatga aatatc                                                    16

```
<210> SEQ ID NO 1708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1708
tactgtctac tatggg                                                    16

<210> SEQ ID NO 1709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1709
cttacatcca cgactt                                                    16

<210> SEQ ID NO 1710
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1710
cagtaactgg tagctc                                                    16

<210> SEQ ID NO 1711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1711
tgtttgattg tgcaga                                                    16

<210> SEQ ID NO 1712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1712
cgccttttat ttccgt                                                    16

<210> SEQ ID NO 1713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1713
ataaccacag cctggg                                                    16

<210> SEQ ID NO 1714
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1714
ataagaatca tcttag                                                   16

<210> SEQ ID NO 1715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1715
actaccgaac gcagtt                                                   16

<210> SEQ ID NO 1716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1716
tagagtggta aggcat                                                   16

<210> SEQ ID NO 1717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1717
ggttggtgta catggt                                                   16

<210> SEQ ID NO 1718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1718
tcctgttaga cagctt                                                   16

<210> SEQ ID NO 1719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1719
ataaagcaca cgggaa                                                   16

<210> SEQ ID NO 1720
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1720
taagagctgt ctcctc                                                   16

<210> SEQ ID NO 1721
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1721
ctaacaaact ttgcag                                                    16

<210> SEQ ID NO 1722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1722
tgtcaccctt ccacgg                                                    16

<210> SEQ ID NO 1723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1723
attggaagac cgcaga                                                    16

<210> SEQ ID NO 1724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1724
ccgctagtaa atgctt                                                    16

<210> SEQ ID NO 1725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1725
aactaaggca aatctc                                                    16

<210> SEQ ID NO 1726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1726
gagtcatgac atccca                                                    16

<210> SEQ ID NO 1727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1727
```
gcagataaat acacat                    16

<210> SEQ ID NO 1728
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1728
tttcccatcg acacag                    16

<210> SEQ ID NO 1729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1729
gctcctactt atcccc                    16

<210> SEQ ID NO 1730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1730
tattgccagg tatctg                    16

<210> SEQ ID NO 1731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1731
caatacatag cagagc                    16

<210> SEQ ID NO 1732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1732
ttagtccgtg ttcagg                    16

<210> SEQ ID NO 1733
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1733
gtagctggtt tgtggg                    16

<210> SEQ ID NO 1734
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1734
catctcttag ggcacc                                                  16

<210> SEQ ID NO 1735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1735
gtttggaagt cgccat                                                  16

<210> SEQ ID NO 1736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1736
aggaagccca atcaag                                                  16

<210> SEQ ID NO 1737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1737
cagattgagt ctcctg                                                  16

<210> SEQ ID NO 1738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1738
ttttacgatc atcatt                                                  16

<210> SEQ ID NO 1739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1739
gcttagaaat tgcagt                                                  16

<210> SEQ ID NO 1740
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1740
agggtaatat tcagac                                                  16
```

<210> SEQ ID NO 1741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1741
tgtagcagac agatca                                                     16

<210> SEQ ID NO 1742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1742
tttaacagct caggta                                                     16

<210> SEQ ID NO 1743
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1743
attctagaca tggcca                                                     16

<210> SEQ ID NO 1744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1744
aaccaatata ctgaga                                                     16

<210> SEQ ID NO 1745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1745
agacatatga catttc                                                     16

<210> SEQ ID NO 1746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1746
acatgacaga ctaact                                                     16

<210> SEQ ID NO 1747
<211> LENGTH: 16
<212> TYPE: DNA
<213> ORGANISM: Artificial sequence
<220> FEATURE:

```
-continued
```

<223> OTHER INFORMATION: Synthetic oligonucleotide

<400> SEQUENCE: 1747
catcaatgct gcactc                                               16

<210> SEQ ID NO 1748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1748
gttgaaggat ggatgg                                               16

<210> SEQ ID NO 1749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1749
agagagatgc ctattt                                               16

<210> SEQ ID NO 1750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1750
ggttccctgt gcagag                                               16

<210> SEQ ID NO 1751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1751
aagaacctga atgcat                                               16

<210> SEQ ID NO 1752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1752
gatgctgaga cgcagg                                               16

<210> SEQ ID NO 1753
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1753
acagactctt ctctag                                               16

```
<210> SEQ ID NO 1754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1754
cctctgaaag aatctg                                                    16

<210> SEQ ID NO 1755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1755
gtagctgcac aaagat                                                    16

<210> SEQ ID NO 1756
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1756
tggtgtcatt tcccaa                                                    16

<210> SEQ ID NO 1757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1757
tttttagtag tcaagg                                                    16

<210> SEQ ID NO 1758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1758
attcaacagg taacaa                                                    16

<210> SEQ ID NO 1759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1759
actaacatct cactga                                                    16

<210> SEQ ID NO 1760
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 1760
agctagtgag aaacaa                                                   16

<210> SEQ ID NO 1761
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1761
cttttattgt tgctaa                                                   16

<210> SEQ ID NO 1762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1762
agtgtacttt aggctc                                                   16

<210> SEQ ID NO 1763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1763
cagccataaa tcttgg                                                   16

<210> SEQ ID NO 1764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1764
aatgacatca tggctt                                                   16

<210> SEQ ID NO 1765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1765
tttattcaat gtggct                                                   16

<210> SEQ ID NO 1766
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1766
ttgggctcaa tgaaat                                                   16

<210> SEQ ID NO 1767
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1767
gcttagtatg aaatat                                                 16

<210> SEQ ID NO 1768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1768
gtactgtcta ctatgg                                                 16

<210> SEQ ID NO 1769
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1769
ctgcttacat ccacga                                                 16

<210> SEQ ID NO 1770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1770
acagtaactg gtagct                                                 16

<210> SEQ ID NO 1771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1771
ctgtttgatt gtgcag                                                 16

<210> SEQ ID NO 1772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1772 gcgccttta tttccg                                                  16

<210> SEQ ID NO 1773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1773
```

```
cctgactata taacca                                                   16

<210> SEQ ID NO 1774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1774
gaccgtgttt ccaaat                                                   16

<210> SEQ ID NO 1775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1775
aactaccgaa cgcagt                                                   16

<210> SEQ ID NO 1776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1776
ggtagagtgg taaggc                                                   16

<210> SEQ ID NO 1777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1777
catagccttc tttctt                                                   16

<210> SEQ ID NO 1778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1778
aatcctgtta gacagc                                                   16

<210> SEQ ID NO 1779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1779
tataaagcac acggga                                                   16

<210> SEQ ID NO 1780
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 1780
aataagagct gtctcc                                                     16

<210> SEQ ID NO 1781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1781
ccctaacaaa ctttgc                                                     16

<210> SEQ ID NO 1782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1782
aatgtcaccc ttccac                                                     16

<210> SEQ ID NO 1783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1783
cattggaaga ccgcag                                                     16

<210> SEQ ID NO 1784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1784
accgctagta aatgct                                                     16

<210> SEQ ID NO 1785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1785
tagaactaag gcaaat                                                     16

<210> SEQ ID NO 1786
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1786
ggagtcatga catccc                                                     16
```

<210> SEQ ID NO 1787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1787
tgagcagata aataca                                                       16

<210> SEQ ID NO 1788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1788
ctttcccatc gacaca                                                       16

<210> SEQ ID NO 1789
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1789
gcgctcctac ttatcc                                                       16

<210> SEQ ID NO 1790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1790
atattgccag gtatct                                                       16

<210> SEQ ID NO 1791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1791
gtgttggttt ataaca                                                       16

<210> SEQ ID NO 1792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1792
acttagtccg tgttca                                                       16

<210> SEQ ID NO 1793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1793
ctgtagctgg tttgtg                                              16

<210> SEQ ID NO 1794
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1794
ccatctctta gggcac                                              16

<210> SEQ ID NO 1795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1795
tgtttggaag tcgcca                                              16

<210> SEQ ID NO 1796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1796
atcagaggaa gcccaa                                              16

<210> SEQ ID NO 1797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1797
accagattga gtctcc                                              16

<210> SEQ ID NO 1798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1798
ctctaatttt acgatc                                              16

<210> SEQ ID NO 1799
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1799
agcttagaaa ttgcag                                              16

<210> SEQ ID NO 1800

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1800
cagggtaata ttcaga                                                      16

<210> SEQ ID NO 1801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1801
tttgtagcag acagat                                                      16

<210> SEQ ID NO 1802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1802
ttttaacagc tcaggt                                                      16

<210> SEQ ID NO 1803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1803
aattctagac atggcc                                                      16

<210> SEQ ID NO 1804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1804
taaccaatat actgag                                                      16

<210> SEQ ID NO 1805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1805
cgcaaaaaga caacga                                                      16

<210> SEQ ID NO 1806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1806
```
gacatgacag actaac 16

<210> SEQ ID NO 1807
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1807
ccatcaatgc tgcact 16

<210> SEQ ID NO 1808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1808
agttgaagga tggatg 16

<210> SEQ ID NO 1809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1809
ctggtaagag agatgc 16

<210> SEQ ID NO 1810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1810
gaggttccct gtgcag 16

<210> SEQ ID NO 1811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1811
caagaacctg aatgca 16

<210> SEQ ID NO 1812
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1812
aggatgctga gacgca 16

<210> SEQ ID NO 1813
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1813
tcacagactc ttctct                                                 16

<210> SEQ ID NO 1814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1814
acctctgaaa gaatct                                                 16

<210> SEQ ID NO 1815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1815
aggtagctgc acaaag                                                 16

<210> SEQ ID NO 1816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1816
cagtctgacc attaat                                                 16

<210> SEQ ID NO 1817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1817
gaaaaaggtg ttctaa                                                 16

<210> SEQ ID NO 1818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1818
aaattcaaca ggtaac                                                 16

<210> SEQ ID NO 1819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1819
ttctactaac atctca                                                 16
```

<210> SEQ ID NO 1820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1820
atgatcatgt ggcggt                                                       16

<210> SEQ ID NO 1821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1821
acttttattg ttgcta                                                       16

<210> SEQ ID NO 1822
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1822
gagtgtactt taggct                                                       16

<210> SEQ ID NO 1823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1823
ctatcaggtg caggag                                                       16

<210> SEQ ID NO 1824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1824
caatgacatc atggct                                                       16

<210> SEQ ID NO 1825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1825
tactttattc aatgtg                                                       16

<210> SEQ ID NO 1826
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1826
attgggctca atgaaa                                                   16

<210> SEQ ID NO 1827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1827
tggcttagta tgaaat                                                   16

<210> SEQ ID NO 1828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1828
tttggcaagg ccagaa                                                   16

<210> SEQ ID NO 1829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1829
gcatagagga agctcg                                                   16

<210> SEQ ID NO 1830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1830
gacagtaact ggtagc                                                   16

<210> SEQ ID NO 1831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1831
ttctgtttga ttgtgc                                                   16

<210> SEQ ID NO 1832
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1832
aggtctgggt atatgt                                                   16
```

```
<210> SEQ ID NO 1833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1833
ccctgactat ataacc                                                    16

<210> SEQ ID NO 1834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1834
ttgaccgtgt ttccaa                                                    16

<210> SEQ ID NO 1835
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1835
aaactaccga acgcag                                                    16

<210> SEQ ID NO 1836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1836
tggtagagtg gtaagg                                                    16

<210> SEQ ID NO 1837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1837
gcatagcctt ctttct                                                    16

<210> SEQ ID NO 1838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1838
caatcctgtt agacag                                                    16

<210> SEQ ID NO 1839
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1839
ttataaagca cacggg                                                   16

<210> SEQ ID NO 1840
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1840
caataagagc tgtctc                                                   16

<210> SEQ ID NO 1841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1841
tgcaggcacc ccagca                                                   16

<210> SEQ ID NO 1842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1842
gaatgtcacc cttcca                                                   16

<210> SEQ ID NO 1843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1843
tcattggaag accgca                                                   16

<210> SEQ ID NO 1844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1844
gaccgctagt aaatgc                                                   16

<210> SEQ ID NO 1845
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1845
ttagaactaa ggcaaa                                                   16

<210> SEQ ID NO 1846
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1846
tggagtcatg acatcc                                                       16

<210> SEQ ID NO 1847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1847
ctgagcagat aaatac                                                       16

<210> SEQ ID NO 1848
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1848
agtcttaatg tggatt                                                       16

<210> SEQ ID NO 1849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1849
agtgtcccca tcccca                                                       16

<210> SEQ ID NO 1850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1850
aatattgcca ggtatc                                                       16

<210> SEQ ID NO 1851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1851
tagtgttggt ttataa                                                       16

<210> SEQ ID NO 1852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1852
```
tgacttagtc cgtgtt                                              16

<210> SEQ ID NO 1853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1853
tctgtagctg gtttgt                                              16

<210> SEQ ID NO 1854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1854
tcccatctct tagggc                                              16

<210> SEQ ID NO 1855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1855
tatgtttgga agtcgc                                              16

<210> SEQ ID NO 1856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1856
aatcagagga agccca                                              16

<210> SEQ ID NO 1857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1857
aaccagattg agtctc                                              16

<210> SEQ ID NO 1858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1858
tctctaattt tacgat                                              16

<210> SEQ ID NO 1859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1859
cagcttagaa attgca                                                    16

<210> SEQ ID NO 1860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1860
ccagggtaat attcag                                                    16

<210> SEQ ID NO 1861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1861
ctttgtagca gacaga                                                    16

<210> SEQ ID NO 1862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1862
tattttaaca gctcag                                                    16

<210> SEQ ID NO 1863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1863
tgcaattcta gacatg                                                    16

<210> SEQ ID NO 1864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1864
actaaccaat atactg                                                    16

<210> SEQ ID NO 1865
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1865
caacagatta ctggac                                                    16

<210> SEQ ID NO 1866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1866
aggacatgac agacta                                                        16

<210> SEQ ID NO 1867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1867
accatcaatg ctgcac                                                        16

<210> SEQ ID NO 1868
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1868
aagttgaagg atggat                                                        16

<210> SEQ ID NO 1869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1869
ttggcatcaa tgaagg                                                        16

<210> SEQ ID NO 1870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1870
agaggttccc tgtgca                                                        16

<210> SEQ ID NO 1871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1871
ccaagaacct gaatgc                                                        16

<210> SEQ ID NO 1872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1872
ggcaggatgc tgagac                                                   16

<210> SEQ ID NO 1873
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1873
ctcacagact cttctc                                                   16

<210> SEQ ID NO 1874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1874
gcacctctga aagaat                                                   16

<210> SEQ ID NO 1875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1875
ggaggtagct gcacaa                                                   16

<210> SEQ ID NO 1876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1876
acagtctgac cattaa                                                   16

<210> SEQ ID NO 1877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1877
ttaggtgaaa aaggtg                                                   16

<210> SEQ ID NO 1878
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1878
tgattcacat aataca                                                   16

<210> SEQ ID NO 1879

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1879
tattctacta acatct                                                         16

<210> SEQ ID NO 1880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1880
aatgatcatg tggcgg                                                         16

<210> SEQ ID NO 1881
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1881
tgacttttat tgttgc                                                         16

<210> SEQ ID NO 1882
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1882
tgagtgtact ttaggc                                                         16

<210> SEQ ID NO 1883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1883
atgctatcag gtgcag                                                         16

<210> SEQ ID NO 1884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1884
gcacaatgac atcatg                                                         16

<210> SEQ ID NO 1885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1885
```
ttactttatt caatgt                                                   16

<210> SEQ ID NO 1886
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1886
tattgggctc aatgaa                                                   16

<210> SEQ ID NO 1887
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1887
tatgggagcc acatgt                                                   16

<210> SEQ ID NO 1888
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1888
cttttggcaa ggccag                                                   16

<210> SEQ ID NO 1889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1889
ttaaacagag gatgca                                                   16

<210> SEQ ID NO 1890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1890
agacagtaac tggtag                                                   16

<210> SEQ ID NO 1891
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1891
tccgttaacc atcaag                                                   16

<210> SEQ ID NO 1892
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1892
ttaggtctgg gtatat                                                      16

<210> SEQ ID NO 1893
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1893
cccctgacta tataac                                                      16

<210> SEQ ID NO 1894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1894
cttgaccgtg tttcca                                                      16

<210> SEQ ID NO 1895
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1895
ttaaactacc gaacgc                                                      16

<210> SEQ ID NO 1896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1896
atggtagagt ggtaag                                                      16

<210> SEQ ID NO 1897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1897
attgcatagc cttctt                                                      16

<210> SEQ ID NO 1898
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1898
ccaatcctgt tagaca                                                      16
```

<210> SEQ ID NO 1899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1899
ctgcttataa agcaca                                                    16

<210> SEQ ID NO 1900
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1900
acaataagag ctgtct                                                    16

<210> SEQ ID NO 1901
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1901
tttgcaggca ccccag                                                    16

<210> SEQ ID NO 1902
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1902
tgaatgtcac ccttcc                                                    16

<210> SEQ ID NO 1903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1903
gcatcattgg aagacc                                                    16

<210> SEQ ID NO 1904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1904
accaagaccg ctagta                                                    16

<210> SEQ ID NO 1905
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1905
tgttagaact aaggca                                                    16

<210> SEQ ID NO 1906
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1906
cctggagtca tgacat                                                    16

<210> SEQ ID NO 1907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1907
tctgagcaga taaata                                                    16

<210> SEQ ID NO 1908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1908
aagtcttaat gtggat                                                    16

<210> SEQ ID NO 1909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1909
ttagtgtccc catccc                                                    16

<210> SEQ ID NO 1910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1910
gaatattgcc aggtat                                                    16

<210> SEQ ID NO 1911
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1911
ttagtgttgg tttata                                                    16

```
<210> SEQ ID NO 1912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1912
tttgacttag tccgtg                                                   16

<210> SEQ ID NO 1913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1913
ctctgtagct ggtttg                                                   16

<210> SEQ ID NO 1914
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1914
ttgatagtga atgtgt                                                   16

<210> SEQ ID NO 1915
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1915
atatgtttgg aagtcg                                                   16

<210> SEQ ID NO 1916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1916
caatcagagg aagccc                                                   16

<210> SEQ ID NO 1917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1917
taaccagatt gagtct                                                   16

<210> SEQ ID NO 1918
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1918
gtctctaatt ttacga                                                         16

<210> SEQ ID NO 1919
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1919
acagcttaga aattgc                                                         16

<210> SEQ ID NO 1920
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1920
ctgtattagc tcaata                                                         16

<210> SEQ ID NO 1921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1921
tctttgtagc agacag                                                         16

<210> SEQ ID NO 1922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1922
ttattttaac agctca                                                         16

<210> SEQ ID NO 1923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1923
ctgcaattct agacat                                                         16

<210> SEQ ID NO 1924
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1924
catttcagag tataag                                                         16

<210> SEQ ID NO 1925
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1925
gatgtgagtg aaataa                                                    16

<210> SEQ ID NO 1926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1926
aaggacatga cagact                                                    16

<210> SEQ ID NO 1927
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1927
ccaccatcaa tgctgc                                                    16

<210> SEQ ID NO 1928
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1928
tttggcatca atgaag                                                    16

<210> SEQ ID NO 1929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1929
tagaggttcc ctgtgc                                                    16

<210> SEQ ID NO 1930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1930
gggcaggatg ctgaga                                                    16

<210> SEQ ID NO 1931
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1931
```
actcacagac tcttct                                                    16

<210> SEQ ID NO 1932
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1932
agcacctctg aaagaa                                                    16

<210> SEQ ID NO 1933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1933
cggaggtagc tgcaca                                                    16

<210> SEQ ID NO 1934
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1934
attctaagaa cctcat                                                    16

<210> SEQ ID NO 1935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1935
aaacaaaccc tccgtc                                                    16

<210> SEQ ID NO 1936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1936
aaatgatcat gtggcg                                                    16

<210> SEQ ID NO 1937
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1937
ctgactttta ttgttg                                                    16

<210> SEQ ID NO 1938
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1938
gtgagtgtac tttagg                                                    16

<210> SEQ ID NO 1939
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1939
aatgctatca ggtgca                                                    16

<210> SEQ ID NO 1940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1940
tgcacaatga catcat                                                    16

<210> SEQ ID NO 1941
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1941
ctacctgtgt cttttta                                                   16

<210> SEQ ID NO 1942
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1942
atatattggg ctcaat                                                    16

<210> SEQ ID NO 1943
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1943
acttttggca aggcca                                                    16

<210> SEQ ID NO 1944
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1944
ccgcaaacaa ggttaa                                                    16
```

<210> SEQ ID NO 1945
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1945
tttaggtctg ggtata 16

<210> SEQ ID NO 1946
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1946
ccccctgact atataa 16

<210> SEQ ID NO 1947
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1947
tcttgaccgt gtttcc 16

<210> SEQ ID NO 1948
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1948
gcattgcata gccttc 16

<210> SEQ ID NO 1949
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1949
aaccaatcct gttaga 16

<210> SEQ ID NO 1950
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1950
tctgcttata aagcac 16

<210> SEQ ID NO 1951
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1951
ctttgcaggc acccca 16

<210> SEQ ID NO 1952
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1952
cttgaatgtc accctt 16

<210> SEQ ID NO 1953
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1953
ttaccaagac cgctag 16

<210> SEQ ID NO 1954
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1954
acttttagta ttaaag 16

<210> SEQ ID NO 1955
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1955
aaagtcttaa tgtgga 16

<210> SEQ ID NO 1956
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1956
cttagtgtcc ccatcc 16

<210> SEQ ID NO 1957
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1957
gttagtgttg gtttat 16

<210> SEQ ID NO 1958

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1958
gtttgactta gtccgt                                                   16

<210> SEQ ID NO 1959
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1959
aatatgtttg gaagtc                                                   16

<210> SEQ ID NO 1960
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1960
agtaaccaga ttgagt                                                   16

<210> SEQ ID NO 1961
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1961
cacagcttag aaattg                                                   16

<210> SEQ ID NO 1962
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1962
cctgtattag ctcaat                                                   16

<210> SEQ ID NO 1963
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1963
cctctttgta gcagac                                                   16

<210> SEQ ID NO 1964
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1964
```
ggttatttta acagct                                                16

<210> SEQ ID NO 1965
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1965
acctgcaatt ctagac                                                16

<210> SEQ ID NO 1966
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1966
aagatgtgag tgaaat                                                16

<210> SEQ ID NO 1967
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1967
aaaggacatg acagac                                                16

<210> SEQ ID NO 1968
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1968
gaggaacttg cttaag                                                16

<210> SEQ ID NO 1969
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1969
ttttggcatc aatgaa                                                16

<210> SEQ ID NO 1970
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1970
tctagcagct catctc                                                16

<210> SEQ ID NO 1971
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1971
ttagcacctc tgaaag                                                    16

<210> SEQ ID NO 1972
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1972
atgtattaga gttaag                                                    16

<210> SEQ ID NO 1973
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1973
cattctaaga acctca                                                    16

<210> SEQ ID NO 1974
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1974
ttagttaggt gaaaaa                                                    16

<210> SEQ ID NO 1975
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1975
cactgattca cataat                                                    16

<210> SEQ ID NO 1976
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1976
tgcaaatgat catgtg                                                    16

<210> SEQ ID NO 1977
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1977
gctgactttt attgtt                                                    16
```

-continued

<210> SEQ ID NO 1978
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1978
agtgagtgta ctttag                                                      16

<210> SEQ ID NO 1979
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1979
ttaatgctat caggtg                                                      16

<210> SEQ ID NO 1980
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1980
atgcacaatg acatca                                                      16

<210> SEQ ID NO 1981
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1981
attctacctg tgtctt                                                      16

<210> SEQ ID NO 1982
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1982
ttggatatat tgggct                                                      16

<210> SEQ ID NO 1983
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1983
tacttttggc aaggcc                                                      16

<210> SEQ ID NO 1984
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1984
gcacagagta ggttaa					16

<210> SEQ ID NO 1985
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1985
tggtagctcc tggcaa					16

<210> SEQ ID NO 1986
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1986
tttccgttaa ccatca					16

<210> SEQ ID NO 1987
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1987
catcttagtg gctggg					16

<210> SEQ ID NO 1988
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1988
gttcttgacc gtgttt					16

<210> SEQ ID NO 1989
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1989
ggttaaacta ccgaac					16

<210> SEQ ID NO 1990
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1990
catggtctgc aaattt					16

-continued

```
<210> SEQ ID NO 1991
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1991
aaaccaatcc tgttag                                                    16

<210> SEQ ID NO 1992
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1992
atctgcttat aaagca                                                    16

<210> SEQ ID NO 1993
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1993
actttgcagg cacccc                                                    16

<210> SEQ ID NO 1994
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1994
gcttgaatgt caccct                                                    16

<210> SEQ ID NO 1995
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1995
tttaccaaga ccgcta                                                    16

<210> SEQ ID NO 1996
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1996
caacttttag tattaa                                                    16

<210> SEQ ID NO 1997
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1997
tcgacacagc atcacc                                                    16

<210> SEQ ID NO 1998
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1998
tcttagtgtc cccatc                                                    16

<210> SEQ ID NO 1999
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1999
ttaggaatat tgccag                                                    16

<210> SEQ ID NO 2000
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2000
gggttagtgt tggttt                                                    16

<210> SEQ ID NO 2001
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2001
tagggcacct caagaa                                                    16

<210> SEQ ID NO 2002
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2002
caaatatgtt tggaag                                                    16

<210> SEQ ID NO 2003
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2003
cccaatcaga ggaagc                                                    16

<210> SEQ ID NO 2004
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 2004
tcatcattat tacctg                                                       16

<210> SEQ ID NO 2005
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2005
ttcagaccag ggtaat                                                       16

<210> SEQ ID NO 2006
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2006
gcctgtatta gctcaa                                                       16

<210> SEQ ID NO 2007
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2007
gcctctttgt agcaga                                                       16

<210> SEQ ID NO 2008
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2008
tactgagagg aaatga                                                       16

<210> SEQ ID NO 2009
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2009
tgtaaagatg tgagtg                                                       16

<210> SEQ ID NO 2010
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2010
```

```
tcaaaggaca tgacag                                                    16

<210> SEQ ID NO 2011
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2011
gagcaacgag gaagga                                                    16

<210> SEQ ID NO 2012
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2012
cctgtcggag gaactt                                                    16

<210> SEQ ID NO 2013
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2013
ttgttttggc atcaat                                                    16

<210> SEQ ID NO 2014
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2014
aatgcatcca aatatc                                                    16

<210> SEQ ID NO 2015
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2015
tggtctagca gctcat                                                    16

<210> SEQ ID NO 2016
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2016
ttacataaga cattat                                                    16

<210> SEQ ID NO 2017
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 2017
ctcaagtgac tcacag                                                    16

<210> SEQ ID NO 2018
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2018
tttagcacct ctgaaa                                                    16

<210> SEQ ID NO 2019
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2019
tttcccaacc agctga                                                    16

<210> SEQ ID NO 2020
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2020
tcatctttgc agacca                                                    16

<210> SEQ ID NO 2021
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2021
tttagttagg tgaaaa                                                    16

<210> SEQ ID NO 2022
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2022
tcactgattc acataa                                                    16

<210> SEQ ID NO 2023
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2023
gagaaacaaa ccctcc                                                    16
```

<210> SEQ ID NO 2024
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2024
gtgcaaatga tcatgt                                                     16

<210> SEQ ID NO 2025
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2025
aagctgactt ttattg                                                     16

<210> SEQ ID NO 2026
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2026
tcttgggatg cacagg                                                     16

<210> SEQ ID NO 2027
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2027
ccttaatgct atcagg                                                     16

<210> SEQ ID NO 2028
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2028
aatgcacaat gacatc                                                     16

<210> SEQ ID NO 2029
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2029
aattctacct gtgtct                                                     16

<210> SEQ ID NO 2030
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 2030
tttggatata ttgggc                                                    16

<210> SEQ ID NO 2031
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2031
ctactatggg agccac                                                    16

<210> SEQ ID NO 2032
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2032
taatactttt ggcaag                                                    16

<210> SEQ ID NO 2033
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2033
ttataggcga gagcac                                                    16

<210> SEQ ID NO 2034
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2034
ctggtagctc ctggca                                                    16

<210> SEQ ID NO 2035
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2035
gattgtgcag acagta                                                    16

<210> SEQ ID NO 2036
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2036
atttccgtta accatc                                                    16

<210> SEQ ID NO 2037
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2037
tgagttttag gtctgg                                                   16

<210> SEQ ID NO 2038
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2038
atcatcttag tggctg                                                   16

<210> SEQ ID NO 2039
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2039
tgttcttgac cgtgtt                                                   16

<210> SEQ ID NO 2040
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2040
aaggttaaac taccga                                                   16

<210> SEQ ID NO 2041
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2041
tacatggtct gcaaat                                                   16

<210> SEQ ID NO 2042
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2042
cattgcattg catagc                                                   16

<210> SEQ ID NO 2043
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2043
```
aaaaccaatc ctgtta                                                   16

<210> SEQ ID NO 2044
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2044
catctgctta taaagc                                                   16

<210> SEQ ID NO 2045
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2045
aaactttgca gcctat                                                   16

<210> SEQ ID NO 2046
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2046
agactttgca ggcacc                                                   16

<210> SEQ ID NO 2047
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2047
ggcttgaatg tcaccc                                                   16

<210> SEQ ID NO 2048
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2048
aatgcttgtc aaaagg                                                   16

<210> SEQ ID NO 2049
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2049
ctttaccaag accgct                                                   16

<210> SEQ ID NO 2050
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 2050
taagtgttag aactaa                                                       16

<210> SEQ ID NO 2051
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2051
accaactttt agtatt                                                       16

<210> SEQ ID NO 2052
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2052
catcgacaca gcatca                                                       16

<210> SEQ ID NO 2053
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2053
ccaaagtctt aatgtg                                                       16

<210> SEQ ID NO 2054
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2054
ccatctctta gtgtcc                                                       16

<210> SEQ ID NO 2055
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2055
cttaggaata ttgcca                                                       16

<210> SEQ ID NO 2056
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2056
agggttagtg ttggtt                                                       16
```

<210> SEQ ID NO 2057
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2057
tctgtttgac ttagtc                                                       16

<210> SEQ ID NO 2058
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2058
cttagggcac ctcaag                                                       16

<210> SEQ ID NO 2059
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2059
taatctggtc atatgg                                                       16

<210> SEQ ID NO 2060
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2060
tgcttacgga gcatag                                                       16

<210> SEQ ID NO 2061
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2061
ctctagacgg gaagct                                                       16

<210> SEQ ID NO 2062
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2062
gatcatcatt attacc                                                       16

<210> SEQ ID NO 2063
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 2063
ttgcagtgcc ctggcc                                                         16

<210> SEQ ID NO 2064
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2064
attcagacca gggtaa                                                         16

<210> SEQ ID NO 2065
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2065
atgcctgtat tagctc                                                         16

<210> SEQ ID NO 2066
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2066
agcctctttg tagcag                                                         16

<210> SEQ ID NO 2067
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2067
gaggttattt taacag                                                         16

<210> SEQ ID NO 2068
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2068
atactgagag gaaatg                                                         16

<210> SEQ ID NO 2069
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2069
atgacatttc agagta                                                         16

```
<210> SEQ ID NO 2070
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2070
gtgtaaagat gtgagt                                                       16

<210> SEQ ID NO 2071
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2071
tgctgcactc aaagag                                                       16

<210> SEQ ID NO 2072
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2072
tcacaagaga ctggac                                                       16

<210> SEQ ID NO 2073
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2073
tggtggacat tggccg                                                       16

<210> SEQ ID NO 2074
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2074
ggtgatggtt gttttg                                                       16

<210> SEQ ID NO 2075
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2075
gaatgcatcc aaatat                                                       16

<210> SEQ ID NO 2076
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 2076
gtggtctagc agctca                                                    16

<210> SEQ ID NO 2077
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2077
cattacataa gacatt                                                    16

<210> SEQ ID NO 2078
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2078
cctcaagtga ctcaca                                                    16

<210> SEQ ID NO 2079
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2079
ctttagcacc tctgaa                                                    16

<210> SEQ ID NO 2080
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2080
atttcccaac cagctg                                                    16

<210> SEQ ID NO 2081
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2081
ttatcatctt tgcaga                                                    16

<210> SEQ ID NO 2082
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2082
ttttagttag gtgaaa                                                    16

<210> SEQ ID NO 2083
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 2083
ctcactgatt cacata                                                       16

<210> SEQ ID NO 2084
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2084
tgagaaacaa accctc                                                       16

<210> SEQ ID NO 2085
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2085
tgtgcaaatg atcatg                                                       16

<210> SEQ ID NO 2086
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2086
taggctcctg ggacct                                                       16

<210> SEQ ID NO 2087
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2087
atcttgggat gcacag                                                       16

<210> SEQ ID NO 2088
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2088
tcatggcttc cagtgt                                                       16

<210> SEQ ID NO 2089
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2089
```

```
ttcaatgtgg cttcta                                                    16

<210> SEQ ID NO 2090
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2090
ttaattctac ctgtgt                                                    16

<210> SEQ ID NO 2091
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2091
tgaaatatct cattag                                                    16

<210> SEQ ID NO 2092
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2092
tgtctactat gggagc                                                    16

<210> SEQ ID NO 2093
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2093
atggtaatac ttttgg                                                    16

<210> SEQ ID NO 2094
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2094
actggtagct cctggc                                                    16

<210> SEQ ID NO 2095
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2095
tgattgtgca gacagt                                                    16

<210> SEQ ID NO 2096
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 2096
tatttccgtt aaccat                                              16

<210> SEQ ID NO 2097
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2097
ctgagtttta ggtctg                                              16

<210> SEQ ID NO 2098
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2098
gaatcatctt agtggc                                              16

<210> SEQ ID NO 2099
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2099
ttgttcttga ccgtgt                                              16

<210> SEQ ID NO 2100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2100
gtggtaaggc atacta                                              16

<210> SEQ ID NO 2101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2101
ggtgtacatg gtctgc                                              16

<210> SEQ ID NO 2102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2102
gcattgcatt gcatag                                              16
```

<210> SEQ ID NO 2103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2103
ggaaaaccaa tcctgt                                                         16

<210> SEQ ID NO 2104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2104
agctgtctcc tctact                                                         16

<210> SEQ ID NO 2105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2105
caaactttgc agccta                                                         16

<210> SEQ ID NO 2106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2106
gagactttgc aggcac                                                         16

<210> SEQ ID NO 2107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2107
tcggcttgaa tgtcac                                                         16

<210> SEQ ID NO 2108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2108
gtaaatgctt gtcaaa                                                         16

<210> SEQ ID NO 2109
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 2109
agtctttacc aagacc                                          16

<210> SEQ ID NO 2110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2110
catgacatcc cagttc                                          16

<210> SEQ ID NO 2111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2111
aaccaacttt tagtat                                          16

<210> SEQ ID NO 2112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2112
ccatcgacac agcatc                                          16

<210> SEQ ID NO 2113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2113
ctacttatcc ccaaag                                          16

<210> SEQ ID NO 2114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2114
gccatctctt agtgtc                                          16

<210> SEQ ID NO 2115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2115
ccttaggaat attgcc                                          16

<210> SEQ ID NO 2116
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2116
gagggttagt gttggt                                                       16

<210> SEQ ID NO 2117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2117
ctggtttgtg ggttct                                                       16

<210> SEQ ID NO 2118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2118
tcttagggca cctcaa                                                       16

<210> SEQ ID NO 2119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2119
ttaatctggt catatg                                                       16

<210> SEQ ID NO 2120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2120
acaaaagcga caaggt                                                       16

<210> SEQ ID NO 2121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2121
ttgagtctcc tgacca                                                       16

<210> SEQ ID NO 2122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2122
```

-continued cgatcatcat tattac                                              16

<210> SEQ ID NO 2123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2123
attgcagtgc cctggc                                              16

<210> SEQ ID NO 2124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2124
tattcagacc agggta                                              16

<210> SEQ ID NO 2125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2125
gatgcctgta ttagct                                              16

<210> SEQ ID NO 2126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2126
gcagcctctt tgtagc                                              16

<210> SEQ ID NO 2127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2127
ctgaggttat tttaac                                              16

<210> SEQ ID NO 2128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2128
tatactgaga ggaaat                                              16

<210> SEQ ID NO 2129
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 2129
atatgacatt tcagag                                                     16

<210> SEQ ID NO 2130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2130
cgtgtaaaga tgtgag                                                     16

<210> SEQ ID NO 2131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2131
aatgctgcac tcaaag                                                     16

<210> SEQ ID NO 2132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2132
taacaaacta tgccta                                                     16

<210> SEQ ID NO 2133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2133
aggaacttgc ttaagt                                                     16

<210> SEQ ID NO 2134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2134
agcagctcat ctccct                                                     16

<210> SEQ ID NO 2135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2135
agttaggtga aaagg                                                      16
```

<210> SEQ ID NO 2136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2136
actgattcac ataata                                                    16

<210> SEQ ID NO 2137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2137
ctatgggagc cacatg                                                    16

<210> SEQ ID NO 2138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2138
cagacagtaa ctggta                                                    16

<210> SEQ ID NO 2139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2139
ttccgttaac catcaa                                                    16

<210> SEQ ID NO 2140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2140
gttaaactac cgaacg                                                    16

<210> SEQ ID NO 2141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2141
ctatggtaga gtggta                                                    16

<210> SEQ ID NO 2142
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 2142
ggacaataag agctgt        16

<210> SEQ ID NO 2143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2143
agcatcattg gaagac        16

<210> SEQ ID NO 2144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2144
gtgttagaac taaggc        16

<210> SEQ ID NO 2145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2145
tttctgagca gataaa        16

<210> SEQ ID NO 2146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2146
taggaatatt gccagg        16

<210> SEQ ID NO 2147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2147
aactctgtag ctggtt        16

<210> SEQ ID NO 2148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2148
tcttgatagt gaatgt        16

```
<210> SEQ ID NO 2149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2149
ccaatcagag gaagcc                                                    16

<210> SEQ ID NO 2150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2150
ctgtctctaa ttttac                                                    16

<210> SEQ ID NO 2151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2151
gacatttcag agtata                                                    16

<210> SEQ ID NO 2152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2152
gcaaatcgga tctttg                                                    16

<210> SEQ ID NO 2153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2153
agaaggtaga ggttcc                                                    16

<210> SEQ ID NO 2154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2154
cagggcagga tgctga                                                    16

<210> SEQ ID NO 2155
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 2155
tgactcacag actctt                                                  16

<210> SEQ ID NO 2156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2156
agaaacaaac cctccg                                                  16

<210> SEQ ID NO 2157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2157
actatgggag ccacat                                                  16

<210> SEQ ID NO 2158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2158
ttgtgcagac agtaac                                                  16

<210> SEQ ID NO 2159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2159
ttttaggtct gggtat                                                  16

<210> SEQ ID NO 2160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2160
attgcattgc atagcc                                                  16

<210> SEQ ID NO 2161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2161
ctttgcagcc tatccc                                                  16

<210> SEQ ID NO 2162
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 2162
tcagcatcat tggaag                                                       16

<210> SEQ ID NO 2163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2163
agtgttagaa ctaagg                                                       16

<210> SEQ ID NO 2164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2164
caaagtctta atgtgg                                                       16

<210> SEQ ID NO 2165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2165
tgtttgactt agtccg                                                       16

<210> SEQ ID NO 2166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2166
aatctggtca tatggt                                                       16

<210> SEQ ID NO 2167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2167
tgcagtgccc tggcct                                                       16

<210> SEQ ID NO 2168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2168
```

```
aggttattt aacagc                                                       16

<210> SEQ ID NO 2169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2169
tgacatttca gagtat                                                      16

<210> SEQ ID NO 2170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2170
tcaatgtggc ttctag                                                      16

<210> SEQ ID NO 2171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2171
attcaatgtg gcttct                                                      16

<210> SEQ ID NO 2172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2172
tattcaatgt ggcttc                                                      16
```

MODULATORS OF PNPLA3 EXPRESSION

SEQUENCE LISTING

The present application is being filed along with a Sequence Listing in electronic format. The Sequence Listing is provided as a file entitled BIOL0317USLSEQ_ST25.txt created Sep. 13, 2018, which is 480 kb in size. The information in the electronic format of the sequence listing is incorporated herein by reference in its entirety.

FIELD

The present embodiments provide methods, compounds, and compositions useful for inhibiting PNPLA3 (patatin like phospholipase domain containing 3; hypothetical protein dJ796I17.1; adiponutrin; DJ796I17.1) expression, and in certain instances, reducing the amount of PNPLA3 protein in a cell or animal, which can be useful for treating, preventing, or ameliorating a disease associated with PNPLA3.

BACKGROUND

Non-alcoholic fatty liver disease (NAFLD) covers a spectrum of liver disease from steatosis to nonalcoholic steatohepatitis (NASH) and cirrhosis. NAFLD is defined as fat accumulation in the liver exceeding 5% by weight, in the absence of significant alcohol consumption, steatogenic medication, or hereditary disorders (Kotronen et al, Arterioscler Thromb. Vasc. Biol. 2008, 28: 27-38).

Non-alcoholic steatohepatitis (NASH) is NAFLD with signs of inflammation and hepatic injury. NASH is defined histologically by macrovesicular steatosis, hepatocellular ballooning, and lobular inflammatory infiltrates (Sanyal, Hepatol. Res. 2011. 41: 670-4). NASH is estimated to affect 2-3% of the general population. In the presence of other pathologies, such as obesity or diabetes, the estimated prevalence increases to 7% and 62% respectively (Hashimoto et al, J. Gastroenterol. 2011. 46(1): 63-69).

PNPLA3 is a 481 amino acid member of the patatin-like phospholipase domain-containing family that is expressed in the ER and on lipid droplets. In humans, PNPLA3 is highly expressed in the liver, whereas adipose tissue expression is five-fold less (Huang et al, Proc. Natl. Acad. Sci. USA 2010. 107: 7892-7).

SUMMARY

Certain embodiments provided herein are compounds and methods for reducing the amount or activity of PNPLA3 mRNA, and in certain embodiments, reducing the amount of PNPLA3 protein in a cell or animal. In certain embodiments, the animal has a liver disease. In certain embodiments, the disease is NASH. In certain embodiments, the disease is NAFLD. In certain embodiments, the disease is hepatic steatosis. In certain embodiments, the disease is liver cirrhosis. In certain embodiments, the disease is hepatocellular carcinoma. In certain embodiments, the disease is alcoholic liver disease. In certain embodiments, the disease is alcoholic steatohepatitis (ASH). In certain embodiments, the disease is HCV hepatitis. In certain embodiments, the disease is chronic hepatitis. In certain embodiments, the disease is hereditary hemochromatosis. In certain embodiments, the disease is primary sclerosing cholangitis. Certain compounds provided herein are directed to compounds and compositions that reduce liver damage, steatosis, liver fibrosis, liver inflammation, liver scarring or cirrhosis, liver failure, liver enlargement, elevated transaminases, or hepatic fat accumulation in an animal.

Certain embodiments provided herein are directed to potent and tolerable compounds and compositions useful for inhibiting PNPLA3 expression, which can be useful for treating, preventing, ameliorating, or slowing progression of liver diseases. Certain embodiments provided herein are directed to compounds and compositions that are more potent or have greater therapeutic value than compounds publicly disclosed.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ION number indicate a combination of nucleobase sequence, chemical modification, and motif.

Definitions

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE) refers to a 2'-O($CH_2$)$_2$—$OCH_3$) in the place of the 2'-OH group of a ribosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within +10% of a value. For example, if it is stated, "the compounds affected about 70% inhibition of PNPLA3", it is implied that PNPLA3 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a ribosyl bicyclic sugar moiety wherein the second ring of the bicyclic sugar is formed via a bridge connecting the 4'-carbon and the 2'-carbon, wherein the bridge has the formula: 4'-CH(CH$_3$)—O-2', and wherein the methyl group of the bridge is in the S configuration.

"cEt nucleoside" means a nucleoside comprising a cEt modified sugar moiety.

"Chemical modification" in a compound describes the substitutions or changes through chemical reaction, of any of the units in the compound relative to the original state of such unit. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded antisense compound" means an antisense compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating PNPLA3 RNA can mean to increase or decrease the level of PNPLA3 RNA and/or PNPLA3 protein in a cell, tissue, organ or organism. A "modulator" effects the change in the cell, tissue, organ or organism. For example, a PNPLA3 compound can be a modulator that decreases the amount of PNPLA3 RNA and/or PNPLA3 protein in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

"Sugar moiety" means an unmodified sugar moiety or a modified sugar moiety. "Unmodified sugar moiety" or "unmodified sugar" means a 2'-OH(H) ribosyl moiety, as found in RNA (an "unmodified RNA sugar moiety"), or a 2'-H(H) moiety, as found in DNA (an "unmodified DNA sugar moiety"). "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen or hydroxyl of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary compounds or nucleic acids.

"Synergy" or "synergize" refers to an effect of a combination that is greater than additive of the effects of each component alone at the same doses.

"PNPLA3" means any nucleic acid or protein of PNPLA3. "PNPLA3 nucleic acid" means any nucleic acid encoding PNPLA3. For example, in certain embodiments, a PNPLA3 nucleic acid includes a DNA sequence encoding PNPLA3, an RNA sequence transcribed from DNA encoding PNPLA3 (including genomic DNA comprising introns and exons), and an mRNA sequence encoding PNPLA3. "PNPLA3 mRNA" means an mRNA encoding a PNPLA3 protein. The target may be referred to in either upper or lower case.

"PNPLA3 specific inhibitor" refers to any agent capable of specifically inhibiting PNPLA3 RNA and/or PNPLA3 protein expression or activity at the molecular level. For example, PNPLA3 specific inhibitors include nucleic acids (including antisense compounds), peptides, antibodies, small molecules, and other agents capable of inhibiting the expression of PNPLA3 RNA and/or PNPLA3 protein.

"Target gene" refers to a gene encoding a target.

"Targeting" means the specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide methods, compounds and compositions for inhibiting PNPLA3 (PNPLA3) expression.

Certain embodiments provide compounds targeted to a PNPLA3 nucleic acid. In certain embodiments, the PNPLA3 nucleic acid has the sequence set forth in RefSeq or GEN- BANK Accession No. NM_025225.2 (incorporated by reference, disclosed herein as SEQ ID NO: 1); NC_000022.11 truncated from nucleotides 43921001 to U.S. Pat. No. 43,954,500 (incorporated by reference, disclosed herein as SEQ ID NO: 2); AK123806.1 (incorporated by reference, disclosed herein as SEQ ID NO: 3); BQ686328.1 (incorporated by reference, disclosed herein as SEQ ID NO: 4); BF762711.1 (incorporated by reference, disclosed herein as SEQ ID NO: 5); DA290491.1 (incorporated by reference, disclosed herein as SEQ ID NO: 6); and the sequences listed as SEQ ID Nos 7, 8, 9, and 10. In certain embodiments, the compound is an antisense compound or oligomeric compound. In certain embodiments, the compound is single-stranded. In certain embodiments, the compound is double-stranded.

In certain embodiments, the compound comprises a modified oligonucleotide 16 linked nucleosides in length. In certain embodiments, the compound is an antisense compound or oligomeric compound.

Certain embodiments provide a compound comprising a modified oligonucleotide 12 to 30 linked nucleosides in length and having a nucleobase sequence comprising the nucleobase sequence of any one of SEQ ID NOs: 17-2169. In certain embodiments, the compound is an antisense compound or oligomeric compound. In certain embodiments, the compound is single-stranded. In certain embodiments, the compound is double-stranded. In certain embodiments, the modified oligonucleotide is 16 to 30 linked nucleosides in length.

Certain embodiments provide a compound comprising a modified oligonucleotide consisting of the nucleobase sequence of any one of SEQ ID NOs: 17-2169. In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 12 to 30 linked nucleosides in length and complementary within nucleobases 5567-5642, 5644-5731, 5567-5731, 5567-5620, 13697-13733, 20553-20676, 20664-20824, 20553-20824, and 25844-25912 of SEQ ID NO: 2, wherein said modified oligonucleotide is at least 85%, at least 90%, at least 95%, or 100% complementary to SEQ ID NO: 2. In certain embodiments, the compound is an antisense compound or oligomeric compound. In certain embodiments, the compound is single-stranded. In certain embodiments, the compound is double-stranded. In certain embodiments, the modified oligonucleotide is 16 to 30 linked nucleosides in length.

In certain embodiments, compounds target nucleotides 5567-5620 of a PNPLA3 nucleic acid. In certain embodiments, compounds target within nucleotides 5567-5642, 5644-5731, 5567-5731, 5567-5620 of a PNPLA3 nucleic acid having the nucleobase sequence of SEQ ID NO: 2. In certain embodiments, compounds have at least an 8, 9, 10, 11, 12, 13, 14, 15, or 16 contiguous nucleobase portion complementary to an equal length portion within nucleotides 5567-5642, 5644-5731, 5567-5731, 5567-5620 of a PNPLA3 nucleic acid having the nucleobase sequence of SEQ ID NO: 2. In certain embodiments, these compounds are antisense compounds, oligomeric compounds, or oligonucleotides.

In certain embodiments, a compound comprises a modified oligonucleotide 12 to 30 linked nucleosides in length and having a nucleobase sequence comprising at least an 8, 9, 10, 11, 12, 13, 14, 15, or 16 contiguous nucleobase portion any one of SEQ ID NOs: 1089, 1757, 141, 1982, 330, 1665, 408, 830, and 899. In certain embodiments, the modified oligonucleotide is 16 to 30 linked nucleosides in length.

In certain embodiments, a compound comprises a modified oligonucleotide 12 to 30 linked nucleosides in length and having a nucleobase sequence comprising any one of SEQ ID NOs: 1089, 1757, 141, 1982, 330, 1665, 408, 830, and 899. In certain embodiments, the modified oligonucleotide is 16 to 30 linked nucleosides in length.

In certain embodiments, a compound comprises a modified oligonucleotide having a nucleobase sequence consisting of any one of SEQ ID NOs: 1089, 1757, 141, 1982, 330, 1665, 408, 830, and 899.

In certain embodiments, compounds targeted to PNPLA3 is ION 975616, 994284, 975605, 994282, 975613, 975617, 975735, 975736, or 975612. Out of over 2,384 compounds that were screened as described in the Examples section below, ION 975616, 994284, 975605, 994282, 975613, 975617, 975735, 975736, and 975612 emerged as the top lead compounds.

In certain embodiments, any of the foregoing modified oligonucleotides comprises at least one modified internucleoside linkage, at least one modified sugar, and/or at least one modified nucleobase.

In certain embodiments, any of the foregoing modified oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH3)-O-2' group, a 4'-CH2-O-2' group, or a 4'-(CH2)2-O-2'group.

In certain embodiments, the modified oligonucleotide comprises at least one modified internucleoside linkage, such as a phosphorothioate internucleoside linkage.

In certain embodiments, any of the foregoing modified oligonucleotides comprises at least one modified nucleobase, such as 5-methylcytosine.

In certain embodiments, any of the foregoing modified oligonucleotides comprises:
  a gap segment consisting of linked deoxynucleosides;
  a 5' wing segment consisting of linked nucleosides; and
  a 3' wing segment consisting of linked nucleosides;
wherein the gap segment is positioned between the 5' wing segment and the 3' wing segment and wherein each nucleoside of each wing segment comprises a modified sugar. In certain embodiments, the modified oligonucleotide is 12 to 30 linked nucleosides in length having a nucleobase sequence comprising the sequence recited in any one of SEQ ID NOs: 1089, 1757, 141, 1982, 330, 1665, 408, 830, and 899. In certain embodiments, the modified oligonucleotide is 16 to 30 linked nucleosides in length having a nucleobase sequence comprising the sequence recited in any one of SEQ ID NOs: 1089, 1757, 141, 1982, 330, 1665, 408, 830, and 899. In certain embodiments, the modified oligonucleotide is 16 linked nucleosides in length having a nucleobase sequence consisting of the sequence recited in any one of SEQ ID NOs: 1089, 1757, 141, 1982, 330, 1665, 408, 830, and 899.

In certain embodiments, a compound comprises or consists of a modified oligonucleotide 12-30 linked nucleobases in length having a nucleobase sequence comprising the sequence recited in any one of SEQ ID NOs: 1089, 1757, 141, 1982, 330, 1665, 408, 830, and 899, wherein the modified oligonucleotide comprises
  a gap segment consisting of ten linked deoxynucleosides;
  a 5' wing segment consisting of three linked nucleosides;
  and a 3' wing segment consisting of three linked nucleosides; wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide, wherein the modified oligonucleotide is 16 linked nucleosides in length and consists of the sequence of SEQ ID NO: 1089, wherein the modified oligonucleotide comprises:

a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment, wherein each nucleoside of each wing segment comprises a cEt sugar; wherein each internucleoside linkage is a phosphorothioate linkage; and wherein each cytosine is a 5-methylcytosine.

In certain embodiments, a compound consists of a modified oligonucleotide and a conjugate group, wherein the modified oligonucleotide is 16 linked nucleosides in length and consists of the sequence of SEQ ID NO: 1089, wherein the modified oligonucleotide comprises:

a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment, wherein each nucleoside of each wing segment comprises a cEt sugar; wherein each internucleoside linkage is a phosphorothioate linkage; wherein each cytosine is a 5-methylcytosine; and wherein the conjugate group is positioned at the 5'end of the modified oligonucleotide and is

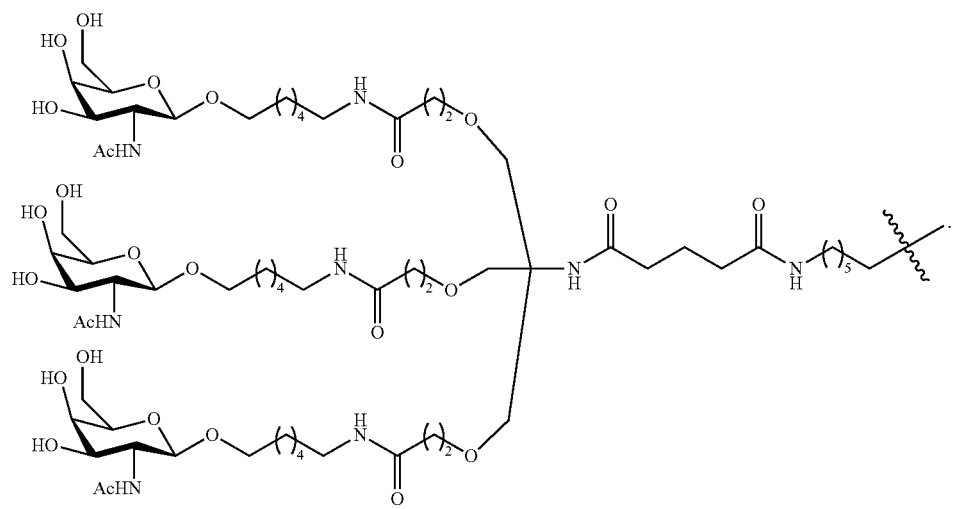

In certain embodiments, a compound comprises or consists of ION 916333 or salt thereof, having the following chemical structure (SEQ ID NO: 1089):
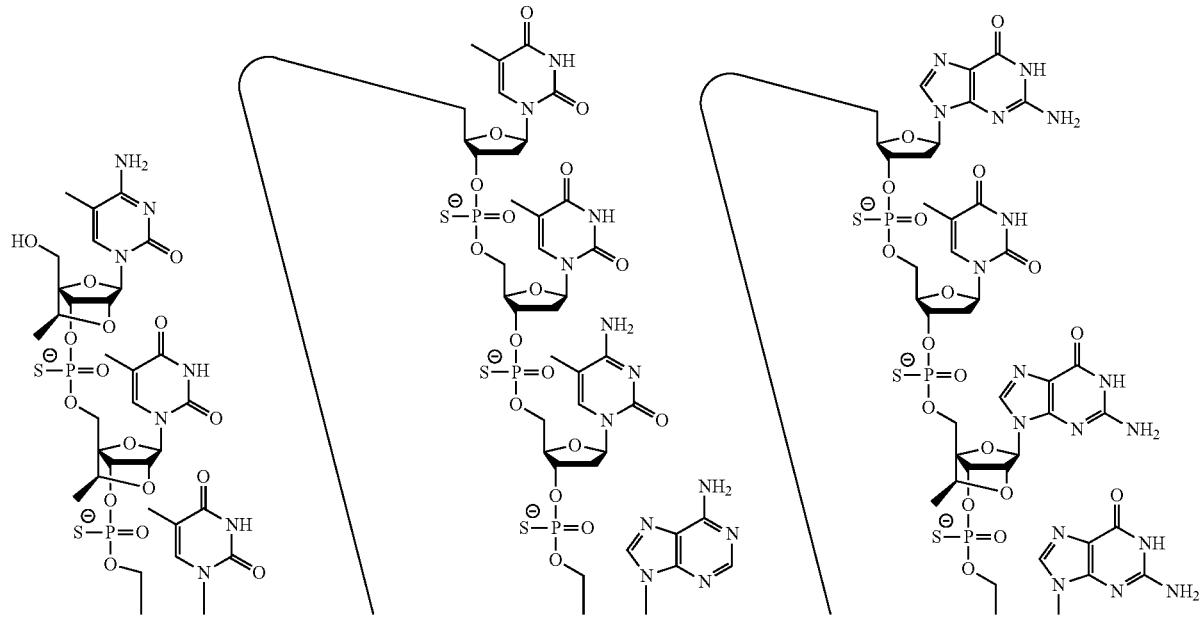
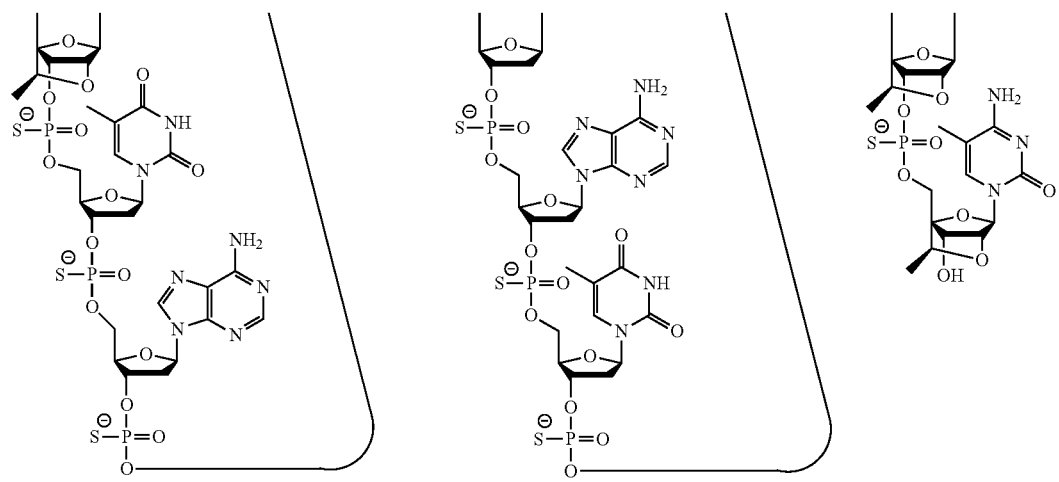

In certain embodiments, a compound comprises or consists of ION 975616 or salt thereof, having the following chemical structure (SEQ ID NO: 1089):
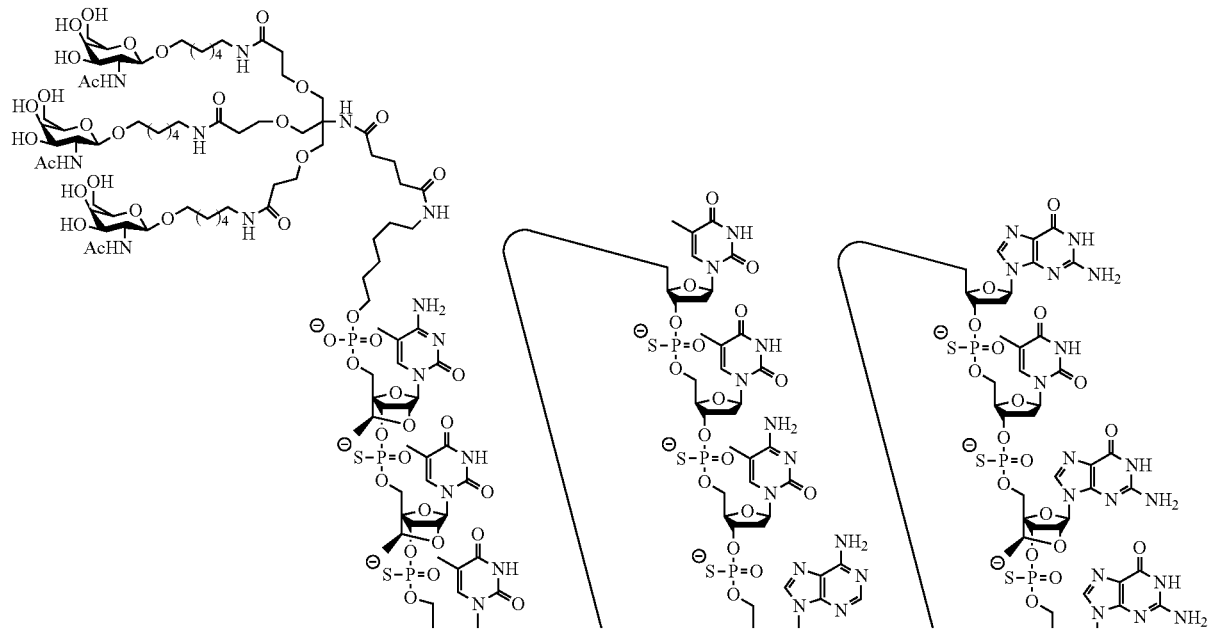
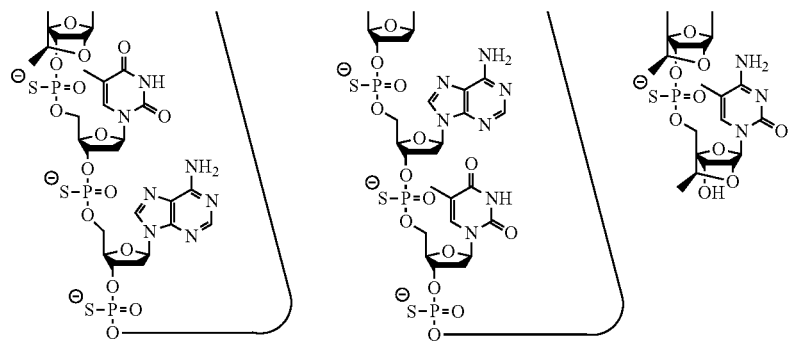

In certain embodiments, a compound comprises or consists of the sodium salt of 975616, having the following chemical structure (SEQ ID NO: 1089):
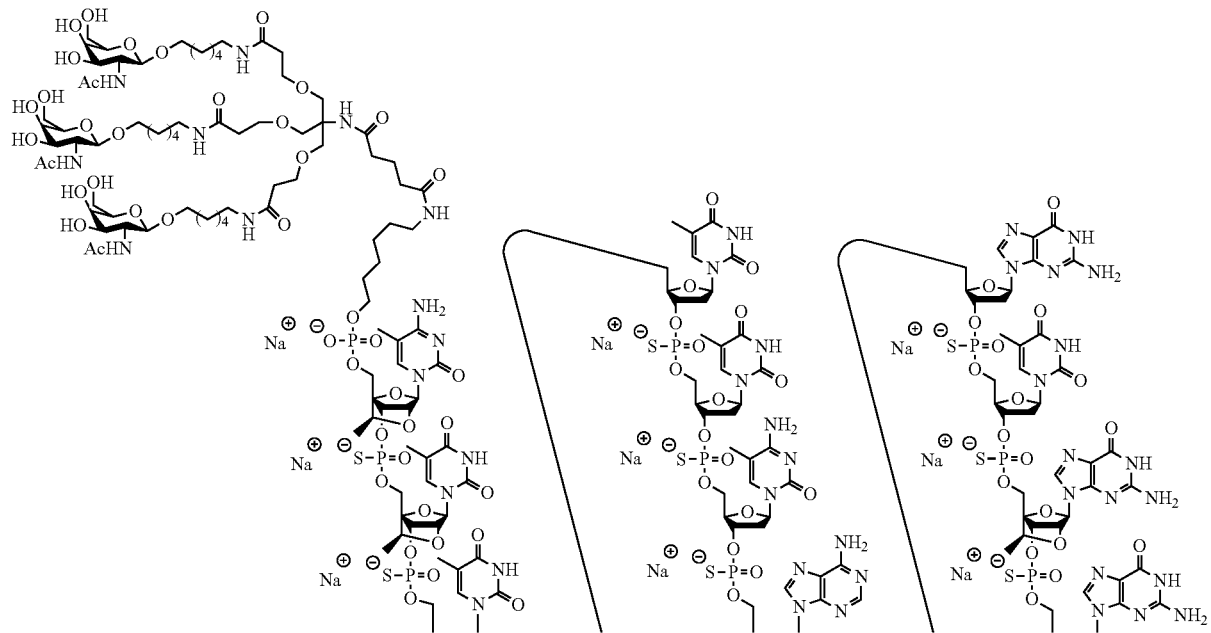
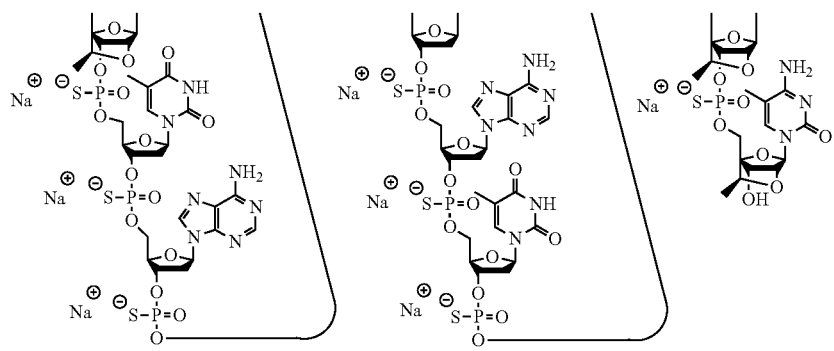

In certain embodiments, a compound comprises or consists of ION 975613 or salt thereof, having the following chemical structure (SEQ ID NO: 330):
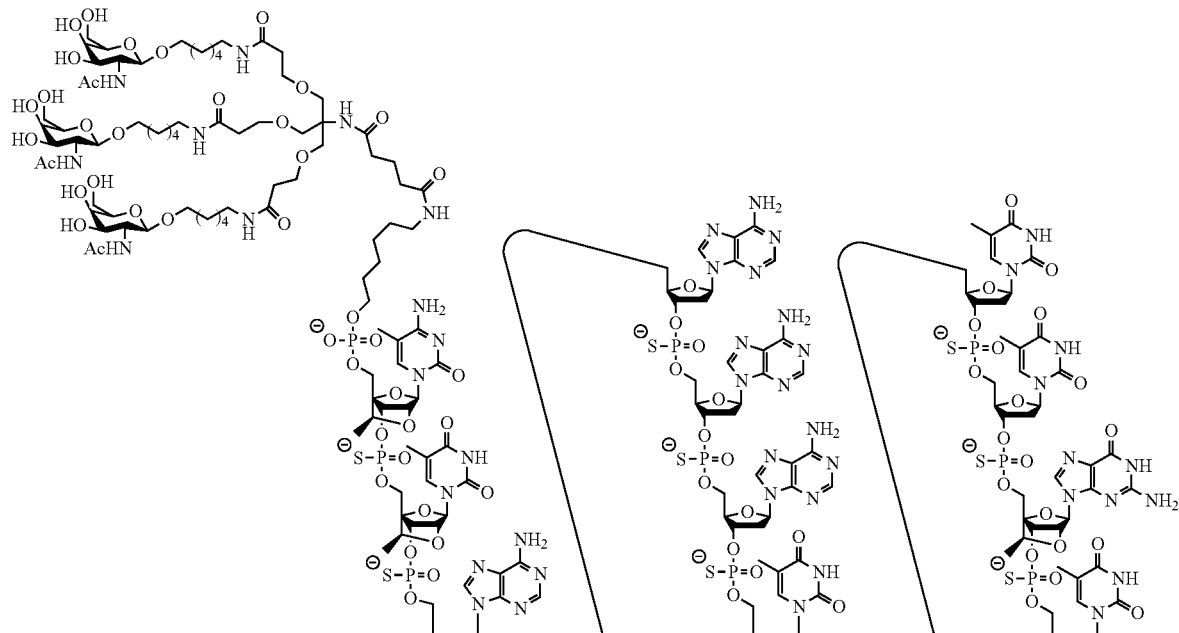
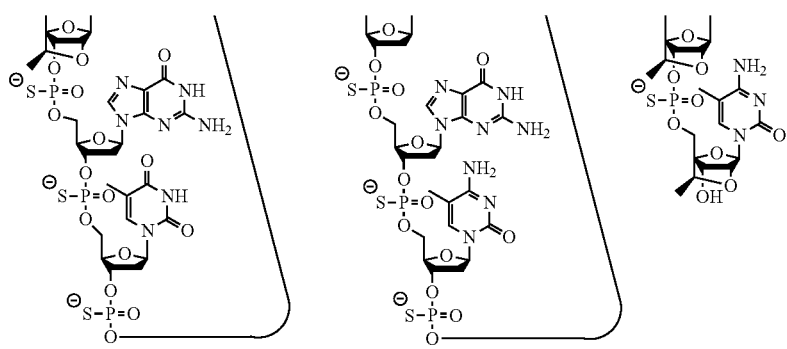

In certain embodiments, a compound comprises or consists of the sodium salt of 975613, having the following chemical structure (SEQ ID NO: 330):
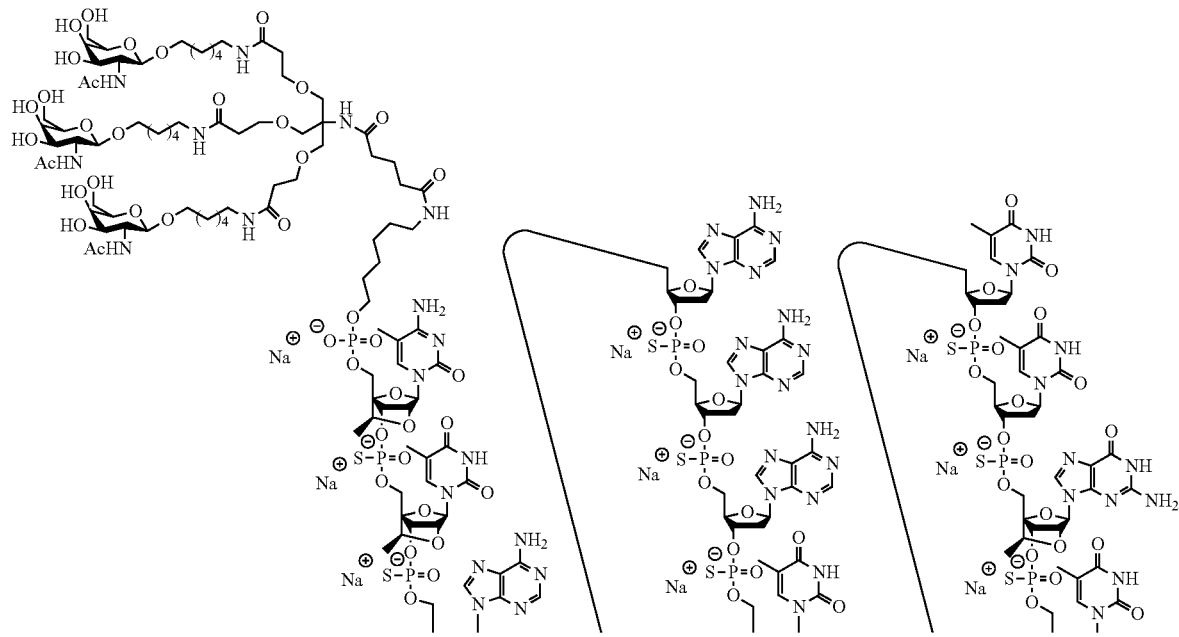
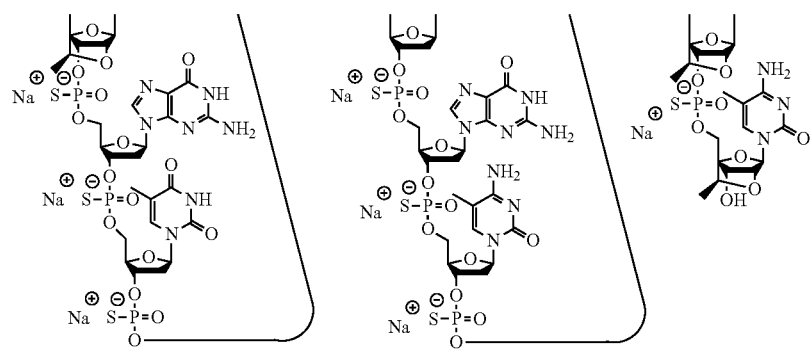

In certain embodiments, a compound comprises or consists of ION 975612 or salt thereof, having the following chemical structure (SEQ ID NO: 899):
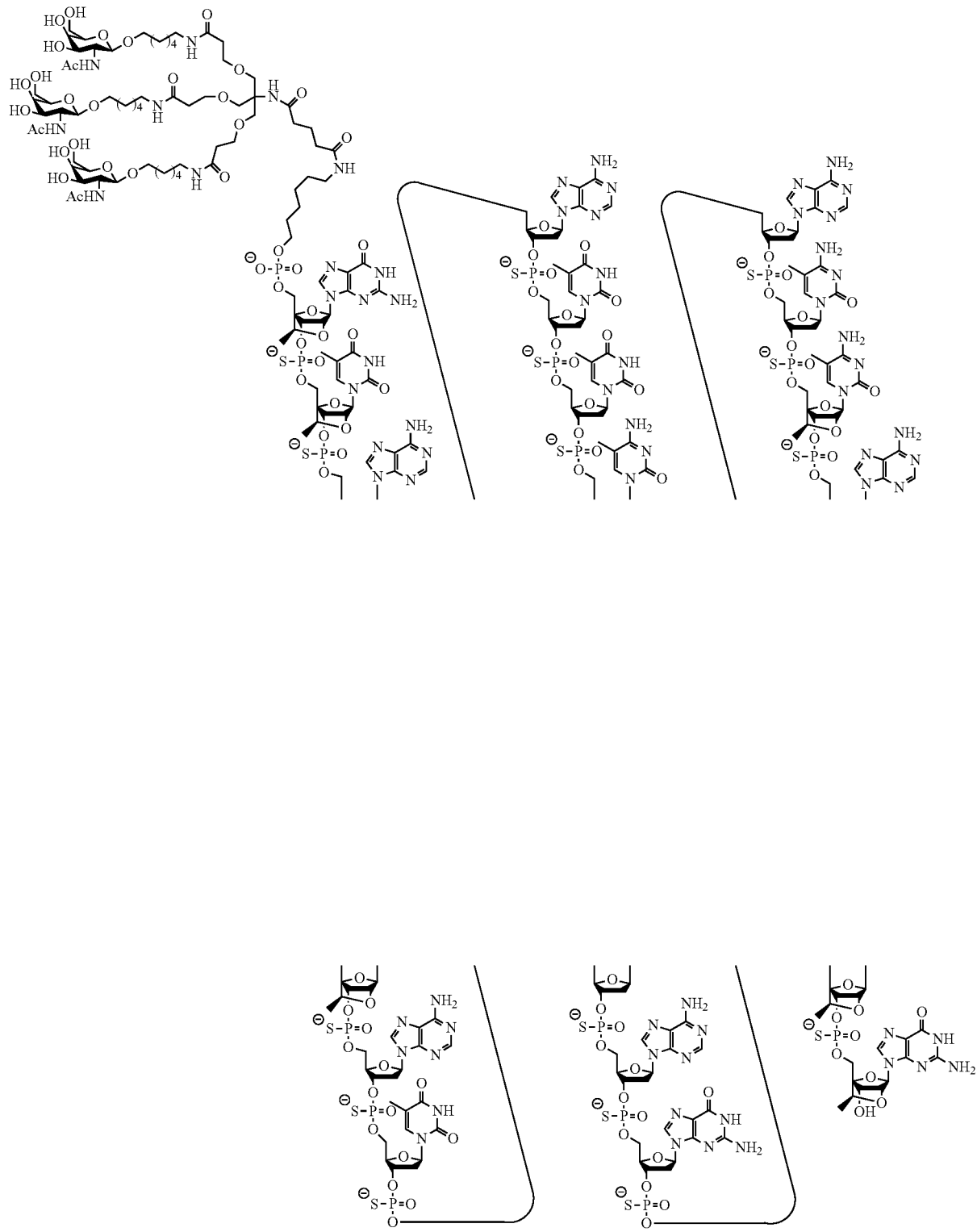

In certain embodiments, a compound comprises or consists of the sodium salt of 975612, having the following chemical structure (SEQ ID NO: 899):
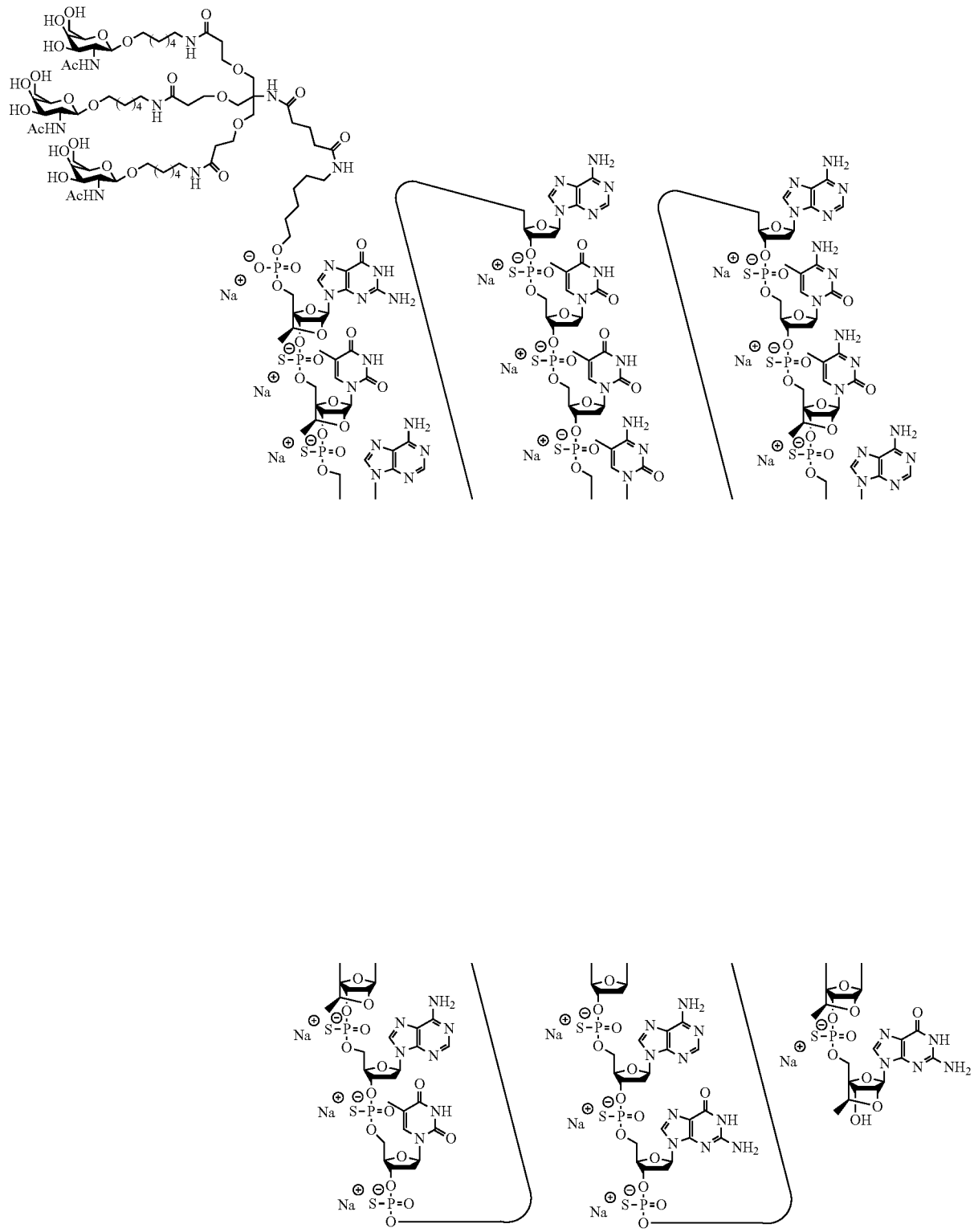

In certain embodiments, a compound comprises or consists of ION 916789 or salt thereof, having the following chemical structure (SEQ ID NO: 899):
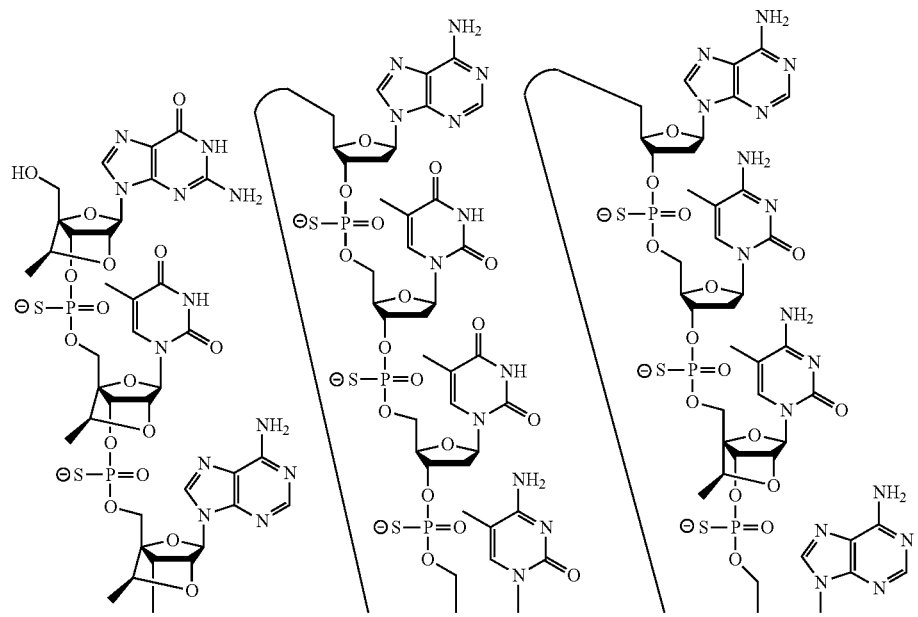
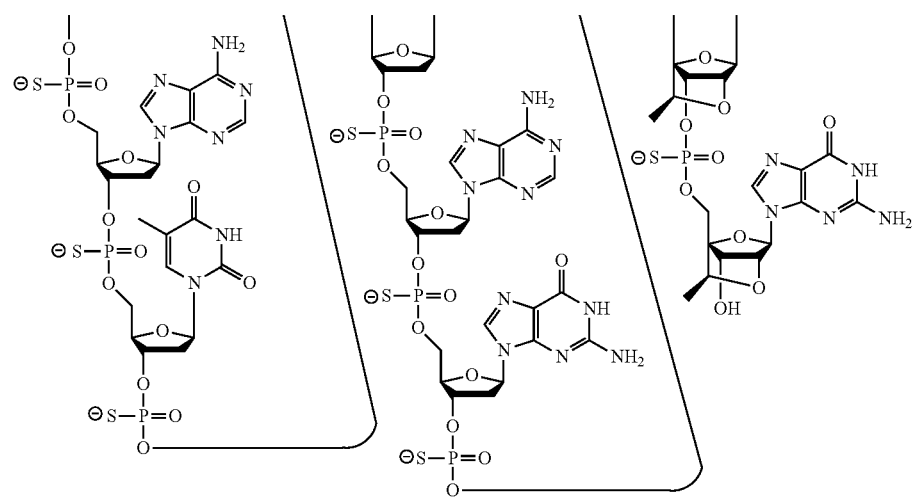

In certain embodiments, a compound comprises or consists of the sodium salt of 916789, having the following chemical structure (SEQ ID NO: 330):
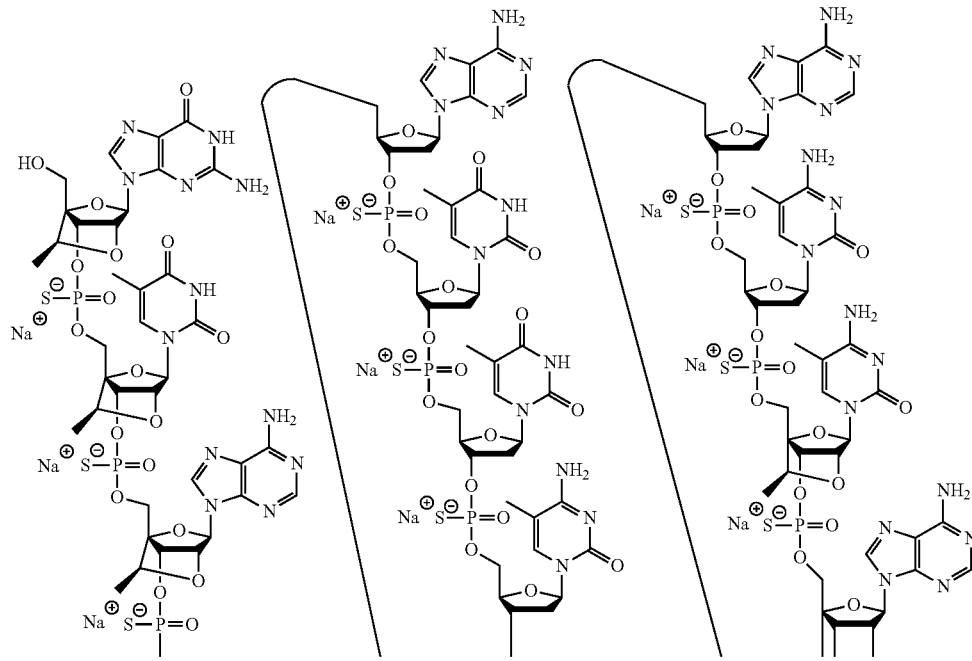
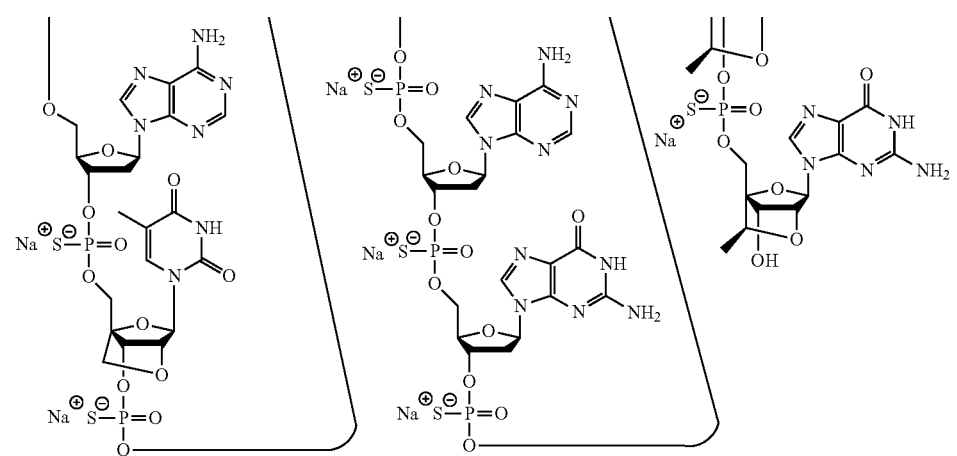

In certain embodiments, a compound comprises or consists of the sodium salt of 916789, having the following chemical structure (SEQ ID NO: 330):
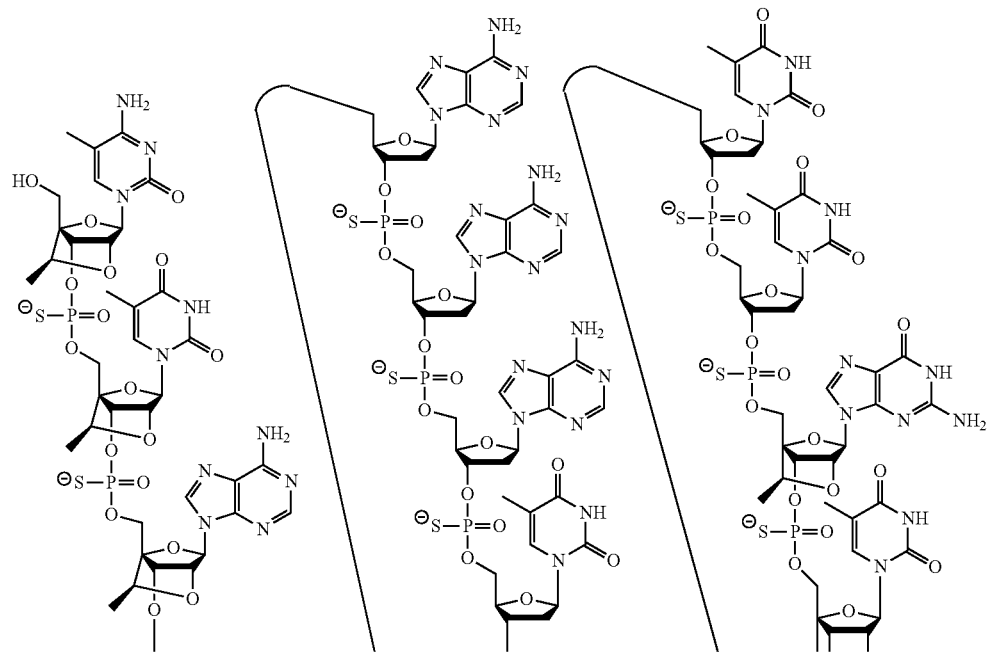
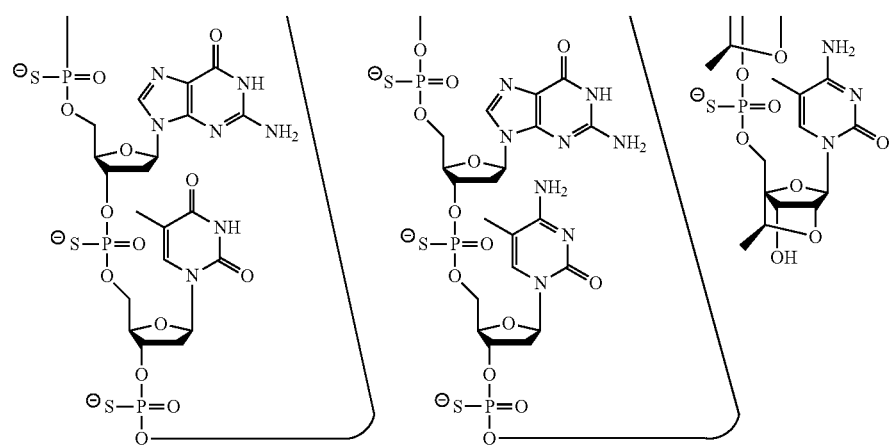

In certain embodiments, a compound comprises or consists of the sodium salt of 916602, having the following chemical structure (SEQ ID NO: 330):

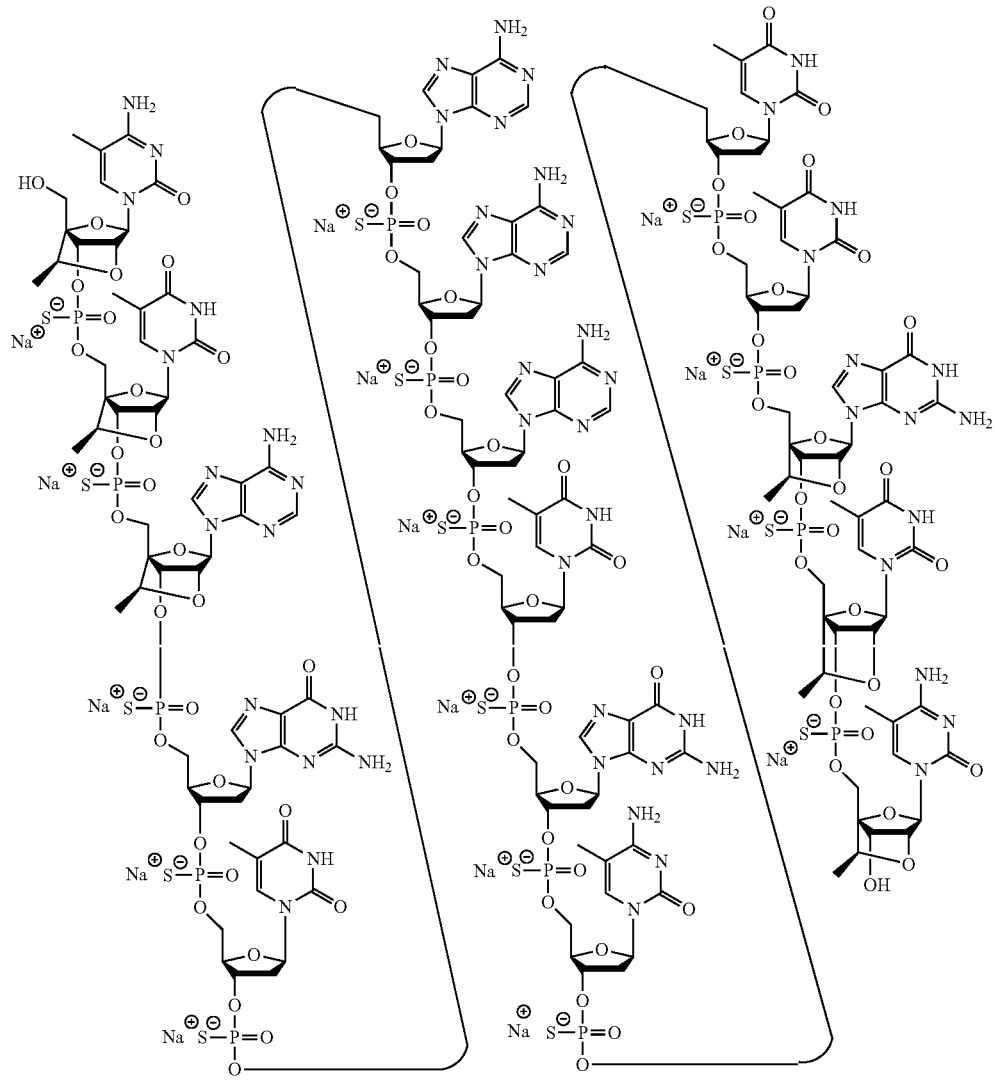

In any of the foregoing embodiments, the compound or oligonucleotide can be at least 85%, at least 90%, at least 95%, at least 98%, at least 99%, or 1000% complementary to a nucleic acid encoding PNPLA3.

In any of the foregoing embodiments, the compound can be single-stranded. In certain embodiments, the compound comprises deoxyribonucleotides. In certain embodiments, the compound is double-stranded. In certain embodiments, the compound is double-stranded and comprises ribonucleotides. In any of the foregoing embodiments, the compound can be an antisense compound or oligomeric compound.

In any of the foregoing embodiments, the compound can be 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length. In certain embodiments, the compound comprises or consists of an oligonucleotide.

In certain embodiments, a compound comprises a modified oligonucleotide described herein and a conjugate group.

In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide. In certain embodiments, the conjugate group comprises at least one N-Acetylgalactosamine (GalNAc), at least two N-Acetylgalactosamines (GalNAcs), or at least three N-Acetylgalactosamines (GalNAcs).

In certain embodiments, compounds or compositions provided herein comprise a pharmaceutically acceptable salt of the modified oligonucleotide. In certain embodiments, the salt is a sodium salt. In certain embodiments, the salt is a potassium salt.

In certain embodiments, the compounds or compositions as described herein are active by virtue of having at least one of an in vitro $IC_{50}$ of less than 2 µM, less than 1.5 µM, less than 1 µM, less than 0.9 µM, less than 0.8 µM, less than 0.7 µM, less than 0.6 µM, less than 0.5 µM, less than 0.4 µM, less than 0.3 µM, less than 0.2 µM, less than 0.1 µM, less than 0.05 µM, less than 0.04 µM, less than 0.03 µM, less than 0.02 µM, or less than 0.01 µM.

In certain embodiments, the compounds or compositions as described herein are highly tolerable as demonstrated by having at least one of an increase in alanine transaminase (ALT) or aspartate transaminase (AST) value of no more than 4 fold, 3 fold, or 2 fold over control animals, or an increase in liver, spleen, or kidney weight of no more than 30%, 20%, 15%, 12%, 10%, 5%, or 2% compared to control animals. In certain embodiments, the compounds or compositions as described herein are highly tolerable as demonstrated by having no increase of ALT or AST over control animals. In certain embodiments, the compounds or compositions as described herein are highly tolerable as demonstrated by having no increase in liver, spleen, or kidney weight over control animals.

Certain embodiments provide a composition comprising the compound of any of the aforementioned embodiments or any pharmaceutically acceptable salt thereof and at least one of a pharmaceutically acceptable carrier or diluent. In certain embodiments, the composition has a viscosity less than about 40 centipoise (cP), less than about 30 centipose (cP), less than about 20 centipoise (cP), less than about 15 centipose (cP), or less than about 10 centipose (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature, or about 20° C., about 21° C., about 22° C., about 23° C., about 24° C., about 25° C., about 26° C., about 27° C., about 28° C., about 29° C., or about 30° C.

Certain Indications

Certain embodiments provided herein relate to methods of inhibiting PNPLA3 expression, which can be useful for treating, preventing, or ameliorating a disease associated with PNPLA3 in an individual, by administration of a compound that targets PNPLA3. In certain embodiments, the compound can be a PNPLA3 specific inhibitor. In certain embodiments, the compound can be an antisense compound, an oligomeric compound, or an oligonucleotide targeted to PNPLA3.

Examples of diseases associated with PNPLA3 treatable, preventable, and/or ameliorable with the methods provided herein include liver disease, NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. Certain compounds provided herein are directed to compounds and compositions that reduce liver damage, steatosis, liver fibrosis, liver inflammation, liver scarring or cirrhosis, liver failure, liver enlargement, elevated transaminases, or hepatic fat accumulation in an animal.

In certain embodiments, a method of treating, preventing, or ameliorating a disease associated with PNPLA3 in an individual comprises administering to the individual a compound comprising a PNPLA3 specific inhibitor, thereby treating, preventing, or ameliorating the disease. In certain embodiments, the individual is identified as having, or at risk of having, a disease associated with PNPLA3. In certain embodiments, the disease is a liver disease. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents liver damage, steatosis, liver fibrosis, cirrhosis, elevated transaminases, or hepatic fat accumulation in an animal.

In certain embodiments, a method of treating, preventing, or ameliorating liver damage, steatosis, liver fibrosis, liver inflammation, liver scarring or cirrhosis, liver failure, liver enlargement, elevated transaminases, or hepatic fat accumulation in an animal comprises administering to the individual a compound comprising a PNPLA3 specific inhibitor, thereby treating, preventing, or ameliorating liver damage, steatosis, liver fibrosis, liver inflammation, liver scarring or cirrhosis, liver failure, liver enlargement, elevated transaminases, or hepatic fat accumulation. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents liver damage, steatosis, liver fibrosis, liver inflammation, liver scarring or cirrhosis, liver failure, liver enlargement, elevated transaminases, or hepatic fat accumulation. In certain embodiments, the individual is identified as having, or at risk of having, a disease associated with PNPLA3.

In certain embodiments, a method of inhibiting expression of PNPLA3 in an individual having, or at risk of having, a disease associated with PNPLA3 comprises administering to the individual a compound comprising a PNPLA3 specific inhibitor, thereby inhibiting expression of PNPLA3 in the individual. In certain embodiments, administering the compound inhibits expression of PNPLA3 in the liver. In certain embodiments, the disease is a liver disease. In certain embodiments, the individual has, or is at risk of having, NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. In certain embodiments, the individual has, or is at risk of having, liver damage, steatosis, liver fibrosis, liver inflammation, liver scarring or cirrhosis, liver failure, liver enlargement, elevated transaminases, or hepatic fat accumulation. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents liver damage, steatosis, liver fibrosis, liver inflammation, liver scarring or cirrhosis, liver failure, liver enlargement, elevated transaminases, or hepatic fat accumulation.

In certain embodiments, a method of inhibiting expression of PNPLA3 in a cell comprises contacting the cell with a compound comprising a PNPLA3 specific inhibitor, thereby inhibiting expression of PNPLA3 in the cell. In certain embodiments, the cell is a hepatocyte. In certain embodiments, the cell is in the liver. In certain embodiments, the cell is in the liver of an individual who has, or is at risk of having, liver damage, steatosis, liver fibrosis, liver inflammation, liver scarring or cirrhosis, liver failure, liver enlargement, elevated transaminases, or hepatic fat accumulation. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or oligomeric compound.

In certain embodiments, a method of reducing or inhibiting liver damage, steatosis, liver fibrosis, liver inflammation, liver scarring or cirrhosis, liver failure, liver enlargement, elevated transaminases, or hepatic fat accumulation in an individual having, or at risk of having, a disease associated with PNPLA3 comprises administering to the individual a compound comprising a PNPLA3 specific inhibitor, thereby reducing or inhibiting liver damage, steatosis, liver fibrosis, liver inflammation, liver scarring or cirrhosis, liver failure, liver enlargement, elevated transaminases, or hepatic fat accumulation in the individual. In certain embodiments, the individual has, or is at risk of having, NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, the individual is identified as having, or at risk of having, a disease associated with PNPLA3.

Certain embodiments are drawn to a compound comprising a PNPLA3 specific inhibitor for use in treating a disease associated with PNPLA3. In certain embodiments, the disease is NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or oligomeric compound. In certain embodiments, the compound is administered to the individual parenterally.

Certain embodiments are drawn to a compound comprising a PNPLA3 specific inhibitor for use in reducing or inhibiting liver damage, steatosis, liver fibrosis, liver inflammation, liver scarring or cirrhosis, liver failure, liver enlargement, elevated transaminases, or hepatic fat accumulation in an individual having, or at risk of having, NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or oligomeric compound.

Certain embodiments are drawn to the use of a compound comprising a PNPLA3 specific inhibitor for the manufacture or preparation of a medicament for treating a disease associated with PNPLA3. Certain embodiments are drawn to the use of a compound comprising a PNPLA3 specific inhibitor for the preparation of a medicament for treating a disease associated with PNPLA3. In certain embodiments, the disease is a liver disease. In certain embodiments, the disease is NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or an oligomeric compound.

Certain embodiments are drawn to the use of a compound comprising a PNPLA3 specific inhibitor for the manufacture or preparation of a medicament for reducing or inhibiting liver damage, steatosis, liver fibrosis, liver inflammation, liver scarring or cirrhosis, liver failure, liver enlargement, elevated transaminases, or hepatic fat accumulation in an individual having, or at risk of having, a liver disease associated with PNPLA3. In certain embodiments, the liver disease is NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. Certain embodiments are drawn to use of a compound comprising a PNPLA3 specific inhibitor for the preparation of a medicament for treating a disease associated with PNPLA3. In certain embodiments, the disease is NAFLD, hepatic steatosis, non-alcoholic steatohepatitis (NASH), liver cirrhosis, hepatocellular carcinoma, alcoholic liver disease, alcoholic steatohepatitis (ASH), HCV hepatitis, chronic hepatitis, hereditary hemochromatosis, or primary sclerosing cholangitis. In certain embodiments, the compound comprises an antisense compound targeted to PNPLA3. In certain embodiments, the compound comprises an oligonucleotide targeted to PNPLA3. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 17-2169. In certain embodiments, a compound comprises a modified oligonucleotide 12 to 30 linked nucleosides in length and having a nucleobase sequence comprising the nucleobase sequence of any one of SEQ ID NOs: 17-2169. In certain embodiments, a compound comprises a modified oligonucleotide consisting of the nucleobase sequence of any one of SEQ ID NOs: 17-2169. In certain embodiments, a compound comprises a modified oligonucleotide 16 to 30 linked nucleosides in length having a nucleobase sequence comprising any one of SEQ ID NOs: 1089, 1757, 141, 1982, 330, 1665, 408, 830, and 899. In certain embodiments, a compound comprises a modified oligonucleotide having a nucleobase sequence consisting of any one of SEQ ID NOs: 1089, 1757, 141, 1982, 330, 1665, 408, 830, and 899. In certain embodiments, the compound is ION 975616, 994284, 975605, 994282, 975613, 975617, 975735, 975736, or 975612. In any of the foregoing embodiments, the compound can be single-stranded or double-stranded. In any of the foregoing embodiments, the compound can be an antisense compound or an oligomeric compound.

In any of the foregoing methods or uses, the compound can be targeted to PNPLA3. In certain embodiments, the compound comprises or consists of a modified oligonucleotide, for example, a modified oligonucleotide 8 to 80 linked nucleosides in length, 10 to 30 linked nucleosides in length, 12 to 30 linked nucleosides in length, or 20 linked nucleosides in length. In certain embodiments, the modified oligonucleotide is at least 80%, at least 85%, at least 90%, at least 95% or 100% complementary to any of the nucleobase sequences recited in SEQ ID NOs: 1-10. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl modified sugar, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the modified oligonucleotide is 12 to 30, 15 to 30, 15 to 25, 15 to 24, 16 to 24, 17 to 24, 18 to 24, 19 to 24, 20 to 24, 19 to 22, 20 to 22, 16 to 20, or 16 or 20 linked nucleosides in length. In certain embodiments, the modified oligonucleotide is at least 80%, at least 85%, at least 90%, at least 95% or 100% complementary to any of the nucleobase sequences recited in SEQ ID NOs: 1-10.

In any of the foregoing methods or uses, the compound comprises or consists of a modified oligonucleotide 16 to 30 linked nucleosides in length and having a nucleobase sequence comprising any one of SEQ ID NOs: 17-2169, wherein the modified oligonucleotide comprises:
  a gap segment consisting of linked 2'-deoxynucleosides;
  a 5' wing segment consisting of linked nucleosides; and
  a 3' wing segment consisting of linked nucleosides;
wherein the gap segment is positioned between the 5' wing segment and the 3' wing segment and wherein each nucleoside of each wing segment comprises a modified sugar.

In any of the foregoing methods or uses, the compound comprises or consists a modified oligonucleotide 16 linked nucleosides in length having a nucleobase sequence comprising the sequence recited in any one of SEQ ID NOs: 1089, 1757, 141, 1982, 330, 1665, 408, 830, and 899, wherein the modified oligonucleotide comprises
  a gap segment consisting of ten linked deoxynucleosides;
  a 5' wing segment consisting of three linked nucleosides; and a 3' wing segment consisting of three linked nucleosides;

wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine. In certain embodiments, the modified oligonucleotide is 16-30 linked nucleosides in length.

In certain embodiments, a compound comprises or consists of ION 916333 or salt thereof, having the following chemical structure (SEQ ID NO: 1089):

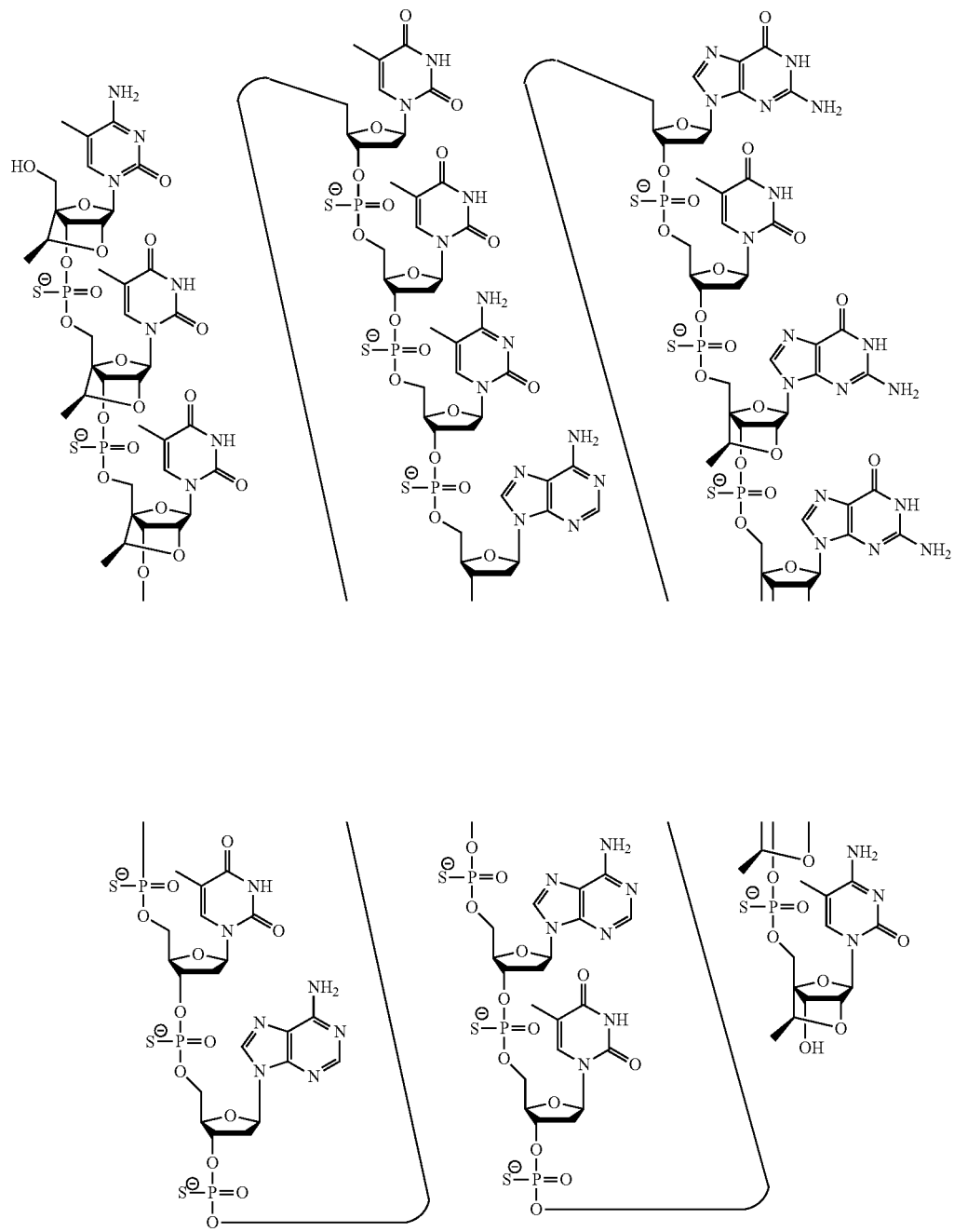

In certain embodiments, a compound comprises or consists of ION 975616 or salt thereof, having the following chemical structure (SEQ ID NO: 1089):
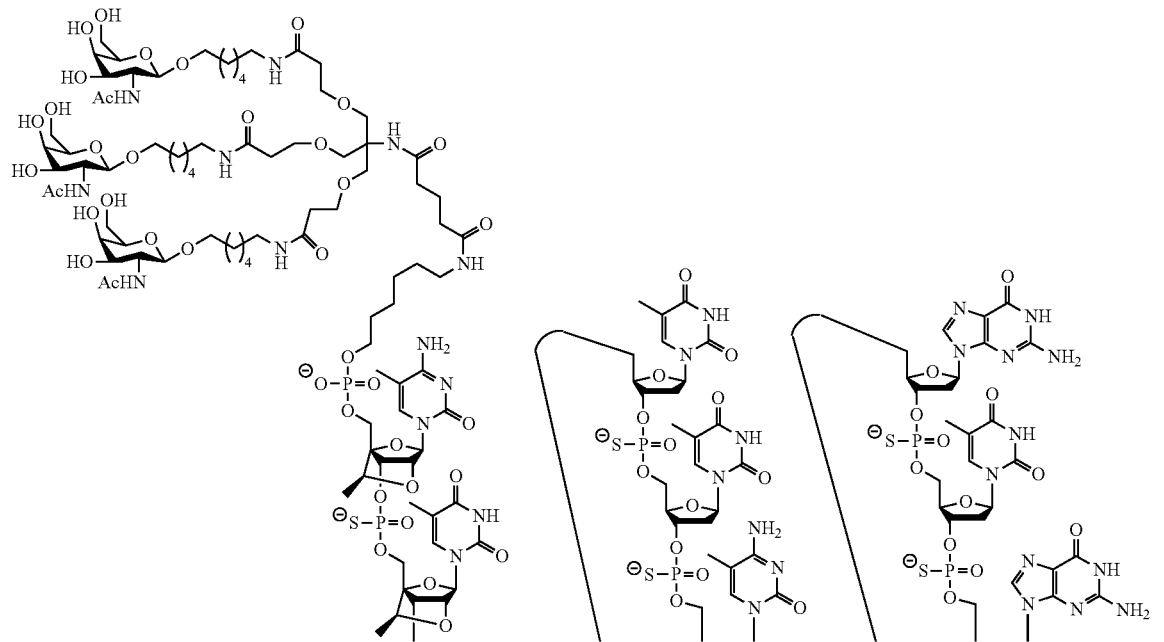
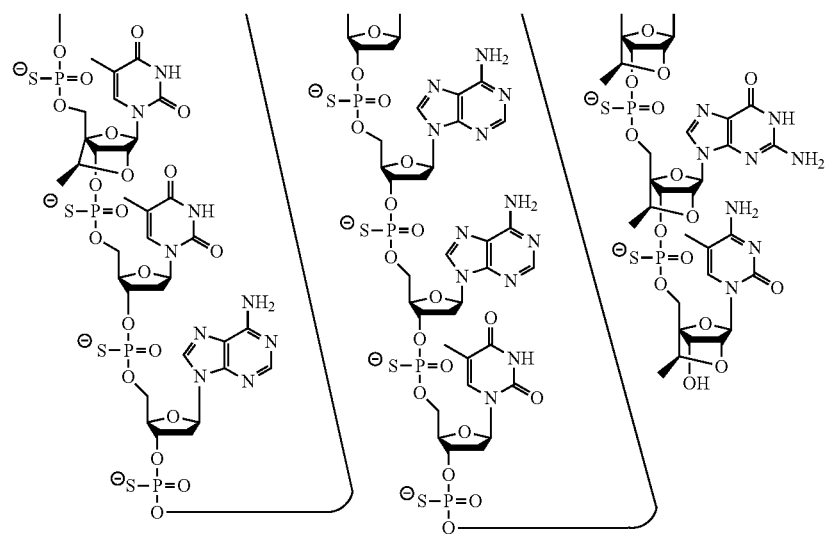

In certain embodiments, a compound comprises or consists of the sodium salt of 975616, having the following chemical structure (SEQ ID NO: 1089):
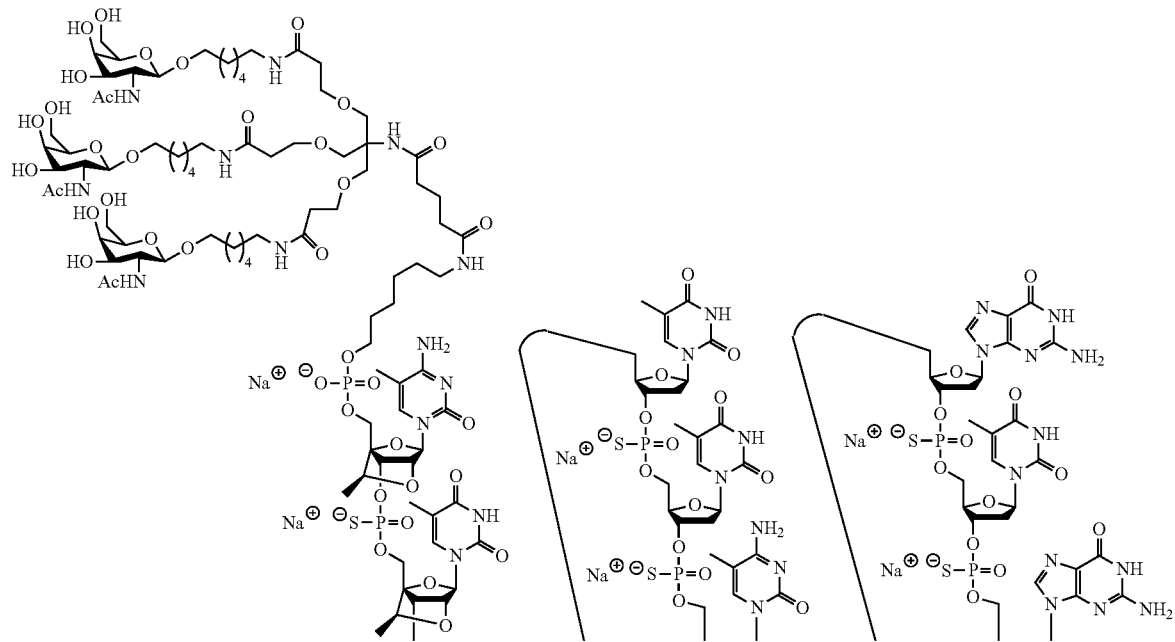
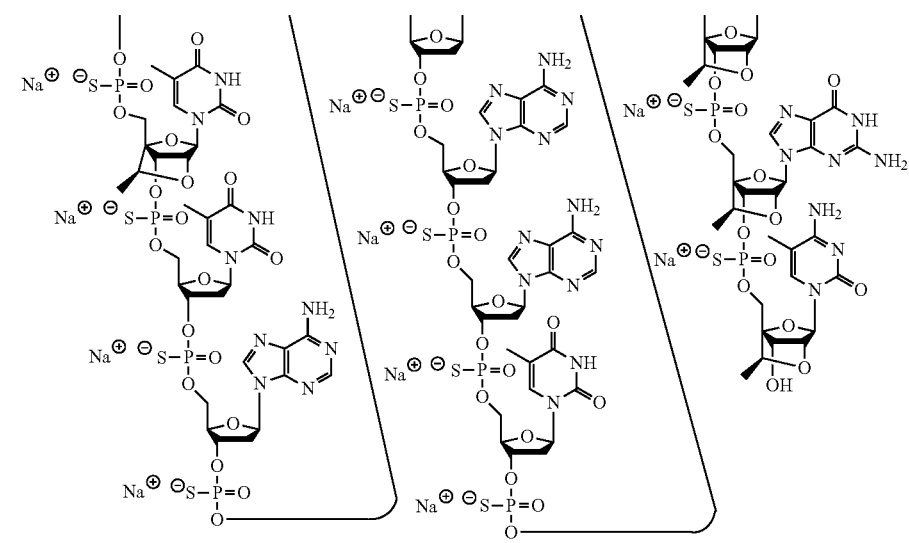

In certain embodiments, a compound comprises or consists of ION 975613 or salt thereof, having the following chemical structure (SEQ ID NO: 330):
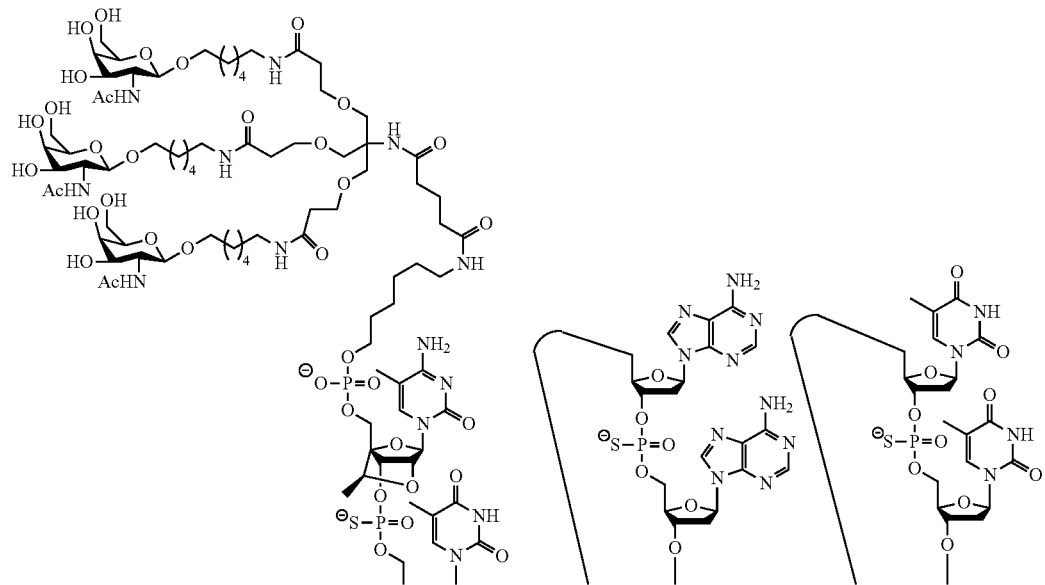
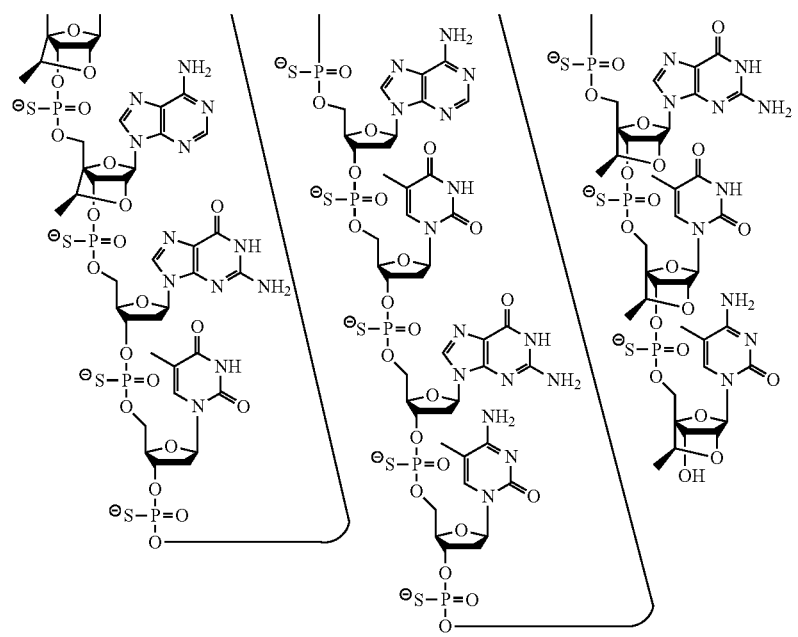

In certain embodiments, a compound comprises or consists of the sodium salt of 975613, having the following chemical structure (SEQ ID NO: 330):
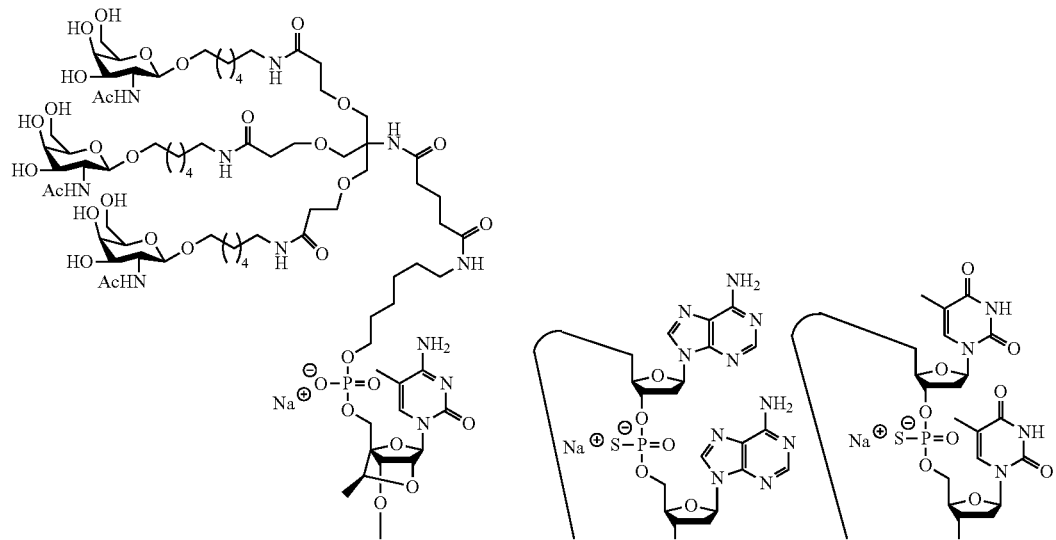
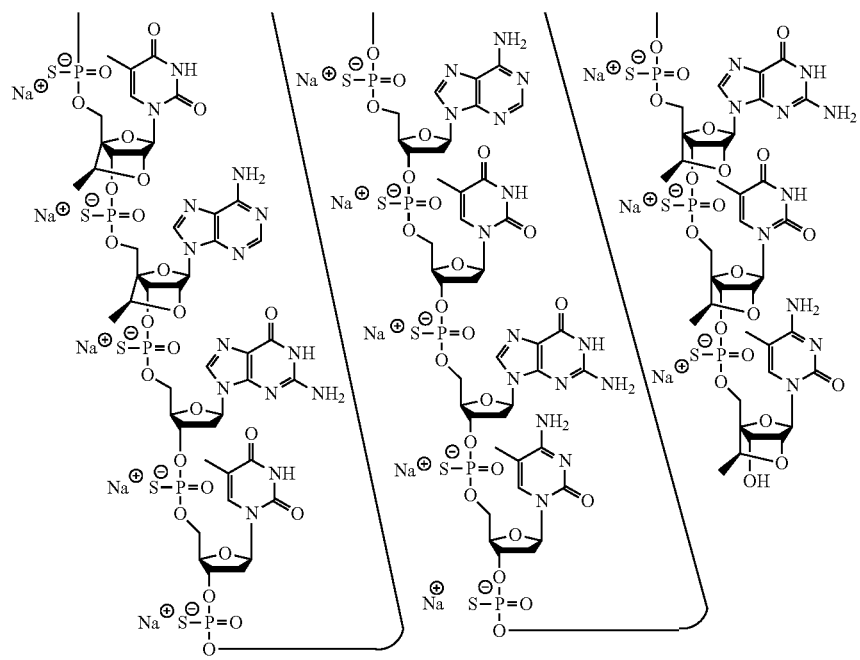

In certain embodiments, a compound comprises or consists of ION 975612 or salt thereof, having the following chemical structure (SEQ ID NO: 899):
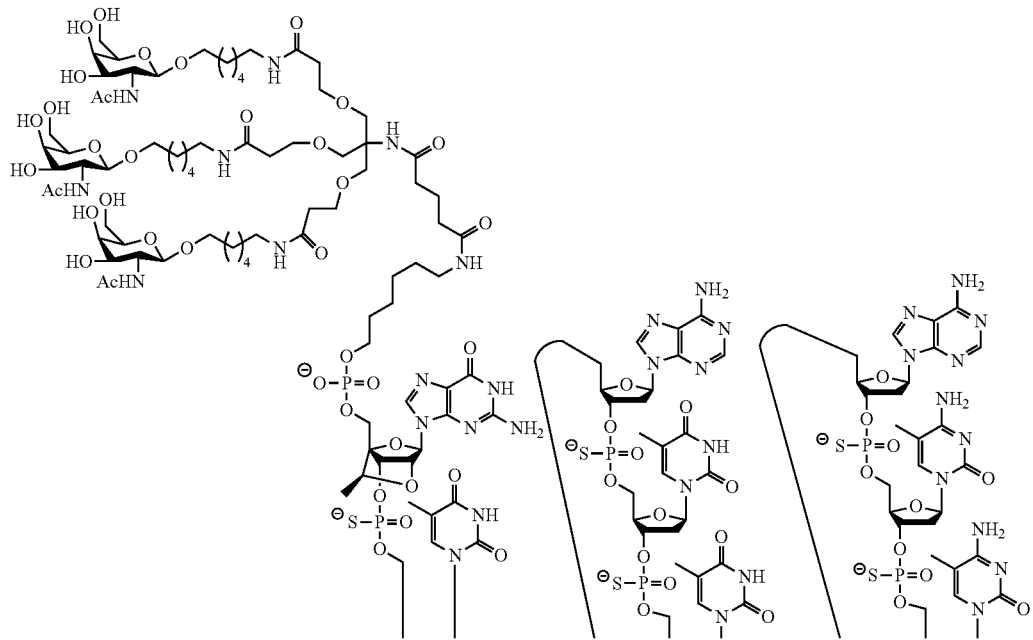
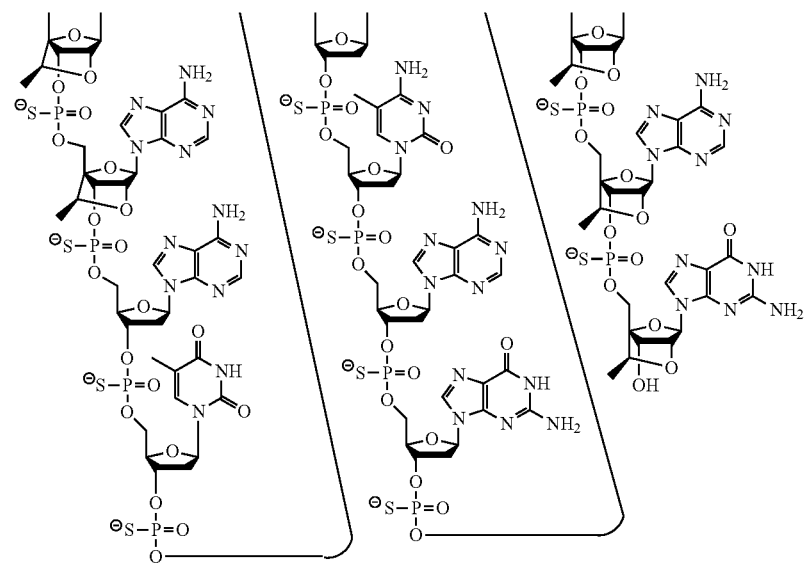

In certain embodiments, a compound comprises or consists of the sodium salt of 975612, having the following chemical structure (SEQ ID NO: 899):
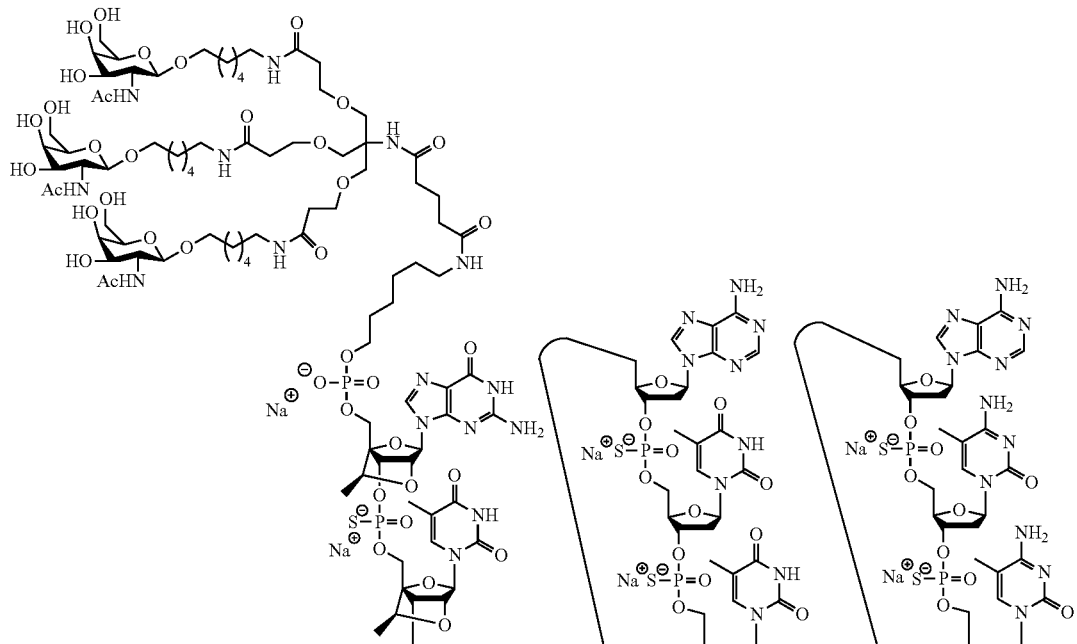
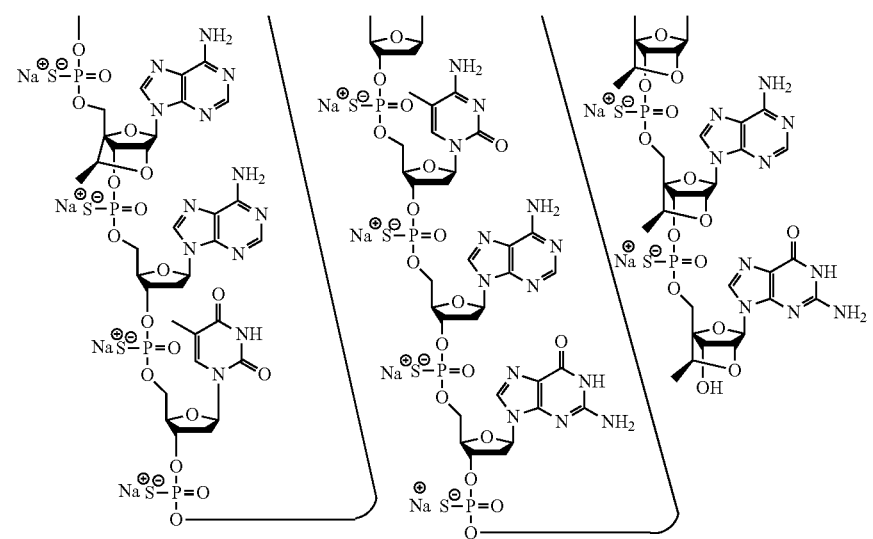

In certain embodiments, a compound comprises or consists of ION 916789 or salt thereof, having the following chemical structure (SEQ ID NO: 899):
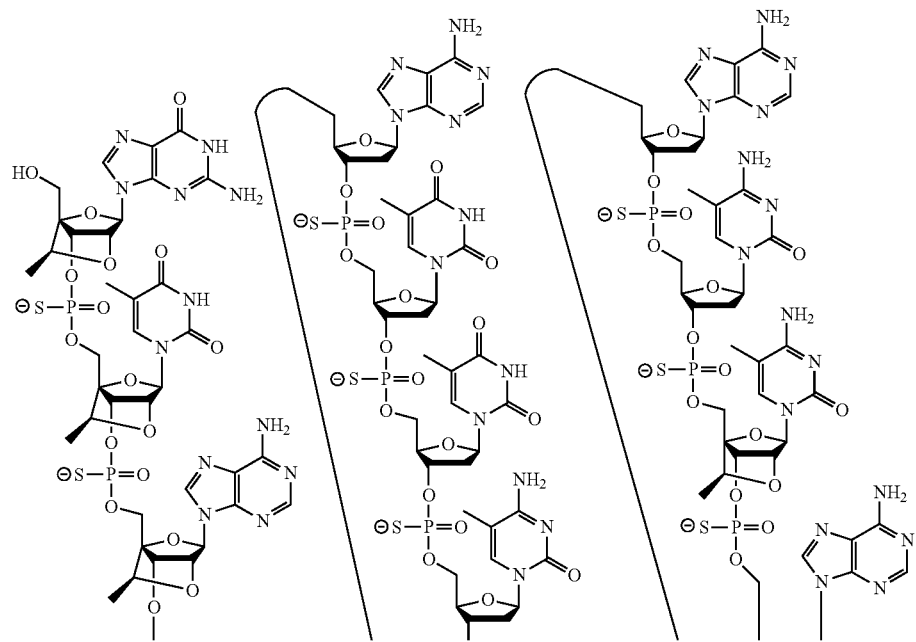
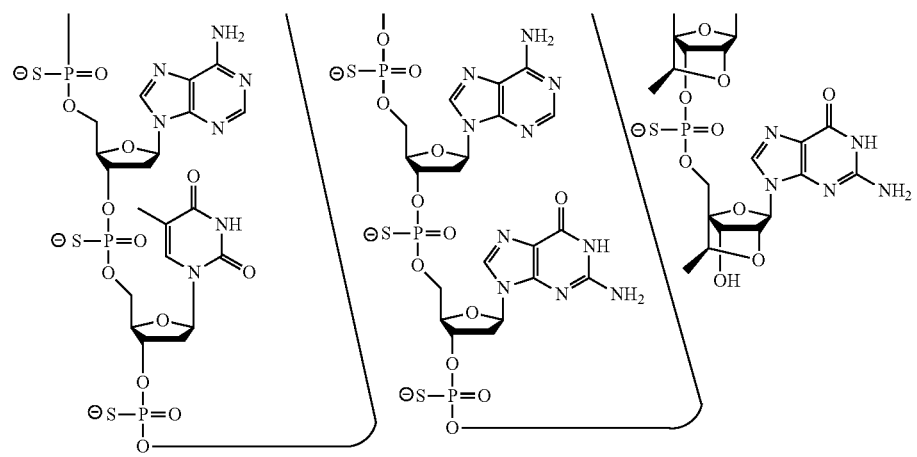

In certain embodiments, a compound comprises or consists of the sodium salt of 916789, having the following chemical structure (SEQ ID NO: 899):
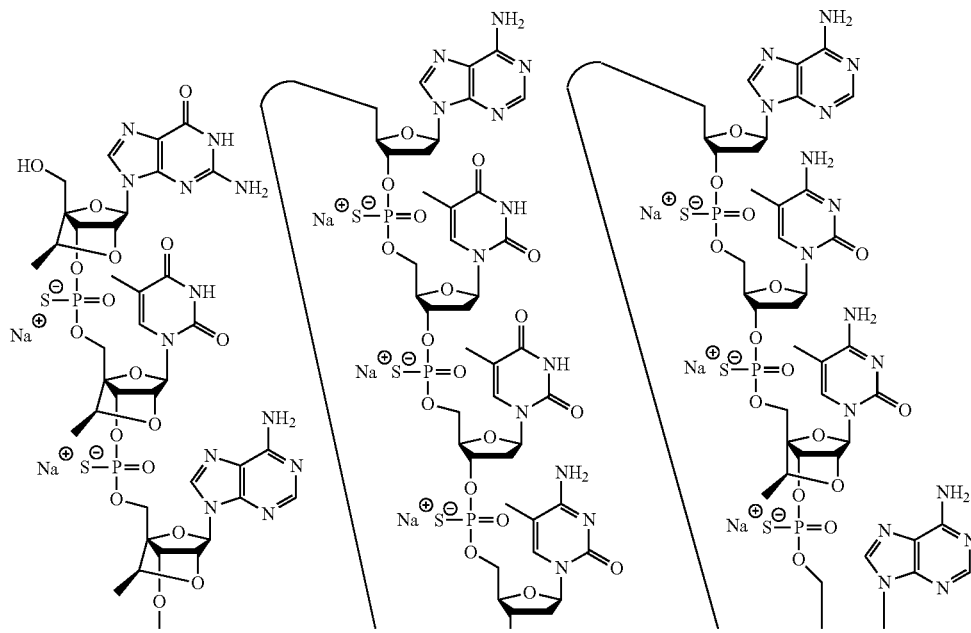
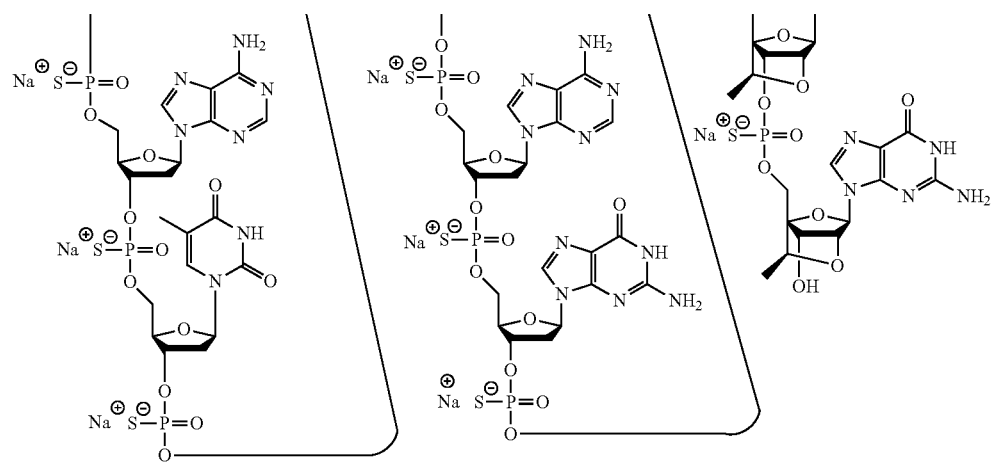

In certain embodiments, a compound comprises or consists of ION 916602 or salt thereof, having the following chemical structure (SEQ ID NO: 330):
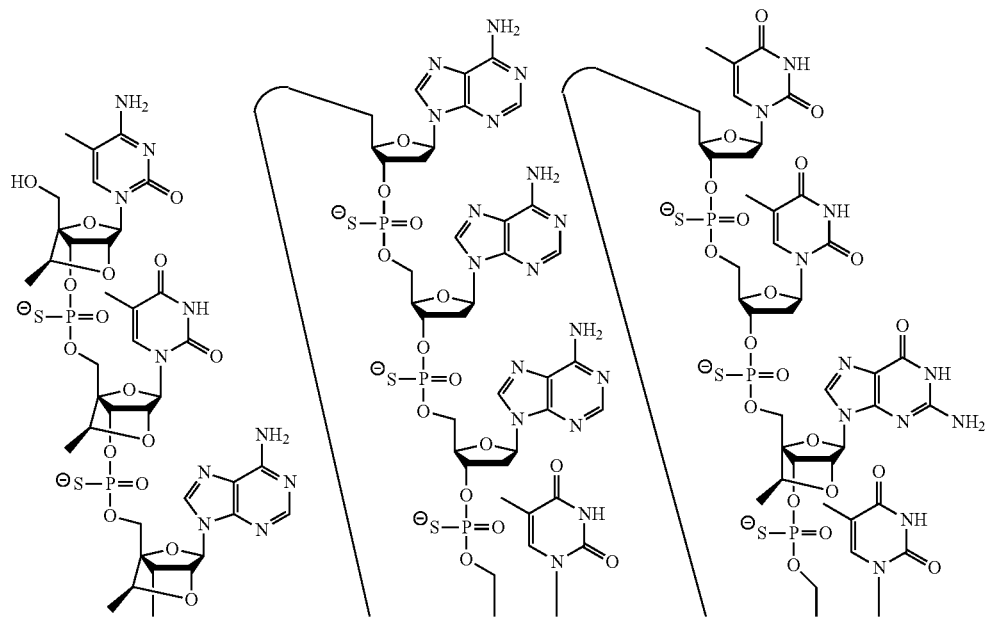
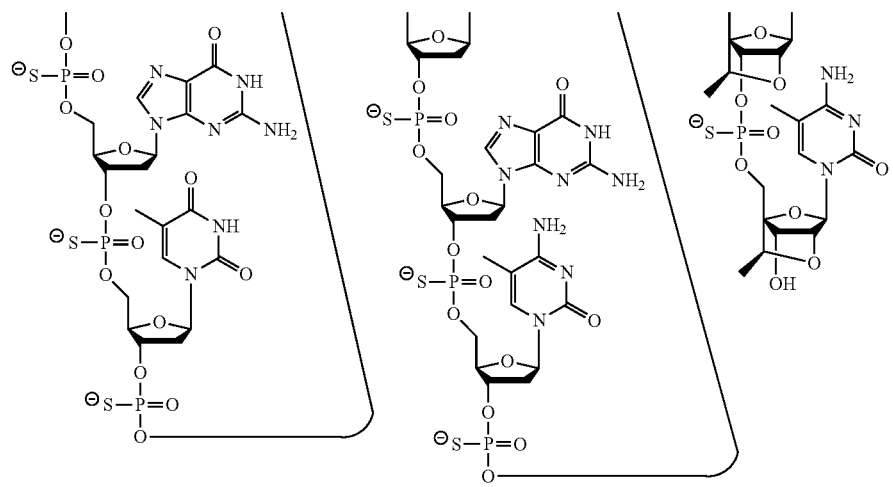

In certain embodiments, a compound comprises or consists of the sodium salt of 916602, having the following chemical structure (SEQ ID NO: 330):

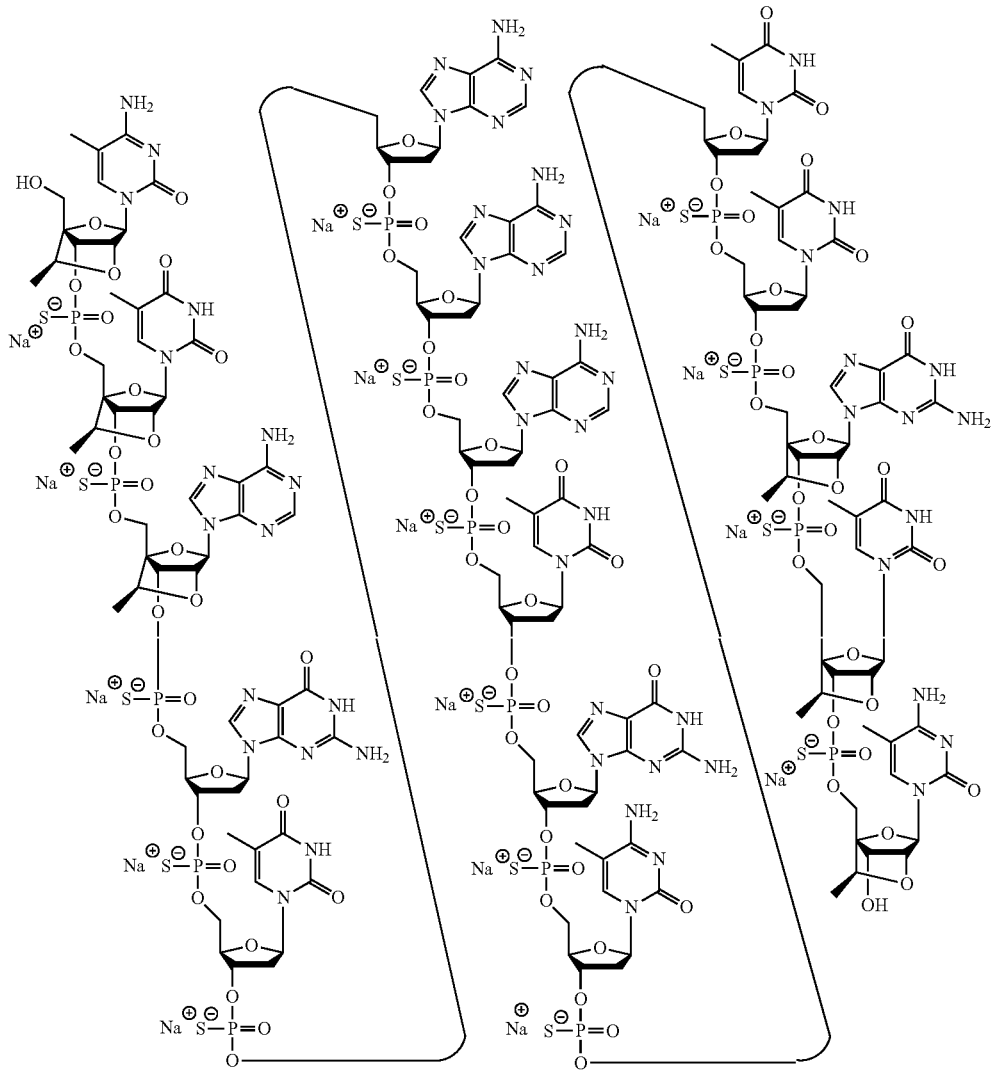

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Certain Compounds

In certain embodiments, compounds described herein can be antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 16-30 linked nucleosides in length and the second modified oligonucleotide is 16-30 linked nucleosides in length. In certain embodiments, one of the modified oligonucleotides has a nucleobase sequence comprising at least 8 contiguous nucleobases of any of SEQ ID NOs: 17-2169.

In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such a double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

Examples of single-stranded and double-stranded compounds include, but are not limited to, oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound described herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, or 20 to 30 subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, or 30 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to a PNPLA3 nucleic acid may have two subunits deleted from the 5' end, or alternatively, may have two subunits deleted from the 3' end of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively, to the 3' end (3' addition) of the compound. Alternatively, the added subunits may be dispersed throughout the compound.

It is possible to increase or decrease the length of a compound, such as an oligonucleotide, and/or introduce mismatch bases without eliminating activity (Woolf et al. *Proc. Natl. Acad. Sci. USA* 1992, 89:7305-7309; Gautschi et al. *J Natl. Cancer Inst*. March 2001, 93:463-471; Maher and Dolnick *Nuc. Acid. Res*. 1998, 16:3341-3358). However, seemingly small changes in oligonucleotide sequence, chemistry and motif can make large differences in one or more of the many properties required for clinical development (Seth et al. *J Med. Chem*. 2009, 52, 10; Egli et al. *J Am. Chem. Soc*. 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence-specific RNAi, for example, short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence-specific RNA interference, such as post transcriptional gene silencing, translational inhibition, or epigenetics.

In certain embodiments, a compound described herein can comprise any of the oligonucleotide sequences targeted to PNPLA3 described herein. In certain embodiments, the compound can be double-stranded. In certain embodiments, the compound comprises a first strand comprising at least an 8, 9, 10, 11, 12, 13, 14, 15, or 16 contiguous nucleobase portion of any one of SEQ ID NOs: 17-2169 and a second strand. In certain embodiments, the compound comprises a first strand comprising the nucleobase sequence of any one of SEQ ID NOs: 17-2169 and a second strand. In certain embodiments, the compound comprises ribonucleotides in which the first strand has uracil (U) in place of thymine (T) in any one of SEQ ID NOs: 17-2169. In certain embodiments, the compound comprises (i) a first strand comprising a nucleobase sequence complementary to the site on PNPLA3 to which any of SEQ ID NOs: 17-2169 is targeted, and (ii) a second strand. In certain embodiments, the compound comprises one or more modified nucleotides in which the 2' position of the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to PNPLA3 described herein. In certain embodiments, the compound is single stranded. In certain embodiments, such a compound is a single-stranded RNAi (ssRNAi) compound.

In certain embodiments, the compound comprises at least an 8, 9, 10, 11, 12, 13, 14, 15, or 16 contiguous nucleobase portion of any one of SEQ ID NOs: 17-2169. In certain embodiments, the compound comprises the nucleobase sequence of any one of SEQ ID NOs: 17-2169. In certain embodiments, the compound comprises ribonucleotides in which uracil (U) is in place of thymine (T) in any one of SEQ ID NOs: 17-2169. In certain embodiments, the compound comprises a nucleobase sequence complementary to the site on PNPLA3 to which any of SEQ ID NOs: 17-2169 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode PNPLA3 include, without limitation, the following: RefSeq or GENBANK Accession Nos. NM_025225.2 (incorporated by reference, disclosed herein as SEQ ID NO: 1); GENBANK Accession No. NC_000022.11 truncated from nucleotides 43921001 to U.S. Pat. No. 43,954,500 (incorporated by reference, disclosed herein as SEQ ID NO: 2); AK123806.1 (incorporated by reference, disclosed herein as SEQ ID NO: 3); BQ686328.1 (incorporated by reference, disclosed herein as SEQ ID NO: 4); BF762711.1 (incorporated by reference, disclosed herein as SEQ ID NO: 5); DA290491.1 (incorporated by reference, disclosed herein as SEQ ID NO: 6); and the sequences listed as SEQ ID Nos. 7, 8, 9, and 10.

Hybridization

In some embodiments, hybridization occurs between a compound disclosed herein and a PNPLA3 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a PNPLA3 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G), unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a PNPLA3 nucleic acid may be tolerated provided that the compound remains able to specifically hybridize to a target nucleic acid. Moreover, a compound may hybridize over one or more segments of a PNPLA3 nucleic acid such that intervening or adjacent segments are not involved in the hybridization event (e.g., a loop structure, mismatch or hairpin structure).

In certain embodiments, the compounds provided herein, or a specified portion thereof are at least, or are up to 70%, 80%, 85%, 86%, 87%, 88%, 89%, 90%, 91%, 92%, 93%, 94%, 95%, 96%, 97%, 98%, 99%, or 100% complementary to a PNPLA3 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a PNPLA3 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a PNPLA3 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. "Fully complementary" can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments, selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a PNPLA3 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a PNPLA3 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of a compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ION number, or portion thereof, in which the compounds comprise an oligonucleotide having one or more mismatched nucleobases.

In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including, but not limited, to substituents at the 2',4', and/or 5' positions. In certain embodiments, the furanosyl sugar moiety is a ribosyl sugar moiety. In certain embodiments, one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include, but are not limited to, alkoxy (e.g., methoxy), alkyl, and those described in Manoharan et al., WO 2015/106128. Examples of 5'-substituent groups suitable for non-bicyclic modified sugar moieties include, but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2'-modified sugar moieties are referred to as 2'-substituted nucleosides or 2'-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include, but are not limited to: 4'-CH$_2$-2',4'-(CH$_2$)$_2$-2',4'-(CH$_2$)$_3$-2',4'-CH$_2$—O-2' ("LNA"), 4'-CH$_2$—S-2',4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2',4'-CH$_2$—N(R)-2',4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2',4'-C(R$_a$R$_b$)—O—N(R)-2',4'-CH$_2$—O—N(R)-2', and 4'-CH$_2$—

N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —[C($R_a$)($R_b$)]$_n$—, —[C($R_a$)($R_b$)]$_n$—O—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J Org. Chem.*, 1998, 63, 10035-10039; Srivastava et al., *J Am. Chem. Soc.*, 2007, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; Allerson et al., US2008/0039618; and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

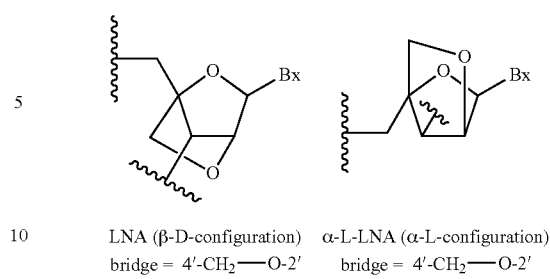

LNA (β-D-configuration)  α-L-LNA (α-L-configuration)
bridge = 4'-CH$_2$—O-2'    bridge = 4'-CH$_2$—O-2'

α-L-methyleneoxy (4'-CH$_2$—O—2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include, but are not limited to, hexitol nucleic acid ("HNA"), anitol nucleic acid ("ANA"), manitol nucleic acid ("MNA") (see e.g., Leumann, CJ. *Bioorg. & Med. Chem.* 2002, 10, 841-854), fluoro HNA:

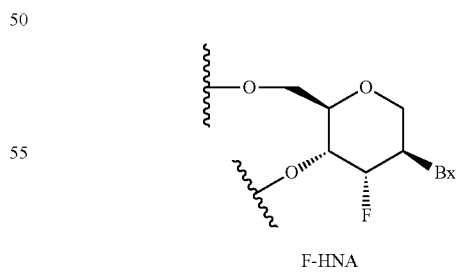

F-HNA ("F-HNA", see e.g., Swayze et al., U.S. Pat. No. 8,088,904; Swayze et al., U.S. Pat. No. 8,440,803; and Swayze et al., U.S. Pat. No. 9,005,906) F-HNA can also be referred to as a F-THP or 3'-fluoro tetrahydropyran, and nucleosides comprising additional modified THP compounds having the formula:

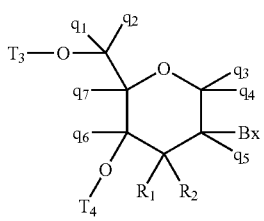

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

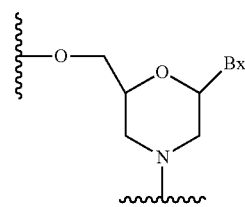

In certain embodiments, morpholinos may be modified, for example, by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include, but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., US2013/130378.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleosides that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($C\equiv C-CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly, 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases, as well as other modified nucleobases include without limitation, Manoharan et al., US2003/0158403, Manoharan et al., US2003/0175906;

Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a PNPLA3 nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., JACS 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

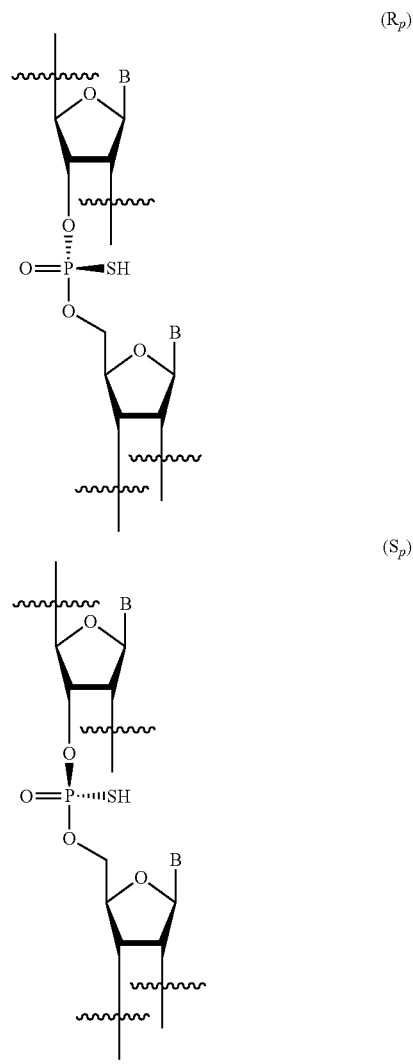

Unless otherwise indicated, chiral internucleoside linkages of modified oligonucleotides described herein can be stereorandom or in a particular stereochemical configuration.

In certain embodiments, compounds targeted to a PNPLA3 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include, but are not limited to, phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include, but are not limited to, methylenemethylimino (—CH$_2$—N(CH$_3$)—O—CH$_2$), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include, but are not limited to, alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O—5'), amide-3 (3'-CH$_2$—C(=O)—N(H)-5'), amide-4 (3'-CH$_2$—N(H)—C(=O)-5'), formacetal (3'-O—CH$_2$—O—5'), methoxypropyl, and thioformacetal (3'-S—CH$_2$—O—5'). Further neutral internucleoside linkages include nonionic linkages comprising siloxane (dialkylsiloxane), carboxylate ester, carboxamide, sulfide, sulfonate ester and amides (See, for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments, the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and, if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments, it is desirable to decrease the number of phosphorothioate internucleoside linkages while retaining nuclease resistance. In certain embodiments, it is desirable to increase the number of phosphodiester internucleoside linkages while retaining nuclease resistance.

3. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleosides comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

a. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include, but are not limited to, any of the sugar modifications discussed herein.

In certain embodiments, modified oligonucleotides comprise or consist of a region having a gapmer motif, which comprises two external regions or "wings" and a central or internal region or "gap". The three regions of a gapmer motif (the 5'-wing, the gap, and the 3'-wing) form a contiguous sequence of nucleosides, wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleosides having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiments, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

b. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments, the block is within 3 nucleosides of the 3'-end of the oligonucleotide. In certain embodiments, the block is at the 5'-end of the oligonucleotide. In certain embodiments, the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

c. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

4. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobases independent of the gapmer pattern of the sugar modifications. Furthermore, in certain instances, an oligonucleotide is described by an overall length or range and by lengths or length ranges of two or more regions (e.g., a regions of nucleosides having specified sugar modifications). In such circumstances, it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide will be 22, which exceeds the upper limit of the overall length of the modified oligonucleotide (20). Herein, if a description of an oligonucleotide is silent with respect to one or more parameters, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and, optionally, one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a pre-mRNA. In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including, but not limited to, pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi: 10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial, or an antibiotic.

2. Conjugate Linkers

Conjugate moieties are attached to oligonucleotides through conjugate linkers. In certain embodiments, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units, such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include, but are not limited to, electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include, but are not limited to, pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include, but are not limited to, substituted or unsubstituted $C_1$-$C_{10}$ alkyl, substituted or unsubstituted $C_2$-$C_{10}$ alkenyl, or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl, and alkynyl.

In certain embodiments, conjugate linkers comprise 1-10 linker-nucleosides. In certain embodiments, such linker-nucleosides are modified nucleosides. In certain embodiments, such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, a compound may comprise a modified oligonucleotide consisting of 8-30 nucleosides and no conjugate group. The total number of contiguous linked nucleosides in such a compound is no more than 30. Unless otherwise indicated, conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances, compounds comprising a particular conjugate moiety are better taken up by a particular cell type, but once the compound has been taken up, it is desirable that the conjugate group be cleaved to release the unconjugated or parent oligonucleotide. Thus, certain conjugates may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amide, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a

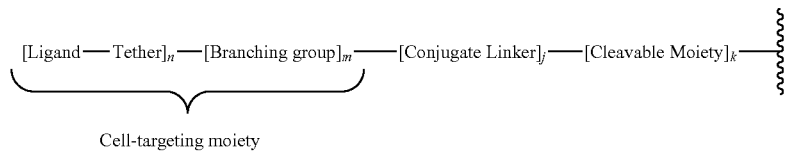

Cell-targeting moiety wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether, and hydroxylamino groups. In certain embodiments, the branching group comprises a branched aliphatic group comprising groups selected from alkyl, amino, oxo, amide, disulfide, polyethylene glycol, ether, thioether, and hydroxylamino groups. In certain such embodiments, the branched aliphatic group comprises groups selected from alkyl, amino, oxo, amide, and ether groups. In certain such embodiments, the branched aliphatic group comprises groups selected from alkyl, amino, and chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactoseamine (GalNAc), mannose, glucose, glucoseamine, and fucose. In certain embodiments, each ligand is N-acetyl galactoseamine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry,* 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups comprise a cell-targeting moiety having the formula:

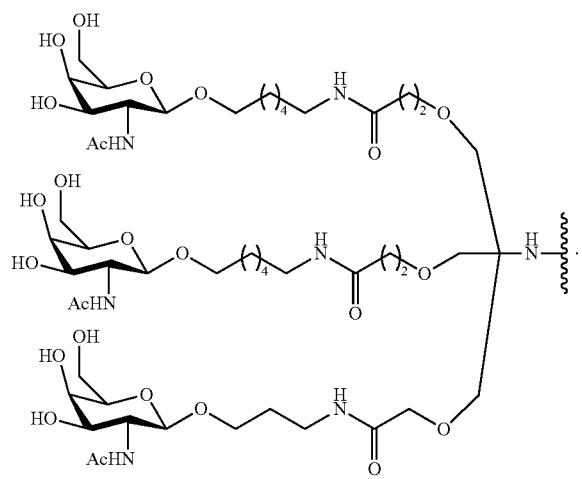

In certain embodiments, conjugate groups comprise a cell-targeting moiety having the formula:

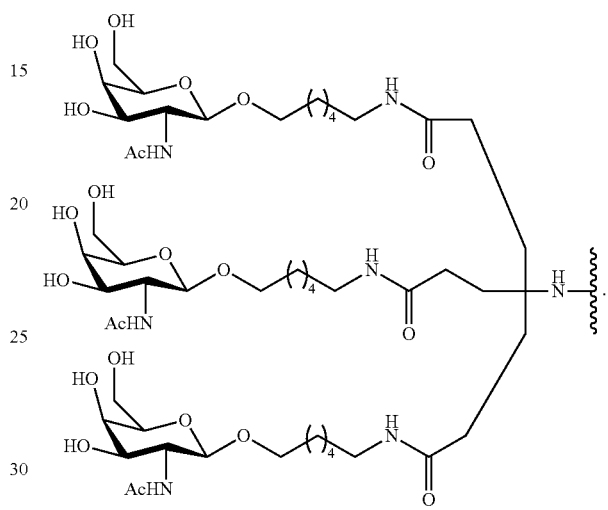

In certain embodiments, conjugate groups comprise a cell-targeting moiety having the formula:

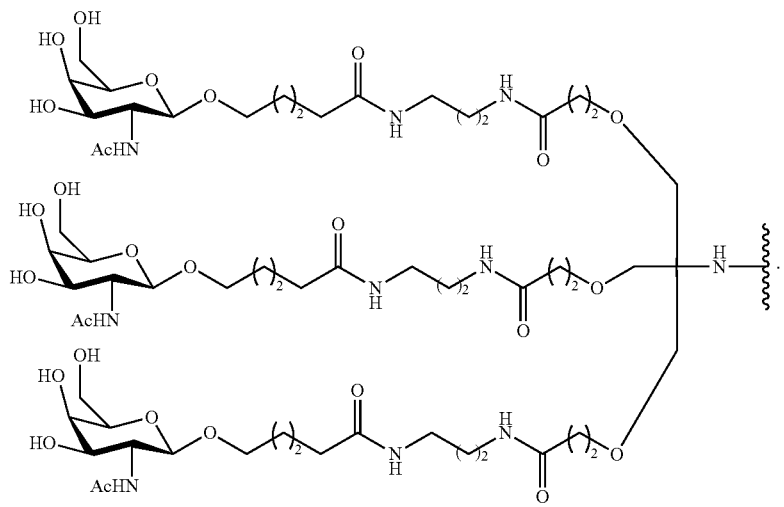

In certain embodiments, compounds described herein comprise a conjugate group described herein as "LICA-1". LICA-1 is shown below without the optional cleavable moiety at the end of the conjugate linker:

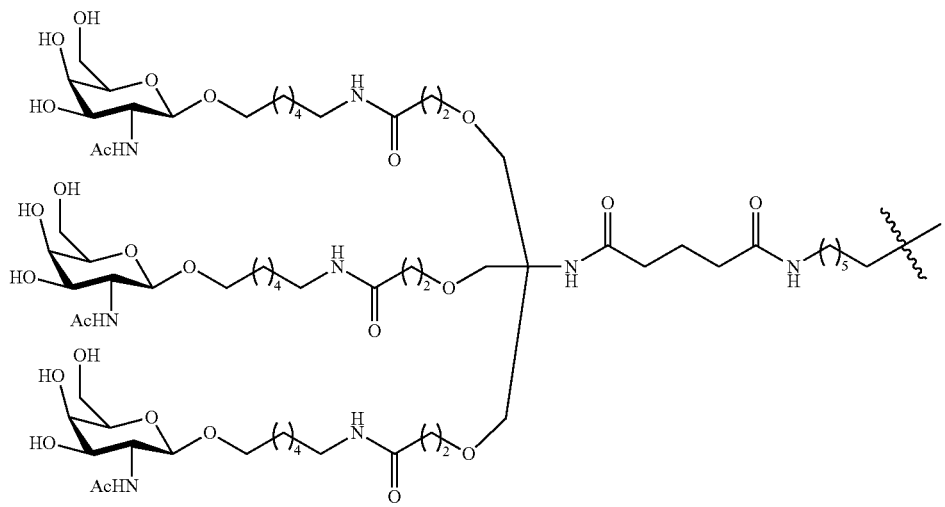

In certain embodiments, compounds described herein comprise LICA-1 and a cleavable moiety within the conjugate linker have the formula:

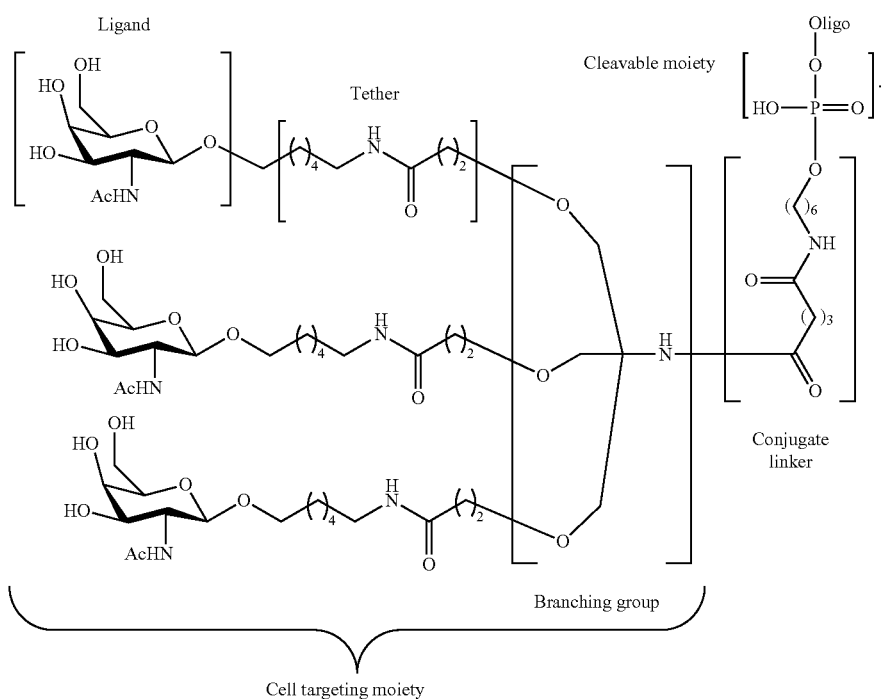

wherein 'oligo' is an oligonucleotide.

Representative publications that teach the preparation of certain of the above noted conjugate groups and compounds comprising conjugate groups, tethers, conjugate linkers, branching groups, ligands, cleavable moieties as well as other modifications include, without limitation, U.S. Pat. Nos. 5,994,517, 6,300,319, 6,660,720, 6,906,182, 7,262, 177, 7,491,805, 8,106,022, 7,723,509, 9,127,276, US 2006/0148740, US 2011/0123520, WO 2013/033230 and WO 2012/037254, Biessen et al., *J. Med. Chem.* 1995, 38, 1846-1852, Lee et al., *Bioorganic & Medicinal Chemistry* 2011, 19, 2494-2500, Rensen et al., *J Biol. Chem.* 2001, 276, 37577-37584, Rensen et al., *J. Med. Chem.* 2004, 47, 5798-5808, Sliedregt et al., *J. Med. Chem.* 1999, 42, 609-

618, and Valentijn et al., *Tetrahedron*, 1997, 53, 759-770, each of which is incorporated by reference herein in its entirety.

In certain embodiments, compounds described herein comprise modified oligonucleotides comprising a gapmer or fully modified motif and a conjugate group comprising at least one, two, or three GalNAc ligands. In certain embodiments, compounds described herein comprise a conjugate group found in any of the following references: Lee, *Carbohydr Res*, 1978, 67, 509-514; Connolly et al., *J Biol Chem*, 1982, 257, 939-945; Pavia et al., *Int J Pep Protein Res*, 1983, 22, 539-548; Lee et al., *Biochem*, 1984, 23, 4255-4261; Lee et al., *Glycoconjugate J*, 1987, 4, 317-328; Toyokuni et al., *Tetrahedron Lett*, 1990, 31, 2673-2676; Biessen et al., *J Med Chem*, 1995, 38, 1538-1546; Valentijn et al., *Tetrahedron*, 1997, 53, 759-770; Kim et al., *Tetrahedron Lett*, 1997, 38, 3487-3490; Lee et al., *Bioconjug Chem*, 1997, 8, 762-765; Kato et al., *Glycobiol*, 2001, 11, 821-829; Rensen et al., *J Biol Chem*, 2001, 276, 37577-37584; Lee et al., *Methods Enzymol*, 2003, 362, 38-43; Westerlind et al., *Glycoconj J*, 2004, 21, 227-241; Lee et al., *BioorgMed Chem Lett*, 2006, 16(19), 5132-5135; Maierhofer et al., *Bioorg Med Chem*, 2007, 15, 7661-7676; Khorev et al., *Bioorg Med Chem*, 2008, 16, 5216-5231; Lee et al., *BioorgMed Chem*, 2011, 19, 2494-2500; Kornilova et al., *Analyt Biochem*, 2012, 425, 43-46; Pujol et al., *Angew Chemie Int Ed Engl*, 2012, 51, 7445-7448; Biessen et al., *J Med Chem*, 1995, 38, 1846-1852; Sliedregt et al., *J Med Chem*, 1999, 42, 609-618; Rensen et al., *J Med Chem*, 2004, 47, 5798-5808; Rensen et al., *Arterioscler Thromb Vasc Biol*, 2006, 26, 169-175; van Rossenberg et al., *Gene Ther*, 2004, 11, 457-464; Sato et al., *JAm Chem Soc*, 2004, 126, 14013-14022; Lee et al., *JOrg Chem*, 2012, 77, 7564-7571; Biessen et al., *FASEB J*, 2000, 14, 1784-1792; Rajur et al., *Bioconjug Chem*, 1997, 8, 935-940; Duff et al., *Methods Enzymol*, 2000, 313, 297-321; Maier et al., *Bioconjug Chem*, 2003, 14, 18-29; Jayaprakash et al., *Org Lett*, 2010, 12, 5410-5413; Manoharan, Antisense Nucleic Acid Drug Dev, 2002, 12, 103-128; Merwin et al., *Bioconjug Chem*, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compounds and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to PNPLA3 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to PNPLA3 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

Certain Selected Compounds

Approximately 2,384 newly designed compounds of various lengths, chemistries, and motifs were tested for their effect on human PNPLA3 mRNA in vitro in several cell types (Example 1). Of 2,384 compounds tested for potency at a single dose in vitro, over 400 selected compounds were tested for dose dependent inhibition in A431 cells (Example 2). Of the over 400 compounds tested by dose response assays, the compounds were further screened for high dose tolerability in a BALB/c mouse model and 87 oligonucleotides were selected for in vivo efficacy in a PNPLA3 transgenic mouse model.

Of the 87 oligonucleotides tested in the transgenic mouse model, 23 oligonucleotides were selected to be further tested for tolerability in preclinical rodel models. In the in vivo rodent tolerability models, body weights and organ weights, liver function markers (such as alanine transaminase, aspartate transaminase and bilirubin), and kidney function markers (such as BUN and creatinine) were measured. In the CD1 mouse model and in the Sprague-Dawley rat model, ION 975591, 975605, 975612, 975613, 975616, 975617, 975735, 975736, 994282, and 994284 were found tolerable (Examples 5 and 6).

These compounds were further tested for efficacy in multi-dose assays in PNPLA3 transgenic mice (Example 7).

IONs 994284, 97605, 975616, 994282, 975613, 975617, 975735, 975736, and 975612 were tested for tolerability in cynomolgus monkeys (Example 8). Treatment with the compounds was well tolerated in the monkeys.

Accordingly, provided herein are compounds with any one or more of the improved properties. In certain embodiments, the compounds as described herein are potent and tolerable.

EXAMPLES

The Examples below describe the screening process to identify lead compounds targeted to PNPLA3. ION 994284, 97605, 975616, 994282, 975613, 975617, 975735, 975736, and 975612 resulted in high potency and tolerability.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to, those in the sequence listing, are intended to encompass nucleic acids containing any combination of natural or modified RNA and/or DNA, including, but not limited to, such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein $^m$C indicates a cytosine base comprising a methyl group at the 5-position.

Certain compounds described herein (e.g. modified oligonucleotides) have one or more asymmetric centers and thus give rise to enantiomers, diastereomers, and other stereoisomeric configurations that may be defined, in terms of absolute stereochemistry, as (R) or (S), as a or R, such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. Likewise, all tautomeric forms of the compounds provided herein are included unless otherwise indicated. Unless otherwise indicated, oligomeric compounds and modified oligonucleotides described herein are intended to include corresponding salt forms.

Compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include, but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human PNPLA3 in A431 Cells

Antisense oligonucleotides were designed targeting a PNPLA3 nucleic acid and were tested for their effects on PNPLA3 mRNA in vitro. The antisense oligonucleotides were tested in a series of experiments that had similar culture conditions. The results for each experiment are presented in separate tables shown below.

The newly designed chimeric antisense oligonucleotides in the Tables below were designed as 3-10-3 cEt gapmers. The gapmers are 16 nucleosides in length, wherein the central gap segment comprises of ten 2'-deoxynucleosides and is flanked by wing segments on the 5' direction and the 3' direction comprising three nucleosides. Each nucleoside in the 5' wing segment and each nucleoside in the 3' wing segment has a cEt sugar modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human PNPLA3 mRNA, designated herein as SEQ ID NO: 1 (GENBANK Accession No. NM_025225.2) or the human PNPLA3 genomic sequence, designated herein as SEQ ID NO: 2 (GENBANK Accession No. NC_000022.11 truncated from nucleotides 43921001 to 43954500). 'n/a' indicates that the antisense oligonucleotide does not target that particular gene sequence with 100% complementarity.

Study 1

Cultured A431 cells at a density of 20,000 cells per well were transfected by free uptake with 4,000 nM antisense oligonucleotide. After a treatment period of approximately 24 hours, RNA was isolated from the cells and PNPLA3 mRNA levels were measured by quantitative real-time PCR. Human primer probe set RTS36070 (forward sequence CCTTGGTATGTTCCTGCTTCA, designated herein as SEQ ID NO: 11; reverse sequence GTTGTCACTCACTCCTCCATC, designated herein as SEQ ID NO: 12; probe sequence TGGCCTTATCCCTCCTTCCTTCAGA, designated herein as SEQ ID NO: 13) was used to measure mRNA levels. PNPLA3 mRNA levels were adjusted according to total RNA content, as measured by RIBOGREEN®. Results are presented as percent inhibition of PNPLA3, relative to untreated control cells.

TABLE 1

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912709 | 27 | 42 | 2765 | 2780 | GGCATTCCCAGCGCGA | 0 | 17 |
| 912710 | 95 | 110 | 2833 | 2848 | TCCTGATCCGCAGCAG | 15 | 18 |
| 912711 | 103 | 118 | 2841 | 2856 | GGCTCGGGTCCTGATC | 0 | 19 |
| 912712 | 131 | 146 | 2869 | 2884 | GTTAGGATCTGGGTCG | 91 | 20 |
| 912713 | 164 | 179 | 2902 | 2917 | GTACATGGCGGCGGCG | 0 | 21 |
| 912714 | 183 | 198 | 2921 | 2936 | TCCAGCCGCGCTCTGC | 23 | 22 |
| 912715 | 196 | 211 | 2934 | 2949 | GCGAAGGACAAGCTCC | 60 | 23 |
| 912716 | 197 | 212 | 2935 | 2950 | CGCGAAGGACAAGCTC | 0 | 24 |
| 912717 | 272 | 287 | 3010 | 3025 | GCGGAGGAGGTGCGGG | 0 | 25 |
| 912718 | 273 | 288 | 3011 | 3026 | CGCGGAGGAGGTGCGG | 0 | 26 |
| 912719 | 274 | 289 | 3012 | 3027 | TCGCGGAGGAGGTGCG | 19 | 27 |
| 912720 | 290 | 305 | 3028 | 3043 | GAACAACATGCGCGCG | 0 | 28 |
| 912721 | 291 | 306 | 3029 | 3044 | CGAACAACATGCGCGC | 7 | 29 |
| 912722 | 292 | 307 | 3030 | 3045 | CCGAACAACATGCGCG | 21 | 30 |
| 912723 | 293 | 308 | 3031 | 3046 | GCCGAACAACATGCGC | 0 | 31 |
| 912724 | 294 | 309 | 3032 | 3047 | CGCCGAACAACATGCG | 0 | 32 |
| 912725 | 323 | 338 | 3061 | 3076 | GCCGACGCAGTGCAAC | 0 | 33 |
| 912726 | 324 | 339 | 3062 | 3077 | CGCCGACGCAGTGCAA | 0 | 34 |
| 912727 | 340 | 355 | 3078 | 3093 | GGGATACCGGAGAGGA | 43 | 35 |
| 912728 | 370 | 385 | 5944 | 5959 | TCTGAGAGGACCTGCA | 53 | 36 |
| 912729 | 375 | 390 | 5949 | 5964 | CAAGATCTGAGAGGAC | 64 | 37 |
| 912730 | 404 | 419 | 5978 | 5993 | GCCAATGTTCCGACTC | 71 | 38 |
| 912731 | 410 | 425 | 5984 | 5999 | GAAGATGCCAATGTTC | 51 | 39 |
| 912732 | 429 | 444 | 6003 | 6018 | TTAAGTTGAAGGATGG | 96 | 40 |
| 912733 | 432 | 447 | 6006 | 6021 | TGCTTAAGTTGAAGGA | 90 | 41 |
| 912734 | 478 | 493 | 6052 | 6067 | TGGACATTGGCCGGGA | 85 | 42 |
| 912735 | 479 | 494 | 6053 | 6068 | GTGGACATTGGCCGGG | 50 | 43 |
| 912736 | 484 | 499 | 6058 | 6073 | AGCTGGTGGACATTGG | 64 | 44 |

TABLE 1-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912737 | 528 | 543 | 6102 | 6117 | CATCAGACACTCTGGT | 5 | 45 |
| 912738 | 531 | 546 | 6105 | 6120 | CCCCATCAGACACTCT | 73 | 46 |
| 912739 | 552 | 567 | 6126 | 6141 | AGTCAGACACCAGAAC | 54 | 47 |
| 912755 | 693 | 708 | 11911 | 11926 | TGGCATCAATGAAGGG | 74 | 48 |
| 912756 | 698 | 713 | 11916 | 11931 | TGTTTTGGCATCAATG | 91 | 49 |
| 912757 | 746 | 761 | 11964 | 11979 | TTTAGGGCAGATGTCG | 89 | 50 |
| 912758 | 747 | 762 | 11965 | 11980 | CTTTAGGGCAGATGTC | 90 | 51 |
| 912759 | 795 | 810 | 12013 | 12028 | GTAGACTGAGCTTGGT | 98 | 52 |
| 912760 | 820 | 835 | 12038 | 12053 | AGGTAGAGGTTCCCTG | 0 | 53 |
| 912761 | 841 | 856 | 12059 | 12074 | GGGACAAAAGCTCTCG | 20 | 54 |
| 912762 | 873 | 888 | 13609 | 13624 | GGCATATCTCTCCCAG | 0 | 55 |
| 912763 | 874 | 889 | 13610 | 13625 | AGGCATATCTCTCCCA | 0 | 56 |
| 912764 | 886 | 901 | 13622 | 13637 | AAATATCCTCGAAGGC | 57 | 57 |
| 912765 | 888 | 903 | 13624 | 13639 | CCAAATATCCTCGAAG | 30 | 58 |
| 912766 | 889 | 904 | 13625 | 13640 | TCCAAATATCCTCGAA | 38 | 59 |
| 912767 | 894 | 909 | 13630 | 13645 | ATGCATCCAAATATCC | 58 | 60 |
| 912768 | 925 | 940 | N/A | N/A | TTGCAGATGCCCTTCT | 15 | 61 |
| 912769 | 968 | 983 | 16088 | 16103 | ATCCATCCCTTCTGAG | 34 | 62 |
| 912770 | 986 | 1001 | 16106 | 16121 | GGGCATGGCGACCTCA | 0 | 63 |
| 912771 | 1004 | 1019 | 16124 | 16139 | ACTCATGTTTGCCCAG | 67 | 64 |
| 912772 | 1068 | 1083 | 16188 | 16203 | GGTCTAGCAGCTCATC | 89 | 65 |
| 912773 | 1075 | 1090 | 16195 | 16210 | CGCAGGTGGTCTAGCA | 0 | 66 |
| 912774 | 1076 | 1091 | 16196 | 16211 | ACGCAGGTGGTCTAGC | 25 | 67 |
| 912775 | 1080 | 1095 | 16200 | 16215 | TGAGACGCAGGTGGTC | 50 | 68 |
| 912776 | 1086 | 1101 | 16206 | 16221 | GGATGCTGAGACGCAG | 67 | 69 |
| 912777 | 1172 | 1187 | 19012 | 19027 | GTATCCACCTTTGTCT | 78 | 70 |
| 912778 | 1178 | 1193 | 19018 | 19033 | GCTCATGTATCCACCT | 79 | 71 |
| 912779 | 1187 | 1202 | 19027 | 19042 | GCAAATCTTGCTCATG | 3 | 72 |
| 912780 | 1188 | 1203 | 19028 | 19043 | TGCAAATCTTGCTCAT | 13 | 73 |
| 912781 | 1189 | 1204 | 19029 | 19044 | TTGCAAATCTTGCTCA | 0 | 74 |
| 912782 | 1195 | 1210 | 19035 | 19050 | AGCAAGTTGCAAATCT | 77 | 75 |
| 912783 | 1199 | 1214 | 19039 | 19054 | GGGTAGCAAGTTGCAA | 74 | 76 |
| 912784 | 1205 | 1220 | 19045 | 19060 | CCTAATGGGTAGCAAG | 62 | 77 |
| 912785 | 1206 | 1221 | 19046 | 19061 | TCCTAATGGGTAGCAA | 79 | 78 |

TABLE 2

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912786 | 1207 | 1222 | 19047 | 19062 | ATCCTAATGGGTAGCA | 81 | 79 |
| 912787 | 1211 | 1226 | 19051 | 19066 | CATTATCCTAATGGGT | 46 | 80 |
| 912788 | 1212 | 1227 | 19052 | 19067 | ACATTATCCTAATGGG | 0 | 81 |
| 912789 | 1213 | 1228 | 19053 | 19068 | GACATTATCCTAATGG | 70 | 82 |
| 912790 | 1220 | 1235 | 19060 | 19075 | TACATAAGACATTATC | 34 | 83 |
| 912791 | 1224 | 1239 | 19064 | 19079 | GCATTACATAAGACAT | 86 | 84 |
| 912792 | 1245 | 1260 | 19085 | 19100 | CCACAGGCAGGGTACA | 76 | 85 |
| 912793 | 1246 | 1261 | 19086 | 19101 | TCCACAGGCAGGGTAC | 28 | 86 |
| 912794 | 1253 | 1268 | 19093 | 19108 | GGCAGATTCCACAGGC | 75 | 87 |
| 912795 | 1259 | 1274 | 19099 | 19114 | CGCAATGGCAGATTCC | 92 | 88 |
| 912796 | 1265 | 1280 | 19105 | 19120 | GACAATCGCAATGGCA | 64 | 89 |
| 912797 | 1266 | 1281 | 19106 | 19121 | GGACAATCGCAATGGC | 75 | 90 |
| 912798 | 1267 | 1282 | 19107 | 19122 | TGGACAATCGCAATGG | 73 | 91 |
| 912799 | 1285 | 1300 | 23690 | 23705 | AGCCATGTCACCAGTC | 67 | 92 |
| 912800 | 1289 | 1304 | 23694 | 23709 | TGGAAGCCATGTCACC | 24 | 93 |
| 912801 | 1290 | 1305 | 23695 | 23710 | CTGGAAGCCATGTCAC | 72 | 94 |
| 912802 | 1297 | 1312 | 23702 | 23717 | GGCATATCTGGAAGCC | 0 | 95 |
| 912803 | 1298 | 1313 | 23703 | 23718 | GGGCATATCTGGAAGC | 0 | 96 |
| 912804 | 1351 | 1366 | 23756 | 23771 | AGCACTCGAGTGAACA | 0 | 97 |
| 912805 | 1386 | 1401 | N/A | N/A | GCATTTGGGACCTGGA | 77 | 98 |
| 912806 | 1387 | 1402 | N/A | N/A | GGCATTTGGGACCTGG | 60 | 99 |
| 912807 | 1388 | 1403 | 25151 | 25166 | TGGCATTTGGGACCTG | 41 | 100 |
| 912808 | 1394 | 1409 | 25157 | 25172 | GCTCACTGGCATTTGG | 44 | 101 |
| 912809 | 1523 | 1538 | 25286 | 25301 | GTTCAGGCTGGACCTG | 49 | 102 |
| 912810 | 1547 | 1562 | 25310 | 25325 | AGGTACTTTATTGCCC | 11 | 103 |
| 912811 | 1550 | 1565 | 25313 | 25328 | AGCAGGTACTTTATTG | 64 | 104 |
| 912812 | 1653 | 1668 | 25416 | 25431 | AACTTTAGCACCTCTG | 91 | 105 |
| 912813 | 1655 | 1670 | 25418 | 25433 | GAAACTTTAGCACCTC | 88 | 106 |
| 912814 | 1656 | 1671 | 25419 | 25434 | GGAAACTTTAGCACCT | 53 | 107 |
| 912815 | 1669 | 1684 | 25432 | 25447 | CTGCACAAAGATGGGA | 80 | 108 |
| 912816 | 1671 | 1686 | 25434 | 25449 | AGCTGCACAAAGATGG | 45 | 109 |
| 912817 | 1685 | 1700 | 25448 | 25463 | AGCAATGCGGAGGTAG | 15 | 110 |
| 912818 | 1740 | 1755 | 25503 | 25518 | ACCAACTCAGCTCAGA | 85 | 111 |
| 912819 | 1741 | 1756 | 25504 | 25519 | AACCAACTCAGCTCAG | 79 | 112 |
| 912820 | 1757 | 1772 | 25520 | 25535 | TCCTAGCTTTTCATAA | 23 | 113 |
| 912821 | 1788 | 1803 | 25551 | 25566 | TGCTGGACCGCTGCAC | 0 | 114 |

TABLE 2-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912822 | 1796 | 1811 | 25559 | 25574 | GAGTTAAGTGCTGGAC | 93 | 115 |
| 912823 | 1802 | 1817 | 25565 | 25580 | GTATTAGAGTTAAGTG | 92 | 116 |
| 912824 | 1803 | 1818 | 25566 | 25581 | TGTATTAGAGTTAAGT | 79 | 117 |
| 912825 | 1806 | 1821 | 25569 | 25584 | TGATGTATTAGAGTTA | 92 | 118 |
| 912826 | 1808 | 1823 | 25571 | 25586 | GCTGATGTATTAGAGT | 80 | 119 |
| 912827 | 1821 | 1836 | 25584 | 25599 | TGAATTAACGCATGCT | 83 | 120 |
| 912828 | 1822 | 1837 | 25585 | 25600 | CTGAATTAACGCATGC | 78 | 121 |
| 912829 | 1870 | 1885 | 25633 | 25648 | AGTAAGGGACCCTCTG | 17 | 122 |
| 912830 | 1871 | 1886 | 25634 | 25649 | CAGTAAGGGACCCTCT | 28 | 123 |
| 912831 | 1872 | 1887 | 25635 | 25650 | TCAGTAAGGGACCCTC | 77 | 124 |
| 912832 | 1874 | 1889 | 25637 | 25652 | AGTCAGTAAGGGACCC | 51 | 125 |
| 912833 | 1893 | 1908 | 25656 | 25671 | ATTAATAGGGCCACGA | 80 | 126 |
| 912834 | 1895 | 1910 | 25658 | 25673 | CCATTAATAGGGCCAC | 90 | 127 |
| 912835 | 1896 | 1911 | 25659 | 25674 | ACCATTAATAGGGCCA | 81 | 128 |
| 912836 | 1906 | 1921 | 25669 | 25684 | GAACAGTCTGACCATT | 82 | 129 |
| 912837 | 1908 | 1923 | 25671 | 25686 | TGGAACAGTCTGACCA | 31 | 130 |
| 912838 | 1909 | 1924 | 25672 | 25687 | CTGGAACAGTCTGACC | 83 | 131 |
| 912839 | 1911 | 1926 | 25674 | 25689 | TGCTGGAACAGTCTGA | 72 | 132 |
| 912840 | 1916 | 1931 | 25679 | 25694 | CCTCATGCTGGAACAG | 83 | 133 |
| 912841 | 1928 | 1943 | 25691 | 25706 | TCATTCTAAGAACCTC | 96 | 134 |
| 912842 | 1945 | 1960 | 25708 | 25723 | ACCCATCCAAACACCT | 16 | 135 |
| 912843 | 1982 | 1997 | 25745 | 25760 | ACACATGGGCCAGCCT | 70 | 136 |
| 912844 | 1989 | 2004 | 25752 | 25767 | CAAGATCACACATGGG | 70 | 137 |
| 912845 | 2057 | 2072 | 25820 | 25835 | GGGACGAACTGCACCC | 0 | 138 |
| 912846 | 2098 | 2113 | 25861 | 25876 | TATCATCTTTGCAGAC | 81 | 139 |
| 912847 | 2116 | 2131 | 25879 | 25894 | GTTTTTAGTAGTCAAG | 91 | 140 |
| 912848 | 2117 | 2132 | 25880 | 25895 | CGTTTTTAGTAGTCAA | 91 | 141 |
| 912849 | 2145 | 2160 | 25908 | 25923 | TATCATCTTGTTACCC | 85 | 142 |
| 912850 | 2148 | 2163 | 25911 | 25926 | GATTATCATCTTGTTA | 70 | 143 |
| 912851 | 2150 | 2165 | 25913 | 25928 | TAGATTATCATCTTGT | 53 | 144 |
| 912852 | 2151 | 2166 | 25914 | 25929 | GTAGATTATCATCTTG | 80 | 145 |
| 912853 | 2152 | 2167 | 25915 | 25930 | AGTAGATTATCATCTT | 84 | 146 |
| 912854 | 2175 | 2190 | 25938 | 25953 | GTGAAAAAGGTGTTCT | 77 | 147 |
| 912855 | 2182 | 2197 | 25945 | 25960 | TAGTTAGGTGAAAAAG | 92 | 148 |
| 912856 | 2188 | 2203 | 25951 | 25966 | TTATTTTAGTTAGGTG | 88 | 149 |

TABLE 2-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912857 | 2190 | 2205 | 25953 | 25968 | CATTATTTTAGTTAGG | 86 | 150 |
| 912858 | 2273 | 2288 | 26036 | 26051 | CTACTAACATCTCACT | 55 | 151 |
| 912859 | 2274 | 2289 | 26037 | 26052 | TCTACTAACATCTCAC | 89 | 152 |
| 912860 | 2278 | 2293 | 26041 | 26056 | TTATTCTACTAACATC | 27 | 153 |
| 912861 | 2280 | 2295 | 26043 | 26058 | GCTTATTCTACTAACA | 79 | 154 |
| 912862 | 2281 | 2296 | 26044 | 26059 | GGCTTATTCTACTAAC | 81 | 155 |
| 912863 | 2632 | 2647 | 26395 | 26410 | GGTGAATGCCCTGCAC | 41 | 156 |

TABLE 3

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912864 | 2703 | 2718 | 26466 | 26481 | TTCAAGTTGTGTGCTC | 90 | 157 |
| 912865 | 2755 | 2770 | 26518 | 26533 | GGGAGAAACTCACTGA | 37 | 158 |
| 912866 | N/A | N/A | 4416 | 4431 | TGCTACTTGCCCCAGC | 2 | 159 |
| 912867 | N/A | N/A | 4421 | 4436 | CACAATGCTACTTGCC | 87 | 160 |
| 912868 | N/A | N/A | 4584 | 4599 | CCCAATGGCAGGGCTT | 58 | 161 |
| 912869 | N/A | N/A | 4592 | 4607 | TGCTCCTACCCAATGG | 46 | 162 |
| 912870 | N/A | N/A | 4766 | 4781 | GACTTTTATTGTTGCT | 95 | 163 |
| 912871 | N/A | N/A | 4883 | 4898 | TTCTATACCAGAGTGA | 89 | 164 |
| 912872 | N/A | N/A | 4884 | 4899 | TTTCTATACCAGAGTG | 89 | 165 |
| 912873 | N/A | N/A | 5405 | 5420 | GTAGATGGCCTTAATG | 83 | 166 |
| 912876 | N/A | N/A | 6155 | 6170 | TACATCCACGACTTCG | 94 | 167 |
| 912877 | N/A | N/A | 6156 | 6171 | TTACATCCACGACTTC | 76 | 168 |
| 912880 | N/A | N/A | 6606 | 6621 | GGAACATTCAGGGTTT | 13 | 169 |
| 912881 | N/A | N/A | 6834 | 6849 | ATTACTTGGGTGCAGG | 55 | 170 |
| 912884 | N/A | N/A | 6838 | 6853 | GCAGATTACTTGGGTG | 45 | 171 |
| 912885 | N/A | N/A | 6931 | 6946 | TGCAGGACAGGTTCCT | 30 | 172 |
| 912888 | N/A | N/A | 7549 | 7564 | CACACTGGGTCACCAC | 55 | 173 |
| 912889 | N/A | N/A | 7552 | 7567 | AGTCACACTGGGTCAC | 61 | 174 |
| 912928 | N/A | N/A | 12273 | 12288 | GGTATATGTTCCCAGG | 87 | 175 |
| 912929 | N/A | N/A | 12314 | 12329 | TATAACCACAGCCTGG | 29 | 176 |
| 912932 | N/A | N/A | 12321 | 12336 | CTGACTATATAACCAC | 81 | 177 |
| 912933 | N/A | N/A | 12666 | 12681 | ATCTTAGTGGCTGGGT | 91 | 178 |

TABLE 3-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912936 | N/A | N/A | 12767 | 12782 | CTTACTATGGTAGAGT | 88 | 179 |
| 912937 | N/A | N/A | 12768 | 12783 | TCTTACTATGGTAGAG | 74 | 180 |
| 912940 | N/A | N/A | 12835 | 12850 | TGCATTGCATAGCCTT | 97 | 181 |
| 912941 | N/A | N/A | 12836 | 12851 | TTGCATTGCATAGCCT | 96 | 182 |
| 912944 | N/A | N/A | 12907 | 12922 | TGCTTATAAAGCACAC | 61 | 183 |
| 912945 | N/A | N/A | 12988 | 13003 | GGAATAAGCCTCCACC | 14 | 184 |
| 912948 | N/A | N/A | 14055 | 14070 | GAAATCTGATTGCTTC | 59 | 185 |
| 912949 | N/A | N/A | 14393 | 14408 | TACTTATCTGCTCACT | 66 | 186 |
| 912952 | N/A | N/A | 14673 14707 | 14688 14722 | TCTCTTAGTGTCCCCA | 90 | 187 |
| 912953 | N/A | N/A | 14674 14708 | 14689 14723 | ATCTCTTAGTGTCCCC | 92 | 188 |
| 912956 | N/A | N/A | 15284 | 15299 | TCACATTCATGCTTGC | 82 | 189 |
| 912957 | N/A | N/A | 15291 | 15306 | GATAACCTCACATTCA | 0 | 190 |
| 912960 | N/A | N/A | 15712 | 15727 | GAGCTAGGTGCTTCAC | 6 | 191 |
| 912961 | N/A | N/A | 15753 | 15768 | ATAACAACTGAACCAC | 85 | 192 |
| 912964 | N/A | N/A | 15937 | 15952 | GTTATTAGCCAAATGC | 92 | 193 |
| 912965 | N/A | N/A | 16468 | 16483 | GGAGACTTGGCAAGGT | 87 | 194 |
| 912968 | N/A | N/A | 16960 | 16975 | ATTCATGACAGCCCTT | 46 | 195 |
| 912969 | N/A | N/A | 17128 | 17143 | ATCGATTTTTCAGAGT | 9 | 196 |
| 912972 | N/A | N/A | 17134 | 17149 | ACAAACATCGATTTTT | 52 | 197 |
| 912973 | N/A | N/A | 17769 | 17784 | CTCTTTAATGACCTCG | 90 | 198 |
| 912976 | N/A | N/A | 18865 | 18880 | GTCAGAGGCACTCACA | 25 | 199 |
| 912977 | N/A | N/A | 18959 | 18974 | AGCTATTATCTCCCAC | 0 | 200 |
| 912980 | N/A | N/A | 19315 | 19330 | AGTTTCTGGGCTTGCA | 90 | 201 |
| 912981 | N/A | N/A | 19382 | 19397 | GGCAATCACAAGAGAC | 73 | 202 |
| 912984 | N/A | N/A | 20286 20316 | 20301 20331 | AGAGGAAGCCCAATCA | 79 | 203 |
| 912985 | N/A | N/A | 20287 20317 | 20302 20332 | CAGAGGAAGCCCAATC | 93 | 204 |
| 912988 | N/A | N/A | 20658 | 20673 | TAGAAATTGCAGTGCC | 92 | 205 |
| 912989 | N/A | N/A | 20731 | 20746 | TCCTATCCATATATTG | 55 | 206 |
| 912992 | N/A | N/A | 21408 | 21423 | GCAATTCTAGACATGG | 88 | 207 |
| 912993 | N/A | N/A | 21558 | 21573 | AGGACTTACACCAAGA | 86 | 208 |
| 912996 | N/A | N/A | 21936 | 21951 | TTCCTAATAAGAGCCC | 24 | 209 |
| 912997 | N/A | N/A | 21946 | 21961 | GTCAAACATCTTCCTA | 66 | 210 |
| 913000 | N/A | N/A | 22077 | 22092 | AAAACTGTAGGATAGG | 47 | 211 |

TABLE 3-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 913001 | N/A | N/A | 22162 | 22177 | GTTACATCCATAAAAC | 0 | 212 |
| 913004 | N/A | N/A | 22169 | 22184 | AGAGAATGTTACATCC | 62 | 213 |
| 913008 | N/A | N/A | 23083 | 23098 | AAAGATTAATCAGGGC | 61 | 214 |
| 913012 | N/A | N/A | 23788 | 23803 | GTATTTACCTGGAGGC | 0 | 215 |
| 913016 | N/A | N/A | 24426 | 24441 | GGCCTATGATTTTCAG | 0 | 216 |

TABLE 4

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912874 | N/A | N/A | 5869 | 5884 | ATACTTTTGGCAAGGC | 96 | 217 |
| 912875 | N/A | N/A | 5870 | 5885 | AATACTTTTGGCAAGG | 91 | 218 |
| 912878 | N/A | N/A | 6159 | 6174 | TGCTTACATCCACGAC | 12 | 219 |
| 912879 | N/A | N/A | 6296 | 6311 | CATCATGTTGGTCTCG | 54 | 220 |
| 912882 | N/A | N/A | 6835 | 6850 | GATTACTTGGGTGCAG | 39 | 221 |
| 912883 | N/A | N/A | 6837 | 6852 | CAGATTACTTGGGTGC | 69 | 222 |
| 912886 | N/A | N/A | 7083 | 7098 | TTTAATGGTGTTTTGG | 87 | 223 |
| 912887 | N/A | N/A | 7478 | 7493 | TCAAATGCCGGTATTC | 52 | 224 |
| 912890 | N/A | N/A | 7587 | 7602 | GTGAACTTCAACTTCC | 56 | 225 |
| 912930 | N/A | N/A | 12317 | 12332 | CTATATAACCACAGCC | 77 | 226 |
| 912931 | N/A | N/A | 12319 | 12334 | GACTATATAACCACAG | 92 | 227 |
| 912934 | N/A | N/A | 12670 | 12685 | AATCATCTTAGTGGCT | 91 | 228 |
| 912935 | N/A | N/A | 12765 | 12780 | TACTATGGTAGAGTGG | 80 | 229 |
| 912938 | N/A | N/A | 12786 | 12801 | GTACATGGTCTGCAAA | 84 | 230 |
| 912939 | N/A | N/A | 12787 | 12802 | TGTACATGGTCTGCAA | 57 | 231 |
| 912942 | N/A | N/A | 12843 | 12858 | GCATGCATTGCATTGC | 16 | 232 |
| 912943 | N/A | N/A | 12885 | 12900 | ACCAATCCTGTTAGAC | 93 | 233 |
| 912946 | N/A | N/A | 13557 | 13572 | GGAGACACCAAGCACC | 42 | 234 |
| 912947 | N/A | N/A | 13751 | 13766 | GCACTAAGTGTTAGAA | 79 | 235 |
| 912950 | N/A | N/A | 14396 | 14411 | GCTTACTTATCTGCTC | 0 | 236 |
| 912951 | N/A | N/A | 14501 | 14516 | GGAGATCCATCCTGCA | 0 | 237 |
| 912954 | N/A | N/A | 14675 14709 | 14690 14724 | CATCTCTTAGTGTCCC | 92 | 238 |
| 912955 | N/A | N/A | 15122 | 15137 | TCCTAATGTCCTCAAC | 9 | 239 |

TABLE 4-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912958 | N/A | N/A | 15293 | 15308 | AAGATAACCTCACATT | 33 | 240 |
| 912959 | N/A | N/A | 15294 | 15309 | CAAGATAACCTCACAT | 22 | 241 |
| 912962 | N/A | N/A | 15754 | 15769 | TATAACAACTGAACCA | 82 | 242 |
| 912963 | N/A | N/A | 15856 | 15871 | GCTTTAAAGCAGGACA | 8 | 243 |
| 912966 | N/A | N/A | 16774 | 16789 | AAAATTGTGGGTTTAG | 68 | 244 |
| 912967 | N/A | N/A | 16850 | 16865 | ATCATTTGGACCATAG | 81 | 245 |
| 912970 | N/A | N/A | 17130 | 17145 | ACATCGATTTTTCAGA | 83 | 246 |
| 912971 | N/A | N/A | 17133 | 17148 | CAAACATCGATTTTTC | 62 | 247 |
| 912974 | N/A | N/A | 17843 | 17858 | GCTTTACAAGCTGGTC | 0 | 248 |
| 912975 | N/A | N/A | 17879 | 17894 | ATCTATGTTCTCCTAG | 0 | 249 |
| 912978 | N/A | N/A | 19125 | 19140 | ACCTAAAATGCTCACC | 0 | 250 |
| 912979 | N/A | N/A | 19198 | 19213 | CCAGACTACATGCCAC | 79 | 251 |
| 912982 | N/A | N/A | 19446 | 19461 | TCTACTAGGCATCTCT | 63 | 252 |
| 912983 | N/A | N/A | 19447 | 19462 | TTCTACTAGGCATCTC | 42 | 253 |
| 912986 | N/A | N/A | 20288 20318 | 20303 20333 | TCAGAGGAAGCCCAAT | 92 | 254 |
| 912987 | N/A | N/A | 20656 | 20671 | GAAATTGCAGTGCCCT | 92 | 255 |
| 912990 | N/A | N/A | 21393 | 21408 | GCCAACCTATCACTGA | 60 | 256 |
| 912991 | N/A | N/A | 21400 | 21415 | AGACATGGCCAACCTA | 32 | 257 |
| 912994 | N/A | N/A | 21565 | 21580 | TGAAATAAGGACTTAC | 67 | 258 |
| 912995 | N/A | N/A | 21934 | 21949 | CCTAATAAGAGCCCCA | 31 | 259 |
| 912998 | N/A | N/A | 22041 | 22056 | GAAATCTGTCAGAGCA | 33 | 260 |
| 912999 | N/A | N/A | 22072 | 22087 | TGTAGGATAGGACTAG | 0 | 261 |
| 913002 | N/A | N/A | 22166 | 22181 | GAATGTTACATCCATA | 53 | 262 |
| 913003 | N/A | N/A | 22168 | 22183 | GAGAATGTTACATCCA | 80 | 263 |
| 913005 | N/A | N/A | 22605 | 22620 | GTGATAAATCTGCAAG | 70 | 264 |
| 913006 | N/A | N/A | 23081 | 23096 | AGATTAATCAGGGCCA | 8 | 265 |
| 913007 | N/A | N/A | 23082 | 23097 | AAGATTAATCAGGGCC | 30 | 266 |
| 913009 | N/A | N/A | 23325 | 23340 | GGTCACATGTGAGCCC | 0 | 267 |
| 913010 | N/A | N/A | 23496 | 23511 | CACTTCTGGTTCAAGA | 13 | 268 |
| 913011 | N/A | N/A | 23580 | 23595 | CCAATCTGATGACTTC | 80 | 269 |
| 913013 | N/A | N/A | 23790 | 23805 | AAGTATTTACCTGGAG | 0 | 270 |
| 913014 | N/A | N/A | 24028 | 24043 | CACTCAAAGAGACTCA | 65 | 271 |
| 913015 | N/A | N/A | 24425 | 24440 | GCCTATGATTTTCAGG | 0 | 272 |
| 913017 | N/A | N/A | 24633 | 24648 | CACTACTGCCCTCTTC | 50 | 273 |

TABLE 4-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 913018 | N/A | N/A | 24983 | 24998 | TGCTGGGCTGATGTCA | 0 | 274 |
| 913019 | N/A | N/A | 25150 | 25165 | GGCATTTGGGACCTGA | 67 | 275 |

TABLE 5

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915343 | 1 | 16 | 2739 | 2754 | GCCCCCCTCGGACCAT | 0 | 276 |
| 915363 | 45 | 60 | 2783 | 2798 | CCTCAGTGTCTCGGCC | 0 | 277 |
| 915383 | 107 | 122 | 2845 | 2860 | AATCGGCTCGGGTCCT | 29 | 278 |
| 915403 | 190 | 205 | 2928 | 2943 | GACAAGCTCCAGCCGC | 64 | 279 |
| 915423 | 249 | 264 | 2987 | 3002 | CGCTCAGGCAGCGGGT | 0 | 280 |
| 915443 | 347 | 362 | N/A | N/A | CTCCAGCGGGATACCG | 6 | 281 |
| 915463 | 386 | 401 | 5960 | 5975 | GGCCTTCCGCACAAGA | 0 | 282 |
| 915483 | 416 | 431 | 5990 | 6005 | TGGATGGAAGATGCCA | 28 | 283 |
| 915503 | 452 | 467 | 6026 | 6041 | GAGACCCTGTCGGAGG | 45 | 284 |
| 915523 | 488 | 503 | 6062 | 6077 | GATGAGCTGGTGGACA | 70 | 285 |
| 915543 | 510 | 525 | 6084 | 6099 | GAGAGATGCCTATTTT | 92 | 286 |
| 915563 | 559 | 574 | 6133 | 6148 | GACCGAAAGTCAGACA | 7 | 287 |
| 915603 | 697 | 712 | 11915 | 11930 | GTTTTGGCATCAATGA | 94 | 288 |
| 915623 | 754 | 769 | 11972 | 11987 | GACTTGACTTTAGGGC | 98 | 289 |
| 915643 | 827 | 842 | 12045 | 12060 | CGAGAGAAGGTAGAGG | 97 | 290 |
| 915663 | 879 | 894 | 13615 | 13630 | CTCGAAGGCATATCTC | 66 | 291 |
| 915683 | 932 | 947 | 16052 | 16067 | GGGCCTGTTGCAGATG | 0 | 292 |
| 915703 | 985 | 1000 | 16105 | 16120 | GGCATGGCGACCTCAG | 6 | 293 |
| 915723 | 1037 | 1052 | 16157 | 16172 | AGCCAAGGCAGCCGAC | 0 | 294 |
| 915743 | 1132 | 1147 | 16252 | 16267 | GCGAGCCTGGGCGAGA | 0 | 295 |
| 915763 | 1177 | 1192 | 19017 | 19032 | CTCATGTATCCACCTT | 88 | 296 |
| 915783 | 1229 | 1244 | 19069 | 19084 | GGGCAGCATTACATAA | 73 | 297 |
| 915803 | 1286 | 1301 | 23691 | 23706 | AAGCCATGTCACCAGT | 34 | 298 |
| 915823 | 1348 | 1363 | 23753 | 23768 | ACTCGAGTGAACACCT | 12 | 299 |
| 915843 | 1405 | 1420 | 25168 | 25183 | GCCTGTTGGCTGCTCA | 1 | 300 |
| 915863 | 1473 | 1488 | 25236 | 25251 | CTGCTGGACAGCCCTT | 0 | 301 |

TABLE 5-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915883 | 1542 | 1557 | 25305 | 25320 | CTTTATTGCCCAAGAA | 72 | 302 |
| 915903 | 1601 | 1616 | 25364 | 25379 | CAGACTCTTCTCTAGT | 49 | 303 |
| 915923 | 1633 | 1648 | 25396 | 25411 | AATCTGCTAGACTCGC | 88 | 304 |
| 915943 | 1686 | 1701 | 25449 | 25464 | CAGCAATGCGGAGGTA | 80 | 305 |
| 915963 | 1768 | 1783 | 25531 | 25546 | GAAAGGTTGCTTCCTA | 84 | 306 |
| 915983 | 1789 | 1804 | 25552 | 25567 | GTGCTGGACCGCTGCA | 11 | 307 |
| 916003 | 1815 | 1830 | 25578 | 25593 | AACGCATGCTGATGTA | 69 | 308 |
| 916023 | 1848 | 1863 | 25611 | 25626 | GCTTCCTGGTGTCATT | 81 | 309 |
| 916043 | 1884 | 1899 | 25647 | 25662 | GCCACGAAACAGTCAG | 67 | 310 |
| 916063 | 1913 | 1928 | 25676 | 25691 | CATGCTGGAACAGTCT | 20 | 311 |
| 916083 | 1954 | 1969 | 25717 | 25732 | AAGGCCCCCACCCATC | 0 | 312 |
| 916103 | 1977 | 1992 | 25740 | 25755 | TGGGCCAGCCTACCCC | 0 | 313 |
| 916123 | 2026 | 2041 | 25789 | 25804 | GGAAGTGGGATCATGC | 55 | 314 |
| 916142 | 2100 | 2115 | 25863 | 25878 | GTTATCATCTTTGCAG | 57 | 315 |
| 916162 | 2139 | 2154 | 25902 | 25917 | CTTGTTACCCCCGCCA | 84 | 316 |
| 916182 | 2264 | 2279 | 26027 | 26042 | TCTCACTGATTCACAT | 83 | 317 |
| 916202 | 2624 | 2639 | 26387 | 26402 | CCCTGCACACTAGATT | 55 | 318 |
| 916222 | 2677 | 2692 | 26440 | 26455 | GAGGCGGAAGCTCCTG | 0 | 319 |
| 916242 | 2707 | 2722 | 26470 | 26485 | CAGGTTCAAGTTGTGT | 83 | 320 |
| 916282 | N/A | N/A | 4225 | 4240 | AAATGTACGGAATCTC | 79 | 321 |
| 916302 | N/A | N/A | 4822 | 4837 | GTGTAAACATTTGTCC | 74 | 322 |
| 916322 | N/A | N/A | 5414 | 5429 | AGCTTTGGTGTAGATG | 49 | 323 |
| 916342 | N/A | N/A | 5801 | 5816 | TACTATGGGAGCCACA | 42 | 324 |
| 916362 | N/A | N/A | 6866 | 6881 | TGAAATTGTAACTGCC | 70 | 325 |
| 916382 | N/A | N/A | 7492 | 7507 | TAGATCGGTGCTGTTC | 27 | 326 |
| 916402 | N/A | N/A | 7785 | 7800 | GTTATAGGCGAGAGCA | 0 | 327 |
| 916562 | N/A | N/A | 12316 | 12331 | TATATAACCACAGCCT | 58 | 328 |
| 916582 | N/A | N/A | 12932 | 12947 | ATAAGAGCTGTCTCCT | 94 | 329 |
| 916602 | N/A | N/A | 13703 | 13718 | CTAGTAAATGCTTGTC | 96 | 330 |
| 916622 | N/A | N/A | 14177 | 14192 | CTAATATTTCTACAGC | 0 | 331 |
| 916642 | N/A | N/A | 14672 | 14687 | CTCTTAGTGTCCCCAT | 95 | 332 |
| 916662 | N/A | N/A | 15542 | 15557 | TTCCATCACAAGGCCT | 50 | 333 |
| 916682 | N/A | N/A | 16317 | 16332 | TCCATAATGCACAAGA | 71 | 334 |
| 916702 | N/A | N/A | 17223 | 17238 | TGTAGCTGGTTTGTGG | 88 | 335 |
| 916722 | N/A | N/A | 18223 | 18238 | AACAGCTACATCAGGC | 44 | 336 |
| 916742 | N/A | N/A | 19249 | 19264 | GGCATTGCACATAGAC | 74 | 337 |

TABLE 5-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916761 | N/A | N/A | 20410 | 20425 | GTAAGCAATGCAGCCA | 88 | 338 |
| 916781 | N/A | N/A | 20659 | 20674 | TTAGAAATTGCAGTGC | 91 | 339 |
| 916801 | N/A | N/A | 20989 | 21004 | AGGTATTAAACTGCCA | 25 | 340 |
| 916821 | N/A | N/A | 21506 | 21521 | GTCCTAAGAGCACTCA | 57 | 341 |
| 916841 | N/A | N/A | 22603 | 22618 | GATAAATCTGCAAGAG | 49 | 342 |
| 916861 | N/A | N/A | 23472 | 23487 | GGGACTTACACTGAAA | 66 | 343 |
| 916881 | N/A | N/A | 24314 | 24329 | GTCAACGCAGACTGCT | 33 | 344 |

TABLE 6

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915344 | 2 | 17 | 2740 | 2755 | CGCCCCCCTCGGACCA | 0 | 345 |
| 915364 | 46 | 61 | 2784 | 2799 | GCCTCAGTGTCTCGGC | 0 | 346 |
| 915384 | 108 | 123 | 2846 | 2861 | GAATCGGCTCGGGTCC | 49 | 347 |
| 915404 | 191 | 206 | 2929 | 2944 | GGACAAGCTCCAGCCG | 9 | 348 |
| 915424 | 250 | 265 | 2988 | 3003 | TCGCTCAGGCAGCGGG | 0 | 349 |
| 915444 | 348 | 363 | N/A | N/A | GCTCCAGCGGGATACC | 0 | 350 |
| 915464 | 387 | 402 | 5961 | 5976 | TGGCCTTCCGCACAAG | 0 | 351 |
| 915484 | 428 | 443 | 6002 | 6017 | TAAGTTGAAGGATGGA | 96 | 352 |
| 915504 | 453 | 468 | 6027 | 6042 | AGAGACCCTGTCGGAG | 80 | 353 |
| 915524 | 489 | 504 | 6063 | 6078 | AGATGAGCTGGTGGAC | 81 | 354 |
| 915544 | 512 | 527 | 6086 | 6101 | AAGAGAGATGCCTATT | 77 | 355 |
| 915564 | 560 | 575 | 6134 | 6149 | GGACCGAAAGTCAGAC | 0 | 356 |
| 915604 | 700 | 715 | 11918 | 11933 | GTTGTTTTGGCATCAA | 91 | 357 |
| 915624 | 755 | 770 | 11973 | 11988 | GGACTTGACTTTAGGG | 81 | 358 |
| 915644 | 828 | 843 | 12046 | 12061 | TCGAGAGAAGGTAGAG | 24 | 359 |
| 915664 | 880 | 895 | 13616 | 13631 | CCTCGAAGGCATATCT | 41 | 360 |
| 915684 | 952 | 967 | 16072 | 16087 | GATGACTTCAGGCCTG | 0 | 361 |
| 915704 | 987 | 1002 | 16107 | 16122 | TGGGCATGGCGACCTC | 0 | 362 |
| 915724 | 1038 | 1053 | 16158 | 16173 | CAGCCAAGGCAGCCGA | 0 | 363 |
| 915744 | 1133 | 1148 | 16253 | 16268 | AGCGAGCCTGGGCGAG | 0 | 364 |
| 915764 | 1179 | 1194 | 19019 | 19034 | TGCTCATGTATCCACC | 56 | 365 |

TABLE 6-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915784 | 1230 | 1245 | 19070 | 19085 | AGGGCAGCATTACATA | 69 | 366 |
| 915804 | 1293 | 1308 | 23698 | 23713 | TATCTGGAAGCCATGT | 6 | 367 |
| 915824 | 1349 | 1364 | 23754 | 23769 | CACTCGAGTGAACACC | 0 | 368 |
| 915844 | 1406 | 1421 | 25169 | 25184 | GGCCTGTTGGCTGCTC | 0 | 369 |
| 915864 | 1477 | 1492 | 25240 | 25255 | GTCTCTGCTGGACAGC | 0 | 370 |
| 915884 | 1545 | 1560 | 25308 | 25323 | GTACTTTATTGCCCAA | 73 | 371 |
| 915904 | 1607 | 1622 | 25370 | 25385 | GACTCACAGACTCTTC | 92 | 372 |
| 915924 | 1634 | 1649 | 25397 | 25412 | GAATCTGCTAGACTCG | 65 | 373 |
| 915944 | 1687 | 1702 | 25450 | 25465 | ACAGCAATGCGGAGGT | 83 | 374 |
| 915964 | 1769 | 1784 | 25532 | 25547 | CGAAAGGTTGCTTCCT | 79 | 375 |
| 915984 | 1790 | 1805 | 25553 | 25568 | AGTGCTGGACCGCTGC | 38 | 376 |
| 916004 | 1816 | 1831 | 25579 | 25594 | TAACGCATGCTGATGT | 79 | 377 |
| 916024 | 1849 | 1864 | 25612 | 25627 | GGCTTCCTGGTGTCAT | 73 | 378 |
| 916044 | 1885 | 1900 | 25648 | 25663 | GGCCACGAAACAGTCA | 40 | 379 |
| 916064 | 1914 | 1929 | 25677 | 25692 | TCATGCTGGAACAGTC | 80 | 380 |
| 916084 | 1958 | 1973 | 25721 | 25736 | TCACAAGGCCCCCACC | 35 | 381 |
| 916104 | 1978 | 1993 | 25741 | 25756 | ATGGGCCAGCCTACCC | 0 | 382 |
| 916124 | 2053 | 2068 | 25816 | 25831 | CGAACTGCACCCCTTC | 38 | 383 |
| 916143 | 2101 | 2116 | 25864 | 25879 | GGTTATCATCTTTGCA | 81 | 384 |
| 916163 | 2140 | 2155 | 25903 | 25918 | TCTTGTTACCCCCGCC | 84 | 385 |
| 916183 | 2265 | 2280 | 26028 | 26043 | ATCTCACTGATTCACA | 86 | 386 |
| 916203 | 2625 | 2640 | 26388 | 26403 | GCCCTGCACACTAGAT | 65 | 387 |
| 916223 | 2678 | 2693 | 26441 | 26456 | GGAGGCGGAAGCTCCT | 0 | 388 |
| 916243 | 2709 | 2724 | 26472 | 26487 | GCCAGGTTCAAGTTGT | 62 | 389 |
| 916283 | N/A | N/A | 4226 | 4241 | CAAATGTACGGAATCT | 52 | 390 |
| 916303 | N/A | N/A | 4864 | 4879 | TACTTTAGGCTCCTGG | 90 | 391 |
| 916323 | N/A | N/A | 5422 | 5437 | AGCATTAGAGCTTTGG | 75 | 392 |
| 916343 | N/A | N/A | 5803 | 5818 | TCTACTATGGGAGCCA | 89 | 393 |
| 916363 | N/A | N/A | 6927 | 6942 | GGACAGGTTCCTTGGA | 0 | 394 |
| 916383 | N/A | N/A | 7493 | 7508 | CTAGATCGGTGCTGTT | 14 | 395 |
| 916403 | N/A | N/A | 7786 | 7801 | AGTTATAGGCGAGAGC | 0 | 396 |
| 916563 | N/A | N/A | 12318 | 12333 | ACTATATAACCACAGC | 90 | 397 |
| 916583 | N/A | N/A | 12936 | 12951 | GACAATAAGAGCTGTC | 0 | 398 |
| 916603 | N/A | N/A | 13704 | 13719 | GCTAGTAAATGCTTGT | 73 | 399 |
| 916623 | N/A | N/A | 14231 | 14246 | CCAACTTTTAGTATTA | 92 | 400 |
| 916643 | N/A | N/A | 14678 | 14693 | AGCCATCTCTTAGTGT | 50 | 401 |

TABLE 6-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916663 | N/A | N/A | 15566 | 15581 | TCTGATGTCGAAGAGG | 68 | 402 |
| 916683 | N/A | N/A | 16341 | 16356 | TCCCATGTGGCAGTAC | 0 | 403 |
| 916703 | N/A | N/A | 17239 | 17254 | TCCAAATGCCCAACTC | 37 | 404 |
| 916723 | N/A | N/A | 18241 | 18256 | GCAAATAATGTGCACA | 22 | 405 |
| 916743 | N/A | N/A | 19250 | 19265 | GGGCATTGCACATAGA | 59 | 406 |
| 916762 | N/A | N/A | 20413 | 20428 | GTAGTAAGCAATGCAG | 69 | 407 |
| 916782 | N/A | N/A | 20660 | 20675 | CTTAGAAATTGCAGTG | 91 | 408 |
| 916802 | N/A | N/A | 21002 | 21017 | ATTTTAACAGCTCAGG | 95 | 409 |
| 916822 | N/A | N/A | 21540 | 21555 | TATGACATTTCAGAGT | 88 | 410 |
| 916842 | N/A | N/A | 22629 | 22644 | AGTACAAGCGCAGCCT | 14 | 411 |
| 916862 | N/A | N/A | 23538 | 23553 | ACAAGGACAAGCCCAC | 37 | 412 |
| 916882 | N/A | N/A | 24339 | 24354 | GAAGTAGCGGCATCCC | 68 | 413 |

TABLE 7

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915345 | 3 | 18 | 2741 | 2756 | CCGCCCCCCTCGGACC | 0 | 414 |
| 915365 | 47 | 62 | 2785 | 2800 | TGCCTCAGTGTCTCGG | 0 | 415 |
| 915385 | 109 | 124 | 2847 | 2862 | GGAATCGGCTCGGGTC | 72 | 416 |
| 915405 | 193 | 208 | 2931 | 2946 | AAGGACAAGCTCCAGC | 41 | 417 |
| 915425 | 251 | 266 | 2989 | 3004 | CTCGCTCAGGCAGCGG | 0 | 418 |
| 915445 | 349 | 364 | N/A | N/A | TGCTCCAGCGGGATAC | 0 | 419 |
| 915465 | 388 | 403 | 5962 | 5977 | CTGGCCTTCCGCACAA | 16 | 420 |
| 915485 | 430 | 445 | 6004 | 6019 | CTTAAGTTGAAGGATG | 27 | 421 |
| 915505 | 454 | 469 | 6028 | 6043 | CAGAGACCCTGTCGGA | 72 | 422 |
| 915525 | 492 | 507 | 6066 | 6081 | CGGAGATGAGCTGGTG | 92 | 423 |
| 915545 | 513 | 528 | 6087 | 6102 | TAAGAGAGATGCCTAT | 57 | 424 |
| 915565 | 561 | 576 | 6135 | 6150 | TGGACCGAAAGTCAGA | 0 | 425 |
| 915605 | 701 | 716 | 11919 | 11934 | GGTTGTTTTGGCATCA | 97 | 426 |
| 915625 | 756 | 771 | 11974 | 11989 | TGGACTTGACTTTAGG | 93 | 427 |
| 915645 | 829 | 844 | 12047 | 12062 | CTCGAGAGAAGGTAGA | 0 | 428 |
| 915665 | 881 | 896 | 13617 | 13632 | TCCTCGAAGGCATATC | 0 | 429 |

TABLE 7-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915685 | 953 | 968 | 16073 | 16088 | GGATGACTTCAGGCCT | 0 | 430 |
| 915705 | 988 | 1003 | 16108 | 16123 | CTGGGCATGGCGACCT | 0 | 431 |
| 915725 | 1039 | 1054 | 16159 | 16174 | ACAGCCAAGGCAGCCG | 0 | 432 |
| 915745 | 1134 | 1149 | 16254 | 16269 | TAGCGAGCCTGGGCGA | 0 | 433 |
| 915765 | 1193 | 1208 | 19033 | 19048 | CAAGTTGCAAATCTTG | 0 | 434 |
| 915785 | 1231 | 1246 | 19071 | 19086 | CAGGGCAGCATTACAT | 74 | 435 |
| 915805 | 1300 | 1315 | 23705 | 23720 | TCGGGCATATCTGGAA | 21 | 436 |
| 915825 | 1350 | 1365 | 23755 | 23770 | GCACTCGAGTGAACAC | 0 | 437 |
| 915845 | 1407 | 1422 | 25170 | 25185 | AGGCCTGTTGGCTGCT | 0 | 438 |
| 915865 | 1480 | 1495 | 25243 | 25258 | TTGGTCTCTGCTGGAC | 21 | 439 |
| 915885 | 1546 | 1561 | 25309 | 25324 | GGTACTTTATTGCCCA | 62 | 440 |
| 915905 | 1609 | 1624 | 25372 | 25387 | GTGACTCACAGACTCT | 81 | 441 |
| 915925 | 1635 | 1650 | 25398 | 25413 | AGAATCTGCTAGACTC | 74 | 442 |
| 915945 | 1688 | 1703 | 25451 | 25466 | CACAGCAATGCGGAGG | 56 | 443 |
| 915965 | 1770 | 1785 | 25533 | 25548 | GCGAAAGGTTGCTTCC | 66 | 444 |
| 915985 | 1791 | 1806 | 25554 | 25569 | AAGTGCTGGACCGCTG | 71 | 445 |
| 916005 | 1817 | 1832 | 25580 | 25595 | TTAACGCATGCTGATG | 69 | 446 |
| 916025 | 1850 | 1865 | 25613 | 25628 | GGGCTTCCTGGTGTCA | 58 | 447 |
| 916045 | 1886 | 1901 | 25649 | 25664 | GGGCCACGAAACAGTC | 9 | 448 |
| 916065 | 1915 | 1930 | 25678 | 25693 | CTCATGCTGGAACAGT | 86 | 449 |
| 916085 | 1959 | 1974 | 25722 | 25737 | ATCACAAGGCCCCCAC | 82 | 450 |
| 916105 | 1979 | 1994 | 25742 | 25757 | CATGGGCCAGCCTACC | 0 | 451 |
| 916125 | 2054 | 2069 | 25817 | 25832 | ACGAACTGCACCCCTT | 84 | 452 |
| 916144 | 2102 | 2117 | 25865 | 25880 | AGGTTATCATCTTTGC | 90 | 453 |
| 916164 | 2141 | 2156 | 25904 | 25919 | ATCTTGTTACCCCCGC | 88 | 454 |
| 916184 | 2266 | 2281 | 26029 | 26044 | CATCTCACTGATTCAC | 91 | 455 |
| 916204 | 2626 | 2641 | 26389 | 26404 | TGCCCTGCACACTAGA | 47 | 456 |
| 916224 | 2680 | 2695 | 26443 | 26458 | GAGGAGGCGGAAGCTC | 0 | 457 |
| 916244 | 2710 | 2725 | 26473 | 26488 | AGCCAGGTTCAAGTTG | 71 | 458 |
| 916284 | N/A | N/A | 4227 | 4242 | TCAAATGTACGGAATC | 40 | 459 |
| 916304 | N/A | N/A | 4865 | 4880 | GTACTTTAGGCTCCTG | 89 | 460 |
| 916324 | N/A | N/A | 5429 | 5444 | ACATATCAGCATTAGA | 87 | 461 |
| 916344 | N/A | N/A | 5804 | 5819 | GTCTACTATGGGAGCC | 90 | 462 |
| 916364 | N/A | N/A | 6966 | 6981 | GAAGATGCATAGAGGA | 0 | 463 |
| 916384 | N/A | N/A | 7550 | 7565 | TCACACTGGGTCACCA | 43 | 464 |
| 916544 | N/A | N/A | 12135 | 12150 | GGCAATCAGGGAGGCA | 32 | 465 |

TABLE 7-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916564 | N/A | N/A | 12320 | 12335 | TGACTATATAACCACA | 92 | 466 |
| 916584 | N/A | N/A | 12951 | 12966 | CCCAATTGCCACTAGG | 83 | 467 |
| 916604 | N/A | N/A | 13718 | 13733 | TCTTTACCAAGACCGC | 92 | 468 |
| 916624 | N/A | N/A | 14245 | 14260 | GACAAATTCATCAACC | 87 | 469 |
| 916644 | N/A | N/A | 14778 | 14793 | CTGTATCCAAAAGGCC | 0 | 470 |
| 916664 | N/A | N/A | 15597 | 15612 | ATACATAGCAGAGCCA | 44 | 471 |
| 916684 | N/A | N/A | 16352 | 16367 | CACCCTATCGCTCCCA | 43 | 472 |
| 916704 | N/A | N/A | 17267 | 17282 | AGTTATGTCTGACTCA | 72 | 473 |
| 916724 | N/A | N/A | 18254 | 18269 | AATATACCCCACAGCA | 40 | 474 |
| 916744 | N/A | N/A | 19288 | 19303 | GTGCATGTGTGGCTTG | 82 | 475 |
| 916763 | N/A | N/A | 20414 | 20429 | TGTAGTAAGCAATGCA | 85 | 476 |
| 916783 | N/A | N/A | 20724 | 20739 | CATATATTGCGGATGA | 24 | 477 |
| 916803 | N/A | N/A | 21005 | 21020 | GTTATTTTAACAGCTC | 95 | 478 |
| 916823 | N/A | N/A | 21561 | 21576 | ATAAGGACTTACACCA | 83 | 479 |
| 916843 | N/A | N/A | 22679 | 22694 | CAGCATGCAACCACCC | 8 | 480 |
| 916863 | N/A | N/A | 23550 | 23565 | TGGGATGCTAGGACAA | 72 | 481 |
| 916883 | N/A | N/A | 24340 | 24355 | GGAAGTAGCGGCATCC | 0 | 482 |

TABLE 8

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915346 | 25 | 40 | 2763 | 2778 | CATTCCCAGCGCGACG | 0 | 483 |
| 915366 | 52 | 67 | 2790 | 2805 | TACCCTGCCTCAGTGT | 0 | 484 |
| 915386 | 112 | 127 | 2850 | 2865 | TCGGGAATCGGCTCGG | 26 | 485 |
| 915406 | 195 | 210 | 2933 | 2948 | CGAAGGACAAGCTCCA | 69 | 486 |
| 915426 | 252 | 267 | 2990 | 3005 | GCTCGCTCAGGCAGCG | 0 | 487 |
| 915446 | 350 | 365 | N/A | N/A | CTGCTCCAGCGGGATA | 0 | 488 |
| 915466 | 389 | 404 | 5963 | 5978 | CCTGGCCTTCCGCACA | 40 | 489 |
| 915486 | 431 | 446 | 6005 | 6020 | GCTTAAGTTGAAGGAT | 88 | 490 |
| 915506 | 455 | 470 | 6029 | 6044 | GCAGAGACCCTGTCGG | 32 | 491 |
| 915526 | 493 | 508 | 6067 | 6082 | CCGGAGATGAGCTGGT | 4 | 492 |
| 915546 | 514 | 529 | 6088 | 6103 | GTAAGAGAGATGCCTA | 94 | 493 |

TABLE 8-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915566 | 562 | 577 | 6136 | 6151 | TTGGACCGAAAGTCAG | 56 | 494 |
| 915606 | 702 | 717 | 11920 | 11935 | TGGTTGTTTTGGCATC | 99 | 495 |
| 915626 | 757 | 772 | 11975 | 11990 | GTGGACTTGACTTTAG | 89 | 496 |
| 915646 | 830 | 845 | 12048 | 12063 | TCTCGAGAGAAGGTAG | 0 | 497 |
| 915666 | 882 | 897 | 13618 | 13633 | ATCCTCGAAGGCATAT | 0 | 498 |
| 915686 | 956 | 971 | 16076 | 16091 | TGAGGATGACTTCAGG | 10 | 499 |
| 915706 | 989 | 1004 | 16109 | 16124 | GCTGGGCATGGCGACC | 10 | 500 |
| 915726 | 1064 | 1079 | 16184 | 16199 | TAGCAGCTCATCTCCC | 67 | 501 |
| 915746 | 1135 | 1150 | 16255 | 16270 | GTAGCGAGCCTGGGCG | 0 | 502 |
| 915766 | 1196 | 1211 | 19036 | 19051 | TAGCAAGTTGCAAATC | 78 | 503 |
| 915786 | 1232 | 1247 | 19072 | 19087 | ACAGGGCAGCATTACA | 87 | 504 |
| 915806 | 1302 | 1317 | 23707 | 23722 | CGTCGGGCATATCTGG | 53 | 505 |
| 915826 | 1352 | 1367 | 23757 | 23772 | CAGCACTCGAGTGAAC | 24 | 506 |
| 915846 | 1408 | 1423 | 25171 | 25186 | GAGGCCTGTTGGCTGC | 0 | 507 |
| 915866 | 1508 | 1523 | 25271 | 25286 | GAGGATGGACCGCGGG | 0 | 508 |
| 915886 | 1549 | 1564 | 25312 | 25327 | GCAGGTACTTTATTGC | 0 | 509 |
| 915906 | 1610 | 1625 | 25373 | 25388 | AGTGACTCACAGACTC | 35 | 510 |
| 915926 | 1636 | 1651 | 25399 | 25414 | AAGAATCTGCTAGACT | 69 | 511 |
| 915946 | 1689 | 1704 | 25452 | 25467 | ACACAGCAATGCGGAG | 69 | 512 |
| 915966 | 1771 | 1786 | 25534 | 25549 | GGCGAAAGGTTGCTTC | 58 | 513 |
| 915986 | 1792 | 1807 | 25555 | 25570 | TAAGTGCTGGACCGCT | 70 | 514 |
| 916006 | 1818 | 1833 | 25581 | 25596 | ATTAACGCATGCTGAT | 73 | 515 |
| 916026 | 1851 | 1866 | 25614 | 25629 | TGGGCTTCCTGGTGTC | 71 | 516 |
| 916046 | 1887 | 1902 | 25650 | 25665 | AGGGCCACGAAACAGT | 61 | 517 |
| 916066 | 1917 | 1932 | 25680 | 25695 | ACCTCATGCTGGAACA | 81 | 518 |
| 916086 | 1960 | 1975 | 25723 | 25738 | CATCACAAGGCCCCCA | 48 | 519 |
| 916106 | 1980 | 1995 | 25743 | 25758 | ACATGGGCCAGCCTAC | 54 | 520 |
| 916126 | 2055 | 2070 | 25818 | 25833 | GACGAACTGCACCCCT | 77 | 521 |
| 916145 | 2105 | 2120 | 25868 | 25883 | TCAAGGTTATCATCTT | 89 | 522 |
| 916165 | 2142 | 2157 | 25905 | 25920 | CATCTTGTTACCCCCG | 89 | 523 |
| 916185 | 2270 | 2285 | 26033 | 26048 | CTAACATCTCACTGAT | 66 | 524 |
| 916205 | 2627 | 2642 | 26390 | 26405 | ATGCCCTGCACACTAG | 62 | 525 |
| 916225 | 2681 | 2696 | 26444 | 26459 | AGAGGAGGCGGAAGCT | 25 | 526 |
| 916245 | 2711 | 2726 | 26474 | 26489 | AAGCCAGGTTCAAGTT | 83 | 527 |
| 916285 | N/A | N/A | 4240 | 4255 | ATTAGGACAAGATTCA | 75 | 528 |
| 916305 | N/A | N/A | 4866 | 4881 | TGTACTTTAGGCTCCT | 93 | 529 |

TABLE 8-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916325 | N/A | N/A | 5430 | 5445 | AACATATCAGCATTAG | 85 | 530 |
| 916345 | N/A | N/A | 5839 | 5854 | CAAGGATGCCACCAAC | 84 | 531 |
| 916365 | N/A | N/A | 6974 | 6989 | TCATTATGGAAGATGC | 0 | 532 |
| 916385 | N/A | N/A | 7602 | 7617 | TTAACAACCCTGTCAG | 1 | 533 |
| 916545 | N/A | N/A | 12151 | 12166 | GTAACTGGTAGCTCCT | 93 | 534 |
| 916565 | N/A | N/A | 12338 | 12353 | ACCCATACTGCACCCC | 79 | 535 |
| 916585 | N/A | N/A | 12957 | 12972 | GCCTATCCCAATTGCC | 70 | 536 |
| 916605 | N/A | N/A | 13719 | 13734 | GTCTTTACCAAGACCG | 23 | 537 |
| 916625 | N/A | N/A | 14248 | 14263 | AACGACAAATTCATCA | 84 | 538 |
| 916645 | N/A | N/A | 14788 | 14803 | TGCAATCCCCCTGTAT | 17 | 539 |
| 916665 | N/A | N/A | 15598 | 15613 | AATACATAGCAGAGCC | 68 | 540 |
| 916685 | N/A | N/A | 16366 | 16381 | TGTCATGGTTGCCTCA | 70 | 541 |
| 916705 | N/A | N/A | 17273 | 17288 | ATAAGGAGTTATGTCT | 80 | 542 |
| 916725 | N/A | N/A | 18255 | 18270 | GAATATACCCCACAGC | 58 | 543 |
| 916745 | N/A | N/A | 19295 | 19310 | GTTACAGGTGCATGTG | 75 | 544 |
| 916764 | N/A | N/A | 20435 | 20450 | AGTCATCTGGAGTCAC | 69 | 545 |
| 916784 | N/A | N/A | 20756 | 20771 | TCAGACAACCCACTGA | 24 | 546 |
| 916804 | N/A | N/A | 21046 | 21061 | AGGAATCTGAATCCTA | 0 | 547 |
| 916824 | N/A | N/A | 21640 | 21655 | GATAATTTCCTAGAGC | 29 | 548 |
| 916844 | N/A | N/A | 22699 | 22714 | GAAATAAGTGCTCAGG | 73 | 549 |
| 916864 | N/A | N/A | 23582 | 23597 | CTCCAATCTGATGACT | 53 | 550 |
| 916884 | N/A | N/A | 24347 | 24362 | GAATTCAGGAAGTAGC | 50 | 551 |

TABLE 9

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915347 | 26 | 41 | 2764 | 2779 | GCATTCCCAGCGCGAC | 0 | 552 |
| 915367 | 58 | 73 | 2796 | 2811 | GCTCTCTACCCTGCCT | 9 | 553 |
| 915387 | 113 | 128 | 2851 | 2866 | ATCGGGAATCGGCTCG | 28 | 554 |
| 915407 | 198 | 213 | 2936 | 2951 | CCGCGAAGGACAAGCT | 0 | 555 |
| 915427 | 253 | 268 | 2991 | 3006 | TGCTCGCTCAGGCAGC | 0 | 556 |
| 915447 | 351 | 366 | N/A | N/A | TCTGCTCCAGCGGGAT | 1 | 557 |
| 915467 | 391 | 406 | 5965 | 5980 | CTCCTGGCCTTCCGCA | 29 | 558 |

TABLE 9-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915487 | 433 | 448 | 6007 | 6022 | TTGCTTAAGTTGAAGG | 94 | 559 |
| 915507 | 456 | 471 | 6030 | 6045 | TGCAGAGACCCTGTCG | 31 | 560 |
| 915527 | 494 | 509 | 6068 | 6083 | GCCGGAGATGAGCTGG | 0 | 561 |
| 915547 | 515 | 530 | 6089 | 6104 | GGTAAGAGAGATGCCT | 0 | 562 |
| 915567 | 563 | 578 | 6137 | 6152 | TTTGGACCGAAAGTCA | 0 | 563 |
| 915607 | 703 | 718 | 11921 | 11936 | ATGGTTGTTTTGGCAT | 35 | 564 |
| 915627 | 758 | 773 | 11976 | 11991 | CGTGGACTTGACTTTA | 85 | 565 |
| 915647 | 831 | 846 | 12049 | 12064 | CTCTCGAGAGAAGGTA | 7 | 566 |
| 915667 | 883 | 898 | 13619 | 13634 | TATCCTCGAAGGCATA | 0 | 567 |
| 915687 | 959 | 974 | 16079 | 16094 | TTCTGAGGATGACTTC | 39 | 568 |
| 915707 | 996 | 1011 | 16116 | 16131 | TTGCCCAGCTGGGCAT | 0 | 569 |
| 915727 | 1065 | 1080 | 16185 | 16200 | CTAGCAGCTCATCTCC | 58 | 570 |
| 915747 | 1136 | 1151 | 16256 | 16271 | TGTAGCGAGCCTGGGC | 16 | 571 |
| 915767 | 1197 | 1212 | 19037 | 19052 | GTAGCAAGTTGCAAAT | 80 | 572 |
| 915787 | 1233 | 1248 | 19073 | 19088 | TACAGGGCAGCATTAC | 71 | 573 |
| 915807 | 1316 | 1331 | 23721 | 23736 | CAACCACAGGACATCG | 0 | 574 |
| 915827 | 1353 | 1368 | 23758 | 23773 | TCAGCACTCGAGTGAA | 0 | 575 |
| 915847 | 1409 | 1424 | 25172 | 25187 | GGAGGCCTGTTGGCTG | 0 | 576 |
| 915867 | 1509 | 1524 | 25272 | 25287 | TGAGGATGGACCGCGG | 14 | 577 |
| 915887 | 1553 | 1568 | 25316 | 25331 | ACCAGCAGGTACTTTA | 29 | 578 |
| 915907 | 1611 | 1626 | 25374 | 25389 | AAGTGACTCACAGACT | 29 | 579 |
| 915927 | 1637 | 1652 | 25400 | 25415 | AAAGAATCTGCTAGAC | 60 | 580 |
| 915947 | 1690 | 1705 | 25453 | 25468 | TACACAGCAATGCGGA | 69 | 581 |
| 915967 | 1772 | 1787 | 25535 | 25550 | AGGCGAAAGGTTGCTT | 0 | 582 |
| 915987 | 1793 | 1808 | 25556 | 25571 | TTAAGTGCTGGACCGC | 82 | 583 |
| 916007 | 1819 | 1834 | 25582 | 25597 | AATTAACGCATGCTGA | 61 | 584 |
| 916027 | 1864 | 1879 | 25627 | 25642 | GGACCCTCTGCACTGG | 43 | 585 |
| 916047 | 1888 | 1903 | 25651 | 25666 | TAGGGCCACGAAACAG | 80 | 586 |
| 916067 | 1918 | 1933 | 25681 | 25696 | AACCTCATGCTGGAAC | 72 | 587 |
| 916087 | 1961 | 1976 | 25724 | 25739 | CCATCACAAGGCCCCC | 63 | 588 |
| 916107 | 1981 | 1996 | 25744 | 25759 | CACATGGGCCAGCCTA | 74 | 589 |
| 916127 | 2056 | 2071 | 25819 | 25834 | GGACGAACTGCACCCC | 5 | 590 |
| 916146 | 2106 | 2121 | 25869 | 25884 | GTCAAGGTTATCATCT | 88 | 591 |
| 916166 | 2143 | 2158 | 25906 | 25921 | TCATCTTGTTACCCCC | 90 | 592 |
| 916186 | 2272 | 2287 | 26035 | 26050 | TACTAACATCTCACTG | 1 | 593 |
| 916206 | 2628 | 2643 | 26391 | 26406 | AATGCCCTGCACACTA | 56 | 594 |

TABLE 9-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916226 | 2682 | 2697 | 26445 | 26460 | GAGAGGAGGCGGAAGC | 10 | 595 |
| 916246 | 2712 | 2727 | 26475 | 26490 | TAAGCCAGGTTCAAGT | 81 | 596 |
| 916286 | N/A | N/A | 4244 | 4259 | TTTCATTAGGACAAGA | 61 | 597 |
| 916306 | N/A | N/A | 4867 | 4882 | GTGTACTTTAGGCTCC | 97 | 598 |
| 916326 | N/A | N/A | 5431 | 5446 | GAACATATCAGCATTA | 52 | 599 |
| 916346 | N/A | N/A | 5872 | 5887 | GTAATACTTTTGGCAA | 75 | 600 |
| 916366 | N/A | N/A | 7069 | 7084 | GGTATTACAAATTATC | 10 | 601 |
| 916386 | N/A | N/A | 7603 | 7618 | CTTAACAACCCTGTCA | 0 | 602 |
| 916546 | N/A | N/A | 12152 | 12167 | AGTAACTGGTAGCTCC | 88 | 603 |
| 916566 | N/A | N/A | 12343 | 12358 | CTAATACCCATACTGC | 84 | 604 |
| 916586 | N/A | N/A | 12966 | 12981 | AACTTTGCAGCCTATC | 85 | 605 |
| 916606 | N/A | N/A | 13739 | 13754 | AGAACTAAGGCAAATC | 85 | 606 |
| 916626 | N/A | N/A | 14257 | 14272 | GTCTTGGCCAACGACA | 0 | 607 |
| 916646 | N/A | N/A | 14793 | 14808 | CAGGATGCAATCCCCC | 45 | 608 |
| 916666 | N/A | N/A | 15601 | 15616 | GCCAATACATAGCAGA | 75 | 609 |
| 916686 | N/A | N/A | 16630 | 16645 | GTCCATGAAATCCAGG | 0 | 610 |
| 916706 | N/A | N/A | 17293 | 17308 | TCTCTTAGGGCACCTC | 87 | 611 |
| 916726 | N/A | N/A | 18256 | 18271 | TGAATATACCCCACAG | 24 | 612 |
| 916746 | N/A | N/A | 19337 | 19352 | AGCTCTAGGAGTCCCC | 63 | 613 |
| 916765 | N/A | N/A | 20513 | 20528 | CCAGATTGAGTCTCCT | 91 | 614 |
| 916785 | N/A | N/A | 20775 | 20790 | AATCAAGTGCCCTCCA | 73 | 615 |
| 916805 | N/A | N/A | 21211 | 21226 | TGTAGCTGTGTGGTGG | 85 | 616 |
| 916825 | N/A | N/A | 21760 | 21775 | TACCATGATCAGGTCA | 0 | 617 |
| 916845 | N/A | N/A | 22713 | 22728 | GTAAAGATGTGAGTGA | 85 | 618 |
| 916865 | N/A | N/A | 23606 | 23621 | GTTTACAAAAGCTGCC | 17 | 619 |
| 916885 | N/A | N/A | 24375 | 24390 | TGAACTCCGGCTCAGT | 0 | 620 |

TABLE 10

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915348 | 28 | 43 | 2766 | 2781 | GGGCATTCCCAGCGCG | 0 | 621 |
| 915368 | 59 | 74 | 2797 | 2812 | CGCTCTCTACCCTGCC | 0 | 622 |
| 915388 | 114 | 129 | 2852 | 2867 | GATCGGGAATCGGCTC | 32 | 623 |

TABLE 10-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915408 | 199 | 214 | 2937 | 2952 | CCCGCGAAGGACAAGC | 6 | 624 |
| 915428 | 275 | 290 | 3013 | 3028 | GTCGCGGAGGAGGTGC | 0 | 625 |
| 915448 | 352 | 367 | N/A | N/A | GTCTGCTCCAGCGGGA | 4 | 626 |
| 915468 | 392 | 407 | 5966 | 5981 | ACTCCTGGCCTTCCGC | 87 | 627 |
| 915488 | 434 | 449 | 6008 | 6023 | CTTGCTTAAGTTGAAG | 0 | 628 |
| 915508 | 457 | 472 | 6031 | 6046 | TTGCAGAGACCCTGTC | 63 | 629 |
| 915528 | 495 | 510 | 6069 | 6084 | TGCCGGAGATGAGCTG | 0 | 630 |
| 915548 | 516 | 531 | 6090 | 6105 | TGGTAAGAGAGATGCC | 18 | 631 |
| 915568 | 564 | 579 | 6138 | 6153 | CTTTGGACCGAAAGTC | 10 | 632 |
| 915608 | 704 | 719 | 11922 | 11937 | GATGGTTGTTTTGGCA | 98 | 633 |
| 915628 | 772 | 787 | 11990 | 12005 | ACATGAAGAAAGTTCG | 41 | 634 |
| 915648 | 832 | 847 | 12050 | 12065 | GCTCTCGAGAGAAGGT | 55 | 635 |
| 915668 | 884 | 899 | 13620 | 13635 | ATATCCTCGAAGGCAT | 33 | 636 |
| 915688 | 962 | 977 | 16082 | 16097 | CCCTTCTGAGGATGAC | 11 | 637 |
| 915708 | 998 | 1013 | 16118 | 16133 | GTTTGCCCAGCTGGGC | 0 | 638 |
| 915728 | 1067 | 1082 | 16187 | 16202 | GTCTAGCAGCTCATCT | 68 | 639 |
| 915748 | 1137 | 1152 | 16257 | 16272 | CTGTAGCGAGCCTGGG | 0 | 640 |
| 915768 | 1198 | 1213 | 19038 | 19053 | GGTAGCAAGTTGCAAA | 90 | 641 |
| 915788 | 1234 | 1249 | 19074 | 19089 | GTACAGGGCAGCATTA | 69 | 642 |
| 915808 | 1317 | 1332 | 23722 | 23737 | GCAACCACAGGACATC | 51 | 643 |
| 915828 | 1354 | 1369 | 23759 | 23774 | ATCAGCACTCGAGTGA | 0 | 644 |
| 915848 | 1410 | 1425 | 25173 | 25188 | GGGAGGCCTGTTGGCT | 17 | 645 |
| 915868 | 1510 | 1525 | 25273 | 25288 | CTGAGGATGGACCGCG | 53 | 646 |
| 915888 | 1554 | 1569 | 25317 | 25332 | CACCAGCAGGTACTTT | 0 | 647 |
| 915908 | 1612 | 1627 | 25375 | 25390 | CAAGTGACTCACAGAC | 91 | 648 |
| 915928 | 1639 | 1654 | 25402 | 25417 | TGAAAGAATCTGCTAG | 59 | 649 |
| 915948 | 1691 | 1706 | 25454 | 25469 | CTACACAGCAATGCGG | 20 | 650 |
| 915968 | 1773 | 1788 | 25536 | 25551 | CAGGCGAAAGGTTGCT | 60 | 651 |
| 915988 | 1794 | 1809 | 25557 | 25572 | GTTAAGTGCTGGACCG | 86 | 652 |
| 916008 | 1820 | 1835 | 25583 | 25598 | GAATTAACGCATGCTG | 88 | 653 |
| 916028 | 1865 | 1880 | 25628 | 25643 | GGGACCCTCTGCACTG | 0 | 654 |
| 916048 | 1889 | 1904 | 25652 | 25667 | ATAGGGCCACGAAACA | 75 | 655 |
| 916068 | 1919 | 1934 | 25682 | 25697 | GAACCTCATGCTGGAA | 72 | 656 |
| 916088 | 1962 | 1977 | 25725 | 25740 | CCCATCACAAGGCCCC | 37 | 657 |
| 916108 | 1984 | 1999 | 25747 | 25762 | TCACACATGGGCCAGC | 84 | 658 |
| 916128 | 2079 | 2094 | 25842 | 25857 | CTGACAGGCAGTGTCG | 10 | 659 |

TABLE 10-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916147 | 2107 | 2122 | 25870 | 25885 | AGTCAAGGTTATCATC | 81 | 660 |
| 916167 | 2144 | 2159 | 25907 | 25922 | ATCATCTTGTTACCCC | 88 | 661 |
| 916187 | 2276 | 2291 | 26039 | 26054 | ATTCTACTAACATCTC | 90 | 662 |
| 916207 | 2629 | 2644 | 26392 | 26407 | GAATGCCCTGCACACT | 72 | 663 |
| 916227 | 2691 | 2706 | 26454 | 26469 | GCTCCAGTGGAGAGGA | 14 | 664 |
| 916247 | 2713 | 2728 | 26476 | 26491 | ATAAGCCAGGTTCAAG | 88 | 665 |
| 916287 | N/A | N/A | 4308 | 4323 | GTGAGAAACAAACCCT | 92 | 666 |
| 916307 | N/A | N/A | 4882 | 4897 | TCTATACCAGAGTGAG | 84 | 667 |
| 916327 | N/A | N/A | 5514 | 5529 | AGGAATGAGTCTCCCA | 17 | 668 |
| 916347 | N/A | N/A | 5873 | 5888 | GGTAATACTTTTGGCA | 70 | 669 |
| 916367 | N/A | N/A | 7106 | 7121 | CGCTTATGAAAGCATC | 0 | 670 |
| 916387 | N/A | N/A | 7605 | 7620 | CCCTTAACAACCCTGT | 28 | 671 |
| 916547 | N/A | N/A | 12167 | 12182 | TTTGATTGTGCAGACA | 98 | 672 |
| 916567 | N/A | N/A | 12345 | 12360 | TCCTAATACCCATACT | 74 | 673 |
| 916587 | N/A | N/A | 12969 | 12984 | ACAAACTTTGCAGCCT | 95 | 674 |
| 916607 | N/A | N/A | 13742 | 13757 | GTTAGAACTAAGGCAA | 94 | 675 |
| 916627 | N/A | N/A | 14301 | 14316 | GAGCAGATAAATACAC | 91 | 676 |
| 916647 | N/A | N/A | 14892 | 14907 | TGGTATCTCGCTTCCT | 0 | 677 |
| 916667 | N/A | N/A | 15613 | 15628 | TAAAGCCACGCAGCCA | 46 | 678 |
| 916687 | N/A | N/A | 16656 | 16671 | CCAGATGCAGGACCCC | 0 | 679 |
| 916707 | N/A | N/A | 17326 | 17341 | AAACTAATGCACCTGG | 43 | 680 |
| 916727 | N/A | N/A | 18257 | 18272 | CTGAATATACCCCACA | 75 | 681 |
| 916747 | N/A | N/A | 19360 | 19375 | AGCTGCTATGTGAGGC | 12 | 682 |
| 916766 | N/A | N/A | 20520 | 20535 | TCAGTAACCAGATTGA | 25 | 683 |
| 916786 | N/A | N/A | 20778 | 20793 | TTTAATCAAGTGCCCT | 81 | 684 |
| 916806 | N/A | N/A | 21216 | 21231 | CAGGATGTAGCTGTGT | 84 | 685 |
| 916826 | N/A | N/A | 21887 | 21902 | TAAGATCCCATCTTAC | 13 | 686 |
| 916846 | N/A | N/A | 22739 | 22754 | AAAGTAAACACCCACC | 42 | 687 |
| 916866 | N/A | N/A | 23625 | 23640 | GCTTACAACACTACCC | 57 | 688 |
| 916886 | N/A | N/A | 24393 | 24408 | GTAATGGGAGCCAGGC | 38 | 689 |

TABLE 11

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915349 | 29 | 44 | 2767 | 2782 | AGGGCATTCCCAGCGC | 0 | 690 |
| 915369 | 60 | 75 | 2798 | 2813 | GCGCTCTCTACCCTGC | 23 | 691 |
| 915389 | 115 | 130 | 2853 | 2868 | GGATCGGGAATCGGCT | 54 | 692 |
| 915409 | 200 | 215 | 2938 | 2953 | GCCCGCGAAGGACAAG | 32 | 693 |
| 915429 | 276 | 291 | 3014 | 3029 | CGTCGCGGAGGAGGTG | 0 | 694 |
| 915449 | 364 | 379 | 5938 | 5953 | AGGACCTGCAGAGTCT | 21 | 695 |
| 915469 | 394 | 409 | 5968 | 5983 | CGACTCCTGGCCTTCC | 59 | 696 |
| 915489 | 435 | 450 | 6009 | 6024 | ACTTGCTTAAGTTGAA | 86 | 697 |
| 915509 | 466 | 481 | 6040 | 6055 | GGGAGGCATTTGCAGA | 57 | 698 |
| 915529 | 496 | 511 | 6070 | 6085 | TTGCCGGAGATGAGCT | 40 | 699 |
| 915549 | 518 | 533 | 6092 | 6107 | TCTGGTAAGAGAGATG | 61 | 700 |
| 915569 | 565 | 580 | 6139 | 6154 | TCTTTGGACCGAAAGT | 9 | 701 |
| 915609 | 705 | 720 | 11923 | 11938 | TGATGGTTGTTTTGGC | 99 | 702 |
| 915629 | 776 | 791 | 11994 | 12009 | GTCCACATGAAGAAAG | 32 | 703 |
| 915649 | 833 | 848 | 12051 | 12066 | AGCTCTCGAGAGAAGG | 36 | 704 |
| 915669 | 885 | 900 | 13621 | 13636 | AATATCCTCGAAGGCA | 55 | 705 |
| 915689 | 969 | 984 | 16089 | 16104 | GATCCATCCCTTCTGA | 20 | 706 |
| 915709 | 999 | 1014 | 16119 | 16134 | TGTTTGCCCAGCTGGG | 5 | 707 |
| 915729 | 1077 | 1092 | 16197 | 16212 | GACGCAGGTGGTCTAG | 0 | 708 |
| 915749 | 1138 | 1153 | N/A | N/A | GCTGTAGCGAGCCTGG | 71 | 709 |
| 915769 | 1200 | 1215 | 19040 | 19055 | TGGGTAGCAAGTTGCA | 81 | 710 |
| 915789 | 1235 | 1250 | 19075 | 19090 | GGTACAGGGCAGCATT | 88 | 711 |
| 915809 | 1318 | 1333 | 23723 | 23738 | TGCAACCACAGGACAT | 40 | 712 |
| 915829 | 1355 | 1370 | 23760 | 23775 | CATCAGCACTCGAGTG | 0 | 713 |
| 915849 | 1424 | 1439 | 25187 | 25202 | CTCAGGTGTGCATGGG | 61 | 714 |
| 915869 | 1511 | 1526 | 25274 | 25289 | CCTGAGGATGGACCGC | 70 | 715 |
| 915889 | 1556 | 1571 | 25319 | 25334 | AGCACCAGCAGGTACT | 35 | 716 |
| 915909 | 1613 | 1628 | 25376 | 25391 | TCAAGTGACTCACAGA | 84 | 717 |
| 915929 | 1645 | 1660 | 25408 | 25423 | CACCTCTGAAAGAATC | 89 | 718 |
| 915949 | 1692 | 1707 | 25455 | 25470 | ACTACACAGCAATGCG | 33 | 719 |
| 915969 | 1774 | 1789 | 25537 | 25552 | ACAGGCGAAAGGTTGC | 88 | 720 |
| 915989 | 1795 | 1810 | 25558 | 25573 | AGTTAAGTGCTGGACC | 84 | 721 |
| 916009 | 1823 | 1838 | 25586 | 25601 | GCTGAATTAACGCATG | 67 | 722 |
| 916029 | 1866 | 1881 | 25629 | 25644 | AGGGACCCTCTGCACT | 15 | 723 |
| 916049 | 1890 | 1905 | 25653 | 25668 | AATAGGGCCACGAAAC | 52 | 724 |
| 916069 | 1920 | 1935 | 25683 | 25698 | AGAACCTCATGCTGGA | 85 | 725 |

TABLE 11-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916089 | 1963 | 1978 | 25726 | 25741 | CCCCATCACAAGGCCC | 20 | 726 |
| 916109 | 1985 | 2000 | 25748 | 25763 | ATCACACATGGGCCAG | 72 | 727 |
| 916129 | 2080 | 2095 | 25843 | 25858 | CCTGACAGGCAGTGTC | 15 | 728 |
| 916148 | 2108 | 2123 | 25871 | 25886 | TAGTCAAGGTTATCAT | 87 | 729 |
| 916168 | 2146 | 2161 | 25909 | 25924 | TTATCATCTTGTTACC | 82 | 730 |
| 916188 | 2279 | 2294 | 26042 | 26057 | CTTATTCTACTAACAT | 87 | 731 |
| 916208 | 2630 | 2645 | 26393 | 26408 | TGAATGCCCTGCACAC | 68 | 732 |
| 916228 | 2692 | 2707 | 26455 | 26470 | TGCTCCAGTGGAGAGG | 80 | 733 |
| 916248 | 2726 | 2741 | 26489 | 26504 | GTCCCTGCAGAAAATA | 0 | 734 |
| 916288 | N/A | N/A | 4337 | 4352 | AGCATACCACACCCCA | 75 | 735 |
| 916308 | N/A | N/A | 5086 | 5101 | GGACATGCTCAGCAGC | 68 | 736 |
| 916328 | N/A | N/A | 5533 | 5548 | TGCTGTAGGCCTCAGC | 0 | 737 |
| 916348 | N/A | N/A | 5874 | 5889 | TGGTAATACTTTTGGC | 86 | 738 |
| 916368 | N/A | N/A | 7132 | 7147 | GTAAATGGAGTCCTTC | 80 | 739 |
| 916388 | N/A | N/A | 7612 | 7627 | CATAATCCCCTTAACA | 32 | 740 |
| 916548 | N/A | N/A | 12195 | 12210 | TTAACCATCAAGGACA | 77 | 741 |
| 916568 | N/A | N/A | 12665 | 12680 | TCTTAGTGGCTGGGTA | 85 | 742 |
| 916588 | N/A | N/A | 12973 | 12988 | CCTAACAAACTTTGCA | 32 | 743 |
| 916608 | N/A | N/A | 13749 | 13764 | ACTAAGTGTTAGAACT | 76 | 744 |
| 916628 | N/A | N/A | 14338 | 14353 | CTGCAGTATCCCTAGC | 0 | 745 |
| 916648 | N/A | N/A | 15012 | 15027 | TCCCATCGGTCATTTC | 45 | 746 |
| 916668 | N/A | N/A | 15682 | 15697 | GAAACCACTATCATCA | 62 | 747 |
| 916688 | N/A | N/A | 16671 | 16686 | GTAATAGGCCAAGTCC | 0 | 748 |
| 916708 | N/A | N/A | 17327 | 17342 | CAAACTAATGCACCTG | 66 | 749 |
| 916728 | N/A | N/A | 18332 | 18347 | CCAATATCATAGCTGA | 85 | 750 |
| 916748 | N/A | N/A | 19376 | 19391 | CACAAGAGACTGGACC | 64 | 751 |
| 916767 | N/A | N/A | 20551 | 20566 | TACTATGGGATGAGTA | 0 | 752 |
| 916787 | N/A | N/A | 20779 | 20794 | TTTTAATCAAGTGCCC | 38 | 753 |
| 916807 | N/A | N/A | 21218 | 21233 | GGCAGGATGTAGCTGT | 63 | 754 |
| 916827 | N/A | N/A | 21947 | 21962 | AGTCAAACATCTTCCT | 50 | 755 |
| 916847 | N/A | N/A | 22759 | 22774 | CAGACTAACTTACTAA | 77 | 756 |
| 916867 | N/A | N/A | 23626 | 23641 | AGCTTACAACACTACC | 13 | 757 |
| 916887 | N/A | N/A | 24505 | 24520 | ATGCTACGGGCTCTCA | 0 | 758 |

TABLE 12

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915350 | 30 | 45 | 2768 | 2783 | CAGGGCATTCCCAGCG | 0 | 759 |
| 915370 | 82 | 97 | 2820 | 2835 | CAGCTCCGCCCGGCGC | 14 | 760 |
| 915390 | 130 | 145 | 2868 | 2883 | TTAGGATCTGGGTCGG | 88 | 761 |
| 915410 | 201 | 216 | 2939 | 2954 | AGCCCGCGAAGGACAA | 0 | 762 |
| 915430 | 295 | 310 | 3033 | 3048 | GCGCCGAACAACATGC | 0 | 763 |
| 915450 | 366 | 381 | 5940 | 5955 | AGAGGACCTGCAGAGT | 83 | 764 |
| 915470 | 395 | 410 | 5969 | 5984 | CCGACTCCTGGCCTTC | 68 | 765 |
| 915490 | 436 | 451 | 6010 | 6025 | AACTTGCTTAAGTTGA | 41 | 766 |
| 915510 | 467 | 482 | 6041 | 6056 | CGGGAGGCATTTGCAG | 44 | 767 |
| 915530 | 497 | 512 | 6071 | 6086 | TTTGCCGGAGATGAGC | 92 | 768 |
| 915550 | 519 | 534 | 6093 | 6108 | CTCTGGTAAGAGAGAT | 20 | 769 |
| 915570 | 566 | 581 | 6140 | 6155 | GTCTTTGGACCGAAAG | 19 | 770 |
| 915590 | 627 | 642 | 7857 | 7872 | GAGGGATAAGGCCACT | 83 | 771 |
| 915610 | 706 | 721 | 11924 | 11939 | GTGATGGTTGTTTTGG | 97 | 772 |
| 915630 | 782 | 797 | 12000 | 12015 | GGTGATGTCCACATGA | 87 | 773 |
| 915650 | 834 | 849 | 12052 | 12067 | AAGCTCTCGAGAGAAG | 44 | 774 |
| 915670 | 887 | 902 | 13623 | 13638 | CAAATATCCTCGAAGG | 0 | 775 |
| 915690 | 970 | 985 | 16090 | 16105 | GGATCCATCCCTTCTG | 0 | 776 |
| 915710 | 1003 | 1018 | 16123 | 16138 | CTCATGTTTGCCCAGC | 68 | 777 |
| 915730 | 1078 | 1093 | 16198 | 16213 | AGACGCAGGTGGTCTA | 0 | 778 |
| 915750 | 1139 | 1154 | N/A | N/A | TGCTGTAGCGAGCCTG | 56 | 779 |
| 915770 | 1201 | 1216 | 19041 | 19056 | ATGGGTAGCAAGTTGC | 79 | 780 |
| 915790 | 1247 | 1262 | 19087 | 19102 | TTCCACAGGCAGGGTA | 48 | 781 |
| 915810 | 1320 | 1335 | 23725 | 23740 | ACTGCAACCACAGGAC | 22 | 782 |
| 915830 | 1356 | 1371 | 23761 | 23776 | ACATCAGCACTCGAGT | 0 | 783 |
| 915850 | 1427 | 1442 | 25190 | 25205 | CTGCTCAGGTGTGCAT | 10 | 784 |
| 915870 | 1512 | 1527 | 25275 | 25290 | ACCTGAGGATGGACCG | 69 | 785 |
| 915890 | 1557 | 1572 | 25320 | 25335 | CAGCACCAGCAGGTAC | 62 | 786 |
| 915910 | 1617 | 1632 | 25380 | 25395 | CTCCTCAAGTGACTCA | 83 | 787 |
| 915930 | 1648 | 1663 | 25411 | 25426 | TAGCACCTCTGAAAGA | 55 | 788 |
| 915950 | 1693 | 1708 | 25456 | 25471 | CACTACACAGCAATGC | 74 | 789 |
| 915970 | 1775 | 1790 | 25538 | 25553 | CACAGGCGAAAGGTTG | 72 | 790 |
| 915990 | 1797 | 1812 | 25560 | 25575 | AGAGTTAAGTGCTGGA | 92 | 791 |
| 916010 | 1824 | 1839 | 25587 | 25602 | AGCTGAATTAACGCAT | 0 | 792 |
| 916030 | 1867 | 1882 | 25630 | 25645 | AAGGGACCCTCTGCAC | 38 | 793 |
| 916050 | 1891 | 1906 | 25654 | 25669 | TAATAGGGCCACGAAA | 53 | 794 |

TABLE 12-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916070 | 1921 | 1936 | 25684 | 25699 | AAGAACCTCATGCTGG | 24 | 795 |
| 916090 | 1964 | 1979 | 25727 | 25742 | CCCCCATCACAAGGCC | 24 | 796 |
| 916110 | 1986 | 2001 | 25749 | 25764 | GATCACACATGGGCCA | 0 | 797 |
| 916130 | 2081 | 2096 | 25844 | 25859 | ACCTGACAGGCAGTGT | 54 | 798 |
| 916149 | 2109 | 2124 | 25872 | 25887 | GTAGTCAAGGTTATCA | 87 | 799 |
| 916169 | 2154 | 2169 | 25917 | 25932 | TAAGTAGATTATCATC | 79 | 800 |
| 916189 | 2282 | 2297 | 26045 | 26060 | AGGCTTATTCTACTAA | 85 | 801 |
| 916209 | 2631 | 2646 | 26394 | 26409 | GTGAATGCCCTGCACA | 59 | 802 |
| 916229 | 2693 | 2708 | 26456 | 26471 | GTGCTCCAGTGGAGAG | 54 | 803 |
| 916249 | 2727 | 2742 | 26490 | 26505 | GGTCCCTGCAGAAAAT | 38 | 804 |
| 916289 | N/A | N/A | 4338 | 4353 | AAGCATACCACACCCC | 79 | 805 |
| 916309 | N/A | N/A | 5278 | 5293 | AATCTTGGGATGCACA | 95 | 806 |
| 916329 | N/A | N/A | 5569 | 5584 | CATCATGGCTTCCAGT | 79 | 807 |
| 916349 | N/A | N/A | 5879 | 5894 | TGGGATGGTAATACTT | 0 | 808 |
| 916369 | N/A | N/A | 7134 | 7149 | AAGTAAATGGAGTCCT | 5 | 809 |
| 916389 | N/A | N/A | 7615 | 7630 | TTGCATAATCCCCTTA | 33 | 810 |
| 916409 | N/A | N/A | 8165 | 8180 | TTAACTAGATCACTGA | 58 | 811 |
| 916429 | N/A | N/A | 9109 | 9124 | TCCTAATGCGAGTCCC | 86 | 812 |
| 916449 | N/A | N/A | 9522 | 9537 | TGCTGCTGGGTGCACT | 45 | 813 |
| 916469 | N/A | N/A | 10199 | 10214 | GGTGATGACACAGCAT | 94 | 814 |
| 916489 | N/A | N/A | 10382 | 10397 | GCCATGTACAACTTTT | 52 | 815 |
| 916509 | N/A | N/A | 11152 | 11167 | TACAATTTGGACAGAG | 71 | 816 |
| 916529 | N/A | N/A | 11546 | 11561 | ACCTATAGGAGTGCCC | 35 | 817 |
| 916549 | N/A | N/A | 12204 | 12219 | TTATTTCCGTTAACCA | 97 | 818 |
| 916569 | N/A | N/A | 12672 | 12687 | AGAATCATCTTAGTGG | 94 | 819 |
| 916589 | N/A | N/A | 12989 | 13004 | CGGAATAAGCCTCCAC | 0 | 820 |
| 916609 | N/A | N/A | 13752 | 13767 | GGCACTAAGTGTTAGA | 57 | 821 |
| 916629 | N/A | N/A | 14375 | 14390 | TCTCACAAGGCTGGCA | 84 | 822 |
| 916649 | N/A | N/A | 15137 | 15152 | GCCATACCGGCTCCCT | 30 | 823 |
| 916669 | N/A | N/A | 15691 | 15706 | GGCCTTACAGAAACCA | 15 | 824 |
| 916689 | N/A | N/A | 16672 | 16687 | AGTAATAGGCCAAGTC | 16 | 825 |
| 916709 | N/A | N/A | 17328 | 17343 | ACAAACTAATGCACCT | 42 | 826 |
| 916729 | N/A | N/A | 18333 | 18348 | TCCAATATCATAGCTG | 32 | 827 |
| 916749 | N/A | N/A | 19445 | 19460 | CTACTAGGCATCTCTA | 32 | 828 |
| 916768 | N/A | N/A | 20553 | 20568 | CTTACTATGGGATGAG | 83 | 829 |
| 916788 | N/A | N/A | 20808 | 20823 | TAATATTCAGACCAGG | 94 | 830 |

TABLE 12-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916808 | N/A | N/A | 21252 | 21267 | CCATGCATGGCACAGT | 4 | 831 |
| 916828 | N/A | N/A | 21968 | 21983 | AGACAGGAATCCAACC | 0 | 832 |
| 916848 | N/A | N/A | 22767 | 22782 | GGACATGACAGACTAA | 96 | 833 |
| 916868 | N/A | N/A | 23637 | 23652 | GCAGACACAACAGCTT | 40 | 834 |
| 916888 | N/A | N/A | 24507 | 24522 | CCATGCTACGGGCTCT | 0 | 835 |

TABLE 13

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915351 | 33 | 48 | 2771 | 2786 | GGCCAGGGCATTCCCA | 0 | 836 |
| 915371 | 83 | 98 | 2821 | 2836 | GCAGCTCCGCCCGGCG | 2 | 837 |
| 915391 | 132 | 147 | 2870 | 2885 | GGTTAGGATCTGGGTC | 54 | 838 |
| 915411 | 222 | 237 | 2960 | 2975 | GGTAGAAGCCCAGGAA | 57 | 839 |
| 915431 | 321 | 336 | 3059 | 3074 | CGACGCAGTGCAACGC | 49 | 840 |
| 915451 | 368 | 383 | 5942 | 5957 | TGAGAGGACCTGCAGA | 0 | 841 |
| 915471 | 400 | 415 | 5974 | 5989 | ATGTTCCGACTCCTGG | 82 | 842 |
| 915491 | 437 | 452 | 6011 | 6026 | GAACTTGCTTAAGTTG | 23 | 843 |
| 915511 | 468 | 483 | 6042 | 6057 | CCGGGAGGCATTTGCA | 0 | 844 |
| 915531 | 498 | 513 | 6072 | 6087 | TTTTGCCGGAGATGAG | 84 | 845 |
| 915551 | 520 | 535 | 6094 | 6109 | ACTCTGGTAAGAGAGA | 5 | 846 |
| 915571 | 567 | 582 | 6141 | 6156 | CGTCTTTGGACCGAAA | 64 | 847 |
| 915611 | 708 | 723 | 11926 | 11941 | CGGTGATGGTTGTTTT | 98 | 848 |
| 915631 | 783 | 798 | 12001 | 12016 | TGGTGATGTCCACATG | 0 | 849 |
| 915651 | 835 | 850 | 12053 | 12068 | AAAGCTCTCGAGAGAA | 35 | 850 |
| 915671 | 890 | 905 | 13626 | 13641 | ATCCAAATATCCTCGA | 42 | 851 |
| 915691 | 971 | 986 | 16091 | 16106 | AGGATCCATCCCTTCT | 0 | 852 |
| 915711 | 1005 | 1020 | 16125 | 16140 | GACTCATGTTTGCCCA | 73 | 853 |
| 915731 | 1079 | 1094 | 16199 | 16214 | GAGACGCAGGTGGTCT | 0 | 854 |
| 915751 | 1140 | 1155 | N/A | N/A | GTGCTGTAGCGAGCCT | 0 | 855 |
| 915771 | 1202 | 1217 | 19042 | 19057 | AATGGGTAGCAAGTTG | 80 | 856 |
| 915791 | 1248 | 1263 | 19088 | 19103 | ATTCCACAGGCAGGGT | 37 | 857 |
| 915811 | 1327 | 1342 | 23732 | 23747 | GTCACCCACTGCAACC | 52 | 858 |
| 915831 | 1357 | 1372 | 23762 | 23777 | CACATCAGCACTCGAG | 29 | 859 |
| 915851 | 1429 | 1444 | 25192 | 25207 | TCCTGCTCAGGTGTGC | 2 | 860 |

TABLE 13-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915871 | 1513 | 1528 | 25276 | 25291 | GACCTGAGGATGGACC | 20 | 861 |
| 915891 | 1558 | 1573 | 25321 | 25336 | TCAGCACCAGCAGGTA | 68 | 862 |
| 915911 | 1620 | 1635 | 25383 | 25398 | CGCCTCCTCAAGTGAC | 48 | 863 |
| 915931 | 1652 | 1667 | 25415 | 25430 | ACTTTAGCACCTCTGA | 93 | 864 |
| 915951 | 1695 | 1710 | 25458 | 25473 | GTCACTACACAGCAAT | 84 | 865 |
| 915971 | 1776 | 1791 | 25539 | 25554 | GCACAGGCGAAAGGTT | 74 | 866 |
| 915991 | 1798 | 1813 | 25561 | 25576 | TAGAGTTAAGTGCTGG | 84 | 867 |
| 916011 | 1825 | 1840 | 25588 | 25603 | CAGCTGAATTAACGCA | 0 | 868 |
| 916031 | 1868 | 1883 | 25631 | 25646 | TAAGGGACCCTCTGCA | 54 | 869 |
| 916051 | 1892 | 1907 | 25655 | 25670 | TTAATAGGGCCACGAA | 75 | 870 |
| 916071 | 1922 | 1937 | 25685 | 25700 | TAAGAACCTCATGCTG | 56 | 871 |
| 916091 | 1965 | 1980 | 25728 | 25743 | CCCCCCATCACAAGGC | 9 | 872 |
| 916111 | 1987 | 2002 | 25750 | 25765 | AGATCACACATGGGCC | 26 | 873 |
| 916131 | 2084 | 2099 | 25847 | 25862 | ACCACCTGACAGGCAG | 80 | 874 |
| 916150 | 2110 | 2125 | 25873 | 25888 | AGTAGTCAAGGTTATC | 92 | 875 |
| 916170 | 2174 | 2189 | 25937 | 25952 | TGAAAAGGTGTTCTA | 49 | 876 |
| 916190 | 2283 | 2298 | 26046 | 26061 | AAGGCTTATTCTACTA | 79 | 877 |
| 916210 | 2633 | 2648 | 26396 | 26411 | AGGTGAATGCCCTGCA | 71 | 878 |
| 916230 | 2694 | 2709 | 26457 | 26472 | TGTGCTCCAGTGGAGA | 75 | 879 |
| 916250 | 2728 | 2743 | 26491 | 26506 | TGGTCCCTGCAGAAAA | 79 | 880 |
| 916290 | N/A | N/A | 4397 | 4412 | TGCCTACTGGCTCACA | 14 | 881 |
| 916310 | N/A | N/A | 5279 | 5294 | AAATCTTGGGATGCAC | 94 | 882 |
| 916330 | N/A | N/A | 5572 | 5587 | TGACATCATGGCTTCC | 93 | 883 |
| 916350 | N/A | N/A | 6158 | 6173 | GCTTACATCCACGACT | 0 | 884 |
| 916370 | N/A | N/A | 7135 | 7150 | CAAGTAAATGGAGTCC | 77 | 885 |
| 916390 | N/A | N/A | 7620 | 7635 | ATCTATTGCATAATCC | 86 | 886 |
| 916550 | N/A | N/A | 12205 | 12220 | TTTATTTCCGTTAACC | 96 | 887 |
| 916570 | N/A | N/A | 12694 | 12709 | TTCTTGACCGTGTTTC | 98 | 888 |
| 916590 | N/A | N/A | 12990 | 13005 | CCGGAATAAGCCTCCA | 47 | 889 |
| 916610 | N/A | N/A | 13822 | 13837 | TGTACAATGGGACGGA | 69 | 890 |
| 916630 | N/A | N/A | 14418 | 14433 | ATCGACACAGCATCAC | 92 | 891 |
| 916650 | N/A | N/A | 15138 | 15153 | TGCCATACCGGCTCCC | 0 | 892 |
| 916670 | N/A | N/A | 15758 | 15773 | GGTTTATAACAACTGA | 89 | 893 |
| 916690 | N/A | N/A | 16722 | 16737 | GCCTTGAGGTGGGTGG | 0 | 894 |
| 916710 | N/A | N/A | 17512 | 17527 | AGTCATGGGATGTGCA | 58 | 895 |
| 916730 | N/A | N/A | 18395 | 18410 | ATGTTTGGAAGTCGCC | 92 | 896 |

TABLE 13-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916750 | N/A | N/A | 19473 | 19488 | AAGGATCCTGCTTCTA | 9 | 897 |
| 916769 | N/A | N/A | 20554 | 20569 | GCTTACTATGGGATGA | 62 | 898 |
| 916789 | N/A | N/A | 20809 | 20824 | GTAATATTCAGACCAG | 96 | 899 |
| 916809 | N/A | N/A | 21254 | 21269 | ATCCATGCATGGCACA | 72 | 900 |
| 916829 | N/A | N/A | 21979 | 21994 | GTCAGACACGGAGACA | 0 | 901 |
| 916849 | N/A | N/A | 23110 | 23125 | GGCTTTTGAAGGAGAG | 84 | 902 |
| 916869 | N/A | N/A | 23787 | 23802 | TATTTACCTGGAGGCG | 0 | 903 |
| 916889 | N/A | N/A | 24612 | 24627 | CAAATCGGATCTTTGC | 44 | 904 |

TABLE 14

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915352 | 34 | 49 | 2772 | 2787 | CGGCCAGGGCATTCCC | 0 | 905 |
| 915372 | 86 | 101 | 2824 | 2839 | GCAGCAGCTCCGCCCG | 48 | 906 |
| 915392 | 135 | 150 | 2873 | 2888 | GCGGGTTAGGATCTGG | 25 | 907 |
| 915412 | 225 | 240 | 2963 | 2978 | CGTGGTAGAAGCCCAG | 2 | 908 |
| 915432 | 322 | 337 | 3060 | 3075 | CCGACGCAGTGCAACG | 31 | 909 |
| 915452 | 371 | 386 | 5945 | 5960 | ATCTGAGAGGACCTGC | 72 | 910 |
| 915472 | 401 | 416 | 5975 | 5990 | AATGTTCCGACTCCTG | 77 | 911 |
| 915492 | 438 | 453 | 6012 | 6027 | GGAACTTGCTTAAGTT | 55 | 912 |
| 915512 | 469 | 484 | 6043 | 6058 | GCCGGGAGGCATTTGC | 3 | 913 |
| 915532 | 499 | 514 | 6073 | 6088 | ATTTTGCCGGAGATGA | 86 | 914 |
| 915552 | 521 | 536 | 6095 | 6110 | CACTCTGGTAAGAGAG | 8 | 915 |
| 915612 | 709 | 724 | 11927 | 11942 | ACGGTGATGGTTGTTT | 87 | 916 |
| 915632 | 787 | 802 | 12005 | 12020 | AGCTTGGTGATGTCCA | 38 | 917 |
| 915652 | 836 | 851 | 12054 | 12069 | AAAAGCTCTCGAGAGA | 0 | 918 |
| 915672 | 891 | 906 | 13627 | 13642 | CATCCAAATATCCTCG | 82 | 919 |
| 915692 | 972 | 987 | 16092 | 16107 | CAGGATCCATCCCTTC | 0 | 920 |
| 915712 | 1006 | 1021 | 16126 | 16141 | AGACTCATGTTTGCCC | 77 | 921 |
| 915732 | 1081 | 1096 | 16201 | 16216 | CTGAGACGCAGGTGGT | 87 | 922 |
| 915752 | 1141 | 1156 | N/A | N/A | AGTGCTGTAGCGAGCC | 1 | 923 |
| 915772 | 1203 | 1218 | 19043 | 19058 | TAATGGGTAGCAAGTT | 77 | 924 |
| 915792 | 1257 | 1272 | 19097 | 19112 | CAATGGCAGATTCCAC | 56 | 925 |

TABLE 14-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915812 | 1328 | 1343 | 23733 | 23748 | GGTCACCCACTGCAAC | 58 | 926 |
| 915832 | 1358 | 1373 | 23763 | 23778 | ACACATCAGCACTCGA | 66 | 927 |
| 915852 | 1430 | 1445 | 25193 | 25208 | GTCCTGCTCAGGTGTG | 52 | 928 |
| 915872 | 1518 | 1533 | 25281 | 25296 | GGCTGGACCTGAGGAT | 0 | 929 |
| 915892 | 1570 | 1585 | 25333 | 25348 | GTGGAGAGCCCCTCAG | 47 | 930 |
| 915912 | 1621 | 1636 | 25384 | 25399 | TCGCCTCCTCAAGTGA | 8 | 931 |
| 915932 | 1654 | 1669 | 25417 | 25432 | AAACTTTAGCACCTCT | 90 | 932 |
| 915952 | 1696 | 1711 | 25459 | 25474 | GGTCACTACACAGCAA | 82 | 933 |
| 915972 | 1777 | 1792 | 25540 | 25555 | TGCACAGGCGAAAGGT | 64 | 934 |
| 915992 | 1799 | 1814 | 25562 | 25577 | TTAGAGTTAAGTGCTG | 91 | 935 |
| 916012 | 1826 | 1841 | 25589 | 25604 | CCAGCTGAATTAACGC | 32 | 936 |
| 916032 | 1869 | 1884 | 25632 | 25647 | GTAAGGGACCCTCTGC | 73 | 937 |
| 916052 | 1894 | 1909 | 25657 | 25672 | CATTAATAGGGCCACG | 81 | 938 |
| 916072 | 1923 | 1938 | 25686 | 25701 | CTAAGAACCTCATGCT | 70 | 939 |
| 916092 | 1966 | 1981 | 25729 | 25744 | ACCCCCCATCACAAGG | 30 | 940 |
| 916112 | 1988 | 2003 | 25751 | 25766 | AAGATCACACATGGGC | 86 | 941 |
| 916132 | 2085 | 2100 | 25848 | 25863 | GACCACCTGACAGGCA | 61 | 942 |
| 916151 | 2111 | 2126 | 25874 | 25889 | TAGTAGTCAAGGTTAT | 88 | 943 |
| 916171 | 2176 | 2191 | 25939 | 25954 | GGTGAAAAGGTGTTC | 84 | 944 |
| 916191 | 2284 | 2299 | 26047 | 26062 | TAAGGCTTATTCTACT | 76 | 945 |
| 916211 | 2634 | 2649 | 26397 | 26412 | GAGGTGAATGCCCTGC | 0 | 946 |
| 916231 | 2695 | 2710 | 26458 | 26473 | GTGTGCTCCAGTGGAG | 87 | 947 |
| 916251 | 2729 | 2744 | 26492 | 26507 | CTGGTCCCTGCAGAAA | 67 | 948 |
| 916291 | N/A | N/A | 4419 | 4434 | CAATGCTACTTGCCCC | 68 | 949 |
| 916311 | N/A | N/A | 5280 | 5295 | TAAATCTTGGGATGCA | 94 | 950 |
| 916331 | N/A | N/A | 5576 | 5591 | ACAATGACATCATGGC | 97 | 951 |
| 916351 | N/A | N/A | 6165 | 6180 | GCAAACTGCTTACATC | 0 | 952 |
| 916371 | N/A | N/A | 7172 | 7187 | GTTAGACGCGCCAGGC | 7 | 953 |
| 916391 | N/A | N/A | 7624 | 7639 | TCTCATCTATTGCATA | 0 | 954 |
| 916551 | N/A | N/A | 12206 | 12221 | TTTTATTTCCGTTAAC | 73 | 955 |
| 916571 | N/A | N/A | 12714 | 12729 | TAAACTACCGAACGCA | 96 | 956 |
| 916591 | N/A | N/A | 12991 | 13006 | CCCGGAATAAGCCTCC | 47 | 957 |
| 916611 | N/A | N/A | 13823 | 13838 | CTGTACAATGGGACGG | 23 | 958 |
| 916631 | N/A | N/A | 14422 | 14437 | TCCCATCGACACAGCA | 95 | 959 |
| 916651 | N/A | N/A | 15206 | 15221 | GGAATATTGCCAGGTA | 95 | 960 |
| 916671 | N/A | N/A | 15759 | 15774 | TGGTTTATAACAACTG | 29 | 961 |

TABLE 14-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916691 | N/A | N/A | 16746 | 16761 | ATTAGGAGAGGTCTCA | 55 | 962 |
| 916711 | N/A | N/A | 17602 | 17617 | CTTGATAGTGAATGTG | 90 | 963 |
| 916731 | N/A | N/A | 18859 | 18874 | GGCACTCACAAAAGCG | 10 | 964 |
| 916751 | N/A | N/A | 20182 | 20197 | CCCTATGTTCTACTTT | 54 | 965 |
| 916770 | N/A | N/A | 20572 | 20587 | CAACATCTCTAGCTGG | 82 | 966 |
| 916790 | N/A | N/A | 20810 | 20825 | GGTAATATTCAGACCA | 0 | 967 |
| 916810 | N/A | N/A | 21265 | 21280 | TGAAGCTACAGATCCA | 74 | 968 |
| 916830 | N/A | N/A | 22042 | 22057 | GGAAATCTGTCAGAGC | 18 | 969 |
| 916850 | N/A | N/A | 23142 | 23157 | GAATCTAGGAAGGCGA | 77 | 970 |
| 916870 | N/A | N/A | 23789 | 23804 | AGTATTTACCTGGAGG | 0 | 971 |
| 916890 | N/A | N/A | 24738 | 24753 | AGCCTTAGGAAGCCTC | 16 | 972 |

TABLE 15

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915353 | 35 | 50 | 2773 | 2788 | TCGGCCAGGGCATTCC | 0 | 973 |
| 915373 | 87 | 102 | 2825 | 2840 | CGCAGCAGCTCCGCCC | 0 | 974 |
| 915393 | 136 | 151 | 2874 | 2889 | CGCGGGTTAGGATCTG | 0 | 975 |
| 915413 | 239 | 254 | 2977 | 2992 | GCGGGTCGCCCCGACG | 0 | 976 |
| 915433 | 325 | 340 | 3063 | 3078 | ACGCCGACGCAGTGCA | 0 | 977 |
| 915453 | 372 | 387 | 5946 | 5961 | GATCTGAGAGGACCTG | 24 | 978 |
| 915473 | 402 | 417 | 5976 | 5991 | CAATGTTCCGACTCCT | 73 | 979 |
| 915493 | 441 | 456 | 6015 | 6030 | GGAGGAACTTGCTTAA | 87 | 980 |
| 915513 | 470 | 485 | 6044 | 6059 | GGCCGGGAGGCATTTG | 0 | 981 |
| 915533 | 500 | 515 | 6074 | 6089 | TATTTTGCCGGAGATG | 75 | 982 |
| 915553 | 522 | 537 | 6096 | 6111 | ACACTCTGGTAAGAGA | 0 | 983 |
| 915613 | 710 | 725 | 11928 | 11943 | CACGGTGATGGTTGTT | 64 | 984 |
| 915633 | 788 | 803 | 12006 | 12021 | GAGCTTGGTGATGTCC | 74 | 985 |
| 915653 | 837 | 852 | 12055 | 12070 | CAAAAGCTCTCGAGAG | 0 | 986 |
| 915673 | 892 | 907 | 13628 | 13643 | GCATCCAAATATCCTC | 81 | 987 |
| 915693 | 973 | 988 | 16093 | 16108 | TCAGGATCCATCCCTT | 10 | 988 |
| 915713 | 1007 | 1022 | 16127 | 16142 | CAGACTCATGTTTGCC | 0 | 989 |
| 915733 | 1082 | 1097 | 16202 | 16217 | GCTGAGACGCAGGTGG | 64 | 990 |
| 915753 | 1142 | 1157 | N/A | N/A | CAGTGCTGTAGCGAGC | 0 | 991 |

TABLE 15-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915773 | 1204 | 1219 | 19044 | 19059 | CTAATGGGTAGCAAGT | 72 | 992 |
| 915793 | 1258 | 1273 | 19098 | 19113 | GCAATGGCAGATTCCA | 57 | 993 |
| 915813 | 1329 | 1344 | 23734 | 23749 | AGGTCACCCACTGCAA | 56 | 994 |
| 915833 | 1359 | 1374 | 23764 | 23779 | GACACATCAGCACTCG | 43 | 995 |
| 915853 | 1431 | 1446 | 25194 | 25209 | AGTCCTGCTCAGGTGT | 66 | 996 |
| 915873 | 1525 | 1540 | 25288 | 25303 | AAGTTCAGGCTGGACC | 54 | 997 |
| 915893 | 1571 | 1586 | 25334 | 25349 | GGTGGAGAGCCCCTCA | 0 | 998 |
| 915913 | 1622 | 1637 | 25385 | 25400 | CTCGCCTCCTCAAGTG | 52 | 999 |
| 915933 | 1660 | 1675 | 25423 | 25438 | GATGGGAAACTTTAGC | 85 | 1000 |
| 915953 | 1697 | 1712 | 25460 | 25475 | GGGTCACTACACAGCA | 78 | 1001 |
| 915973 | 1778 | 1793 | 25541 | 25556 | CTGCACAGGCGAAAGG | 35 | 1002 |
| 915993 | 1800 | 1815 | 25563 | 25578 | ATTAGAGTTAAGTGCT | 63 | 1003 |
| 916013 | 1827 | 1842 | 25590 | 25605 | ACCAGCTGAATTAACG | 66 | 1004 |
| 916033 | 1873 | 1888 | 25636 | 25651 | GTCAGTAAGGGACCCT | 52 | 1005 |
| 916053 | 1897 | 1912 | 25660 | 25675 | GACCATTAATAGGGCC | 51 | 1006 |
| 916073 | 1924 | 1939 | 25687 | 25702 | TCTAAGAACCTCATGC | 55 | 1007 |
| 916093 | 1967 | 1982 | 25730 | 25745 | TACCCCCATCACAAG | 15 | 1008 |
| 916113 | 1990 | 2005 | 25753 | 25768 | ACAAGATCACACATGG | 72 | 1009 |
| 916133 | 2086 | 2101 | 25849 | 25864 | AGACCACCTGACAGGC | 79 | 1010 |
| 916152 | 2112 | 2127 | 25875 | 25890 | TTAGTAGTCAAGGTTA | 84 | 1011 |
| 916172 | 2177 | 2192 | 25940 | 25955 | AGGTGAAAAAGGTGTT | 88 | 1012 |
| 916192 | 2285 | 2300 | 26048 | 26063 | TTAAGGCTTATTCTAC | 82 | 1013 |
| 916212 | 2635 | 2650 | 26398 | 26413 | TGAGGTGAATGCCCTG | 58 | 1014 |
| 916232 | 2696 | 2711 | 26459 | 26474 | TGTGTGCTCCAGTGGA | 89 | 1015 |
| 916252 | 2730 | 2745 | 26493 | 26508 | GCTGGTCCCTGCAGAA | 44 | 1016 |
| 916272 | N/A | N/A | 3328 | 3343 | GGGACGCACGAGAGTC | 0 | 1017 |
| 916292 | N/A | N/A | 4432 | 4447 | GTCAATAGCTTCACAA | 86 | 1018 |
| 916312 | N/A | N/A | 5281 | 5296 | ATAAATCTTGGGATGC | 92 | 1019 |
| 916332 | N/A | N/A | 5577 | 5592 | CACAATGACATCATGG | 95 | 1020 |
| 916352 | N/A | N/A | 6170 | 6185 | GATAAGCAAACTGCTT | 19 | 1021 |
| 916372 | N/A | N/A | 7192 | 7207 | GAGGATGCAACTGGCT | 84 | 1022 |
| 916392 | N/A | N/A | 7644 | 7659 | TCGGACTTCAGGCCCA | 0 | 1023 |
| 916552 | N/A | N/A | 12208 | 12223 | CCTTTTATTTCCGTTA | 97 | 1024 |
| 916572 | N/A | N/A | 12745 | 12760 | GCATACTAAAACCACC | 85 | 1025 |
| 916592 | N/A | N/A | 13375 | 13390 | GACTTTGCAGGCACCC | 92 | 1026 |
| 916612 | N/A | N/A | 13909 | 13924 | TGACATCCCAGTTCAA | 30 | 1027 |

TABLE 15-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916632 | N/A | N/A | 14427 | 14442 | TACTTTCCCATCGACA | 81 | 1028 |
| 916652 | N/A | N/A | 15207 | 15222 | AGGAATATTGCCAGGT | 88 | 1029 |
| 916672 | N/A | N/A | 15768 | 15783 | GGTTAGTGTTGGTTTA | 92 | 1030 |
| 916692 | N/A | N/A | 16790 | 16805 | CATTCGATGGAGGTTC | 58 | 1031 |
| 916712 | N/A | N/A | 17629 | 17644 | GGCGGATTTCCCCACT | 11 | 1032 |
| 916732 | N/A | N/A | 18894 | 18909 | TAAAATACGCCCGTCC | 7 | 1033 |
| 916752 | N/A | N/A | 20183 | 20198 | TCCCTATGTTCTACTT | 32 | 1034 |
| 916771 | N/A | N/A | 20574 | 20589 | ATCAACATCTCTAGCT | 46 | 1035 |
| 916791 | N/A | N/A | 20811 | 20826 | GGGTAATATTCAGACC | 43 | 1036 |
| 916811 | N/A | N/A | 21313 | 21328 | TTTACTAGAGACTCTG | 69 | 1037 |
| 916831 | N/A | N/A | 22071 | 22086 | GTAGGATAGGACTAGA | 45 | 1038 |
| 916851 | N/A | N/A | 23219 | 23234 | ATAAATGCCTGACCAC | 64 | 1039 |
| 916871 | N/A | N/A | 23861 | 23876 | TGTTTCTAGAATGTCG | 68 | 1040 |
| 916891 | N/A | N/A | 24873 | 24888 | GCCTATCAGTTTCCCC | 0 | 1041 |

TABLE 16

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915354 | 36 | 51 | 2774 | 2789 | CTCGGCCAGGGCATTC | 0 | 1042 |
| 915374 | 89 | 104 | 2827 | 2842 | TCCGCAGCAGCTCCGC | 60 | 1043 |
| 915394 | 137 | 152 | 2875 | 2890 | GCGCGGGTTAGGATCT | 0 | 1044 |
| 915414 | 240 | 255 | 2978 | 2993 | AGCGGGTCGCCCCGAC | 21 | 1045 |
| 915434 | 337 | 352 | 3075 | 3090 | ATACCGGAGAGGACGC | 85 | 1046 |
| 915454 | 374 | 389 | 5948 | 5963 | AAGATCTGAGAGGACC | 24 | 1047 |
| 915474 | 403 | 418 | 5977 | 5992 | CCAATGTTCCGACTCC | 95 | 1048 |
| 915494 | 442 | 457 | 6016 | 6031 | CGGAGGAACTTGCTTA | 93 | 1049 |
| 915514 | 471 | 486 | 6045 | 6060 | TGGCCGGAGGCATTT | 0 | 1050 |
| 915534 | 501 | 516 | 6075 | 6090 | CTATTTGCCGGAGAT | 87 | 1051 |
| 915554 | 523 | 538 | 6097 | 6112 | GACACTCTGGTAAGAG | 26 | 1052 |
| 915614 | 711 | 726 | 11929 | 11944 | ACACGGTGATGGTTGT | 46 | 1053 |
| 915634 | 791 | 806 | 12009 | 12024 | ACTGAGCTTGGTGATG | 87 | 1054 |
| 915654 | 838 | 853 | 12056 | 12071 | ACAAAGCTCTCGAGA | 0 | 1055 |
| 915674 | 900 | 915 | 13636 | 13651 | ACCTGAATGCATCCAA | 93 | 1056 |

TABLE 16-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915694 | 974 | 989 | 16094 | 16109 | CTCAGGATCCATCCCT | 43 | 1057 |
| 915714 | 1008 | 1023 | 16128 | 16143 | CCAGACTCATGTTTGC | 0 | 1058 |
| 915734 | 1083 | 1098 | 16203 | 16218 | TGCTGAGACGCAGGTG | 50 | 1059 |
| 915754 | 1143 | 1158 | N/A | N/A | TCAGTGCTGTAGCGAG | 42 | 1060 |
| 915774 | 1208 | 1223 | 19048 | 19063 | TATCCTAATGGGTAGC | 53 | 1061 |
| 915794 | 1260 | 1275 | 19100 | 19115 | TCGCAATGGCAGATTC | 67 | 1062 |
| 915814 | 1333 | 1348 | 23738 | 23753 | TGTGAGGTCACCCACT | 0 | 1063 |
| 915834 | 1360 | 1375 | 23765 | 23780 | AGACACATCAGCACTC | 24 | 1064 |
| 915854 | 1432 | 1447 | 25195 | 25210 | CAGTCCTGCTCAGGTG | 54 | 1065 |
| 915874 | 1526 | 1541 | 25289 | 25304 | GAAGTTCAGGCTGGAC | 75 | 1066 |
| 915894 | 1572 | 1587 | 25335 | 25350 | AGGTGGAGAGCCCCTC | 0 | 1067 |
| 915914 | 1623 | 1638 | 25386 | 25401 | ACTCGCCTCCTCAAGT | 0 | 1068 |
| 915934 | 1661 | 1676 | 25424 | 25439 | AGATGGGAAACTTTAG | 84 | 1069 |
| 915954 | 1724 | 1739 | 25487 | 25502 | GGCTGGGATCCTCCAC | 24 | 1070 |
| 915974 | 1779 | 1794 | 25542 | 25557 | GCTGCACAGGCGAAAG | 56 | 1071 |
| 915994 | 1801 | 1816 | 25564 | 25579 | TATTAGAGTTAAGTGC | 75 | 1072 |
| 916014 | 1828 | 1843 | 25591 | 25606 | AACCAGCTGAATTAAC | 55 | 1073 |
| 916034 | 1875 | 1890 | 25638 | 25653 | CAGTCAGTAAGGGACC | 70 | 1074 |
| 916054 | 1898 | 1913 | 25661 | 25676 | TGACCATTAATAGGGC | 74 | 1075 |
| 916074 | 1925 | 1940 | 25688 | 25703 | TTCTAAGAACCTCATG | 22 | 1076 |
| 916094 | 1968 | 1983 | 25731 | 25746 | CTACCCCCCATCACAA | 0 | 1077 |
| 916114 | 1992 | 2007 | 25755 | 25770 | CCACAAGATCACACAT | 0 | 1078 |
| 916134 | 2087 | 2102 | 25850 | 25865 | CAGACCACCTGACAGG | 78 | 1079 |
| 916153 | 2113 | 2128 | 25876 | 25891 | TTTAGTAGTCAAGGTT | 93 | 1080 |
| 916173 | 2178 | 2193 | 25941 | 25956 | TAGGTGAAAAGGTGT | 89 | 1081 |
| 916193 | 2306 | 2321 | 26069 | 26084 | ACCCAACCGATTTTTT | 61 | 1082 |
| 916213 | 2636 | 2651 | 26399 | 26414 | CTGAGGTGAATGCCCT | 73 | 1083 |
| 916233 | 2697 | 2712 | 26460 | 26475 | TTGTGTGCTCCAGTGG | 92 | 1084 |
| 916253 | 2746 | 2761 | 26509 | 26524 | TCACTGACCATGTGGG | 16 | 1085 |
| 916273 | N/A | N/A | 3362 | 3377 | CTTCATGCACGGGCGC | 37 | 1086 |
| 916293 | N/A | N/A | 4462 | 4477 | GCATAATCTCCTGCCT | 0 | 1087 |
| 916313 | N/A | N/A | 5284 | 5299 | GCCATAAATCTTGGGA | 37 | 1088 |
| 916333 | N/A | N/A | 5605 | 5620 | CTTTATTCAATGTGGC | 97 | 1089 |
| 916353 | N/A | N/A | 6529 | 6544 | TACAACTGCCTGTGTT | 0 | 1090 |
| 916373 | N/A | N/A | 7218 | 7233 | AAAGCTTCCGCAAACA | 51 | 1091 |
| 916393 | N/A | N/A | 7657 | 7672 | CTAACATACACCCTCG | 0 | 1092 |

TABLE 16-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916553 | N/A | N/A | 12225 | 12240 | AGCTTCTGGGACAAGC | 10 | 1093 |
| 916573 | N/A | N/A | 12746 | 12761 | GGCATACTAAAACCAC | 55 | 1094 |
| 916593 | N/A | N/A | 13397 | 13412 | TTGAATGTCACCCTTC | 91 | 1095 |
| 916613 | N/A | N/A | 13914 | 13929 | AGTCATGACATCCCAG | 93 | 1096 |
| 916633 | N/A | N/A | 14442 | 14457 | TCTCATTGGCACCTGT | 86 | 1097 |
| 916653 | N/A | N/A | 15252 | 15267 | CCCTATCAGATGCCCT | 81 | 1098 |
| 916673 | N/A | N/A | 15799 | 15814 | CATATCTGGTTTCATG | 0 | 1099 |
| 916693 | N/A | N/A | 16842 | 16857 | GACCATAGCACTGTCT | 0 | 1100 |
| 916713 | N/A | N/A | 17737 | 17752 | ATTAATCTGGTCATAT | 0 | 1101 |
| 916733 | N/A | N/A | 18898 | 18913 | TCCATAAAATACGCCC | 69 | 1102 |
| 916753 | N/A | N/A | 20195 | 20210 | GAAAGATGGAATTCCC | 86 | 1103 |
| 916772 | N/A | N/A | 20604 | 20619 | TACGATCATCATTATT | 91 | 1104 |
| 916792 | N/A | N/A | 20841 | 20856 | GTATTAGCTCAATATT | 0 | 1105 |
| 916812 | N/A | N/A | 21314 | 21329 | GTTTACTAGAGACTCT | 64 | 1106 |
| 916832 | N/A | N/A | 22080 | 22095 | GTAAAAACTGTAGGAT | 0 | 1107 |
| 916852 | N/A | N/A | 23220 | 23235 | GATAAATGCCTGACCA | 29 | 1108 |
| 916872 | N/A | N/A | 24011 | 24026 | CCGACGGGAAGTCTTC | 0 | 1109 |
| 916892 | N/A | N/A | 24874 | 24889 | GGCCTATCAGTTTCCC | 0 | 1110 |

TABLE 17

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915355 | 37 | 52 | 2775 | 2790 | TCTCGGCCAGGGCATT | 0 | 1111 |
| 915375 | 90 | 105 | 2828 | 2843 | ATCCGCAGCAGCTCCG | 52 | 1112 |
| 915395 | 138 | 153 | 2876 | 2891 | GGCGCGGGTTAGGATC | 0 | 1113 |
| 915415 | 241 | 256 | 2979 | 2994 | CAGCGGGTCGCCCCGA | 8 | 1114 |
| 915435 | 338 | 353 | 3076 | 3091 | GATACCGGAGAGGACG | 30 | 1115 |
| 915455 | 378 | 393 | 5952 | 5967 | GCACAAGATCTGAGAG | 72 | 1116 |
| 915475 | 405 | 420 | 5979 | 5994 | TGCCAATGTTCCGACT | 0 | 1117 |
| 915495 | 443 | 458 | 6017 | 6032 | TCGGAGGAACTTGCTT | 69 | 1118 |
| 915515 | 472 | 487 | 6046 | 6061 | TTGGCCGGGAGGCATT | 9 | 1119 |
| 915535 | 502 | 517 | 6076 | 6091 | CCTATTTTGCCGGAGA | 96 | 1120 |
| 915555 | 524 | 539 | 6098 | 6113 | AGACACTCTGGTAAGA | 2 | 1121 |
| 915615 | 712 | 727 | 11930 | 11945 | GACACGGTGATGGTTG | 32 | 1122 |

TABLE 17-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915635 | 792 | 807 | 12010 | 12025 | GACTGAGCTTGGTGAT | 93 | 1123 |
| 915655 | 839 | 854 | 12057 | 12072 | GACAAAAGCTCTCGAG | 40 | 1124 |
| 915675 | 901 | 916 | 13637 | 13652 | AACCTGAATGCATCCA | 92 | 1125 |
| 915695 | 975 | 990 | 16095 | 16110 | CCTCAGGATCCATCCC | 0 | 1126 |
| 915715 | 1011 | 1026 | 16131 | 16146 | AATCCAGACTCATGTT | 67 | 1127 |
| 915735 | 1088 | 1103 | 16208 | 16223 | CAGGATGCTGAGACGC | 86 | 1128 |
| 915755 | 1144 | 1159 | N/A | N/A | CTCAGTGCTGTAGCGA | 25 | 1129 |
| 915775 | 1209 | 1224 | 19049 | 19064 | TTATCCTAATGGGTAG | 23 | 1130 |
| 915795 | 1261 | 1276 | 19101 | 19116 | ATCGCAATGGCAGATT | 0 | 1131 |
| 915815 | 1337 | 1352 | 23742 | 23757 | CACCTGTGAGGTCACC | 35 | 1132 |
| 915835 | 1361 | 1376 | 23766 | 23781 | CAGACACATCAGCACT | 54 | 1133 |
| 915855 | 1433 | 1448 | 25196 | 25211 | CCAGTCCTGCTCAGGT | 23 | 1134 |
| 915875 | 1530 | 1545 | 25293 | 25308 | AGAAGAAGTTCAGGCT | 81 | 1135 |
| 915895 | 1574 | 1589 | 25337 | 25352 | AAAGGTGGAGAGCCCC | 76 | 1136 |
| 915915 | 1624 | 1639 | 25387 | 25402 | GACTCGCCTCCTCAAG | 75 | 1137 |
| 915935 | 1674 | 1689 | 25437 | 25452 | GGTAGCTGCACAAAGA | 76 | 1138 |
| 915955 | 1726 | 1741 | 25489 | 25504 | GAGGCTGGGATCCTCC | 0 | 1139 |
| 915975 | 1780 | 1795 | 25543 | 25558 | CGCTGCACAGGCGAAA | 0 | 1140 |
| 915995 | 1805 | 1820 | 25568 | 25583 | GATGTATTAGAGTTAA | 82 | 1141 |
| 916015 | 1829 | 1844 | 25592 | 25607 | CAACCAGCTGAATTAA | 59 | 1142 |
| 916035 | 1876 | 1891 | 25639 | 25654 | ACAGTCAGTAAGGGAC | 81 | 1143 |
| 916055 | 1899 | 1914 | 25662 | 25677 | CTGACCATTAATAGGG | 49 | 1144 |
| 916075 | 1929 | 1944 | 25692 | 25707 | GTCATTCTAAGAACCT | 81 | 1145 |
| 916095 | 1969 | 1984 | 25732 | 25747 | CCTACCCCCCATCACA | 21 | 1146 |
| 916115 | 1995 | 2010 | 25758 | 25773 | ACCCCACAAGATCACA | 0 | 1147 |
| 916135 | 2088 | 2103 | 25851 | 25866 | GCAGACCACCTGACAG | 44 | 1148 |
| 916154 | 2131 | 2146 | 25894 | 25909 | CCCCGCCATGGAGACG | 68 | 1149 |
| 916174 | 2180 | 2195 | 25943 | 25958 | GTTAGGTGAAAAAGGT | 90 | 1150 |
| 916194 | 2308 | 2323 | 26071 | 26086 | GCACCCAACCGATTTT | 83 | 1151 |
| 916214 | 2637 | 2652 | 26400 | 26415 | GCTGAGGTGAATGCCC | 52 | 1152 |
| 916234 | 2698 | 2713 | 26461 | 26476 | GTTGTGTGCTCCAGTG | 88 | 1153 |
| 916254 | 2747 | 2762 | 26510 | 26525 | CTCACTGACCATGTGG | 13 | 1154 |
| 916274 | N/A | N/A | 3524 | 3539 | GCAAATCGGCCCCTCG | 3 | 1155 |
| 916294 | N/A | N/A | 4463 | 4478 | GGCATAATCTCCTGCC | 0 | 1156 |
| 916314 | N/A | N/A | 5324 | 5339 | TGGCATGCAAGACCAC | 0 | 1157 |
| 916334 | N/A | N/A | 5606 | 5621 | ACTTTATTCAATGTGG | 95 | 1158 |

TABLE 17-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916354 | N/A | N/A | 6556 | 6571 | GTTTATGTCACTCTGG | 68 | 1159 |
| 916374 | N/A | N/A | 7245 | 7260 | GAACAGACAAGTGCTG | 38 | 1160 |
| 916394 | N/A | N/A | 7658 | 7673 | ACTAACATACACCCTC | 31 | 1161 |
| 916554 | N/A | N/A | 12249 | 12264 | ATAATCAGGGTGGTGC | 0 | 1162 |
| 916574 | N/A | N/A | 12747 | 12762 | AGGCATACTAAAACCA | 47 | 1163 |
| 916594 | N/A | N/A | 13500 | 13515 | GAATCATGCAAGCTCT | 50 | 1164 |
| 916614 | N/A | N/A | 13996 | 14011 | TAAACTAAGGGTCACA | 37 | 1165 |
| 916634 | N/A | N/A | 14497 | 14512 | ATCCATCCTGCATGAG | 76 | 1166 |
| 916654 | N/A | N/A | 15254 | 15269 | GGCCCTATCAGATGCC | 0 | 1167 |
| 916674 | N/A | N/A | 15802 | 15817 | CTACATATCTGGTTTC | 0 | 1168 |
| 916694 | N/A | N/A | 16844 | 16859 | TGGACCATAGCACTGT | 60 | 1169 |
| 916714 | N/A | N/A | 17738 | 17753 | TATTAATCTGGTCATA | 18 | 1170 |
| 916734 | N/A | N/A | 18926 | 18941 | CCACTTTACTCTGTTG | 64 | 1171 |
| 916754 | N/A | N/A | 20210 | 20225 | AACTATGCCTAGAACG | 43 | 1172 |
| 916773 | N/A | N/A | 20606 | 20621 | TTTACGATCATCATTA | 77 | 1173 |
| 916793 | N/A | N/A | 20842 | 20857 | TGTATTAGCTCAATAT | 0 | 1174 |
| 916813 | N/A | N/A | 21319 | 21334 | TGGGAGTTTACTAGAG | 66 | 1175 |
| 916833 | N/A | N/A | 22118 | 22133 | AGAGAGTACTCTTGGA | 11 | 1176 |
| 916853 | N/A | N/A | 23222 | 23237 | CTGATAAATGCCTGAC | 78 | 1177 |
| 916873 | N/A | N/A | 24038 | 24053 | ATCAATGCTGCACTCA | 88 | 1178 |
| 916893 | N/A | N/A | 24889 | 24904 | ACGAATCCCTGGAGGG | 0 | 1179 |

TABLE 18

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915356 | 38 | 53 | 2776 | 2791 | GTCTCGGCCAGGGCAT | 0 | 1180 |
| 915376 | 93 | 108 | 2831 | 2846 | CTGATCCGCAGCAGCT | 28 | 1181 |
| 915396 | 165 | 180 | 2903 | 2918 | CGTACATGGCGGCGGC | 0 | 1182 |
| 915416 | 242 | 257 | 2980 | 2995 | GCAGCGGGTCGCCCCG | 0 | 1183 |
| 915436 | 339 | 354 | 3077 | 3092 | GGATACCGGAGAGGAC | 64 | 1184 |
| 915456 | 379 | 394 | 5953 | 5968 | CGCACAAGATCTGAGA | 79 | 1185 |
| 915476 | 406 | 421 | 5980 | 5995 | ATGCCAATGTTCCGAC | 83 | 1186 |
| 915496 | 444 | 459 | 6018 | 6033 | GTCGGAGGAACTTGCT | 35 | 1187 |

TABLE 18-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915516 | 473 | 488 | 6047 | 6062 | ATTGGCCGGGAGGCAT | 0 | 1188 |
| 915536 | 503 | 518 | 6077 | 6092 | GCCTATTTTGCCGGAG | 77 | 1189 |
| 915556 | 525 | 540 | 6099 | 6114 | CAGACACTCTGGTAAG | 62 | 1190 |
| 915616 | 730 | 745 | 11948 | 11963 | TACTCCCCATAGAAGG | 8 | 1191 |
| 915636 | 794 | 809 | 12012 | 12027 | TAGACTGAGCTTGGTG | 90 | 1192 |
| 915656 | 840 | 855 | 12058 | 12073 | GGACAAAAGCTCTCGA | 60 | 1193 |
| 915676 | 902 | 917 | 13638 | 13653 | GAACCTGAATGCATCC | 72 | 1194 |
| 915696 | 978 | 993 | 16098 | 16113 | CGACCTCAGGATCCAT | 0 | 1195 |
| 915716 | 1012 | 1027 | 16132 | 16147 | GAATCCAGACTCATGT | 0 | 1196 |
| 915736 | 1089 | 1104 | 16209 | 16224 | GCAGGATGCTGAGACG | 55 | 1197 |
| 915756 | 1145 | 1160 | N/A | N/A | ACTCAGTGCTGTAGCG | 12 | 1198 |
| 915776 | 1210 | 1225 | 19050 | 19065 | ATTATCCTAATGGGTA | 28 | 1199 |
| 915796 | 1262 | 1277 | 19102 | 19117 | AATCGCAATGGCAGAT | 0 | 1200 |
| 915816 | 1339 | 1354 | 23744 | 23759 | AACACCTGTGAGGTCA | 56 | 1201 |
| 915836 | 1365 | 1380 | 23770 | 23785 | GGAGCAGACACATCAG | 53 | 1202 |
| 915856 | 1434 | 1449 | 25197 | 25212 | GCCAGTCCTGCTCAGG | 21 | 1203 |
| 915876 | 1531 | 1546 | 25294 | 25309 | AAGAAGAAGTTCAGGC | 85 | 1204 |
| 915896 | 1575 | 1590 | 25338 | 25353 | GAAAGGTGGAGAGCCC | 78 | 1205 |
| 915916 | 1626 | 1641 | 25389 | 25404 | TAGACTCGCCTCCTCA | 32 | 1206 |
| 915936 | 1676 | 1691 | 25439 | 25454 | GAGGTAGCTGCACAAA | 91 | 1207 |
| 915956 | 1737 | 1752 | 25500 | 25515 | AACTCAGCTCAGAGGC | 46 | 1208 |
| 915976 | 1781 | 1796 | 25544 | 25559 | CCGCTGCACAGGCGAA | 0 | 1209 |
| 915996 | 1807 | 1822 | 25570 | 25585 | CTGATGTATTAGAGTT | 93 | 1210 |
| 916016 | 1830 | 1845 | 25593 | 25608 | CCAACCAGCTGAATTA | 21 | 1211 |
| 916036 | 1877 | 1892 | 25640 | 25655 | AACAGTCAGTAAGGGA | 82 | 1212 |
| 916056 | 1900 | 1915 | 25663 | 25678 | TCTGACCATTAATAGG | 13 | 1213 |
| 916076 | 1930 | 1945 | 25693 | 25708 | TGTCATTCTAAGAACC | 40 | 1214 |
| 916096 | 1970 | 1985 | 25733 | 25748 | GCCTACCCCCATCAC | 18 | 1215 |
| 916116 | 1996 | 2011 | 25759 | 25774 | CACCCCACAAGATCAC | 50 | 1216 |
| 916136 | 2089 | 2104 | 25852 | 25867 | TGCAGACCACCTGACA | 58 | 1217 |
| 916155 | 2132 | 2147 | 25895 | 25910 | CCCCCGCCATGGAGAC | 33 | 1218 |
| 916175 | 2224 | 2239 | 25987 | 26002 | CGCTTCCTTACATTTT | 89 | 1219 |
| 916195 | 2309 | 2324 | 26072 | 26087 | TGCACCCAACCGATTT | 64 | 1220 |
| 916215 | 2638 | 2653 | 26401 | 26416 | GGCTGAGGTGAATGCC | 0 | 1221 |
| 916235 | 2699 | 2714 | 26462 | 26477 | AGTTGTGTGCTCCAGT | 85 | 1222 |
| 916255 | 2748 | 2763 | 26511 | 26526 | ACTCACTGACCATGTG | 0 | 1223 |

TABLE 18-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916275 | N/A | N/A | 3555 | 3570 | GGCCAAAGCCCCACTC | 0 | 1224 |
| 916295 | N/A | N/A | 4464 | 4479 | GGGCATAATCTCCTGC | 0 | 1225 |
| 916315 | N/A | N/A | 5342 | 5357 | GGCTGATCTGCACTCT | 84 | 1226 |
| 916335 | N/A | N/A | 5626 | 5641 | TAATTCTACCTGTGTC | 92 | 1227 |
| 916355 | N/A | N/A | 6557 | 6572 | AGTTTATGTCACTCTG | 27 | 1228 |
| 916375 | N/A | N/A | 7321 | 7336 | ACACTTTGCGAAGCAC | 27 | 1229 |
| 916395 | N/A | N/A | 7660 | 7675 | GAACTAACATACACCC | 1 | 1230 |
| 916555 | N/A | N/A | 12252 | 12267 | CCCATAATCAGGGTGG | 0 | 1231 |
| 916575 | N/A | N/A | 12758 | 12773 | GTAGAGTGGTAAGGCA | 95 | 1232 |
| 916595 | N/A | N/A | 13502 | 13517 | AAGAATCATGCAAGCT | 34 | 1233 |
| 916615 | N/A | N/A | 13997 | 14012 | TTAAACTAAGGGTCAC | 65 | 1234 |
| 916635 | N/A | N/A | 14549 | 14564 | TTAATGTGGATTCACG | 76 | 1235 |
| 916655 | N/A | N/A | 15295 | 15310 | CCAAGATAACCTCACA | 64 | 1236 |
| 916675 | N/A | N/A | 15806 | 15821 | CCATCTACATATCTGG | 26 | 1237 |
| 916695 | N/A | N/A | 16854 | 16869 | CACAATCATTTGGACC | 72 | 1238 |
| 916715 | N/A | N/A | 17739 | 17754 | GTATTAATCTGGTCAT | 87 | 1239 |
| 916735 | N/A | N/A | 19113 | 19128 | CACCTCTGGACAATCG | 29 | 1240 |
| 916755 | N/A | N/A | 20212 | 20227 | CAAACTATGCCTAGAA | 70 | 1241 |
| 916774 | N/A | N/A | 20608 | 20623 | ATTTTACGATCATCAT | 91 | 1242 |
| 916794 | N/A | N/A | 20846 | 20861 | TGCCTGTATTAGCTCA | 90 | 1243 |
| 916814 | N/A | N/A | 21345 | 21360 | CACATAAAGTCAAACG | 87 | 1244 |
| 916834 | N/A | N/A | 22124 | 22139 | AGAACAAGAGAGTACT | 3 | 1245 |
| 916854 | N/A | N/A | 23250 | 23265 | CACATAAAGGACCCCC | 54 | 1246 |
| 916874 | N/A | N/A | 24126 | 24141 | CGCTATCTGACACTCC | 87 | 1247 |
| 916894 | N/A | N/A | 24896 | 24911 | TCCACCAACGAATCCC | 50 | 1248 |

TABLE 19

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915357 | 39 | 54 | 2777 | 2792 | TGTCTCGGCCAGGGCA | 0 | 1249 |
| 915377 | 94 | 109 | 2832 | 2847 | CCTGATCCGCAGCAGC | 0 | 1250 |
| 915397 | 182 | 197 | 2920 | 2935 | CCAGCCGCGCTCTGCG | 0 | 1251 |
| 915417 | 243 | 258 | 2981 | 2996 | GGCAGCGGGTCGCCCC | 0 | 1252 |
| 915437 | 341 | 356 | 3079 | 3094 | CGGGATACCGGAGAGG | 57 | 1253 |

TABLE 19-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915457 | 380 | 395 | 5954 | 5969 | CCGCACAAGATCTGAG | 71 | 1254 |
| 915477 | 407 | 422 | 5981 | 5996 | GATGCCAATGTTCCGA | 93 | 1255 |
| 915497 | 445 | 460 | 6019 | 6034 | TGTCGGAGGAACTTGC | 85 | 1256 |
| 915517 | 474 | 489 | 6048 | 6063 | CATTGGCCGGGAGGCA | 0 | 1257 |
| 915537 | 504 | 519 | 6078 | 6093 | TGCCTATTTTGCCGGA | 44 | 1258 |
| 915557 | 526 | 541 | 6100 | 6115 | TCAGACACTCTGGTAA | 26 | 1259 |
| 915617 | 732 | 747 | 11950 | 11965 | CGTACTCCCCATAGAA | 66 | 1260 |
| 915637 | 796 | 811 | 12014 | 12029 | CGTAGACTGAGCTTGG | 98 | 1261 |
| 915657 | 857 | 872 | 12075 | 12090 | CACCTTGAGATCCGGG | 0 | 1262 |
| 915677 | 903 | 918 | 13639 | 13654 | AGAACCTGAATGCATC | 78 | 1263 |
| 915697 | 979 | 994 | 16099 | 16114 | GCGACCTCAGGATCCA | 1 | 1264 |
| 915717 | 1031 | 1046 | 16151 | 16166 | GGCAGCCGACTCCGGG | 19 | 1265 |
| 915737 | 1109 | 1124 | 16229 | 16244 | CAGGATGCTCTCATCC | 0 | 1266 |
| 915757 | 1146 | 1161 | N/A | N/A | CACTCAGTGCTGTAGC | 33 | 1267 |
| 915777 | 1214 | 1229 | 19054 | 19069 | AGACATTATCCTAATG | 42 | 1268 |
| 915797 | 1263 | 1278 | 19103 | 19118 | CAATCGCAATGGCAGA | 49 | 1269 |
| 915817 | 1340 | 1355 | 23745 | 23760 | GAACACCTGTGAGGTC | 44 | 1270 |
| 915837 | 1398 | 1413 | 25161 | 25176 | GGCTGCTCACTGGCAT | 18 | 1271 |
| 915857 | 1435 | 1450 | 25198 | 25213 | GGCCAGTCCTGCTCAG | 0 | 1272 |
| 915877 | 1534 | 1549 | 25297 | 25312 | CCCAAGAAGAAGTTCA | 76 | 1273 |
| 915897 | 1576 | 1591 | 25339 | 25354 | GGAAAGGTGGAGAGCC | 24 | 1274 |
| 915917 | 1627 | 1642 | 25390 | 25405 | CTAGACTCGCCTCCTC | 77 | 1275 |
| 915937 | 1679 | 1694 | 25442 | 25457 | GCGGAGGTAGCTGCAC | 16 | 1276 |
| 915957 | 1738 | 1753 | 25501 | 25516 | CAACTCAGCTCAGAGG | 61 | 1277 |
| 915977 | 1782 | 1797 | 25545 | 25560 | ACCGCTGCACAGGCGA | 34 | 1278 |
| 915997 | 1809 | 1824 | 25572 | 25587 | TGCTGATGTATTAGAG | 83 | 1279 |
| 916017 | 1831 | 1846 | 25594 | 25609 | CCCAACCAGCTGAATT | 42 | 1280 |
| 916037 | 1878 | 1893 | 25641 | 25656 | AAACAGTCAGTAAGGG | 92 | 1281 |
| 916057 | 1901 | 1916 | 25664 | 25679 | GTCTGACCATTAATAG | 64 | 1282 |
| 916077 | 1931 | 1946 | 25694 | 25709 | CTGTCATTCTAAGAAC | 41 | 1283 |
| 916097 | 1971 | 1986 | 25734 | 25749 | AGCCTACCCCCCATCA | 0 | 1284 |
| 916117 | 1997 | 2012 | 25760 | 25775 | CCACCCCACAAGATCA | 0 | 1285 |
| 916137 | 2090 | 2105 | 25853 | 25868 | TTGCAGACCACCTGAC | 65 | 1286 |
| 916156 | 2133 | 2148 | 25896 | 25911 | ACCCCCGCCATGGAGA | 54 | 1287 |
| 916176 | 2225 | 2240 | 25988 | 26003 | ACGCTTCCTTACATTT | 84 | 1288 |
| 916196 | 2310 | 2325 | 26073 | 26088 | CTGCACCCAACCGATT | 58 | 1289 |

TABLE 19-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916216 | 2639 | 2654 | 26402 | 26417 | GGGCTGAGGTGAATGC | 46 | 1290 |
| 916236 | 2700 | 2715 | 26463 | 26478 | AAGTTGTGTGCTCCAG | 86 | 1291 |
| 916256 | 2751 | 2766 | 26514 | 26529 | GAAACTCACTGACCAT | 41 | 1292 |
| 916276 | N/A | N/A | 4068 | 4083 | GGAAACAACTTTCCTC | 0 | 1293 |
| 916296 | N/A | N/A | 4730 | 4745 | GATCATGTGGCGGTCT | 68 | 1294 |
| 916316 | N/A | N/A | 5364 | 5379 | CACTTACTGGCCTGGC | 30 | 1295 |
| 916336 | N/A | N/A | 5645 | 5660 | ATATTGGGCTCAATGA | 89 | 1296 |
| 916356 | N/A | N/A | 6575 | 6590 | ATCACTGGAGGTGTAC | 0 | 1297 |
| 916376 | N/A | N/A | 7328 | 7343 | CAGGATCACACTTTGC | 17 | 1298 |
| 916396 | N/A | N/A | 7661 | 7676 | GGAACTAACATACACC | 0 | 1299 |
| 916556 | N/A | N/A | 12272 | 12287 | GTATATGTTCCCAGGT | 81 | 1300 |
| 916576 | N/A | N/A | 12788 | 12803 | GTGTACATGGTCTGCA | 94 | 1301 |
| 916596 | N/A | N/A | 13529 | 13544 | ATCATTGGAAGACCGC | 89 | 1302 |
| 916616 | N/A | N/A | 13998 | 14013 | GTTAAACTAAGGGTCA | 85 | 1303 |
| 916636 | N/A | N/A | 14550 | 14565 | CTTAATGTGGATTCAC | 91 | 1304 |
| 916656 | N/A | N/A | 15351 | 15366 | TCCAACTTCAGGCTGA | 74 | 1305 |
| 916676 | N/A | N/A | 15819 | 15834 | AGCTTTGTGGGCTCCA | 69 | 1306 |
| 916696 | N/A | N/A | 16982 | 16997 | GTTTAATAAGGGCACC | 63 | 1307 |
| 916716 | N/A | N/A | 17740 | 17755 | CGTATTAATCTGGTCA | 93 | 1308 |
| 916736 | N/A | N/A | 19126 | 19141 | CACCTAAAATGCTCAC | 17 | 1309 |
| 916756 | N/A | N/A | 20213 | 20228 | ACAAACTATGCCTAGA | 58 | 1310 |
| 916775 | N/A | N/A | 20609 | 20624 | AATTTTACGATCATCA | 78 | 1311 |
| 916795 | N/A | N/A | 20927 | 20942 | GACAGATCAGCACTCG | 80 | 1312 |
| 916815 | N/A | N/A | 21407 | 21422 | CAATTCTAGACATGGC | 88 | 1313 |
| 916835 | N/A | N/A | 22338 | 22353 | TGCACCTACCCTTTTC | 39 | 1314 |
| 916855 | N/A | N/A | 23251 | 23266 | ACACATAAAGGACCCC | 48 | 1315 |
| 916875 | N/A | N/A | 24241 | 24256 | GCATTACCAGGCACCT | 61 | 1316 |
| 916895 | N/A | N/A | 24912 | 24927 | GACATCACAGGTGTTG | 5 | 1317 |

TABLE 20

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915358 | 40 | 55 | 2778 | 2793 | GTGTCTCGGCCAGGGC | 0 | 1318 |
| 915378 | 96 | 111 | 2834 | 2849 | GTCCTGATCCGCAGCA | 0 | 1319 |
| 915398 | 184 | 199 | 2922 | 2937 | CTCCAGCCGCGCTCTG | 14 | 1320 |
| 915418 | 244 | 259 | 2982 | 2997 | AGGCAGCGGGTCGCCC | 0 | 1321 |
| 915438 | 342 | 357 | 3080 | 3095 | GCGGGATACCGGAGAG | 44 | 1322 |
| 915458 | 381 | 396 | 5955 | 5970 | TCCGCACAAGATCTGA | 41 | 1323 |
| 915478 | 408 | 423 | 5982 | 5997 | AGATGCCAATGTTCCG | 95 | 1324 |
| 915498 | 446 | 461 | 6020 | 6035 | CTGTCGGAGGAACTTG | 40 | 1325 |
| 915518 | 475 | 490 | 6049 | 6064 | ACATTGGCCGGGAGGC | 5 | 1326 |
| 915538 | 505 | 520 | 6079 | 6094 | ATGCCTATTTTGCCGG | 61 | 1327 |
| 915558 | 527 | 542 | 6101 | 6116 | ATCAGACACTCTGGTA | 0 | 1328 |
| 915618 | 748 | 763 | 11966 | 11981 | ACTTTAGGGCAGATGT | 87 | 1329 |
| 915638 | 818 | 833 | 12036 | 12051 | GTAGAGGTTCCCTGTG | 87 | 1330 |
| 915658 | 859 | 874 | N/A | N/A | AGCACCTTGAGATCCG | 0 | 1331 |
| 915678 | 926 | 941 | N/A | N/A | GTTGCAGATGCCCTTC | 24 | 1332 |
| 915698 | 980 | 995 | 16100 | 16115 | GGCGACCTCAGGATCC | 0 | 1333 |
| 915718 | 1032 | 1047 | 16152 | 16167 | AGGCAGCCGACTCCGG | 8 | 1334 |
| 915738 | 1114 | 1129 | 16234 | 16249 | GTGTCCAGGATGCTCT | 41 | 1335 |
| 915758 | 1147 | 1162 | N/A | N/A | TCACTCAGTGCTGTAG | 59 | 1336 |
| 915778 | 1217 | 1232 | 19057 | 19072 | ATAAGACATTATCCTA | 85 | 1337 |
| 915798 | 1264 | 1279 | 19104 | 19119 | ACAATCGCAATGGCAG | 66 | 1338 |
| 915818 | 1342 | 1357 | 23747 | 23762 | GTGAACACCTGTGAGG | 58 | 1339 |
| 915838 | 1400 | 1415 | 25163 | 25178 | TTGGCTGCTCACTGGC | 79 | 1340 |
| 915858 | 1436 | 1451 | 25199 | 25214 | GGGCCAGTCCTGCTCA | 0 | 1341 |
| 915878 | 1535 | 1550 | 25298 | 25313 | GCCCAAGAAGAAGTTC | 54 | 1342 |
| 915898 | 1590 | 1605 | 25353 | 25368 | CTAGTGAAAAACTGGG | 34 | 1343 |
| 915918 | 1628 | 1643 | 25391 | 25406 | GCTAGACTCGCCTCCT | 33 | 1344 |
| 915938 | 1680 | 1695 | 25443 | 25458 | TGCGGAGGTAGCTGCA | 0 | 1345 |
| 915958 | 1756 | 1771 | 25519 | 25534 | CCTAGCTTTTCATAAA | 0 | 1346 |
| 915978 | 1783 | 1798 | 25546 | 25561 | GACCGCTGCACAGGCG | 24 | 1347 |
| 915998 | 1810 | 1825 | 25573 | 25588 | ATGCTGATGTATTAGA | 86 | 1348 |
| 916018 | 1832 | 1847 | 25595 | 25610 | TCCCAACCAGCTGAAT | 3 | 1349 |
| 916038 | 1879 | 1894 | 25642 | 25657 | GAAACAGTCAGTAAGG | 64 | 1350 |
| 916058 | 1902 | 1917 | 25665 | 25680 | AGTCTGACCATTAATA | 86 | 1351 |
| 916078 | 1933 | 1948 | 25696 | 25711 | ACCTGTCATTCTAAGA | 18 | 1352 |
| 916098 | 1972 | 1987 | 25735 | 25750 | CAGCCTACCCCCCATC | 41 | 1353 |

TABLE 20-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916118 | 1999 | 2014 | 25762 | 25777 | CTCCACCCCACAAGAT | 0 | 1354 |
| 916138 | 2092 | 2107 | 25855 | 25870 | CTTTGCAGACCACCTG | 65 | 1355 |
| 916157 | 2134 | 2149 | 25897 | 25912 | TACCCCCGCCATGGAG | 57 | 1356 |
| 916177 | 2237 | 2252 | 26000 | 26015 | CAACAGGTAACAACGC | 88 | 1357 |
| 916197 | 2579 | 2594 | 26342 | 26357 | GTCAGACTTTCACTCA | 81 | 1358 |
| 916217 | 2659 | 2674 | 26422 | 26437 | GTGCTTGGCTCCTGCC | 43 | 1359 |
| 916237 | 2701 | 2716 | 26464 | 26479 | CAAGTTGTGTGCTCCA | 73 | 1360 |
| 916257 | 2769 | 2784 | 26532 | 26547 | CATCGCCACACATGGG | 61 | 1361 |
| 916277 | N/A | N/A | 4105 | 4120 | AGGAAGGGTCCCAAAC | 0 | 1362 |
| 916297 | N/A | N/A | 4731 | 4746 | TGATCATGTGGCGGTC | 80 | 1363 |
| 916317 | N/A | N/A | 5391 | 5406 | TGCTATCAGGTGCAGG | 60 | 1364 |
| 916337 | N/A | N/A | 5646 | 5661 | TATATTGGGCTCAATG | 71 | 1365 |
| 916357 | N/A | N/A | 6594 | 6609 | GTTTACAAACATGGAC | 26 | 1366 |
| 916377 | N/A | N/A | 7464 | 7479 | TCATTAGCATCACCGG | 33 | 1367 |
| 916397 | N/A | N/A | 7662 | 7677 | GGGAACTAACATACAC | 0 | 1368 |
| 916557 | N/A | N/A | 12274 | 12289 | GGGTATATGTTCCCAG | 0 | 1369 |
| 916577 | N/A | N/A | 12830 | 12845 | TGCATAGCCTTCTTTC | 84 | 1370 |
| 916597 | N/A | N/A | 13530 | 13545 | CATCATTGGAAGACCG | 62 | 1371 |
| 916617 | N/A | N/A | 14016 | 14031 | TCTTTAACTTCGGCCC | 70 | 1372 |
| 916637 | N/A | N/A | 14551 | 14566 | TCTTAATGTGGATTCA | 88 | 1373 |
| 916657 | N/A | N/A | 15388 | 15403 | TCAGACAACCACAGCT | 66 | 1374 |
| 916677 | N/A | N/A | 15852 | 15867 | TAAAGCAGGACACACG | 74 | 1375 |
| 916697 | N/A | N/A | 17077 | 17092 | AGACATGTTGGTGTCT | 0 | 1376 |
| 916717 | N/A | N/A | 17788 | 17803 | CCCCAGTCTTTTATTC | 0 | 1377 |
| 916737 | N/A | N/A | 19140 | 19155 | GGAAGACACGGAGCCA | 20 | 1378 |
| 916757 | N/A | N/A | 20240 | 20255 | CCTAACTGCTGGCTCT | 85 | 1379 |
| 916776 | N/A | N/A | 20610 | 20625 | TAATTTTACGATCATC | 76 | 1380 |
| 916796 | N/A | N/A | 20939 | 20954 | CTCTTTGTAGCAGACA | 90 | 1381 |
| 916816 | N/A | N/A | 21439 | 21454 | CAATATACTGAGAGGA | 92 | 1382 |
| 916836 | N/A | N/A | 22392 | 22407 | GTAGACATCCTTCCCG | 65 | 1383 |
| 916856 | N/A | N/A | 23252 | 23267 | GACACATAAAGGACCC | 59 | 1384 |
| 916876 | N/A | N/A | 24242 | 24257 | TGCATTACCAGGCACC | 37 | 1385 |
| 916896 | N/A | N/A | 24913 | 24928 | GGACATCACAGGTGTT | 19 | 1386 |

TABLE 21

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915359 | 41 | 56 | 2779 | 2794 | AGTGTCTCGGCCAGGG | 0 | 1387 |
| 915379 | 97 | 112 | 2835 | 2850 | GGTCCTGATCCGCAGC | 0 | 1388 |
| 915399 | 185 | 200 | 2923 | 2938 | GCTCCAGCCGCGCTCT | 26 | 1389 |
| 915419 | 245 | 260 | 2983 | 2998 | CAGGCAGCGGGTCGCC | 0 | 1390 |
| 915439 | 343 | 358 | 3081 | 3096 | AGCGGGATACCGGAGA | 69 | 1391 |
| 915459 | 382 | 397 | 5956 | 5971 | TTCCGCACAAGATCTG | 71 | 1392 |
| 915479 | 409 | 424 | 5983 | 5998 | AAGATGCCAATGTTCC | 93 | 1393 |
| 915499 | 448 | 463 | 6022 | 6037 | CCCTGTCGGAGGAACT | 30 | 1394 |
| 915519 | 477 | 492 | 6051 | 6066 | GGACATTGGCCGGGAG | 88 | 1395 |
| 915539 | 506 | 521 | 6080 | 6095 | GATGCCTATTTTGCCG | 60 | 1396 |
| 915559 | 529 | 544 | 6103 | 6118 | CCATCAGACACTCTGG | 30 | 1397 |
| 915579 | 595 | 610 | 7825 | 7840 | CAGGAACATACCAAGG | 98 | 1398 |
| 915599 | 674 | 689 | 11892 | 11907 | GTTGTCACTCACTCCT | 98 | 1399 |
| 915619 | 749 | 764 | 11967 | 11982 | GACTTTAGGGCAGATG | 96 | 1400 |
| 915639 | 819 | 834 | 12037 | 12052 | GGTAGAGGTTCCCTGT | 92 | 1401 |
| 915659 | 860 | 875 | N/A | N/A | CAGCACCTTGAGATCC | 0 | 1402 |
| 915679 | 928 | 943 | N/A | N/A | CTGTTGCAGATGCCCT | 58 | 1403 |
| 915699 | 981 | 996 | 16101 | 16116 | TGGCGACCTCAGGATC | 40 | 1404 |
| 915719 | 1033 | 1048 | 16153 | 16168 | AAGGCAGCCGACTCCG | 0 | 1405 |
| 915739 | 1115 | 1130 | 16235 | 16250 | GGTGTCCAGGATGCTC | 40 | 1406 |
| 915759 | 1148 | 1163 | N/A | N/A | TTCACTCAGTGCTGTA | 29 | 1407 |
| 915779 | 1219 | 1234 | 19059 | 19074 | ACATAAGACATTATCC | 86 | 1408 |
| 915799 | 1268 | 1283 | 19108 | 19123 | CTGGACAATCGCAATG | 42 | 1409 |
| 915819 | 1344 | 1359 | 23749 | 23764 | GAGTGAACACCTGTGA | 81 | 1410 |
| 915839 | 1401 | 1416 | 25164 | 25179 | GTTGGCTGCTCACTGG | 85 | 1411 |
| 915859 | 1437 | 1452 | 25200 | 25215 | AGGGCCAGTCCTGCTC | 0 | 1412 |
| 915879 | 1538 | 1553 | 25301 | 25316 | ATTGCCCAAGAAGAAG | 54 | 1413 |
| 915899 | 1591 | 1606 | 25354 | 25369 | TCTAGTGAAAAACTGG | 0 | 1414 |
| 915919 | 1629 | 1644 | 25392 | 25407 | TGCTAGACTCGCCTCC | 72 | 1415 |
| 915939 | 1681 | 1696 | 25444 | 25459 | ATGCGGAGGTAGCTGC | 39 | 1416 |
| 915959 | 1764 | 1779 | 25527 | 25542 | GGTTGCTTCCTAGCTT | 87 | 1417 |
| 915979 | 1784 | 1799 | 25547 | 25562 | GGACCGCTGCACAGGC | 0 | 1418 |
| 915999 | 1811 | 1826 | 25574 | 25589 | CATGCTGATGTATTAG | 35 | 1419 |
| 916019 | 1833 | 1848 | 25596 | 25611 | TTCCCAACCAGCTGAA | 0 | 1420 |
| 916039 | 1880 | 1895 | 25643 | 25658 | CGAAACAGTCAGTAAG | 80 | 1421 |
| 916059 | 1905 | 1920 | 25668 | 25683 | AACAGTCTGACCATTA | 85 | 1422 |

TABLE 21-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916079 | 1934 | 1949 | 25697 | 25712 | CACCTGTCATTCTAAG | 45 | 1423 |
| 916099 | 1973 | 1988 | 25736 | 25751 | CCAGCCTACCCCCCAT | 53 | 1424 |
| 916119 | 2022 | 2037 | 25785 | 25800 | GTGGGATCATGCTATT | 76 | 1425 |
| 916139 | 2093 | 2108 | 25856 | 25871 | TCTTTGCAGACCACCT | 85 | 1426 |
| 916158 | 2135 | 2150 | 25898 | 25913 | TTACCCCGCCATGGA | 0 | 1427 |
| 916178 | 2238 | 2253 | 26001 | 26016 | TCAACAGGTAACAACG | 87 | 1428 |
| 916198 | 2620 | 2635 | 26383 | 26398 | GCACACTAGATTATTT | 66 | 1429 |
| 916218 | 2673 | 2688 | 26436 | 26451 | CGGAAGCTCCTGCTGT | 27 | 1430 |
| 916238 | 2702 | 2717 | 26465 | 26480 | TCAAGTTGTGTGCTCC | 91 | 1431 |
| 916258 | 2770 | 2785 | 26533 | 26548 | TCATCGCCACACATGG | 49 | 1432 |
| 916278 | N/A | N/A | 4211 | 4226 | TCATTTCCAGGAGTAC | 75 | 1433 |
| 916298 | N/A | N/A | 4735 | 4750 | CAAATGATCATGTGGC | 93 | 1434 |
| 916318 | N/A | N/A | 5394 | 5409 | TAATGCTATCAGGTGC | 95 | 1435 |
| 916338 | N/A | N/A | 5648 | 5663 | GATATATTGGGCTCAA | 97 | 1436 |
| 916358 | N/A | N/A | 6596 | 6611 | GGGTTTACAAACATGG | 75 | 1437 |
| 916378 | N/A | N/A | 7465 | 7480 | TTCATTAGCATCACCG | 78 | 1438 |
| 916398 | N/A | N/A | 7686 | 7701 | GTTAATCCATGGGTCA | 49 | 1439 |
| 916418 | N/A | N/A | 8992 | 9007 | AGCCTAAACTTCCTCC | 63 | 1440 |
| 916438 | N/A | N/A | 9318 | 9333 | AGAAGAGCCGCCCTGC | 77 | 1441 |
| 916458 | N/A | N/A | 9795 | 9810 | GCAAGACTAGCAAGTG | 85 | 1442 |
| 916478 | N/A | N/A | 10301 | 10316 | AGCATGCGGTATGTAC | 67 | 1443 |
| 916498 | N/A | N/A | 10849 | 10864 | CACACAATTTCTAGGG | 82 | 1444 |
| 916518 | N/A | N/A | 11346 | 11361 | TTGACAATTAGAACCA | 96 | 1445 |
| 916538 | N/A | N/A | 11711 | 11726 | ACAAATCCTTACCGAG | 54 | 1446 |
| 916558 | N/A | N/A | 12285 | 12300 | GTTTTAGGTCTGGGTA | 94 | 1447 |
| 916578 | N/A | N/A | 12831 | 12846 | TTGCATAGCCTTCTTT | 93 | 1448 |
| 916598 | N/A | N/A | 13660 | 13675 | CATACATACCCTTCTC | 9 | 1449 |
| 916618 | N/A | N/A | 14025 | 14040 | CGCAGAAACTCTTTAA | 89 | 1450 |
| 916638 | N/A | N/A | 14552 | 14567 | GTCTTAATGTGGATTC | 93 | 1451 |
| 916658 | N/A | N/A | 15421 | 15436 | AGCATTGGCACACTGG | 70 | 1452 |
| 916678 | N/A | N/A | 15857 | 15872 | GGCTTTAAAGCAGGAC | 62 | 1453 |
| 916698 | N/A | N/A | 17079 | 17094 | GCAGACATGTTGGTGT | 2 | 1454 |
| 916718 | N/A | N/A | 17839 | 17854 | TACAAGCTGGTCCTTG | 0 | 1455 |
| 916738 | N/A | N/A | 19211 | 19226 | GACAATCCAGGTCCCA | 70 | 1456 |
| 916758 | N/A | N/A | 20285 | 20300 | GAGGAAGCCCAATCAA | 81 | 1457 |
| 916777 | N/A | N/A | 20611 | 20626 | CTAATTTTACGATCAT | 81 | 1458 |

TABLE 21-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916797 | N/A | N/A | 20984 | 20999 | TTAAACTGCCAAGTCC | 83 | 1459 |
| 916817 | N/A | N/A | 21440 | 21455 | CCAATATACTGAGAGG | 96 | 1460 |
| 916837 | N/A | N/A | 22406 | 22421 | GGTAGCACCGCCAAGT | 0 | 1461 |
| 916857 | N/A | N/A | 23301 | 23316 | CACCATGGAGAGGTCT | 0 | 1462 |
| 916877 | N/A | N/A | 24243 | 24258 | TTGCATTACCAGGCAC | 17 | 1463 |
| 916897 | N/A | N/A | 24934 | 24949 | GCTACCTGGACACCTC | 47 | 1464 |

TABLE 22

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 841947 | 2094 | 2109 | 25857 | 25872 | ATCTTTGCAGACCACC | 89 | 1464 |
| 912986 | N/A | N/A | 20288 20318 | 20303 20333 | TCAGAGGAAGCCCAAT | 92 | 254 |
| 915360 | 42 | 57 | 2780 | 2795 | CAGTGTCTCGGCCAGG | 0 | 1466 |
| 915380 | 98 | 113 | 2836 | 2851 | GGGTCCTGATCCGCAG | 0 | 1467 |
| 915400 | 186 | 201 | 2924 | 2939 | AGCTCCAGCCGCGCTC | 0 | 1468 |
| 915420 | 246 | 261 | 2984 | 2999 | TCAGGCAGCGGGTCGC | 78 | 1469 |
| 915440 | 344 | 359 | 3082 | 3097 | CAGCGGGATACCGGAG | 72 | 1470 |
| 915460 | 383 | 398 | 5957 | 5972 | CTTCCGCACAAGATCT | 0 | 1471 |
| 915480 | 411 | 426 | 5985 | 6000 | GGAAGATGCCAATGTT | 94 | 1472 |
| 915500 | 449 | 464 | 6023 | 6038 | ACCCTGTCGGAGGAAC | 40 | 1473 |
| 915520 | 480 | 495 | 6054 | 6069 | GGTGGACATTGGCCGG | 38 | 1474 |
| 915540 | 507 | 522 | 6081 | 6096 | AGATGCCTATTTTGCC | 76 | 1475 |
| 915560 | 556 | 571 | 6130 | 6145 | CGAAAGTCAGACACCA | 69 | 1476 |
| 915620 | 750 | 765 | 11968 | 11983 | TGACTTTAGGGCAGAT | 89 | 1477 |
| 915640 | 821 | 836 | 12039 | 12054 | AAGGTAGAGGTTCCCT | 10 | 1478 |
| 915660 | 875 | 890 | 13611 | 13626 | AAGGCATATCTCTCCC | 47 | 1479 |
| 915680 | 929 | 944 | N/A | N/A | CCTGTTGCAGATGCCC | 22 | 1480 |
| 915700 | 982 | 997 | 16102 | 16117 | ATGGCGACCTCAGGAT | 58 | 1481 |
| 915720 | 1034 | 1049 | 16154 | 16169 | CAAGGCAGCCGACTCC | 63 | 1482 |
| 915740 | 1121 | 1136 | 16241 | 16256 | CGAGAGGGTGTCCAGG | 0 | 1483 |
| 915760 | 1149 | 1164 | N/A | N/A | CTTCACTCAGTGCTGT | 13 | 1484 |
| 915780 | 1226 | 1241 | 19066 | 19081 | CAGCATTACATAAGAC | 94 | 1485 |
| 915800 | 1270 | 1285 | 19110 | 19125 | CTCTGGACAATCGCAA | 55 | 1486 |

TABLE 22-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915820 | 1345 | 1360 | 23750 | 23765 | CGAGTGAACACCTGTG | 83 | 1487 |
| 915840 | 1402 | 1417 | 25165 | 25180 | TGTTGGCTGCTCACTG | 77 | 1488 |
| 915860 | 1470 | 1485 | 25233 | 25248 | CTGGACAGCCCTTGGG | 29 | 1489 |
| 915880 | 1539 | 1554 | 25302 | 25317 | TATTGCCCAAGAAGAA | 18 | 1490 |
| 915900 | 1598 | 1613 | 25361 | 25376 | ACTCTTCTCTAGTGAA | 67 | 1491 |
| 915920 | 1630 | 1645 | 25393 | 25408 | CTGCTAGACTCGCCTC | 88 | 1492 |
| 915940 | 1682 | 1697 | 25445 | 25460 | AATGCGGAGGTAGCTG | 0 | 1493 |
| 915960 | 1765 | 1780 | 25528 | 25543 | AGGTTGCTTCCTAGCT | 55 | 1494 |
| 915980 | 1785 | 1800 | 25548 | 25563 | TGGACCGCTGCACAGG | 82 | 1495 |
| 916000 | 1812 | 1827 | 25575 | 25590 | GCATGCTGATGTATTA | 52 | 1496 |
| 916020 | 1837 | 1852 | 25600 | 25615 | TCATTTCCCAACCAGC | 94 | 1497 |
| 916040 | 1881 | 1896 | 25644 | 25659 | ACGAAACAGTCAGTAA | 79 | 1498 |
| 916060 | 1907 | 1922 | 25670 | 25685 | GGAACAGTCTGACCAT | 22 | 1499 |
| 916080 | 1936 | 1951 | 25699 | 25714 | AACACCTGTCATTCTA | 71 | 1500 |
| 916100 | 1974 | 1989 | 25737 | 25752 | GCCAGCCTACCCCCCA | 23 | 1501 |
| 916120 | 2023 | 2038 | 25786 | 25801 | AGTGGGATCATGCTAT | 0 | 1502 |
| 916159 | 2136 | 2151 | 25899 | 25914 | GTTACCCCGCCATGG | 47 | 1503 |
| 916179 | 2239 | 2254 | 26002 | 26017 | TTCAACAGGTAACAAC | 84 | 1504 |
| 916199 | 2621 | 2636 | 26384 | 26399 | TGCACACTAGATTATT | 0 | 1505 |
| 916219 | 2674 | 2689 | 26437 | 26452 | GCGGAAGCTCCTGCTG | 6 | 1506 |
| 916239 | 2704 | 2719 | 26467 | 26482 | GTTCAAGTTGTGTGCT | 85 | 1507 |
| 916259 | 2771 | 2786 | 26534 | 26549 | CTCATCGCCACACATG | 85 | 1508 |
| 916279 | N/A | N/A | 4218 | 4233 | CGGAATCTCATTTCCA | 0 | 1509 |
| 916299 | N/A | N/A | 4736 | 4751 | GCAAATGATCATGTGG | 93 | 1510 |
| 916319 | N/A | N/A | 5396 | 5411 | CTTAATGCTATCAGGT | 83 | 1511 |
| 916339 | N/A | N/A | 5649 | 5664 | GGATATATTGGGCTCA | 96 | 1512 |
| 916359 | N/A | N/A | 6597 | 6612 | AGGGTTTACAAACATG | 32 | 1513 |
| 916379 | N/A | N/A | 7466 | 7481 | ATTCATTAGCATCACC | 52 | 1514 |
| 916399 | N/A | N/A | 7687 | 7702 | GGTTAATCCATGGGTC | 0 | 1515 |
| 916559 | N/A | N/A | 12286 | 12301 | AGTTTTAGGTCTGGGT | 89 | 1516 |
| 916579 | N/A | N/A | 12833 | 12848 | CATTGCATAGCCTTCT | 96 | 1517 |
| 916599 | N/A | N/A | 13661 | 13676 | CCATACATACCCTTCT | 21 | 1518 |
| 916619 | N/A | N/A | 14077 | 14092 | ACCCACACCTGACTGG | 16 | 1519 |
| 916639 | N/A | N/A | 14572 | 14587 | CGCTCCTACTTATCCC | 96 | 1520 |
| 916659 | N/A | N/A | 15427 | 15442 | TCTTACAGCATTGGCA | 38 | 1521 |
| 916679 | N/A | N/A | 15973 | 15988 | CATCTACCAAACTGCA | 73 | 1522 |

TABLE 22-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916699 | N/A | N/A | 17135 | 17150 | AACAAACATCGATTTT | 47 | 1523 |
| 916719 | N/A | N/A | 17844 | 17859 | AGCTTTACAAGCTGGT | 0 | 1524 |
| 916739 | N/A | N/A | 19213 | 19228 | ACGACAATCCAGGTCC | 14 | 1525 |
| 916778 | N/A | N/A | 20612 | 20627 | TCTAATTTTACGATCA | 92 | 1526 |
| 916798 | N/A | N/A | 20985 | 21000 | ATTAAACTGCCAAGTC | 72 | 1527 |
| 916818 | N/A | N/A | 21441 | 21456 | ACCAATATACTGAGAG | 92 | 1528 |
| 916838 | N/A | N/A | 22409 | 22424 | AGCGGTAGCACCGCCA | 0 | 1529 |
| 916858 | N/A | N/A | 23323 | 23338 | TCACATGTGAGCCCAG | 46 | 1530 |
| 916878 | N/A | N/A | 24271 | 24286 | GTACAACAGAGGGTGG | 19 | 1531 |
| 916898 | N/A | N/A | 24978 | 24993 | GGCTGATGTCACCACC | 32 | 1532 |

TABLE 23

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915361 | 43 | 58 | 2781 | 2796 | TCAGTGTCTCGGCCAG | 0 | 1533 |
| 915381 | 105 | 120 | 2843 | 2858 | TCGGCTCGGGTCCTGA | 0 | 1534 |
| 915401 | 188 | 203 | 2926 | 2941 | CAAGCTCCAGCCGCGC | 22 | 1535 |
| 915421 | 247 | 262 | 2985 | 3000 | CTCAGGCAGCGGGTCG | 48 | 1536 |
| 915441 | 345 | 360 | 3083 | 3098 | CCAGCGGGATACCGGA | 0 | 1537 |
| 915461 | 384 | 399 | 5958 | 5973 | CCTTCCGCACAAGATC | 59 | 1538 |
| 915481 | 414 | 429 | 5988 | 6003 | GATGGAAGATGCCAAT | 83 | 1539 |
| 915501 | 450 | 465 | 6024 | 6039 | GACCCTGTCGGAGGAA | 26 | 1540 |
| 915521 | 482 | 497 | 6056 | 6071 | CTGGTGGACATTGGCC | 0 | 1541 |
| 915541 | 508 | 523 | 6082 | 6097 | GAGATGCCTATTTTGC | 92 | 1542 |
| 915561 | 557 | 572 | 6131 | 6146 | CCGAAAGTCAGACACC | 0 | 1543 |
| 915601 | 691 | 706 | 11909 | 11924 | GCATCAATGAAGGGTA | 91 | 1544 |
| 915621 | 751 | 766 | 11969 | 11984 | TTGACTTTAGGGCAGA | 85 | 1545 |
| 915641 | 822 | 837 | 12040 | 12055 | GAAGGTAGAGGTTCCC | 74 | 1546 |
| 915661 | 876 | 891 | 13612 | 13627 | GAAGGCATATCTCTCC | 32 | 1547 |
| 915681 | 930 | 945 | 16050 | 16065 | GCCTGTTGCAGATGCC | 0 | 1548 |
| 915701 | 983 | 998 | 16103 | 16118 | CATGGCGACCTCAGGA | 0 | 1549 |
| 915721 | 1035 | 1050 | 16155 | 16170 | CCAAGGCAGCCGACTC | 79 | 1550 |
| 915741 | 1122 | 1137 | 16242 | 16257 | GCGAGAGGGTGTCCAG | 0 | 1551 |
| 915761 | 1150 | 1165 | 18990 | 19005 | TCTTCACTCAGTGCTG | 41 | 1552 |

TABLE 23-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915781 | 1227 | 1242 | 19067 | 19082 | GCAGCATTACATAAGA | 75 | 1553 |
| 915801 | 1273 | 1288 | N/A | N/A | AGTCTCTGGACAATCG | 0 | 1554 |
| 915821 | 1346 | 1361 | 23751 | 23766 | TCGAGTGAACACCTGT | 52 | 1555 |
| 915841 | 1403 | 1418 | 25166 | 25181 | CTGTTGGCTGCTCACT | 80 | 1556 |
| 915861 | 1471 | 1486 | 25234 | 25249 | GCTGGACAGCCCTTGG | 0 | 1557 |
| 915881 | 1540 | 1555 | 25303 | 25318 | TTATTGCCCAAGAAGA | 75 | 1558 |
| 915901 | 1599 | 1614 | 25362 | 25377 | GACTCTTCTCTAGTGA | 67 | 1559 |
| 915921 | 1631 | 1646 | 25394 | 25409 | TCTGCTAGACTCGCCT | 50 | 1560 |
| 915941 | 1683 | 1698 | 25446 | 25461 | CAATGCGGAGGTAGCT | 39 | 1561 |
| 915961 | 1766 | 1781 | 25529 | 25544 | AAGGTTGCTTCCTAGC | 71 | 1562 |
| 915981 | 1786 | 1801 | 25549 | 25564 | CTGGACCGCTGCACAG | 0 | 1563 |
| 916001 | 1813 | 1828 | 25576 | 25591 | CGCATGCTGATGTATT | 73 | 1564 |
| 916021 | 1840 | 1855 | 25603 | 25618 | GTGTCATTTCCCAACC | 61 | 1565 |
| 916041 | 1882 | 1897 | 25645 | 25660 | CACGAAACAGTCAGTA | 34 | 1566 |
| 916061 | 1910 | 1925 | 25673 | 25688 | GCTGGAACAGTCTGAC | 82 | 1567 |
| 916081 | 1942 | 1957 | 25705 | 25720 | CATCCAAACACCTGTC | 69 | 1568 |
| 916101 | 1975 | 1990 | 25738 | 25753 | GGCCAGCCTACCCCCC | 2 | 1569 |
| 916121 | 2024 | 2039 | 25787 | 25802 | AAGTGGGATCATGCTA | 26 | 1570 |
| 916140 | 2095 | 2110 | 25858 | 25873 | CATCTTTGCAGACCAC | 92 | 1571 |
| 916160 | 2137 | 2152 | 25900 | 25915 | TGTTACCCCCGCCATG | 51 | 1572 |
| 916180 | 2257 | 2272 | 26020 | 26035 | GATTCACATAATACAA | 87 | 1573 |
| 916200 | 2622 | 2637 | 26385 | 26400 | CTGCACACTAGATTAT | 0 | 1574 |
| 916220 | 2675 | 2690 | 26438 | 26453 | GGCGGAAGCTCCTGCT | 0 | 1575 |
| 916240 | 2705 | 2720 | 26468 | 26483 | GGTTCAAGTTGTGTGC | 69 | 1576 |
| 916260 | 2772 | 2787 | 26535 | 26550 | TCTCATCGCCACACAT | 72 | 1577 |
| 916280 | N/A | N/A | 4220 | 4235 | TACGGAATCTCATTTC | 80 | 1578 |
| 916300 | N/A | N/A | 4791 | 4806 | GGCCACCTTGGGATAC | 17 | 1579 |
| 916320 | N/A | N/A | 5398 | 5413 | GCCTTAATGCTATCAG | 67 | 1580 |
| 916340 | N/A | N/A | 5650 | 5665 | TGGATATATTGGGCTC | 97 | 1581 |
| 916360 | N/A | N/A | 6603 | 6618 | ACATTCAGGGTTTACA | 18 | 1582 |
| 916380 | N/A | N/A | 7468 | 7483 | GTATTCATTAGCATCA | 51 | 1583 |
| 916400 | N/A | N/A | 7688 | 7703 | AGGTTAATCCATGGGT | 29 | 1584 |
| 916560 | N/A | N/A | 12287 | 12302 | GAGTTTTAGGTCTGGG | 95 | 1585 |
| 916580 | N/A | N/A | 12905 | 12920 | CTTATAAAGCACACGG | 95 | 1586 |
| 916600 | N/A | N/A | 13683 | 13698 | GGGCATGGCTGATCCT | 8 | 1587 |
| 916620 | N/A | N/A | 14099 | 14114 | CAAACTTGTCTAGTGG | 67 | 1588 |

TABLE 23-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916640 | N/A | N/A | 14600 | 14615 | TCGCATCCATGGGTCC | 83 | 1589 |
| 916660 | N/A | N/A | 15429 | 15444 | GCTCTTACAGCATTGG | 51 | 1590 |
| 916680 | N/A | N/A | 15974 | 15989 | CCATCTACCAAACTGC | 61 | 1591 |
| 916700 | N/A | N/A | 17195 | 17210 | GACTTAGTCCGTGTTC | 49 | 1592 |
| 916720 | N/A | N/A | 17883 | 17898 | CAGCATCTATGTTCTC | 67 | 1593 |
| 916740 | N/A | N/A | 19239 | 19254 | ATAGACTGTGAGCTGT | 82 | 1594 |
| 916759 | N/A | N/A | 20354 | 20369 | GACCATTCTGCTCCCC | 20 | 1595 |
| 916779 | N/A | N/A | 20632 | 20647 | GCCCATACCTTTTATC | 47 | 1596 |
| 916799 | N/A | N/A | 20987 | 21002 | GTATTAAACTGCCAAG | 81 | 1597 |
| 916819 | N/A | N/A | 21444 | 21459 | CTAACCAATATACTGA | 73 | 1598 |
| 916839 | N/A | N/A | 22506 | 22521 | GGCTGGTGATGAAACA | 0 | 1599 |
| 916859 | N/A | N/A | 23345 | 23360 | CCTCATGGTTTGCTGT | 31 | 1600 |
| 916879 | N/A | N/A | 24273 | 24288 | CAGTACAACAGAGGGT | 81 | 1601 |
| 916899 | N/A | N/A | 25064 | 25079 | CACATTGCCGGCCAGT | 58 | 1602 |

TABLE 24

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915362 | 44 | 59 | 2782 | 2797 | CTCAGTGTCTCGGCCA | 0 | 1603 |
| 915382 | 106 | 121 | 2844 | 2859 | ATCGGCTCGGGTCCTG | 30 | 1604 |
| 915402 | 189 | 204 | 2927 | 2942 | ACAAGCTCCAGCCGCG | 24 | 1605 |
| 915422 | 248 | 263 | 2986 | 3001 | GCTCAGGCAGCGGGTC | 33 | 1606 |
| 915442 | 346 | 361 | N/A | N/A | TCCAGCGGGATACCGG | 0 | 1607 |
| 915462 | 385 | 400 | 5959 | 5974 | GCCTTCCGCACAAGAT | 60 | 1608 |
| 915482 | 415 | 430 | 5989 | 6004 | GGATGGAAGATGCCAA | 60 | 1609 |
| 915502 | 451 | 466 | 6025 | 6040 | AGACCCTGTCGGAGGA | 75 | 1610 |
| 915522 | 487 | 502 | 6061 | 6076 | ATGAGCTGGTGGACAT | 74 | 1611 |
| 915542 | 509 | 524 | 6083 | 6098 | AGAGATGCCTATTTTG | 91 | 1612 |
| 915562 | 558 | 573 | 6132 | 6147 | ACCGAAAGTCAGACAC | 0 | 1613 |
| 915602 | 692 | 707 | 11910 | 11925 | GGCATCAATGAAGGGT | 88 | 1614 |
| 915622 | 752 | 767 | 11970 | 11985 | CTTGACTTTAGGGCAG | 86 | 1615 |
| 915642 | 824 | 839 | 12042 | 12057 | GAGAAGGTAGAGGTTC | 81 | 1616 |
| 915662 | 878 | 893 | 13614 | 13629 | TCGAAGGCATATCTCT | 16 | 1617 |

TABLE 24-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915682 | 931 | 946 | 16051 | 16066 | GGCCTGTTGCAGATGC | 0 | 1618 |
| 915702 | 984 | 999 | 16104 | 16119 | GCATGGCGACCTCAGG | 24 | 1619 |
| 915722 | 1036 | 1051 | 16156 | 16171 | GCCAAGGCAGCCGACT | 0 | 1620 |
| 915742 | 1123 | 1138 | 16243 | 16258 | GGCGAGAGGGTGTCCA | 0 | 1621 |
| 915762 | 1173 | 1188 | 19013 | 19028 | TGTATCCACCTTTGTC | 85 | 1622 |
| 915782 | 1228 | 1243 | 19068 | 19083 | GGCAGCATTACATAAG | 73 | 1623 |
| 915802 | 1283 | 1298 | N/A | N/A | CCATGTCACCAGTCTC | 59 | 1624 |
| 915822 | 1347 | 1362 | 23752 | 23767 | CTCGAGTGAACACCTG | 0 | 1625 |
| 915842 | 1404 | 1419 | 25167 | 25182 | CCTGTTGGCTGCTCAC | 88 | 1626 |
| 915862 | 1472 | 1487 | 25235 | 25250 | TGCTGGACAGCCCTTG | 0 | 1627 |
| 915882 | 1541 | 1556 | 25304 | 25319 | TTTATTGCCCAAGAAG | 38 | 1628 |
| 915902 | 1600 | 1615 | 25363 | 25378 | AGACTCTTCTCTAGTG | 60 | 1629 |
| 915922 | 1632 | 1647 | 25395 | 25410 | ATCTGCTAGACTCGCC | 86 | 1630 |
| 915942 | 1684 | 1699 | 25447 | 25462 | GCAATGCGGAGGTAGC | 38 | 1631 |
| 915962 | 1767 | 1782 | 25530 | 25545 | AAAGGTTGCTTCCTAG | 77 | 1632 |
| 915982 | 1787 | 1802 | 25550 | 25565 | GCTGGACCGCTGCACA | 79 | 1633 |
| 916002 | 1814 | 1829 | 25577 | 25592 | ACGCATGCTGATGTAT | 72 | 1634 |
| 916022 | 1841 | 1856 | 25604 | 25619 | GGTGTCATTTCCCAAC | 80 | 1635 |
| 916042 | 1883 | 1898 | 25646 | 25661 | CCACGAAACAGTCAGT | 87 | 1636 |
| 916062 | 1912 | 1927 | 25675 | 25690 | ATGCTGGAACAGTCTG | 78 | 1637 |
| 916082 | 1943 | 1958 | 25706 | 25721 | CCATCCAAACACCTGT | 64 | 1638 |
| 916102 | 1976 | 1991 | 25739 | 25754 | GGGCCAGCCTACCCCC | 0 | 1639 |
| 916122 | 2025 | 2040 | 25788 | 25803 | GAAGTGGGATCATGCT | 71 | 1640 |
| 916141 | 2097 | 2112 | 25860 | 25875 | ATCATCTTTGCAGACC | 91 | 1641 |
| 916161 | 2138 | 2153 | 25901 | 25916 | TTGTTACCCCCGCCAT | 89 | 1642 |
| 916181 | 2259 | 2274 | 26022 | 26037 | CTGATTCACATAATAC | 91 | 1643 |
| 916201 | 2623 | 2638 | 26386 | 26401 | CCTGCACACTAGATTA | 59 | 1644 |
| 916221 | 2676 | 2691 | 26439 | 26454 | AGGCGGAAGCTCCTGC | 0 | 1645 |
| 916241 | 2706 | 2721 | 26469 | 26484 | AGGTTCAAGTTGTGTG | 87 | 1646 |
| 916281 | N/A | N/A | 4224 | 4239 | AATGTACGGAATCTCA | 83 | 1647 |
| 916301 | N/A | N/A | 4810 | 4825 | GTCCATGTGGGTGTCC | 74 | 1648 |
| 916321 | N/A | N/A | 5399 | 5414 | GGCCTTAATGCTATCA | 13 | 1649 |
| 916341 | N/A | N/A | 5711 | 5726 | TAGTATGAAATATCTC | 96 | 1650 |
| 916361 | N/A | N/A | 6862 | 6877 | ATTGTAACTGCCAGGC | 0 | 1651 |
| 916381 | N/A | N/A | 7471 | 7486 | CCGGTATTCATTAGCA | 0 | 1652 |
| 916401 | N/A | N/A | 7728 | 7743 | GAGCAGGGCAACAAAC | 22 | 1653 |

TABLE 24-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 916561 | N/A | N/A | 12315 | 12330 | ATATAACCACAGCCTG | 54 | 1654 |
| 916581 | N/A | N/A | 12906 | 12921 | GCTTATAAAGCACACG | 94 | 1655 |
| 916601 | N/A | N/A | 13702 | 13717 | TAGTAAATGCTTGTCA | 95 | 1656 |
| 916621 | N/A | N/A | 14123 | 14138 | GGCAGAAATGTGCTCT | 60 | 1657 |
| 916641 | N/A | N/A | 14632 | 14647 | CTTCATGCCATCCTGT | 83 | 1658 |
| 916661 | N/A | N/A | 15430 | 15445 | TGCTCTTACAGCATTG | 0 | 1659 |
| 916681 | N/A | N/A | 16262 | 16277 | GGTACCTGTAGCGAGC | 0 | 1660 |
| 916701 | N/A | N/A | 17197 | 17212 | TTGACTTAGTCCGTGT | 93 | 1661 |
| 916721 | N/A | N/A | 18220 | 18235 | AGCTACATCAGGCTGG | 0 | 1662 |
| 916741 | N/A | N/A | 19244 | 19259 | TGCACATAGACTGTGA | 0 | 1663 |
| 916760 | N/A | N/A | 20373 | 20388 | GACTGCTGAGCCAAGC | 61 | 1664 |
| 916780 | N/A | N/A | 20657 | 20672 | AGAAATTGCAGTGCCC | 92 | 1665 |
| 916800 | N/A | N/A | 20988 | 21003 | GGTATTAAACTGCCAA | 0 | 1666 |
| 916820 | N/A | N/A | 21447 | 21462 | TCACTAACCAATATAC | 47 | 1667 |
| 916840 | N/A | N/A | 22602 | 22617 | ATAAATCTGCAAGAGC | 62 | 1668 |
| 916860 | N/A | N/A | 23369 | 23384 | TCTCATGGTCAAGACC | 52 | 1669 |
| 916880 | N/A | N/A | 24305 | 24320 | GACTGCTAGGCTTCAC | 54 | 1670 |
| 916900 | N/A | N/A | 25100 | 25115 | CGCTGCTGCAGTGTGC | 34 | 1671 |

Human primer probe set RTS36075 (forward sequence TGAGGCTGGAGGGAGATG, designated herein as SEQ ID NO: 14; reverse sequence GCTCATGTATCCACCTTTGTCT, designated herein as SEQ ID NO: 15; probe sequence CTAGACCACCTGCGTCTCAGCATC, designated herein as SEQ ID NO: 16) was also used to measure mRNA levels. PNPLA3 mRNA levels were adjusted according to total RNA content, as measured by RIBOGREEN®. Results are presented as percent inhibition of PNPLA3, relative to untreated control cells.

TABLE 25

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 898558 | 581 | 596 | N/A | N/A | GGCATCCACGACTTCG | 87 | 1672 |
| 912709 | 27 | 42 | 2765 | 2780 | GGCATTCCCAGCGCGA | 0 | 17 |
| 912710 | 95 | 110 | 2833 | 2848 | TCCTGATCCGCAGCAG | 0 | 18 |
| 912711 | 103 | 118 | 2841 | 2856 | GGCTCGGGTCCTGATC | 0 | 19 |
| 912712 | 131 | 146 | 2869 | 2884 | GTTAGGATCTGGGTCG | 76 | 20 |
| 912713 | 164 | 179 | 2902 | 2917 | GTACATGGCGGCGGCG | 0 | 21 |
| 912714 | 183 | 198 | 2921 | 2936 | TCCAGCCGCGCTCTGC | 29 | 22 |
| 912715 | 196 | 211 | 2934 | 2949 | GCGAAGGACAAGCTCC | 31 | 23 |
| 912716 | 197 | 212 | 2935 | 2950 | CGCGAAGGACAAGCTC | 0 | 24 |

TABLE 25-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912717 | 272 | 287 | 3010 | 3025 | GCGGAGGAGGTGCGGG | 0 | 25 |
| 912718 | 273 | 288 | 3011 | 3026 | CGCGGAGGAGGTGCGG | 0 | 26 |
| 912719 | 274 | 289 | 3012 | 3027 | TCGCGGAGGAGGTGCG | 16 | 27 |
| 912720 | 290 | 305 | 3028 | 3043 | GAACAACATGCGCGCG | 0 | 28 |
| 912721 | 291 | 306 | 3029 | 3044 | CGAACAACATGCGCGC | 2 | 29 |
| 912722 | 292 | 307 | 3030 | 3045 | CCGAACAACATGCGCG | 0 | 30 |
| 912723 | 293 | 308 | 3031 | 3046 | GCCGAACAACATGCGC | 0 | 31 |
| 912724 | 294 | 309 | 3032 | 3047 | CGCCGAACAACATGCG | 0 | 32 |
| 912725 | 323 | 338 | 3061 | 3076 | GCCGACGCAGTGCAAC | 0 | 33 |
| 912726 | 324 | 339 | 3062 | 3077 | CGCCGACGCAGTGCAA | 0 | 34 |
| 912727 | 340 | 355 | 3078 | 3093 | GGGATACCGGAGAGGA | 32 | 35 |
| 912728 | 370 | 385 | 5944 | 5959 | TCTGAGAGGACCTGCA | 31 | 36 |
| 912729 | 375 | 390 | 5949 | 5964 | CAAGATCTGAGAGGAC | 60 | 37 |
| 912730 | 404 | 419 | 5978 | 5993 | GCCAATGTTCCGACTC | 52 | 38 |
| 912731 | 410 | 425 | 5984 | 5999 | GAAGATGCCAATGTTC | 31 | 39 |
| 912732 | 429 | 444 | 6003 | 6018 | TTAAGTTGAAGGATGG | 93 | 40 |
| 912733 | 432 | 447 | 6006 | 6021 | TGCTTAAGTTGAAGGA | 82 | 41 |
| 912734 | 478 | 493 | 6052 | 6067 | TGGACATTGGCCGGGA | 73 | 42 |
| 912735 | 479 | 494 | 6053 | 6068 | GTGGACATTGGCCGGG | 44 | 43 |
| 912736 | 484 | 499 | 6058 | 6073 | AGCTGGTGGACATTGG | 29 | 44 |
| 912737 | 528 | 543 | 6102 | 6117 | CATCAGACACTCTGGT | 0 | 45 |
| 912738 | 531 | 546 | 6105 | 6120 | CCCCATCAGACACTCT | 55 | 46 |
| 912739 | 552 | 567 | 6126 | 6141 | AGTCAGACACCAGAAC | 23 | 47 |
| 912740 | 582 | 597 | N/A | N/A | AGGCATCCACGACTTC | 40 | 1673 |
| 912741 | 584 | 599 | N/A | N/A | CAAGGCATCCACGACT | 55 | 1674 |
| 912742 | 591 | 606 | N/A | N/A | AACATACCAAGGCATC | 59 | 1675 |
| 912743 | 593 | 608 | N/A | N/A | GGAACATACCAAGGCA | 69 | 1676 |
| 912744 | 594 | 609 | 7824 | 7839 | AGGAACATACCAAGGC | 85 | 1677 |
| 912745 | 625 | 640 | 7855 | 7870 | GGGATAAGGCCACTGT | 71 | 1678 |
| 912746 | 626 | 641 | 7856 | 7871 | AGGGATAAGGCCACTG | 12 | 1679 |
| 912747 | 630 | 645 | 7860 | 7875 | AAGGAGGGATAAGGCC | 0 | 1680 |
| 912748 | 652 | 667 | N/A | N/A | ACATATCGCACGCCTC | 35 | 1681 |
| 912749 | 653 | 668 | N/A | N/A | CACATATCGCACGCCT | 3 | 1682 |
| 912750 | 654 | 669 | N/A | N/A | CCACATATCGCACGCC | 27 | 1683 |
| 912751 | 656 | 671 | N/A | N/A | ATCCACATATCGCACG | 24 | 1684 |
| 912752 | 660 | 675 | 11878 | 11893 | CTCCATCCACATATCG | 87 | 1685 |

TABLE 25-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
| --- | --- | --- | --- | --- | --- | --- | --- |
| 912753 | 689 | 704 | 11907 | 11922 | ATCAATGAAGGGTACG | 79 | 1686 |
| 912754 | 690 | 705 | 11908 | 11923 | CATCAATGAAGGGTAC | 63 | 1687 |
| 912755 | 693 | 708 | 11911 | 11926 | TGGCATCAATGAAGGG | 68 | 48 |
| 912756 | 698 | 713 | 11916 | 11931 | TGTTTTGGCATCAATG | 88 | 49 |
| 912757 | 746 | 761 | 11964 | 11979 | TTTAGGGCAGATGTCG | 75 | 50 |
| 912758 | 747 | 762 | 11965 | 11980 | CTTTAGGGCAGATGTC | 82 | 51 |
| 912759 | 795 | 810 | 12013 | 12028 | GTAGACTGAGCTTGGT | 96 | 52 |
| 912760 | 820 | 835 | 12038 | 12053 | AGGTAGAGGTTCCCTG | 0 | 53 |
| 912761 | 841 | 856 | 12059 | 12074 | GGGACAAAAGCTCTCG | 0 | 54 |
| 912762 | 873 | 888 | 13609 | 13624 | GGCATATCTCTCCCAG | 0 | 55 |
| 912763 | 874 | 889 | 13610 | 13625 | AGGCATATCTCTCCCA | 0 | 56 |
| 912764 | 886 | 901 | 13622 | 13637 | AAATATCCTCGAAGGC | 71 | 57 |
| 912765 | 888 | 903 | 13624 | 13639 | CCAAATATCCTCGAAG | 37 | 58 |
| 912766 | 889 | 904 | 13625 | 13640 | TCCAAATATCCTCGAA | 0 | 59 |
| 912767 | 894 | 909 | 13630 | 13645 | ATGCATCCAAATATCC | 42 | 60 |
| 912768 | 925 | 940 | N/A | N/A | TTGCAGATGCCCTTCT | 5 | 61 |
| 912769 | 968 | 983 | 16088 | 16103 | ATCCATCCCTTCTGAG | 6 | 62 |
| 912770 | 986 | 1001 | 16106 | 16121 | GGGCATGGCGACCTCA | 0 | 63 |
| 912771 | 1004 | 1019 | 16124 | 16139 | ACTCATGTTTGCCCAG | 67 | 64 |
| 912782 | 1195 | 1210 | 19035 | 19050 | AGCAAGTTGCAAATCT | 71 | 75 |
| 912783 | 1199 | 1214 | 19039 | 19054 | GGGTAGCAAGTTGCAA | 37 | 76 |
| 912784 | 1205 | 1220 | 19045 | 19060 | CCTAATGGGTAGCAAG | 25 | 77 |
| 912785 | 1206 | 1221 | 19046 | 19061 | TCCTAATGGGTAGCAA | 64 | 78 |

TABLE 26

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
| --- | --- | --- | --- | --- | --- | --- | --- |
| 912786 | 1207 | 1222 | 19047 | 19062 | ATCCTAATGGGTAGCA | 65 | 79 |
| 912787 | 1211 | 1226 | 19051 | 19066 | CATTATCCTAATGGGT | 43 | 80 |
| 912788 | 1212 | 1227 | 19052 | 19067 | ACATTATCCTAATGGG | 0 | 81 |
| 912789 | 1213 | 1228 | 19053 | 19068 | GACATTATCCTAATGG | 59 | 82 |
| 912790 | 1220 | 1235 | 19060 | 19075 | TACATAAGACATTATC | 8 | 83 |
| 912791 | 1224 | 1239 | 19064 | 19079 | GCATTACATAAGACAT | 86 | 84 |

TABLE 26-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912792 | 1245 | 1260 | 19085 | 19100 | CCACAGGCAGGGTACA | 58 | 85 |
| 912793 | 1246 | 1261 | 19086 | 19101 | TCCACAGGCAGGGTAC | 5 | 86 |
| 912794 | 1253 | 1268 | 19093 | 19108 | GGCAGATTCCACAGGC | 68 | 87 |
| 912795 | 1259 | 1274 | 19099 | 19114 | CGCAATGGCAGATTCC | 84 | 88 |
| 912796 | 1265 | 1280 | 19105 | 19120 | GACAATCGCAATGGCA | 63 | 89 |
| 912797 | 1266 | 1281 | 19106 | 19121 | GGACAATCGCAATGGC | 54 | 90 |
| 912798 | 1267 | 1282 | 19107 | 19122 | TGGACAATCGCAATGG | 59 | 91 |
| 912799 | 1285 | 1300 | 23690 | 23705 | AGCCATGTCACCAGTC | 51 | 92 |
| 912800 | 1289 | 1304 | 23694 | 23709 | TGGAAGCCATGTCACC | 32 | 93 |
| 912801 | 1290 | 1305 | 23695 | 23710 | CTGGAAGCCATGTCAC | 44 | 94 |
| 912802 | 1297 | 1312 | 23702 | 23717 | GGCATATCTGGAAGCC | 0 | 95 |
| 912803 | 1298 | 1313 | 23703 | 23718 | GGGCATATCTGGAAGC | 0 | 96 |
| 912804 | 1351 | 1366 | 23756 | 23771 | AGCACTCGAGTGAACA | 6 | 97 |
| 912805 | 1386 | 1401 | N/A | N/A | GCATTTGGGACCTGGA | 54 | 98 |
| 912806 | 1387 | 1402 | N/A | N/A | GGCATTTGGGACCTGG | 33 | 99 |
| 912807 | 1388 | 1403 | 25151 | 25166 | TGGCATTTGGGACCTG | 0 | 100 |
| 912808 | 1394 | 1409 | 25157 | 25172 | GCTCACTGGCATTTGG | 7 | 101 |
| 912809 | 1523 | 1538 | 25286 | 25301 | GTTCAGGCTGGACCTG | 17 | 102 |
| 912810 | 1547 | 1562 | 25310 | 25325 | AGGTACTTTATTGCCC | 30 | 103 |
| 912811 | 1550 | 1565 | 25313 | 25328 | AGCAGGTACTTTATTG | 55 | 104 |
| 912812 | 1653 | 1668 | 25416 | 25431 | AACTTTAGCACCTCTG | 87 | 105 |
| 912813 | 1655 | 1670 | 25418 | 25433 | GAAACTTTAGCACCTC | 85 | 106 |
| 912814 | 1656 | 1671 | 25419 | 25434 | GGAAACTTTAGCACCT | 26 | 107 |
| 912815 | 1669 | 1684 | 25432 | 25447 | CTGCACAAAGATGGGA | 66 | 108 |
| 912816 | 1671 | 1686 | 25434 | 25449 | AGCTGCACAAAGATGG | 41 | 109 |
| 912817 | 1685 | 1700 | 25448 | 25463 | AGCAATGCGGAGGTAG | 35 | 110 |
| 912818 | 1740 | 1755 | 25503 | 25518 | ACCAACTCAGCTCAGA | 76 | 111 |
| 912819 | 1741 | 1756 | 25504 | 25519 | AACCAACTCAGCTCAG | 77 | 112 |
| 912820 | 1757 | 1772 | 25520 | 25535 | TCCTAGCTTTTCATAA | 18 | 113 |
| 912821 | 1788 | 1803 | 25551 | 25566 | TGCTGGACCGCTGCAC | 1 | 114 |
| 912822 | 1796 | 1811 | 25559 | 25574 | GAGTTAAGTGCTGGAC | 90 | 115 |
| 912823 | 1802 | 1817 | 25565 | 25580 | GTATTAGAGTTAAGTG | 86 | 116 |
| 912824 | 1803 | 1818 | 25566 | 25581 | TGTATTAGAGTTAAGT | 79 | 117 |
| 912825 | 1806 | 1821 | 25569 | 25584 | TGATGTATTAGAGTTA | 89 | 118 |
| 912826 | 1808 | 1823 | 25571 | 25586 | GCTGATGTATTAGAGT | 79 | 119 |
| 912827 | 1821 | 1836 | 25584 | 25599 | TGAATTAACGCATGCT | 73 | 120 |

TABLE 26-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 912828 | 1822 | 1837 | 25585 | 25600 | CTGAATTAACGCATGC | 69 | 121 |
| 912829 | 1870 | 1885 | 25633 | 25648 | AGTAAGGGACCCTCTG | 0 | 122 |
| 912830 | 1871 | 1886 | 25634 | 25649 | CAGTAAGGGACCCTCT | 44 | 123 |
| 912831 | 1872 | 1887 | 25635 | 25650 | TCAGTAAGGGACCCTC | 67 | 124 |
| 912832 | 1874 | 1889 | 25637 | 25652 | AGTCAGTAAGGGACCC | 50 | 125 |
| 912833 | 1893 | 1908 | 25656 | 25671 | ATTAATAGGGCCACGA | 78 | 126 |
| 912834 | 1895 | 1910 | 25658 | 25673 | CCATTAATAGGGCCAC | 72 | 127 |
| 912835 | 1896 | 1911 | 25659 | 25674 | ACCATTAATAGGGCCA | 65 | 128 |
| 912836 | 1906 | 1921 | 25669 | 25684 | GAACAGTCTGACCATT | 82 | 129 |
| 912837 | 1908 | 1923 | 25671 | 25686 | TGGAACAGTCTGACCA | 39 | 130 |
| 912838 | 1909 | 1924 | 25672 | 25687 | CTGGAACAGTCTGACC | 84 | 131 |
| 912839 | 1911 | 1926 | 25674 | 25689 | TGCTGGAACAGTCTGA | 72 | 132 |
| 912840 | 1916 | 1931 | 25679 | 25694 | CCTCATGCTGGAACAG | 84 | 133 |
| 912841 | 1928 | 1943 | 25691 | 25706 | TCATTCTAAGAACCTC | 87 | 134 |
| 912842 | 1945 | 1960 | 25708 | 25723 | ACCCATCCAAACACCT | 18 | 135 |
| 912843 | 1982 | 1997 | 25745 | 25760 | ACACATGGGCCAGCCT | 46 | 136 |
| 912844 | 1989 | 2004 | 25752 | 25767 | CAAGATCACACATGGG | 71 | 137 |
| 912845 | 2057 | 2072 | 25820 | 25835 | GGGACGAACTGCACCC | 0 | 138 |
| 912846 | 2098 | 2113 | 25861 | 25876 | TATCATCTTTGCAGAC | 68 | 139 |
| 912847 | 2116 | 2131 | 25879 | 25894 | GTTTTTAGTAGTCAAG | 90 | 140 |
| 912848 | 2117 | 2132 | 25880 | 25895 | CGTTTTTAGTAGTCAA | 94 | 141 |
| 912849 | 2145 | 2160 | 25908 | 25923 | TATCATCTTGTTACCC | 87 | 142 |
| 912850 | 2148 | 2163 | 25911 | 25926 | GATTATCATCTTGTTA | 60 | 143 |
| 912851 | 2150 | 2165 | 25913 | 25928 | TAGATTATCATCTTGT | 50 | 144 |
| 912852 | 2151 | 2166 | 25914 | 25929 | GTAGATTATCATCTTG | 72 | 145 |
| 912853 | 2152 | 2167 | 25915 | 25930 | AGTAGATTATCATCTT | 79 | 146 |
| 912854 | 2175 | 2190 | 25938 | 25953 | GTGAAAAGGTGTTCT | 64 | 147 |
| 912855 | 2182 | 2197 | 25945 | 25960 | TAGTTAGGTGAAAAG | 77 | 148 |
| 912856 | 2188 | 2203 | 25951 | 25966 | TTATTTAGTTAGGTG | 82 | 149 |
| 912857 | 2190 | 2205 | 25953 | 25968 | CATTATTTAGTTAGG | 77 | 150 |
| 912858 | 2273 | 2288 | 26036 | 26051 | CTACTAACATCTCACT | 48 | 151 |
| 912859 | 2274 | 2289 | 26037 | 26052 | TCTACTAACATCTCAC | 91 | 152 |
| 912860 | 2278 | 2293 | 26041 | 26056 | TTATTCTACTAACATC | 37 | 153 |
| 912861 | 2280 | 2295 | 26043 | 26058 | GCTTATTCTACTAACA | 77 | 154 |
| 912862 | 2281 | 2296 | 26044 | 26059 | GGCTTATTCTACTAAC | 70 | 155 |
| 912863 | 2632 | 2647 | 26395 | 26410 | GGTGAATGCCCTGCAC | 42 | 156 |

Study 2

Cultured A431 cells at a density of 5,000 cells per well were transfected by free uptake with 1,000 nM antisense oligonucleotide. After a treatment period of approximately 24 hours, RNA was isolated from the cells and PNPLA3 mRNA levels were measured by quantitative real-time PCR. Human primer probe set RTS36070 was used to measure mRNA levels. PNPLA3 mRNA levels were adjusted according to total RNA content, as measured by RIBOGREENR. Results are presented as percent inhibition of PNPLA3, relative to untreated control cells.

TABLE 27

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 97 | 702 |
| 959270 | 413 | 428 | 5987 | 6002 | ATGGAAGATGCCAATG | 32 | 1688 |
| 959280 | 491 | 506 | 6065 | 6080 | GGAGATGAGCTGGTGG | 66 | 1689 |
| 959290 | 793 | 808 | 12011 | 12026 | AGACTGAGCTTGGTGA | 78 | 1690 |
| 959300 | 899 | 914 | 13635 | 13650 | CCTGAATGCATCCAAA | 69 | 1691 |
| 959310 | 1084 | 1099 | 16204 | 16219 | ATGCTGAGACGCAGGT | 0 | 1692 |
| 959320 | 1256 | 1271 | 19096 | 19111 | AATGGCAGATTCCACA | 25 | 1693 |
| 959330 | 1642 | 1657 | 25405 | 25420 | CTCTGAAAGAATCTGC | 75 | 1694 |
| 959340 | 1659 | 1674 | 25422 | 25437 | ATGGGAAACTTTAGCA | 77 | 1695 |
| 959350 | 1839 | 1854 | 25602 | 25617 | TGTCATTTCCCAACCA | 79 | 1696 |
| 959360 | 2114 | 2129 | 25877 | 25892 | TTTTAGTAGTCAAGGT | 88 | 1697 |
| 959370 | 2223 | 2238 | 25986 | 26001 | GCTTCCTTACATTTTT | 85 | 1698 |
| 959380 | 2269 | 2284 | 26032 | 26047 | TAACATCTCACTGATT | 42 | 1699 |
| 959390 | N/A | N/A | 4311 | 4326 | CTAGTGAGAAACAAAC | 0 | 1700 |
| 959400 | N/A | N/A | 4761 | 4776 | TTATTGTTGCTAAACC | 32 | 1701 |
| 959410 | N/A | N/A | 4863 | 4878 | ACTTTAGGCTCCTGGG | 60 | 1702 |
| 959420 | N/A | N/A | 5285 | 5300 | AGCCATAAATCTTGGG | 24 | 1703 |
| 959430 | N/A | N/A | 5573 | 5588 | ATGACATCATGGCTTC | 93 | 1704 |
| 959440 | N/A | N/A | 5603 | 5618 | TTATTCAATGTGGCTT | 95 | 1705 |
| 959450 | N/A | N/A | 5640 | 5655 | GGGCTCAATGAAATTA | 12 | 1706 |
| 959460 | N/A | N/A | 5713 | 5728 | CTTAGTATGAAATATC | 86 | 1707 |
| 959470 | N/A | N/A | 5808 | 5823 | TACTGTCTACTATGGG | 91 | 1708 |
| 959480 | N/A | N/A | 6157 | 6172 | CTTACATCCACGACTT | 35 | 1709 |
| 959660 | N/A | N/A | 12153 | 12168 | CAGTAACTGGTAGCTC | 74 | 1710 |
| 959670 | N/A | N/A | 12169 | 12184 | TGTTTGATTGTGCAGA | 95 | 1711 |
| 959680 | N/A | N/A | 12210 | 12225 | CGCCTTTTATTTCCGT | 92 | 1712 |
| 959690 | N/A | N/A | 12313 | 12328 | ATAACCACAGCCTGGG | 66 | 1713 |
| 959700 | N/A | N/A | 12675 | 12690 | ATAAGAATCATCTTAG | 7 | 1714 |
| 959710 | N/A | N/A | 12711 | 12726 | ACTACCGAACGCAGTT | 41 | 1715 |

TABLE 27-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959720 | N/A | N/A | 12757 | 12772 | TAGAGTGGTAAGGCAT | 84 | 1716 |
| 959730 | N/A | N/A | 12793 | 12808 | GGTTGGTGTACATGGT | 96 | 1717 |
| 959740 | N/A | N/A | 12880 | 12895 | TCCTGTTAGACAGCTT | 93 | 1718 |
| 959750 | N/A | N/A | 12902 | 12917 | ATAAAGCACACGGGAA | 86 | 1719 |
| 959760 | N/A | N/A | 12931 | 12946 | TAAGAGCTGTCTCCTC | 85 | 1720 |
| 959770 | N/A | N/A | 12972 | 12987 | CTAACAAACTTTGCAG | 79 | 1721 |
| 959780 | N/A | N/A | 13392 | 13407 | TGTCACCCTTCCACGG | 15 | 1722 |
| 959790 | N/A | N/A | 13526 | 13541 | ATTGGAAGACCGCAGA | 43 | 1723 |
| 959800 | N/A | N/A | 13706 | 13721 | CCGCTAGTAAATGCTT | 44 | 1724 |
| 959810 | N/A | N/A | 13737 | 13752 | AACTAAGGCAAATCTC | 77 | 1725 |
| 959820 | N/A | N/A | 13915 | 13930 | GAGTCATGACATCCCA | 89 | 1726 |
| 959830 | N/A | N/A | 14299 | 14314 | GCAGATAAATACACAT | 93 | 1727 |
| 959840 | N/A | N/A | 14424 | 14439 | TTTCCCATCGACACAG | 78 | 1728 |
| 959850 | N/A | N/A | 14571 | 14586 | GCTCCTACTTATCCCC | 76 | 1729 |
| 959860 | N/A | N/A | 15202 | 15217 | TATTGCCAGGTATCTG | 64 | 1730 |
| 959870 | N/A | N/A | 15599 | 15614 | CAATACATAGCAGAGC | 23 | 1731 |
| 959880 | N/A | N/A | 17192 | 17207 | TTAGTCCGTGTTCAGG | 90 | 1732 |
| 959890 | N/A | N/A | 17222 | 17237 | GTAGCTGGTTTGTGGG | 20 | 1733 |
| 959900 | N/A | N/A | 17295 | 17310 | CATCTCTTAGGGCACC | 79 | 1734 |
| 959910 | N/A | N/A | 18393 | 18408 | GTTTGGAAGTCGCCAT | 77 | 1735 |
| 959920 | N/A | N/A | 20284 | 20299 | AGGAAGCCCAATCAAG | 85 | 1736 |
| 959930 | N/A | N/A | 20512 | 20527 | CAGATTGAGTCTCCTG | 10 | 1737 |
| 959940 | N/A | N/A | 20607 | 20622 | TTTTACGATCATCATT | 72 | 1738 |
| 959950 | N/A | N/A | 20661 | 20676 | GCTTAGAAATTGCAGT | 75 | 1739 |
| 959960 | N/A | N/A | 20812 | 20827 | AGGGTAATATTCAGAC | 86 | 1740 |
| 959970 | N/A | N/A | 20934 | 20949 | TGTAGCAGACAGATCA | 74 | 1741 |
| 959980 | N/A | N/A | 21000 | 21015 | TTTAACAGCTCAGGTA | 66 | 1742 |
| 959990 | N/A | N/A | 21405 | 21420 | ATTCTAGACATGGCCA | 51 | 1743 |
| 960000 | N/A | N/A | 21442 | 21457 | AACCAATATACTGAGA | 71 | 1744 |
| 960010 | N/A | N/A | 21545 | 21560 | AGACATATGACATTTC | 91 | 1745 |
| 960020 | N/A | N/A | 22765 | 22780 | ACATGACAGACTAACT | 55 | 1746 |
| 960030 | N/A | N/A | 24039 | 24054 | CATCAATGCTGCACTC | 13 | 1747 |

TABLE 28

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 98 | 702 |
| 959271 | 425 | 440 | 5999 | 6014 | GTTGAAGGATGGATGG | 90 | 1748 |
| 959281 | 511 | 526 | 6085 | 6100 | AGAGAGATGCCTATTT | 73 | 1749 |
| 959291 | 813 | 828 | 12031 | 12046 | GGTTCCCTGTGCAGAG | 79 | 1750 |
| 959301 | 904 | 919 | 13640 | 13655 | AAGAACCTGAATGCAT | 48 | 1751 |
| 959311 | 1085 | 1100 | 16205 | 16220 | GATGCTGAGACGCAGG | 0 | 1752 |
| 959321 | 1602 | 1617 | 25365 | 25380 | ACAGACTCTTCTCTAG | 45 | 1753 |
| 959331 | 1643 | 1658 | 25406 | 25421 | CCTCTGAAAGAATCTG | 81 | 1754 |
| 959341 | 1673 | 1688 | 25436 | 25451 | GTAGCTGCACAAAGAT | 69 | 1755 |
| 959351 | 1842 | 1857 | 25605 | 25620 | TGGTGTCATTTCCCAA | 19 | 1756 |
| 959361 | 2115 | 2130 | 25878 | 25893 | TTTTTAGTAGTCAAGG | 91 | 1757 |
| 959371 | 2240 | 2255 | 26003 | 26018 | ATTCAACAGGTAACAA | 69 | 1758 |
| 959381 | 2271 | 2286 | 26034 | 26049 | ACTAACATCTCACTGA | 33 | 1759 |
| 959391 | N/A | N/A | 4313 | 4328 | AGCTAGTGAGAAACAA | 47 | 1760 |
| 959401 | N/A | N/A | 4764 | 4779 | CTTTTATTGTTGCTAA | 77 | 1761 |
| 959411 | N/A | N/A | 4868 | 4883 | AGTGTACTTTAGGCTC | 90 | 1762 |
| 959421 | N/A | N/A | 5286 | 5301 | CAGCCATAAATCTTGG | 0 | 1763 |
| 959431 | N/A | N/A | 5574 | 5589 | AATGACATCATGGCTT | 74 | 1764 |
| 959441 | N/A | N/A | 5604 | 5619 | TTTATTCAATGTGGCT | 96 | 1765 |
| 959451 | N/A | N/A | 5642 | 5657 | TTGGGCTCAATGAAAT | 0 | 1766 |
| 959461 | N/A | N/A | 5714 | 5729 | GCTTAGTATGAAATAT | 78 | 1767 |
| 959471 | N/A | N/A | 5809 | 5824 | GTACTGTCTACTATGG | 78 | 1768 |
| 959481 | N/A | N/A | 6160 | 6175 | CTGCTTACATCCACGA | 4 | 1769 |
| 959661 | N/A | N/A | 12154 | 12169 | ACAGTAACTGGTAGCT | 72 | 1770 |
| 959671 | N/A | N/A | 12170 | 12185 | CTGTTTGATTGTGCAG | 50 | 1771 |
| 959681 | N/A | N/A | 12211 | 12226 | GCGCCTTTTATTTCCG | 14 | 1772 |
| 959691 | N/A | N/A | 12322 | 12337 | CCTGACTATATAACCA | 56 | 1773 |
| 959701 | N/A | N/A | 12689 | 12704 | GACCGTGTTTCCAAAT | 97 | 1774 |
| 959711 | N/A | N/A | 12712 | 12727 | AACTACCGAACGCAGT | 48 | 1775 |
| 959721 | N/A | N/A | 12759 | 12774 | GGTAGAGTGGTAAGGC | 95 | 1776 |
| 959731 | N/A | N/A | 12828 | 12843 | CATAGCCTTCTTTCTT | 93 | 1777 |
| 959741 | N/A | N/A | 12882 | 12897 | AATCCTGTTAGACAGC | 90 | 1778 |
| 959751 | N/A | N/A | 12903 | 12918 | TATAAAGCACACGGGA | 82 | 1779 |
| 959761 | N/A | N/A | 12933 | 12948 | AATAAGAGCTGTCTCC | 87 | 1780 |
| 959771 | N/A | N/A | 12974 | 12989 | CCCTAACAAACTTTGC | 62 | 1781 |
| 959781 | N/A | N/A | 13394 | 13409 | AATGTCACCCTTCCAC | 90 | 1782 |

TABLE 28-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959791 | N/A | N/A | 13527 | 13542 | CATTGGAAGACCGCAG | 76 | 1783 |
| 959801 | N/A | N/A | 13707 | 13722 | ACCGCTAGTAAATGCT | 35 | 1784 |
| 959811 | N/A | N/A | 13740 | 13755 | TAGAACTAAGGCAAAT | 65 | 1785 |
| 959821 | N/A | N/A | 13916 | 13931 | GGAGTCATGACATCCC | 42 | 1786 |
| 959831 | N/A | N/A | 14302 | 14317 | TGAGCAGATAAATACA | 75 | 1787 |
| 959841 | N/A | N/A | 14425 | 14440 | CTTTCCCATCGACACA | 79 | 1788 |
| 959851 | N/A | N/A | 14573 | 14588 | GCGCTCCTACTTATCC | 0 | 1789 |
| 959861 | N/A | N/A | 15203 | 15218 | ATATTGCCAGGTATCT | 67 | 1790 |
| 959871 | N/A | N/A | 15763 | 15778 | GTGTTGGTTTATAACA | 13 | 1791 |
| 959881 | N/A | N/A | 17194 | 17209 | ACTTAGTCCGTGTTCA | 45 | 1792 |
| 959891 | N/A | N/A | 17224 | 17239 | CTGTAGCTGGTTTGTG | 42 | 1793 |
| 959901 | N/A | N/A | 17296 | 17311 | CCATCTCTTAGGGCAC | 53 | 1794 |
| 959911 | N/A | N/A | 18394 | 18409 | TGTTTGGAAGTCGCCA | 87 | 1795 |
| 959921 | N/A | N/A | 20289 | 20304 | ATCAGAGGAAGCCCAA | 84 | 1796 |
| 959931 | N/A | N/A | 20514 | 20529 | ACCAGATTGAGTCTCC | 91 | 1797 |
| 959941 | N/A | N/A | 20613 | 20628 | CTCTAATTTTACGATC | 70 | 1798 |
| 959951 | N/A | N/A | 20662 | 20677 | AGCTTAGAAATTGCAG | 0 | 1799 |
| 959961 | N/A | N/A | 20813 | 20828 | CAGGGTAATATTCAGA | 87 | 1800 |
| 959971 | N/A | N/A | 20936 | 20951 | TTTGTAGCAGACAGAT | 18 | 1801 |
| 959981 | N/A | N/A | 21001 | 21016 | TTTTAACAGCTCAGGT | 71 | 1802 |
| 959991 | N/A | N/A | 21406 | 21421 | AATTCTAGACATGGCC | 25 | 1803 |
| 960001 | N/A | N/A | 21443 | 21458 | TAACCAATATACTGAG | 72 | 1804 |
| 960011 | N/A | N/A | 22023 | 22038 | CGCAAAAAGACAACGA | 16 | 1805 |
| 960021 | N/A | N/A | 22766 | 22781 | GACATGACAGACTAAC | 76 | 1806 |
| 960031 | N/A | N/A | 24040 | 24055 | CCATCAATGCTGCACT | 61 | 1807 |

TABLE 29

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 97 | 702 |
| 959272 | 426 | 441 | 6000 | 6015 | AGTTGAAGGATGGATG | 76 | 1808 |
| 959282 | 517 | 532 | 6091 | 6106 | CTGGTAAGAGAGATGC | 64 | 1809 |
| 959292 | 815 | 830 | 12033 | 12048 | GAGGTTCCCTGTGCAG | 81 | 1810 |
| 959302 | 905 | 920 | 13641 | 13656 | CAAGAACCTGAATGCA | 65 | 1811 |

TABLE 29-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959312 | 1087 | 1102 | 16207 | 16222 | AGGATGCTGAGACGCA | 66 | 1812 |
| 959322 | 1604 | 1619 | 25367 | 25382 | TCACAGACTCTTCTCT | 50 | 1813 |
| 959332 | 1644 | 1659 | 25407 | 25422 | ACCTCTGAAAGAATCT | 69 | 1814 |
| 959342 | 1675 | 1690 | 25438 | 25453 | AGGTAGCTGCACAAAG | 78 | 1815 |
| 959352 | 1903 | 1918 | 25666 | 25681 | CAGTCTGACCATTAAT | 77 | 1816 |
| 959362 | 2173 | 2188 | 25936 | 25951 | GAAAAAGGTGTTCTAA | 85 | 1817 |
| 959372 | 2242 | 2257 | 26005 | 26020 | AAATTCAACAGGTAAC | 62 | 1818 |
| 959382 | 2275 | 2290 | 26038 | 26053 | TTCTACTAACATCTCA | 80 | 1819 |
| 959392 | N/A | N/A | 4732 | 4747 | ATGATCATGTGGCGGT | 80 | 1820 |
| 959402 | N/A | N/A | 4765 | 4780 | ACTTTTATTGTTGCTA | 86 | 1821 |
| 959412 | N/A | N/A | 4869 | 4884 | GAGTGTACTTTAGGCT | 94 | 1822 |
| 959422 | N/A | N/A | 5389 | 5404 | CTATCAGGTGCAGGAG | 93 | 1823 |
| 959432 | N/A | N/A | 5575 | 5590 | CAATGACATCATGGCT | 90 | 1824 |
| 959442 | N/A | N/A | 5607 | 5622 | TACTTTATTCAATGTG | 0 | 1825 |
| 959452 | N/A | N/A | 5643 | 5658 | ATTGGGCTCAATGAAA | 35 | 1826 |
| 959462 | N/A | N/A | 5716 | 5731 | TGGCTTAGTATGAAAT | 80 | 1827 |
| 959472 | N/A | N/A | 5864 | 5879 | TTTGGCAAGGCCAGAA | 0 | 1828 |
| 959482 | N/A | N/A | 6960 | 6975 | GCATAGAGGAAGCTCG | 32 | 1829 |
| 959662 | N/A | N/A | 12155 | 12170 | GACAGTAACTGGTAGC | 92 | 1830 |
| 959672 | N/A | N/A | 12172 | 12187 | TTCTGTTTGATTGTGC | 97 | 1831 |
| 959682 | N/A | N/A | 12280 | 12295 | AGGTCTGGGTATATGT | 93 | 1832 |
| 959692 | N/A | N/A | 12323 | 12338 | CCCTGACTATATAACC | 32 | 1833 |
| 959702 | N/A | N/A | 12691 | 12706 | TTGACCGTGTTTCCAA | 94 | 1834 |
| 959712 | N/A | N/A | 12713 | 12728 | AAACTACCGAACGCAG | 92 | 1835 |
| 959722 | N/A | N/A | 12760 | 12775 | TGGTAGAGTGGTAAGG | 94 | 1836 |
| 959732 | N/A | N/A | 12829 | 12844 | GCATAGCCTTCTTTCT | 87 | 1837 |
| 959742 | N/A | N/A | 12883 | 12898 | CAATCCTGTTAGACAG | 13 | 1838 |
| 959752 | N/A | N/A | 12904 | 12919 | TTATAAAGCACACGGG | 87 | 1839 |
| 959762 | N/A | N/A | 12934 | 12949 | CAATAAGAGCTGTCTC | 81 | 1840 |
| 959772 | N/A | N/A | 13370 | 13385 | TGCAGGCACCCCAGCA | 0 | 1841 |
| 959782 | N/A | N/A | 13395 | 13410 | GAATGTCACCCTTCCA | 90 | 1842 |
| 959792 | N/A | N/A | 13528 | 13543 | TCATTGGAAGACCGCA | 84 | 1843 |
| 959802 | N/A | N/A | 13708 | 13723 | GACCGCTAGTAAATGC | 57 | 1844 |
| 959812 | N/A | N/A | 13741 | 13756 | TTAGAACTAAGGCAAA | 78 | 1845 |
| 959822 | N/A | N/A | 13917 | 13932 | TGGAGTCATGACATCC | 0 | 1846 |
| 959832 | N/A | N/A | 14303 | 14318 | CTGAGCAGATAAATAC | 74 | 1847 |

TABLE 29-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959842 | N/A | N/A | 14553 | 14568 | AGTCTTAATGTGGATT | 76 | 1848 |
| 959852 | N/A | N/A | 14667 | 14682 | AGTGTCCCCATCCCCA | 54 | 1849 |
| 959862 | N/A | N/A | 15204 | 15219 | AATATTGCCAGGTATC | 56 | 1850 |
| 959872 | N/A | N/A | 15765 | 15780 | TAGTGTTGGTTTATAA | 89 | 1851 |
| 959882 | N/A | N/A | 17196 | 17211 | TGACTTAGTCCGTGTT | 43 | 1852 |
| 959892 | N/A | N/A | 17225 | 17240 | TCTGTAGCTGGTTTGT | 61 | 1853 |
| 959902 | N/A | N/A | 17298 | 17313 | TCCCATCTCTTAGGGC | 24 | 1854 |
| 959912 | N/A | N/A | 18396 | 18411 | TATGTTTGGAAGTCGC | 91 | 1855 |
| 959922 | N/A | N/A | 20290 | 20305 | AATCAGAGGAAGCCCA | 40 | 1856 |
| 959932 | N/A | N/A | 20515 | 20530 | AACCAGATTGAGTCTC | 72 | 1857 |
| 959942 | N/A | N/A | 20614 | 20629 | TCTCTAATTTTACGAT | 23 | 1858 |
| 959952 | N/A | N/A | 20663 | 20678 | CAGCTTAGAAATTGCA | 24 | 1859 |
| 959962 | N/A | N/A | 20814 | 20829 | CCAGGGTAATATTCAG | 87 | 1860 |
| 959972 | N/A | N/A | 20937 | 20952 | CTTTGTAGCAGACAGA | 50 | 1861 |
| 959982 | N/A | N/A | 21003 | 21018 | TATTTTAACAGCTCAG | 94 | 1862 |
| 959992 | N/A | N/A | 21409 | 21424 | TGCAATTCTAGACATG | 12 | 1863 |
| 960002 | N/A | N/A | 21445 | 21460 | ACTAACCAATATACTG | 55 | 1864 |
| 960012 | N/A | N/A | 22541 | 22556 | CAACAGATTACTGGAC | 28 | 1865 |
| 960022 | N/A | N/A | 22768 | 22783 | AGGACATGACAGACTA | 66 | 1866 |
| 960032 | N/A | N/A | 24041 | 24056 | ACCATCAATGCTGCAC | 79 | 1867 |

TABLE 30

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 98 | 702 |
| 959273 | 427 | 442 | 6001 | 6016 | AAGTTGAAGGATGGAT | 86 | 1868 |
| 959283 | 694 | 709 | 11912 | 11927 | TTGGCATCAATGAAGG | 73 | 1869 |
| 959293 | 816 | 831 | 12034 | 12049 | AGAGGTTCCCTGTGCA | 80 | 1870 |
| 959303 | 906 | 921 | 13642 | 13657 | CCAAGAACCTGAATGC | 65 | 1871 |
| 959313 | 1090 | 1105 | 16210 | 16225 | GGCAGGATGCTGAGAC | 43 | 1872 |
| 959323 | 1605 | 1620 | 25368 | 25383 | CTCACAGACTCTTCTC | 81 | 1873 |
| 959333 | 1646 | 1661 | 25409 | 25424 | GCACCTCTGAAAGAAT | 51 | 1874 |
| 959343 | 1677 | 1692 | 25440 | 25455 | GGAGGTAGCTGCACAA | 73 | 1875 |

TABLE 30-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959353 | 1904 | 1919 | 25667 | 25682 | ACAGTCTGACCATTAA | 85 | 1876 |
| 959363 | 2179 | 2194 | 25942 | 25957 | TTAGGTGAAAAAGGTG | 91 | 1877 |
| 959373 | 2258 | 2273 | 26021 | 26036 | TGATTCACATAATACA | 71 | 1878 |
| 959383 | 2277 | 2292 | 26040 | 26055 | TATTCTACTAACATCT | 38 | 1879 |
| 959393 | N/A | N/A | 4733 | 4748 | AATGATCATGTGGCGG | 93 | 1880 |
| 959403 | N/A | N/A | 4767 | 4782 | TGACTTTTATTGTTGC | 87 | 1881 |
| 959413 | N/A | N/A | 4870 | 4885 | TGAGTGTACTTTAGGC | 94 | 1882 |
| 959423 | N/A | N/A | 5392 | 5407 | ATGCTATCAGGTGCAG | 0 | 1883 |
| 959433 | N/A | N/A | 5578 | 5593 | GCACAATGACATCATG | 86 | 1884 |
| 959443 | N/A | N/A | 5608 | 5623 | TTACTTTATTCAATGT | 9 | 1885 |
| 959453 | N/A | N/A | 5644 | 5659 | TATTGGGCTCAATGAA | 80 | 1886 |
| 959463 | N/A | N/A | 5798 | 5813 | TATGGGAGCCACATGT | 4 | 1887 |
| 959473 | N/A | N/A | 5866 | 5881 | CTTTTGGCAAGGCCAG | 0 | 1888 |
| 959483 | N/A | N/A | 7199 | 7214 | TTAAACAGAGGATGCA | 31 | 1889 |
| 959663 | N/A | N/A | 12156 | 12171 | AGACAGTAACTGGTAG | 75 | 1890 |
| 959673 | N/A | N/A | 12199 | 12214 | TCCGTTAACCATCAAG | 95 | 1891 |
| 959683 | N/A | N/A | 12282 | 12297 | TTAGGTCTGGGTATAT | 94 | 1892 |
| 959693 | N/A | N/A | 12324 | 12339 | CCCCTGACTATATAAC | 0 | 1893 |
| 959703 | N/A | N/A | 12692 | 12707 | CTTGACCGTGTTTCCA | 97 | 1894 |
| 959713 | N/A | N/A | 12715 | 12730 | TTAAACTACCGAACGC | 95 | 1895 |
| 959723 | N/A | N/A | 12761 | 12776 | ATGGTAGAGTGGTAAG | 77 | 1896 |
| 959733 | N/A | N/A | 12832 | 12847 | ATTGCATAGCCTTCTT | 95 | 1897 |
| 959743 | N/A | N/A | 12884 | 12899 | CCAATCCTGTTAGACA | 83 | 1898 |
| 959753 | N/A | N/A | 12908 | 12923 | CTGCTTATAAAGCACA | 2 | 1899 |
| 959763 | N/A | N/A | 12935 | 12950 | ACAATAAGAGCTGTCT | 85 | 1900 |
| 959773 | N/A | N/A | 13372 | 13387 | TTTGCAGGCACCCCAG | 63 | 1901 |
| 959783 | N/A | N/A | 13396 | 13411 | TGAATGTCACCCTTCC | 53 | 1902 |
| 959793 | N/A | N/A | 13531 | 13546 | GCATCATTGGAAGACC | 86 | 1903 |
| 959803 | N/A | N/A | 13713 | 13728 | ACCAAGACCGCTAGTA | 38 | 1904 |
| 959813 | N/A | N/A | 13743 | 13758 | TGTTAGAACTAAGGCA | 79 | 1905 |
| 959823 | N/A | N/A | 13919 | 13934 | CCTGGAGTCATGACAT | 7 | 1906 |
| 959833 | N/A | N/A | 14304 | 14319 | TCTGAGCAGATAAATA | 39 | 1907 |
| 959843 | N/A | N/A | 14554 | 14569 | AAGTCTTAATGTGGAT | 84 | 1908 |
| 959853 | N/A | N/A | 14669 | 14684 | TTAGTGTCCCCATCCC | 78 | 1909 |
| 959863 | N/A | N/A | 15205 | 15220 | GAATATTGCCAGGTAT | 86 | 1910 |
| 959873 | N/A | N/A | 15766 | 15781 | TTAGTGTTGGTTTATA | 92 | 1911 |

TABLE 30-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959883 | N/A | N/A | 17198 | 17213 | TTTGACTTAGTCCGTG | 86 | 1912 |
| 959893 | N/A | N/A | 17226 | 17241 | CTCTGTAGCTGGTTTG | 82 | 1913 |
| 959903 | N/A | N/A | 17601 | 17616 | TTGATAGTGAATGTGT | 83 | 1914 |
| 959913 | N/A | N/A | 18397 | 18412 | ATATGTTTGGAAGTCG | 91 | 1915 |
| 959923 | N/A | N/A | 20291 | 20306 | CAATCAGAGGAAGCCC | 34 | 1916 |
| 959933 | N/A | N/A | 20516 | 20531 | TAACCAGATTGAGTCT | 66 | 1917 |
| 959943 | N/A | N/A | 20615 | 20630 | GTCTCTAATTTTACGA | 53 | 1918 |
| 959953 | N/A | N/A | 20664 | 20679 | ACAGCTTAGAAATTGC | 89 | 1919 |
| 959963 | N/A | N/A | 20843 | 20858 | CTGTATTAGCTCAATA | 67 | 1920 |
| 959973 | N/A | N/A | 20938 | 20953 | TCTTTGTAGCAGACAG | 84 | 1921 |
| 959983 | N/A | N/A | 21004 | 21019 | TTATTTTAACAGCTCA | 92 | 1922 |
| 959993 | N/A | N/A | 21410 | 21425 | CTGCAATTCTAGACAT | 29 | 1923 |
| 960003 | N/A | N/A | 21535 | 21550 | CATTTCAGAGTATAAG | 46 | 1924 |
| 960013 | N/A | N/A | 22708 | 22723 | GATGTGAGTGAAATAA | 69 | 1925 |
| 960023 | N/A | N/A | 22769 | 22784 | AAGGACATGACAGACT | 68 | 1926 |
| 960033 | N/A | N/A | 24043 | 24058 | CCACCATCAATGCTGC | 58 | 1927 |

TABLE 31

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 99 | 702 |
| 959284 | 695 | 710 | 11913 | 11928 | TTTGGCATCAATGAAG | 69 | 1928 |
| 959294 | 817 | 832 | 12035 | 12050 | TAGAGGTTCCCTGTGC | 83 | 1929 |
| 959314 | 1091 | 1106 | 16211 | 16226 | GGGCAGGATGCTGAGA | 22 | 1930 |
| 959324 | 1606 | 1621 | 25369 | 25384 | ACTCACAGACTCTTCT | 68 | 1931 |
| 959334 | 1647 | 1662 | 25410 | 25425 | AGCACCTCTGAAAGAA | 67 | 1932 |
| 959344 | 1678 | 1693 | 25441 | 25456 | CGGAGGTAGCTGCACA | 85 | 1933 |
| 959354 | 1926 | 1941 | 25689 | 25704 | ATTCTAAGAACCTCAT | 51 | 1934 |
| 959384 | N/A | N/A | 4303 | 4318 | AAACAAACCCTCCGTC | 10 | 1935 |
| 959394 | N/A | N/A | 4734 | 4749 | AAATGATCATGTGGCG | 94 | 1936 |
| 959404 | N/A | N/A | 4768 | 4783 | CTGACTTTATTGTTG | 74 | 1937 |
| 959414 | N/A | N/A | 4871 | 4886 | GTGAGTGTACTTTAGG | 98 | 1938 |
| 959424 | N/A | N/A | 5393 | 5408 | AATGCTATCAGGTGCA | 31 | 1939 |
| 959434 | N/A | N/A | 5579 | 5594 | TGCACAATGACATCAT | 88 | 1940 |

TABLE 31-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959444 | N/A | N/A | 5621 | 5636 | CTACCTGTGTCTTTTA | 90 | 1941 |
| 959454 | N/A | N/A | 5647 | 5662 | ATATATTGGGCTCAAT | 81 | 1942 |
| 959474 | N/A | N/A | 5867 | 5882 | ACTTTTGGCAAGGCCA | 17 | 1943 |
| 959484 | N/A | N/A | 7211 | 7226 | CCGCAAACAAGGTTAA | 22 | 1944 |
| 959684 | N/A | N/A | 12283 | 12298 | TTTAGGTCTGGGTATA | 93 | 1945 |
| 959694 | N/A | N/A | 12325 | 12340 | CCCCCTGACTATATAA | 18 | 1946 |
| 959704 | N/A | N/A | 12693 | 12708 | TCTTGACCGTGTTTCC | 97 | 1947 |
| 959734 | N/A | N/A | 12834 | 12849 | GCATTGCATAGCCTTC | 96 | 1948 |
| 959744 | N/A | N/A | 12886 | 12901 | AACCAATCCTGTTAGA | 59 | 1949 |
| 959754 | N/A | N/A | 12909 | 12924 | TCTGCTTATAAAGCAC | 100 | 1950 |
| 959774 | N/A | N/A | 13373 | 13388 | CTTTGCAGGCACCCCA | 72 | 1951 |
| 959784 | N/A | N/A | 13398 | 13413 | CTTGAATGTCACCCTT | 92 | 1952 |
| 959804 | N/A | N/A | 13715 | 13730 | TTACCAAGACCGCTAG | 47 | 1953 |
| 959824 | N/A | N/A | 14228 | 14243 | ACTTTTAGTATTAAAG | 0 | 1954 |
| 959844 | N/A | N/A | 14555 | 14570 | AAAGTCTTAATGTGGA | 88 | 1955 |
| 959854 | N/A | N/A | 14670 | 14685 | CTTAGTGTCCCCATCC | 76 | 1956 |
| 959874 | N/A | N/A | 15767 | 15782 | GTTAGTGTTGGTTTAT | 95 | 1957 |
| 959884 | N/A | N/A | 17199 | 17214 | GTTTGACTTAGTCCGT | 96 | 1958 |
| 959914 | N/A | N/A | 18398 | 18413 | AATATGTTTGGAAGTC | 87 | 1959 |
| 959934 | N/A | N/A | 20518 | 20533 | AGTAACCAGATTGAGT | 96 | 1960 |
| 959954 | N/A | N/A | 20665 | 20680 | CACAGCTTAGAAATTG | 88 | 1961 |
| 959964 | N/A | N/A | 20844 | 20859 | CCTGTATTAGCTCAAT | 92 | 1962 |
| 959974 | N/A | N/A | 20940 | 20955 | CCTCTTTGTAGCAGAC | 84 | 1963 |
| 959984 | N/A | N/A | 21006 | 21021 | GGTTATTTTAACAGCT | 85 | 1964 |
| 959994 | N/A | N/A | 21412 | 21427 | ACCTGCAATTCTAGAC | 61 | 1965 |
| 960014 | N/A | N/A | 22710 | 22725 | AAGATGTGAGTGAAAT | 70 | 1966 |
| 960024 | N/A | N/A | 22770 | 22785 | AAAGGACATGACAGAC | 87 | 1967 |

TABLE 32

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959275 | 440 | 455 | 6014 | 6029 | GAGGAACTTGCTTAAG | 81 | 1968 |
| 959285 | 696 | 711 | 11914 | 11929 | TTTTGGCATCAATGAA | 62 | 1969 |

TABLE 32-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959305 | 1066 | 1081 | 16186 | 16201 | TCTAGCAGCTCATCTC | 64 | 1970 |
| 959335 | 1649 | 1664 | 25412 | 25427 | TTAGCACCTCTGAAAG | 72 | 1971 |
| 959345 | 1804 | 1819 | 25567 | 25582 | ATGTATTAGAGTTAAG | 77 | 1972 |
| 959355 | 1927 | 1942 | 25690 | 25705 | CATTCTAAGAACCTCA | 71 | 1973 |
| 959365 | 2183 | 2198 | 25946 | 25961 | TTAGTTAGGTGAAAAA | 81 | 1974 |
| 959375 | 2261 | 2276 | 26024 | 26039 | CACTGATTCACATAAT | 70 | 1975 |
| 959395 | N/A | N/A | 4737 | 4752 | TGCAAATGATCATGTG | 66 | 1976 |
| 959405 | N/A | N/A | 4769 | 4784 | GCTGACTTTTATTGTT | 84 | 1977 |
| 959415 | N/A | N/A | 4872 | 4887 | AGTGAGTGTACTTTAG | 94 | 1978 |
| 959425 | N/A | N/A | 5395 | 5410 | TTAATGCTATCAGGTG | 81 | 1979 |
| 959435 | N/A | N/A | 5580 | 5595 | ATGCACAATGACATCA | 86 | 1980 |
| 959445 | N/A | N/A | 5624 | 5639 | ATTCTACCTGTGTCTT | 97 | 1981 |
| 959455 | N/A | N/A | 5651 | 5666 | TTGGATATATTGGGCT | 97 | 1982 |
| 959475 | N/A | N/A | 5868 | 5883 | TACTTTTGGCAAGGCC | 70 | 1983 |
| 959485 | N/A | N/A | 7697 | 7712 | GCACAGAGTAGGTTAA | 72 | 1984 |
| 959655 | N/A | N/A | 12146 | 12161 | TGGTAGCTCCTGGCAA | 55 | 1985 |
| 959675 | N/A | N/A | 12201 | 12216 | TTTCCGTTAACCATCA | 94 | 1986 |
| 959695 | N/A | N/A | 12667 | 12682 | CATCTTAGTGGCTGGG | 93 | 1987 |
| 959705 | N/A | N/A | 12695 | 12710 | GTTCTTGACCGTGTTT | 97 | 1988 |
| 959715 | N/A | N/A | 12717 | 12732 | GGTTAAACTACCGAAC | 11 | 1989 |
| 959725 | N/A | N/A | 12783 | 12798 | CATGGTCTGCAAATTT | 89 | 1990 |
| 959745 | N/A | N/A | 12887 | 12902 | AAACCAATCCTGTTAG | 46 | 1991 |
| 959755 | N/A | N/A | 12910 | 12925 | ATCTGCTTATAAAGCA | 42 | 1992 |
| 959775 | N/A | N/A | 13374 | 13389 | ACTTTGCAGGCACCCC | 87 | 1993 |
| 959785 | N/A | N/A | 13399 | 13414 | GCTTGAATGTCACCCT | 94 | 1994 |
| 959805 | N/A | N/A | 13716 | 13731 | TTTACCAAGACCGCTA | 86 | 1995 |
| 959825 | N/A | N/A | 14230 | 14245 | CAACTTTTAGTATTAA | 0 | 1996 |
| 959835 | N/A | N/A | 14417 | 14432 | TCGACACAGCATCACC | 62 | 1997 |
| 959855 | N/A | N/A | 14671 | 14686 | TCTTAGTGTCCCCATC | 78 | 1998 |
| 959865 | N/A | N/A | 15209 | 15224 | TTAGGAATATTGCCAG | 93 | 1999 |
| 959875 | N/A | N/A | 15769 | 15784 | GGGTTAGTGTTGGTTT | 94 | 2000 |
| 959895 | N/A | N/A | 17288 | 17303 | TAGGGCACCTCAAGAA | 0 | 2001 |
| 959915 | N/A | N/A | 18400 | 18415 | CAAATATGTTTGGAAG | 50 | 2002 |
| 959925 | N/A | N/A | 20293 | 20308 | CCCAATCAGAGGAAGC | 41 | 2003 |
| 959935 | N/A | N/A | 20599 | 20614 | TCATCATTATTACCTG | 91 | 2004 |
| 959955 | N/A | N/A | 20803 | 20818 | TTCAGACCAGGGTAAT | 91 | 2005 |

TABLE 32-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959965 | N/A | N/A | 20845 | 20860 | GCCTGTATTAGCTCAA | 90 | 2006 |
| 959975 | N/A | N/A | 20941 | 20956 | GCCTCTTTGTAGCAGA | 0 | 2007 |
| 959995 | N/A | N/A | 21434 | 21449 | TACTGAGAGGAAATGA | 64 | 2008 |
| 960015 | N/A | N/A | 22714 | 22729 | TGTAAAGATGTGAGTG | 78 | 2009 |
| 960025 | N/A | N/A | 22772 | 22787 | TCAAAGGACATGACAG | 80 | 2010 |
| 960037 | N/A | N/A | 22590 | 22605 | GAGCAACGAGGAAGGA | 68 | 2011 |

TABLE 33

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 98 | 702 |
| 959276 | 447 | 462 | 6021 | 6036 | CCTGTCGGAGGAACTT | 37 | 2012 |
| 959286 | 699 | 714 | 11917 | 11932 | TTGTTTTGGCATCAAT | 73 | 2013 |
| 959296 | 895 | 910 | 13631 | 13646 | AATGCATCCAAATATC | 0 | 2014 |
| 959306 | 1069 | 1084 | 16189 | 16204 | TGGTCTAGCAGCTCAT | 25 | 2015 |
| 959316 | 1221 | 1236 | 19061 | 19076 | TTACATAAGACATTAT | 35 | 2016 |
| 959326 | 1614 | 1629 | 25377 | 25392 | CTCAAGTGACTCACAG | 85 | 2017 |
| 959336 | 1650 | 1665 | 25413 | 25428 | TTTAGCACCTCTGAAA | 24 | 2018 |
| 959346 | 1834 | 1849 | 25597 | 25612 | TTTCCCAACCAGCTGA | 60 | 2019 |
| 959356 | 2096 | 2111 | 25859 | 25874 | TCATCTTTGCAGACCA | 90 | 2020 |
| 959366 | 2184 | 2199 | 25947 | 25962 | TTTAGTTAGGTGAAAA | 57 | 2021 |
| 959376 | 2262 | 2277 | 26025 | 26040 | TCACTGATTCACATAA | 86 | 2022 |
| 959386 | N/A | N/A | 4306 | 4321 | GAGAAACAAACCCTCC | 0 | 2023 |
| 959396 | N/A | N/A | 4738 | 4753 | GTGCAAATGATCATGT | 69 | 2024 |
| 959406 | N/A | N/A | 4771 | 4786 | AAGCTGACTTTTATTG | 57 | 2025 |
| 959416 | N/A | N/A | 5276 | 5291 | TCTTGGGATGCACAGG | 49 | 2026 |
| 959426 | N/A | N/A | 5397 | 5412 | CCTTAATGCTATCAGG | 0 | 2027 |
| 959436 | N/A | N/A | 5581 | 5596 | AATGCACAATGACATC | 69 | 2028 |
| 959446 | N/A | N/A | 5625 | 5640 | AATTCTACCTGTGTCT | 82 | 2029 |
| 959456 | N/A | N/A | 5652 | 5667 | TTTGGATATATTGGGC | 95 | 2030 |
| 959466 | N/A | N/A | 5802 | 5817 | CTACTATGGGAGCCAC | 64 | 2031 |
| 959476 | N/A | N/A | 5871 | 5886 | TAATACTTTTGGCAAG | 29 | 2032 |
| 959486 | N/A | N/A | 7784 | 7799 | TTATAGGCGAGAGCAC | 0 | 2033 |
| 959656 | N/A | N/A | 12147 | 12162 | CTGGTAGCTCCTGGCA | 44 | 2034 |

TABLE 33-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959666 | N/A | N/A | 12164 | 12179 | GATTGTGCAGACAGTA | 95 | 2035 |
| 959676 | N/A | N/A | 12202 | 12217 | ATTTCCGTTAACCATC | 93 | 2036 |
| 959686 | N/A | N/A | 12288 | 12303 | TGAGTTTTAGGTCTGG | 96 | 2037 |
| 959696 | N/A | N/A | 12669 | 12684 | ATCATCTTAGTGGCTG | 91 | 2038 |
| 959706 | N/A | N/A | 12696 | 12711 | TGTTCTTGACCGTGTT | 98 | 2039 |
| 959716 | N/A | N/A | 12719 | 12734 | AAGGTTAAACTACCGA | 6 | 2040 |
| 959726 | N/A | N/A | 12785 | 12800 | TACATGGTCTGCAAAT | 90 | 2041 |
| 959736 | N/A | N/A | 12838 | 12853 | CATTGCATTGCATAGC | 96 | 2042 |
| 959746 | N/A | N/A | 12888 | 12903 | AAAACCAATCCTGTTA | 47 | 2043 |
| 959756 | N/A | N/A | 12911 | 12926 | CATCTGCTTATAAAGC | 81 | 2044 |
| 959766 | N/A | N/A | 12967 | 12982 | AAACTTTGCAGCCTAT | 93 | 2045 |
| 959776 | N/A | N/A | 13376 | 13391 | AGACTTTGCAGGCACC | 90 | 2046 |
| 959786 | N/A | N/A | 13400 | 13415 | GGCTTGAATGTCACCC | 69 | 2047 |
| 959796 | N/A | N/A | 13697 | 13712 | AATGCTTGTCAAAAGG | 70 | 2048 |
| 959806 | N/A | N/A | 13717 | 13732 | CTTTACCAAGACCGCT | 82 | 2049 |
| 959816 | N/A | N/A | 13747 | 13762 | TAAGTGTTAGAACTAA | 30 | 2050 |
| 959826 | N/A | N/A | 14232 | 14247 | ACCAACTTTTAGTATT | 79 | 2051 |
| 959836 | N/A | N/A | 14419 | 14434 | CATCGACACAGCATCA | 59 | 2052 |
| 959846 | N/A | N/A | 14557 | 14572 | CCAAAGTCTTAATGTG | 53 | 2053 |
| 959856 | N/A | N/A | 14676 | 14691 | CCATCTCTTAGTGTCC | 88 | 2054 |
| 959866 | N/A | N/A | 15210 | 15225 | CTTAGGAATATTGCCA | 87 | 2055 |
| 959876 | N/A | N/A | 15770 | 15785 | AGGGTTAGTGTTGGTT | 89 | 2056 |
| 959886 | N/A | N/A | 17202 | 17217 | TCTGTTTGACTTAGTC | 70 | 2057 |
| 959896 | N/A | N/A | 17290 | 17305 | CTTAGGGCACCTCAAG | 30 | 2058 |
| 959906 | N/A | N/A | 17735 | 17750 | TAATCTGGTCATATGG | 43 | 2059 |
| 959916 | N/A | N/A | 18445 | 18460 | TGCTTACGGAGCATAG | 0 | 2060 |
| 959926 | N/A | N/A | 20472 | 20487 | CTCTAGACGGGAAGCT | 31 | 2061 |
| 959936 | N/A | N/A | 20601 | 20616 | GATCATCATTATTACC | 71 | 2062 |
| 959946 | N/A | N/A | 20652 | 20667 | TTGCAGTGCCCTGGCC | 31 | 2063 |
| 959956 | N/A | N/A | 20804 | 20819 | ATTCAGACCAGGGTAA | 87 | 2064 |
| 959966 | N/A | N/A | 20847 | 20862 | ATGCCTGTATTAGCTC | 65 | 2065 |
| 959976 | N/A | N/A | 20942 | 20957 | AGCCTCTTTGTAGCAG | 5 | 2066 |
| 959986 | N/A | N/A | 21008 | 21023 | GAGGTTATTTTAACAG | 69 | 2067 |
| 959996 | N/A | N/A | 21435 | 21450 | ATACTGAGAGGAAATG | 68 | 2068 |
| 960006 | N/A | N/A | 21539 | 21554 | ATGACATTTCAGAGTA | 88 | 2069 |
| 960016 | N/A | N/A | 22715 | 22730 | GTGTAAAGATGTGAGT | 84 | 2070 |

TABLE 33-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 960026 | N/A | N/A | 24033 | 24048 | TGCTGCACTCAAAGAG | 0 | 2071 |
| 960038 | N/A | N/A | 19377 | 19392 | TCACAAGAGACTGGAC | 31 | 2072 |

TABLE 34

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 98 | 702 |
| 959277 | 481 | 496 | 6055 | 6070 | TGGTGGACATTGGCCG | 5 | 2073 |
| 959287 | 707 | 722 | 11925 | 11940 | GGTGATGGTTGTTTTG | 85 | 2074 |
| 959297 | 896 | 911 | 13632 | 13647 | GAATGCATCCAAATAT | 0 | 2075 |
| 959307 | 1070 | 1085 | 16190 | 16205 | GTGGTCTAGCAGCTCA | 66 | 2076 |
| 959317 | 1223 | 1238 | 19063 | 19078 | CATTACATAAGACATT | 46 | 2077 |
| 959327 | 1615 | 1630 | 25378 | 25393 | CCTCAAGTGACTCACA | 83 | 2078 |
| 959337 | 1651 | 1666 | 25414 | 25429 | CTTTAGCACCTCTGAA | 71 | 2079 |
| 959347 | 1835 | 1850 | 25598 | 25613 | ATTTCCCAACCAGCTG | 49 | 2080 |
| 959357 | 2099 | 2114 | 25862 | 25877 | TTATCATCTTTGCAGA | 48 | 2081 |
| 959367 | 2185 | 2200 | 25948 | 25963 | TTTTAGTTAGGTGAAA | 43 | 2082 |
| 959377 | 2263 | 2278 | 26026 | 26041 | CTCACTGATTCACATA | 79 | 2083 |
| 959387 | N/A | N/A | 4307 | 4322 | TGAGAAACAAACCCTC | 0 | 2084 |
| 959397 | N/A | N/A | 4739 | 4754 | TGTGCAAATGATCATG | 82 | 2085 |
| 959407 | N/A | N/A | 4859 | 4874 | TAGGCTCCTGGGACCT | 0 | 2086 |
| 959417 | N/A | N/A | 5277 | 5292 | ATCTTGGGATGCACAG | 89 | 2087 |
| 959427 | N/A | N/A | 5567 | 5582 | TCATGGCTTCCAGTGT | 78 | 2088 |
| 959437 | N/A | N/A | 5600 | 5615 | TTCAATGTGGCTTCTA | 96 | 2089 |
| 959447 | N/A | N/A | 5627 | 5642 | TTAATTCTACCTGTGT | 72 | 2090 |
| 959457 | N/A | N/A | 5706 | 5721 | TGAAATATCTCATTAG | 77 | 2091 |
| 959467 | N/A | N/A | 5805 | 5820 | TGTCTACTATGGGAGC | 83 | 2092 |
| 959477 | N/A | N/A | 5875 | 5890 | ATGGTAATACTTTTGG | 75 | 2093 |
| 959657 | N/A | N/A | 12148 | 12163 | ACTGGTAGCTCCTGGC | 78 | 2094 |
| 959667 | N/A | N/A | 12165 | 12180 | TGATTGTGCAGACAGT | 97 | 2095 |
| 959677 | N/A | N/A | 12203 | 12218 | TATTTCCGTTAACCAT | 91 | 2096 |
| 959687 | N/A | N/A | 12289 | 12304 | CTGAGTTTTAGGTCTG | 96 | 2097 |
| 959697 | N/A | N/A | 12671 | 12686 | GAATCATCTTAGTGGC | 94 | 2098 |

TABLE 34-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959707 | N/A | N/A | 12697 | 12712 | TTGTTCTTGACCGTGT | 98 | 2099 |
| 959717 | N/A | N/A | 12753 | 12768 | GTGGTAAGGCATACTA | 35 | 2100 |
| 959727 | N/A | N/A | 12789 | 12804 | GGTGTACATGGTCTGC | 97 | 2101 |
| 959737 | N/A | N/A | 12839 | 12854 | GCATTGCATTGCATAG | 92 | 2102 |
| 959747 | N/A | N/A | 12890 | 12905 | GGAAAACCAATCCTGT | 69 | 2103 |
| 959757 | N/A | N/A | 12927 | 12942 | AGCTGTCTCCTCTACT | 70 | 2104 |
| 959767 | N/A | N/A | 12968 | 12983 | CAAACTTTGCAGCCTA | 95 | 2105 |
| 959777 | N/A | N/A | 13377 | 13392 | GAGACTTTGCAGGCAC | 88 | 2106 |
| 959787 | N/A | N/A | 13402 | 13417 | TCGGCTTGAATGTCAC | 67 | 2107 |
| 959797 | N/A | N/A | 13700 | 13715 | GTAAATGCTTGTCAAA | 91 | 2108 |
| 959807 | N/A | N/A | 13720 | 13735 | AGTCTTTACCAAGACC | 0 | 2109 |
| 959817 | N/A | N/A | 13911 | 13926 | CATGACATCCCAGTTC | 29 | 2110 |
| 959827 | N/A | N/A | 14233 | 14248 | AACCAACTTTTAGTAT | 27 | 2111 |
| 959837 | N/A | N/A | 14420 | 14435 | CCATCGACACAGCATC | 89 | 2112 |
| 959847 | N/A | N/A | 14567 | 14582 | CTACTTATCCCCAAAG | 16 | 2113 |
| 959857 | N/A | N/A | 14677 | 14692 | GCCATCTCTTAGTGTC | 36 | 2114 |
| 959867 | N/A | N/A | 15211 | 15226 | CCTTAGGAATATTGCC | 75 | 2115 |
| 959877 | N/A | N/A | 15771 | 15786 | GAGGGTTAGTGTTGGT | 93 | 2116 |
| 959887 | N/A | N/A | 17218 | 17233 | CTGGTTTGTGGGTTCT | 75 | 2117 |
| 959897 | N/A | N/A | 17291 | 17306 | TCTTAGGGCACCTCAA | 53 | 2118 |
| 959907 | N/A | N/A | 17736 | 17751 | TTAATCTGGTCATATG | 0 | 2119 |
| 959917 | N/A | N/A | 18852 | 18867 | ACAAAAGCGACAAGGT | 33 | 2120 |
| 959927 | N/A | N/A | 20508 | 20523 | TTGAGTCTCCTGACCA | 65 | 2121 |
| 959937 | N/A | N/A | 20602 | 20617 | CGATCATCATTATTAC | 87 | 2122 |
| 959947 | N/A | N/A | 20653 | 20668 | ATTGCAGTGCCCTGGC | 69 | 2123 |
| 959957 | N/A | N/A | 20805 | 20820 | TATTCAGACCAGGGTA | 89 | 2124 |
| 959967 | N/A | N/A | 20848 | 20863 | GATGCCTGTATTAGCT | 72 | 2125 |
| 959977 | N/A | N/A | 20944 | 20959 | GCAGCCTCTTTGTAGC | 0 | 2126 |
| 959987 | N/A | N/A | 21010 | 21025 | CTGAGGTTATTTTAAC | 40 | 2127 |
| 959997 | N/A | N/A | 21436 | 21451 | TATACTGAGAGGAAAT | 47 | 2128 |
| 960007 | N/A | N/A | 21541 | 21556 | ATATGACATTTCAGAG | 91 | 2129 |
| 960017 | N/A | N/A | 22716 | 22731 | CGTGTAAAGATGTGAG | 87 | 2130 |
| 960027 | N/A | N/A | 24035 | 24050 | AATGCTGCACTCAAAG | 31 | 2131 |
| 960039 | N/A | N/A | 20215 | 20230 | TAACAAACTATGCCTA | 44 | 2132 |

TABLE 35

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 98 | 702 |
| 959274 | 439 | 454 | 6013 | 6028 | AGGAACTTGCTTAAGT | 73 | 2133 |
| 959284 | 695 | 710 | 11913 | 11928 | TTTGGCATCAATGAAG | 60 | 1928 |
| 959294 | 817 | 832 | 12035 | 12050 | TAGAGGTTCCCTGTGC | 77 | 1929 |
| 959304 | 1063 | 1078 | 16183 | 16198 | AGCAGCTCATCTCCCT | 62 | 2134 |
| 959314 | 1091 | 1106 | 16211 | 16226 | GGGCAGGATGCTGAGA | 13 | 1930 |
| 959324 | 1606 | 1621 | 25369 | 25384 | ACTCACAGACTCTTCT | 72 | 1931 |
| 959334 | 1647 | 1662 | 25410 | 25425 | AGCACCTCTGAAAGAA | 65 | 1932 |
| 959344 | 1678 | 1693 | 25441 | 25456 | CGGAGGTAGCTGCACA | 86 | 1933 |
| 959354 | 1926 | 1941 | 25689 | 25704 | ATTCTAAGAACCTCAT | 54 | 1934 |
| 959364 | 2181 | 2196 | 25944 | 25959 | AGTTAGGTGAAAAAGG | 92 | 2135 |
| 959374 | 2260 | 2275 | 26023 | 26038 | ACTGATTCACATAATA | 78 | 2136 |
| 959384 | N/A | N/A | 4303 | 4318 | AAACAAACCCTCCGTC | 2 | 1935 |
| 959394 | N/A | N/A | 4734 | 4749 | AAATGATCATGTGGCG | 94 | 1936 |
| 959404 | N/A | N/A | 4768 | 4783 | CTGACTTTTATTGTTG | 72 | 1937 |
| 959414 | N/A | N/A | 4871 | 4886 | GTGAGTGTACTTTAGG | 97 | 1938 |
| 959424 | N/A | N/A | 5393 | 5408 | AATGCTATCAGGTGCA | 31 | 1939 |
| 959434 | N/A | N/A | 5579 | 5594 | TGCACAATGACATCAT | 87 | 1940 |
| 959444 | N/A | N/A | 5621 | 5636 | CTACCTGTGTCTTTTA | 90 | 1941 |
| 959454 | N/A | N/A | 5647 | 5662 | ATATATTGGGCTCAAT | 80 | 1942 |
| 959464 | N/A | N/A | 5799 | 5814 | CTATGGGAGCCACATG | 24 | 2137 |
| 959474 | N/A | N/A | 5867 | 5882 | ACTTTTGGCAAGGCCA | 23 | 1943 |
| 959484 | N/A | N/A | 7211 | 7226 | CCGCAAACAAGGTTAA | 0 | 1944 |
| 959664 | N/A | N/A | 12157 | 12172 | CAGACAGTAACTGGTA | 96 | 2138 |
| 959674 | N/A | N/A | 12200 | 12215 | TTCCGTTAACCATCAA | 97 | 2139 |
| 959684 | N/A | N/A | 12283 | 12298 | TTTAGGTCTGGGTATA | 93 | 1945 |
| 959694 | N/A | N/A | 12325 | 12340 | CCCCCTGACTATATAA | 26 | 1946 |
| 959704 | N/A | N/A | 12693 | 12708 | TCTTGACCGTGTTTCC | 98 | 1947 |
| 959714 | N/A | N/A | 12716 | 12731 | GTTAAACTACCGAACG | 35 | 2140 |
| 959724 | N/A | N/A | 12763 | 12778 | CTATGGTAGAGTGGTA | 93 | 2141 |
| 959734 | N/A | N/A | 12834 | 12849 | GCATTGCATAGCCTTC | 97 | 1948 |
| 959744 | N/A | N/A | 12886 | 12901 | AACCAATCCTGTTAGA | 55 | 1949 |
| 959754 | N/A | N/A | 12909 | 12924 | TCTGCTTATAAAGCAC | 0 | 1950 |
| 959764 | N/A | N/A | 12937 | 12952 | GGACAATAAGAGCTGT | 91 | 2142 |
| 959774 | N/A | N/A | 13373 | 13388 | CTTTGCAGGCACCCCA | 72 | 1951 |
| 959784 | N/A | N/A | 13398 | 13413 | CTTGAATGTCACCCTT | 92 | 1952 |

TABLE 35-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959794 | N/A | N/A | 13532 | 13547 | AGCATCATTGGAAGAC | 92 | 2143 |
| 959804 | N/A | N/A | 13715 | 13730 | TTACCAAGACCGCTAG | 57 | 1953 |
| 959814 | N/A | N/A | 13744 | 13759 | GTGTTAGAACTAAGGC | 94 | 2144 |
| 959824 | N/A | N/A | 14228 | 14243 | ACTTTTAGTATTAAAG | 0 | 1954 |
| 959834 | N/A | N/A | 14306 | 14321 | TTTCTGAGCAGATAAA | 66 | 2145 |
| 959844 | N/A | N/A | 14555 | 14570 | AAAGTCTTAATGTGGA | 87 | 1955 |
| 959854 | N/A | N/A | 14670 | 14685 | CTTAGTGTCCCCATCC | 77 | 1956 |
| 959864 | N/A | N/A | 15208 | 15223 | TAGGAATATTGCCAGG | 89 | 2146 |
| 959874 | N/A | N/A | 15767 | 15782 | GTTAGTGTTGGTTTAT | 94 | 1957 |
| 959884 | N/A | N/A | 17199 | 17214 | GTTTGACTTAGTCCGT | 95 | 1958 |
| 959894 | N/A | N/A | 17228 | 17243 | AACTCTGTAGCTGGTT | 41 | 2147 |
| 959904 | N/A | N/A | 17603 | 17618 | TCTTGATAGTGAATGT | 73 | 2148 |
| 959914 | N/A | N/A | 18398 | 18413 | AATATGTTTGGAAGTC | 89 | 1959 |
| 959924 | N/A | N/A | 20292 | 20307 | CCAATCAGAGGAAGCC | 58 | 2149 |
| 959934 | N/A | N/A | 20518 | 20533 | AGTAACCAGATTGAGT | 81 | 1960 |
| 959944 | N/A | N/A | 20617 | 20632 | CTGTCTCTAATTTTAC | 75 | 2150 |
| 959954 | N/A | N/A | 20665 | 20680 | CACAGCTTAGAAATTG | 87 | 1961 |
| 959964 | N/A | N/A | 20844 | 20859 | CCTGTATTAGCTCAAT | 92 | 1962 |
| 959974 | N/A | N/A | 20940 | 20955 | CCTCTTTGTAGCAGAC | 83 | 1963 |
| 959984 | N/A | N/A | 21006 | 21021 | GGTTATTTTAACAGCT | 85 | 1964 |
| 959994 | N/A | N/A | 21412 | 21427 | ACCTGCAATTCTAGAC | 54 | 1965 |
| 960004 | N/A | N/A | 21537 | 21552 | GACATTTCAGAGTATA | 93 | 2151 |
| 960014 | N/A | N/A | 22710 | 22725 | AAGATGTGAGTGAAAT | 69 | 1966 |
| 960024 | N/A | N/A | 22770 | 22785 | AAAGGACATGACAGAC | 75 | 1967 |
| 960034 | N/A | N/A | 24613 | 24628 | GCAAATCGGATCTTTG | 32 | 2152 |

TABLE 36

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 915609 | 705 | 720 | 11923 | 11938 | TGATGGTTGTTTTGGC | 98 | 702 |
| 959275 | 440 | 455 | 6014 | 6029 | GAGGAACTTGCTTAAG | 80 | 1968 |
| 959285 | 696 | 711 | 11914 | 11929 | TTTTGGCATCAATGAA | 63 | 1969 |
| 959295 | 823 | 838 | 12041 | 12056 | AGAAGGTAGAGGTTCC | 48 | 2153 |
| 959305 | 1066 | 1081 | 16186 | 16201 | TCTAGCAGCTCATCTC | 66 | 1970 |

TABLE 36-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959315 | 1093 | 1108 | 16213 | 16228 | CAGGGCAGGATGCTGA | 2 | 2154 |
| 959325 | 1608 | 1623 | 25371 | 25386 | TGACTCACAGACTCTT | 60 | 2155 |
| 959335 | 1649 | 1664 | 25412 | 25427 | TTAGCACCTCTGAAAG | 54 | 1971 |
| 959345 | 1804 | 1819 | 25567 | 25582 | ATGTATTAGAGTTAAG | 79 | 1972 |
| 959355 | 1927 | 1942 | 25690 | 25705 | CATTCTAAGAACCTCA | 68 | 1973 |
| 959365 | 2183 | 2198 | 25946 | 25961 | TTAGTTAGGTGAAAAA | 69 | 1974 |
| 959375 | 2261 | 2276 | 26024 | 26039 | CACTGATTCACATAAT | 73 | 1975 |
| 959385 | N/A | N/A | 4305 | 4320 | AGAAACAAACCCTCCG | 70 | 2156 |
| 959395 | N/A | N/A | 4737 | 4752 | TGCAAATGATCATGTG | 69 | 1976 |
| 959405 | N/A | N/A | 4769 | 4784 | GCTGACTTTTATTGTT | 83 | 1977 |
| 959415 | N/A | N/A | 4872 | 4887 | AGTGAGTGTACTTTAG | 94 | 1978 |
| 959425 | N/A | N/A | 5395 | 5410 | TTAATGCTATCAGGTG | 82 | 1979 |
| 959435 | N/A | N/A | 5580 | 5595 | ATGCACAATGACATCA | 84 | 1980 |
| 959445 | N/A | N/A | 5624 | 5639 | ATTCTACCTGTGTCTT | 95 | 1981 |
| 959455 | N/A | N/A | 5651 | 5666 | TTGGATATATTGGGCT | 97 | 1982 |
| 959465 | N/A | N/A | 5800 | 5815 | ACTATGGGAGCCACAT | 26 | 2157 |
| 959475 | N/A | N/A | 5868 | 5883 | TACTTTTGGCAAGGCC | 69 | 1983 |
| 959485 | N/A | N/A | 7697 | 7712 | GCACAGAGTAGGTTAA | 70 | 1984 |
| 959655 | N/A | N/A | 12146 | 12161 | TGGTAGCTCCTGGCAA | 50 | 1985 |
| 959665 | N/A | N/A | 12162 | 12177 | TTGTGCAGACAGTAAC | 87 | 2158 |
| 959675 | N/A | N/A | 12201 | 12216 | TTTCCGTTAACCATCA | 95 | 1986 |
| 959685 | N/A | N/A | 12284 | 12299 | TTTTAGGTCTGGGTAT | 81 | 2159 |
| 959695 | N/A | N/A | 12667 | 12682 | CATCTTAGTGGCTGGG | 91 | 1987 |
| 959705 | N/A | N/A | 12695 | 12710 | GTTCTTGACCGTGTTT | 97 | 1988 |
| 959715 | N/A | N/A | 12717 | 12732 | GGTTAAACTACCGAAC | 26 | 1989 |
| 959725 | N/A | N/A | 12783 | 12798 | CATGGTCTGCAAATTT | 89 | 1990 |
| 959735 | N/A | N/A | 12837 | 12852 | ATTGCATTGCATAGCC | 95 | 2160 |
| 959745 | N/A | N/A | 12887 | 12902 | AAACCAATCCTGTTAG | 54 | 1991 |
| 959755 | N/A | N/A | 12910 | 12925 | ATCTGCTTATAAAGCA | 43 | 1992 |
| 959765 | N/A | N/A | 12964 | 12979 | CTTTGCAGCCTATCCC | 95 | 2161 |
| 959775 | N/A | N/A | 13374 | 13389 | ACTTTGCAGGCACCCC | 86 | 1993 |
| 959785 | N/A | N/A | 13399 | 13414 | GCTTGAATGTCACCCT | 95 | 1994 |
| 959795 | N/A | N/A | 13534 | 13549 | TCAGCATCATTGGAAG | 60 | 2162 |
| 959805 | N/A | N/A | 13716 | 13731 | TTTACCAAGACCGCTA | 82 | 1995 |
| 959815 | N/A | N/A | 13745 | 13760 | AGTGTTAGAACTAAGG | 93 | 2163 |
| 959825 | N/A | N/A | 14230 | 14245 | CAACTTTTAGTATTAA | 9 | 1996 |

TABLE 36-continued

Inhibition of PNPLA3 mRNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | PNPLA3 % Inhibition | SEQ ID NO |
|---|---|---|---|---|---|---|---|
| 959835 | N/A | N/A | 14417 | 14432 | TCGACACAGCATCACC | 59 | 1997 |
| 959845 | N/A | N/A | 14556 | 14571 | CAAAGTCTTAATGTGG | 84 | 2164 |
| 959855 | N/A | N/A | 14671 | 14686 | TCTTAGTGTCCCCATC | 78 | 1998 |
| 959865 | N/A | N/A | 15209 | 15224 | TTAGGAATATTGCCAG | 91 | 1999 |
| 959875 | N/A | N/A | 15769 | 15784 | GGGTTAGTGTTGGTTT | 93 | 2000 |
| 959885 | N/A | N/A | 17200 | 17215 | TGTTTGACTTAGTCCG | 96 | 2165 |
| 959895 | N/A | N/A | 17288 | 17303 | TAGGGCACCTCAAGAA | 0 | 2001 |
| 959905 | N/A | N/A | 17734 | 17749 | AATCTGGTCATATGGT | 42 | 2166 |
| 959915 | N/A | N/A | 18400 | 18415 | CAAATATGTTTGGAAG | 55 | 2002 |
| 959925 | N/A | N/A | 20293 | 20308 | CCCAATCAGAGGAAGC | 57 | 2003 |
| 959935 | N/A | N/A | 20599 | 20614 | TCATCATTATTACCTG | 93 | 2004 |
| 959945 | N/A | N/A | 20651 | 20666 | TGCAGTGCCCTGGCCT | 40 | 2167 |
| 959955 | N/A | N/A | 20803 | 20818 | TTCAGACCAGGGTAAT | 93 | 2005 |
| 959965 | N/A | N/A | 20845 | 20860 | GCCTGTATTAGCTCAA | 88 | 2006 |
| 959975 | N/A | N/A | 20941 | 20956 | GCCTCTTTGTAGCAGA | 0 | 2007 |
| 959985 | N/A | N/A | 21007 | 21022 | AGGTTATTTTAACAGC | 94 | 2168 |
| 959995 | N/A | N/A | 21434 | 21449 | TACTGAGAGGAAATGA | 65 | 2008 |
| 960005 | N/A | N/A | 21538 | 21553 | TGACATTTCAGAGTAT | 87 | 2169 |
| 960015 | N/A | N/A | 22714 | 22729 | TGTAAAGATGTGAGTG | 75 | 2009 |
| 960025 | N/A | N/A | 22772 | 22787 | TCAAAGGACATGACAG | 78 | 2010 |
| 960037 | N/A | N/A | 22590 | 22605 | GAGCAACGAGGAAGGA | 64 | 2011 |

Example 2: Dose-Dependent Antisense Inhibition of Human PNPLA3 in A431 Cells

Gapmers from Example 1 exhibiting significant in vitro inhibition of PNPLA3 mRNA were selected and tested at various doses in A431 cells. The antisense oligonucleotides were tested in a series of experiments that had similar culture conditions. The results for each experiment are presented in separate tables shown below. Cells were plated at a density of 10,000 cells per well and transfected free uptake with different concentrations of antisense oligonucleotide, as specified in the Tables below. After a treatment period of approximately 16 hours, RNA was isolated from the cells and PNPLA3 mRNA levels were measured by quantitative real-time PCR. Human primer probe set RTS36070 was used to measure mRNA levels. PNPLA3 mRNA levels were adjusted according to total RNA content, as measured by RIBOGREEN®. Results are presented as percent inhibition of PNPLA3, relative to untreated control cells.

The half maximal inhibitory concentration ($IC_{50}$) of each oligonucleotide is also presented. PNPLA3 mRNA levels were significantly reduced in a dose-dependent manner in antisense oligonucleotide treated cells.

TABLE 37

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | $IC_{50}$ (µM) |
| 912712 | 27 | 67 | 76 | 74 | 0.2 |
| 912732 | 54 | 78 | 88 | 87 | <0.1 |
| 912733 | 45 | 74 | 85 | 88 | <0.1 |
| 912734 | 33 | 64 | 80 | 83 | 0.1 |
| 912756 | 46 | 72 | 89 | 92 | <0.1 |
| 912757 | 31 | 62 | 78 | 86 | 0.2 |
| 912758 | 38 | 70 | 85 | 90 | 0.1 |
| 912759 | 66 | 92 | 97 | 98 | <0.1 |
| 912772 | 46 | 63 | 79 | 88 | 0.1 |
| 912795 | 40 | 64 | 83 | 84 | 0.1 |
| 912812 | 43 | 81 | 88 | 88 | <0.1 |
| 912822 | 81 | 83 | 92 | 86 | <0.1 |
| 912823 | 67 | 80 | 91 | 86 | <0.1 |
| 912825 | 58 | 80 | 86 | 88 | <0.1 |
| 912834 | 37 | 75 | 81 | 84 | 0.1 |
| 912841 | 17 | 62 | 79 | 69 | 0.3 |
| 912847 | 70 | 83 | 90 | 91 | <0.1 |

TABLE 37-continued

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | IC$_{50}$ (μM) |
| 912848 | 80 | 89 | 90 | 90 | <0.1 |
| 912855 | 48 | 62 | 77 | 80 | 0.1 |

TABLE 38

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | IC$_{50}$ (μM) |
| 912759 | 68 | 94 | 94 | 98 | <0.1 |
| 912813 | 57 | 84 | 90 | 87 | <0.1 |
| 912856 | 60 | 81 | 91 | 88 | <0.1 |
| 912859 | 48 | 79 | 81 | 72 | <0.1 |
| 912864 | 60 | 88 | 90 | 90 | <0.1 |
| 912870 | 67 | 81 | 91 | 94 | <0.1 |
| 912871 | 21 | 67 | 84 | 89 | 0.2 |
| 912872 | 18 | 73 | 90 | 92 | 0.2 |
| 912876 | 43 | 70 | 87 | 92 | 0.1 |
| 912933 | 68 | 89 | 90 | 90 | <0.1 |
| 912940 | 86 | 91 | 95 | 96 | <0.1 |
| 912941 | 87 | 94 | 96 | 96 | <0.1 |
| 912952 | 68 | 85 | 90 | 91 | <0.1 |
| 912953 | 80 | 90 | 95 | 93 | <0.1 |
| 912964 | 59 | 78 | 88 | 91 | <0.1 |
| 912973 | 53 | 70 | 87 | 91 | <0.1 |
| 912980 | 54 | 77 | 84 | 88 | <0.1 |
| 912985 | 23 | 61 | 81 | 87 | 0.2 |
| 912988 | 65 | 83 | 86 | 89 | <0.1 |

TABLE 39

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | IC$_{50}$ (μM) |
| 912759 | 72 | 95 | 97 | 99 | <0.1 |
| 912874 | 78 | 90 | 96 | 97 | <0.1 |
| 912875 | 64 | 83 | 92 | 94 | <0.1 |
| 912886 | 49 | 78 | 85 | 92 | <0.1 |
| 912931 | 68 | 88 | 94 | 95 | <0.1 |
| 912934 | 57 | 83 | 90 | 92 | <0.1 |
| 912936 | 50 | 78 | 89 | 89 | <0.1 |
| 912938 | 57 | 73 | 85 | 87 | <0.1 |
| 912943 | 64 | 84 | 90 | 93 | <0.1 |
| 912954 | 80 | 92 | 93 | 94 | <0.1 |
| 912970 | 44 | 73 | 86 | 90 | <0.1 |
| 912986 | 56 | 78 | 91 | 92 | <0.1 |
| 912987 | 79 | 90 | 92 | 88 | <0.1 |
| 912992 | 21 | 59 | 74 | 81 | 0.3 |
| 915603 | 50 | 88 | 96 | 98 | <0.1 |
| 915623 | 81 | 96 | 98 | 98 | <0.1 |
| 915643 | 67 | 89 | 94 | 96 | <0.1 |
| 916602 | 79 | 92 | 95 | 96 | <0.1 |
| 916642 | 44 | 83 | 91 | 93 | <0.1 |

TABLE 40

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | IC$_{50}$ (μM) |
| 912759 | 73 | 94 | 98 | 99 | <0.1 |
| 915484 | 67 | 87 | 93 | 95 | <0.1 |
| 915543 | 34 | 69 | 87 | 90 | 0.1 |
| 915604 | 54 | 78 | 91 | 95 | <0.1 |
| 915763 | 63 | 80 | 87 | 87 | <0.1 |
| 915904 | 50 | 83 | 92 | 94 | <0.1 |
| 915923 | 63 | 74 | 82 | 87 | <0.1 |
| 916183 | 33 | 78 | 89 | 91 | 0.1 |
| 916303 | 58 | 73 | 84 | 91 | <0.1 |
| 916343 | 15 | 72 | 76 | 87 | 0.2 |
| 916563 | 46 | 74 | 90 | 95 | <0.1 |
| 916582 | 48 | 74 | 89 | 91 | <0.1 |
| 916623 | 64 | 81 | 91 | 94 | <0.1 |
| 916702 | 45 | 70 | 78 | 79 | <0.1 |
| 916761 | 46 | 75 | 85 | 88 | <0.1 |
| 916781 | 55 | 79 | 86 | 87 | <0.1 |
| 916782 | 62 | 87 | 91 | 93 | <0.1 |
| 916802 | 66 | 88 | 94 | 91 | <0.1 |
| 916822 | 29 | 72 | 83 | 87 | 0.1 |

TABLE 41

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | IC$_{50}$ (μM) |
| 912759 | 72 | 95 | 98 | 99 | <0.1 |
| 915525 | 51 | 76 | 88 | 84 | <0.1 |
| 915546 | 39 | 79 | 90 | 94 | 0.1 |
| 915605 | 59 | 84 | 96 | 96 | <0.1 |
| 915606 | 74 | 94 | 99 | 98 | <0.1 |
| 915625 | 72 | 82 | 91 | 95 | <0.1 |
| 915944 | 36 | 71 | 75 | 83 | 0.1 |
| 916065 | 36 | 62 | 78 | 79 | 0.1 |
| 916144 | 71 | 86 | 90 | 92 | <0.1 |
| 916163 | 36 | 67 | 81 | 74 | 0.1 |
| 916164 | 82 | 88 | 89 | 92 | <0.1 |
| 916184 | 60 | 79 | 87 | 89 | <0.1 |
| 916304 | 46 | 65 | 80 | 84 | 0.1 |
| 916324 | 57 | 77 | 87 | 92 | <0.1 |
| 916344 | 41 | 70 | 83 | 88 | 0.1 |
| 916564 | 38 | 66 | 88 | 94 | 0.1 |
| 916604 | 67 | 87 | 95 | 96 | <0.1 |
| 916624 | 43 | 59 | 79 | 87 | 0.1 |
| 916803 | 67 | 84 | 93 | 92 | <0.1 |

TABLE 42

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | IC$_{50}$ (μM) |
| 912759 | 70 | 94 | 98 | 99 | <0.1 |
| 915486 | 35 | 64 | 82 | 90 | 0.1 |
| 915487 | 62 | 89 | 94 | 95 | <0.1 |
| 915626 | 67 | 83 | 92 | 94 | <0.1 |
| 915786 | 65 | 84 | 88 | 88 | <0.1 |
| 916145 | 53 | 66 | 85 | 87 | <0.1 |
| 916146 | 62 | 77 | 86 | 86 | <0.1 |
| 916165 | 71 | 86 | 89 | 88 | <0.1 |
| 916166 | 71 | 83 | 87 | 88 | <0.1 |
| 916305 | 57 | 86 | 90 | 92 | <0.1 |

TABLE 42-continued

Multi-dose assay of 3-10-3 cEt gapmers in A431 cells

| Compound Number | PNPLA3 % Inhibition | | | | IC$_{50}$ (μM) |
|---|---|---|---|---|---|
| | 62.5 nM | 250 nM | 1,000 nM | 4,000 nM | |
| 916306 | 86 | 96 | 98 | 98 | <0.1 |
| 916325 | 59 | 78 | 83 | 86 | <0.1 |
| 916345 | 21 | 47 | 67 | 73 | 0.4 |
| 916545 | 63 | 88 | 95 | 94 | <0.1 |
| 916546 | 66 | 85 | 92 | 95 | <0.1 |
| 916625 | 47 | 71 | 84 | 92 | <0.1 |
| 916706 | 22 | 65 | 80 | 85 | 0.2 |
| 916765 | 67 | 85 | 92 | 93 | <0.1 |
| 916845 | 38 | 71 | 80 | 87 | 0.1 |

TABLE 43

Multi-dose assay of 3-10-3 cEt gapmers in A431 cells

| Compound Number | PNPLA3 % Inhibition | | | | IC$_{50}$ (μM) |
|---|---|---|---|---|---|
| | 62.5 nM | 250 nM | 1,000 nM | 4,000 nM | |
| 912759 | 97 | 99 | 100 | 100 | <0.1 |
| 915608 | 66 | 91 | 97 | 97 | <0.1 |
| 915609 | 71 | 97 | 99 | 99 | <0.1 |
| 915627 | 0 | 26 | 53 | 62 | 1.3 |
| 915768 | 39 | 69 | 86 | 91 | 0.1 |
| 915908 | 49 | 70 | 80 | 85 | <0.1 |
| 915987 | 47 | 60 | 75 | 78 | 0.1 |
| 916008 | 45 | 69 | 84 | 83 | <0.1 |
| 916187 | 71 | 82 | 88 | 92 | <0.1 |
| 916247 | 34 | 72 | 83 | 84 | 0.1 |
| 916287 | 31 | 70 | 90 | 91 | 0.1 |
| 916547 | 79 | 93 | 97 | 97 | <0.1 |
| 916566 | 8 | 45 | 73 | 81 | 0.5 |
| 916586 | 47 | 67 | 89 | 91 | <0.1 |
| 916587 | 48 | 81 | 90 | 94 | <0.1 |
| 916606 | 18 | 64 | 87 | 90 | 0.2 |
| 916607 | 72 | 94 | 94 | 95 | <0.1 |
| 916627 | 18 | 51 | 82 | 79 | 0.3 |
| 916805 | 18 | 65 | 78 | 81 | 0.2 |

TABLE 44

Multi-dose assay of 3-10-3 cEt gapmers in A431 cells

| Compound Number | PNPLA3 % Inhibition | | | | IC$_{50}$ (μM) |
|---|---|---|---|---|---|
| | 62.5 nM | 250 nM | 1,000 nM | 4,000 nM | |
| 912759 | 64 | 92 | 97 | 99 | <0.1 |
| 915610 | 74 | 94 | 98 | 99 | <0.1 |
| 915789 | 35 | 72 | 82 | 85 | 0.1 |
| 915909 | 52 | 69 | 82 | 86 | <0.1 |
| 915929 | 13 | 32 | 60 | 59 | 1.0 |
| 915969 | 39 | 54 | 74 | 74 | 0.2 |
| 915989 | 46 | 67 | 81 | 86 | 0.1 |
| 916069 | 24 | 59 | 75 | 56 | 0.3 |
| 916148 | 42 | 71 | 85 | 80 | <0.1 |
| 916168 | 28 | 54 | 74 | 68 | 0.3 |
| 916188 | 22 | 42 | 72 | 70 | 0.4 |
| 916309 | 30 | 77 | 91 | 96 | 0.1 |
| 916348 | 41 | 57 | 65 | 73 | 0.1 |
| 916549 | 64 | 85 | 94 | 96 | <0.1 |
| 916568 | 54 | 66 | 81 | 87 | <0.1 |
| 916569 | 60 | 86 | 92 | 95 | <0.1 |
| 916728 | 22 | 50 | 68 | 73 | 0.4 |
| 916788 | 60 | 89 | 94 | 96 | <0.1 |
| 916848 | 49 | 75 | 89 | 95 | <0.1 |

TABLE 45

Multi-dose assay of 3-10-3 cEt gapmers in A431 cells

| Compound Number | PNPLA3 % Inhibition | | | | IC$_{50}$ (μM) |
|---|---|---|---|---|---|
| | 62.5 nM | 250 nM | 1,000 nM | 4,000 nM | |
| 912759 | 81 | 93 | 98 | 100 | <0.1 |
| 915390 | 9 | 40 | 67 | 77 | 0.6 |
| 915611 | 46 | 80 | 93 | 88 | <0.1 |
| 915630 | 52 | 69 | 81 | 82 | <0.1 |
| 915910 | 44 | 64 | 79 | 80 | 0.1 |
| 915931 | 83 | 88 | 89 | 86 | <0.1 |
| 916149 | 73 | 87 | 89 | 83 | <0.1 |
| 916150 | 51 | 68 | 77 | 84 | <0.1 |
| 916189 | 60 | 73 | 77 | 79 | <0.1 |
| 916310 | 45 | 77 | 88 | 95 | <0.1 |
| 916330 | 48 | 67 | 84 | 86 | <0.1 |
| 916550 | 62 | 85 | 94 | 97 | <0.1 |
| 916570 | 89 | 96 | 98 | 98 | <0.1 |
| 916629 | 26 | 53 | 73 | 86 | 0.3 |
| 916630 | 52 | 68 | 87 | 91 | <0.1 |
| 916670 | 43 | 77 | 78 | 85 | <0.1 |
| 916730 | 61 | 74 | 82 | 86 | <0.1 |
| 916768 | 35 | 57 | 67 | 72 | 0.2 |
| 916789 | 79 | 92 | 96 | 96 | <0.1 |

TABLE 46

Multi-dose assay of 3-10-3 cEt gapmers in A431 cells

| Compound Number | PNPLA3 % Inhibition | | | | IC$_{50}$ (μM) |
|---|---|---|---|---|---|
| | 62.5 nM | 250 nM | 1,000 nM | 4,000 nM | |
| 912759 | 76 | 94 | 96 | 99 | <0.1 |
| 915532 | 31 | 66 | 82 | 92 | 0.1 |
| 915612 | 54 | 77 | 86 | 90 | <0.1 |
| 915732 | 42 | 63 | 80 | 84 | 0.1 |
| 915932 | 45 | 71 | 88 | 89 | <0.1 |
| 915951 | 26 | 58 | 71 | 74 | 0.3 |
| 915991 | 67 | 84 | 85 | 85 | <0.1 |
| 915992 | 54 | 78 | 86 | 87 | <0.1 |
| 916112 | 35 | 67 | 76 | 78 | 0.1 |
| 916151 | 51 | 79 | 87 | 90 | <0.1 |
| 916311 | 36 | 70 | 81 | 87 | 0.1 |
| 916331 | 56 | 85 | 93 | 95 | <0.1 |
| 916332 | 82 | 91 | 94 | 96 | <0.1 |
| 916390 | 30 | 41 | 68 | 64 | 0.5 |
| 916552 | 79 | 93 | 96 | 97 | <0.1 |
| 916571 | 53 | 78 | 90 | 94 | <0.1 |
| 916631 | 48 | 77 | 86 | 90 | <0.1 |
| 916651 | 81 | 89 | 94 | 95 | <0.1 |
| 916711 | 37 | 66 | 85 | 91 | 0.1 |

TABLE 47

Multi-dose assay of 3-10-3 cEt gapmers in A431 cells

| Compound Number | PNPLA3 % Inhibition | | | | IC$_{50}$ (μM) |
|---|---|---|---|---|---|
| | 62.5 nM | 250 nM | 1,000 nM | 4,000 nM | |
| 912759 | 58 | 90 | 98 | 99 | <0.1 |
| 915474 | 51 | 79 | 90 | 93 | <0.1 |
| 915493 | 48 | 58 | 83 | 80 | 0.1 |
| 915494 | 46 | 73 | 86 | 90 | <0.1 |
| 915674 | 49 | 72 | 89 | 93 | <0.1 |
| 915933 | 40 | 63 | 75 | 79 | 0.1 |
| 916153 | 68 | 86 | 89 | 91 | <0.1 |
| 916172 | 85 | 89 | 87 | 87 | <0.1 |
| 916173 | 81 | 90 | 91 | 88 | <0.1 |
| 916292 | 64 | 83 | 92 | 92 | <0.1 |

TABLE 47-continued

Multi-dose assay of 3-10-3 cEt gapmers in A431 cells

| Compound Number | PNPLA3 % Inhibition | | | | $IC_{50}$ ($\mu$M) |
|---|---|---|---|---|---|
| | 62.5 nM | 250 nM | 1,000 nM | 4,000 nM | |
| 916312 | 60 | 84 | 91 | 92 | <0.1 |
| 916333 | 75 | 92 | 96 | 96 | <0.1 |
| 916572 | 29 | 62 | 79 | 88 | 0.2 |
| 916592 | 52 | 74 | 89 | 90 | <0.1 |
| 916593 | 25 | 67 | 83 | 93 | 0.2 |
| 916613 | 46 | 75 | 89 | 92 | <0.1 |
| 916652 | 65 | 83 | 91 | 88 | <0.1 |
| 916672 | 73 | 89 | 93 | 90 | <0.1 |
| 916772 | 50 | 61 | 83 | 89 | <0.1 |

TABLE 48

Multi-dose assay of 3-10-3 cEt gapmers in A431 cells

| Compound Number | PNPLA3 % Inhibition | | | | $IC_{50}$ ($\mu$M) |
|---|---|---|---|---|---|
| | 62.5 nM | 250 nM | 1,000 nM | 4,000 nM | |
| 912759 | 50 | 89 | 96 | 99 | <0.1 |
| 915534 | 0 | 33 | 66 | 57 | 1.1 |
| 915535 | 51 | 81 | 92 | 96 | <0.1 |
| 915634 | 18 | 67 | 79 | 84 | 0.2 |
| 915635 | 44 | 72 | 86 | 91 | 0.1 |
| 915675 | 36 | 68 | 82 | 90 | 0.1 |
| 915735 | 45 | 68 | 73 | 84 | 0.1 |
| 915936 | 36 | 67 | 78 | 83 | 0.1 |
| 915995 | 78 | 87 | 90 | 89 | <0.1 |
| 915996 | 83 | 91 | 93 | 92 | <0.1 |
| 916174 | 80 | 84 | 86 | 81 | <0.1 |
| 916175 | 55 | 82 | 86 | 89 | <0.1 |
| 916334 | 50 | 82 | 92 | 94 | <0.1 |
| 916335 | 52 | 76 | 89 | 93 | <0.1 |
| 916575 | 62 | 88 | 93 | 93 | <0.1 |
| 916753 | 49 | 69 | 76 | 74 | <0.1 |
| 916774 | 49 | 72 | 86 | 91 | <0.1 |
| 916794 | 26 | 64 | 85 | 85 | 0.2 |
| 916873 | 16 | 49 | 72 | 82 | 0.4 |

TABLE 49

Multi-dose assay of 3-10-3 cEt gapmers in A431 cells

| Compound Number | PNPLA3 % Inhibition | | | | $IC_{50}$ ($\mu$M) |
|---|---|---|---|---|---|
| | 62.5 nM | 250 nM | 1,000 nM | 4,000 nM | |
| 912759 | 57 | 90 | 97 | 99 | <0.1 |
| 915477 | 47 | 65 | 88 | 93 | 0.1 |
| 915478 | 47 | 78 | 90 | 95 | <0.1 |
| 915497 | 63 | 68 | 79 | 86 | <0.1 |
| 915637 | 67 | 91 | 97 | 98 | <0.1 |
| 916037 | 15 | 47 | 70 | 61 | 0.6 |
| 916236 | 80 | 87 | 90 | 88 | <0.1 |
| 916336 | 52 | 67 | 81 | 87 | <0.1 |
| 916576 | 50 | 76 | 89 | 93 | <0.1 |
| 916596 | 55 | 82 | 93 | 94 | <0.1 |
| 916636 | 42 | 71 | 87 | 90 | 0.1 |
| 916637 | 56 | 85 | 90 | 93 | <0.1 |
| 916715 | 27 | 38 | 68 | 68 | 0.5 |
| 916716 | 35 | 77 | 89 | 93 | 0.1 |
| 916796 | 14 | 62 | 84 | 89 | 0.3 |
| 916814 | 22 | 44 | 70 | 79 | 0.4 |
| 916815 | 56 | 79 | 87 | 89 | <0.1 |
| 916816 | 33 | 72 | 83 | 93 | 0.1 |
| 916874 | 5 | 34 | 61 | 70 | 0.8 |

TABLE 50

Multi-dose assay of 3-10-3 cEt gapmers in A431 cells

| Compound Number | PNPLA3 % Inhibition | | | | $IC_{50}$ ($\mu$M) |
|---|---|---|---|---|---|
| | 62.5 nM | 250 nM | 1,000 nM | 4,000 nM | |
| 912759 | 56 | 91 | 97 | 100 | <0.1 |
| 915479 | 38 | 70 | 89 | 94 | 0.1 |
| 915618 | 42 | 63 | 75 | 85 | 0.1 |
| 915619 | 65 | 87 | 96 | 97 | <0.1 |
| 915638 | 31 | 64 | 80 | 82 | 0.2 |
| 915639 | 33 | 78 | 88 | 93 | 0.1 |
| 915778 | 41 | 50 | 78 | 87 | 0.2 |
| 916058 | 26 | 34 | 73 | 81 | 0.4 |
| 916177 | 38 | 55 | 83 | 82 | 0.1 |
| 916238 | 84 | 91 | 93 | 93 | <0.1 |
| 916298 | 79 | 87 | 92 | 94 | <0.1 |
| 916318 | 59 | 71 | 91 | 94 | <0.1 |
| 916338 | 71 | 91 | 94 | 92 | <0.1 |
| 916558 | 73 | 89 | 94 | 94 | <0.1 |
| 916577 | 41 | 66 | 78 | 82 | 0.1 |
| 916578 | 69 | 85 | 91 | 93 | <0.1 |
| 916638 | 46 | 84 | 90 | 92 | <0.1 |
| 916757 | 33 | 60 | 82 | 88 | 0.2 |
| 916817 | 31 | 67 | 82 | 87 | 0.1 |

TABLE 51

Multi-dose assay of 3-10-3 cEt gapmers in A431 cells

| Compound Number | PNPLA3 % Inhibition | | | | $IC_{50}$ ($\mu$M) |
|---|---|---|---|---|---|
| | 62.5 nM | 250 nM | 1,000 nM | 4,000 nM | |
| 841947 | 50 | 78 | 89 | 92 | <0.1 |
| 912759 | 75 | 50 | 85 | 99 | <0.1 |
| 912986 | 54 | 78 | 90 | 95 | <0.1 |
| 915480 | 61 | 87 | 94 | 97 | <0.1 |
| 915519 | 47 | 77 | 86 | 85 | <0.1 |
| 915620 | 46 | 75 | 88 | 91 | <0.1 |
| 915780 | 24 | 76 | 92 | 94 | 0.1 |
| 915920 | 23 | 65 | 79 | 82 | 0.2 |
| 916020 | 45 | 80 | 85 | 81 | <0.1 |
| 916299 | 59 | 87 | 92 | 93 | <0.1 |
| 916339 | 88 | 95 | 97 | 97 | <0.1 |
| 916340 | 83 | 96 | 97 | 98 | <0.1 |
| 916559 | 41 | 68 | 83 | 89 | 0.1 |
| 916579 | 71 | 86 | 96 | 96 | <0.1 |
| 916618 | 59 | 90 | 95 | 96 | <0.1 |
| 916618 | 10 | 47 | 70 | 78 | 0.5 |
| 916639 | 38 | 58 | 80 | 86 | 0.1 |
| 916778 | 68 | 87 | 92 | 94 | <0.1 |
| 916818 | 60 | 77 | 90 | 91 | <0.1 |

TABLE 52

Multi-dose assay of 3-10-3 cEt gapmers in A431 cells

| Compound Number | PNPLA3 % Inhibition | | | | $IC_{50}$ ($\mu$M) |
|---|---|---|---|---|---|
| | 62.5 nM | 250 nM | 1,000 nM | 4,000 nM | |
| 912759 | 60 | 0 | 85 | 99 | 0.3 |
| 915541 | 48 | 71 | 89 | 91 | <0.1 |
| 915542 | 50 | 72 | 86 | 93 | <0.1 |
| 915601 | 8 | 53 | 84 | 84 | 0.3 |
| 915602 | 1 | 56 | 77 | 91 | 0.4 |
| 915621 | 21 | 54 | 75 | 80 | 0.3 |
| 915622 | 0 | 44 | 73 | 84 | 0.5 |
| 915922 | 27 | 64 | 79 | 85 | 0.2 |
| 916042 | 6 | 57 | 89 | 88 | 0.3 |
| 916140 | 43 | 82 | 90 | 89 | <0.1 |

TABLE 52-continued

Multi-dose assay of 3-10-3 cEt gapmers in A431 cells

| | PNPLA3 % Inhibition | | | | |
|---|---|---|---|---|---|
| Compound Number | 62.5 nM | 250 nM | 1,000 nM | 4,000 nM | $IC_{50}$ (μM) |
| 916141 | 72 | 88 | 93 | 91 | <0.1 |
| 916180 | 33 | 62 | 69 | 83 | 0.2 |
| 916181 | 53 | 80 | 89 | 92 | <0.1 |
| 916341 | 0 | 78 | 94 | 94 | 0.3 |
| 916560 | 72 | 91 | 95 | 94 | <0.1 |
| 916581 | 38 | 76 | 91 | 91 | 0.1 |
| 916601 | 44 | 80 | 88 | 90 | <0.1 |
| 916701 | 61 | 83 | 91 | 93 | <0.1 |
| 916780 | 75 | 91 | 93 | 94 | <0.1 |

TABLE 53

Multi-dose assay of 3-10-3 cEt gapmers in A431 cells

| | PNPLA3 % Inhibition | | | | |
|---|---|---|---|---|---|
| Compound Number | 15.6 nM | 62.5 nM | 250 nM | 1,000 nM | $IC_{50}$ (μM) |
| 915609 | 52 | 86 | 96 | 99 | <0.01 |
| 959430 | 42 | 76 | 90 | 95 | <0.01 |
| 959440 | 39 | 73 | 92 | 98 | 0.02 |
| 959470 | 46 | 73 | 89 | 94 | <0.01 |
| 959670 | 52 | 90 | 96 | 98 | <0.01 |
| 959680 | 50 | 75 | 91 | 96 | <0.01 |
| 959730 | 83 | 96 | 98 | 98 | <0.01 |
| 959740 | 50 | 70 | 90 | 96 | <0.01 |
| 959820 | 40 | 69 | 85 | 92 | 0.02 |
| 959830 | 46 | 69 | 93 | 97 | 0.02 |
| 959880 | 34 | 62 | 85 | 93 | 0.03 |
| 960010 | 48 | 78 | 92 | 95 | <0.01 |

TABLE 54

Multi-dose assay of 3-10-3 cEt gapmers in A431 cells

| | PNPLA3 % Inhibition | | | | |
|---|---|---|---|---|---|
| Compound Number | 15.6 nM | 62.5 nM | 250 nM | 1,000 nM | $IC_{50}$ (μM) |
| 915609 | 53 | 87 | 98 | 99 | <0.01 |
| 959271 | 55 | 74 | 91 | 91 | <0.01 |
| 959360 | 7 | 43 | 79 | 85 | 0.1 |
| 959361 | 60 | 87 | 93 | 94 | <0.01 |
| 959411 | 56 | 76 | 91 | 94 | <0.01 |
| 959441 | 50 | 81 | 93 | 97 | <0.01 |
| 959460 | 0 | 29 | 75 | 90 | 0.2 |
| 959701 | 62 | 91 | 97 | 98 | <0.01 |
| 959721 | 80 | 94 | 97 | 97 | <0.01 |
| 959731 | 25 | 64 | 82 | 91 | 0.05 |
| 959741 | 41 | 65 | 83 | 91 | 0.02 |
| 959750 | 0 | 26 | 65 | 87 | 0.2 |
| 959761 | 28 | 60 | 84 | 91 | 0.05 |
| 959781 | 39 | 58 | 75 | 87 | 0.04 |
| 959911 | 20 | 54 | 78 | 90 | 0.1 |
| 959921 | 37 | 61 | 83 | 91 | 0.03 |
| 959931 | 48 | 72 | 89 | 92 | <0.01 |
| 959960 | 11 | 51 | 79 | 90 | 0.1 |
| 959961 | 38 | 64 | 85 | 92 | 0.03 |

TABLE 55

Multi-dose assay of 3-10-3 cEt gapmers in A431 cells

| | PNPLA3 % Inhibition | | | | |
|---|---|---|---|---|---|
| Compound Number | 15.6 nM | 62.5 nM | 250 nM | 1,000 nM | $IC_{50}$ (μM) |
| 915609 | 11 | 71 | 93 | 98 | 0.1 |
| 959412 | 52 | 77 | 90 | 94 | <0.01 |
| 959413 | 34 | 82 | 95 | 97 | 0.02 |
| 959422 | 15 | 50 | 80 | 87 | 0.1 |
| 959432 | 33 | 60 | 86 | 95 | 0.04 |
| 959662 | 0 | 53 | 84 | 92 | 0.1 |
| 959672 | 54 | 85 | 95 | 97 | <0.01 |
| 959673 | 18 | 62 | 88 | 95 | 0.1 |
| 959682 | 46 | 77 | 90 | 91 | <0.01 |
| 959702 | 39 | 71 | 91 | 96 | 0.02 |
| 959703 | 81 | 96 | 99 | 99 | <0.01 |
| 959712 | 4 | 30 | 75 | 92 | 0.1 |
| 959713 | 0 | 53 | 86 | 96 | 0.1 |
| 959722 | 33 | 80 | 90 | 94 | 0.02 |
| 959733 | 31 | 68 | 92 | 96 | 0.03 |
| 959782 | 35 | 63 | 86 | 94 | 0.03 |
| 959872 | 29 | 64 | 77 | 89 | 0.04 |
| 959912 | 25 | 69 | 89 | 92 | 0.04 |
| 959982 | 21 | 61 | 83 | 91 | 0.1 |

TABLE 56

Multi-dose assay of 3-10-3 cEt gapmers in A431 cells

| | PNPLA3 % Inhibition | | | | |
|---|---|---|---|---|---|
| Compound Number | 15.6 nM | 62.5 nM | 250 nM | 1,000 nM | $IC_{50}$ (μM) |
| 915609 | 2 | 73 | 93 | 98 | 0.1 |
| 959363 | 49 | 82 | 91 | 91 | <0.01 |
| 959393 | 38 | 71 | 87 | 95 | 0.02 |
| 959394 | 27 | 73 | 91 | 97 | 0.03 |
| 959414 | 69 | 94 | 98 | 99 | <0.01 |
| 959664 | 51 | 77 | 95 | 98 | <0.01 |
| 959674 | 43 | 74 | 95 | 98 | 0.02 |
| 959683 | 14 | 71 | 90 | 96 | 0.05 |
| 959704 | 57 | 92 | 98 | 99 | <0.01 |
| 959724 | 0 | 68 | 90 | 95 | 0.1 |
| 959734 | 71 | 93 | 98 | 98 | <0.01 |
| 959814 | 24 | 76 | 90 | 95 | 0.03 |
| 959873 | 38 | 53 | 83 | 90 | 0.04 |
| 959874 | 51 | 82 | 95 | 97 | <0.01 |
| 959884 | 44 | 77 | 94 | 97 | <0.01 |
| 959913 | 18 | 50 | 85 | 92 | 0.1 |
| 959953 | 6 | 51 | 85 | 92 | 0.1 |
| 959983 | 22 | 54 | 81 | 92 | 0.1 |
| 960004 | 10 | 71 | 92 | 96 | 0.1 |

TABLE 57

Multi-dose assay of 3-10-3 cEt gapmers in A431 cells

| | PNPLA3 % Inhibition | | | | |
|---|---|---|---|---|---|
| Compound Number | 15.6 nM | 62.5 nM | 250 nM | 1,000 nM | $IC_{50}$ (μM) |
| 915609 | 12 | 69 | 93 | 98 | 0.1 |
| 959364 | 32 | 72 | 89 | 91 | 0.03 |
| 959415 | 21 | 70 | 91 | 96 | 0.04 |
| 959444 | 6 | 47 | 82 | 91 | 0.1 |
| 959445 | 32 | 70 | 92 | 97 | 0.03 |
| 959455 | 61 | 87 | 95 | 97 | <0.01 |
| 959675 | 20 | 56 | 80 | 94 | 0.1 |
| 959684 | 8 | 47 | 83 | 86 | 0.1 |
| 959705 | 77 | 95 | 98 | 99 | <0.01 |
| 959735 | 12 | 67 | 90 | 95 | 0.1 |

TABLE 57-continued

Multi-dose assay of 3-10-3 cEt gapmers in A431 cells

| Compound Number | PNPLA3 % Inhibition | | | | $IC_{50}$ (μM) |
|---|---|---|---|---|---|
| | 15.6 nM | 62.5 nM | 250 nM | 1,000 nM | |
| 959764 | 4 | 32 | 80 | 92 | 0.1 |
| 959765 | 1 | 59 | 88 | 93 | 0.1 |
| 959784 | 3 | 35 | 75 | 90 | 0.1 |
| 959785 | 27 | 72 | 92 | 96 | 0.03 |
| 959794 | 0 | 0 | 53 | 83 | 0.3 |
| 959864 | 26 | 61 | 84 | 91 | 0.05 |
| 959885 | 49 | 81 | 95 | 96 | <0.01 |
| 959914 | 7 | 43 | 76 | 89 | 0.1 |
| 959964 | 17 | 55 | 83 | 91 | 0.1 |

TABLE 58

Multi-dose assay of 3-10-3 cEt gapmers in A431 cells

| Compound Number | PNPLA3 % Inhibition | | | | $IC_{50}$ (μM) |
|---|---|---|---|---|---|
| | 15.6 nM | 62.5 nM | 250 nM | 1,000 nM | |
| 915609 | 0 | 73 | 95 | 97 | 0.1 |
| 959456 | 66 | 90 | 97 | 98 | <0.01 |
| 959666 | 29 | 60 | 89 | 97 | 0.04 |
| 959676 | 15 | 44 | 81 | 93 | 0.1 |
| 959686 | 71 | 92 | 97 | 97 | <0.01 |
| 959695 | 40 | 75 | 91 | 93 | 0.02 |
| 959696 | 21 | 81 | 90 | 92 | 0.03 |
| 959706 | 81 | 95 | 98 | 98 | <0.01 |
| 959725 | 8 | 55 | 76 | 84 | 0.1 |
| 959726 | 0 | 59 | 88 | 91 | 0.1 |
| 959736 | 46 | 84 | 94 | 98 | <0.01 |
| 959766 | 22 | 57 | 83 | 94 | 0.1 |
| 959776 | 1 | 53 | 87 | 93 | 0.1 |
| 959815 | 31 | 67 | 89 | 91 | 0.03 |
| 959865 | 6 | 49 | 84 | 91 | 0.1 |
| 959875 | 34 | 74 | 91 | 92 | 0.02 |
| 959935 | 22 | 55 | 84 | 94 | 0.1 |
| 959955 | 0 | 55 | 83 | 89 | 0.1 |
| 959985 | 29 | 71 | 88 | 93 | 0.03 |

TABLE 59

Multi-dose assay of 3-10-3 cEt gapmers in A431 cells

| Compound Number | PNPLA3 % Inhibition | | | | $IC_{50}$ (μm) |
|---|---|---|---|---|---|
| | 15.6 nM | 62.5 nM | 250 nM | 1,000 nM | |
| 915609 | 37 | 80 | 96 | 99 | 0.02 |
| 959356 | 40 | 71 | 87 | 88 | 0.02 |
| 959417 | 25 | 58 | 83 | 92 | 0.1 |
| 959437 | 65 | 88 | 94 | 95 | <0.01 |
| 959667 | 37 | 69 | 90 | 95 | 0.02 |
| 959677 | 29 | 56 | 82 | 92 | 0.05 |
| 959687 | 51 | 79 | 93 | 97 | <0.01 |
| 959697 | 51 | 75 | 93 | 95 | <0.01 |
| 959707 | 81 | 94 | 98 | 98 | <0.01 |
| 959727 | 71 | 92 | 96 | 96 | <0.01 |
| 959737 | 45 | 75 | 89 | 94 | <0.01 |
| 959767 | 47 | 76 | 93 | 96 | <0.01 |
| 959797 | 32 | 59 | 87 | 94 | 0.04 |
| 959856 | 13 | 35 | 67 | 80 | 0.1 |
| 959876 | 38 | 75 | 89 | 90 | 0.02 |
| 959877 | 40 | 81 | 89 | 94 | <0.01 |
| 959956 | 25 | 25 | 66 | 85 | 0.1 |

TABLE 59-continued

Multi-dose assay of 3-10-3 cEt gapmers in A431 cells

| Compound Number | PNPLA3 % Inhibition | | | | $IC_{50}$ (μm) |
|---|---|---|---|---|---|
| | 15.6 nM | 62.5 nM | 250 nM | 1,000 nM | |
| 960006 | 13 | 40 | 68 | 83 | 0.1 |
| 960007 | 24 | 59 | 88 | 91 | 0.05 |

Example 3: Tolerability of Modified Oligonucleotides Targeting Human PNPLA3 in BALB/c Mice BALB/c mice are a multipurpose mouse model frequently utilized for safety and efficacy testing. The mice were treated with antisense oligonucleotides selected from studies described above and evaluated for changes in the levels of various plasma chemistry markers.

Ionis oligonucleotides selected from the studies above were conjugated with 3'-THA-$C_6$-GalNAC$_3$-(3R,5S)-5-(hydroxymethyl) pyrrolidin-3-ol phosphate endcap (henceforth referred to as 3'-THA).

Treatment

Groups of 6- to 7-week-old male mice were injected subcutaneously once with 200 mg/kg of modified oligonucleotides. One group of male BALB/c mice was injected with PBS. Mice were euthanized 72-96 hours after the single dose and plasma was harvested for further analysis.

To evaluate the effect of modified oligonucleotides on liver function, plasma levels of transaminases were measured using an automated clinical chemistry analyzer (Beckman Coulter AU480, Brea, CA). Modified oligonucleotides that caused changes in the levels of transaminases outside the expected range for antisense oligonucleotides were excluded in further studies. The oligonucleotides which were considered tolerable in this study and were selected for further evaluation are presented in the Table below. 'Parent Oligo' indicates the Ionis oligonucleotide that has been described in the studies above and that was conjugated with 3'-THA and tested in this study.

TABLE 60

Antisense oligonucleotides in BALB/c mouse study

| Compound ID | Parent oligo ID |
|---|---|
| 975746 | 916339 |
| 975747 | 912941 |
| 975748 | 916306 |
| 975755 | 916332 |
| 975760 | 912848 |
| 975764 | 916298 |
| 975766 | 916552 |
| 975767 | 916789 |
| 975768 | 916602 |
| 975770 | 912874 |
| 975771 | 916333 |
| 975772 | 916780 |
| 975775 | 916672 |
| 975777 | 916558 |
| 975780 | 916607 |
| 975783 | 916338 |
| 975788 | 912847 |
| 975790 | 916778 |
| 975792 | 912870 |
| 975794 | 916802 |
| 975797 | 916637 |

TABLE 60-continued

Antisense oligonucleotides in BALB/c mouse study

| Compound ID | Parent oligo ID |
|---|---|
| 975799 | 912732 |
| 975800 | 912733 |
| 975803 | 912813 |
| 975804 | 912823 |
| 975805 | 912834 |
| 975806 | 912855 |
| 975807 | 912856 |
| 975808 | 912864 |
| 975809 | 912871 |
| 975810 | 912872 |
| 975811 | 912875 |
| 975813 | 912931 |
| 975814 | 912934 |
| 975815 | 912936 |
| 975816 | 912938 |
| 975817 | 912943 |
| 975820 | 912988 |
| 975822 | 915486 |
| 975829 | 915619 |
| 975836 | 915780 |
| 975840 | 915989 |
| 975844 | 916151 |
| 975849 | 916292 |
| 975850 | 916299 |
| 975851 | 916303 |
| 975852 | 916309 |
| 975853 | 916310 |
| 975854 | 916312 |
| 975855 | 916318 |
| 975856 | 916324 |
| 975857 | 916331 |
| 975858 | 916334 |
| 975859 | 916335 |
| 975860 | 916336 |
| 975861 | 916549 |
| 975862 | 916550 |
| 975864 | 916563 |
| 975865 | 916564 |
| 975866 | 916568 |
| 975868 | 916571 |
| 975869 | 916575 |
| 975870 | 916580 |
| 975871 | 916581 |
| 975873 | 916586 |
| 975875 | 916601 |
| 975878 | 916624 |
| 975879 | 916625 |
| 975880 | 916636 |
| 975881 | 916638 |
| 975883 | 916670 |
| 975886 | 916711 |
| 975887 | 916716 |
| 975888 | 916774 |
| 975889 | 916781 |
| 975890 | 916782 |
| 975891 | 916788 |
| 975893 | 916815 |
| 975894 | 916816 |
| 975895 | 916817 |
| 975896 | 916818 |
| 975897 | 916822 |
| 975898 | 916845 |
| 994288 | 959455 |
| 994289 | 960010 |
| 994290 | 959361 |
| 994291 | 959271 |

Example 4: Effect of Antisense Inhibition of PNPLA3 in Transgenic Mouse Model A PNPLA3 transgenic mouse model from wild-type C57BL/6 generated by the University of California, Irvine was used. The mouse model comprises a genomic construct containing the entire PNPLA3 gene fosmid, generously provided by the University of Washington. The efficacy of Ionis oligonucleotides was evaluated in this model.

Treatment

Transgenic mice were maintained on a 12-hour light/dark cycle and were fed ad libitum normal Purina mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

The hPNPLA3 Tg mice were divided into groups of 2 mice each. Groups received subcutaneous injections of Ionis oligonucleotide at a dose of 2.5 mg/kg on days 1 and 8. One group of 4 mice received subcutaneous injections of PBS on days 1 and 8. The saline-injected group served as the control group to which oligonucleotide-treated groups were compared.

RNA Analysis

On day 10, RNA was extracted from liver for real-time PCR analysis of measurement of mRNA expression of PNPLA3. Primer probe sets RTS36070 and RTS36075 were both used to measure PNPLA3 mRNA levels. Results are presented as percent change of mRNA, relative to PBS control, normalized with RIBOGREEN®. As presented in the Table below, treatment with Ionis antisense oligonucleotides resulted in significant reduction of PNPLA3 mRNA in comparison to the PBS control. '0' indicates that the oligonucleotides did not inhibit mRNA expression.

TABLE 61

Percent inhibition of PNPLA3 mRNA in the transgenic mice liver relative to the PBS control

| Compound ID | Inhibition (%) measured with RTS36070 | Inhibition (%) measured with RTS36075 |
|---|---|---|
| 975746 | 99 | 99 |
| 975747 | 99 | 99 |
| 975748 | 98 | 98 |
| 975755 | 99 | 99 |
| 975760 | 96 | 97 |
| 975764 | 75 | 83 |
| 975766 | 99 | 99 |
| 975767 | 98 | 98 |
| 975768 | 98 | 98 |
| 975770 | 97 | 97 |
| 975771 | 98 | 99 |
| 975772 | 96 | 96 |
| 975775 | 90 | 91 |
| 975777 | 85 | 89 |
| 975780 | 44 | 63 |
| 975783 | 87 | 90 |
| 975788 | 0 | 26 |
| 975790 | 0 | 0 |
| 975792 | 9 | 34 |
| 975794 | 44 | 50 |
| 975797 | 0 | 0 |
| 975799 | 0 | 0 |
| 975800 | 0 | 5 |
| 975803 | 68 | 68 |
| 975804 | 11 | 38 |
| 975805 | 0 | 0 |
| 975806 | 0 | 0 |
| 975807 | 0 | 0 |
| 975808 | 47 | 58 |
| 975809 | 0 | 19 |
| 975810 | 12 | 22 |
| 975811 | 19 | 32 |

TABLE 61-continued

Percent inhibition of PNPLA3 mRNA in the transgenic mice liver relative to the PBS control

| Compound ID | Inhibition (%) measured with RTS36070 | Inhibition (%) measured with RTS36075 |
|---|---|---|
| 975813 | 36 | 39 |
| 975814 | 48 | 54 |
| 975815 | 78 | 77 |
| 975816 | 56 | 56 |
| 975817 | 84 | 86 |
| 975820 | 35 | 45 |
| 975822 | 0 | 0 |
| 975829 | 98 | 98 |
| 975836 | 85 | 91 |
| 975840 | 19 | 44 |
| 975844 | 21 | 31 |
| 975849 | 88 | 89 |
| 975850 | 41 | 48 |
| 975851 | 5 | 18 |
| 975852 | 24 | 41 |
| 975853 | 0 | 0 |
| 975854 | 0 | 0 |
| 975855 | 0 | 0 |
| 975856 | 45 | 31 |
| 975857 | 73 | 67 |
| 975858 | 58 | 40 |
| 975860 | 92 | 92 |
| 975861 | 66 | 49 |
| 975862 | 46 | 36 |
| 975864 | 16 | 21 |
| 975865 | 0 | 0 |
| 975866 | 40 | 41 |
| 975868 | 56 | 48 |
| 975869 | 30 | 19 |
| 975870 | 0 | 14 |
| 975871 | 0 | 0 |
| 975875 | 75 | 73 |
| 975878 | 18 | 12 |
| 975879 | 7 | 0 |
| 975880 | 0 | 0 |
| 975881 | 54 | 54 |
| 975883 | 77 | 80 |
| 975886 | 18 | 28 |
| 975887 | 49 | 57 |
| 975888 | 10 | 9 |
| 975889 | 90 | 91 |
| 975890 | 96 | 98 |
| 975891 | 97 | 98 |
| 975893 | 95 | 95 |
| 975894 | 85 | 87 |
| 975895 | 89 | 89 |
| 975896 | 91 | 89 |
| 975898 | 94 | 95 |
| 975897 | 96 | 97 |
| 975873 | 99 | 99 |
| 994288 | 99 | 99 |
| 994289 | 98 | 99 |
| 994290 | 98 | 99 |
| 994291 | 95 | 95 |
| 975859 | 95 | 96 |

Example 5: Tolerability of Modified Oligonucleotides Targeting Human PNPLA3 in CD1 Mice CD1 ® mice (Charles River, MA) are a multipurpose mice model, frequently utilized for safety and efficacy testing. The mice were treated with Ionis antisense oligonucleotides selected from studies described above and evaluated for changes in the levels of various plasma chemistry markers.

Ionis oligonucleotides selected from the studies above were conjugated with 5'-Trishexylamino-(THA)-$C_6$GalNAC3 endcap (henceforth referred to as 5'-THA). The Ionis oligonucleotides tested are presented in the Table below. 'Unconjugated parent ION No.' refers to the Ionis oligonucleotide described in the in vitro studies above with the same sequence. '3'-THA counterpart ION No.' refers to the 3'-THA conjugated oligonucleotide with the same sequence and evaluated in the mice studies above.

TABLE 62

5'-THA oligonucleotides tested in CD1 mice tolerability study

| Compound ID | Unconjugated parent ION No. | 3'-THA counterpart ION No | Sequence | SEQ ID NO |
|---|---|---|---|---|
| 975591 | 916339 | 975746 | GGATATATTGGGCTCA | 1512 |
| 975592 | 912941 | 975747 | TTGCATTGCATAGCCT | 182 |
| 975593 | 916306 | 975748 | GTGTACTTTAGGCTCC | 598 |
| 975600 | 916332 | 975755 | CACAATGACATCATGG | 1020 |
| 975605 | 912848 | 975760 | CGTTTTTAGTAGTCAA | 141 |
| 975611 | 916552 | 975766 | CCTTTTATTTCCGTTA | 1024 |
| 975612 | 916789 | 975767 | GTAATATTCAGACCAG | 899 |
| 975613 | 916602 | 975768 | CTAGTAAATGCTTGTC | 330 |
| 975615 | 912874 | 975770 | ATACTTTTGGCAAGGC | 217 |
| 975616 | 916333 | 975771 | CTTTATTCAATGTGGC | 1089 |

TABLE 62-continued

5'-THA oligonucleotides tested in CD1 mice tolerability study

| Compound ID | Unconjugated parent ION No. | 3'-THA counterpart ION No | Sequence | SEQ ID NO |
|---|---|---|---|---|
| 975617 | 916780 | 975772 | AGAAATTGCAGTGCCC | 1665 |
| 975674 | 915619 | 975829 | GACTTTAGGGCAGATG | 1400 |
| 975704 | 916335 | 975859 | TAATTCTACCTGTGTC | 1227 |
| 975718 | 916586 | 975873 | AACTTTGCAGCCTATC | 605 |
| 975735 | 916782 | 975890 | CTTAGAAATTGCAGTG | 408 |
| 975736 | 916788 | 975891 | TAATATTCAGACCAGG | 830 |
| 975738 | 916815 | 975893 | CAATTCTAGACATGGC | 1313 |
| 975742 | 916822 | 975897 | TATGACATTTCAGAGT | 410 |
| 975743 | 916845 | 975898 | GTAAAGATGTGAGTGA | 618 |
| 994282 | 959455 | 994288 | TTGGATATATTGGGCT | 1982 |
| 994283 | 960010 | 994289 | AGACATATGACATTTC | 1745 |
| 994284 | 959361 | 994290 | TTTTTAGTAGTCAAGG | 1757 |
| 994285 | 959271 | 994291 | GTTGAAGGATGGATGG | 1748 |

Treatment

Groups of four CD1 mice each were weekly injected subcutaneously with 15 mg/kg of Ionis oligonucleotides for 6 weeks, with one loading dose at day 4 (total 8 doses). One group of male CD1 mice was injected subcutaneously for 6 weeks with PBS. Mice were euthanized 48 hours after the last dose, and organs and plasma were harvested for further analysis.

Plasma Chemistry Markers

To evaluate the effect of Ionis oligonucleotides on liver and kidney function, plasma levels of transaminases (ALT and AST), albumin, total bilirubin, and creatinine were measured at week 3 using an automated clinical chemistry analyzer (Beckman Coulter AU480, Brea, CA). The results are presented in the Table below. Ionis oligonucleotides that caused changes in the levels of any of the liver or kidney function markers outside the expected range for antisense oligonucleotides were excluded in further studies.

TABLE 63

Plasma chemistry marker levels in CD1 mice at week 3

| | Albumin (g/dL) | ALT (IU/L) | AST (IU/L) | Total bilirubin (mg/dL) | Creatinine (mg/dL) |
|---|---|---|---|---|---|
| PBS | 2.9 | 31 | 64 | 0.4 | 0.1 |
| 975611 | 2.7 | 640 | 385 | 0.3 | 0.1 |
| 994282 | 2.4 | 76 | 83 | 0.3 | 0.1 |
| 975592 | 3.0 | 786 | 942 | 0.5 | 0.1 |
| 975600 | 2.7 | 334 | 431 | 0.3 | 0.1 |
| 975591 | 2.6 | 62 | 115 | 0.4 | 0.1 |
| 975718 | 2.4 | 1717 | 2183 | 1.2 | 0.1 |
| 994284 | 2.7 | 41 | 97 | 0.3 | 0.1 |
| 994283 | 2.8 | 216 | 154 | 0.3 | 0.1 |
| 975616 | 3.0 | 69 | 137 | 0.3 | 0.1 |
| 975612 | 2.7 | 47 | 218 | 0.4 | 0.1 |
| 975674 | 2.9 | 134 | 114 | 0.4 | 0.1 |
| 975613 | 2.8 | 60 | 277 | 0.3 | 0.1 |
| 975593 | 2.7 | 429 | 405 | 0.4 | 0.1 |
| 975736 | 2.9 | 46 | 63 | 0.2 | 0.2 |
| 975735 | 2.5 | 46 | 79 | 0.2 | 0.1 |
| 975742 | 2.6 | 152 | 96 | 0.2 | 0.1 |
| 975615 | 2.9 | 207 | 189 | 0.4 | 0.1 |
| 975617 | 2.9 | 65 | 70 | 0.3 | 0.1 |
| 975605 | 2.9 | 67 | 92 | 0.3 | 0.1 |
| 975704 | 2.4 | 33 | 61 | 0.2 | 0.1 |
| 975738 | 2.6 | 43 | 67 | 0.2 | 0.1 |
| 975743 | 2.9 | 119 | 126 | 0.4 | 0.1 |
| 994285 | 2.8 | 400 | 353 | 0.2 | 0.1 |

Hematology Assays

Blood obtained from selected mouse groups at week 6 were sent to IDEXX BioResearch for measurement of platelet count. The results are presented in the tables below. Ionis oligonucleotides that caused changes in the platelet count outside the expected range for antisense oligonucleotides were excluded in further studies.

TABLE 64

Platelet count in CD1 mice

| | Platelet ($\times 10^3/\mu L$) |
|---|---|
| PBS | 1067 |
| 975605 | 1202 |
| 975612 | 1200 |
| 975613 | 1417 |
| 975616 | 1178 |
| 975617 | 922 |
| 975674 | 618 |
| 975591 | 941 |

TABLE 64-continued

Platelet count in CD1 mice

| | Platelet (×10³/μL) |
|---|---|
| 975743 | 1127 |
| 994282 | 1384 |
| 994284 | 1255 |
| 975704 | 939 |
| 975735 | 1039 |
| 975736 | 1116 |
| 975738 | 1126 |
| 975742 | 808 |

Example 6: Tolerability of Modified Oligonucleotides Targeting Human PNPLA3 in Sprague-Dawley Rats Sprague-Dawley rats are a multipurpose model used for safety and efficacy evaluations. The rats were treated with Ionis antisense oligonucleotides from the studies described in the Examples above and evaluated for changes in the levels of various plasma chemistry markers.

Treatment

Male Sprague-Dawley rats were maintained on a 12-hour light/dark cycle and fed ad libitum with Purina normal rat chow, diet 5001. Groups of 4 Sprague-Dawley rats each were weekly injected subcutaneously with 15 mg/kg of Ionis oligonucleotide for 6 weeks, with one loading dose on day 4 (total 8 doses). Forty eight hours after the last dose, rats were euthanized and organs and plasma were harvested for further analysis.

Plasma Chemistry Markers

To evaluate the effect of Ionis oligonucleotides on hepatic function, plasma levels of transaminases were measured using an automated clinical chemistry analyzer (Beckman Coulter AU480, Brea, CA). Plasma levels of ALT (alanine transaminase) and AST (aspartate transaminase) were measured and the results are presented in the Table below expressed in IU/L. Plasma levels of bilirubin, creatinine, albumin, and BUN were also measured using the same clinical chemistry analyzer and the results are also presented in the Table below expressed in mg/dL. Ionis oligonucleotides that caused changes in the levels of any markers of liver function outside the expected range for antisense oligonucleotides were excluded in further studies.

TABLE 65

Plasma chemistry markers in Sprague-Dawley rats

| | Albumin (g/dL) | ALT (IU/L) | AST (IU/L) | Total bilirubin (mg/dL) | Creatinine (mg/dL) | BUN (mg/dL) |
|---|---|---|---|---|---|---|
| PBS | 3 | 35 | 81 | 0.2 | 0.2 | 12 |
| 975591 | 3 | 57 | 161 | 0.2 | 0.3 | 14 |
| 975605 | 4 | 62 | 176 | 0.3 | 0.2 | 14 |
| 975612 | 3 | 106 | 153 | 0.2 | 0.3 | 13 |
| 975613 | 3 | 32 | 94 | 0.2 | 0.2 | 12 |
| 975616 | 4 | 31 | 106 | 0.2 | 0.3 | 13 |
| 975617 | 3 | 49 | 263 | 0.2 | 0.2 | 12 |
| 975735 | 3 | 44 | 128 | 0.2 | 0.2 | 14 |
| 975736 | 3 | 73 | 293 | 0.3 | 0.3 | 14 |
| 994282 | 3 | 41 | 135 | 0.1 | 0.3 | 12 |
| 994284 | 3 | 32 | 95 | 0.1 | 0.2 | 13 |

Kidney Function

To evaluate the effect of Ionis oligonucleotides on kidney function, urinary levels of protein and creatinine were measured using an automated clinical chemistry analyzer (Beckman Coulter AU480, Brea, CA). The ratios of total protein to creatinine are presented in the Table below. Ionis oligonucleotides that caused changes in the levels of the ratio outside the expected range for antisense oligonucleotides were excluded in further studies.

TABLE 66

Total protein to creatinine ratio in Sprague-Dawley rats

| PBS | 1.5 |
|---|---|
| 975591 | 2.0 |
| 975605 | 1.6 |
| 975612 | 1.9 |
| 975613 | 2.3 |
| 975616 | 2.0 |
| 975617 | 1.4 |
| 975735 | 2.2 |
| 975736 | 1.1 |
| 994282 | 2.1 |
| 994284 | 2.1 |

Organ Weights

Liver, heart, spleen and kidney weights were measured at the end of the study, and are presented in the Table below. Ionis oligonucleotides that caused any changes in organ weights outside the expected range for antisense oligonucleotides were excluded from further studies.

TABLE 67

Organ weights (g)

| | Liver | Kidney | Spleen |
|---|---|---|---|
| Saline | 16 | 3 | 1 |
| 975591 | 16 | 4 | 1 |
| 975605 | 21 | 3 | 1 |
| 975612 | 12 | 3 | 1 |
| 975613 | 16 | 3 | 1 |
| 975616 | 15 | 3 | 1 |
| 975617 | 19 | 4 | 2 |
| 975735 | 14 | 4 | 1 |
| 975736 | 15 | 3 | 1 |
| 994282 | 14 | 3 | 1 |
| 994284 | 15 | 3 | 1 |

Example 7: Effect of Antisense Inhibition of PNPLA3 in Transgenic Mouse Model Ionis oligonucleotides were tested in a multi-dose assay in the hPNPLA3 Tg model.

Treatment

Transgenic mice were maintained on a 12-hour light/dark cycle and were fed ad libitum normal Purina mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Study 1

The hPNPLA3 Tg mice were divided into groups of 4 mice each. Groups received subcutaneous injections of Ionis oligonucleotide at a weekly dose of 5 mg/kg, 1 mg/kg, or 0.25 mg/kg administered on days 1, 5, 8, 15, and 23. One group of 4 mice received subcutaneous injections of PBS on days 1, 5, 8, 15, and 23. The saline-injected group served as the control group to which oligonucleotide-treated groups were compared.

RNA Analysis

On day 26, RNA was extracted from liver for real-time PCR analysis of measurement of mRNA expression of PNPLA3. Primer probe sets RTS36070 and RTS36075 were both used to measure PNPLA3 mRNA levels. Results are presented as percent change of mRNA, relative to PBS control, normalized with RIBOGREEN©. As presented in the Table below, treatment with Ionis antisense oligonucleotides resulted in significant dose-dependent reduction of PNPLA3 mRNA in comparison to the PBS control.

TABLE 68

Percent inhibition of PNPLA3 mRNA in the transgenic mice liver relative to the PBS control

|  | mg/kg/wk | Inhibition measured by RTS36070 | Inhibition measured by RTS36075 | $EC_{50}$ (µg/g) |
|---|---|---|---|---|
| 975605 | 5 | 93 | 90 | 2.2 |
|  | 1 | 66 | 57 |  |
|  | 0.25 | 45 | 46 |  |
| 975612 | 5 | 98 | 99 | 3.1 |
|  | 1 | 89 | 88 |  |
|  | 0.25 | 34 | 44 |  |
| 975613 | 5 | 98 | 97 | 1.0 |
|  | 1 | 87 | 85 |  |
|  | 0.25 | 58 | 56 |  |
| 975616 | 5 | 93 | 93 | 0.5 |
|  | 1 | 85 | 87 |  |
|  | 0.25 | 60 | 63 |  |
| 975617 | 5 | 97 | 97 | 0.3 |
|  | 1 | 76 | 78 |  |
|  | 0.25 | 55 | 53 |  |
| 975735 | 5 | 97 | 98 | 1.5 |
|  | 1 | 74 | 75 |  |
|  | 0.25 | 29 | 33 |  |
| 975736 | 5 | 98 | 98 | 0.9 |
|  | 1 | 73 | 71 |  |
|  | 0.25 | 44 | 45 |  |
| 994282 | 5 | 98 | 98 | 0.2 |
|  | 1 | 91 | 80 |  |
|  | 0.25 | 62 | 58 |  |
| 994284 | 5 | 99 | 100 | 0.3 |
|  | 1 | 89 | 88 |  |
|  | 0.25 | 53 | 47 |  |

Study 2

The hPNPLA3 Tg mice were divided into groups of 4 mice each. Groups received subcutaneous injections of Ionis oligonucleotide at a weekly dose of 5 mg/kg, 2.5 mg/kg, 1 mg/kg, 0.5 mg/kg, or 0.25 mg/kg administered on days 1, 5, 8, 15, and 23. One group of 4 mice received subcutaneous injections of PBS on days 1, 5, 8, 15, and 23. The saline-injected group served as the control group to which oligonucleotide-treated groups were compared.

RNA Analysis

On day 26, RNA was extracted from liver for real-time PCR analysis of measurement of mRNA expression of PNPLA3. Primer probe sets RTS36070 and RTS36075 were both used to measure PNPLA3 mRNA levels. Results are presented as percent change of mRNA, relative to PBS control, normalized with RIBOGREEN®. As presented in the Table below, treatment with Ionis antisense oligonucleotides resulted in significant dose-dependent reduction of PNPLA3 mRNA in comparison to the PBS control.

TABLE 69

Percent inhibition of PNPLA3 mRNA in the transgenic mice liver relative to the PBS control

|  | mg/kg/wk | Inhibition measured by RTS36070 | Inhibition measured by RTS36075 | $EC_{50}$ (µg/g) | $EC_{90}$ (µg/g) |
|---|---|---|---|---|---|
| 975612 | 5 | 96 | 97 | 1.0 | 8.6 |
|  | 2.5 | 98 | 98 |  |  |
|  | 1 | 95 | 96 |  |  |
|  | 0.5 | 82 | 83 |  |  |
|  | 0.25 | 43 | 44 |  |  |
| 975613 | 5 | 99 | 99 | 0.9 | 7.7 |
|  | 2.5 | 99 | 99 |  |  |
|  | 1 | 91 | 91 |  |  |
|  | 0.5 | 82 | 83 |  |  |
|  | 0.25 | 69 | 74 |  |  |
| 975616 | 5 | 96 | 96 | 1.0 | 9.4 |
|  | 2.5 | 94 | 93 |  |  |
|  | 1 | 89 | 89 |  |  |
|  | 0.5 | 81 | 81 |  |  |
|  | 0.25 | 73 | 60 |  |  |

Example 8: Effect of Modified Oligonucleotides Targeting Human PNPLA3 in Cynomolgus Monkeys Cynomolgus monkeys were treated with Ionis antisense oligonucleotides selected from studies described in the Examples above. Antisense oligonucleotide tolerability was evaluated.

Treatment

Prior to the study, the monkeys were kept in quarantine during which the animals were observed daily for general health. The monkeys were 2-4 years old and weighed 2-4 kg. Nine groups of 5 randomly assigned male cynomolgus monkeys each were injected subcutaneously with Ionis oligonucleotide or PBS in a clock-wise rotation between four different sites on the back. The monkeys were dosed twice per week (days 1, 5, 9, and 14) for the first 2 weeks, and then subsequently once a week for 10 weeks with 10 mg/kg of Ionis oligonucleotide on days 21, 28, 35, 42, 49, 56, 63, 70, 77, and 84. A control group of 5 cynomolgus monkeys was injected with PBS in a similar manner and served as the control group.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. Scheduled euthanasia of the animals was conducted on day 86 approximately 48 hours after the last dose by exsanguination while under deep anesthesia. The protocols described in the Example were approved by the Institutional Animal Care and Use Committee (IACUC).

Body and Organ Weight Measurements

To evaluate the effect of Ionis oligonucleotides on the overall health of the animals, body and organ weights were measured. Body weights and organ weights were measured on day 86 and the data is presented in the Table below. The results indicate that effect of treatment with antisense oligonucleotides on body and organ weights was within the expected range for antisense oligonucleotides. Specifically, treatment with ION 945616 was well tolerated in terms of the body and organ weights of the monkeys.

TABLE 70

Final body and organ weights in cynomolgus monkey

|  | Body Wt (kg) | Spleen (g) | Kidney (g) | Liver with gallbladder (g) |
|---|---|---|---|---|
| PBS Control | 2797 | 2.6 | 13.1 | 53 |
| 994284 | 2789 | 3.3 | 14.7 | 69 |
| 975605 | 2685 | 4.1 | 12.2 | 58 |
| 975616 | 2868 | 3.1 | 12.9 | 63 |
| 994282 | 2782 | 4.4 | 12.1 | 62 |
| 975613 | 2704 | 3.0 | 13.5 | 60 |
| 975617 | 2761 | 3.8 | 14.1 | 61 |
| 975735 | 2765 | 4.1 | 15.5 | 67 |
| 975736 | 2844 | 3.0 | 14.1 | 66 |
| 975612 | 2711 | 2.8 | 13.2 | 60 |

Liver Function

To evaluate the effect of Ionis oligonucleotides on hepatic function, blood samples were collected from all the study groups on day 86. The monkeys were fasted overnight prior to blood collection. Blood was collected in tubes without anticoagulant for serum separation. The tubes were kept at room temperature for a minimum of 90 minutes and then centrifuged at 3000 rpm for 10 minutes to obtain serum. Levels of various liver function markers were measured using a Toshiba 200FR NEO chemistry analyzer (Toshiba Co., Japan). Plasma levels of ALT and AST were measured and the results are presented in the Table below, expressed in IU/L. Bilirubin, a liver function marker, was similarly measured and is presented in the Table below, expressed in mg/dL. The results indicate that antisense oligonucleotides had no effect on liver function outside the expected range for antisense oligonucleotides.

TABLE 71

Liver function markers in cynomolgus monkey plasma

|  | ALT (IU/L) | AST (IU/L) | Bilirubin (mg/dL) | Albumin (g/dL) |
|---|---|---|---|---|
| PBS Control | 38 | 55 | 0.2 | 4.3 |
| 994284 | 64 | 48 | 0.2 | 3.7 |
| 975605 | 48 | 54 | 0.3 | 4.0 |
| 975616 | 54 | 57 | 0.3 | 3.9 |
| 994282 | 89 | 53 | 0.3 | 4.0 |
| 975613 | 60 | 71 | 0.4 | 4.0 |
| 975617 | 65 | 61 | 0.3 | 4.0 |
| 975735 | 59 | 79 | 0.3 | 4.1 |
| 975736 | 70 | 56 | 0.3 | 3.9 |
| 975612 | 61 | 66 | 0.3 | 3.9 |

Kidney Function

To evaluate the effect of Ionis oligonucleotides on kidney function, blood samples were collected from all the study groups on day 86. The monkeys were fasted overnight prior to blood collection. Blood was collected in tubes without anticoagulant for serum separation. The tubes were kept at room temperature for a minimum of 90 minutes and then centrifuged at 3000 rpm for 10 minutes to obtain serum. Levels of BUN and creatinine were measured using a Toshiba 200FR NEO chemistry analyzer (Toshiba Co., Japan). Results are presented in the Table below, expressed in mg/dL.

The plasma chemistry data indicate that most of the Ionis oligonucleotides did not have any effect on the kidney function outside the expected range for antisense oligonucleotides.

TABLE 72

Plasma BUN and creatinine levels (mg/dL) in cynomolgus monkeys

|  | BUN | Creatinine |
|---|---|---|
| PBS Control | 23 | 0.8 |
| 994284 | 24 | 0.8 |
| 975605 | 27 | 0.7 |
| 975616 | 21 | 0.8 |
| 994282 | 24 | 0.8 |
| 975613 | 23 | 0.9 |
| 975617 | 21 | 0.7 |
| 975735 | 20 | 0.8 |
| 975736 | 23 | 0.8 |
| 975612 | 20 | 0.8 |

Hematology

To evaluate any effect of Ionis oligonucleotides in cynomolgus monkeys on hematologic parameters, blood samples of approximately 0.5 mL of blood was collected from each of the available study animals on day 86. The samples were collected in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA2120i hematology analyzer (Siemens, USA).

The data indicate the oligonucleotides did not cause any changes in hematologic parameters outside the expected range for antisense oligonucleotides at this dose.

TABLE 73

Blood cell counts in cynomolgus monkeys

|  | RBC ($\times 10^6/\mu L$) | Platelets ($\times 10^3/\mu L$) | WBC ($\times 10^3/\mu L$) | Neutrophils ($\times 10^3/\mu L$) | Lymphocytes ($\times 10^3/\mu L$) | Monocytes ($\times 10^3/\mu L$) |
|---|---|---|---|---|---|---|
| PBS Control | 6.0 | 342 | 12 | 3.2 | 7.8 | 0.3 |
| 994284 | 6.0 | 410 | 10 | 2.7 | 6.7 | 0.3 |
| 975605 | 5.8 | 326 | 10 | 4.8 | 4.5 | 0.4 |
| 975616 | 6.0 | 362 | 10 | 3.4 | 5.8 | 0.3 |
| 994282 | 5.8 | 359 | 10 | 3.9 | 5.5 | 0.3 |
| 975613 | 5.5 | 327 | 8 | 2.6 | 5.5 | 0.2 |
| 975617 | 6.1 | 358 | 10 | 3.1 | 6.4 | 0.3 |

TABLE 73-continued

Blood cell counts in cynomolgus monkeys

|  | RBC (×10$^6$/μL) | Platelets (×10$^3$/μL) | WBC (×10$^3$/μL) | Neutrophils (×10$^3$/μL) | Lymphocytes (×10$^3$/μL) | Monocytes (×10$^3$/μL) |
| --- | --- | --- | --- | --- | --- | --- |
| 975735 | 5.9 | 241 | 13 | 5.4 | 6.6 | 0.4 |
| 975736 | 5.8 | 360 | 10 | 3.5 | 6.4 | 0.2 |
| 975612 | 6.2 | 421 | 11 | 5.1 | 5.7 | 0.2 |

TABLE 74

Hematologic parameters in cynomolgus monkeys

|  | Hemoglobin (g/dL) | HCT (%) |
| --- | --- | --- |
| PBS Control | 14 | 49 |
| 994284 | 14 | 48 |
| 975605 | 14 | 46 |
| 975616 | 14 | 49 |
| 994282 | 14 | 47 |
| 975613 | 13 | 46 |
| 975617 | 14 | 49 |
| 975735 | 14 | 48 |
| 975736 | 14 | 48 |
| 975612 | 14 | 49 |

Pro-Inflammatory Proteins Analysis

To evaluate any inflammatory effect of Ionis oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP), which is synthesized in the liver and which serves as a marker of inflammation, and complement $C_3$ were measured using a Toshiba 200FR NEO chemistry analyzer (Toshiba Co., Japan).

Example 9: Measurement of Viscosity of Antisense Oligonucleotides Targeting Human PNPLA3

The viscosity of select antisense oligonucleotides from the studies described above was measured with the aim of screening out antisense oligonucleotides which have a viscosity of more than 40 centipoise (cP). Oligonucleotides having a viscosity greater than 40 cP would have less than optimal viscosity.

Oligonucleotides (32-35 mg) were weighed into a glass vial, 120 μL of water was added and the antisense oligonucleotide was dissolved into solution by heating the vial at 50° C. Part (75 μL) of the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in the Table below, where the concentration of each antisense oligonucleotide was 200 mg/ml, and indicate that most of the antisense oligonucleotides solutions are optimal in their viscosity under the criterion stated above.

TABLE 75

Viscosity of antisense oligonucleotides at 200 mg/mL

|  | Viscosity (cP) |
| --- | --- |
| 994284 | 21 |
| 975605 | 19 |
| 975616 | 20 |
| 994282 | 30 |
| 975613 | 24 |
| 975617 | 22 |
| 975735 | 15 |
| 975736 | 49 |
| 975612 | 25 |

Example 10: Design of Oligonucleotides at the Site of ION 975616

Additional antisense oligonucleotides were designed targeting a PNPLA3 nucleic acid that overlap the target site of ION 916333, which is the unconjugated version of ION 975616, and with different chemical modifications and motifs.

The newly designed chimeric antisense oligonucleotides in the Tables below were designed as 3-10-3 cEt gapmers or deoxy, MOE, and cEt oligonucleotides. The 3-10-3 cEt gapmers are 16 nucleosides in length, wherein the central gap segment comprises of ten 2'-deoxynucleosides and is flanked by wing segments on the 5' direction and the 3' direction comprising three nucleosides. Each nucleoside in the 5' wing segment and each nucleoside in the 3' wing segment has a cEt sugar modification. The internucleoside linkages throughout each gapmer are phosphorothioate (P=S) linkages. All cytosine residues throughout each gapmer are 5-methylcytosines. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; 'd' indicates deoxyribose; the number after the 'd' indicates the number of deoxyribose; and 'e' indicates a MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence (SEQ ID NO: 2).

TABLE 76

Modified oligonucleotides targeting human PNPLA3

| Start Site | Stop Site | Sequence | Compound Number | Chemistry | SEQ ID NO |
|---|---|---|---|---|---|
| 5599 | 5614 | TCAATGTGGCTTCTAG | 995553 | kkk-d10-kkk | 2170 |
| 5600 | 5615 | TTCAATGTGGCTTCTA | 959437 | kkk-d10-kkk | 2089 |
| 5601 | 5616 | ATTCAATGTGGCTTCT | 959438 | kkk-d10-kkk | 2171 |
| 5602 | 5617 | TATTCAATGTGGCTTC | 959439 | kkk-d10-kkk | 2172 |
| 5603 | 5618 | TTATTCAATGTGGCTT | 959440 | kkk-d10-kkk | 1705 |
| 5603 | 5618 | TTATTCAATGTGGCTT | 995696 | k-d10-kekek | 1705 |
| 5603 | 5618 | TTATTCAATGTGGCTT | 995906 | kk-d9-eeekk | 1705 |
| 5603 | 5618 | TTATTCAATGTGGCTT | 996116 | kk-d9-ekeke | 1705 |
| 5604 | 5619 | TTTATTCAATGTGGCT | 959441 | kkk-d10-kkk | 1765 |
| 5604 | 5619 | TTTATTCAATGTGGCT | 995697 | k-d10-kekek | 1765 |
| 5604 | 5619 | TTTATTCAATGTGGCT | 995907 | kk-d9-eeekk | 1765 |
| 5604 | 5619 | TTTATTCAATGTGGCT | 996117 | kk-d9-ekeke | 1765 |
| 5605 | 5620 | CTTTATTCAATGTGGC | 916333 | kkk-d10-kkk | 1089 |
| 5605 | 5620 | CTTTATTCAATGTGGC | 995698 | k-d10-kekek | 1089 |
| 5605 | 5620 | CTTTATTCAATGTGGC | 995908 | kk-d9-eeekk | 1089 |
| 5605 | 5620 | CTTTATTCAATGTGGC | 996118 | kk-d9-ekeke | 1089 |
| 5605 | 5620 | CTTTATTCAATGTGGC | 996277 | kek-d9-eekk | 1089 |
| 5606 | 5621 | ACTTTATTCAATGTGG | 916334 | kkk-d10-kkk | 1158 |
| 5606 | 5621 | ACTTTATTCAATGTGG | 995699 | k-d10-kekek | 1158 |
| 5606 | 5621 | ACTTTATTCAATGTGG | 995909 | kk-d9-eeekk | 1158 |
| 5606 | 5621 | ACTTTATTCAATGTGG | 996119 | kk-d9-ekeke | 1158 |
| 5607 | 5622 | TACTTTATTCAATGTG | 959442 | kkk-d10-kkk | 1825 |
| 5608 | 5623 | TTACTTTATTCAATGT | 959443 | kkk-d10-kkk | 1885 |

The oligonucleotides were tested in a series of experiments. Cultured A-431 cells at a density of 10,000 cells per well were treated using free uptake with modified oligonucleotides diluted to different concentrations. After a treatment period of approximately 48 hours, PNPLA3 mRNA levels were measured as previously described using the Human PNPLA3 primer-probe set RTS36070. PNPLA3 mRNA levels were adjusted according to total RNA content, as measured by RIBOGREEN®. The $IC_{50}$ ratios of the assays are presented in the tables below, which is the ratio of the $IC_{50}$ of a benchmark oligonucleotide to the $IC_{50}$ of the oligonucleotide. Hence, a bigger value of the ratio indicates that the oligonucleotide is more active than the benchmark.

TABLE XX

Efficacy of modified oligonucleotides targeting human PNPLA3

| Start Site | Stop Site | Compound Number | Chemistry | $IC_{50}$ ratio |
|---|---|---|---|---|
| 5600 | 5615 | 959437 | kkk-d10-kkk | 1.42 |
| 5601 | 5616 | 959438 | kkk-d10-kkk | 0.49 |
| 5602 | 5617 | 959439 | kkk-d10-kkk | 0.36 |
| 5603 | 5618 | 959440 | kkk-d10-kkk | 0.55 |
| 5603 | 5618 | 995906 | kk-d9-eeekk | 1.42 |
| 5604 | 5619 | 959441 | kkk-d10-kkk | 1.66 |
| 5605 | 5620 | 916333 | kkk-d10-kkk | 1.96 |
| 5605 | 5620 | 995908 | kk-d9-eeekk | 0.70 |
| 5606 | 5621 | 916334 | kkk-d10-kkk | 0.95 |
| 5606 | 5621 | 995909 | kk-d9-eeekk | 1.47 |

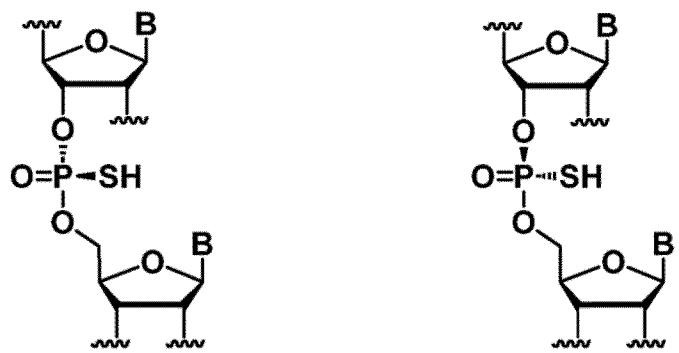

What is claimed:

1. A compound comprising a modified oligonucleotide 16 to 30 linked nucleosides in length having a nucleobase sequence comprising the nucleobase sequence SEQ ID NO: 1089, or a pharmaceutically acceptable salt thereof.

2. The compound of claim 1, wherein the modified oligonucleotide is 16 linked nucleosides having a nucleobase sequence comprising the nucleobase sequence SEQ ID NO: 1089, or a pharmaceutically acceptable salt thereof.

3. The compound of claim 1, wherein the modified oligonucleotide comprises at least one modified internucleoside linkage, and/or at least one modified sugar, and/or at least one modified nucleobase.

4. The compound of claim 3, wherein the at least one modified internucleoside linkage is a phosphorothioate internucleoside linkage.

5. The compound of claim 3, wherein the at least one modified sugar is a bicyclic sugar.

6. The compound of claim 5, wherein the bicyclic sugar comprises a
a 4'-$CH_2$—O—2' group or a 4'-$CH(CH_3)$—O—2' group or a 4'-$(CH_2)_2$—O-2' group.

7. The compound of claim 3, wherein the at least one modified sugar comprises a 2'-O$(CH)_2$—$OCH_3$ group or a 2'-O—$CH_3$ group.

8. The compound of claim 3, wherein the at least one modified nucleobase is a 5-methylcytosine.

9. The compound of claim 1, wherein the modified oligonucleotide comprises:
a gap segment consisting of ten linked deoxynucleosides;
a 5' wing segment consisting of three linked nucleosides; and
a 3' wing segment consisting of three linked nucleosides; and
wherein the gap segment is positioned between the 5' wing segment and the 3' wing segment, wherein each nucleoside of each wing segment comprises a cEt sugar; wherein each internucleoside linkage is a phosphorothioate linkage; wherein each cytosine is a 5-methylcytosine.

10. The compound of claim 1, wherein the compound further comprises a conjugate group.

11. The compound of claim 10, wherein the conjugate group is positioned at the 5'end of the modified oligonucleotide and is

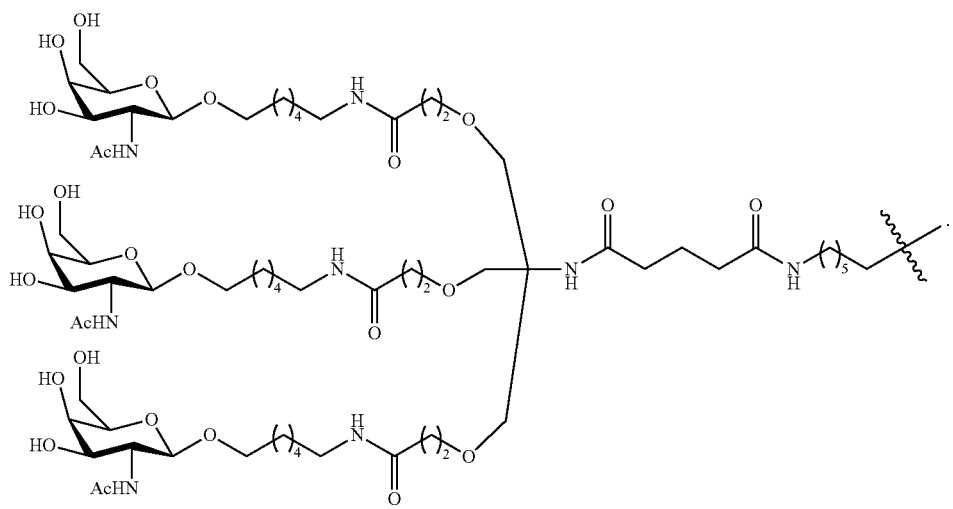
12. The compound of claim 1, wherein the pharmaceutically acceptable salt is a sodium salt.
13. The compound of claim 1, wherein the pharmaceutically acceptable salt is a potassium salt.
14. A composition comprising the compound of claim 1 and a pharmaceutically acceptable carrier.
* * * * *

UNITED STATES PATENT AND TRADEMARK OFFICE
CERTIFICATE OF CORRECTION

PATENT NO. : 11,781,143 B2
APPLICATION NO. : 16/936060
DATED : October 10, 2023
INVENTOR(S) : Susan M. Freier and Huynh-Hoa Bui Page 1 of 46

It is certified that error appears in the above-identified patent and that said Letters Patent is hereby corrected as shown below:

In the Specification

In Columns 15-16, please delete the structure:

"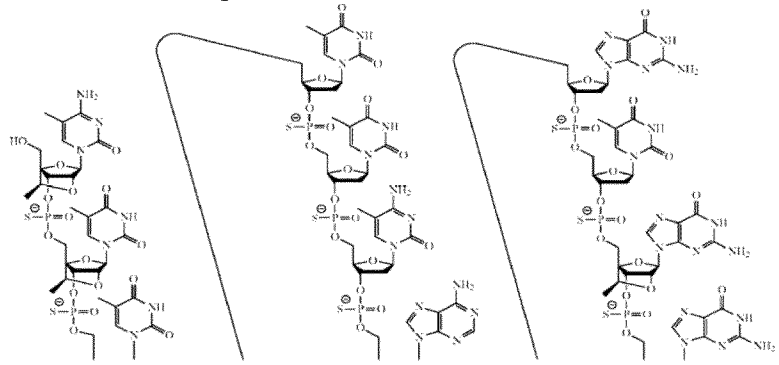

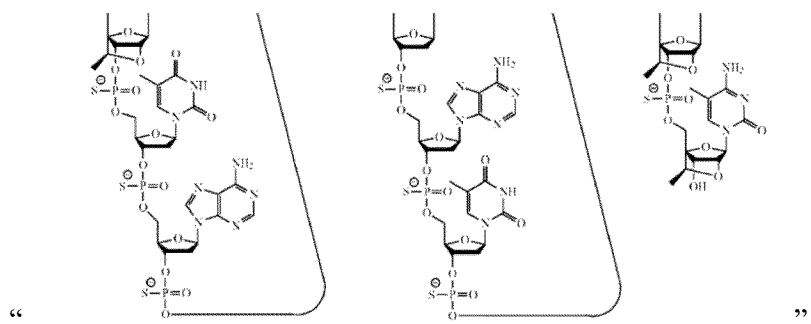"

Signed and Sealed this
Twenty-ninth Day of October, 2024

Katherine Kelly Vidal
*Director of the United States Patent and Trademark Office*

And replace with the correct structure:
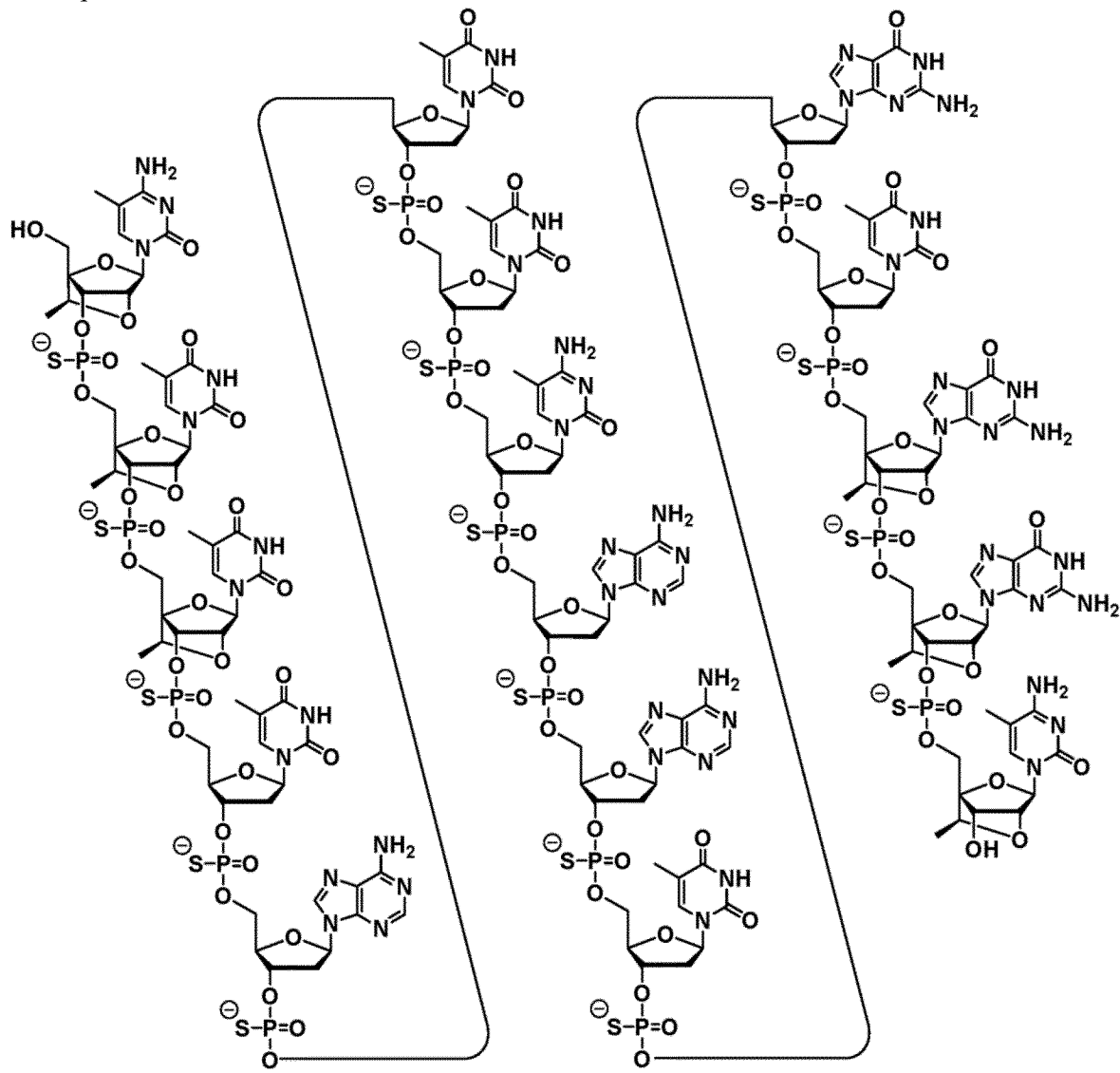

CERTIFICATE OF CORRECTION (continued)
U.S. Pat. No. 11,781,143 B2

In Columns 17-18, please delete the structure:

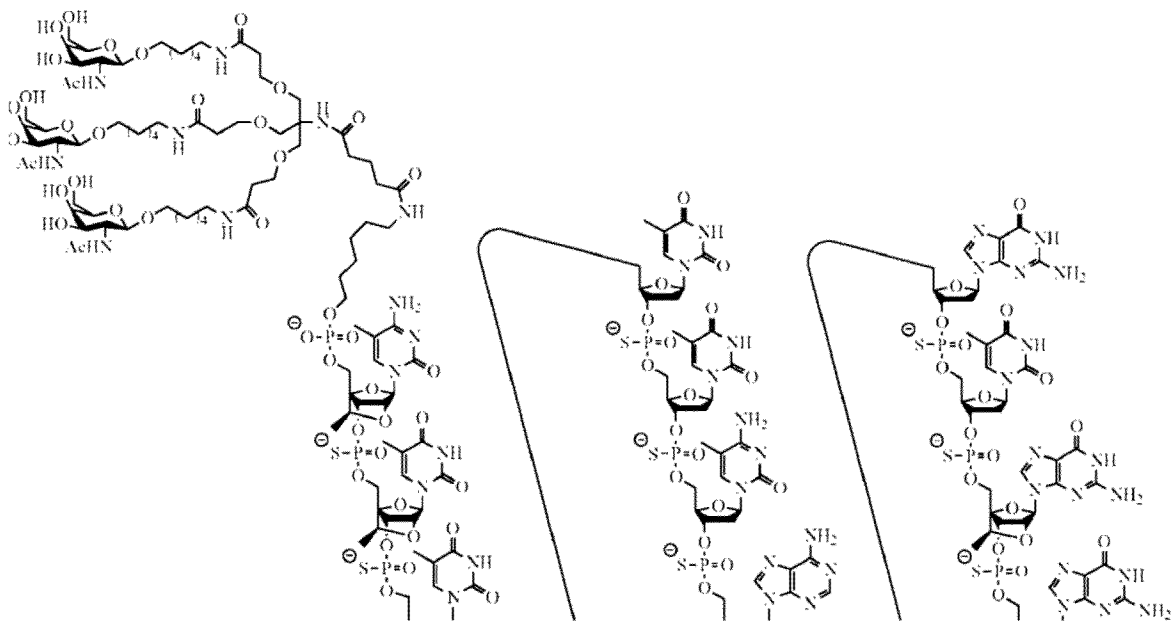

"

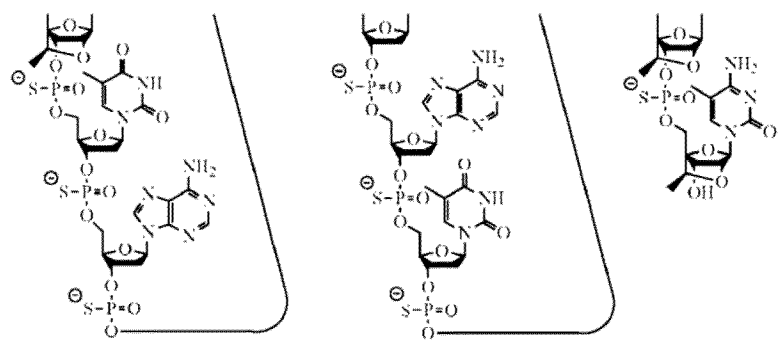

"

CERTIFICATE OF CORRECTION (continued)
U.S. Pat. No. 11,781,143 B2

And replace with the correct structure:

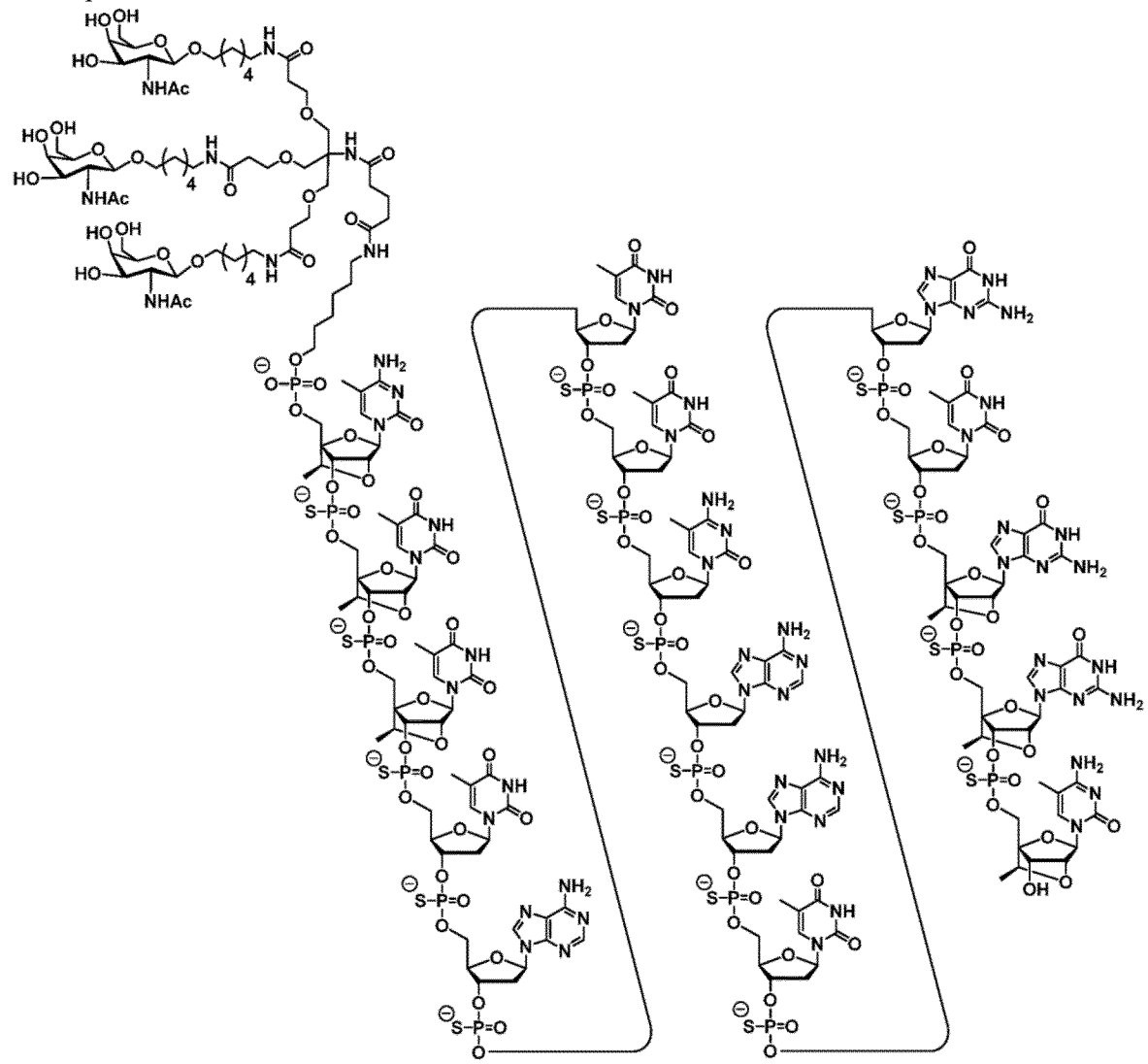

CERTIFICATE OF CORRECTION (continued)
U.S. Pat. No. 11,781,143 B2

In Columns 19-20, please delete the structure:

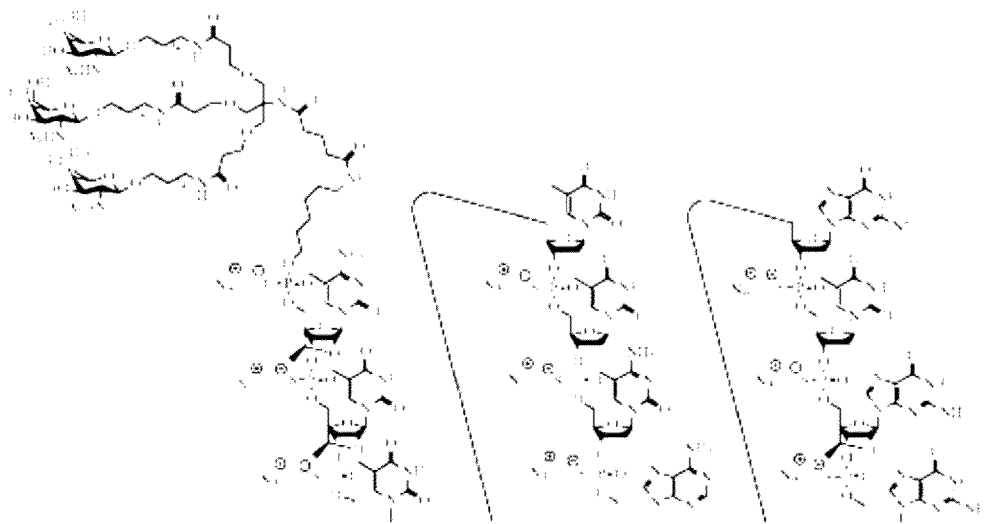

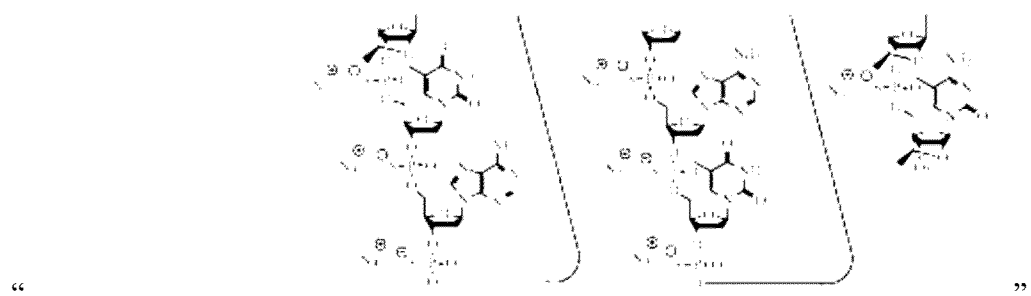

"                                                                                "

And replace with the correct structure:
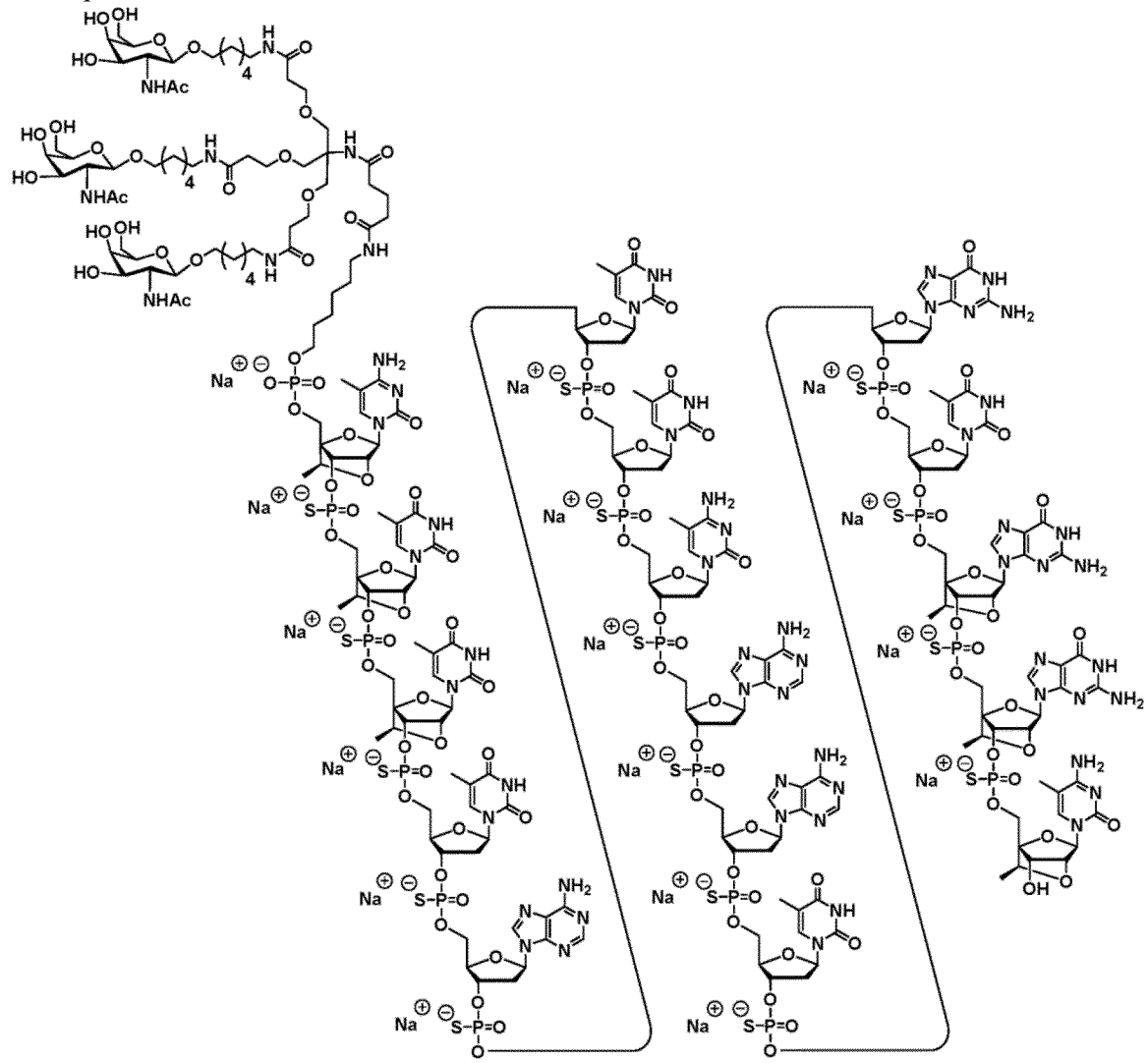

CERTIFICATE OF CORRECTION (continued)
U.S. Pat. No. 11,781,143 B2

In Columns 21-22, please delete the structure:

"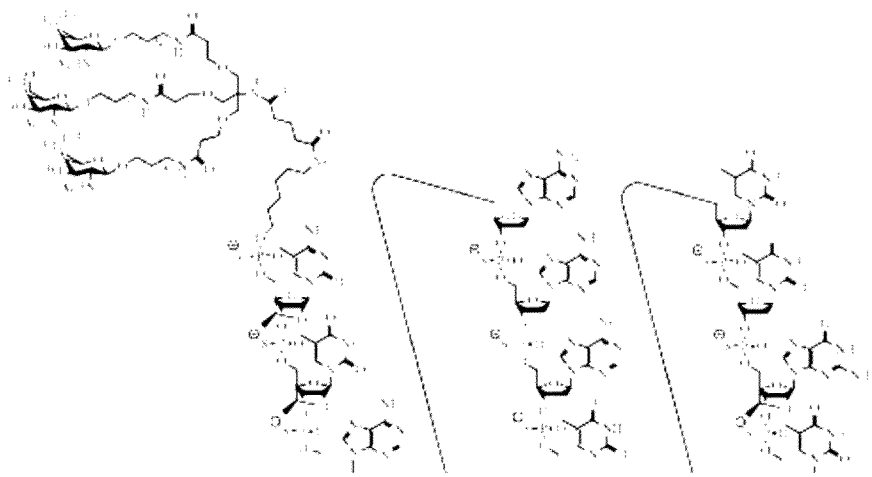

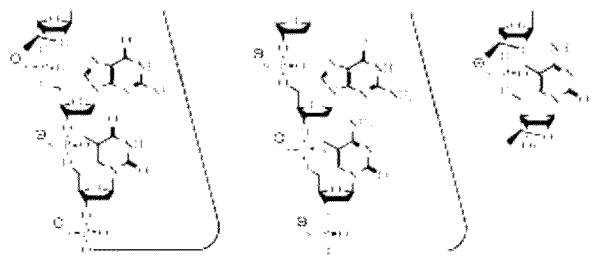"

And replace with the correct structure:
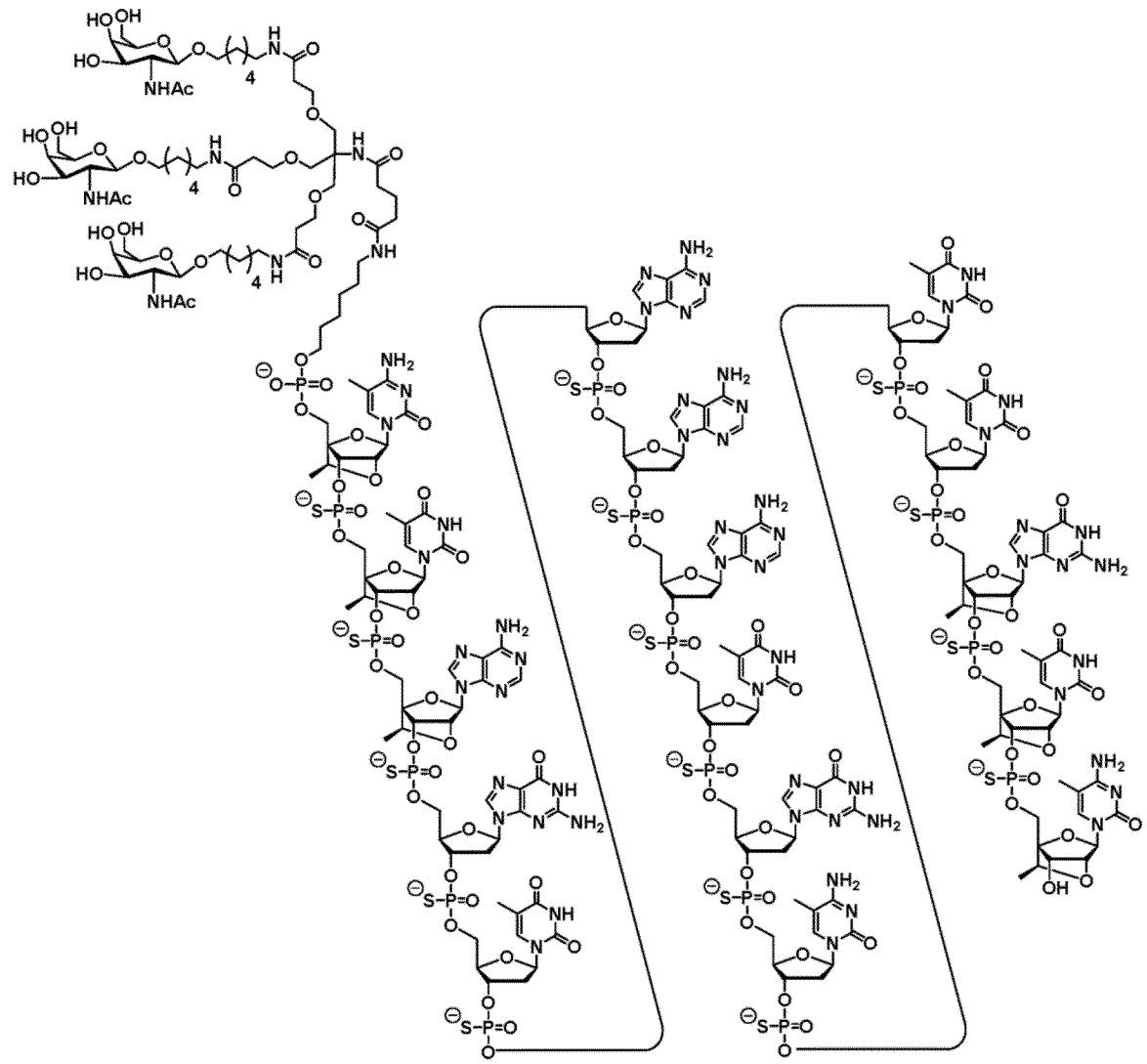

In Columns 23-24, please delete the structure:
"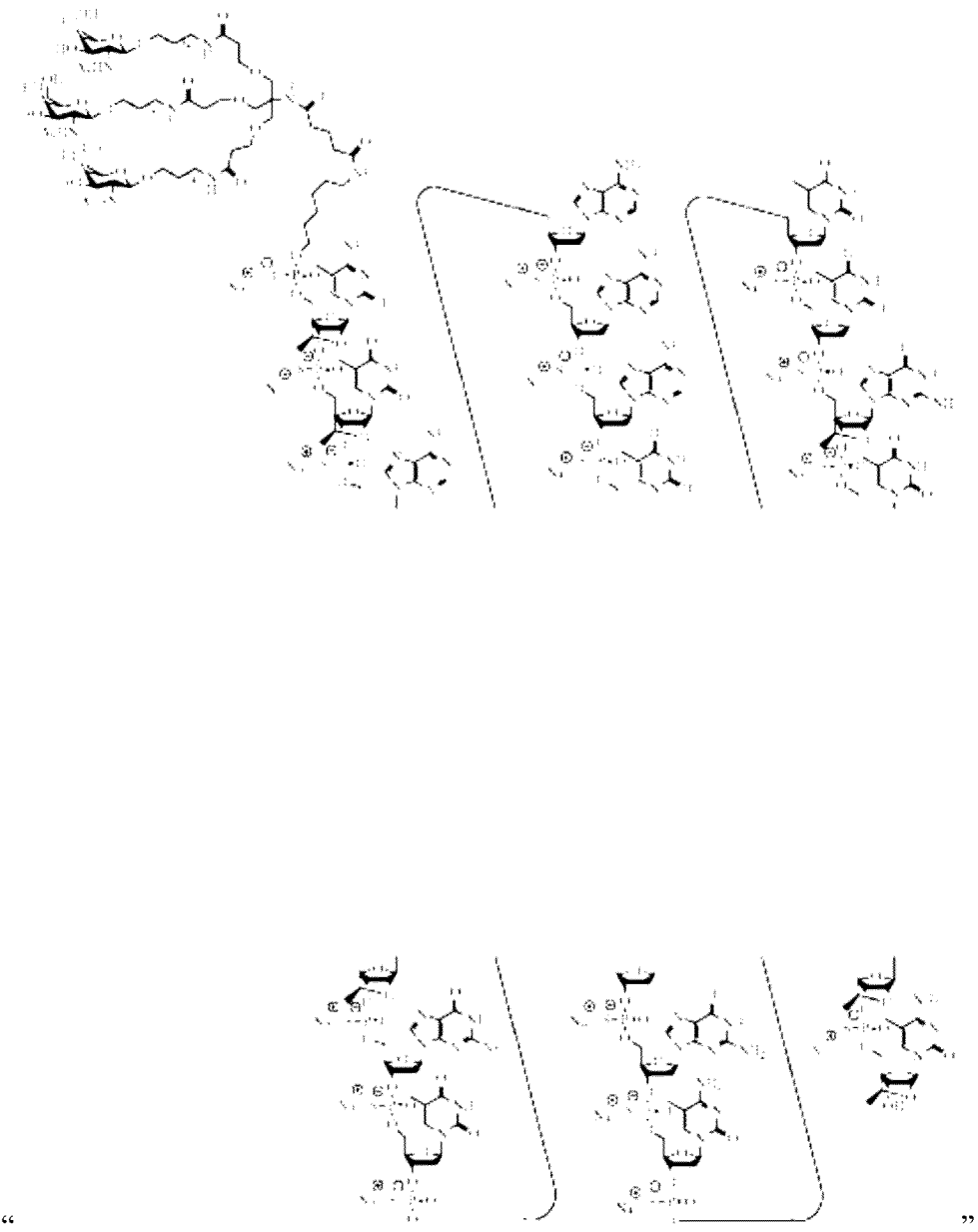"

And replace with the correct structure:
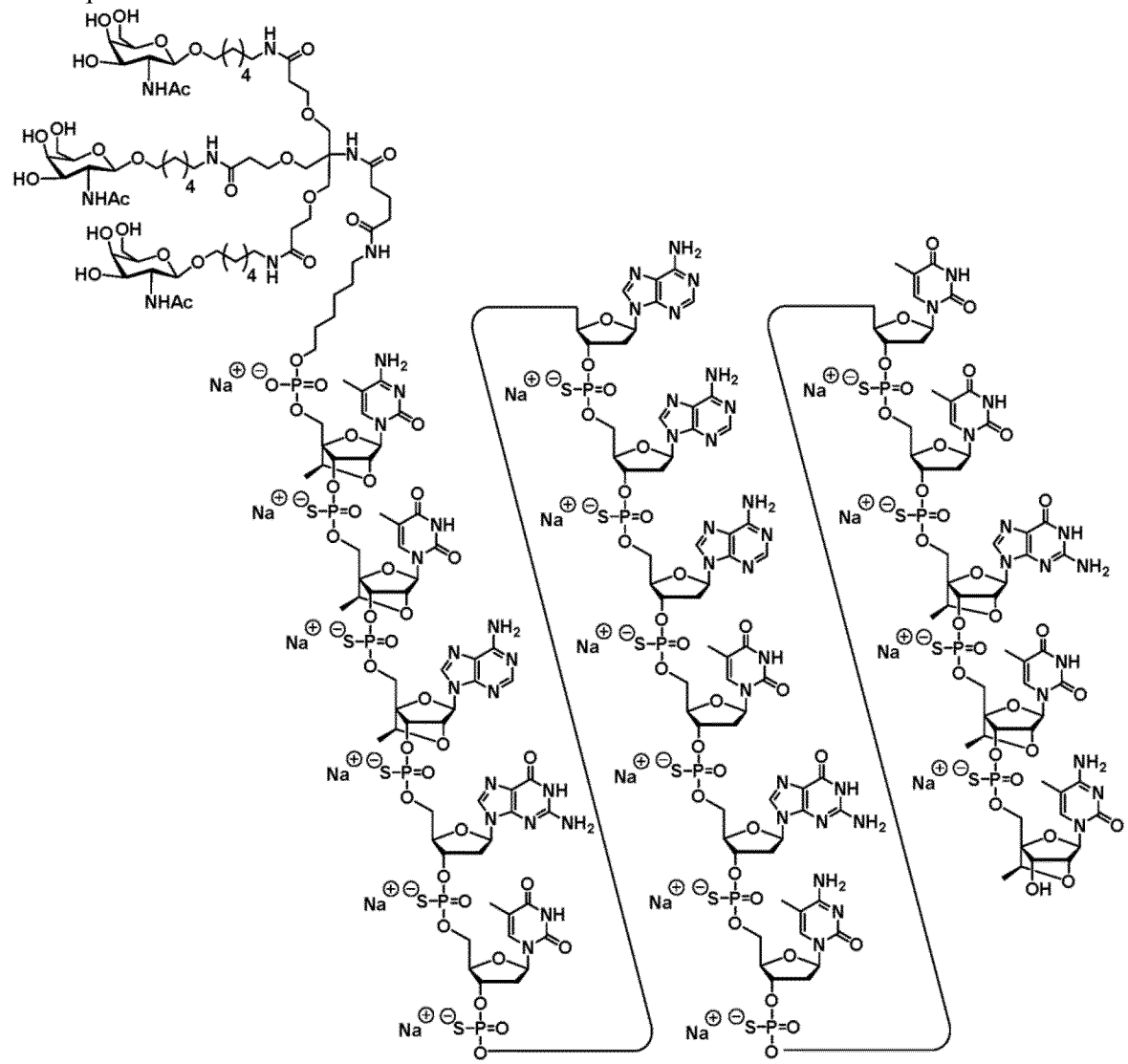

In Columns 25-26, please delete the structure:
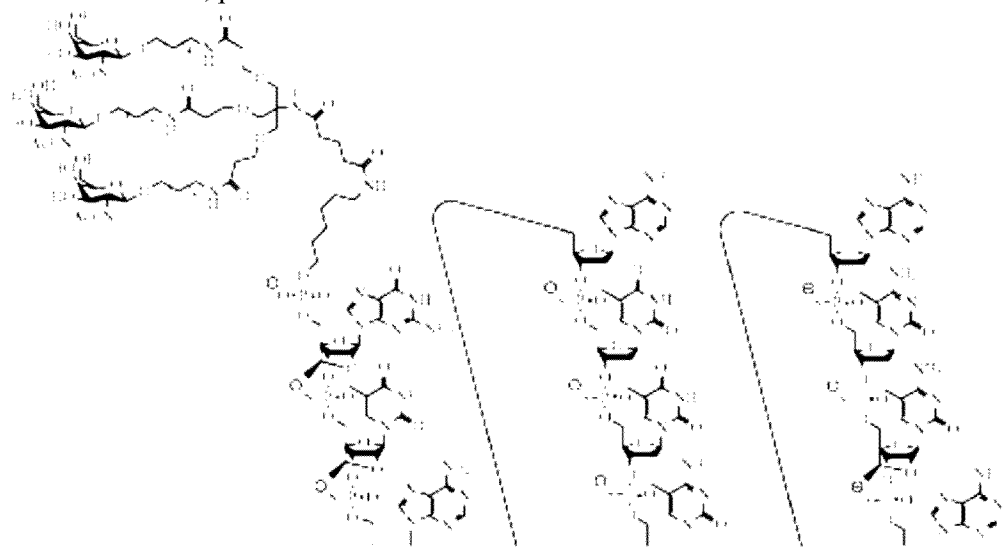
"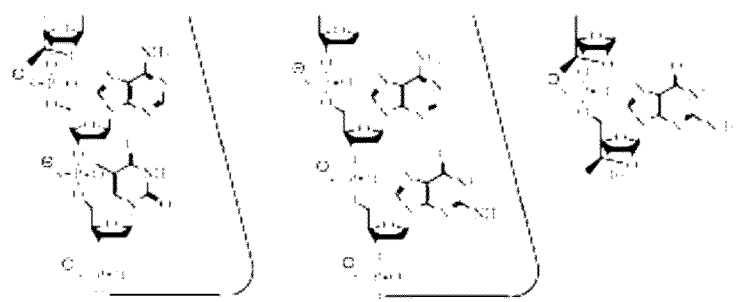"

And replace with the correct structure:
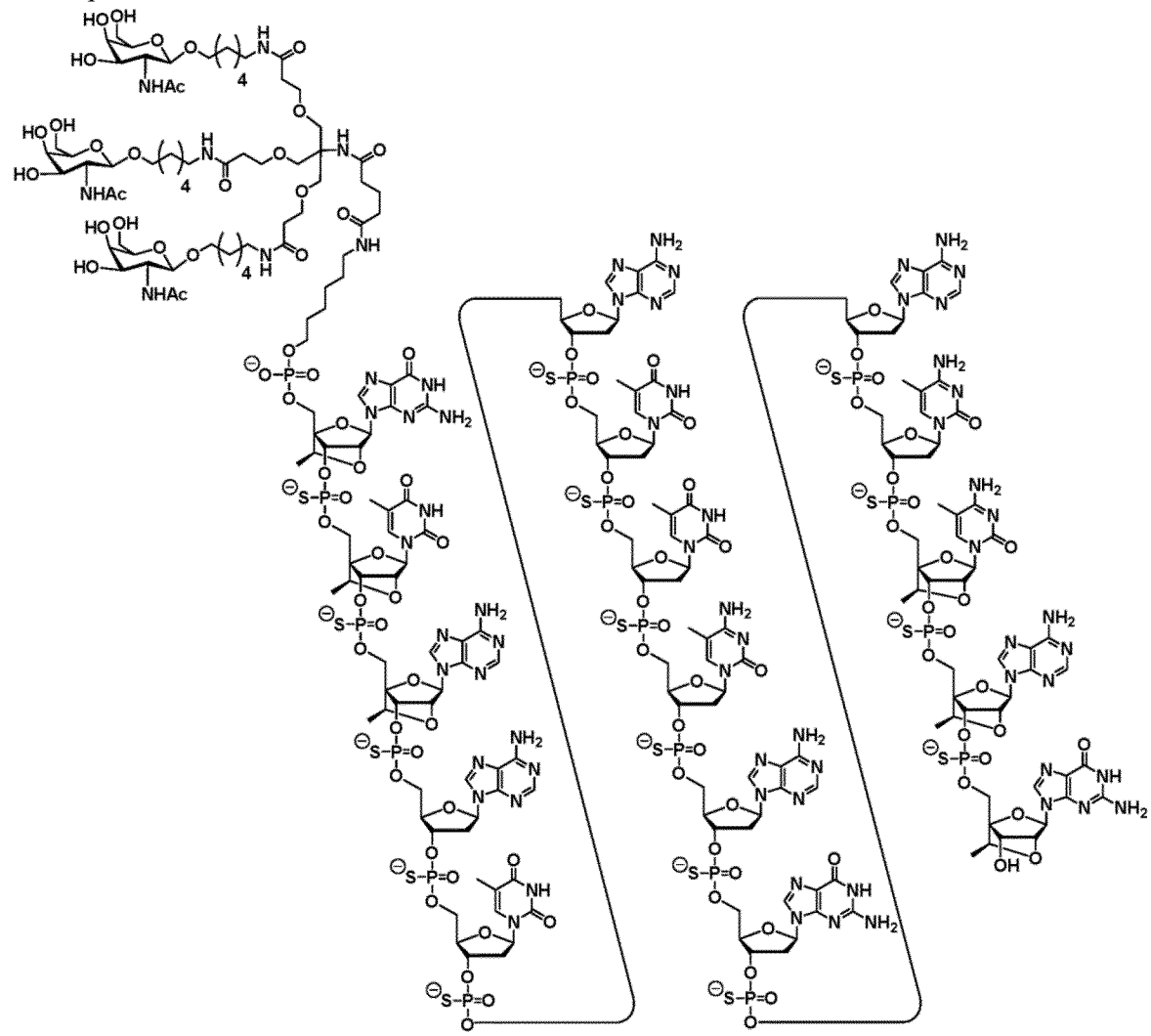

In Columns 27-28, please delete the structure:
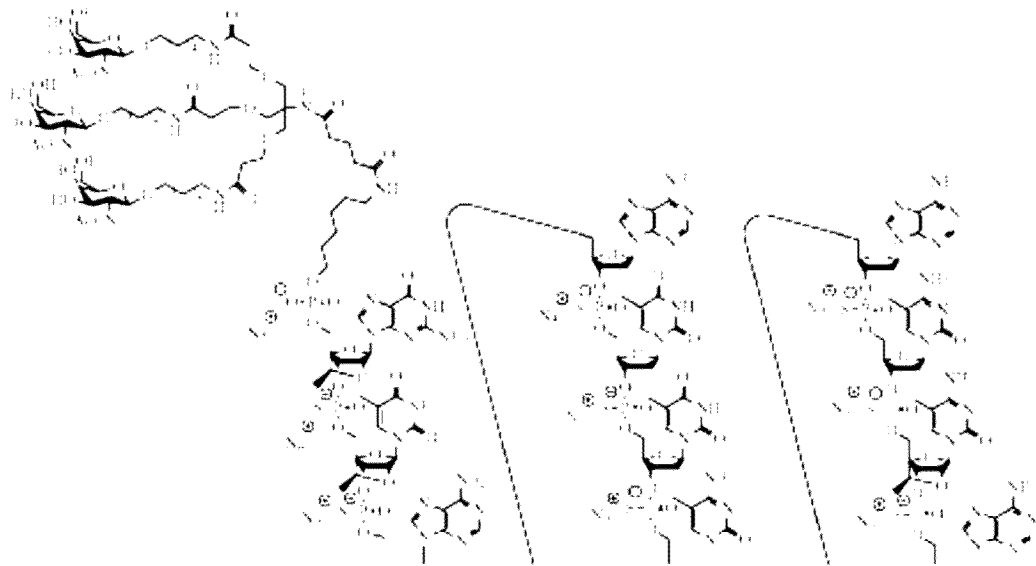
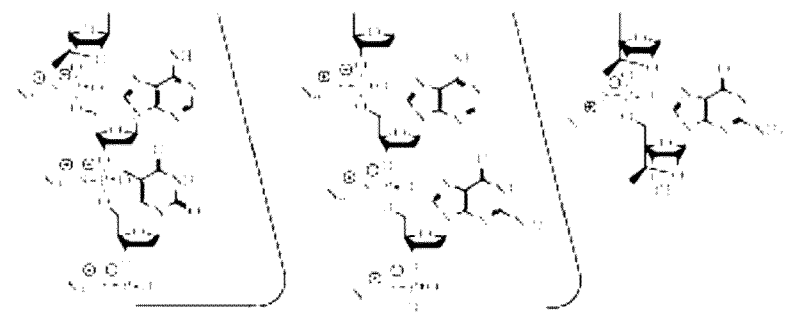

And replace with the correct structure:
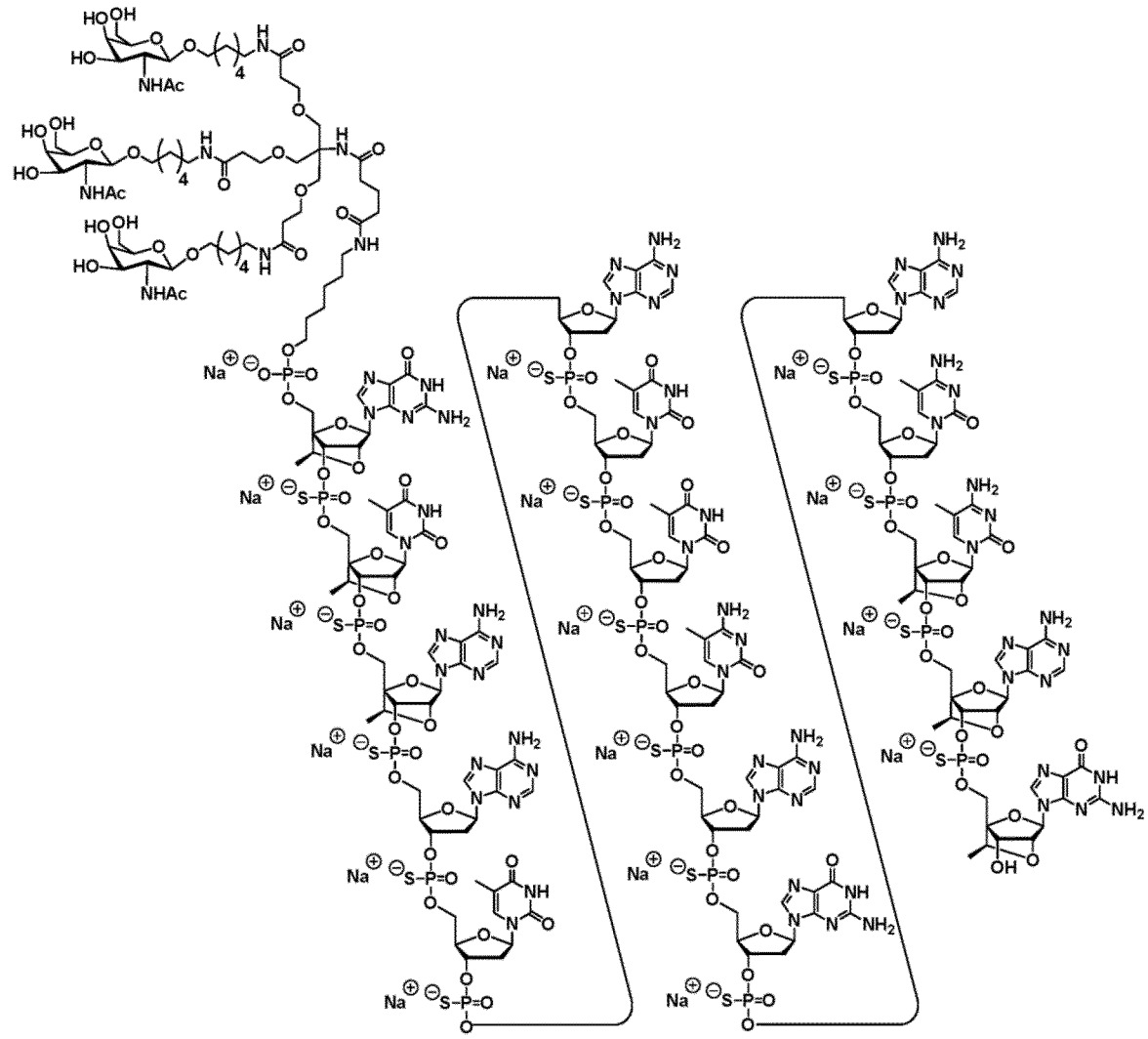

CERTIFICATE OF CORRECTION (continued)
U.S. Pat. No. 11,781,143 B2

In Columns 29-30, please delete the structure:

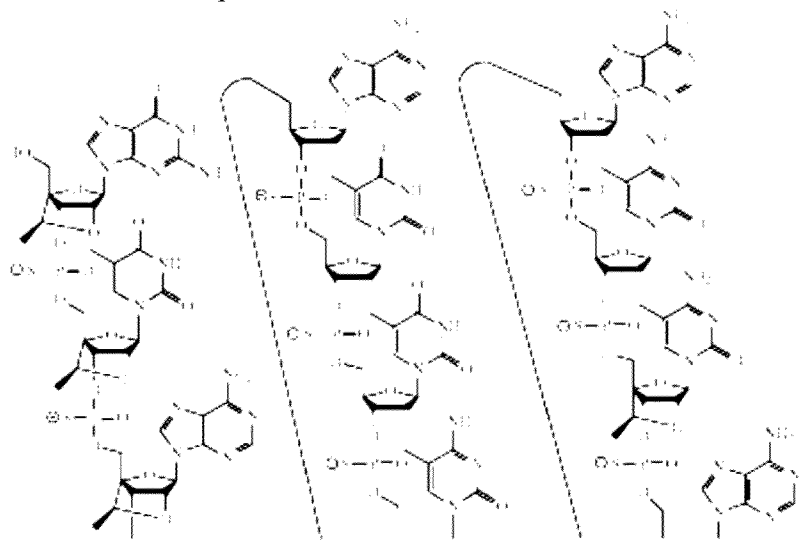

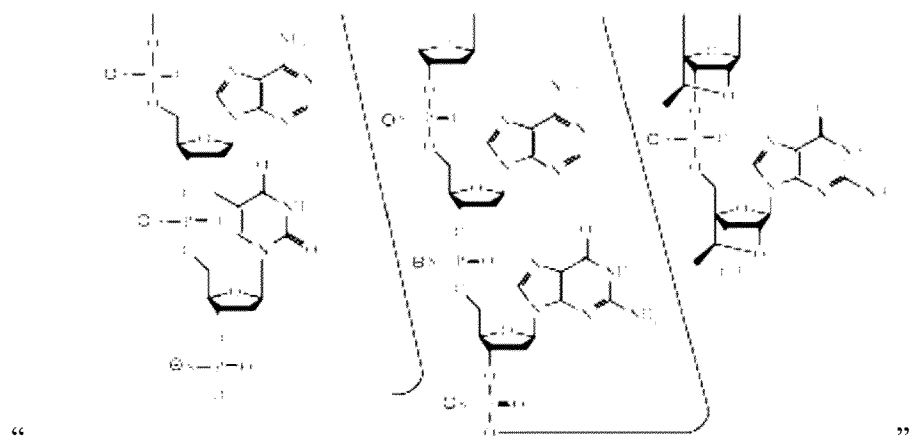

And replace with the correct structure:
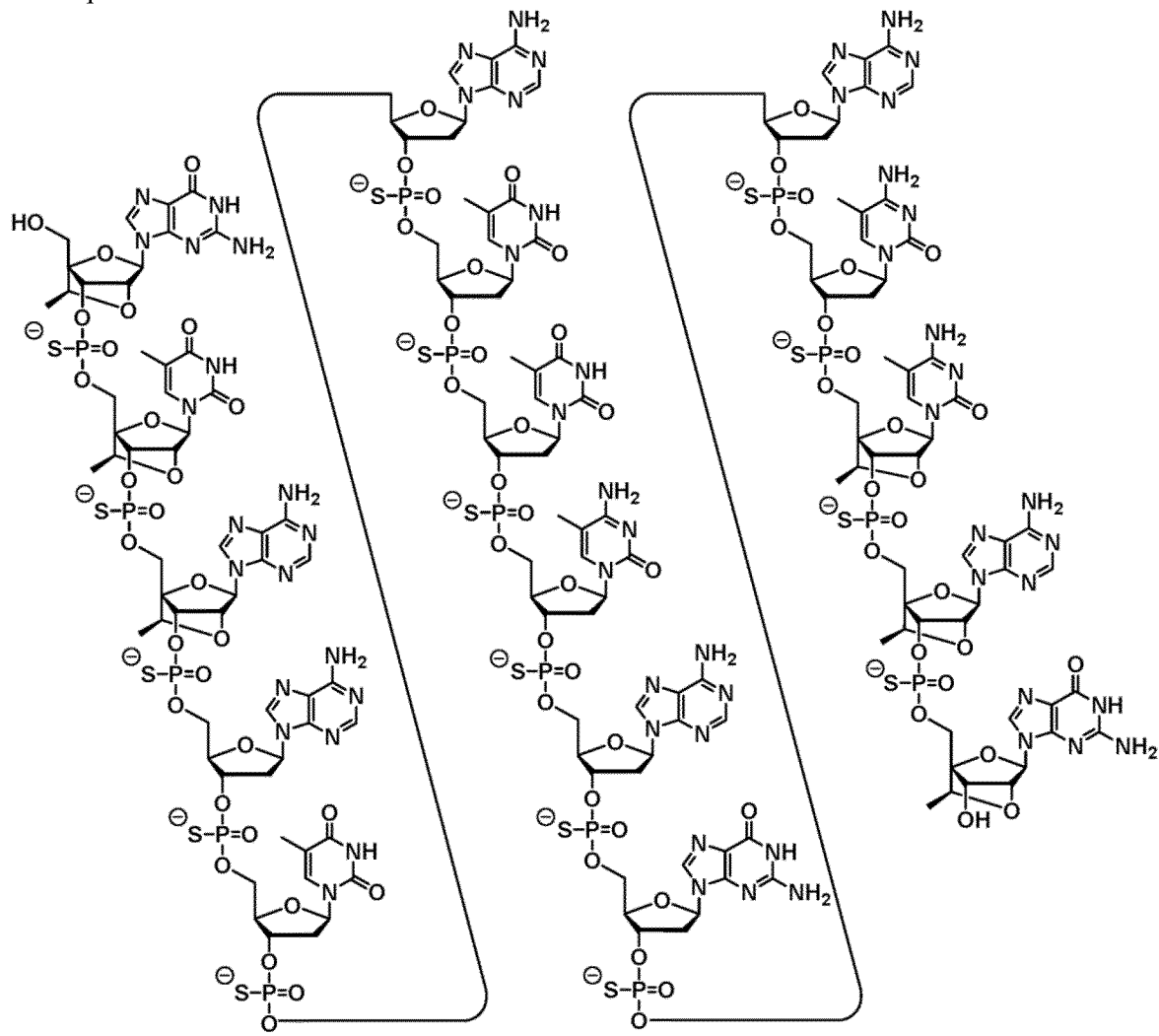

CERTIFICATE OF CORRECTION (continued)
U.S. Pat. No. 11,781,143 B2

In Columns 31-32, please delete the text and structure:
"In certain embodiments, a compound comprises or consists of the sodium salt of 916789, having the following chemical structure (SEQ ID NO: 330):

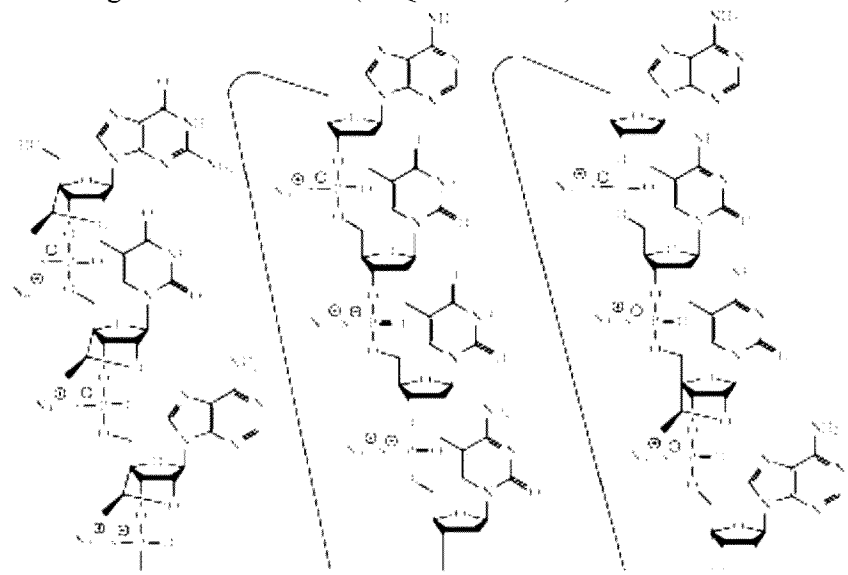

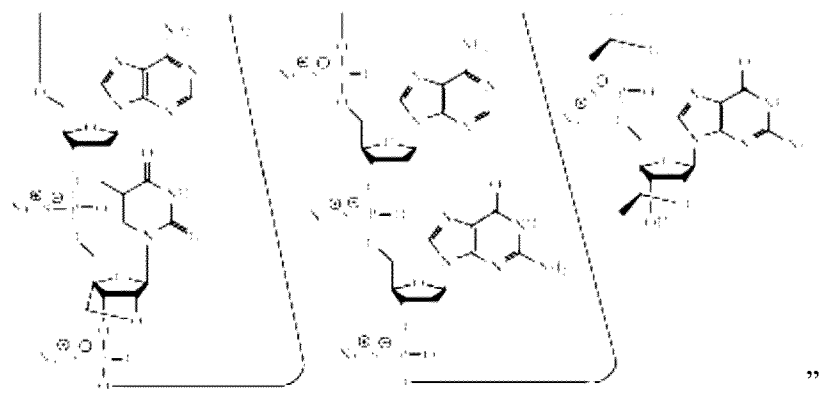

"

And replace with the correct text and structure:

In certain embodiments, a compound comprises or consists of the sodium salt of 916789, having the following chemical structure (SEQ ID NO: 899):
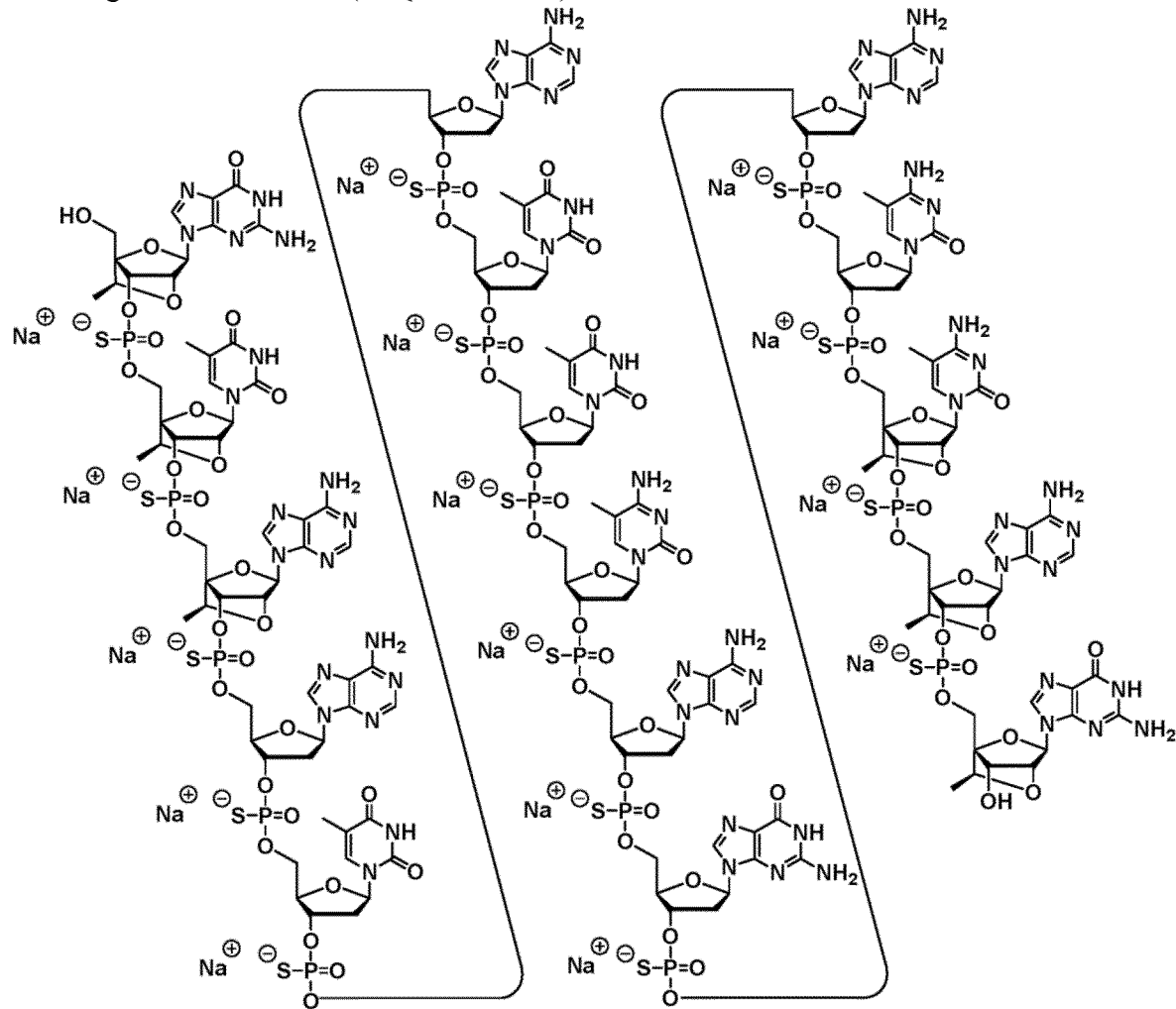
In Columns 33-34, please delete the text and structure:

"In certain embodiments, a compound comprises or consists of the sodium salt of 916789, having the following chemical structure (SEQ ID NO: 330):
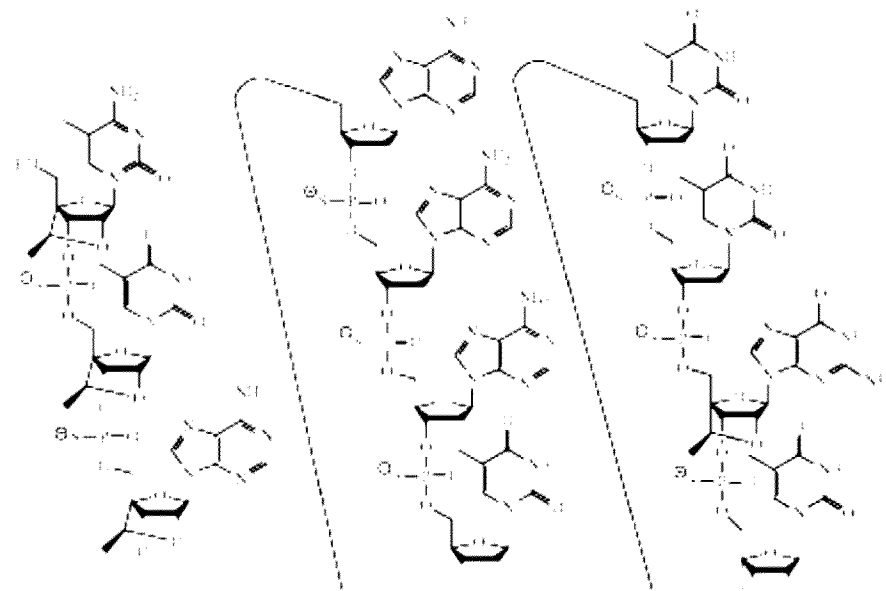
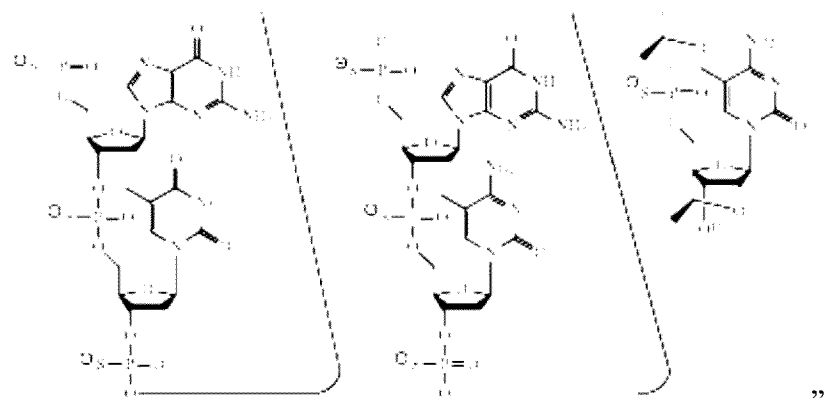
"
And replace with the correct text and structure:

In certain embodiments, a compound comprises or consists of ION 916603 or salt thereof, having the following chemical structure (SEQ ID NO: 330):
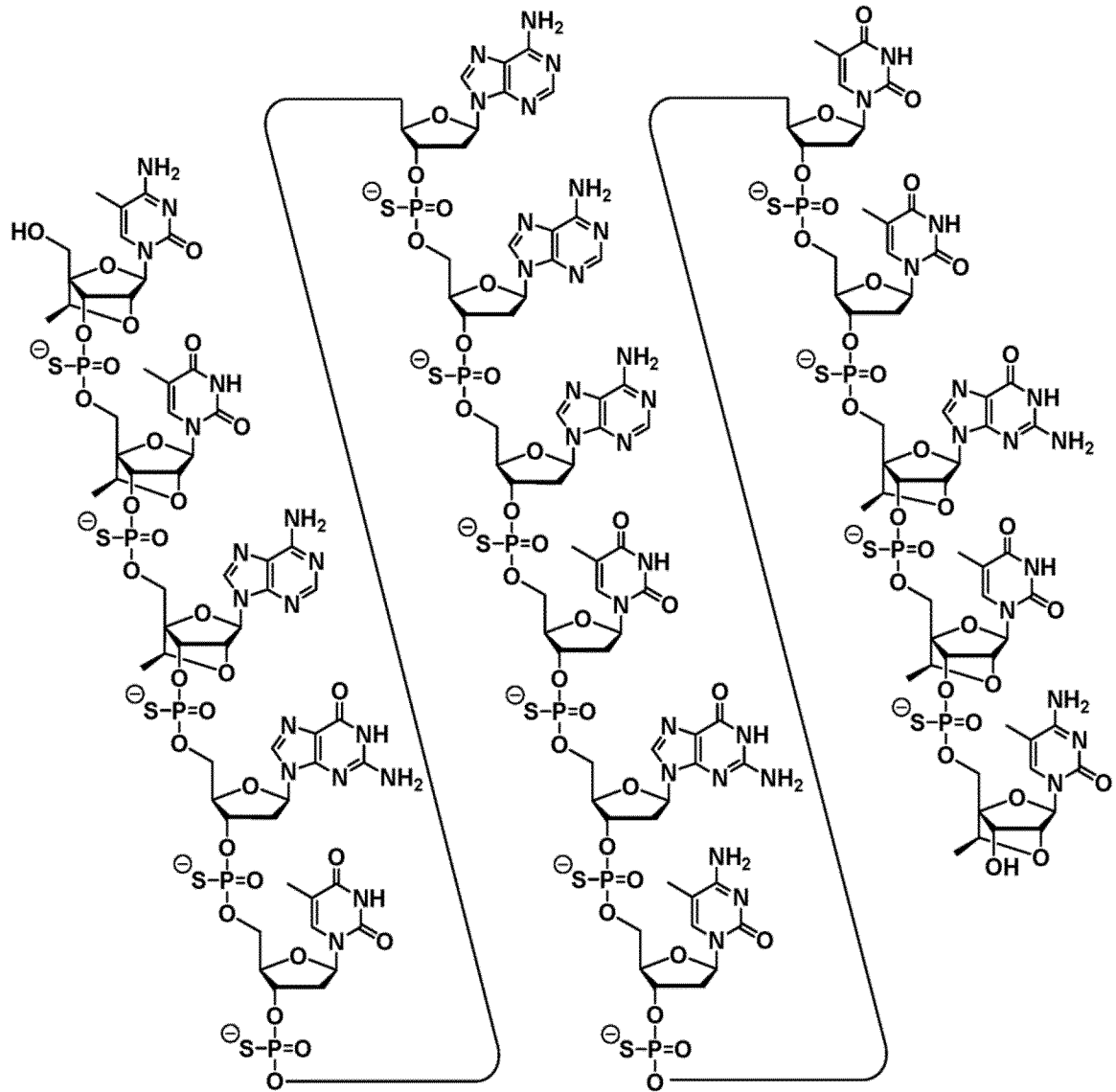
In Columns 35-36, please delete the structure:

CERTIFICATE OF CORRECTION (continued)
U.S. Pat. No. 11,781,143 B2

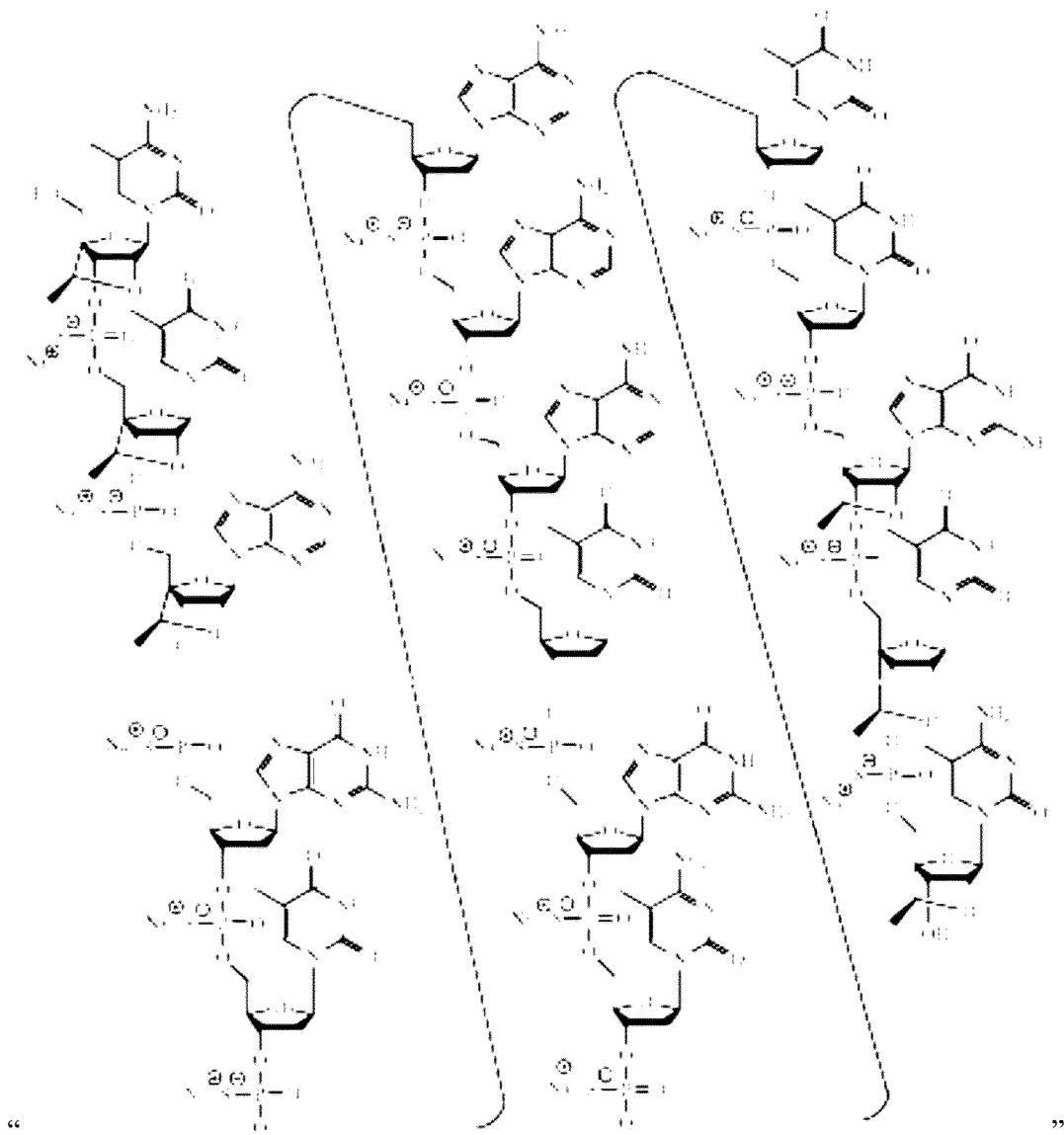

And replace with the correct structure:

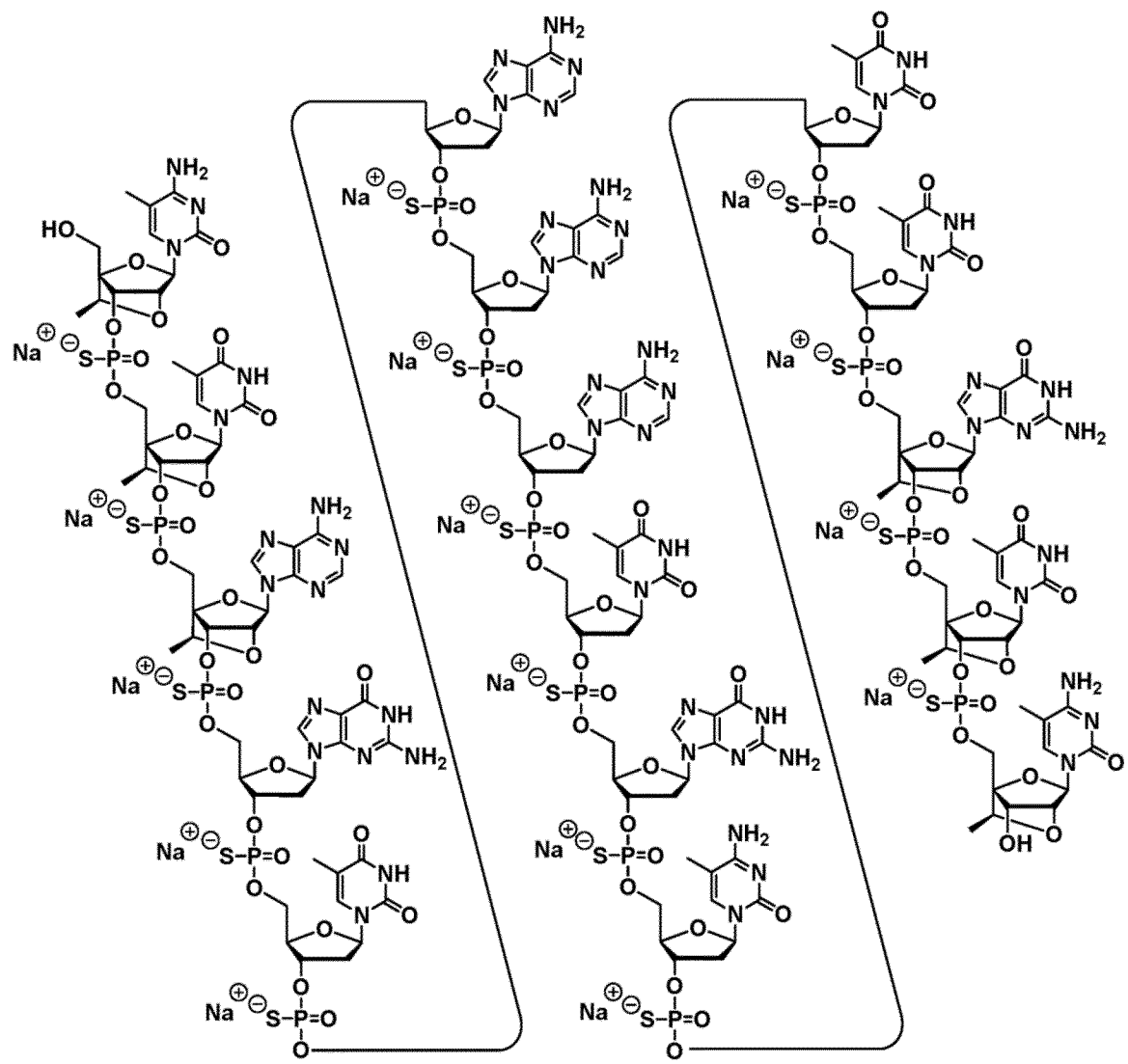
In Columns 45-46, please delete the structure:

"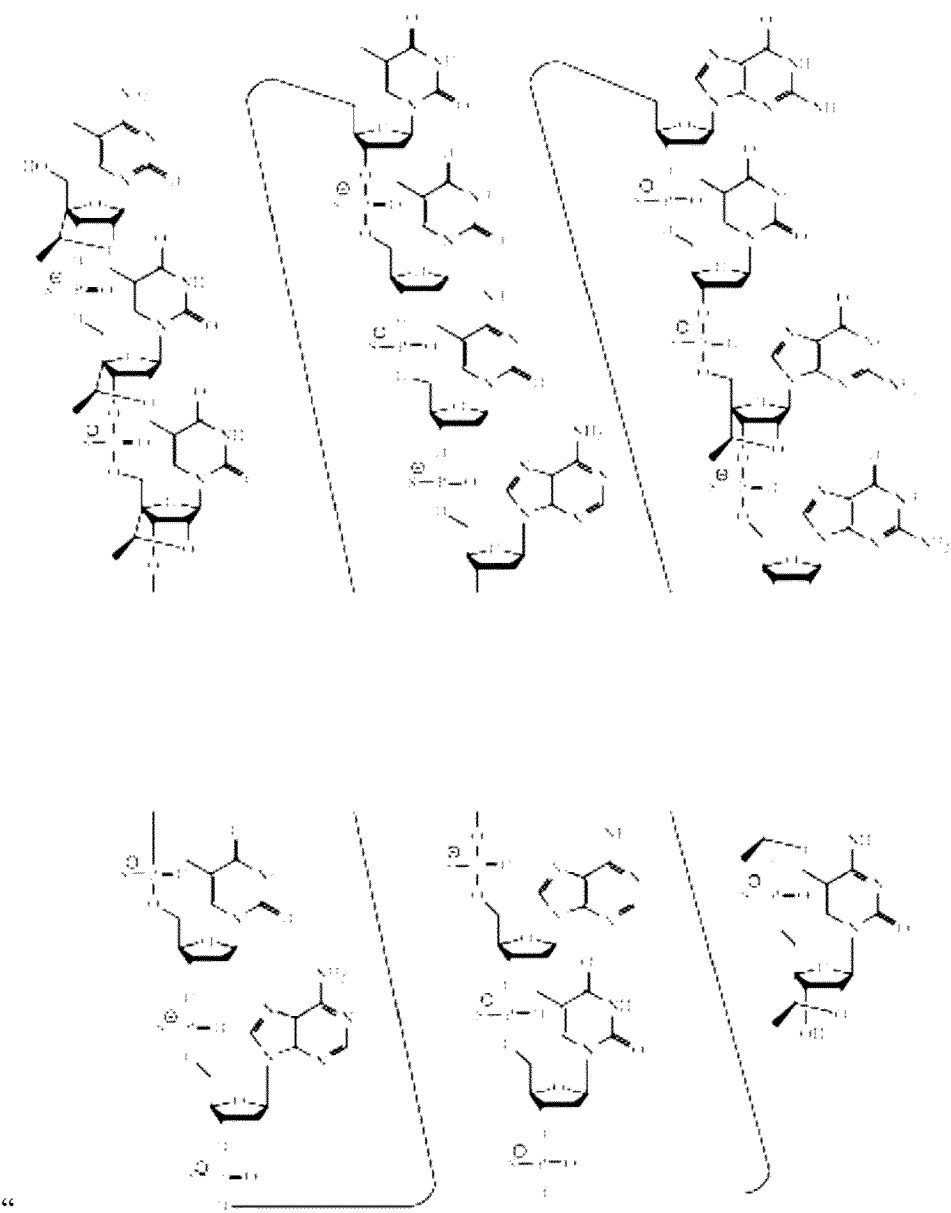"
And replace with the correct structure:

CERTIFICATE OF CORRECTION (continued)
U.S. Pat. No. 11,781,143 B2

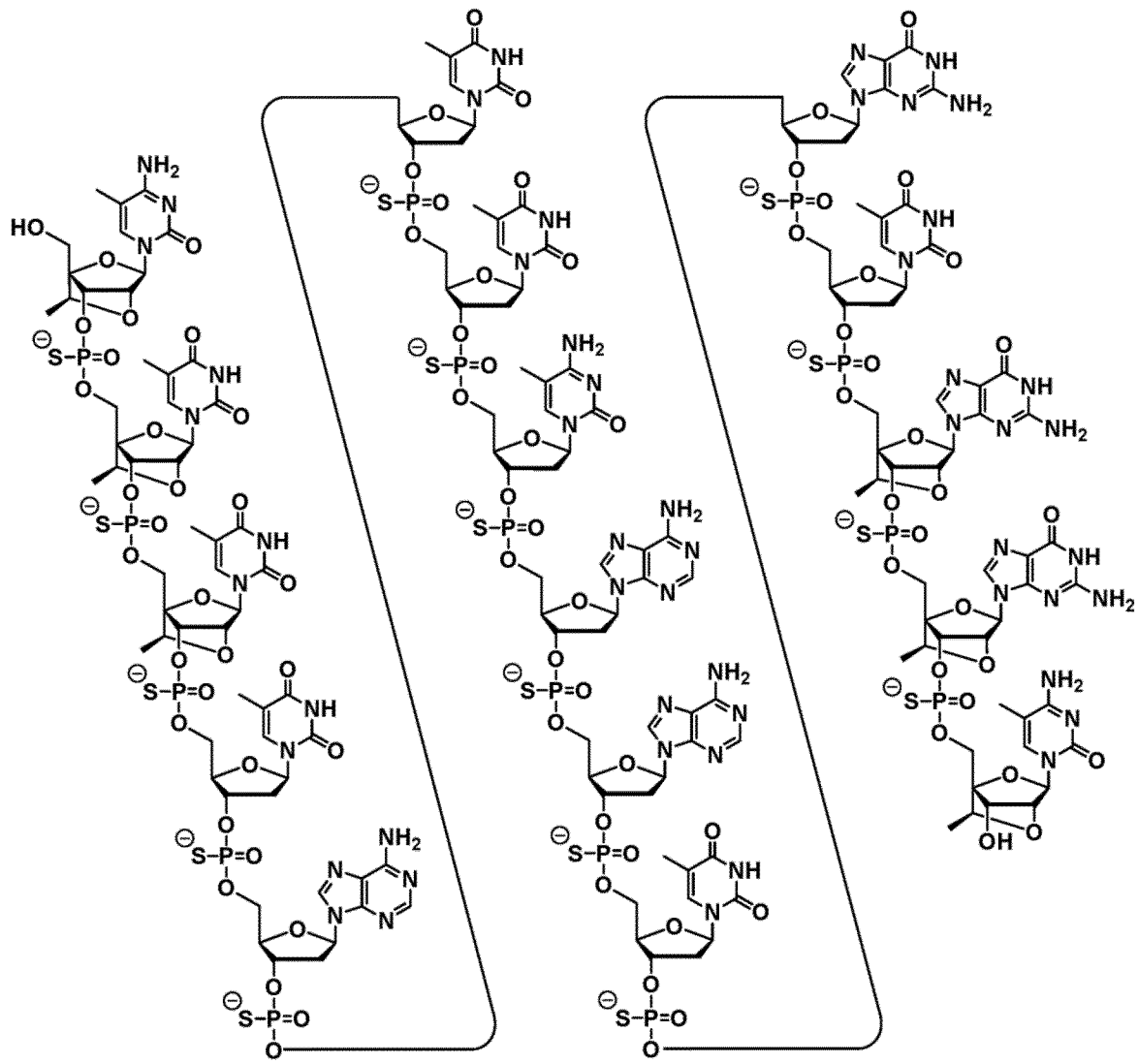

In Column 47-48, please delete the structure:

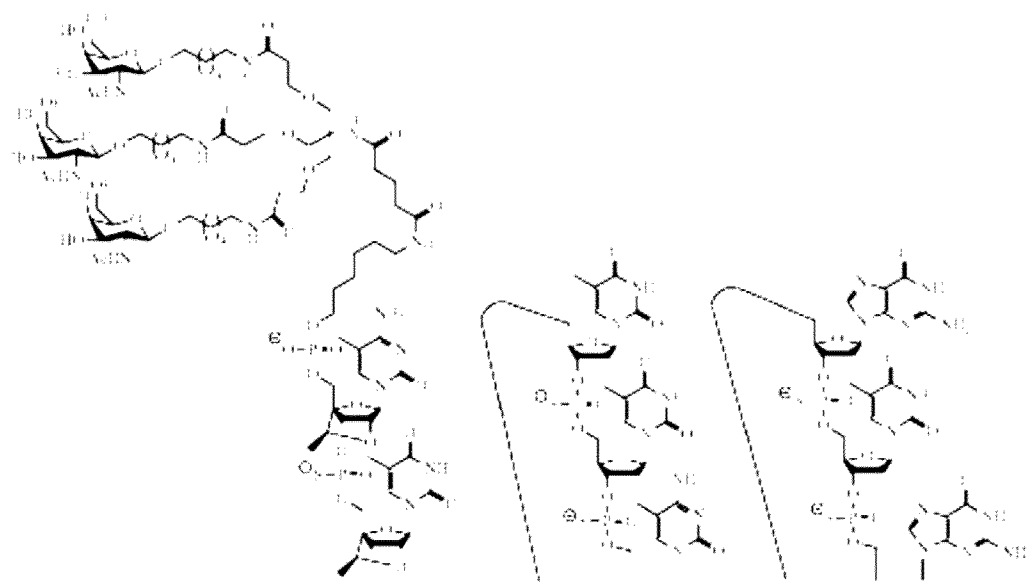
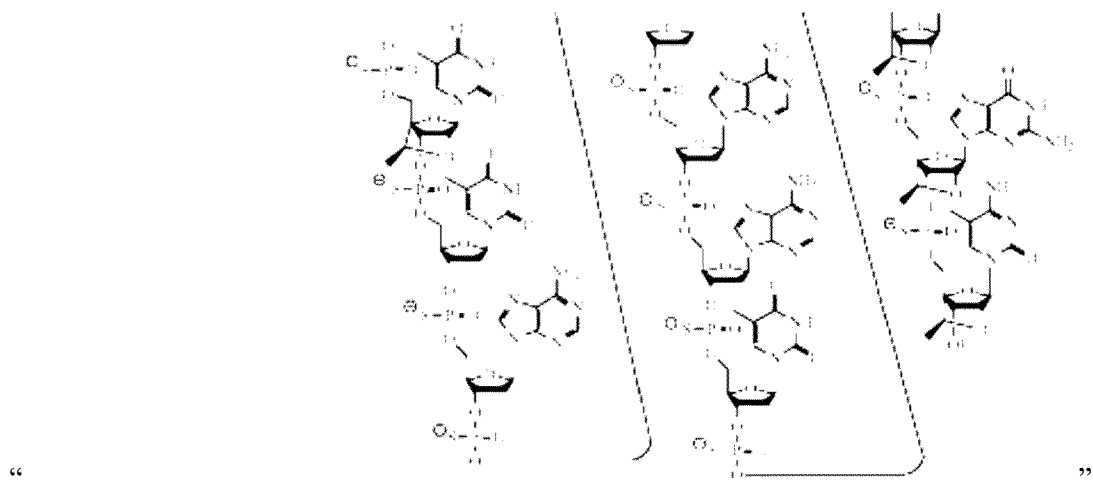
"                                                                                              "
And replace with the correct structure:

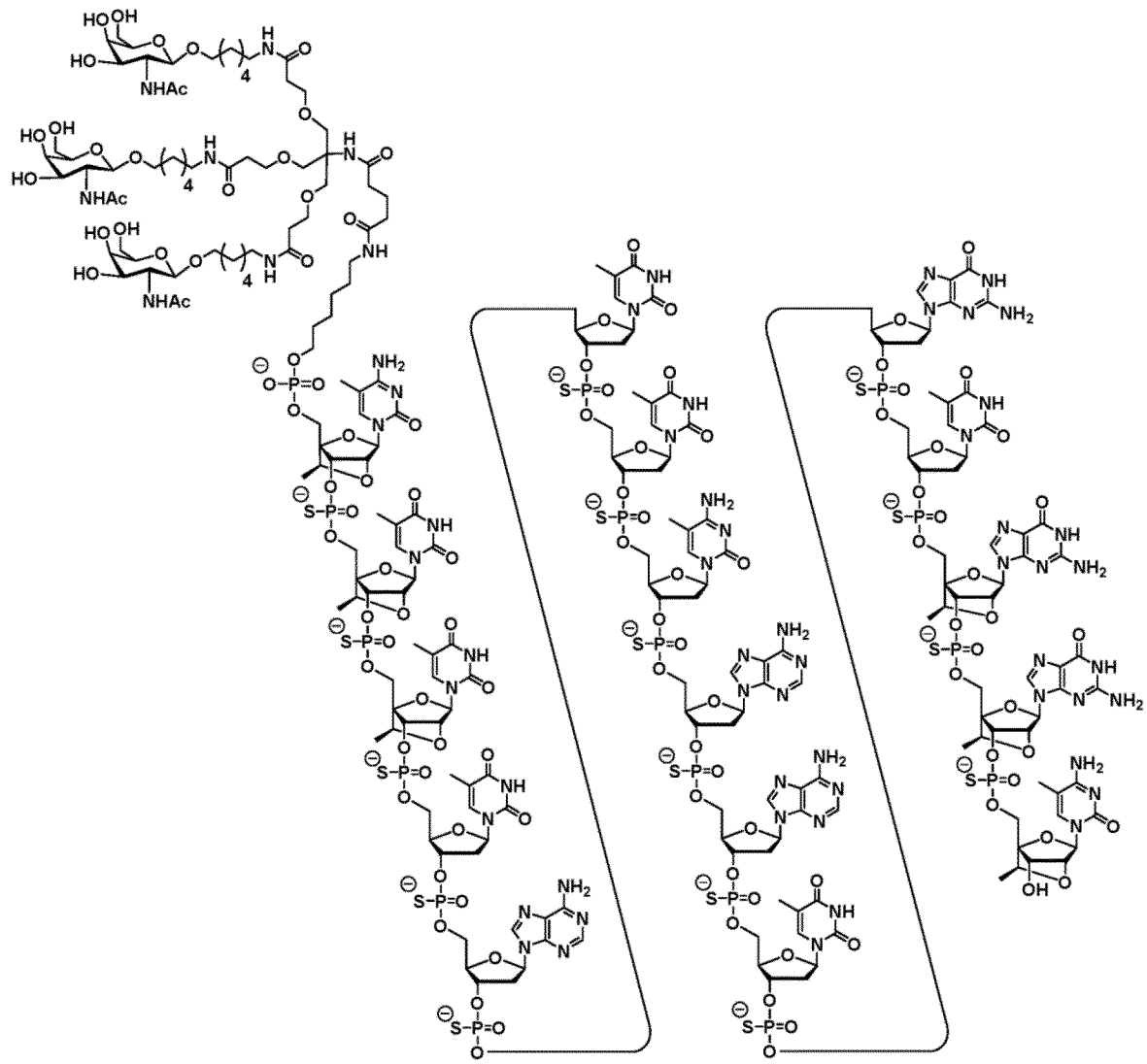
In Columns 49-50, please delete the structure:

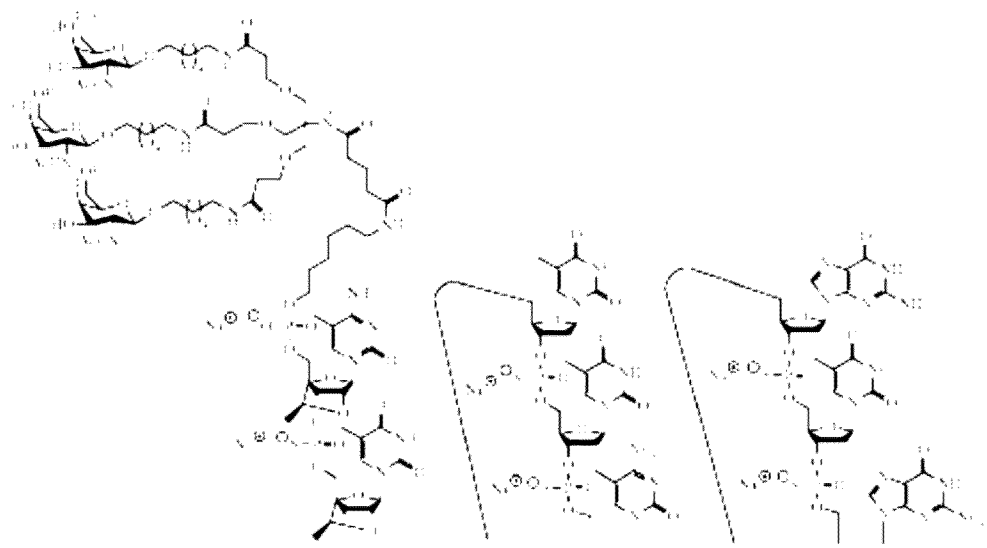
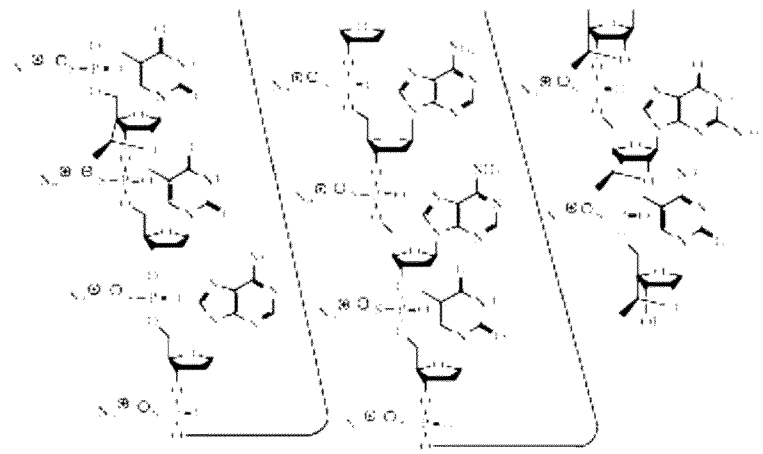
And replace with the correct structure:

CERTIFICATE OF CORRECTION (continued)
U.S. Pat. No. 11,781,143 B2

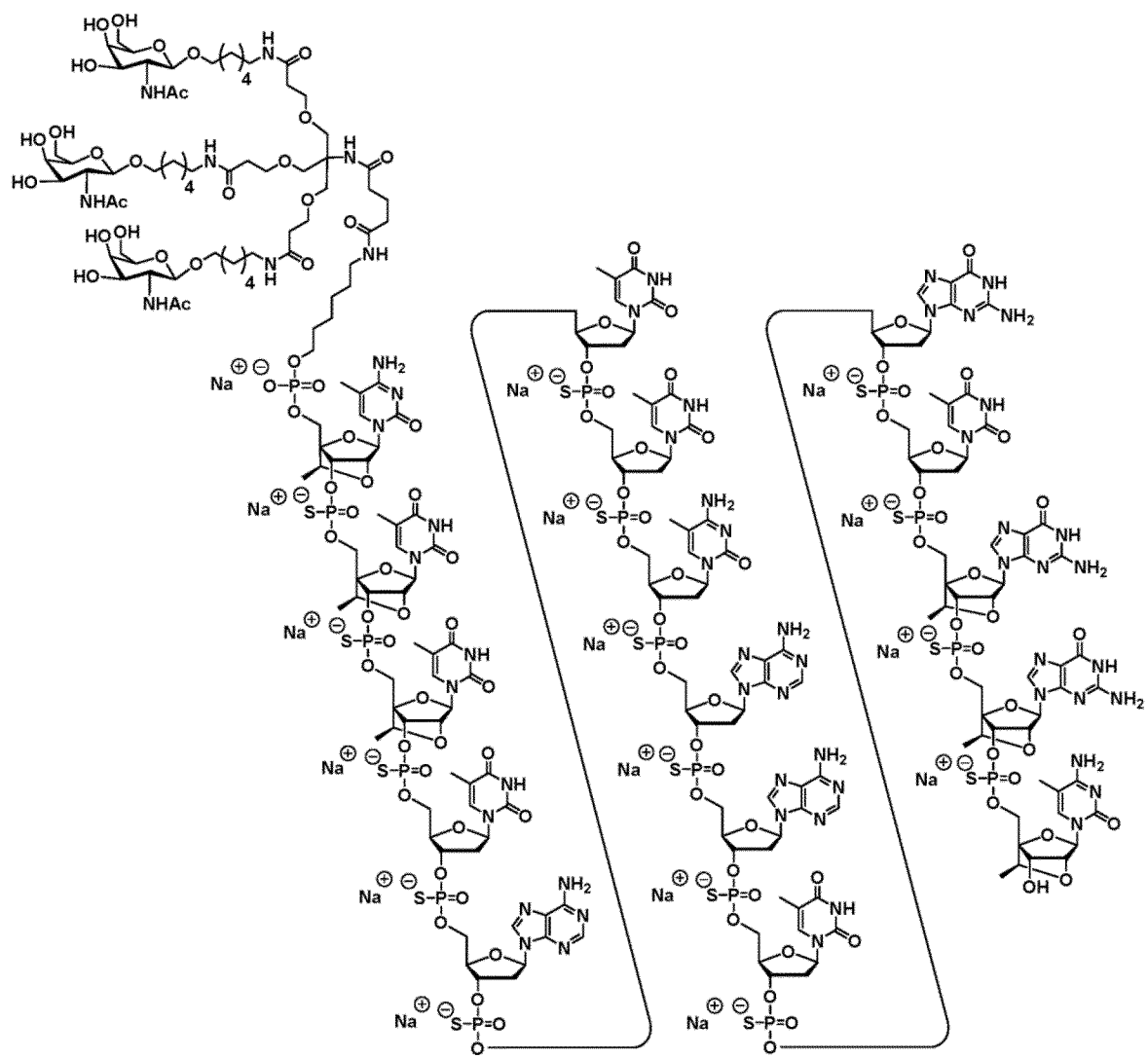

In Columns 51-52, please delete the structure:

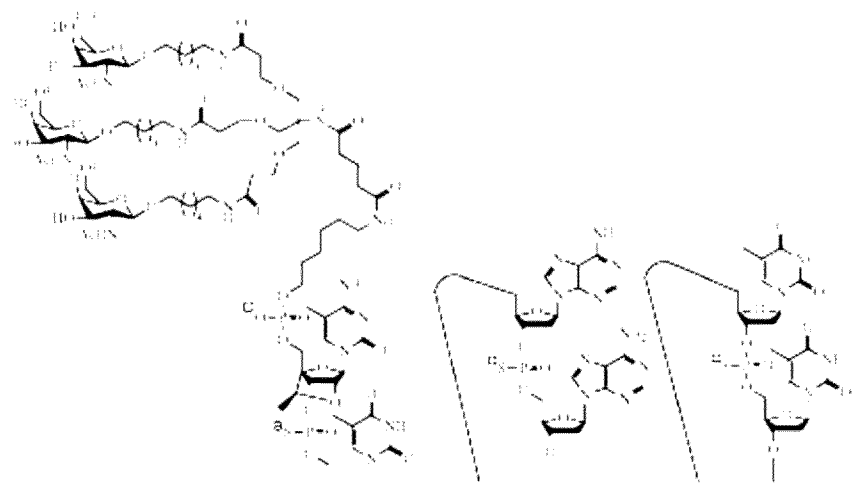
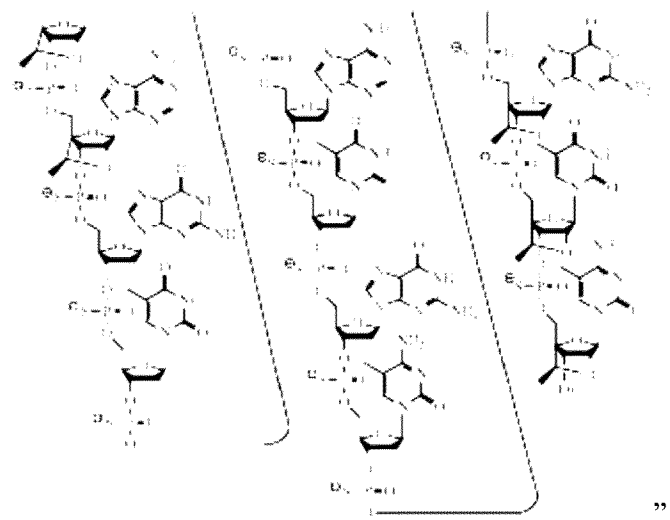
"                                            "
And replace with the correct structure:

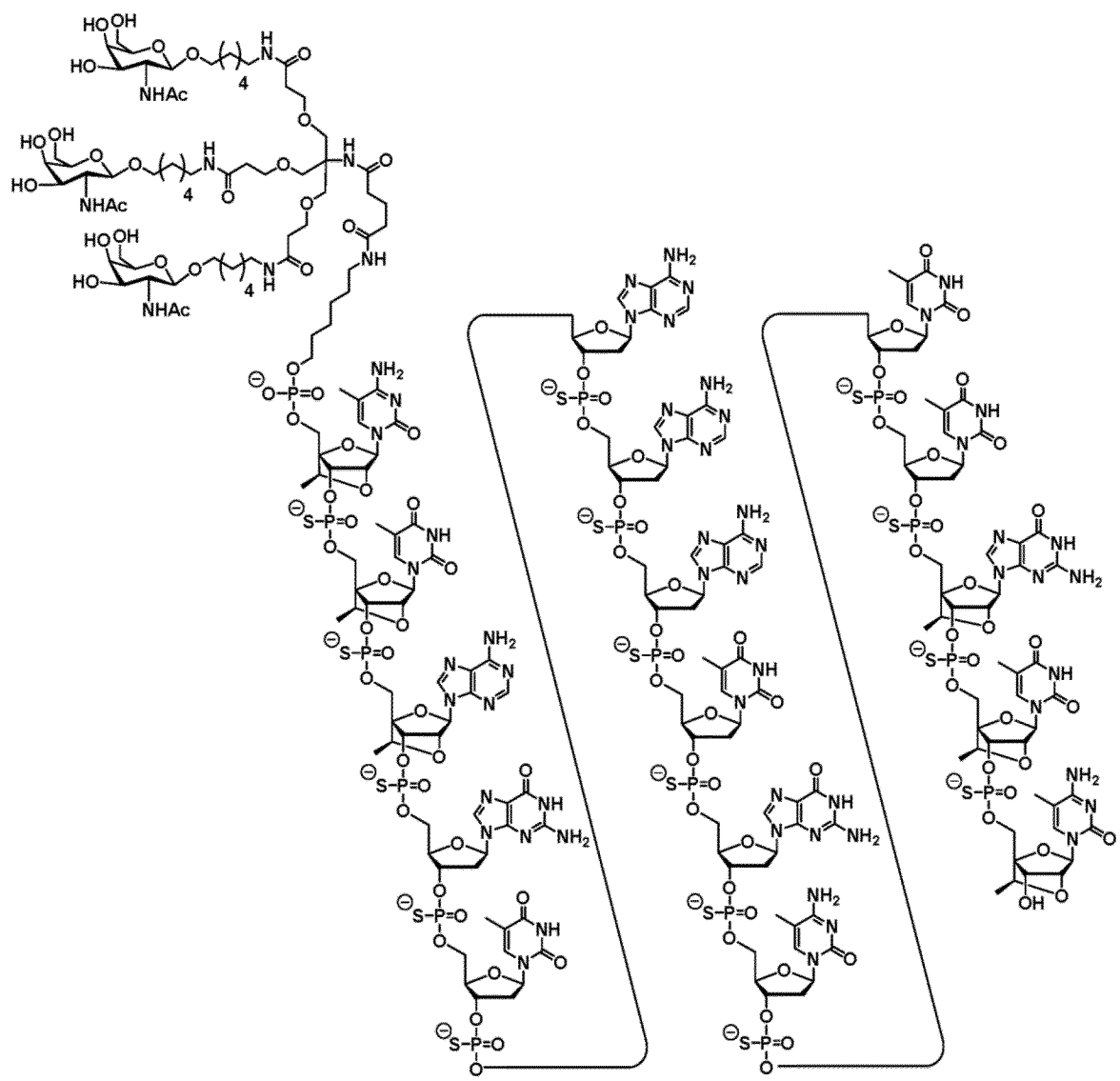
In Columns 53-54, please delete the structure:

CERTIFICATE OF CORRECTION (continued)
U.S. Pat. No. 11,781,143 B2

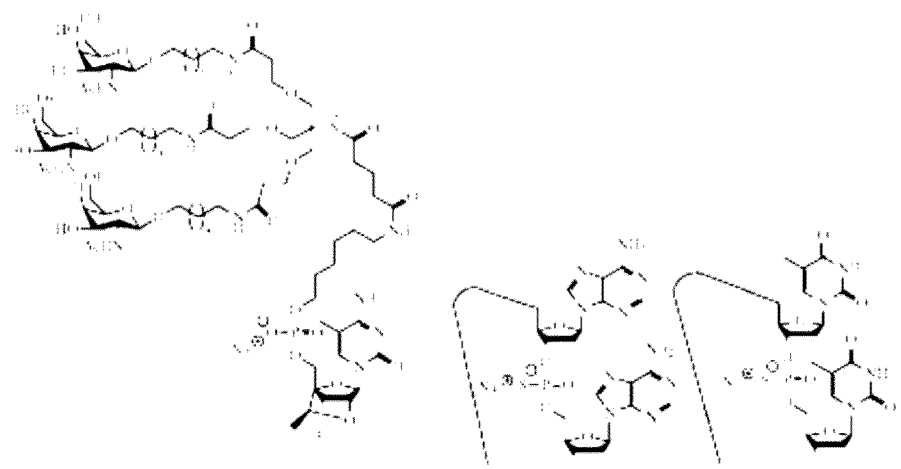

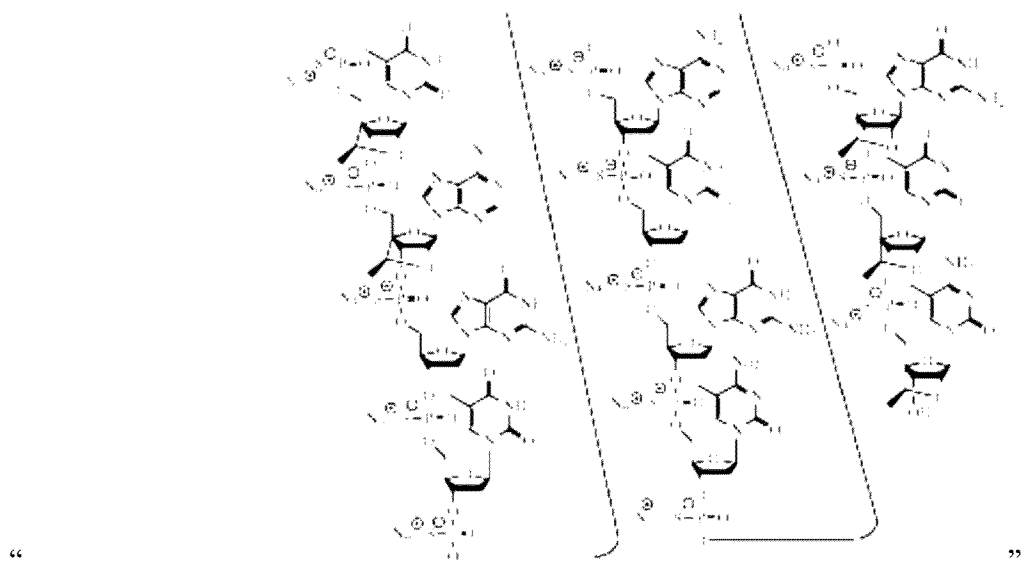

"                                                                           "

And replace with the correct structure:

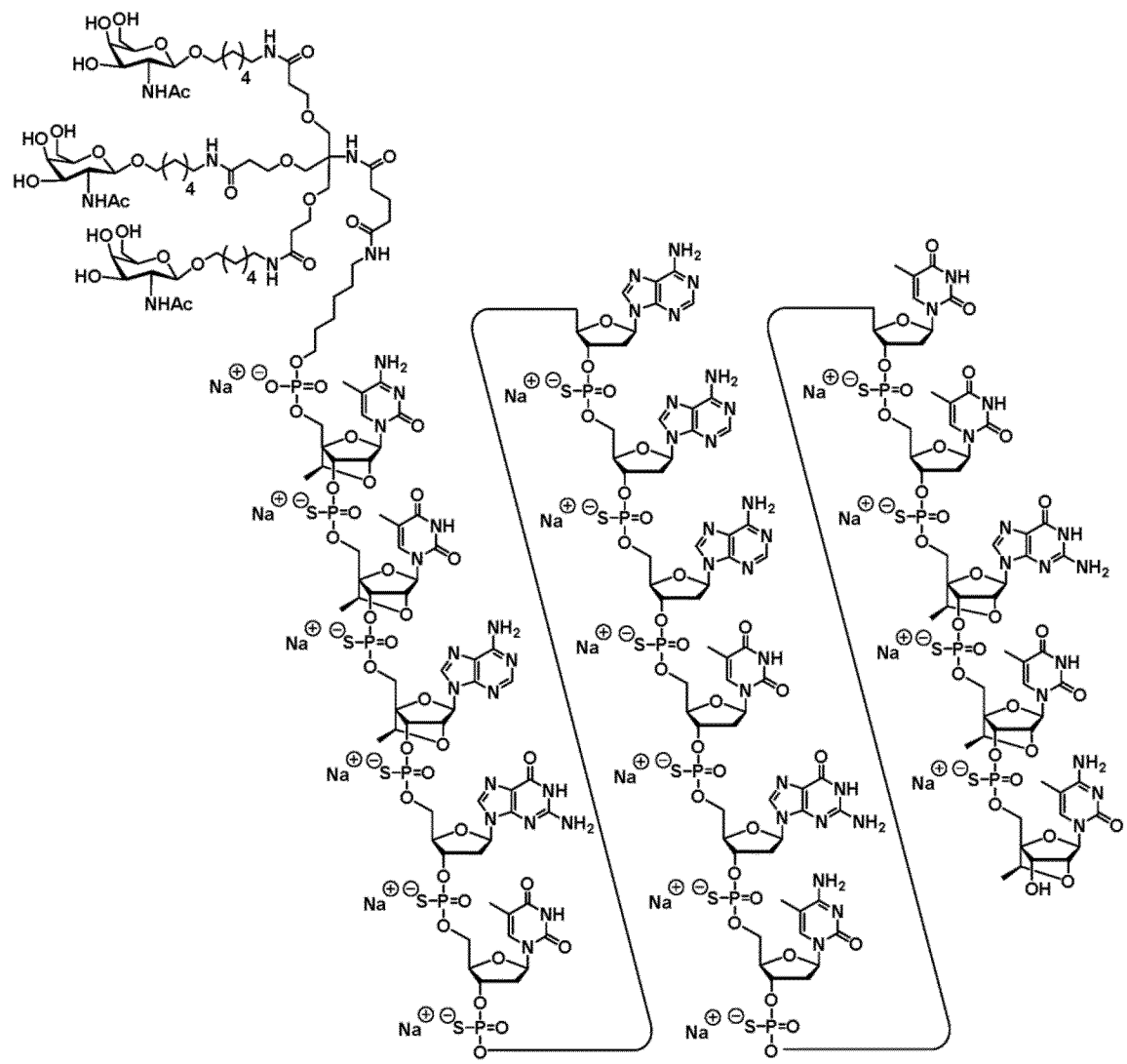

In Columns 55-56, please delete the structure:
"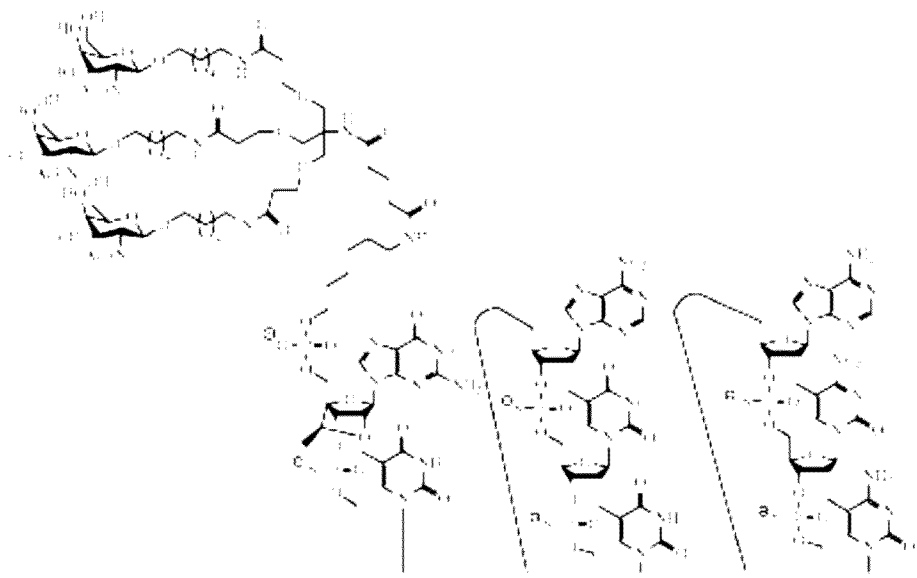
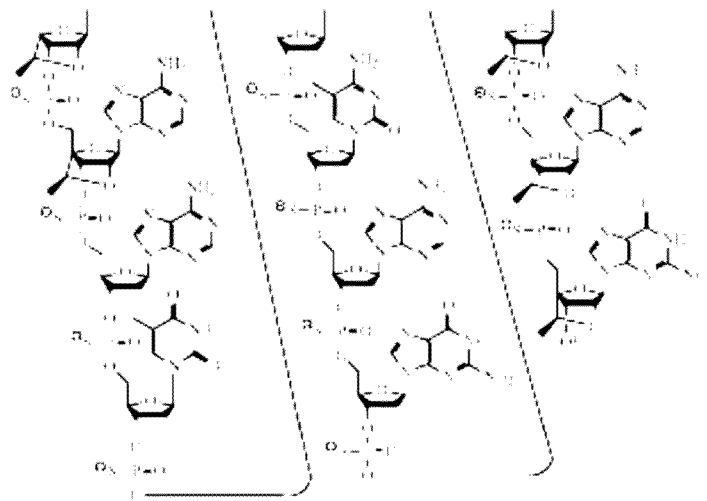"

And replace with the correct structure:
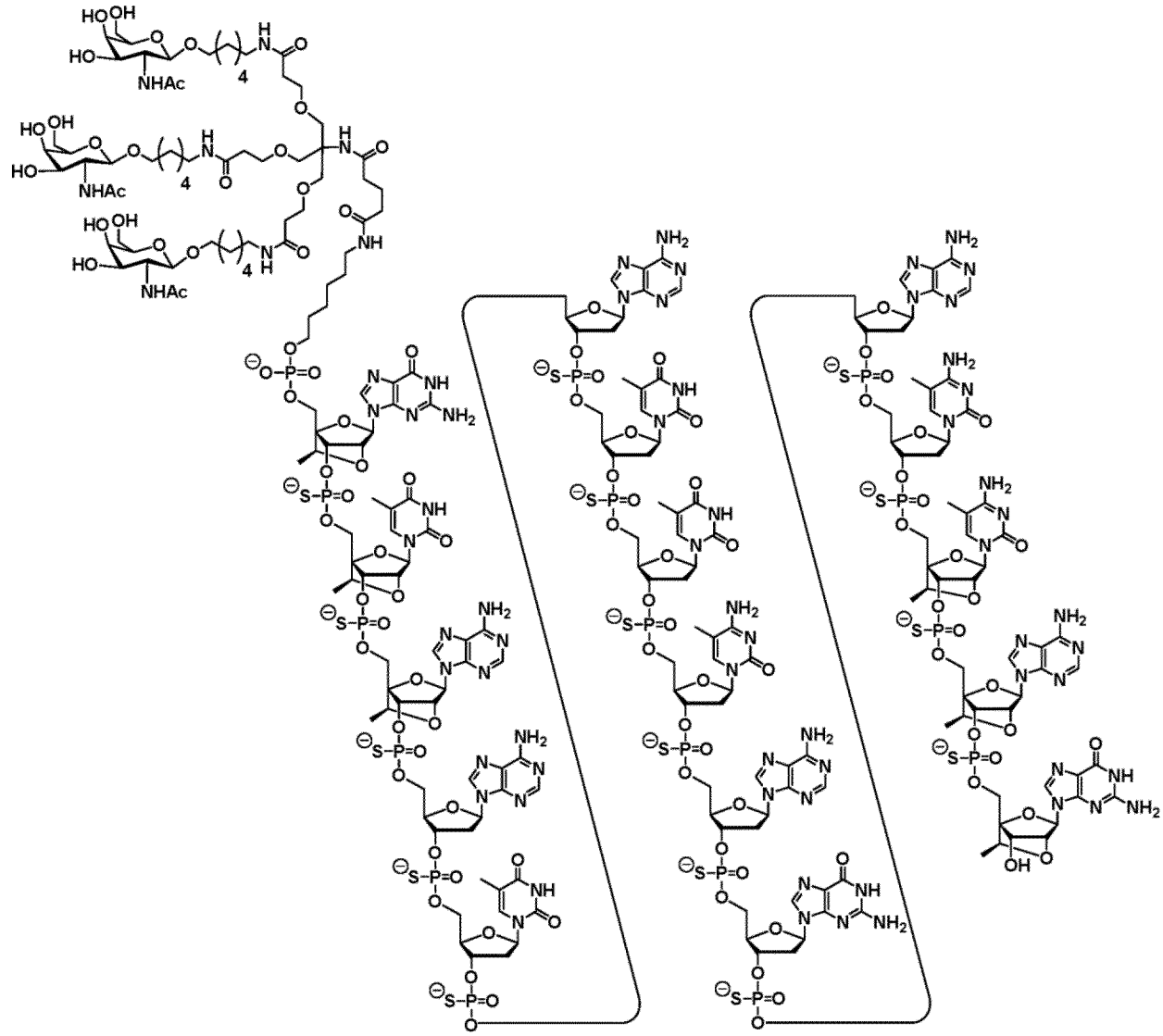

CERTIFICATE OF CORRECTION (continued)
U.S. Pat. No. 11,781,143 B2

In Columns 57-58, please delete the structure:

"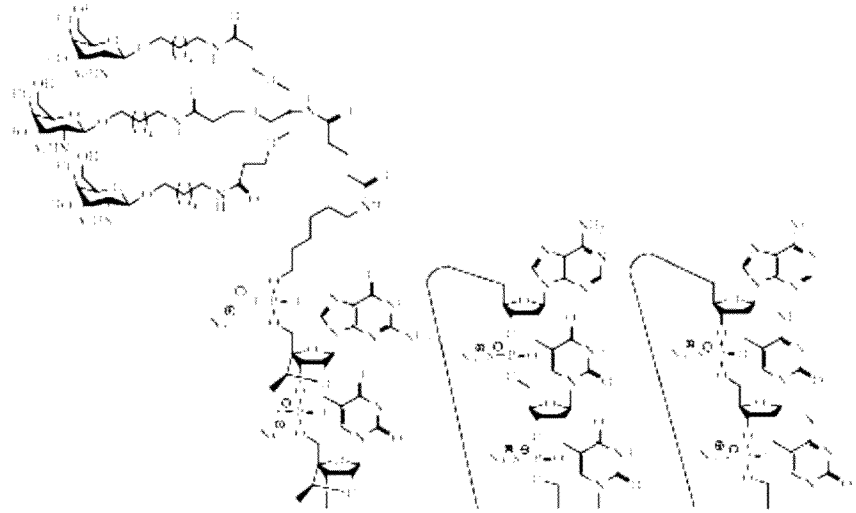

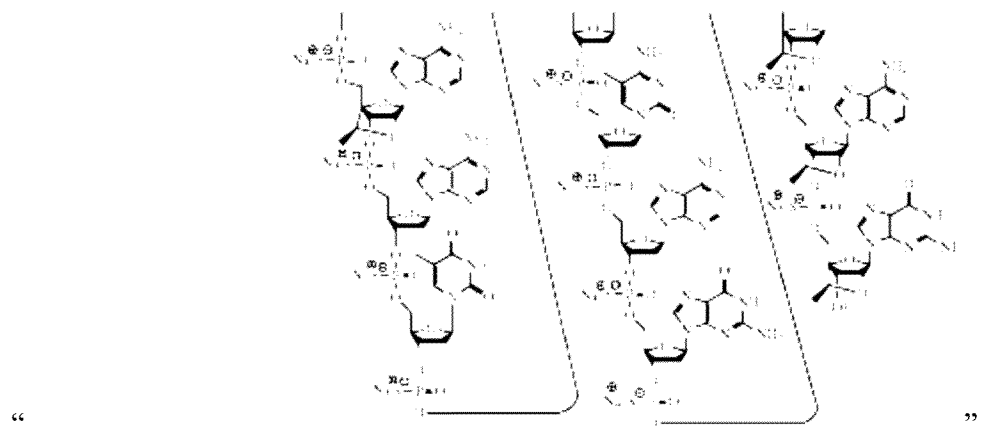"

And replace with the correct structure:
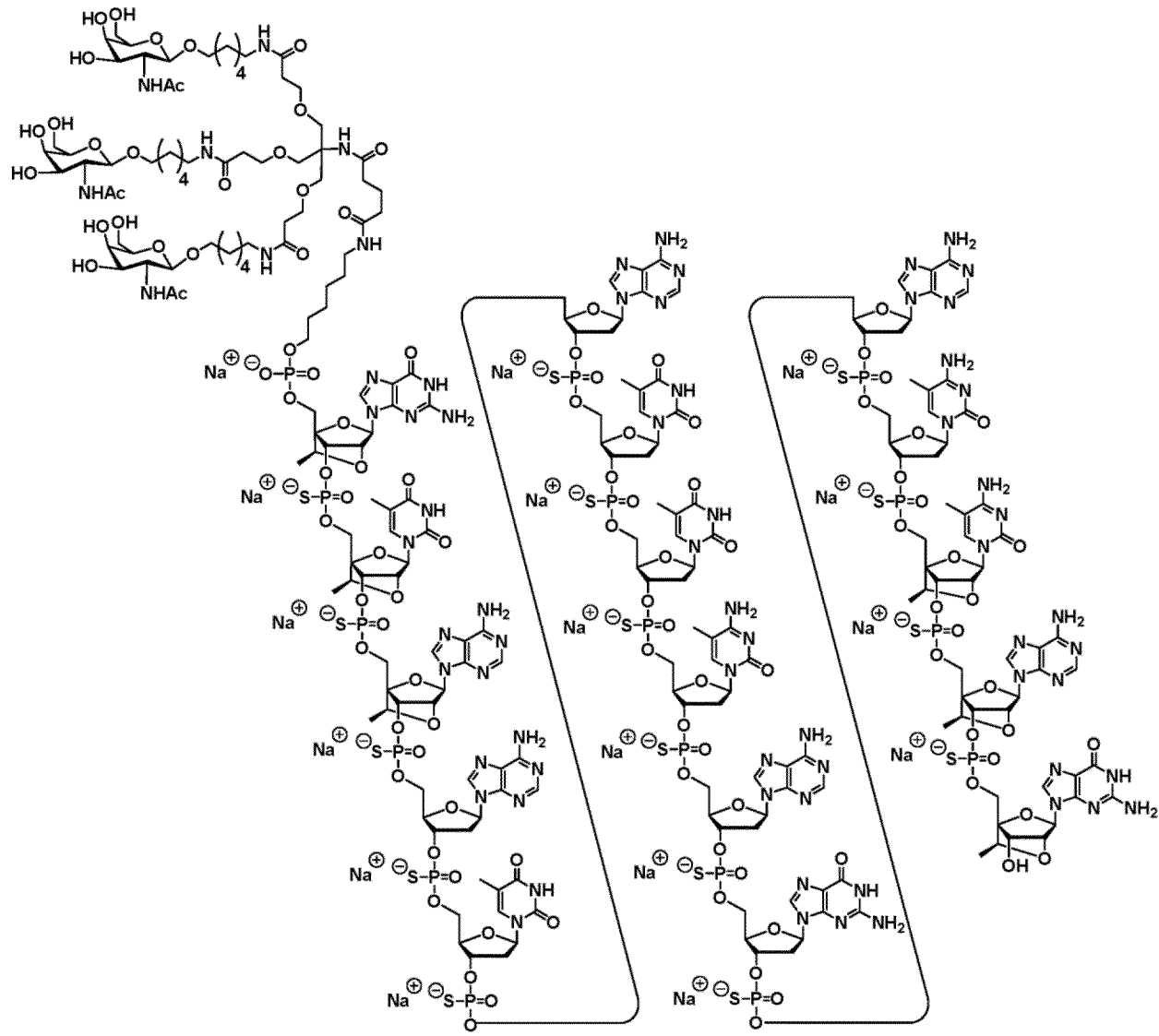

CERTIFICATE OF CORRECTION (continued)
U.S. Pat. No. 11,781,143 B2

In Columns 59-60, please delete the structure:

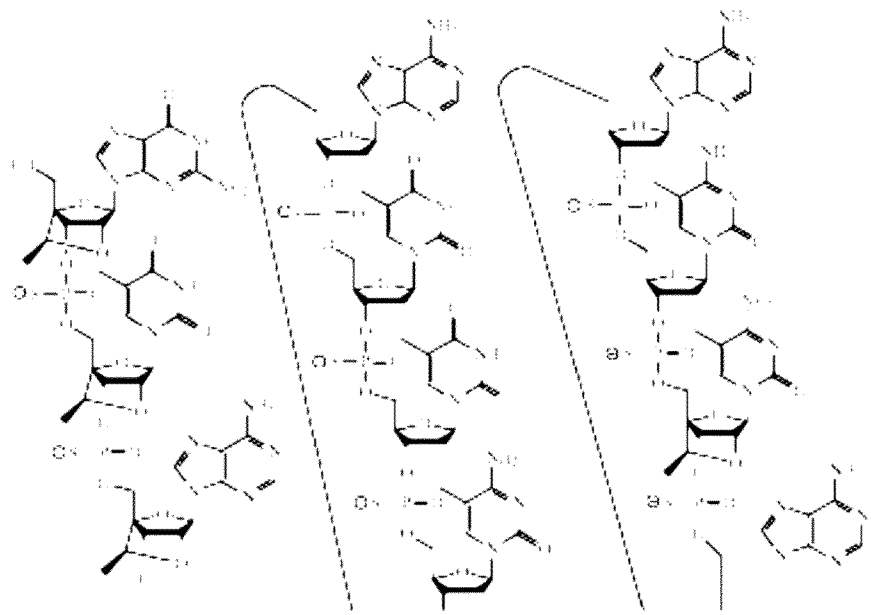

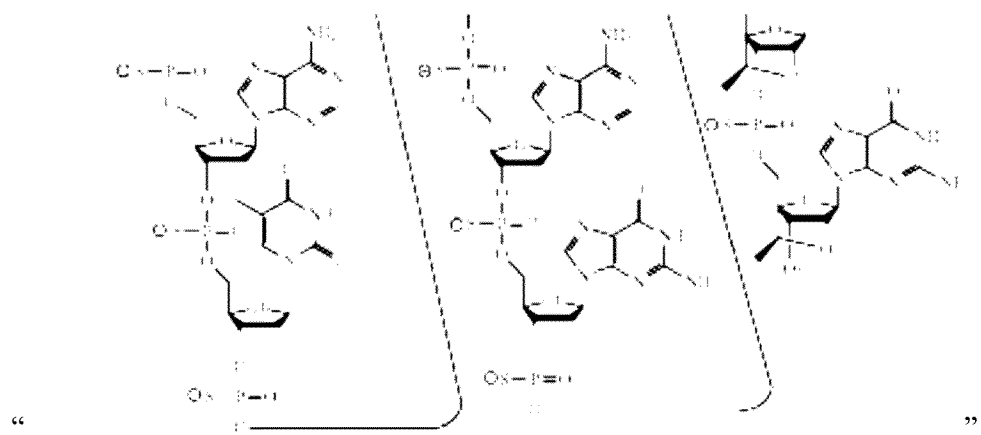

" "

And replace with the correct structure:
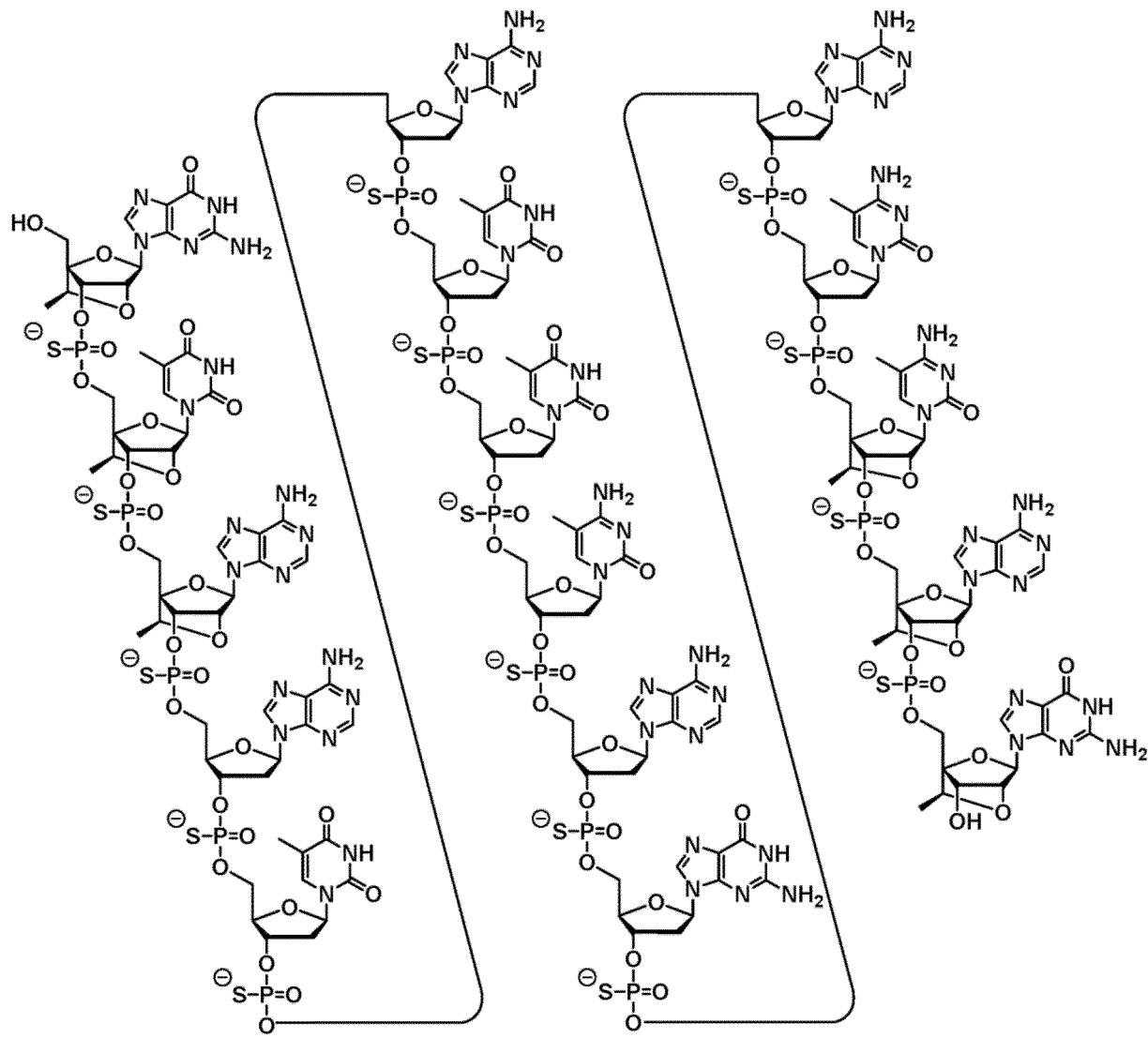
In Columns 61-62, please delete the structure:

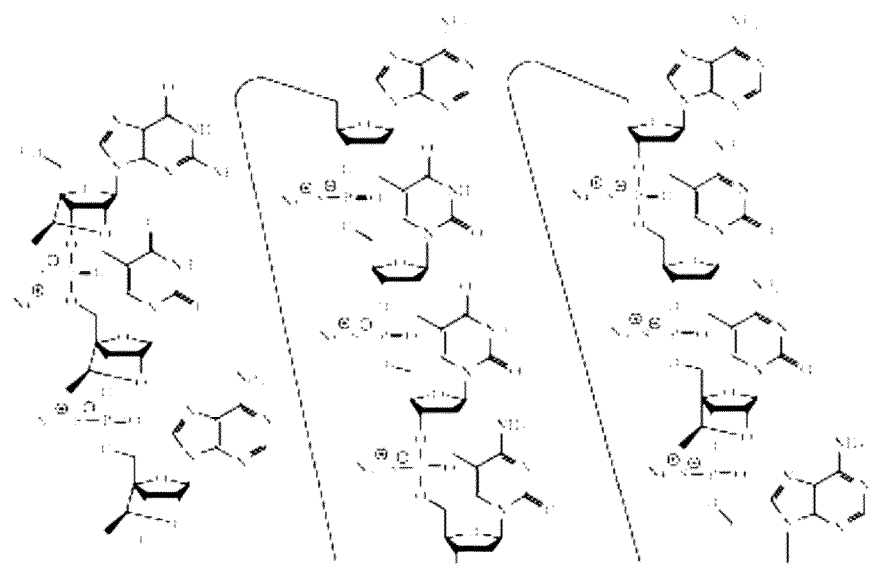
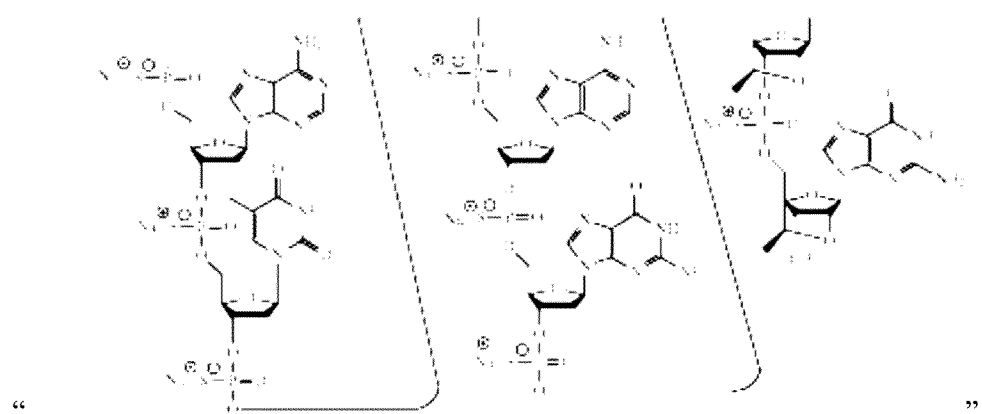
And replace with the correct structure:

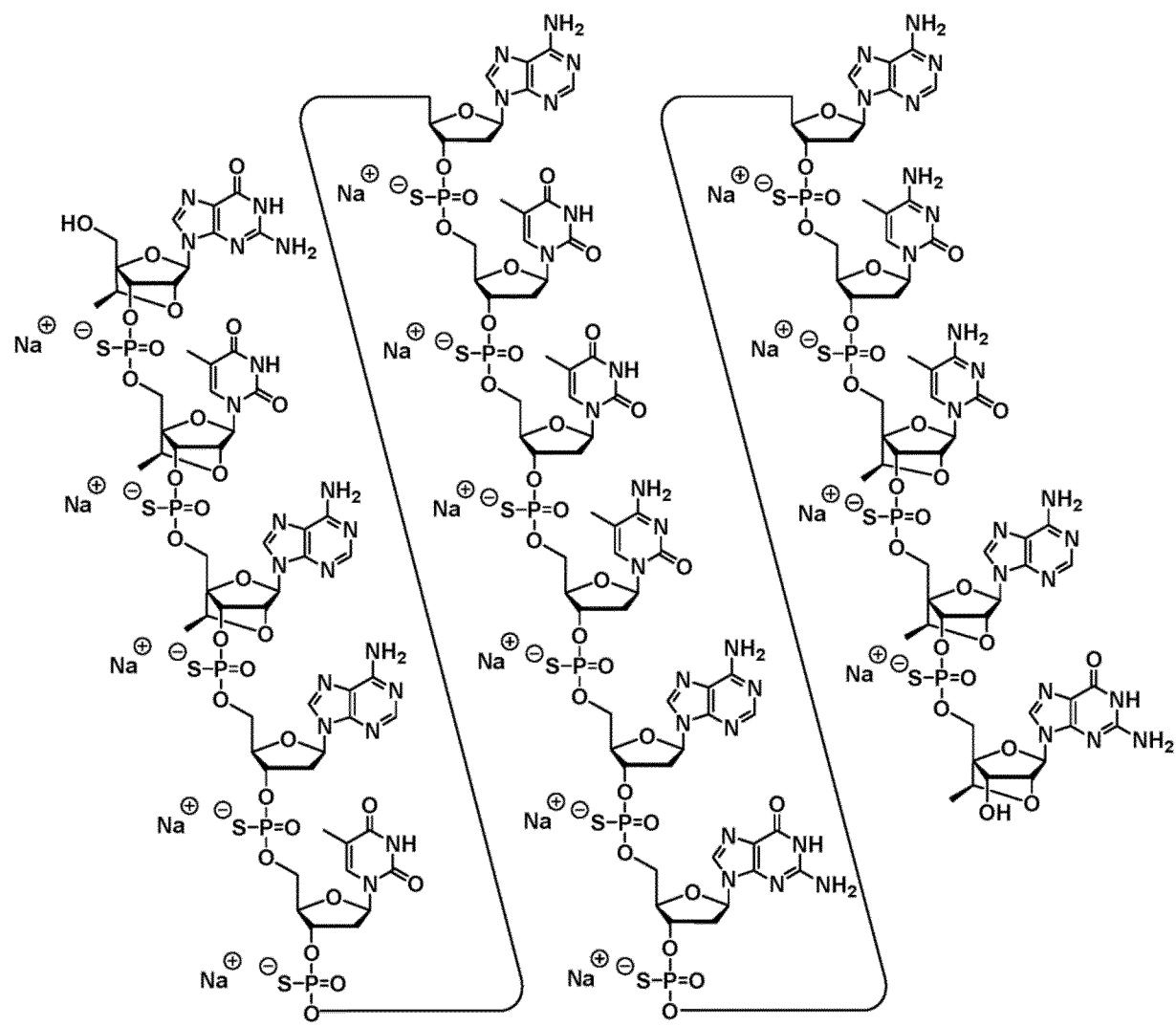

In Columns 63-64, please delete the structure:
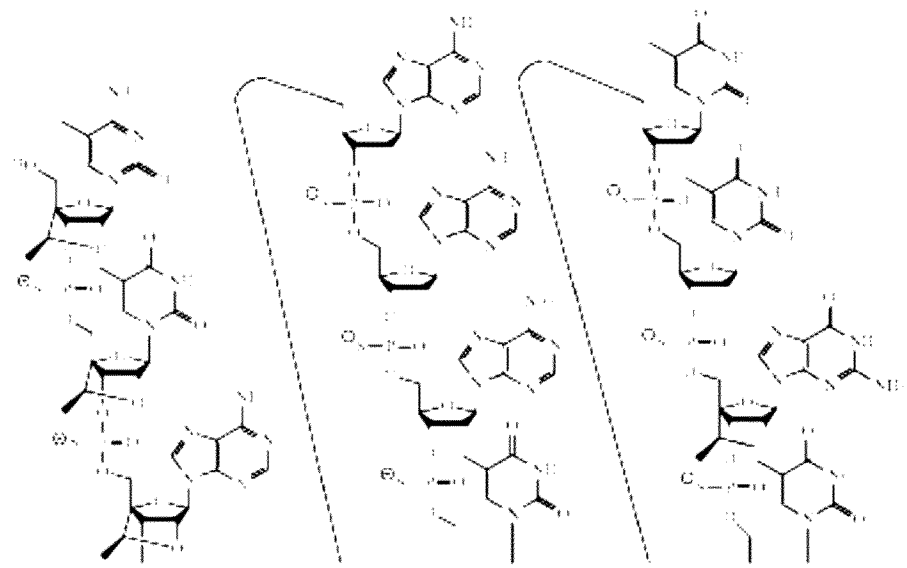
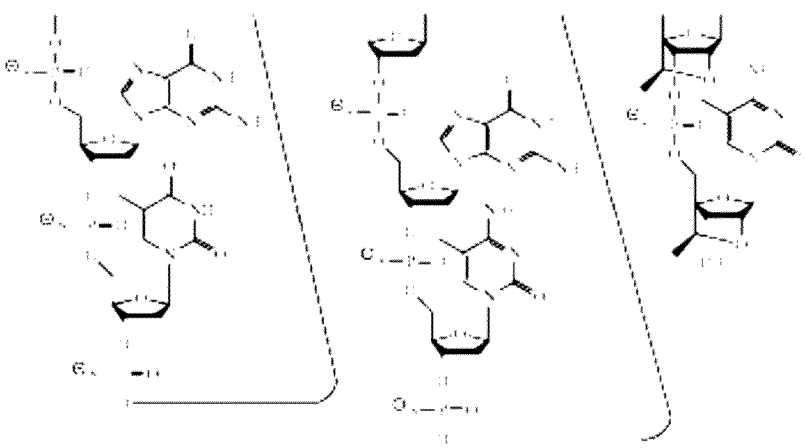

And replace with the correct structure:
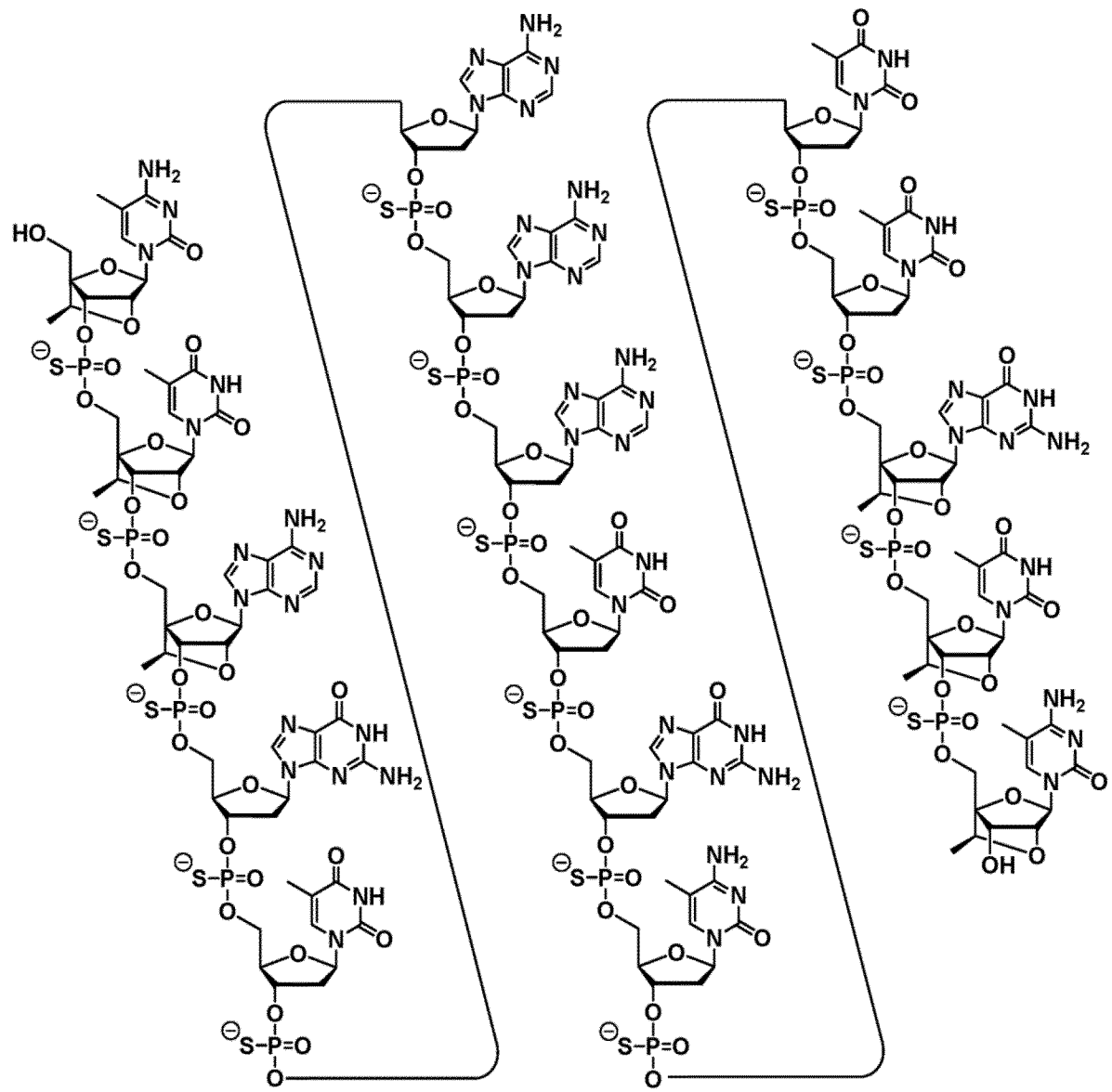

In Columns 65-66, please delete the structure:

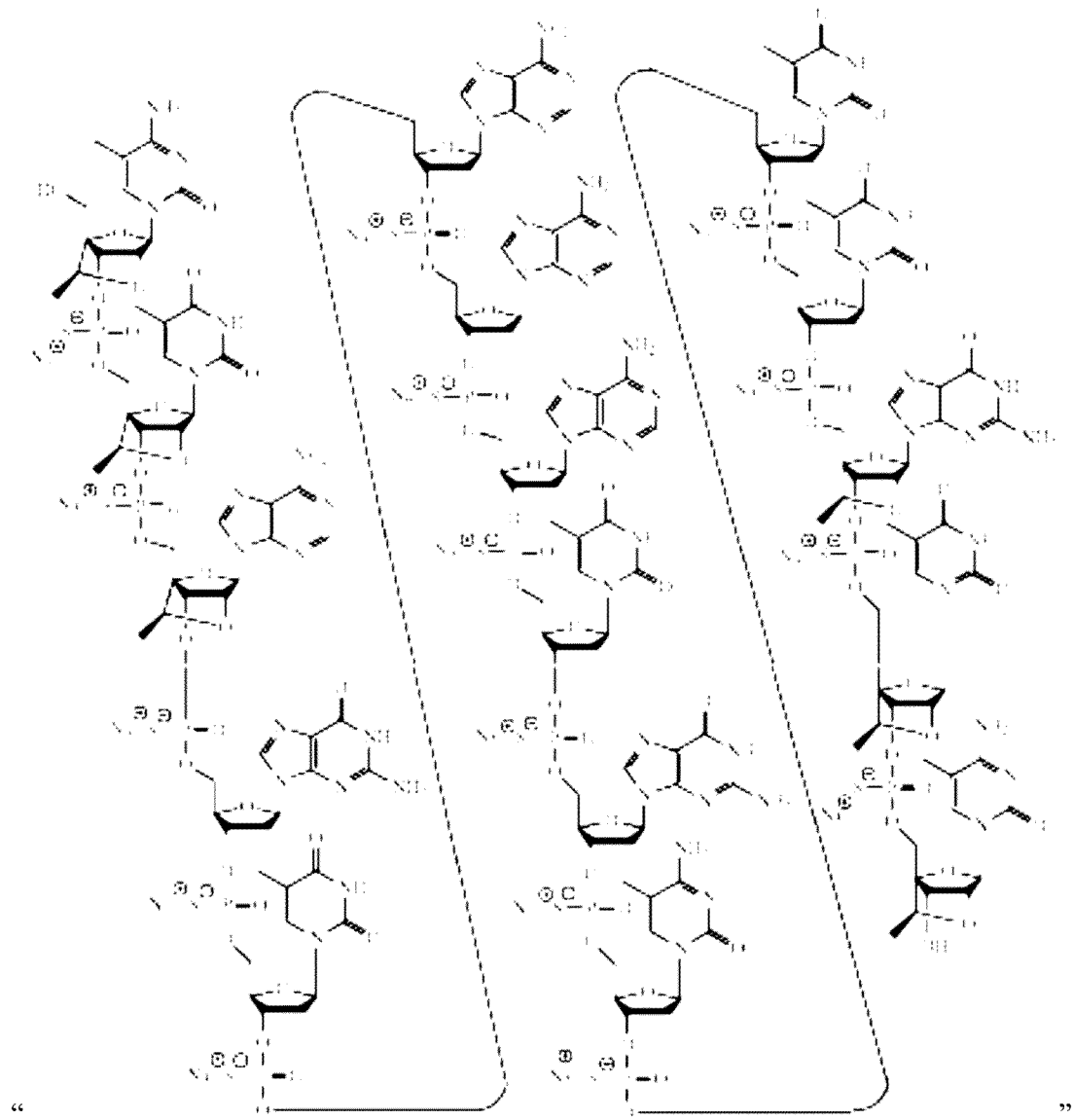

"                                                                                                                                                              "

CERTIFICATE OF CORRECTION (continued)
U.S. Pat. No. 11,781,143 B2

And replace with the correct structure:

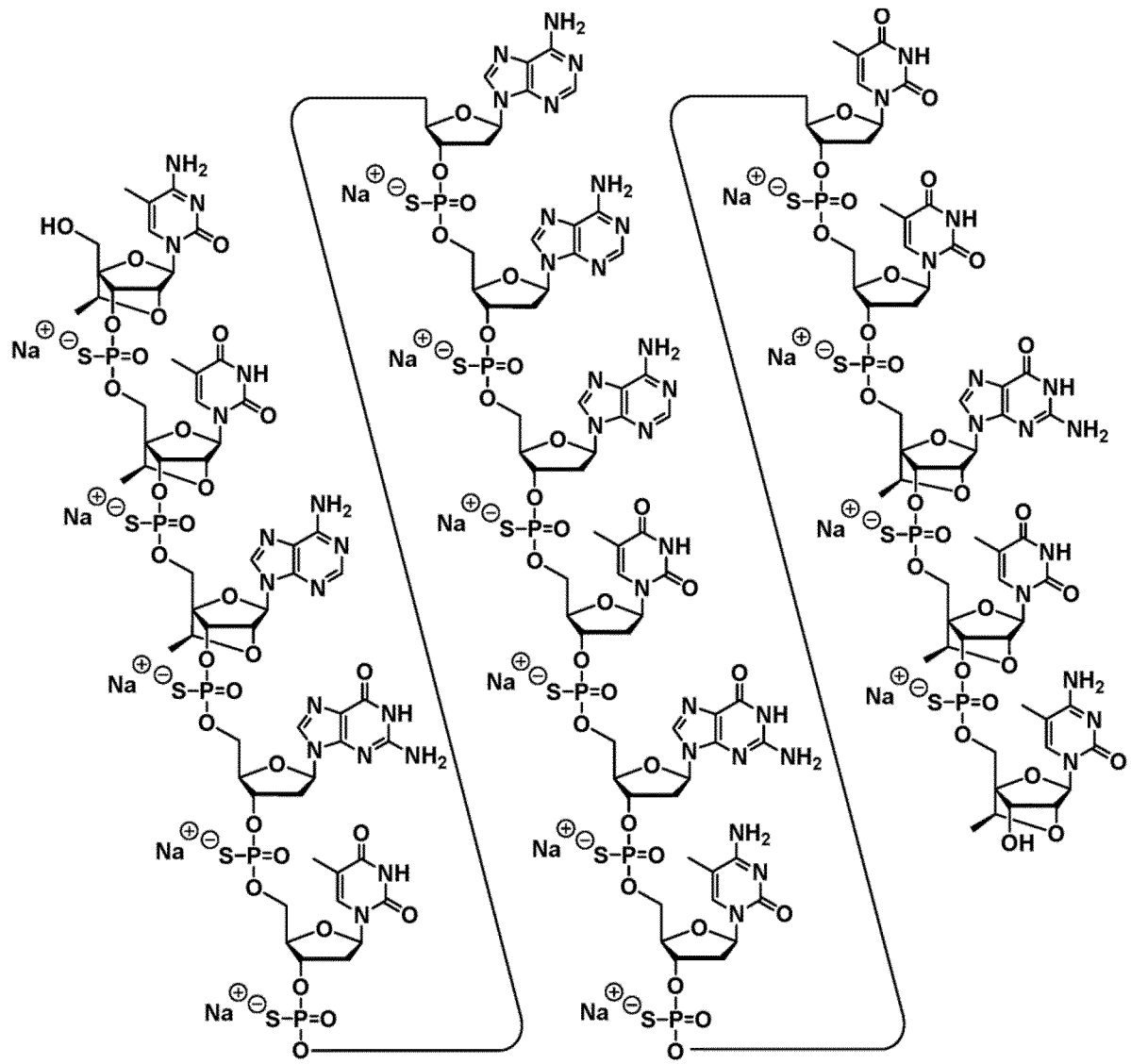

In Column 82, please delete the structure:

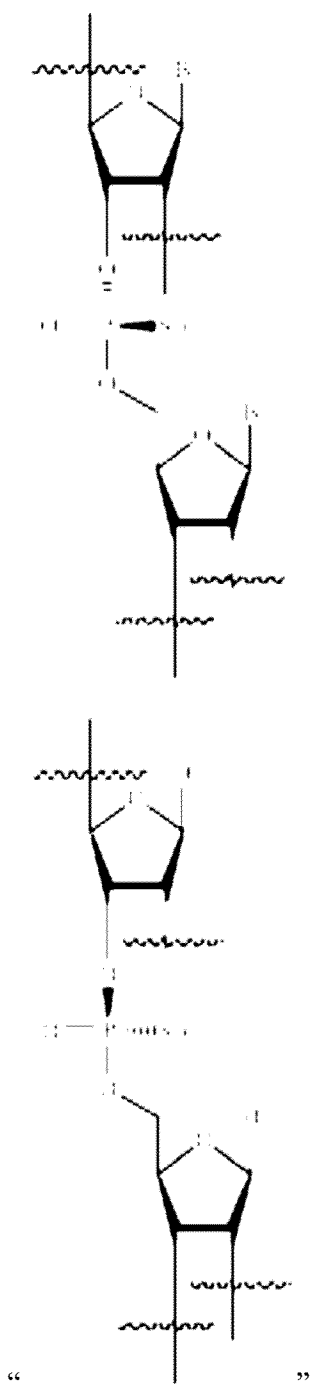
And replace with the correct structure: